US012595230B2

(12) United States Patent
Bernardelli et al.

(10) Patent No.: US 12,595,230 B2
(45) Date of Patent: Apr. 7, 2026

(54) SUBSTITUTED 6,7-DIHYDRO-5H-BENZO[7]ANNULENE COMPOUNDS AND THEIR DERIVATIVES, PROCESSES FOR THEIR PREPARATION AND THERAPEUTIC USES THEREOF

(71) Applicant: Sanofi, Paris (FR)

(72) Inventors: Patrick Bernardelli, Paris (FR); Marc Bianciotto, Paris (FR); Victor Certal, Paris (FR); Alice Da Rocha, Paris (FR); Béatrice De Bruin, Paris (FR); Youssef El Ahmad, Paris (FR); Frank Halley, Paris (FR); Patrick Mougenot, Paris (FR); Eric Nicolai, Paris (FR); Anne-Marie Periers, Paris (FR); Frédéric Petit, Paris (FR); Franck Slowinski, Paris (FR); Corinne Terrier, Paris (FR)

(73) Assignee: SANOFI, Paris (FR)

( * ) Notice: Subject to any disclaimer, the term of this patent is extended or adjusted under 35 U.S.C. 154(b) by 435 days.

(21) Appl. No.: 18/032,500

(22) PCT Filed: Oct. 19, 2021

(86) PCT No.: PCT/EP2021/078883

§ 371 (c)(1),
(2) Date: Apr. 18, 2023

(87) PCT Pub. No.: WO2022/084280

PCT Pub. Date: Apr. 28, 2022

(65) Prior Publication Data

US 2023/0382854 A1 Nov. 30, 2023

(30) Foreign Application Priority Data

Oct. 19, 2020 (EP) .................................... 20306236
Sep. 16, 2021 (EP) .................................... 21306281

(51) Int. Cl.
*C07D 205/04* (2006.01)
*A61P 35/00* (2006.01)
(Continued)

(52) U.S. Cl.
CPC ............ *C07D 205/04* (2013.01); *A61P 35/00* (2018.01); *C07D 205/12* (2013.01);
(Continued)

(58) Field of Classification Search
None
See application file for complete search history.

(56) References Cited

U.S. PATENT DOCUMENTS 6,495,607 B2 12/2002 Bohlmann et al.
7,429,681 B2 9/2008 Pinney et al.
(Continued)

FOREIGN PATENT DOCUMENTS

CN 1309635 A 8/2001
CN 106924210 A 7/2017
(Continued)

OTHER PUBLICATIONS

Ashizawa, Kazuhide, "Optimization of salt and crystalline forms, and crystallization techniques," Pharm Tech Japan, 2002, vol. 18, No. 10, pp. 81-96 (machine translation of excerpts).
Hirayama, Noriaki, "Handbook for organic compounds crystal preparation," 2008, pp. 17-23, 37-40, 45-51, 57-65 (machine translation of excerpts).
Rabion, A., et al., Pending U.S. Appl. No. 18/924,400, filed Oct. 23, 2024.
André, F., et al., Alpelisib for PIK3CA-Mutated, Hormone Receptor—Positive Advanced Breast Cancer, The New England Journal of Medicine, vol. 380, No. 20, May 16, 2019, 12 pages (1929-1940).
Anstead, Gregory, M. et al., "2,3-Diarylindenes and 2,3-Diarylindenones: Synthesis, Molecular Structure, Photochemistry, Estrogen Receptor Binding Activity, and Comparisons with Related Triarylethylenes", Journal of Medicinal Chemistry, 1988, vol. 31, No. 7, pp. 1316-1326.
(Continued)

*Primary Examiner* — Sarah Pihonak
*Assistant Examiner* — Donna M Nestor
(74) *Attorney, Agent, or Firm* — McNeill PLLC

(57) ABSTRACT

Disclosed herein are compounds of the formula (I), or pharmaceutically acceptable salts thereof wherein R1 and R2 represent a hydrogen atom or a deuterium atom; R3 represents a hydrogen atom, a —COOH group or a —OH group; R3' and R3" represent a hydrogen atom, a methyl group, a methoxy group, a chlorine atom, a fluorine atom, or a cyano group; R4 and R5 represent a hydrogen atom, a halogen atom, a —IMH2 group, a $(C_1\text{-}C_3)$alkyl group, a (C1-C3)alkoxy group, or a —OH group; or R4 and R5 together form an oxo group or R4 and R5 together form a $=NOCH_3$ group or a $(C_3\text{-}C_5)$cycloalkyl group; R7 represents a hydrogen atom, a methyl group, a —OH group or a fluorine atom; R6 represents a phenyl group, a fused phenyl group, a bicyclic group comprising 5 to 12 carbon atoms, a heteroaryl group comprising 2 to 9 carbon atoms and comprising from 1 to 3 heteroatoms, a cycloalkyl group comprising 3 to 7 carbon atoms, a (C3-C6) cycloalkyl (C1-C3) alkyl group, a 3 to 8 membered-heterocycloalkyl group, a (C1-C6)alkyl group or a phenyl $(C_1\text{-}C_2)$ alkyl group; X represents $—CH_2—$, —O— or —S—; Y represents —CH=, —N= or —CR"=; R8 represents a $(C_1\text{-}C_3)$ alkyl group, a halogen atom, a cyano group, or a $(C_1\text{-}C_3)$ fluoroalkyl group; R9 represents a hydrogen atom or a fluorine atom; RIO and RIO' represent a hydrogen atom or a fluorine atom; R11 represents a hydrogen atom a $(C_1\text{-}C_3)$ alkyl group or a cyclopropyl group; n is 0, 1 or 2, and m is 0 or 1. Further disclosed are process for preparing the same, pharmaceutical compositions comprising them as well as said compounds of formula (I) for use as an inhibitor and degrader of estrogen receptors, in particular in the treatment
(Continued)

of ovulatory dysfunction, cancer, endometriosis, osteoporosis, benign prostatic hypertrophy or inflammation.

(I)

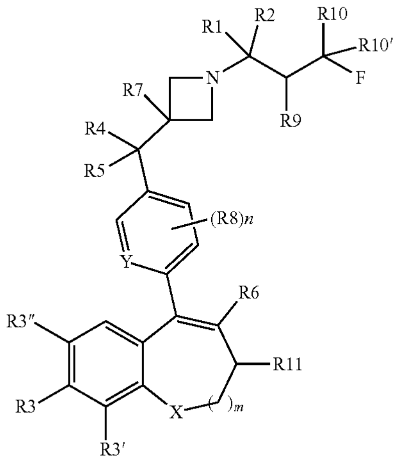

32 Claims, No Drawings

(51) Int. Cl.
*C07D 205/12* (2006.01)
*C07D 401/06* (2006.01)
*C07D 401/10* (2006.01)
*C07D 403/10* (2006.01)

(52) U.S. Cl.
CPC ......... *C07D 401/06* (2013.01); *C07D 401/10* (2013.01); *C07D 403/10* (2013.01)

(56) References Cited

U.S. PATENT DOCUMENTS

| | | | |
|---|---|---|---|
| 7,612,114 | B2 | 11/2009 | Hamaoka et al. |
| 7,799,824 | B2 | 9/2010 | Lagu et al. |
| 8,299,112 | B2 | 10/2012 | Smith et al. |
| 9,309,211 | B2 | 4/2016 | Xiao et al. |
| 9,540,361 | B2 | 1/2017 | Dijcks et al. |
| 9,714,221 | B1 | 7/2017 | Bouaboula et al. |
| 9,845,291 | B2 | 12/2017 | Liang et al. |
| 10,570,090 | B2 | 2/2020 | Bouaboula et al. |
| 10,966,963 | B2 | 4/2021 | Labadie et al. |
| 11,149,031 | B2 | 10/2021 | Bouaboula et al. |
| 11,214,541 | B2 | 1/2022 | Bouaboula et al. |
| 11,260,057 | B2 | 3/2022 | Bouaboula et al. |
| 11,713,296 | B2 | 8/2023 | Malpart et al. |
| 12,157,721 | B2 | 12/2024 | Rabion et al. |
| 2012/0130219 | A1 | 5/2012 | Zhao et al. |
| 2013/0252890 | A1 | 9/2013 | Wintermantel et al. |
| 2015/0080438 | A1 | 3/2015 | Wintermantel et al. |
| 2015/0157606 | A1 | 6/2015 | Maneval et al. |
| 2016/0184311 | A1 | 6/2016 | Chen et al. |
| 2017/0197915 | A9 | 7/2017 | Liang et al. |
| 2017/0233340 | A1 | 8/2017 | Bouaboula et al. |
| 2018/0153828 | A1 | 6/2018 | Garner et al. |
| 2019/0167652 | A1 | 6/2019 | Abrams et al. |
| 2020/0155521 | A1 | 5/2020 | Schwartz et al. |
| 2020/0352905 | A1 | 11/2020 | Cartot-Cotton et al. |
| 2020/0361918 | A1 | 11/2020 | Bouaboula et al. |
| 2020/0392081 | A1 | 12/2020 | Bouaboula et al. |
| 2021/0188771 | A1 | 6/2021 | Rabion et al. |
| 2021/0188772 | A1 | 6/2021 | Malpart et al. |
| 2022/0073460 | A1 | 3/2022 | Bouaboula et al. |
| 2022/0204488 | A1 | 6/2022 | Bouaboula et al. |
| 2022/0362248 | A1 | 11/2022 | Bouaboula et al. |
| 2023/0028566 | A1 | 1/2023 | Billot et al. |
| 2023/0089371 | A1 | 3/2023 | Bouaboula et al. |
| 2023/0115865 | A1 | 4/2023 | Boisnard et al. |
| 2023/0404971 | A1 | 12/2023 | Bouaboula et al. |
| 2024/0091194 | A1 | 3/2024 | Cartot-Cotton et al. |
| 2024/0101512 | A1 | 3/2024 | Bernardelli et al. |
| 2024/0197692 | A1 | 6/2024 | Bouaboula et al. |
| 2024/0197739 | A1 | 6/2024 | Bouaboula et al. |
| 2025/0042849 | A1 | 2/2025 | Rabion et al. |

FOREIGN PATENT DOCUMENTS

| | | | |
|---|---|---|---|
| CN | 109896991 | A | 6/2019 |
| EA | 023947 | B1 | 7/2016 |
| EP | 1229036 | A1 | 8/2002 |
| EP | 3434272 | A1 | 1/2019 |
| JP | 2002520388 | A | 7/2002 |
| JP | 2005528320 | A | 9/2005 |
| JP | 2008512348 | A | 4/2008 |
| JP | 2008546706 | A | 12/2008 |
| JP | 2011500538 | A | 1/2011 |
| JP | 2013530973 | A | 8/2013 |
| JP | 2015500814 | A | 1/2015 |
| JP | 2018537406 | A | 12/2018 |
| WO | 1992015579 | A1 | 9/1992 |
| WO | 2000003979 | A1 | 1/2000 |
| WO | 2003016270 | A2 | 2/2003 |
| WO | 2003091239 | A1 | 11/2003 |
| WO | 2004058682 | A1 | 7/2004 |
| WO | 2006012135 | A1 | 2/2006 |
| WO | 2006138427 | A2 | 12/2006 |
| WO | 2009047343 | A1 | 4/2009 |
| WO | 2009101634 | A2 | 8/2009 |
| WO | 2012037410 | A2 | 3/2012 |
| WO | 2012037411 | A2 | 3/2012 |
| WO | 2012068284 | A2 | 5/2012 |
| WO | 2013097773 | A1 | 7/2013 |
| WO | 2015028409 | A1 | 3/2015 |
| WO | 2016051374 | A1 | 4/2016 |
| WO | 2016097071 | A1 | 6/2016 |
| WO | 2016097072 | A1 | 6/2016 |
| WO | 2016176666 | A1 | 11/2016 |
| WO | 2017140669 | A1 | 8/2017 |
| WO | 2018091153 | A1 | 5/2018 |
| WO | 2019020559 | A1 | 1/2019 |
| WO | 2019106604 | A1 | 6/2019 |
| WO | 2019144132 | A1 | 7/2019 |
| WO | 2020014435 | A1 | 1/2020 |
| WO | 2020049153 | A1 | 3/2020 |
| WO | 2020112765 | A1 | 6/2020 |
| WO | 2020225375 | A1 | 11/2020 |
| WO | 2021116074 | A1 | 6/2021 |
| WO | 2021127043 | A1 | 6/2021 |
| WO | 2021170793 | A1 | 9/2021 |
| WO | 2021178846 | A1 | 9/2021 |
| WO | 2022084298 | A1 | 4/2022 |
| WO | 2022106711 | A1 | 5/2022 |
| WO | 2022218956 | A1 | 10/2022 |
| WO | 2022218958 | A1 | 10/2022 |

OTHER PUBLICATIONS

Bardia, A., et al., Dose-escalation study of SAR439859, an oral selective estrogen receptor (ER) degrader (SERD), in postmenopausal women with ER+/HER2− metastatic breast cancer (mBC), Journal of Clinical Oncology, vol. 37, Suppl. 15, p. 1054 (May 20, 2019).

Bernardelli, P., et al., Pending U.S. Appl. No. 18/032,502, filed Apr. 18, 2023.

Billot, P. et al., Pending U.S. Appl. No. 17/783,364, filed Jun. 8, 2022.

Boinsard, S., et al., Pending U.S. Appl. No. 17/765,169, filed Mar. 30, 2022.

Bouaboula, M. et al., Pending U.S. Appl. No. 18/037,949, filed May 19, 2023.

(56) References Cited

OTHER PUBLICATIONS

Bouaboula, M. et al., U.S. Appl. No. 16/414,558, filed May 16, 2019 (Issued).
Bouaboula, M., et al., Pending U.S. Appl. No. 16/634,089, filed Jan. 24, 2020. (Issued).
Bouaboula, M., et al., Pending U.S. Appl. No. 17/460,629, filed Aug. 30, 2021.
Bouaboula, M., et al., Pending U.S. Appl. No. 17/532,051, filed Nov. 22, 2021.
Bouaboula, M., et al., Pending U.S. Appl. No. 17/579,187, filed Jan. 19, 2022.
Bouaboula, M., et al., Pending U.S. Appl. No. 17/802,223, filed Aug. 25, 2022.
Bouaboula, M., et al., U.S. Appl. No. 16/743,504, filed Jan. 15, 2020 (Abandoned).
Bouaboula, M., et al., U.S. Appl. No. 17/124,852, filed Dec. 17, 2020. (Issued).
Campone, M., et al., "Abstract P5-11-02: Dose-escalation study of SAR439859, an oral selective estrogen receptor degrader, in post-menopausal women with estrogen receptor-positive and human epidermal growth factor receptor 2-negative metastatic breast cancer," Cancer Research, vol. 80, Suppl. 4, pp. 1-4 (Feb. 2020).
Cancer [online]—Medline Plus, [Retrieved on Jul. 6, 2007] Retrieved from the Internet, URL: http://www.nlm.nih.gov/medlineplus/cancer.html, pp. 1-10.
Cartot-Cotton, S., et al., Pending U.S. Appl. No. 16/870,031, filed May 8, 2020.
Chandarlapaty, S., et al., "277MO SAR439859, an oral selective estrogen receptor (ER) degrader (SERD), in ER +/ HER2− metastatic breast cancer (mBC): Biomarker analyses from a phase I/II study", Annals of Oncology, vol. 31, No. S4, Sep. 1, 2020, p. S351.
Deroo, B.J., et al., "Estrogen Receptors and Human Disease", The Journal of Clinical Investigation, vol. 116, No. 3, pp. 561-570 (2006).
El-Ahmad, Y., et al., "Discovery of 6-(2,4-Dichlorophenyl)-5-[4-[(3S)-1-(3-fluoropropyl)-pyrrolidin-3-yl]-oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," Journal of Medicinal Chemistry, vol. 63, No. 2, pp. 512-528 (2019).
Extended European Search Report issued in European Application No. 19305593.6 on Oct. 30, 2019, 7 pages.
Franks, et al., "Selective Estrogen Receptor Modulators: Cannabinoid Receptor Inverse Agonists with Differential CB1 and CB2 Selectively," Frontiers in Pharmacology, vol. 7, No. 503, pp. 1-16 (2016).
Golub et al., "Molecular Classification of Cancer: Class Discovery and Class Prediction by Gene Expression Monitoring", Science, vol. 286, pp. 531-537 (1999).
Gould, P., "Salt selection for basic drugs," International Journal of Pharmaceutics, vol. 33, pp. 201-217 (1986).
International Search Report for International Application No. PCT/EP2017/053282, mailed Jul. 6, 2017.
International Search Report for International Application No. PCT/EP2017/068446, mailed Sep. 12, 2017.
International Search Report for International Application No. PCT/EP2018/069901, mailed Oct. 12, 2018.
International Search Report for International Application No. PCT/EP2019/073823, mailed Oct. 10, 2019.
International Search Report for International Application No. PCT/EP2019/073827, mailed Oct. 9, 2019.
International Search Report for International Application No. PCT/EP2020/062743, mailed Aug. 10, 2020.
International Search Report for International Application No. PCT/EP2020/085011, mailed Jan. 25, 2021.
International Search Report for International Application No. PCT/EP2021/054815, mailed May 12, 2021.
International Search Report for International Application No. PCT/EP2021/078916, mailed Dec. 9, 2021.
International Search Report for International Application No. PCT/EP2021/082583, mailed Feb. 25, 2022.
Jordan, Craig V., "Antiestrogens and Selective Estrogen Receptor Modulators as Multifunctional Medicines. 1. Receptor Interactions," Journal of Medicinal Chemistry,vol. 46, No. 6, pp. 883-908 (2003).
Lala, P.K., et al., "Role of Nitric Oxide in Tumor Progression: Lessons From Experimental Tumors", Cancer Metastasis Reviews, Mar. 1998, vol. 17, No. 1, pp. 91-106.
Littke, A.F., et al., "Versatile Catalysts for the Suzuki Cross-Coupling of Arylboronic Acids with Aryl and Vinyl Halides and Triflates under Mild Conditions," Journal of the American Chemical Society, 122(17): 4020-4028 (2000).
Malpart, J., et al., Pending U.S. Appl. No. 17/193,776, filed Mar. 5, 2021.
Mannava, M.K.C., et al., "Enhanced Bioavailability in the Oxalate Salt of the Antituberculosis Drug Ethionamide," Crystal Growth & Design, vol. 16(3), pp. 1591-1598, (2016).
McCague, Raymond et al., "Nonisomerizable Analogues of (Z)- and (E)-4-Hydroxytamoxifen. Synthesis and Endocrinological Properties of Substituted Diphenylbenzocycloheptenes", Journal of Medicinal Chemistry, vol. 31, No. 7, pp. 1285-1290 (1988).
Miller, Chris P., "SERMs: Evolutionary Chemistry, Revolutionary Biology," Current Pharmaceutical Design, vol. 8, No. 23, pp. 2089-2111 (2002).
Pickar, et al., "SERMs: Progress and future perspectives," Maturitas, Elsevier, vol. 67, pp. 129-138 (2010).
Rabion, A., et al., Pending U.S. Appl. No. 17/193,706, filed Mar. 5, 2021.
RN 1861739-57-2, Registry Database Compound, 2016.
Ruff, et al., "Estrogen Receptor Transcription and Transactivation Structure-Function Relationship in DNA- and Ligand-Binding Domains of Estrogen Receptors", Breast Cancer Research, 2000, vol. 2, No. 5, pp. 353-359.
Translation of Office Action issued in Japanese Application No. 2018-515615, mailed on Sep. 18, 2018, 3 pages.
Translation of Search Report issued in Chinese Application No. 201780023008.0, mailed Apr. 23, 2020, 3 pages.
Ullrich, et al., "Estrogen receptor modulator review," Expert Opinion, vol. 16, No. 5, pp. 559-572 (2006).
Anonymous, "Phase 1 / 2 Study of Amcenestrant (SAR439859) Single Agent and in Combination With Other Anti-cancer Therapies in Postmenopausal Women With Estrogen Receptor Positive Advanced Breast Cancer," Sep. 15, 2017, URL: https://www.clinicaltrials.gov/ct2/show/NCT03284957.
Besret, et al., "Translational strategy using multiple nuclear imaging biomarkers to evaluate target engagement and early therapeutic efficacy of SAR439859, a novel selective estrogen receptor degrader", EJNMMI Research, Biomed Central Ltd, London, UK, vol. 10, No. 1, Jun. 29, 2020, pp. 1-13.
Bouaboula, M., et al., Pending U.S. Appl. No. 18/286,496, filed Oct. 11, 2023.
Bouaboula, M., et al., Pending U.S. Appl. No. 18/286,510, filed Oct. 11, 2023.
International Search Report for International Application No. PCT/EP2022/059700, mailed Jul. 8, 2022.
International Search Report for International Application No. PCT/EP2022/059704, mailed Jul. 21, 2022.
Robinson, Dan, R. et al., "Activating ESR1 mutations in hormone-resistant metastatic breast cancer", Nat. Genet., Dec. 2013, 45(12), 1446-1451.
Toy, Weiyi, et al., "Activating ESR1 mutations differentially impact the efficacy of ER antagonists", Cancer Discovery, Mar. 2017, 7(3), 277-287.
Iorfida, M., et al., Fulvestrant in combination with CDK4/6 inhibitors for HER2-metastatic breast cancers: current perspectives, Breast Cancer: Targets and Therapy, Mar. 18, 2020, 13 pages.

SUBSTITUTED 6,7-DIHYDRO-5H-BENZO[7]ANNULENE COMPOUNDS AND THEIR DERIVATIVES, PROCESSES FOR THEIR PREPARATION AND THERAPEUTIC USES THEREOF

CROSS-REFERENCE TO RELATED APPLICATIONS

This application is a national phase entry pursuant to 35 U.S.C. § 371 of International Application No. PCT/EP2021/078883, filed Oct. 19, 2021, which claims the benefit of priority to European Application No. 20306236.9, filed Oct. 19, 2020, and European Application No. 21306281.3, filed Sep. 16, 2021, the entire contents of each of which are incorporated by reference herein in their entirety for any purpose.

Disclosed herein are novel substituted 6,7-dihydro-5H-benzo[7]annulene derivatives, the processes for their preparation, as well as the therapeutic uses thereof, in particular as anticancer agents via selective antagonism and degradation of estrogen receptors.

The Estrogen Receptors (ER) belong to the steroid/nuclear receptor superfamily involved in the regulation of eukaryotic gene expression, cellular proliferation and in target tissues. ERs are in two forms: the estrogen receptor alpha (ERα) and the estrogen receptor beta (ERβ) respectively encoded by the ESR1 and the ESR2 genes. ERα and ERβ are ligand-activated transcription factors which are activated by the hormone estrogen (the most potent estrogen produced in the body is 17β-estradiol). In the absence of hormone, ERs are largely located in the cytosol of the cell. When the hormone estrogen binds to ERs, ERs migrate from the cytosol to the nucleus of the cell, form dimers and then bind to specific genomic sequences called Estrogen Response Elements (ERE). The DNA/ER complex interacts with co-regulators to modulate the transcription of target genes.

ERα is mainly expressed in reproductive tissues such as uterus, ovary, breast, bone and white adipose tissue. Abnormal ERα signaling leads to development of a variety of diseases, such as cancers, metabolic and cardiovascular diseases, neurodegenerative diseases, inflammation diseases and osteoporosis.

ERα is expressed in not more than 10% of normal breast epithelium but approximately 50-80% of breast tumors. Such breast tumors with high level of ERα are classified as ERα-positive breast tumors. The etiological role of estrogen in breast cancer is well established and modulation of ERα signaling remains the mainstay of breast cancer treatment for the majority ERα-positive breast tumors. Currently, several strategies for inhibiting the estrogen axis in breast cancer exist, including: 1—blocking estrogen synthesis by aromatase inhibitors that are used to treat early and advanced ERα-positive breast cancer patients; 2—antagonizing estrogen ligand binding to ERα by tamoxifen which is used to treat ERα-positive breast cancer patients in both pre- and post-menopausal setting; 3—antagonizing and downregulating ERα levels by fulvestrant, which is used to treat breast cancer in patients that have progressed despite endocrine therapies such as tamoxifen or aromatase inhibitors.

Although these endocrine therapies have contributed enormously to reduction in breast cancer development, about more than one-third of ERα-positive patients display de novo resistance or develop resistance over time to such existing therapies. Several mechanisms have been described to explain resistance to such hormone therapies. For example, hypersensitivity of ERα to low estrogen level in treatment with aromatase inhibitors, the switch of tamoxifen effects from antagonist to agonist effects in tamoxifen treatments or multiple growth factor receptor signaling pathways. Acquired mutations in ERα occurring after initiation of hormone therapies may also play a role in treatment failure and cancer progression. Certain mutations in ERα, particularly those identified in the Ligand Binding Domain (LBD), result in the ability to bind to DNA in the absence of ligand and confer hormone independence in cells harboring such mutant receptors.

Most of the endocrine therapy resistance mechanisms identified rely on ERα-dependent activity. One of the new strategies to counterforce such resistance is to shut down the ERα signaling by removing ERα from the tumor cells using Selective Estrogen Receptors Degraders (SERDs). Clinical and preclinical data showed that a significant number of the resistance pathways can be circumvented by the use of SERDs.

There is still a need to provide SERDs with good degradation efficacy.

Documents WO2017/140669 and WO2018/091153 disclose some substituted 6,7-dihydro-5H-benzo[7]annulene compounds and substituted N-(3-fluoropropyl)-pyrrolidine derivatives useful as SERDs.

The inventors have now found novel compounds able to selectively antagonize and degrade the estrogen receptors (SERDs compounds), for use in cancer treatment.

Disclosed herein are compounds of the formula (I), or pharmaceutically acceptable salts thereof:

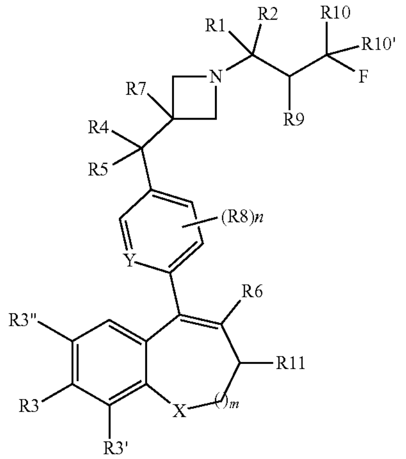

wherein:

R1 and R2 independently represent a hydrogen atom or a deuterium atom;

R3 represents a hydrogen atom, a —COOH group or a —OH group;

R3' and R3" independently represent a hydrogen atom, a methyl group, a methoxy group, a chlorine atom, a fluorine atom, or a cyano group;

R4 and R5 independently represent a hydrogen atom, a fluorine atom, a —$NH_2$ group, a ($C_1$-$C_3$)alkyl group such as a methyl group, a ($C_1$-$C_3$)alkoxy group such as a methoxy group or an ethoxy group, or a —OH group; or R4 and R5 together form an oxo group or R4 and R5 together form a =$NOCH_3$ group or a ($C_3$-$C_5$)cycloalkyl group with the carbon atom to which they are attached;

R7 represents a hydrogen atom, a methyl group, a —OH group or a fluorine atom; or alternatively R4 and R7 together form a cyclopropyl group together with the bond to which they are attached, that gives with the adjacent azetidine group an azaspiro[2.3]hexane;

R6 represents a group selected from:

- a phenyl group, said phenyl group being optionally substituted by 1 to 3 substituents independently selected from a halogen atom; a $(C_1-C_6)$alkyl group optionally substituted with a cyano group or a —OH group; a $(C_1-C_6)$fluoroalkyl group; a $(C_3-C_6)$cycloalkyl group; a $(C_1-C_6)$alkoxy group; a $(C_1-C_6)$fluoroalkoxy group; a cyano group; a trifluoromethylsulfonyl group; a $(C_1-C_4)$alkylthio group; a $(C_1-C_4)$fluoroalkylthio group; a $(C_1-C_4)$alkylsulfonyl group; and a —OH group;
- a fused phenyl group, selected from phenyl groups fused with a $(C_3-C_6)$cycloalkyl, which $(C_3-C_6)$cycloalkyl ring optionally comprises an unsaturation and wherein the fused phenyl is optionally substituted with 1 to 3 substituents independently selected from a $(C_1-C_3)$ alkyl group, a hydroxy group, a halogen atom, a $(C_1-C_6)$fluoroalkyl group and a $(C_1-C_3)$alkoxy group;
- a bicyclic group comprising 5 to 12 carbon atoms, optionally comprising 1 to 2 unsaturations; optionally substituted with 1 to 4 substituents independently selected from: a fluorine atom, a —OH group, a $(C_1-C_3)$-alkyl group, a $(C_1-C_3)$fluoroalkyl group, a $(C_1-C_3)$alkoxy group, a $(C_1-C_3)$fluoroalkoxy group and an oxo group;
- a heteroaryl group comprising 2 to 9 carbon atoms and comprising from 1 to 3 heteroatoms independently selected from oxygen, nitrogen and sulfur, and at least 5 atoms including carbon atoms and heteroatoms, such as a pyridyl group, a pyridone group or a pyrrolyl group, said heteroaryl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a cyano group, a carbamoyl group and a —OH group;
- a cycloalkyl group comprising 3 to 7 carbon atoms, said cycloalkyl group being saturated or partially saturated and being optionally substituted with 1 to 4 substituents independently selected from:
  - a fluorine atom, a —OH group, a $(C_1-C_3)$alkyl group, a $(C_1-C_3)$fluoroalkyl group, a $(C_1-C_3)$ alkoxy group, a $(C_1-C_3)$fluoroalkoxy group, an oxo group,
  - a $(C_3-C_6)$cycloalkyl group, and a phenyl group, said $(C_3-C_6)$cycloalkyl or phenyl groups being optionally substituted with one or two halogen atom(s) or $(C_1-C_3)$alkyl group(s);
- a $(C_3-C_6)$cycloalkyl$(C_1-C_3)$alkyl group, optionally substituted on the cycloalkyl with 1 to 4 substituents independently selected from: a fluorine atom, a —OH group, a $(C_1-C_4)$alkyl group, a $(C_1-C_3)$fluoroalkyl group, a $(C_1-C_3)$fluoroalkoxy group and an oxo group;
- a 3 to 8 membered-heterocycloalkyl group comprising 1 or 2 heteroatoms independently selected from oxygen, nitrogen and sulfur, such as a tetrahydropyranyl or a tetrahydrofuranyl group, said heterocycloalkyl group being saturated or partially saturated and being optionally substituted with 1 to 3 substituents independently selected from: a fluorine atom, a $(C_1-C_3)$alkyl group, a $(C_1-C_3)$fluoroalkyl group, a $(C_1-C_3)$fluoroalkoxy group, an oxo group, a $(C_1-C_3)$ alkoxy group and a —OH group;
- a $(C_1-C_6)$alkyl group, such as an isobutyl group or an ethylbutyl group, said alkyl group being optionally substituted with 1 to 4 substituents independently selected from: a fluorine atom, a $(C_1-C_3)$alkoxy group, a $(C_1-C_3)$fluoroalkoxy group and a —OH group; and
- a phenyl$(C_1-C_2)$alkyl group, said phenyl group being optionally substituted with 1 to 3 substituents independently selected from a halogen atom; a $(C_1-C_3)$ alkyl group; a $(C_1-C_3)$fluoroalkyl group; a $(C_1-C_3)$ alkoxy group; a $(C_1-C_3)$ fluoroalkoxy group; a cyano group; and a —OH group;

X represents —$CH_2$—, —O— or —S—;

Y represents —CH═, —N═ or —CR"═, wherein R" represents a $(C_1-C_3)$alkyl group or a halogen atom, such as a fluorine or a chlorine atom, a cyano group, or a $(C_1-C_3)$fluoroalkyl group, such as a trifluoromethyl;

R8 independently represents a $(C_1-C_3)$alkyl group, such as a methyl group, a halogen atom, such as a fluorine atom, a cyano group, or a $(C_1-C_3)$fluoroalkyl group, such as a trifluoromethyl;

R9 represents a hydrogen atom or a fluorine atom;

R10 and R10' independently represent a hydrogen atom or a fluorine atom;

R11 represents a hydrogen atom, or a $(C_1-C_3)$alkyl group or a cyclopropyl;

n is 0, 1 or 2, and m is 0 or 1.

The compounds of formula (I) can contain one or more asymmetric carbon atoms. They may therefore exist in the form of enantiomers.

The compounds of formula (I) may be present as well under tautomer forms.

The compounds of formula (I) may exist in the form of bases, acids, zwitterion or of addition salts with acids or bases. Hence, herein are provided compounds of formula (I) or pharmaceutically acceptable salts thereof.

These salts may be prepared with pharmaceutically acceptable acids or bases, although the salts of other acids or bases useful, for example, for purifying or isolating the compounds of formula (I) are also provided.

Among suitable salts of the compounds of formula (I), hydrochloride may be cited.

As used herein, the terms below have the following definitions unless otherwise mentioned throughout the instant specification:

- a halogen atom: a fluorine, a chlorine, a bromine or an iodine atom, and in particular a fluorine and a chlorine atom;
- an oxo: a "═O" group;
- an alkyl group: a linear or branched saturated hydrocarbon-based aliphatic group comprising, unless otherwise mentioned, from 1 to 6 carbon atoms (noted "$(C_1-C_6)$-alkyl"). By way of examples, mention may be made of, but not limited to: methyl, ethyl, propyl, isopropyl, butyl, isobutyl, sec-butyl, tert-butyl, pentyl, isopentyl, hexyl and isohexyl groups, and the like;
- a cycloalkyl group: a monocyclic alkyl group comprising, unless otherwise mentioned, from 3 to 7 carbon atoms, saturated or partially unsaturated and unsubstituted or substituted. By way of examples, mention may be made of, but not limited to: cyclopropyl, cyclobutyl, cyclopentyl, cyclobutenyl, cyclopentenyl, cyclohexyl, cyclohexenyl, cycloheptyl, cycloheptenyl, groups and the like, in particular a cyclopentyl, a cyclohexyl, a cycloheptyl, a cycloheptenyl, or a cyclohexenyl;

a cycloalkylalkyl group: an alkyl group substituted with a cyclic alkyl group as defined above. Mention may be made of, but not limited to: cyclobutylmethyl;

a heterocycloalkyl group: a 3 to 8-membered cycloalkyl group, saturated of partially unsaturated, comprising 1 to 2 heteroatoms independently selected from oxygen, nitrogen and sulfur, in particular being oxygen or nitrogen. By way of examples, mention may be made of, but not limited to: morpholinyl, piperazinyl, piperidinyl, pyrrolidinyl, aziridinyl, oxanyl, oxetanyl, tetrahydropyranyl, morpholinyl, tetrahydrofuranyl, oxepanyl, diazepanyl, dioxanyl, tetrahydropyranyl, and tetrahydrothiopyranyl. The heterocycloalkyl is advantageously tetrahydrofuranyl or tetrahydropyranyl.

a fluoroalkyl group: an alkyl group as previously defined where the alkyl group is substituted with at least one fluorine atom. In other terms, at least one hydrogen atom of the alkyl group is replaced by a fluorine atom. By way of example, mention may be made of $—CH_2F$, $—CHF_2$, $CH_2CHF_2$, $—CH_2CH_2F$ and the like. When all the hydrogen atoms belonging to the alkyl group are replaced by fluorine atoms, the fluoroalkyl group can be named perfluoroalkyl group. By way of example, mention may be made of trifluoromethyl group or trifluoroethyl group and the like;

an alkoxy group: an —O-alkyl group where the alkyl group is as previously defined. By way of examples, mention may be made of, but not limited to: methoxy, ethoxy, propoxy, isopropoxy, linear, secondary or tertiary butoxy, isobutoxy, pentoxy or hexoxy groups, and the like;

a fluoroalkoxy group: an —O-alkyl group where the alkyl group is as previously defined and where the alkyl group is substituted with at least one fluorine atom. In other terms, at least one hydrogen atom of the alkyl group is replaced by a fluorine atom. By way of example, mention may be made of $—OCH_2F$, $—OCHF_2$, $—OCH_2CH_2F$ and the like. When all the hydrogen atoms belonging to the alkyl group are replaced by fluorine atoms, the fluoroalkoxy group can be named perfluoroalkoxy group. By way of example, mention may be made of trifluoromethoxy group and the like;

a $(C_1-C_4)$alkylthio group also named a $(C_1-C_4)$alkylsulfanyl group: a —S-alkyl group where the alkyl group is as previously defined. By way of examples, mention may be made of, but not limited to: methylthio, ethylthio, propylthio, isopropylthio, linear, secondary or tertiary butylthio, isobutylthio, and the like;

a $(C_1-C_4)$alkylsulfonyl group: a $—SO_2$-alkyl group where the alkyl group is as previously defined. By way of examples, mention may be made of, but not limited to $—SO_2CH_3$, $—SO_2CH_2CH_3$ and the like;

a $(C_1-C_4)$fluoroalkylthio group also named a $(C_1-C_4)$ fluoroalkylsulfanyl group: a —S-fluoroalkyl group where the fluoroalkyl group is as previously defined. By way of examples, mention may be made of, but not limited to: fluoromethylthio, difluoromethylthio, trifluoromethylthio and the like;

a fused phenyl: a bicyclic radical comprising from 7 to 10 carbon atoms and that contains a phenyl moiety. Said phenyl moiety may be fused to a $(C_3-C_6)$cycloalkyl group, i.e. the phenyl moiety may share a bond with said $(C_3-C_6)$cycloalkyl group. The fused phenyl group may be bound to the rest of the molecule by its phenyl moiety. It may be substituted. Examples are, but are not limited to indanyl, bicyclo[4.2.0]octa-1(6),2,4-trienyl, tetrahydronaphthalenyl and the like;

a heteroaryl group: a cyclic 5 to 10-membered aromatic group containing between 2 and 9 carbon atoms and containing between 1 and 3 heteroatoms, such as nitrogen, oxygen or sulfur. Such nitrogen atom may be substituted with an oxygen atom in order to form a —N—O bond. Such —N—O bond can be in a form of a N-oxide ($—N^+—O^-$). Said heteroaryl group may be monocyclic or bicyclic. By way of examples of heteroaryl groups, mention may be made of, but not limited to: thiophene, furan, thiadiazole, thiazole, imidazole, pyridazine, triazine, pyrazine, oxadiazole, pyrazole, isothiazole, oxazole, isoxazole, pyridine, pyrimidine, benzotriazole, benzoxazole, pyrrolo[2,3-b]pyridine, benzimidazole, benzoxadiazole, benzothiazole, benzothiadiazole, benzofuran, indole, isoquinoline, indazole, benzisoxazole, benzisothiazole, pyridone groups and the like. The heteroaryl group is advantageously pyridine, pyrrole, imidazole, pyrazine, furane, thiazole, pyrazole, thiadiazole, pyridazine, pyridone and pyrimidine, and more particularly pyridine, pyridone and pyrrole;

a bicyclic group, generally comprising 5 to 12 carbon atoms, is a hydrocarbon group selected from groups comprising two rings connected through:

a single common atom: a "spirobicyclic ring". Such spiro bicyclic alkyl generally comprises 5 to 11 carbon atoms referring to a "spiro$(C_5-C_{11})$bicyclic ring". The rings may be saturated or partially unsaturated. Such spirobicyclic ring may be unsubstituted or substituted, in particular by at least one $(C_1-C_3)$ alkyl group such as methyl or a fluorine. By way of examples of spiro$(C_5-C_{11})$bicyclic ring as for the definition of R6, mention may be made of, but not limited to: spiro[2.3]hexane, spiro[3.3]heptane, spiro[3.3]heptene, spiro[2.5]octane and 7-azaspiro[3.5]nonane. The spiro$(C_5-C_{11})$bicyclic ring is advantageously spiro[3.3]heptane or spiro[3.3]heptene still for the R6 group.

two common atoms. In that case the bicyclic group comprises 7 to 12 carbon atoms and optionally comprises 1 to 2 unsaturations. By way of examples of such bicyclic groups, mention may be made of, but not limited to: cis-1,3a,4,5,6,6a-hexahydropentalenyl group, bicyclo[3.1.0]hexan-1-yl, bicyclo[4.1.0]heptanyl and octahydropentalenyl.

three or more common atoms. In that case the bicyclic group comprises 6 to 10 carbon atoms, such bicyclic group may be referred to as a "bridged $(C_6-C_{10})$ cycloalkyl" group, the rings share three or more atoms and the bridge contains at least one atom, for example 1, 2 or 3 atoms and preferentially 1 atom. By way of examples of such bridged cycloalkyl groups, mention may be made of, but not limited to bicyclo[3.2.1]octan-3-yl and bicyclo[2.2.1]heptan-2-yl.

A zwitterion means: a globally neutral molecule with a positive and a negative electrical charge and having an acidic group and a basic group.

In another embodiment, in the compounds of formula (I) as defined above, R1 and R2 are a hydrogen atom.

In another embodiment, in the compounds of formula (I) as defined above, R3 is —COOH.

In another embodiment, in the compounds of formula (I) as defined above, X represents $—CH_2—$.

In another embodiment, in the compounds of formula (I) as defined above, R4 and R5 represent independently from each other a hydrogen atom, a fluorine atom, a methyl group, a methoxy group, an ethoxy group, a —$NH_2$ group or a —OH group; or R4 and R5 together form an oxo group, a =$NOCH_3$ group or a cyclopropyl group with the carbon atom to which they are attached or alternatively R4 and R7 together form a cyclopropyl group together with the bond to which they are attached, in particular both of R4 and R5 represent hydrogen atoms or a fluorine atom, or one of R4 and R5 represents a hydrogen atom and the other a fluorine atom or a —OH group, or one of R4 and R5 represents a methyl group and the other a hydroxy group or a fluorine atom, more particularly R4 and R5 both represent a hydrogen atom.

In another embodiment, in the compounds of formula (I) as defined above, R4 and R5 represent a hydrogen atom, a —$NH_2$ group, a methyl group, a methoxy group, an ethoxy group.

In another embodiment, in the compounds of formula (I) as defined above, R4 and R5 both represent a hydrogen atom.

In another embodiment, in the compounds of formula (I) as defined above, R7 represents a hydrogen atom, a —OH group, a methyl group or a fluorine atom, more particularly a hydrogen atom.

In another embodiment, in the compounds of formula (I) as defined above, R6 represents R6 represents a phenyl group, said phenyl group being optionally substituted with 1 to 3 substituents independently selected from a chlorine atom, a fluorine atom, a methyl group, an ethyl group, a trifluoromethyl group, a 2,2,2-trifluoroethyl group, a hydroxy methyl group, a 2-hydroxyethyl group, a fluoromethyl group, a difluoromethyl group, a 2,2-difluoroethyl group, a methoxy group, an ethoxy group, a cyano group, a cyanomethyl group, a trifluoromethylsulfonyl group, a methylsulfanyl group, a difluoromethylsulfanyl group, a methylsulfonyl group and a difluoromethoxy group.

In another embodiment, in the compounds of formula (I) as defined above, R6 represents a fused phenyl group, selected from a bicyclo[4.2.0]octa-trienyl group and an indanyl group, said groups being optionally substituted with one or two fluorine atoms.

In another embodiment, in the compounds of formula (I) as defined above, R6 represents

- a pyridyl group, said pyridyl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a carbamoyl and a —OH group, and more particularly selected from a methyl group, a methoxy group, a fluorine atom, a chlorine atom, a trifluoromethyl group, a difluoromethyl group, a methoxy group and a carbamoyl group,
- a pyridone, optionally substituted with 1 to 3 substituents independently selected from a halogen atom, a $(C_1-C_3)$ alkyl group, a $(C_1-C_3)$fluoroalkyl group, a $(C_1-C_3)$ alkoxy group and a $(C_1-C_3)$fluoroalkoxy group, and more particularly selected from a methyl group, a methoxy group, a fluorine atom, a chlorine atom, a trifluoromethyl group and a difluoromethyl group or
- a pyrrole group, optionally substituted with 1 or 2 substituents selected from a $(C_1-C_6)$alkyl group, such as a methyl group.

In another embodiment, in the compounds of formula (I) as defined above, R6 represents a cycloalkyl group selected from a cyclohexyl group, a cyclopentyl group, a cycloheptyl group, a cycloheptenyl group and a cyclohexenyl group, said cycloalkyl group being optionally substituted with 1 to 4 substituents independently selected from:

- a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, an oxo group,
- a $(C_3-C_6)$cycloalkyl group and a phenyl group, said $(C_3-C_6)$cycloalkyl or phenyl groups being optionally substituted with one or two halogen atom(s) or a $(C_1-C_3)$alkyl group, said cycloalkyl being advantageously substituted with 1 to 2 substituents independently selected from:

- a fluorine atom, a methyl group, and
- a cyclohexyl group substituted by two halogen atoms, in particular fluor atoms.

In another embodiment, in the compounds of formula (I) as defined above, R6 represents a heterocycloalkyl group, and more particularly a tetrahydropyranyl group, said heterocycloalkyl group being optionally substituted with 1 to 3 substituents independently selected from: a $(C_1-C_6)$alkyl group, a fluorine atom and a —OH group.

In another embodiment, in the compounds of formula (I) as defined above, R6 represents a bicyclic group selected from

- a spiro[3.3]hept-1-ene or a spiro[3.3]hept-2-ane group, said group being optionally substituted with 1 to 4 substituents independently selected from: a $(C_1-C_3)$ alkyl group, a fluorine atom, a $(C_1-C_3)$alkoxy group, a $(C_1-C_3)$fluoroalkoxy group and a —OH group, and in particular optionally substituted with 1 or 2 fluorine atoms,
- a bicyclo[2.2.1]heptan-2-yl or a bicyclo[3.2.1]octan-3-yl group, said group being optionally substituted with 1 to 4 substituents independently selected from: a $(C_1-C_3)$ alkyl group, a fluorine atom, a $(C_1-C_3)$alkoxy group, a $(C_1-C_3)$fluoroalkoxy group and a —OH group.

In another embodiment, in the compounds of formula (I) as defined above, R6 represents a $(C_1-C_6)$alkyl group selected from an ethyl, an isobutyl group and an ethylbutyl, said alkyl group being optionally substituted with 1 to 4 substituents independently selected from: a fluorine atom, a $(C_1-C_3)$alkoxy group, a $(C_1-C_3)$fluoroalkoxy group and a —OH group, and in particular optionally substituted with 1 or 3 fluorine atoms.

In another embodiment, in the compounds of formula (I) as defined above, R6 represents a cis-1,3a,4,5,6,6a-hexahydropentalenyl group.

In another embodiment, in the compounds of formula (I) as defined above, R6 represents a cyclobutylmethyl group.

In another embodiment, in the compounds of formula (I) as defined above, R6 represents a phenyl$(C_1-C_2)$alkyl group, in particular chosen from a phenylmethyl or a phenylethyl.

In another embodiment, in the compounds of formula (I) as defined above, R3' and R3" represent a hydrogen atom.

In another embodiment, in the compounds of formula (I) as defined above, R8 independently represents a methyl group or a fluorine atom and n is 0, 1 or 2.

In another embodiment, in the compounds of formula (I) as defined above, Y represents —CH=, —$C(CH_3)$=, —CF= or —N=, and in particular —CH= or —N=.

In another embodiment, in the compounds of formula (I) as defined above, R9 represents a hydrogen atom.

In another embodiment, in the compounds of formula (I) as defined above, R10 and R10' represent a hydrogen atom.

In another embodiment, in the compounds of formula (I) as defined above, R11 represents a hydrogen atom.

In another embodiment, in the compounds of formula (I) as defined above, m is 1.

In another embodiment, in the compounds of formula (I) R3 is a COOH group and R6 is a phenyl group comprising two or three substitutions independently selected from a chlorine atom, a fluorine atom, a trifluoromethyl group and a methyl group, at least one of the substitutions comprising a halogen atom. In such embodiment, R3' and R3" are in particular hydrogen atoms. Still in such embodiment, R1, R2, R4; R5, R7, R9, R10, R10' and R11 are hydrogen atoms. In such embodiment, Y is a —CH═ group and n is equal to 0. Still in such embodiment, X is a —$CH_2$— group. Still in such embodiment, m is 1.

In addition to said embodiment, further embodiments are herein provided.

A further embodiment provides compounds of the formula (I'), or pharmaceutically acceptable salts thereof:

(I')

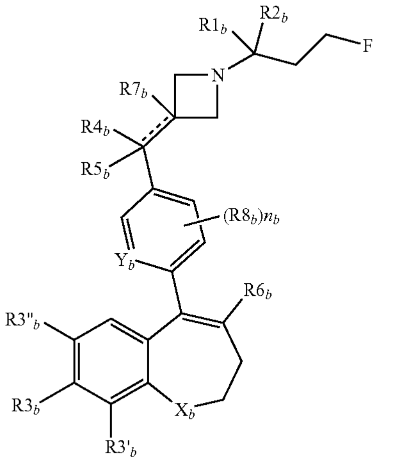

wherein:

- - - - represents a double or single bond, and when it is a double bond, then $R4_b$ and $R7_b$ do not exist;

$R1_b$ and $R2_b$ represent independently a hydrogen atom or a deuterium atom;

$R3_b$ represents a hydrogen atom, a —COOH group or a —OH group;

$R3'_b$ and $R3''_b$ independently represent a hydrogen atom, a methyl, a chlorine or a fluorine atom;

$R4_b$ and $R5_b$ represent independently a hydrogen atom, a halogen atom, a —$NH_2$ group, a methyl group or a —OH group; or R4 and R5 together form an oxo group;

$R6_b$ represents a group selected from:

a phenyl group, said phenyl group being optionally substituted with 1 to 3 substituents independently selected from a halogen atom, a ($C_1$-$C_6$)alkyl group, a ($C_1$-$C_6$)haloalkyl group, a ($C_1$-$C_6$)alkoxy group, a ($C_1$-$C_6$)haloalkoxy group and a —OH group;

a heteroaryl group comprising 2 to 9 carbon atoms and comprising from 1 to 3 heteroatoms independently selected from oxygen, nitrogen and sulfur, and at least 5 atoms including carbon atoms and heteroatoms, such as a pyridyl group, said heteroaryl group being optionally substituted by 1 to 3 substituents independently selected from a halogen atom, a ($C_1$-$C_6$)alkyl group, a ($C_1$-$C_6$)haloalkyl group, a ($C_1$-$C_6$) alkoxy group, a ($C_1$-$C_6$)haloalkoxy group and a —OH group;

a cycloalkyl group comprising 3 to 9 carbon atoms, said cycloalkyl group being saturated or partially saturated and being optionally substituted with 1 to 4 substituents independently selected from: a fluorine atom, a —OH group, a ($C_1$-$C_6$)-alkyl group and an oxo group;

a 4 to 7 membered-heterocycloalkyl group comprising 1 or 2 heteroatoms independently selected from oxygen, nitrogen and sulfur, such as a tetrahydropyran group, said heterocycloalkyl group being optionally substituted with 1 to 3 substituents independently selected from: a fluorine atom, a ($C_1$-$C_6$) alkoxy group, a ($C_1$-$C_6$)haloalkoxy group and a —OH group;

a spiro($C_5$-$C_{11}$)bicyclic ring, such as a spiro[3.3]heptane or spiro[3.3]heptane), said spiro($C_5$-$C_{11}$)bicyclic ring being optionally substituted with 1 to 4 substituents independently selected from: a ($C_1$-$C_6$) alkyl group, a fluorine atom, a ($C_1$-$C_6$)alkoxy group, a ($C_1$-$C_6$)haloalkoxy group and a —OH group;

a ($C_1$-$C_6$)alkyl group, such as isobutyl, said alkyl group being optionally substituted with 1 to 4 substituents independently selected from: a fluorine atom, a ($C_1$-$C_6$)alkoxy group, a ($C_1$-$C_6$)haloalkoxy group and a —OH group;

$R7_b$ represents a hydrogen atom or a halogen atom;

$X_b$ represents —$CH_2$—, —O— or —S—;

$Y_b$ represents —CH—, —N— or —$CR''_b$—, wherein $R''_b$ represents a ($C_1$-$C_4$)alkyl group or a halogen atom, such as a fluorine or a chlorine atom;

$R8_b$ independently represents a ($C_1$-$C_4$)alkyl group, such as methyl, or a halogen atom, such as fluorine; and $n_b$ is 0, 1 or 2.

The compounds of formula (I') can contain one or more asymmetric carbon atoms. They may therefore exist in the form of enantiomers.

The compounds of formula (I') may be present as well under tautomer forms.

The compounds of formula (I') may exist in the form of bases, acids, zwitterion or of addition salts with acids or bases. Hence, herein are provided compounds of formula (I') or pharmaceutically acceptable salts thereof.

These salts may be prepared with pharmaceutically acceptable acids or bases, although the salts of other acids or bases useful, for example, for purifying or isolating the compounds of formula (I') are also provided.

Among suitable salts of the compounds of formula (I'), hydrochloride may be cited.

In an embodiment, in the compound of formula (I') as defined above, - - - - represents a single bond.

In another embodiment, in the compounds of formula (I') as defined above, $R1_b$ and $R2_b$ are a hydrogen atom.

In another embodiment, in the compounds of formula (I) as defined above, $R3_b$ is —COOH.

In another embodiment, in the compounds of formula (I') as defined above, $X_b$ represents —$CH_2$—.

In another embodiment, in the compounds of formula (I') as defined above, $R4_b$ and $R5_b$ represent independently a hydrogen atom, a fluorine atom, a —$NH_2$ group, a methyl group or a —OH group, in particular represent independently a hydrogen atom, a fluorine atom or a —OH group; or $R4_b$ and $R5_b$ together form an oxo group, in particular both of $R4_b$ and $R5_b$ represent hydrogen atoms or a fluorine atom, or one of $R4_b$ and $R5_b$ represents a hydrogen atom and the other a fluorine atom or a —OH group, more particularly $R4_b$ and $R5_b$ both represent a hydrogen atom.

In another embodiment, in the compounds of formula (I') as defined above, $R7_b$ represents a hydrogen atom or a fluorine atom, more particularly a hydrogen atom.

In another embodiment, in the compounds of formula (I') as defined above, $R6_b$ represents a phenyl group, said phenyl group being optionally substituted with 1 to 3 substituents independently selected from a chlorine atom, a fluorine atom, a methyl group, a trifluoromethyl group, a methoxy group and a difluoromethoxy group.

In another embodiment, in the compounds of formula (I') as defined above, $R6_b$ represents a pyridyl group, said pyridyl group being optionally substituted by 1 to 3 substituents independently selected from a halogen atom, a $(C_1-C_6)$alkyl group, a $(C_1-C_6)$haloalkyl group, a $(C_1-C_6)$alkoxy group, a $(C_1-C_6)$haloalkoxy group and a —OH group, and more particularly selected from a methoxy group.

In another embodiment, in the compounds of formula (I') as defined above, $R6_b$ represents a cycloalkyl group selected from a cyclohexyl group, a cyclopentyl group and a cyclohexenyl group, said cycloalkyl group being optionally substituted with 1 to 4 substituents independently selected from: a fluorine atom and a methyl group.

In another embodiment, in the compounds of formula (I') as defined above, $R6_b$ represents a tetrahydropyran group, said tetrahydropyran group being optionally substituted with 1 to 3 substituents independently selected from: a fluorine atom, a $(C_1-C_6)$alkoxy group, a $(C_1-C_6)$haloalkoxy group and a —OH group.

In another embodiment, in the compounds of formula (I') as defined above, $R6_b$ represents a spiro[3.3]hept-1-ene or a spiro[3.3]hept-2-ane group, said spiro[3.3]hept-1-ene or spiro[3.3]hept-2-ane group being optionally substituted with 1 to 4 substituents independently selected from: a $(C_1-C_6)$alkyl group, a fluorine atom, a $(C_1-C_6)$alkoxy group, a $(C_1-C_6)$haloalkoxy group and a —OH group, and in particular optionally substituted with 1 or 2 fluorine atoms.

In another embodiment, in the compounds of formula (I') as defined above, $R6_b$ represents an isobutyl group, said isobutyl group being optionally substituted with 1 to 4 substituents independently selected from: a fluorine atom, a $(C_1-C_6)$alkoxy group, a $(C_1-C_6)$haloalkoxy group and a —OH group, and in particular optionally substituted with 1 to 3 fluorine atoms.

In another embodiment, in the compounds of formula (I') as defined above, $R8_b$ independently represents a methyl group or a fluorine atom and n is 0, 1 or 2.

In another embodiment, in the compounds of formula (I') as defined above, $Y_b$ represents —CH—, —C($CH_3$)—, —CF— or —N—, and in particular —CH— or —N—.

Among the compounds of formula (I) described herein, mention may be made in particular of the following compounds or a pharmaceutically acceptable salt thereof, in particular hydrochloride salt thereof:

9-(4-((1-(3-fluoropropyl)azetidin-3-yl)methyl)phenyl)-8-phenyl-6,7-dihydro-5H-benzo[7]annulene-3-carboxylic acid, (1)

8-(2,4-dichlorophenyl)-9-(4-((1-(3-fluoropropyl)azetidin-3-yl)methyl)phenyl)-6,7-dihydro-5H-benzo[7]annulene-3-carboxylic acid, (2)

8-(2-chlorophenyl)-9-(4-((1-(3-fluoropropyl)azetidin-3-yl)methyl)phenyl)-6,7-dihydro-5H-benzo[7]annulene-3-carboxylic acid, (3)

8-(4,4-difluorocyclohexyl)-9-(4-((1-(3-fluoropropyl)azetidin-3-yl)methyl)phenyl)-6,7-dihydro-5H-benzo[7]annulene-3-carboxylic acid, (4)

8-(4,4-difluorocyclohex-1-en-1-yl)-9-(4-((1-(3-fluoropropyl)azetidin-3-yl)methyl)phenyl)-6,7-dihydro-5H-benzo[7]annulene-3-carboxylic acid, (5)

8-cyclopentyl-9-(4-((1-(3-fluoropropyl)azetidin-3-yl)methyl)phenyl)-6,7-dihydro-5H-benzo[7]annulene-3-carboxylic acid, (6)

8-(2-chloro-4-methylphenyl)-9-(4-((1-(3-fluoropropyl)azetidin-3-yl)methyl)phenyl)-6,7-dihydro-5H-benzo[7]annulene-3-carboxylic acid, (7)

8-(2-chloro-4-fluorophenyl)-9-(4-((1-(3-fluoropropyl)azetidin-3-yl)methyl)phenyl)-6,7-dihydro-5H-benzo[7]annulene-3-carboxylic acid, (8)

8-(2-chloro-3-fluorophenyl)-9-(4-((1-(3-fluoropropyl)azetidin-3-yl)methyl)phenyl)-6,7-dihydro-5H-benzo[7]annulene-3-carboxylic acid, (9)

8-(2,4-dimethylphenyl)-9-(4-((1-(3-fluoropropyl)azetidin-3-yl)methyl)phenyl)-6,7-dihydro-5H-benzo[7]annulene-3-carboxylic acid, (10)

8-(2-fluoro-4-methylphenyl)-9-(4-((1-(3-fluoropropyl)azetidin-3-yl)methyl)phenyl)-6,7-dihydro-5H-benzo[7]annulene-3-carboxylic acid, (11)

8-(4-chloro-2-fluorophenyl)-9-(4-((1-(3-fluoropropyl)azetidin-3-yl)methyl)phenyl)-6,7-dihydro-5H-benzo[7]annulene-3-carboxylic acid, (12)

8-(4,4-dimethylcyclohexyl)-9-(4-((1-(3-fluoropropyl)azetidin-3-yl)methyl)phenyl)-6,7-dihydro-5H-benzo[7]annulene-3-carboxylic acid, (13)

9-(4-((1-(3-fluoropropyl)azetidin-3-yl)methyl)phenyl)-8-((1s,4s)-4-methylcyclohexyl)-6,7-dihydro-5H-benzo[7]annulene-3-carboxylic acid, (14)

9-(4-((1-(3-fluoropropyl)azetidin-3-yl)methyl)phenyl)-8-((1r,4r)-4-methylcyclohexyl)-6,7-dihydro-5H-benzo[7]annulene-3-carboxylic acid, (15)

8-(2-fluoro-4-methoxyphenyl)-9-(4-((1-(3-fluoropropyl)azetidin-3-yl)methyl)phenyl)-6,7-dihydro-5H-benzo[7]annulene-3-carboxylic acid, (16)

9-(4-((1-(3-fluoropropyl)azetidin-3-yl)methyl)phenyl)-8-(2-methyl-4-(trifluoromethyl)phenyl)-6,7-dihydro-5H-benzo[7]annulene-3-carboxylic acid, (17)

9-(4-((1-(3-fluoropropyl)azetidin-3-yl)methyl)phenyl)-8-(6-methoxypyridin-3-yl)-6,7-dihydro-5H-benzo[7]annulene-3-carboxylic acid, (18)

8-(2,3-dichlorophenyl)-9-(4-((1-(3-fluoropropyl)azetidin-3-yl)methyl)phenyl)-6,7-dihydro-5H-benzo[7]annulene-3-carboxylic acid, (19)

8-(4-(difluoromethoxy)-2-methylphenyl)-9-(4-((1-(3-fluoropropyl)azetidin-3-yl)methyl)phenyl)-6,7-dihydro-5H-benzo[7]annulene-3-carboxylic acid, (20)

9-(4-((1-(3-fluoropropyl)azetidin-3-yl)methyl)phenyl)-8-(2-methoxypyridin-4-yl)-6,7-dihydro-5H-benzo[7]annulene-3-carboxylic acid, (21)

8-(2,3-difluorophenyl)-9-(4-((1-(3-fluoropropyl)azetidin-3-yl)methyl)phenyl)-6,7-dihydro-5H-benzo[7]annulene-3-carboxylic acid, (22)

9-(4-((1-(3-fluoropropyl)azetidin-3-yl)methyl)phenyl)-8-(2-(trifluoromethyl)phenyl)-6,7-dihydro-5H-benzo[7]annulene-3-carboxylic acid, (23)

8-(2-chloro-4-methoxyphenyl)-9-(4-((1-(3-fluoropropyl)azetidin-3-yl)methyl)phenyl)-6,7-dihydro-5H-benzo[7]annulene-3-carboxylic acid, (24)

8-(4-chloro-2-methylphenyl)-9-(4-((1-(3-fluoropropyl)azetidin-3-yl)methyl)phenyl)-6,7-dihydro-5H-benzo[7]annulene-3-carboxylic acid, (25)

8-(4-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, (26)

8-(4-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, (27)

8-(3-fluoro-2-methylphenyl)-9-(4-((1-(3-fluoropropyl)azetidin-3-yl)methyl)phenyl)-6,7-dihydro-5H-benzo[7]annulene-3-carboxylic acid, (28)

9-(4-((1-(3-fluoropropyl)azetidin-3-yl)methyl)phenyl)-8-(4-methoxy-2-methylphenyl)-6,7-dihydro-5H-benzo[7]annulene-3-carboxylic acid, (29)

8-(2-chloro-3-methylphenyl)-9-(4-((1-(3-fluoropropyl)azetidin-3-yl)methyl)phenyl)-6,7-dihydro-5H-benzo[7]annulene-3-carboxylic acid, (30)

8-(2-fluoro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid, (31)

8-(3-chloro-2-fluorophenyl)-9-(4-((1-(3-fluoropropyl)azetidin-3-yl)methyl)phenyl)-6,7-dihydro-5H-benzo[7]annulene-3-carboxylic acid, (32)

8-(4-fluoro-2-methylphenyl)-9-(4-((1-(3-fluoropropyl)azetidin-3-yl)methyl)phenyl)-6,7-dihydro-5H-benzo[7]annulene-3-carboxylic acid, (33)

8-(2-chloro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid, (34)

8-(2-fluorophenyl)-9-(4-((1-(3-fluoropropyl)azetidin-3-yl)methyl)phenyl)-6,7-dihydro-5H-benzo[7]annulene-3-carboxylic acid, (35)

8-(4-fluoro-2-methoxyphenyl)-9-(4-((1-(3-fluoropropyl)azetidin-3-yl)methyl)phenyl)-6,7-dihydro-5H-benzo[7]annulene-3-carboxylic acid, (36)

9-(4-((1-(3-fluoropropyl)azetidin-3-yl)methyl)phenyl)-8-isobutyl-6,7-dihydro-5H-benzo[7]annulene-3-carboxylic acid, (37)

9-(4-((1-(3-fluoropropyl)azetidin-3-yl)methyl)phenyl)-8-(tetrahydro-2H-pyran-4-yl)-6,7-dihydro-5H-benzo[7]annulene-3-carboxylic acid, (38)

8-(2,4-dichlorophenyl)-9-(4-(1-(3-fluoropropyl)azetidine-3-carbonyl)phenyl)-6,7-dihydro-5H-benzo[7]annulene-3-carboxylic acid, (39)

8-(2,4-dichlorophenyl)-9-(4-(difluoro(1-(3-fluoropropyl)azetidin-3-yl)methyl)phenyl)-6,7-dihydro-5H-benzo[7]annulene-3-carboxylic acid, (40)

8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylic acid, (41) and (42)

8-(2,4-dichlorophenyl)-9-(4-(fluoro(1-(3-fluoropropyl)azetidin-3-yl)methyl)phenyl)-6,7-dihydro-5H-benzo[7]annulene-3-carboxylic acid, (43) and (44)

8-(3,4-difluorophenyl)-9-(4-((1-(3-fluoropropyl)azetidin-3-yl)methyl)phenyl)-6,7-dihydro-5H-benzo[7]annulene-3-carboxylic acid, (45)

8-(2,4-dichlorophenyl)-9-(4-((3-fluoro-1-(3-fluoropropyl)azetidin-3-yl)methyl)phenyl)-6,7-dihydro-5H-benzo[7]annulene-3-carboxylic acid, (46)

8-(2,4-dichlorophenyl)-9-(2-fluoro-4-((1-(3-fluoropropyl)azetidin-3-yl)methyl)phenyl)-6,7-dihydro-5H-benzo[7]annulene-3-carboxylic acid, (47)

8-(2,4-dichlorophenyl)-9-(4-((1-(3-fluoropropyl)azetidin-3-yl)methyl)-3-methylphenyl)-6,7-dihydro-5H-benzo[7]annulene-3-carboxylic acid, (48)

4-(2-chlorophenyl)-5-(4-((1-(3-fluoropropyl)azetidin-3-yl)methyl)phenyl)-2,3-dihydrobenzo[b]oxepine-8-carboxylic acid, (49)

8-(6,6-difluorospiro[3.3]hept-1-en-2-yl)-9-(4-((1-(3-fluoropropyl)azetidin-3-yl)methyl)phenyl)-6,7-dihydro-5H-benzo[7]annulene-3-carboxylic acid, (50)

8-(6,6-difluorospiro[3.3]heptan-2-yl)-9-(4-((1-(3-fluoropropyl)azetidin-3-yl)methyl)phenyl)-6,7-dihydro-5H-benzo[7]annulene-3-carboxylic acid, (51), and 4-(2,4-dichlorophenyl)-5-(4-((1-(3-fluoropropyl)azetidin-3-yl)methyl)phenyl)-2,3-dihydrobenzo[b]thiepine-8-carboxylic acid, (52), 8-(bicyclo[4.2.0]octa-1(6),2,4-trien-2-yl)-9-(4-((1-(3-fluoropropyl)azetidin-3-yl)methyl)phenyl)-6,7-dihydro-5H-benzo[7]annulene-3-carboxylic acid (53), 8-(1,1-difluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride (54), 8-(7-fluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride (55), 8-(5-fluoro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid (56), 8-(2-(difluoromethyl)-4-methylphenyl)-9-(4-((1-(3-fluoropropyl)azetidin-3-yl)methyl)phenyl)-6,7-dihydro-5H-benzo[7]annulene-3-carboxylic acid hydrochloride (57), 8-(3-chloro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid (58), 8-(2-chloro-4-fluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride (59), 8-(3-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid (60), 8-(3,4-bis(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid (61), 8-(4-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid, formic acid (62), 9-(4-(difluoro(1-(3-fluoropropyl)azetidin-3-yl)methyl)phenyl)-8-(cis-4-methylcyclohexyl)-6,7-dihydro-5H-benzo[7]annulene-3-carboxylic acid (63), 9-(4-(difluoro(1-(3-fluoropropyl)azetidin-3-yl)methyl)phenyl)-8-(trans-4-methylcyclohexyl)-6,7-dihydro-5H-benzo[7]annulene-3-carboxylic acid (64), 8-(3-fluorophenyl)-9-(4-((1-(3-fluoropropyl)azetidin-3-yl)methyl)phenyl)-6,7-dihydro-5H-benzo[7]annulene-3-carboxylic acid (65), 8-(3-fluoro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid (66), 8-(3-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride (67), 9-(4-((1-(3-fluoropropyl)azetidin-3-yl)methyl)phenyl)-8-(2-methyl-3-(trifluoromethyl)phenyl)-6,7-dihydro-5H-benzo[7]annulene-3-carboxylic acid hydrochloride (68), 8-(4-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid (69), 8-(5-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid (70), 8-(3-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid (71), 8-(5-chloro-3-(trifluoromethyl)pyridin-2-yl)-9-(3-fluoro-4-((1-(3-fluoropropyl)azetidin-3-yl)methyl)phenyl)-6,7-dihydro-5H-benzo[7]annulene-3-carboxylic acid (72), 8-(4-chloro-3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid (73),
8-(4-chloro-3-methylphenyl)-9-(4-((1-(3-fluoropropyl)azetidin-3-yl)methyl)phenyl)-6,7-dihydro-5H-benzo[7]annulene-3-carboxylic acid hydrochloride (74),
8-(2-chloro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (75),
8-(4-chloro-2-(difluoromethyl)phenyl)-4-fluoro-9-(4-((1-(3-fluoropropyl)azetidin-3-yl)methyl)phenyl)-6,7-dihydro-5H-benzo[7]annulene-3-carboxylic acid hydrochloride (76),
8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid isomer 1 (77),
8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid isomer 2 (78),
8-(4-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride (79),
8-(2-fluoro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (80),
8-(2,4-difluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride (81),
8-(5-chloro-3-(difluoromethyl)pyridin-2-yl)-9-(4-((1-(3-fluoropropyl)azetidin-3-yl)methyl)phenyl)-6,7-dihydro-5H-benzo[7]annulene-3-carboxylic acid hydrochloride (82),
8-(3-fluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride (83),
8-(3-chloro-4-methylphenyl)-9-(4-((1-(3-fluoropropyl)azetidin-3-yl)methyl)phenyl)-6,7-dihydro-5H-benzo[7]annulene-3-carboxylic acid hydrochloride (84),
8-(3,4-dimethylphenyl)-9-(4-((1-(3-fluoropropyl)azetidin-3-yl)methyl)phenyl)-6,7-dihydro-5H-benzo[7]annulene-3-carboxylic acid hydrochloride (85),
8-(3-chloro-2-(trifluoromethyl)phenyl)-9-(2-fluoro-4-((1-(3-fluoropropyl)azetidin-3-yl)methyl)phenyl)-6,7-dihydro-5H-benzo[7]annulene-3-carboxylic acid hydrochloride (86),
8-(2-chloro-3-fluorophenyl)-4-fluoro-9-(4-((1-(3-fluoropropyl)azetidin-3-yl)methyl)phenyl)-6,7-dihydro-5H-benzo[7]annulene-3-carboxylic acid, formic acid (87),
8-(3-chloro-4-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid (88),
8-(5-chloro-4-(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid, formic acid (89),
8-(3-chloro-4-fluorophenyl)-9-(4-((1-(3-fluoropropyl)azetidin-3-yl)methyl)phenyl)-6,7-dihydro-5H-benzo[7]annulene-3-carboxylic acid hydrochloride (90),
8-(2-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride (91),
8-(2,4-dichlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid (92),
8-(6-(difluoromethyl)-2,3-difluorophenyl)-9-(4-((1-(3-fluoropropyl)azetidin-3-yl)methyl)phenyl)-6,7-dihydro-5H-benzo[7]annulene-3-carboxylic acid, formic acid (93),
8-(3-chlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid (94),
8-(6-(difluoromethyl)-4-methylpyridin-3-yl)-9-(4-((1-(3-fluoropropyl)azetidin-3-yl)methyl)phenyl)-6,7-dihydro-5H-benzo[7]annulene-3-carboxylic acid (95),
8-(3,3-dimethylcyclohexyl)-9-(4-((1-(3-fluoropropyl)azetidin-3-yl)methyl)phenyl)-6,7-dihydro-5H-benzo[7]annulene-3-carboxylic acid hydrochloride Isomer 1 (96),
8-(3,3-dimethylcyclohexyl)-9-(4-((1-(3-fluoropropyl)azetidin-3-yl)methyl)phenyl)-6,7-dihydro-5H-benzo[7]annulene-3-carboxylic acid hydrochloride Isomer 2 (97),
8-(5-fluoro-2-methylphenyl)-9-(4-((1-(3-fluoropropyl)azetidin-3-yl)methyl)phenyl)-6,7-dihydro-5H-benzo[7]annulene-3-carboxylic acid, formic acid (98),
8-(4-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride (99),
8-(2-cyano-4-fluorophenyl)-9-(4-((1-(3-fluoropropyl)azetidin-3-yl)methyl)phenyl)-6,7-dihydro-5H-benzo[7]annulene-3-carboxylic acid hydrochloride (100),
8-(4-chloro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride (101),
8-(3-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride (102),
9-(4-(fluoro(1-(3-fluoropropyl)azetidin-3-yl)methyl)phenyl)-8-(3-fluoro-2-methylphenyl)-6,7-dihydro-5H-benzo[7]annulene-3-carboxylic acid Isomer 1 (103),
9-(4-(fluoro(1-(3-fluoropropyl)azetidin-3-yl)methyl)phenyl)-8-(4-fluoro-2-methylphenyl)-6,7-dihydro-5H-benzo[7]annulene-3-carboxylic acid Isomer 2 (104),
8-(2-carbamoylpyridin-4-yl)-9-(4-((1-(3-fluoropropyl)azetidin-3-yl)methyl)phenyl)-6,7-dihydro-5H-benzo[7]annulene-3-carboxylic acid hydrochloride (105),
8-(3-chloro-2-(trifluoromethyl)phenyl)-9-(4-(fluoro(1-(3-fluoropropyl)azetidin-3-yl)methyl)phenyl)-6,7-dihydro-5H-benzo[7]annulene-3-carboxylic acid Isomer 2 (106),
8-(2-chloro-4-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 (107),
9-(4-((1-(3-fluoropropyl)azetidin-3-yl)methyl)phenyl)-8-(trans-3-methylcyclohexyl)-6,7-dihydro-5H-benzo[7]annulene-3-carboxylic acid hydrochloride (108),
9-(4-((1-(3-fluoropropyl)azetidin-3-yl)methyl)phenyl)-8-(cis-3-methylcyclohexyl)-6,7-dihydro-5H-benzo[7]annulene-3-carboxylic acid hydrochloride (109),
9-(4-((1-(3-fluoropropyl)azetidin-3-yl)methyl)phenyl)-8-(1H-pyrrol-2-yl)-6,7-dihydro-5H-benzo[7]annulene-3-carboxylic acid (110),
8-(4-chloro-2-fluorophenyl)-9-(4-(fluoro(1-(3-fluoropropyl)azetidin-3-yl)methyl)phenyl)-6,7-dihydro-5H-benzo[7]annulene-3-carboxylic acid (111),
8-(4-chloro-2-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 (112),
8-(4-ethyl-2-methylphenyl)-9-(4-((1-(3-fluoropropyl)azetidin-3-yl)methyl)phenyl)-6,7-dihydro-5H-benzo[7]annulene-3-carboxylic acid (113),
9-(4-((1-(3-fluoropropyl)azetidin-3-yl)methyl)phenyl)-8-(4-((trifluoromethyl)sulfonyl)phenyl)-6,7-dihydro-5H-benzo[7]annulene-3-carboxylic acid hydrochloride (114), 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylic acid hydrochloride (115), 9-(4-((1-(3-fluoropropyl)azetidin-3-yl)methyl)phenyl)-8-mesityl-6,7-dihydro-5H-benzo[7]annulene-3-carboxylic acid (116), 8-(4-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (117), 8-(3-chlorophenyl)-9-(4-((1-(3-fluoropropyl)azetidin-3-yl)methyl)phenyl)-6,7-dihydro-5H-benzo[7]annulene-3-carboxylic acid hydrochloride (118), 8-(4-cyano-2-methylphenyl)-9-(4-((1-(3-fluoropropyl)azetidin-3-yl)methyl)phenyl)-6,7-dihydro-5H-benzo[7]annulene-3-carboxylic acid hydrochloride (119), 8-(2-fluoro-4-(methylthio)phenyl)-9-(4-((1-(3-fluoropropyl)azetidin-3-yl)methyl)phenyl)-6,7-dihydro-5H-benzo[7]annulene-3-carboxylic acid hydrochloride (120), 8-(2,4-dichlorophenyl)-9-(2,5-difluoro-4-((1-(3-fluoropropyl)azetidin-3-yl)methyl)phenyl)-6,7-dihydro-5H-benzo[7]annulene-3-carboxylic acid (121), 8-(2,4-dimethylphenyl)-9-(4-(fluoro(1-(3-fluoropropyl)azetidin-3-yl)methyl)phenyl)-6,7-dihydro-5H-benzo[7]annulene-3-carboxylic acid Isomer 2 (122), 8-(2-chloro-3-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 (123), 8-(2-chloro-4-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride (124), 8-(2-chloro-4-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 2 (125), 8-(2-chloro-3-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 2 (126), 9-(4-(fluoro(1-(3-fluoropropyl)azetidin-3-yl)methyl)phenyl)-8-(2-fluoro-4-methylphenyl)-6,7-dihydro-5H-benzo[7]annulene-3-carboxylic acid Isomer 2 (127), 8-(4-chloro-3-fluoro-2-methylphenyl)-9-(4-((1-(3-fluoropropyl)azetidin-3-yl)methyl)phenyl)-6,7-dihydro-5H-benzo[7]annulene-3-carboxylic acid hydrochloride (128), 8-(3,4-difluoro-2-methylphenyl)-9-(4-((1-(3-fluoropropyl)azetidin-3-yl)methyl)phenyl)-6,7-dihydro-5H-benzo[7]annulene-3-carboxylic acid hydrochloride (129), 8-(2-fluoro-4-(methylsulfonyl)phenyl)-9-(4-((1-(3-fluoropropyl)azetidin-3-yl)methyl)phenyl)-6,7-dihydro-5H-benzo[7]annulene-3-carboxylic acid hydrochloride (130), 9-(4-((1-(3-fluoropropyl)azetidin-3-yl)methyl)phenyl)-8-(1-methyl-1H-pyrrol-2-yl)-6,7-dihydro-5H-benzo[7]annulene-3-carboxylic acid hydrochloride (131), 8-(2,6-dimethylpyridin-3-yl)-9-(3-fluoro-4-((1-(3-fluoropropyl)azetidin-3-yl)methyl)phenyl)-6,7-dihydro-5H-benzo[7]annulene-3-carboxylic acid (132), 8-(4-chloro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, formic acid (133), 8-(2,5-difluorophenyl)-9-(4-((1-(3-fluoropropyl)azetidin-3-yl)methyl)phenyl)-6,7-dihydro-5H-benzo[7]annulene-3-carboxylic acid, formic acid (134), 9-(3-fluoro-4-((1-(3-fluoropropyl)azetidin-3-yl)methyl)phenyl)-8-(2-fluoro-4-methylphenyl)-6,7-dihydro-5H-benzo[7]annulene-3-carboxylic acid (135), 8-(4-fluoro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride (136), 8-(3-cyano-2-methylphenyl)-9-(4-((1-(3-fluoropropyl)azetidin-3-yl)methyl)phenyl)-6,7-dihydro-5H-benzo[7]annulene-3-carboxylic acid (137), 8-(4-((difluoromethyl)thio)phenyl)-9-(4-((1-(3-fluoropropyl)azetidin-3-yl)methyl)phenyl)-6,7-dihydro-5H-benzo[7]annulene-3-carboxylic acid hydrochloride (138), 8-(4-fluoro-2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride (139), 8-(4-fluorophenyl)-9-(4-((1-(3-fluoropropyl)azetidin-3-yl)methyl)phenyl)-6,7-dihydro-5H-benzo[7]annulene-3-carboxylic acid hydrochloride (140), 8-(2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride (141), 8-(2,4-dichlorophenyl)-9-(3,5-difluoro-4-((1-(3-fluoropropyl)azetidin-3-yl)methyl)phenyl)-6,7-dihydro-5H-benzo[7]annulene-3-carboxylic acid (142), 8-(2,6-dimethylpyridin-3-yl)-9-(4-((1-(3-fluoropropyl)azetidin-3-yl)methyl)phenyl)-6,7-dihydro-5H-benzo[7]annulene-3-carboxylic acid hydrochloride (143), 8-(4-chloro-2-(cyanomethyl)phenyl)-9-(4-((1-(3-fluoropropyl)azetidin-3-yl)methyl)phenyl)-6,7-dihydro-5H-benzo[7]annulene-3-carboxylic acid, formic acid (144), 8-(2-chloro-4-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride (145), 8-(2-(fluoromethyl)phenyl)-9-(4-((1-(3-fluoropropyl)azetidin-3-yl)methyl)phenyl)-6,7-dihydro-5H-benzo[7]annulene-3-carboxylic acid (146), 8-(3-cyanophenyl)-9-(4-((1-(3-fluoropropyl)azetidin-3-yl)methyl)phenyl)-6,7-dihydro-5H-benzo[7]annulene-3-carboxylic acid, formic acid (147), 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylic acid (148), 8-(2-ethyl-4-fluorophenyl)-9-(4-((1-(3-fluoropropyl)azetidin-3-yl)methyl)phenyl)-6,7-dihydro-5H-benzo[7]annulene-3-carboxylic acid hydrochloride (149), 9-(4-((1-(3-fluoropropyl)azetidin-3-yl)methyl)phenyl)-8-(o-tolyl)-6,7-dihydro-5H-benzo[7]annulene-3-carboxylic acid hydrochloride (150), 8-(2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride (151), 8-(2-ethylphenyl)-9-(4-((1-(3-fluoropropyl)azetidin-3-yl)methyl)phenyl)-6,7-dihydro-5H-benzo[7]annulene-3-carboxylic acid hydrochloride (152), 9-(4-((1-(3-fluoropropyl)azetidin-3-yl)methyl)phenyl)-8-(2,4,6-trifluorophenyl)-6,7-dihydro-5H-benzo[7]annulene-3-carboxylic acid hydrochloride (153), 8-(4-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid (154), 8-(2-cyano-5-methylphenyl)-9-(4-((1-(3-fluoropropyl)azetidin-3-yl)methyl)phenyl)-6,7-dihydro-5H-benzo[7]annulene-3-carboxylic acid (155), 8-(5-cyano-2-methylphenyl)-9-(4-((1-(3-fluoropropyl)azetidin-3-yl)methyl)phenyl)-6,7-dihydro-5H-benzo[7]annulene-3-carboxylic acid (156), 8-(2-cyano-6-methylphenyl)-9-(4-((1-(3-fluoropropyl)azetidin-3-yl)methyl)phenyl)-6,7-dihydro-5H-benzo[7]annulene-3-carboxylic acid (157), 8-(2-cyano-4-methylphenyl)-9-(4-((1-(3-fluoropropyl)azetidin-3-yl)methyl)phenyl)-6,7-dihydro-5H-benzo[7]annulene-3-carboxylic acid (158), 8-(4,6-bis(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid (159), 8-(2-chloro-4-fluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride (160), 8-(2,3-difluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride (161), 8-(cyclohept-1-en-1-yl)-9-(4-((1-(3-fluoropropyl)azetidin-3-yl)methyl)phenyl)-6,7-dihydro-5H-benzo[7]annulene-3-carboxylic acid (162), 8-cycloheptyl-9-(4-((1-(3-fluoropropyl)azetidin-3-yl)methyl)phenyl)-6,7-dihydro-5H-benzo[7]annulene-3-carboxylic acid hydrochloride (163), 8-(2-(difluoromethyl)-4-fluorophenyl)-9-(4-((1-(3-fluoropropyl)azetidin-3-yl)methyl)phenyl)-6,7-dihydro-5H-benzo[7]annulene-3-carboxylic acid (164), 8-(3-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid (165), 8-(2-cyano-3-methylphenyl)-9-(4-((1-(3-fluoropropyl)azetidin-3-yl)methyl)phenyl)-6,7-dihydro-5H-benzo[7]annulene-3-carboxylic acid (166), 8-(2,4-dichlorophenyl)-9-(4-((1-(3-fluoropropyl)azetidin-3-yl)methyl)-3,5-dimethylphenyl)-6,7-dihydro-5H-benzo[7]annulene-3-carboxylic acid hydrochloride (167), 9-(4-(difluoro(1-(3-fluoropropyl)azetidin-3-yl)methyl)phenyl)-8-isobutyl-6,7-dihydro-5H-benzo[7]annulene-3-carboxylic acid (168), 8-(2,4-difluorophenyl)-9-(4-((1-(3-fluoropropyl)azetidin-3-yl)methyl)phenyl)-6,7-dihydro-5H-benzo[7]annulene-3-carboxylic acid hydrochloride (169), 8-(4-chloro-2-cyanophenyl)-9-(4-((1-(3-fluoropropyl)azetidin-3-yl)methyl)phenyl)-6,7-dihydro-5H-benzo[7]annulene-3-carboxylic acid hydrochloride (170), 8-(4-chloro-2,3-difluorophenyl)-9-(4-((1-(3-fluoropropyl)azetidin-3-yl)methyl)phenyl)-6,7-dihydro-5H-benzo[7]annulene-3-carboxylic acid hydrochloride (171), 8-(3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride (172), 8-(2-chloro-3-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride (173), 8-(4-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride (174), 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 1 (175), 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 2 (176), 9-(4-(fluoro(1-(3-fluoropropyl)azetidin-3-yl)methyl)phenyl)-8-(2-fluoro-4-methylphenyl)-6,7-dihydro-5H-benzo[7]annulene-3-carboxylic acid Isomer 1 (177), 8-(4-chloro-2-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 1 (178), 8-(2-chloro-4-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 (179), 8-(2-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (180), 8-(2,4-dimethylphenyl)-9-(4-(fluoro(1-(3-fluoropropyl)azetidin-3-yl)methyl)phenyl)-6,7-dihydro-5H-benzo[7]annulene-3-carboxylic acid Isomer 1 (181), 8-(2-chloro-3-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 1 (182), 8-(4-chloro-2-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 (183), 8-(2,4-dichlorophenyl)-9-(4-((1-(3-fluoropropyl)-3-methylazetidin-3-yl)methyl)phenyl)-6,7-dihydro-5H-benzo[7]annulene-3-carboxylic acid (184), 9-(4-(fluoro(1-(3-fluoropropyl)azetidin-3-yl)methyl)phenyl)-8-(3-fluoro-2-methylphenyl)-6,7-dihydro-5H-benzo[7]annulene-3-carboxylic acid Isomer 1 (185), 9-(4-(fluoro(1-(3-fluoropropyl)azetidin-3-yl)methyl)phenyl)-8-(4-fluoro-2-methylphenyl)-6,7-dihydro-5H-benzo[7]annulene-3-carboxylic acid Isomer 1 (186), 8-(2-chloro-4-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 1 (187), 8-(2-chloro-3-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 (188), 8-(2-chloro-4-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (189), 9-(4-(difluoro(1-(3-fluoropropyl)azetidin-3-yl)methyl)phenyl)-8-(4-fluoro-2-(trifluoromethyl)phenyl)-6,7-dihydro-5H-benzo[7]annulene-3-carboxylic acid (190), 9-(4-(difluoro(1-(3-fluoropropyl)azetidin-3-yl)methyl)phenyl)-8-(2-(trifluoromethyl)phenyl)-6,7-dihydro-5H-benzo[7]annulene-3-carboxylic acid (191), 8-(4-chlorophenyl)-9-(4-((1-(3-fluoropropyl)azetidin-3-yl)methyl)phenyl)-6,7-dihydro-5H-benzo[7]annulene-3-carboxylic acid hydrochloride (192), 9-(4-((1-(3-fluoropropyl)azetidin-3-yl)methyl)phenyl)-8-(4-methylpyridin-3-yl)-6,7-dihydro-5H-benzo[7]annulene-3-carboxylic acid (193), 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 1 (194), 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 2 (195), (E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid (196), (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid (197), 9-(4-(difluoro(1-(3-fluoropropyl)azetidin-3-yl)methyl)phenyl)-8-(3-fluoro-2-methylphenyl)-6,7-dihydro-5H-benzo[7]annulene-3-carboxylic acid (198), 8-(4-chloro-2-methylphenyl)-9-(4-(difluoro(1-(3-fluoropropyl)azetidin-3-yl)methyl)phenyl)-6,7-dihydro-5H-benzo[7]annulene-3-carboxylic acid (199), 9-(4-(difluoro(1-(3-fluoropropyl)azetidin-3-yl)methyl)phenyl)-8-(4-fluoro-2-methylphenyl)-6,7-dihydro-5H-benzo[7]annulene-3-carboxylic acid (200), 8-(4-ethoxy-2-methylphenyl)-9-(4-((1-(3-fluoropropyl)azetidin-3-yl)methyl)phenyl)-6,7-dihydro-5H-benzo[7]annulene-3-carboxylic acid hydrochloride (201), 8-(5-chloro-2-fluorophenyl)-9-(4-((1-(3-fluoropropyl)azetidin-3-yl)methyl)phenyl)-6,7-dihydro-5H-benzo[7]annulene-3-carboxylic acid hydrochloride (202), 8-(5-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (203), 8-(2-fluoro-5-methylphenyl)-9-(4-((1-(3-fluoropropyl)azetidin-3-yl)methyl)phenyl)-6,7-dihydro-5H-benzo[7]annulene-3-carboxylic acid hydrochloride (204), 8-(2-chlorophenyl)-2-fluoro-9-(4-((1-(3-fluoropropyl)azetidin-3-yl)methyl)phenyl)-6,7-dihydro-5H-benzo[7]annulene-3-carboxylic acid (205), 8-(2,4-dichlorophenyl)-2-fluoro-9-(4-((1-(3-fluoropropyl)azetidin-3-yl)methyl)phenyl)-6,7-dihydro-5H-benzo[7]annulene-3-carboxylic acid (206), 8-(3,4-dichlorophenyl)-9-(4-((1-(3-fluoropropyl)azetidin-3-yl)methyl)phenyl)-6,7-dihydro-5H-benzo[7]annulene-3-carboxylic acid hydrochloride (207), 8-(2,4-dichlorophenyl)-9-(4-((1-(3-fluoropropyl-1,1-d2)azetidin-3-yl)methyl)phenyl)-6,7-dihydro-5H-benzo[7]annulene-3-carboxylic acid hydrochloride (208), 8-(1,5-dimethyl-6-oxo-1,6-dihydropyridin-3-yl)-9-(4-((1-(3-fluoropropyl)azetidin-3-yl)methyl)phenyl)-6,7-dihydro-5H-benzo[7]annulene-3-carboxylic acid (209), 8-(2,3-difluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride (210), 8-(2,4-dichloro-3-fluorophenyl)-9-(4-((1-(3-fluoropropyl)azetidin-3-yl)methyl)phenyl)-6,7-dihydro-5H-benzo[7]annulene-3-carboxylic acid hydrochloride (211), 8-(3-chloro-2-methylphenyl)-9-(4-((1-(3-fluoropropyl)azetidin-3-yl)methyl)phenyl)-6,7-dihydro-5H-benzo[7]annulene-3-carboxylic acid hydrochloride (212), 9-(4-((1-(3-fluoropropyl)azetidin-3-yl)methyl)phenyl)-8-(4-methyl-2-(trifluoromethyl)phenyl)-6,7-dihydro-5H-benzo[7]annulene-3-carboxylic acid hydrochloride (213), 9-(4-((1-(3-fluoropropyl)azetidin-3-yl)methyl)phenyl)-8-(4-(trifluoromethyl)pyridin-3-yl)-6,7-dihydro-5H-benzo[7]annulene-3-carboxylic acid (214), 8-(2,4-dichlorophenyl)-9-(4-(1-(1-(3-fluoropropyl)azetidin-3-yl)cyclopropyl)phenyl)-6,7-dihydro-5H-benzo[7]annulene-3-carboxylic acid hydrochloride (215), 8-(2-chloro-4-fluorophenyl)-2,4-difluoro-9-(4-((1-(3-fluoropropyl)azetidin-3-yl)methyl)phenyl)-6,7-dihydro-5H-benzo[7]annulene-3-carboxylic acid (216), 8-(2-chloro-4-methylphenyl)-2,4-difluoro-9-(4-((1-(3-fluoropropyl)azetidin-3-yl)methyl)phenyl)-6,7-dihydro-5H-benzo[7]annulene-3-carboxylic acid (217), 8-(5-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid (218), 8-(5-chloro-3-fluoropyridin-2-yl)-9-(4-((1-(3-fluoropropyl)azetidin-3-yl)methyl)phenyl)-6,7-dihydro-5H-benzo[7]annulene-3-carboxylic acid (219), 8-(2-chloro-6-fluorophenyl)-9-(4-((1-(3-fluoropropyl)azetidin-3-yl)methyl)phenyl)-6,7-dihydro-5H-benzo[7]annulene-3-carboxylic acid (220), 8-(4-chloro-2-(difluoromethyl)phenyl)-9-(4-((1-(3-fluoropropyl)azetidin-3-yl)methyl)phenyl)-6,7-dihydro-5H-benzo[7]annulene-3-carboxylic acid (221), 8-(2,6-difluorophenyl)-9-(4-((1-(3-fluoropropyl)azetidin-3-yl)methyl)phenyl)-6,7-dihydro-5H-benzo[7]annulene-3-carboxylic acid (222), 8-(2,4-dichlorophenyl)-9-(4-((1-(3,3-difluoropropyl)azetidin-3-yl)methyl)phenyl)-6,7-dihydro-5H-benzo[7]annulene-3-carboxylic acid (223), 8-(2-chlorophenyl)-2,4-difluoro-9-(4-((1-(3-fluoropropyl)azetidin-3-yl)oxy)phenyl)-6,7-dihydro-5H-benzo[7]annulene-3-carboxylic acid (224), 8-(2,4-dichlorophenyl)-2,4-difluoro-9-(4-((1-(3-fluoropropyl)azetidin-3-yl)methyl)phenyl)-6,7-dihydro-5H-benzo[7]annulene-3-carboxylic acid (225), 8-(3-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid (226), 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid
Isomer 1 (227), 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 2 (228), 8-(2,4-dichlorophenyl)-9-(4-(ethoxy(1-(3-fluoropropyl)azetidin-3-yl)methyl)phenyl)-6,7-dihydro-5H-benzo[7]annulene-3-carboxylic acid Isomer 1 (229), 8-(2,4-dichlorophenyl)-9-(4-(ethoxy(1-(3-fluoropropyl)azetidin-3-yl)methyl)phenyl)-6,7-dihydro-5H-benzo[7]annulene-3-carboxylic acid Isomer 2 (230), 8-(2-ethylbutyl)-9-(4-((1-(3-fluoropropyl)azetidin-3-yl)methyl)phenyl)-6,7-dihydro-5H-benzo[7]annulene-3-carboxylic acid (231), 8-(3-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid (232), 8-(2,4-dichlorophenyl)-9-(4-((1-(3-fluoropropyl)-3-hydroxyazetidin-3-yl)methyl)phenyl)-6,7-dihydro-5H-benzo[7]annulene-3-carboxylic acid (233), 8-(3,5-dichloropyridin-2-yl)-9-(4-((1-(3-fluoropropyl)azetidin-3-yl)methyl)phenyl)-6,7-dihydro-5H-benzo[7]annulene-3-carboxylic acid (234), 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid Isomer 1 (235), 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid Isomer 2 (236), 8-(4-chloro-2-(trifluoromethyl)phenyl)-9-(4-((3-fluoro-1-(3-fluoropropyl)azetidin-3-yl)methyl)phenyl)-6,7-dihydro-5H-benzo[7]annulene-3-carboxylic acid (237), 9-(4-((3-fluoro-1-(3-fluoropropyl)azetidin-3-yl)methyl)phenyl)-8-(2-(trifluoromethyl)phenyl)-6,7-dihydro-5H-benzo[7]annulene-3-carboxylic acid (238), 8-(2,4-dichlorophenyl)-9-(3-fluoro-4-((1-(3-fluoropropyl)azetidin-3-yl)methyl)phenyl)-6,7-dihydro-5H-benzo[7]annulene-3-carboxylic acid (239), 8-(2,4-dichlorophenyl)-9-(4-((1-(3-fluoropropyl)azetidin-3-yl)methyl)-2-methylphenyl)-6,7-dihydro-5H-benzo[7]annulene-3-carboxylic acid (240), 9-(4-((3-fluoro-1-(3-fluoropropyl)azetidin-3-yl)methyl)phenyl)-8-(4-fluoro-2-(trifluoromethyl)phenyl)-6,7-dihydro-5H-benzo[7]annulene-3-carboxylic acid (241), 8-(2-chloro-4-fluorophenyl)-9-(4-((3-fluoro-1-(3-fluoropropyl)azetidin-3-yl)methyl)phenyl)-6,7-dihydro-5H-benzo[7]annulene-3-carboxylic acid (242), 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 1 (243), 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 2 (244), 2-cyano-8-(2,4-dichlorophenyl)-9-(4-((1-(3-fluoropropyl)azetidin-3-yl)methyl)phenyl)-6,7-dihydro-5H-benzo[7]annulene-3-carboxylic acid (245), 4-cyano-8-(2,4-dichlorophenyl)-9-(4-((1-(3-fluoropropyl)azetidin-3-yl)methyl)phenyl)-6,7-dihydro-5H-benzo[7]annulene-3-carboxylic acid, formic acid (246),
4-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid (247),
2-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid (248),
8-(2,4-dichlorophenyl)-9-(4-((1-(3-fluoropropyl)azetidin-3-yl)methyl)phenyl)-2-methyl-6,7-dihydro-5H-benzo[7]annulene-3-carboxylic acid (249),
8-(2,4-dichlorophenyl)-9-(4-((1-(3-fluoropropyl)azetidin-3-yl)methyl)phenyl)-4-methyl-6,7-dihydro-5H-benzo[7]annulene-3-carboxylic acid hydrochloride (250),
sodium 8-(3-(difluoromethyl)-5-fluorophenyl)-9-(4-((1-(3-fluoropropyl)azetidin-3-yl)methyl)phenyl)-6,7-dihydro-5H-benzo[7]annulene-3-carboxylate (251),
8-(2-chlorophenyl)-9-(5-((1-(3-fluoropropyl)azetidin-3-yl)methyl)pyridin-2-yl)-6,7-dihydro-5H-benzo[7]annulene-3-carboxylic acid (252),
8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic acid (253),
8-(2,4-dichlorophenyl)-9-(4-((1-(3-fluoropropyl)azetidin-3-yl)methyl)phenyl)-6,7-dihydro-5H-benzo[7]annulen-3-ol (254),
8-(2-chlorophenyl)-9-(4-((1-(3-fluoropropyl)azetidin-3-yl)methyl)phenyl)-6,7-dihydro-5H-benzo[7]annulen-3-ol (255),
8-(2-methyl-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid (256),
8-(2-chloro-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid (257),
8-(4-fluoro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid (258),
8-(3-chloro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid (259),
8-(3-chloro-2-methylphenyl)-9-(4-((1-(3,3,3-trifluoropropyl)azetidin-3-yl)methyl)phenyl)-6,7-dihydro-5H-benzo[7]annulene-3-carboxylic acid (260),
8-(2,4-dichlorophenyl)-9-(4-((1-(3,3,3-trifluoropropyl)azetidin-3-yl)methyl)phenyl)-6,7-dihydro-5H-benzo[7]annulene-3-carboxylic acid (261),
6-(2,4-dichlorophenyl)-5-(4-((1-(3-fluoropropyl)azetidin-3-yl)methyl)phenyl)-7,8-dihydronaphthalene-2-carboxylic acid hydrochloride (262),
4-(4-chloro-2-methylphenyl)-5-(4-((1-(3-fluoropropyl)azetidin-3-yl)methyl)phenyl)-2,3-dihydrobenzo[b]oxepine-8-carboxylic acid (263),
sodium 4-(2-chloro-4-fluorophenyl)-5-(4-((1-(3-fluoropropyl)azetidin-3-yl)methyl)phenyl)-2,3-dihydrobenzo[b]oxepine-8-carboxylate (264),
8-(2-chloro-4-methylphenyl)-2,4-difluoro-9-(4-((1-(3-fluoropropyl)azetidin-3-yl)methyl)phenyl)-6,7-dihydro-5H-benzo[7]annulen-3-ol (265),
8-(3,5-difluorophenyl)-9-(4-((1-(3-fluoropropyl)azetidin-3-yl)methyl)phenyl)-6,7-dihydro-5H-benzo[7]annulene-3-carboxylic acid (266),
9-(4-((1-(3-fluoropropyl)azetidin-3-yl)methyl)phenyl)-8-(3,4,5-trifluorophenyl)-6,7-dihydro-5H-benzo[7]annulene-3-carboxylic acid (267),
9-(4-((1-(3-fluoropropyl)azetidin-3-yl)methyl)phenyl)-8-(2-methoxy-6-(trifluoromethyl)pyridin-3-yl)-6,7-dihydro-5H-benzo[7]annulene-3-carboxylic acid (268),
8-(4-fluoro-2-methylphenyl)-9-(4-((1-(3-fluoropropyl)azetidin-3-yl)methyl)phenyl)-4-methoxy-6,7-dihydro-5H-benzo[7]annulene-3-carboxylic acid (269),
8-(2,4-difluorophenyl)-9-(4-((1-(3-fluoropropyl)azetidin-3-yl)methyl)phenyl)-4-methoxy-6,7-dihydro-5H-benzo[7]annulene-3-carboxylic acid (270),
8-(2,4-dichlorophenyl)-9-(4-((1-(3-fluoropropyl)azetidin-3-yl)methyl)phenyl)-4-methoxy-6,7-dihydro-5H-benzo[7]annulene-3-carboxylic acid (271),
8-(4-fluoro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid (272),
sodium 8-(5-(difluoromethyl)-2-fluorophenyl)-9-(4-((1-(3-fluoropropyl)azetidin-3-yl)methyl)phenyl)-6,7-dihydro-5H-benzo[7]annulene-3-carboxylate (273),
sodium 9-(4-((1-(3-fluoropropyl)azetidin-3-yl)methyl)phenyl)-8-(2-methoxy-6-(trifluoromethyl)pyridin-4-yl)-6,7-dihydro-5H-benzo[7]annulene-3-carboxylate (274),
8-(3,4-difluoro-2-methylphenyl)-9-(4-((1-(3,3-difluoropropyl)azetidin-3-yl)methyl)phenyl)-6,7-dihydro-5H-benzo[7]annulene-3-carboxylic acid (275),
9-(4-((1-(3,3-difluoropropyl)azetidin-3-yl)methyl)phenyl)-8-(4-fluoro-2-(trifluoromethyl)phenyl)-6,7-dihydro-5H-benzo[7]annulene-3-carboxylic acid (276),
8-(2-chloro-3-methylphenyl)-9-(4-((1-(3,3-difluoropropyl)azetidin-3-yl)methyl)phenyl)-6,7-dihydro-5H-benzo[7]annulene-3-carboxylic acid (277),
9-(4-((1-(3,3-difluoropropyl)azetidin-3-yl)methyl)phenyl)-8-(3-fluoro-2-(trifluoromethyl)phenyl)-6,7-dihydro-5H-benzo[7]annulene-3-carboxylic acid (278),
9-(4-((1-(3,3-difluoropropyl)azetidin-3-yl)methyl)phenyl)-8-(4-fluoro-2-methylphenyl)-6,7-dihydro-5H-benzo[7]annulene-3-carboxylic acid (279),
8-(3-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid (280),
8-(2,4-difluorophenyl)-9-(4-((1-(3,3-difluoropropyl)azetidin-3-yl)methyl)phenyl)-6,7-dihydro-5H-benzo[7]annulene-3-carboxylic acid (281),
8-(4-chloro-2-methylphenyl)-9-(4-((1-(3,3-difluoropropyl)azetidin-3-yl)methyl)phenyl)-6,7-dihydro-5H-benzo[7]annulene-3-carboxylic acid (282),
8-(4-fluoro-2-(trifluoromethyl)phenyl)-9-(4-((1-(3-fluoropropyl)azetidin-3-yl)methyl)phenyl)-4-methoxy-6,7-dihydro-5H-benzo[7]annulene-3-carboxylic acid hydrochloride (283),
8-(2-(difluoromethyl)-4,6-difluorophenyl)-9-(4-((1-(3-fluoropropyl)azetidin-3-yl)methyl)phenyl)-6,7-dihydro-5H-benzo[7]annulene-3-carboxylic acid hydrochloride (284),
9-(4-((1-(3,3-difluoropropyl)azetidin-3-yl)methyl)phenyl)-8-(4-fluoro-2,3-dimethylphenyl)-6,7-dihydro-5H-benzo[7]annulene-3-carboxylic acid (285),
8-(2-chloro-3-(trifluoromethyl)phenyl)-9-(4-((1-(3,3-difluoropropyl)azetidin-3-yl)methyl)phenyl)-6,7-dihydro-5H-benzo[7]annulene-3-carboxylic acid (286),
9-(4-((1-(3,3-difluoropropyl)azetidin-3-yl)methyl)phenyl)-8-(2-methyl-3-(trifluoromethyl)phenyl)-6,7-dihydro-5H-benzo[7]annulene-3-carboxylic acid (287),
9-(4-((1-(3,3-difluoropropyl)azetidin-3-yl)methyl)phenyl)-8-(2-fluoro-3-(trifluoromethyl)phenyl)-6,7-dihydro-5H-benzo[7]annulene-3-carboxylic acid (288),
8-(4-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid (289), 8-(4-fluoro-3-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid (290), 8-(5-chloro-3-(trifluoromethyl)pyridin-2-yl)-9-(4-((1-(3,3-difluoropropyl)azetidin-3-yl)methyl)phenyl)-6,7-dihydro-5H-benzo[7]annulene-3-carboxylic acid (291), 8-(4-chloro-3-fluoro-2-methylphenyl)-9-(4-((1-(3,3-difluoropropyl)azetidin-3-yl)methyl)phenyl)-6,7-dihydro-5H-benzo[7]annulene-3-carboxylic acid (292), 8-(3-chloro-2-methylphenyl)-9-(4-((1-(3,3-difluoropropyl)azetidin-3-yl)methyl)phenyl)-6,7-dihydro-5H-benzo[7]annulene-3-carboxylic acid (293), 8-(cyclobutylmethyl)-9-(4-((1-(3-fluoropropyl)azetidin-3-yl)methyl)phenyl)-6,7-dihydro-5H-benzo[7]annulene-3-carboxylic acid (294), 8-(2-fluoro-5-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid (295), 8-(2-(difluoromethyl)-3-fluorophenyl)-9-(4-((1-(3-fluoropropyl)azetidin-3-yl)methyl)phenyl)-6,7-dihydro-5H-benzo[7]annulene-3-carboxylic acid (296), 8-(3-(2,2-difluoroethyl)phenyl)-9-(4-((1-(3-fluoropropyl)azetidin-3-yl)methyl)phenyl)-6,7-dihydro-5H-benzo[7]annulene-3-carboxylic acid (297), 9-(4-((1-(3-fluoropropyl)azetidin-3-yl)methyl)phenyl)-8-(3-(2,2,2-trifluoroethyl)phenyl)-6,7-dihydro-5H-benzo[7]annulene-3-carboxylic acid (298), sodium 9-(4-((1-(3-fluoropropyl)azetidin-3-yl)methyl)phenyl)-8-(cis-1,3a,4,5,6,6a-hexahydropentalen-2-yl)-6,7-dihydro-5H-benzo[7]annulene-3-carboxylate (299), 8-(6-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid (300), 9-(4-((1-(3-fluoropropyl)azetidin-3-yl)methyl)phenyl)-8-(2-(2,2,2-trifluoroethyl)phenyl)-6,7-dihydro-5H-benzo[7]annulene-3-carboxylic acid (301), 8-(2,4-dichlorophenyl)-9-(4-((1-(3-fluoropropyl)azetidin-3-yl)methyl)phenyl)-7-methyl-6,7-dihydro-5H-benzo[7]annulene-3-carboxylic acid Isomer 1 (302), 8-(2,4-dichlorophenyl)-9-(4-((1-(3-fluoropropyl)azetidin-3-yl)methyl)phenyl)-7-methyl-6,7-dihydro-5H-benzo[7]annulene-3-carboxylic acid Isomer 2 (303), 3-(4-(8-(2-chlorophenyl)-6,7-dihydro-5H-benzo[7]annulen-9-yl)benzyl)-1-(3-fluoropropyl)azetidine (304), 8-(2,4-dichlorophenyl)-2,4-difluoro-9-(4-((1-(3-fluoropropyl)azetidin-3-yl)methyl)phenyl)-6,7-dihydro-5H-benzo[7]annulen-3-ol (305), 9-(4-((1-(3-fluoropropyl)azetidin-3-yl)methyl)phenyl)-8-(6-methoxy-5-(trifluoromethyl)pyridin-3-yl)-6,7-dihydro-5H-benzo[7]annulene-3-carboxylic acid (306)

8-(bicyclo[2.2.1]heptan-2-yl)-9-(4-((1-(3-fluoropropyl)azetidin-3-yl)methyl)phenyl)-6,7-dihydro-5H-benzo[7]annulene-3-carboxylic acid, mixture of isomers (307)

3-(2,4-dichlorophenyl)-4-(4-((1-(3-fluoropropyl)azetidin-3-yl)methyl)phenyl)-2H-thiochromene-7-carboxylic acid (308)

8-(4-fluoro-2,3-dimethylphenyl)-9-(4-((1-(3-fluoropropyl)azetidin-3-yl)methyl)phenyl)-7-methyl-6,7-dihydro-5H-benzo[7]annulene-3-carboxylic acid, racemic mixture (309)

9-(4-((1-(3-fluoropropyl)azetidin-3-yl)methyl)phenyl)-7-methyl-8-(2-methyl-3-(trifluoromethyl)phenyl)-6,7-dihydro-5H-benzo[7]annulene-3-carboxylic acid, racemic mixture (310)

8-benzyl-9-(4-((1-(3-fluoropropyl)azetidin-3-yl)methyl)phenyl)-6,7-dihydro-5H-benzo[7]annulene-3-carboxylic acid (311)

8-(4-fluoro-2-(trifluoromethyl)phenyl)-9-(4-((1-(3-fluoropropyl)azetidin-3-yl)methyl)phenyl)-7-methyl-6,7-dihydro-5H-benzo[7]annulene-3-carboxylic acid, racemic mixture (312)

9-(4-((1-(3-fluoropropyl)azetidin-3-yl)methyl)phenyl)-8-(3-methyl-2-(trifluoromethyl)phenyl)-6,7-dihydro-5H-benzo[7]annulene-3-carboxylic acid hydrochloride (313)

3-(2,4-difluorophenyl)-4-(4-((1-(3-fluoropropyl)azetidin-3-yl)methyl)phenyl)-2H-thiochromene-7-carboxylic acid (314)

8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid (315)

8-(bicyclo[3.2.1]octan-3-yl)-9-(4-((1-(3-fluoropropyl)azetidin-3-yl)methyl)phenyl)-6,7-dihydro-5H-benzo[7]annulene-3-carboxylic acid (316)

8-(4-chlorophenyl)-9-(4-((1-(3-fluoropropyl)azetidin-3-yl)methyl)phenyl)-7-isopropyl-6,7-dihydro-5H-benzo[7]annulene-3-carboxylic acid, racemic mixture (317)

9-(4-((1-(3-fluoropropyl)azetidin-3-yl)methyl)phenyl)-8-(4-(trifluoromethyl)phenyl)-6,7-dihydro-5H-benzo[7]annulene-3-carboxylic acid hydrochloride (318)

9-(4-((1-(3-fluoropropyl)azetidin-3-yl)methyl)phenyl)-8-(3-(2-hydroxyethyl)phenyl)-6,7-dihydro-5H-benzo[7]annulene-3-carboxylic acid (319)

9-(4-((1-(3-fluoropropyl)azetidin-3-yl)methyl)phenyl)-8-(3-(hydroxymethyl)phenyl)-6,7-dihydro-5H-benzo[7]annulene-3-carboxylic acid (320)

8-(2,4-dichlorophenyl)-9-(4-((1-(3-fluoropropyl)azetidin-3-yl)methyl)phenyl)-7-isopropyl-6,7-dihydro-5H-benzo[7]annulene-3-carboxylic acid, Isomer 1 (321)

8-(2,4-dichlorophenyl)-9-(4-((1-(3-fluoropropyl)azetidin-3-yl)methyl)phenyl)-7-isopropyl-6,7-dihydro-5H-benzo[7]annulene-3-carboxylic acid, Isomer 2 (322)

9-(4-((1-(3-fluoropropyl)azetidin-3-yl)methyl)phenyl)-8-(3-(trifluoromethyl)phenyl)-6,7-dihydro-5H-benzo[7]annulene-3-carboxylic acid (323)

8-(4-chlorophenyl)-7-cyclopropyl-9-(4-((1-(3-fluoropropyl)azetidin-3-yl)methyl)phenyl)-6,7-dihydro-5H-benzo[7]annulene-3-carboxylic acid, racemic mixture (324)

8-(4-fluorophenyl)-9-(4-((1-(3-fluoropropyl)azetidin-3-yl)methyl)phenyl)-7-methyl-6,7-dihydro-5H-benzo[7]annulene-3-carboxylic acid, racemic mixture (325)

8-(3,4-difluorophenyl)-9-(4-((1-(3-fluoropropyl)azetidin-3-yl)methyl)phenyl)-7-methyl-6,7-dihydro-5H-benzo[7]annulene-3-carboxylic acid, racemic mixture (326)

8-(4-chlorophenyl)-9-(4-((1-(3-fluoropropyl)azetidin-3-yl)methyl)phenyl)-7-methyl-6,7-dihydro-5H-benzo[7]annulene-3-carboxylic acid, Isomer 1 (327)

18-(4-chlorophenyl)-9-(4-((1-(3-fluoropropyl)azetidin-3-yl)methyl)phenyl)-7-methyl-6,7-dihydro-5H-benzo[7]annulene-3-carboxylic acid, Isomer 2 (328)

8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, Isomer 1 (329)
8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, Isomer 2 (330)
8-((1R,2S)-2-(4,4-difluorocyclohexyl)cyclopropyl)-9-(4-((1-(3-fluoropropyl)azetidin-3-yl)methyl)phenyl)-6,7-dihydro-5H-benzo[7]annulene-3-carboxylic acid (331)
8-(5-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride (332)
9-(4-((1-(3-fluoropropyl)azetidin-3-yl)methyl)phenyl)-7-methyl-8-(3-(trifluoromethyl)phenyl)-6,7-dihydro-5H-benzo[7]annulene-3-carboxylic acid, Mixture of isomers (333)
8-(3-chloro-2-methoxyphenyl)-9-(4-((1-(3-fluoropropyl)azetidin-3-yl)methyl)phenyl)-6,7-dihydro-5H-benzo[7]annulene-3-carboxylic acid (334)
8-(3-fluoro-2-methoxyphenyl)-9-(4-((1-(3-fluoropropyl)azetidin-3-yl)methyl)phenyl)-6,7-dihydro-5H-benzo[7]annulene-3-carboxylic acid (335)
9-(4-((1-(3-fluoropropyl)azetidin-3-yl)methyl)phenyl)-8-(octahydropentalen-2-yl)-6,7-dihydro-5H-benzo[7]annulene-3-carboxylic acid, Isomer 1 (336).

Another embodiment is a compound selected from the above list, or a pharmaceutically acceptable salt thereof, for use in therapy, especially as an inhibitor and degrader of estrogen receptors.

Another embodiment is a compound selected from the above list, or a pharmaceutically acceptable salt thereof, for use in the treatment of cancer, especially breast cancer.

Another embodiment is a method of inhibiting and degrading estrogen receptors, comprising administering to a subject in need thereof, in particular a human, a therapeutically effective amount of a compound selected from the above list, or a pharmaceutically acceptable salt thereof.

Another embodiment is a method of treating ovulatory dysfunction, cancer, endometriosis, osteoporosis, benign prostatic hypertrophy or inflammation, comprising administering to a subject in need thereof, in particular a human, a therapeutically effective amount of a compound selected from the above list, or a pharmaceutically acceptable salt thereof.

Another embodiment is a method of treating cancer, comprising administering to a subject in need thereof, in particular a human, a therapeutically effective amount of a compound selected from the above list, or a pharmaceutically acceptable salt thereof.

Another embodiment is a pharmaceutical composition comprising as active principle an effective dose of a compound selected from the above list, or a pharmaceutically acceptable salt thereof, and also at least one pharmaceutically acceptable excipient.

The compounds of the formula (I) can be prepared by the following processes.

The compounds of the formula (I) and other related compounds having different substituents are synthesized using techniques and materials described below or otherwise known by the skilled person in the art. In addition, solvents, temperatures and other reaction conditions presented below may vary as deemed appropriate to the skilled person in the art.

General below methods for the preparation of compounds of formula (I) optionally modified by the use of appropriate reagents and conditions for the introduction of the various moieties found in the formula (I) as described below.

The following abbreviations and empirical formulae are used:

MeCN Acetonitrile
$NH_4Cl$ Ammonium chloride
$NH_4OH$ Ammonium hydroxide
9-BBN 9-borabicyclo[3.3.1]nonane
CO Carbon monoxide
$Cs_2CO_3$ Cesium carbonate
DCM Dichloromethane
DIEA Diisopropylethylamine
DMF N,N-dimethylformamide
DMSO Dimethyl sulfoxide
Dppf 1,1'-Bis(diphenylphosphino)ferrocene
EtOH Ethanol
EtOAc Ethyl acetate
$H_2$ Hydrogen
HCl Hydrochloric acid
HPLC High performance liquid chromatography
$LiAlH_4$ Lithium aluminium hydride
LiHMDS Lithium hexamethyldisilazane
MeOH Methanol
$MgSO_4$ Magnesium sulfate
m-CPBA Meta-chloroperbenzoic acid
MTBE Methyl tert-butyl ether
n-BuLi n-Butyllithium
Pd/C Palladium on carbon
$K_2CO_3$ Potassium carbonate
KHMDS Potassium hexamethyldisilazane
KOH Potassium hydroxide
$NaBH_4$ Sodium borohydride
NaCl Sodium chloride
$NaHCO_3$Sodium bicarbonate
NaH Sodium hydride
NaHMDS Sodium hexamethyldisilazane
NaOH Sodium hydroxide
$Na_2SO_4$ Sodium sulfate
$NaHSO_3$ Sodium bisulfate
SCX Strong cation exchange
$Pd(dppf)Cl_2$ [1,1'-Bis(diphenylphosphino)ferrocene]dichloropalladium(II)
$Pd(PPh_3)_2Cl_2$ bis (triphenylphosphine) palladium(II) dichloride
PhOK Potassium phenolate
SFC Supercritical Fluid Chromatography
TEA Triethylamine
TFA Trifluoroacetic acid
THF Tetrahydrofuran
$PPh_3$ Triphenylphosphine
RT Room temperature
Ar Argon
DABCO 1,4-diazabicyclo[2.2.2]octane SCHEME 1a - Part - 1: Preparation of compounds of the formula (I) - General process
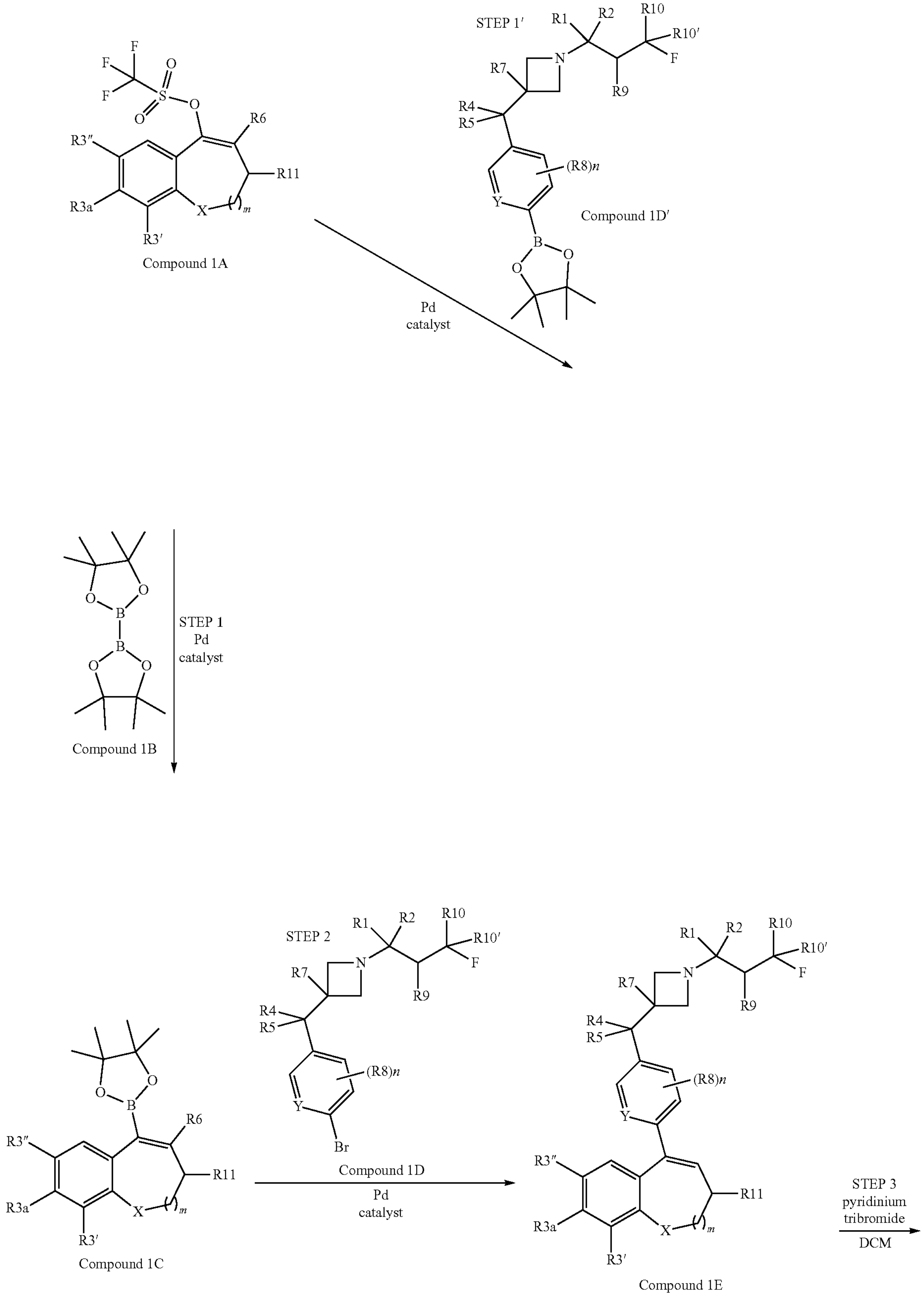

-continued
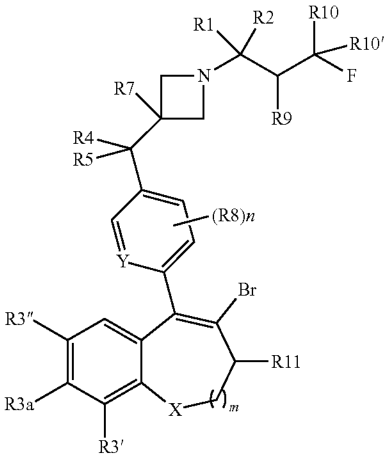
Compound 1F
SCHEME 1a - Part - 2:
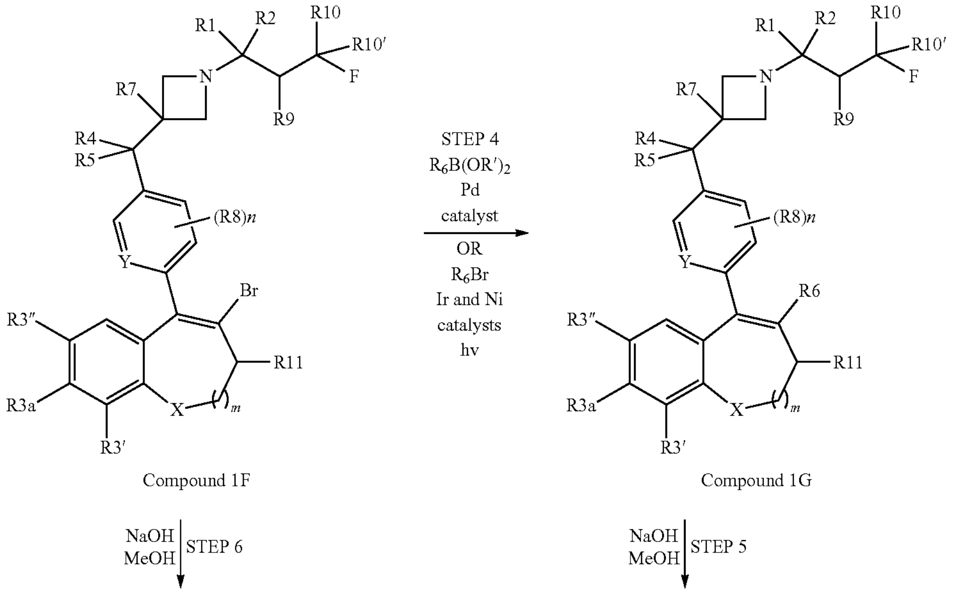
Compound 1F
Compound 1G -continued

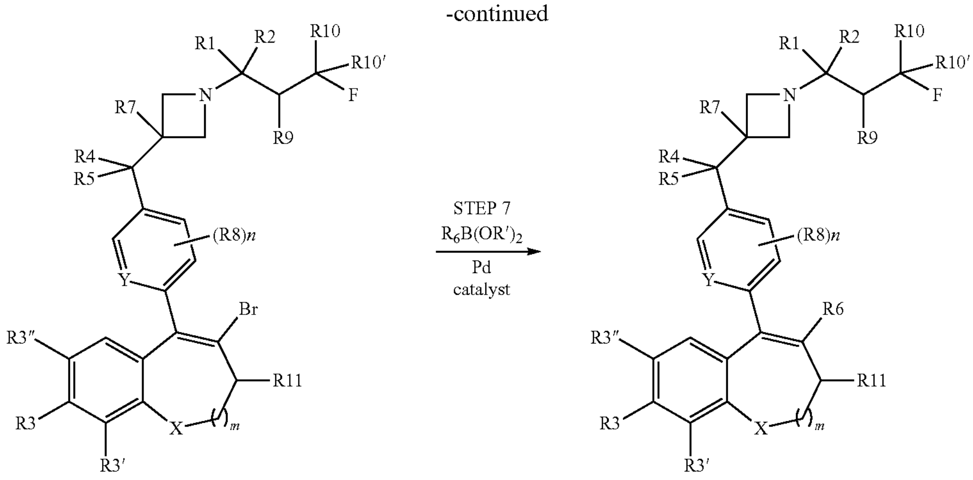

Compound 1Fa

Compound 1

According to SCHEME 1a—Part—1 and Part—2, in which R3a is H, a carboxylic ester such as COOMe, COOEt, or protected OH as O-pivaloyl for example, R1, R2, R3, R3', R3", R4, R5, R6, R7, R8, R9, R10, R10', R11, n, m, X and Y are defined as described above, compound 1A (prepared according to WO2017140669 when X═C), can be converted in STEP 1 to compound 1C by treatment with compound 1B in the presence of a palladium catalyst, for example bis (triphenylphosphine) palladium(II) dichloride $Pd(PPh_3)_2Cl_2$, and a phosphine such as triphenylphosphine in solution in toluene by heating up to reflux of solvent in presence of a base such as KOPh.

Compound 1C can be converted in STEP 2 to compound 1E by treatment with compound 1D in a Suzuki coupling reaction using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Alternatively, compound 1E can be obtained in STEP 1' by Suzuki coupling between compound 1A and compound 1D' using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Compound 1E can be converted in STEP 3 to compound 1F by treatment for example with pyridinium tribromide in DCM or THF at room temperature.

This bromo derivative intermediate 1F can then be subjected in STEP 4 to a second Suzuki coupling with a suitable boronic reagent $R6B(OR')_2$, wherein —$B(OR')_2$ is a boronic acid or a pinacolate ester and R6 is defined as above, using for example $Pd(dppf)Cl_2$, complex with DCM, as catalyst, in a mixture of dioxane and water as solvent and in the presence of a base, for example $Cs_2CO_3$, at room temperature or by heating up to reflux to give compound 1G. When R6 is a substituted cycloalkene, heterocycloalkene or aliphatic ethylene, it may be reduced by hydrogenation with a catalyst such as Pd/C under hydrogen pressure ($H_2$) around 5 bars for example at temperature up to 70° C. to give the corresponding saturated compound 1G.

Alternatively, compound 1F can be subjected to a photocatalyzed coupling reaction with R6Br, where R6 is an alkyl group, a cycloalkyl or a spiro bicyclic alkyl as defined above, using catalysts such as $(Ir[dF(CF_3)ppy]_2(dtbpy))PF_6$ and nickel(II) chloride ethylene glycol dimethyl ether complex in presence of tris(trimethylsilyl)silane and bases such as 4,4'-di-tert-butyl-2,2'-bipyridine and sodium carbonate to give the corresponding compound 1G.

Compound 1G can be converted in STEP 5 to compound of formula (I) in presence of a source of hydroxide ions such as NaOH in solution in methanol (MeOH).

Intermediate 1F can be converted in STEP 6 to compound 1Fa in the presence of a source of hydroxide ions such as NaOH in solution in methanol (MeOH).

This compound 1Fa can be converted in STEP 7 to compound I through Suzuki conditions using a suitable boronic reagent $R6B(OR')_2$, wherein —$B(OR')_2$ is a boronic acid or a pinacolate ester and R6 is as above defined, using for example $Pd(dppf)Cl_2$, complex with DCM, as catalyst, in a mixture of dioxane and water as solvent and in the presence of a base, for example $Cs_2CO_3$, at room temperature or by heating up to reflux of solvents. When R6 is a substituted cycloalkene, heterocycloalkene or aliphatic ethylene, it may be reduced by hydrogenation with a catalyst, such as Pd/C under hydrogen ($H_2$) pressure around 5 bars, for example at temperature up to 70° C., to give the corresponding saturated compound I.

When R3a is COOMe, COOEt, or a protected OH such as O-pivaloyl, deprotection can be performed in STEP 5 by treatment with an aqueous solution of sodium hydroxide (NaOH) 2N or lithium hydroxide (LiOH) in MeOH. When R3 is COOH, extraction of the product could give the sodium salt of compound I. The acidification with an aqueous solution of HCl 2N to pH 6-7 could give the neutral form of compound I. The acidification with an aqueous solution of HCl 2N to pH 1-2 could give the hydrochloride salt of compound I. The purification using HPLC in presence of formic acid or trifluoroacetic acid in the eluent could give the formate or trifluoroacetate salt of compound I.

Herein is also provided a process for preparing a compound of formula (I) as defined above, wherein a compound of formula 1G

1G

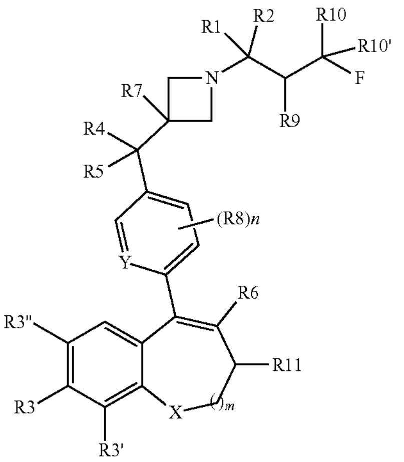

wherein R1, R2, R3", R3", R4, R5, R6, R7, Y, R8, R9, R10, R10', R11, n, m, X are as defined above and R3a is carboxylic ester such as COOMe, COOEt, or protected OH with O-pivaloyl for example, is converted to compound of formula (I), in presence of a source of hydroxide ions, such as NaOH in solution in methanol, said step being optionally preceded by a step for obtaining compound 1G, wherein a compound of formula 1F

1F

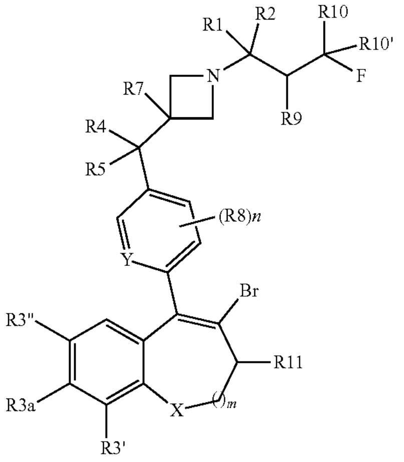

wherein, R1, R2, R3", R3", R4, R5, R7, Y, R8, R9, R10, R10', R11, n, m, X are as described above and R3a is as defined above, is subjected to a Suzuki coupling with a boronic reagent R6-B(OR')$_2$, wherein —B(OR')$_2$ is a boronic acid or a pinacolate ester and R6 is as defined above.

Herein is also provided a process for preparing a compound of formula (I) as described above, wherein a compound of formula 1Fa 1Fa

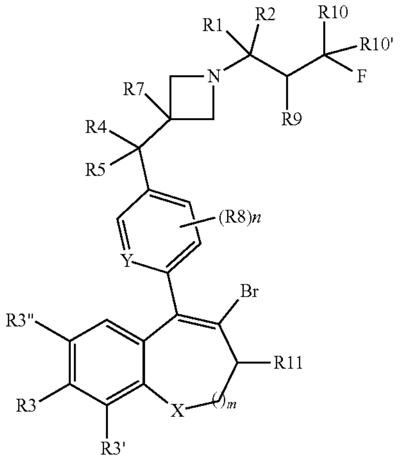

wherein R1, R2, R3, R3', R3", R4, R5, R7, Y, R8, R9, R10, R10', R11, n, m, X are as described above, is submitted to a Suzuki coupling with a boronic reagent R6-B(OR')$_2$, wherein —B(OR')$_2$ is a boronic acid or a pinacolate ester and R6 is defined above, said step being optionally preceded by a step for obtaining compound 1Fa, wherein a compound of formula 1F

1F

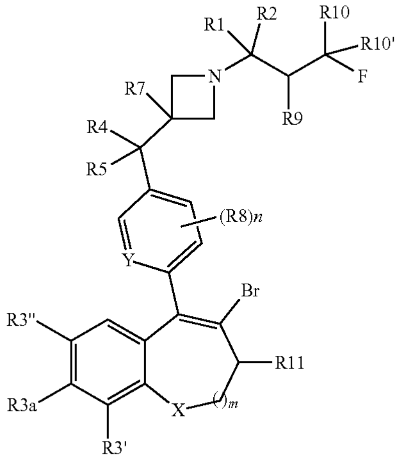

wherein R1, R2, R3', R3", R4, R5, R7, Y, R8, R9, R10, R10', R11, n, m, X are as described above and R3a is as defined above, is converted to a compound 1Fa in the presence of a source of hydroxide ions, such as NaOH in solution in methanol.

Herein are also provided the intermediate compounds selected from compounds of formula 1E, 1F, 1G and 1Fa, or any of its pharmaceutically acceptable salt,

1E

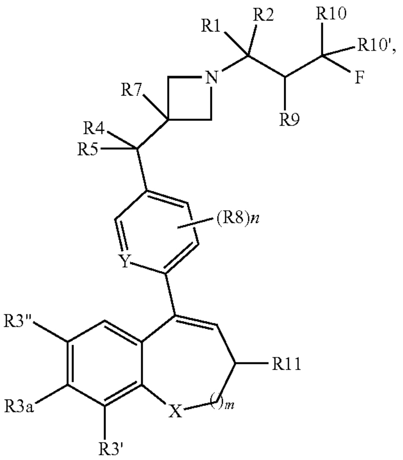

1F

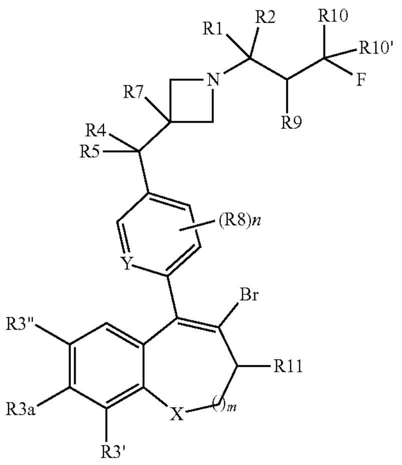

1G

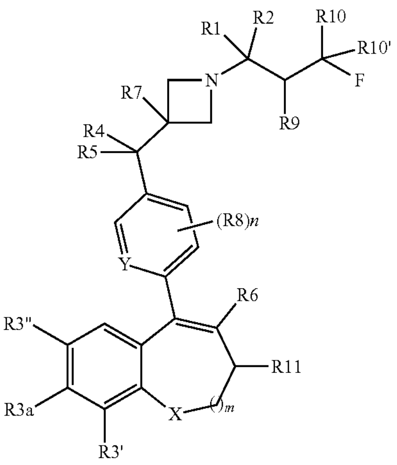

and

-continued

1Fa

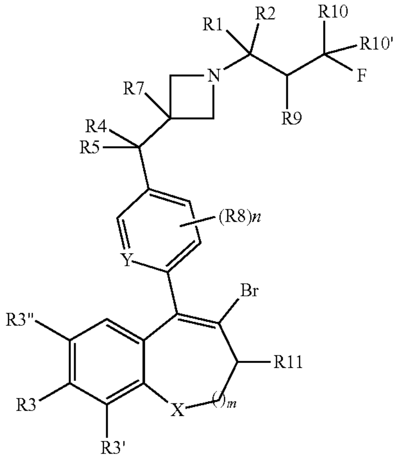

wherein R1, R2, R3, R3', R3", R4, R5, R7, Y, R8, R9, R10, R10', R11, n, m, X are as defined above and R3a is carboxylic ester such as COOMe, COOEt, or protected OH with O-pivaloyl.

Herein is further provided the intermediate compound of formulas 1D and 1D', or any of their pharmaceutically acceptable salt

1D

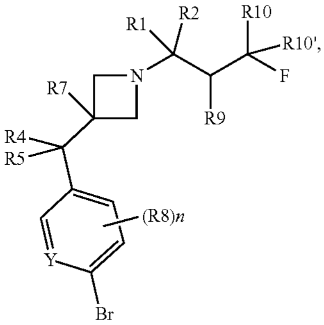

1D'

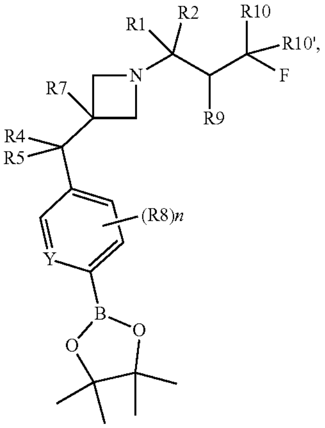

wherein R1, R2, R4, R5, R7, R8, R9, R10, R10', n and Y are as described above.

In another aspect, herein is also provided a process for the preparation of a compound of formula (I), wherein R3 is a —COOH group, comprising a deprotection step of a compound of formula IG as defined above, optionally followed by a purification step.

Said purification step may for example consist, as illustrated in step 2 of example 1 herein after, in an acidification step, for example with an aqueous solution of hydrochloric acid.
SCHEME 1b - Part - 1: Preparation of compounds of the formula (I) - General process
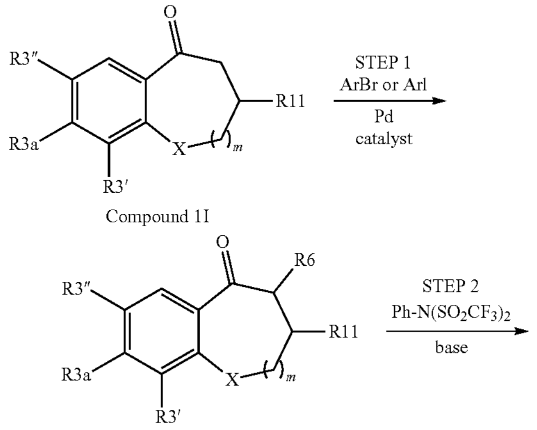
Compound 1I
Compound 1J
-continued
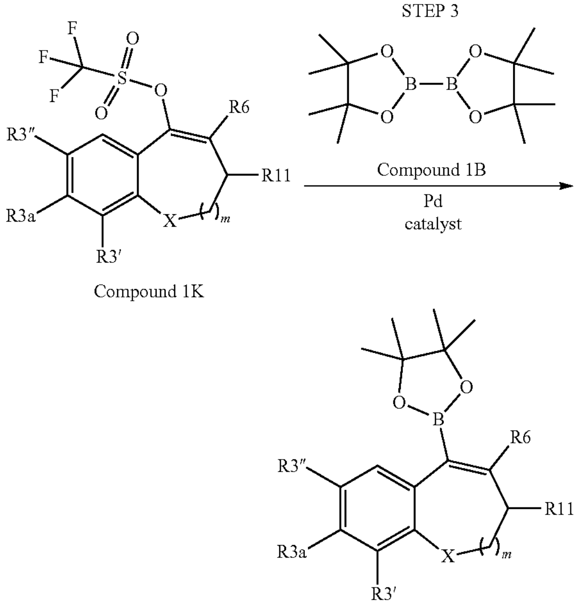
Compound 1K
Compound 1L
SCHEME 1b - Part - 2
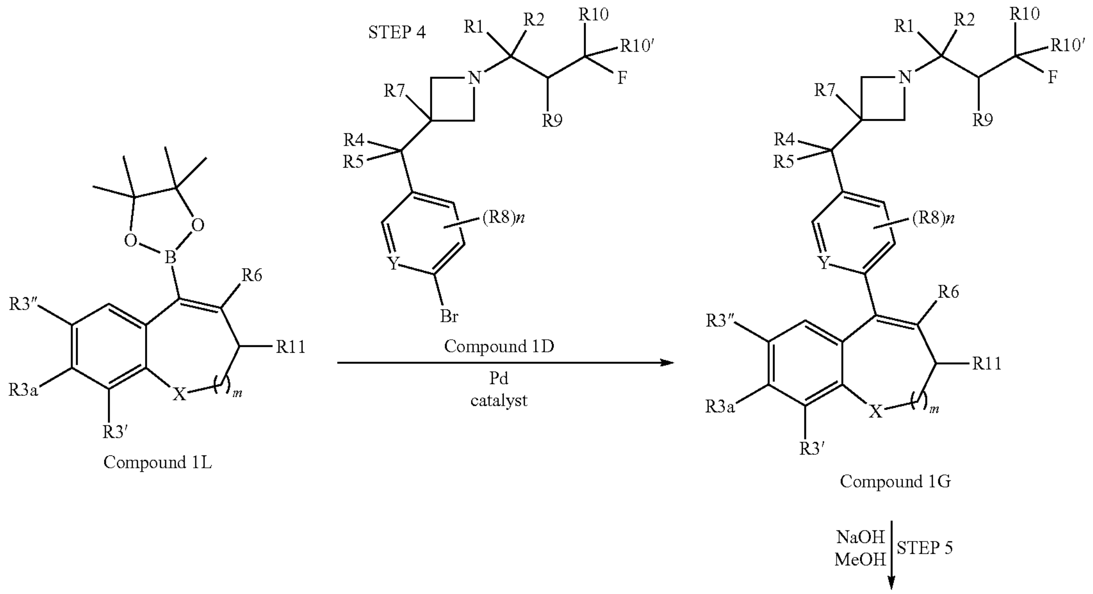
Compound 1L
Compound 1G -continued

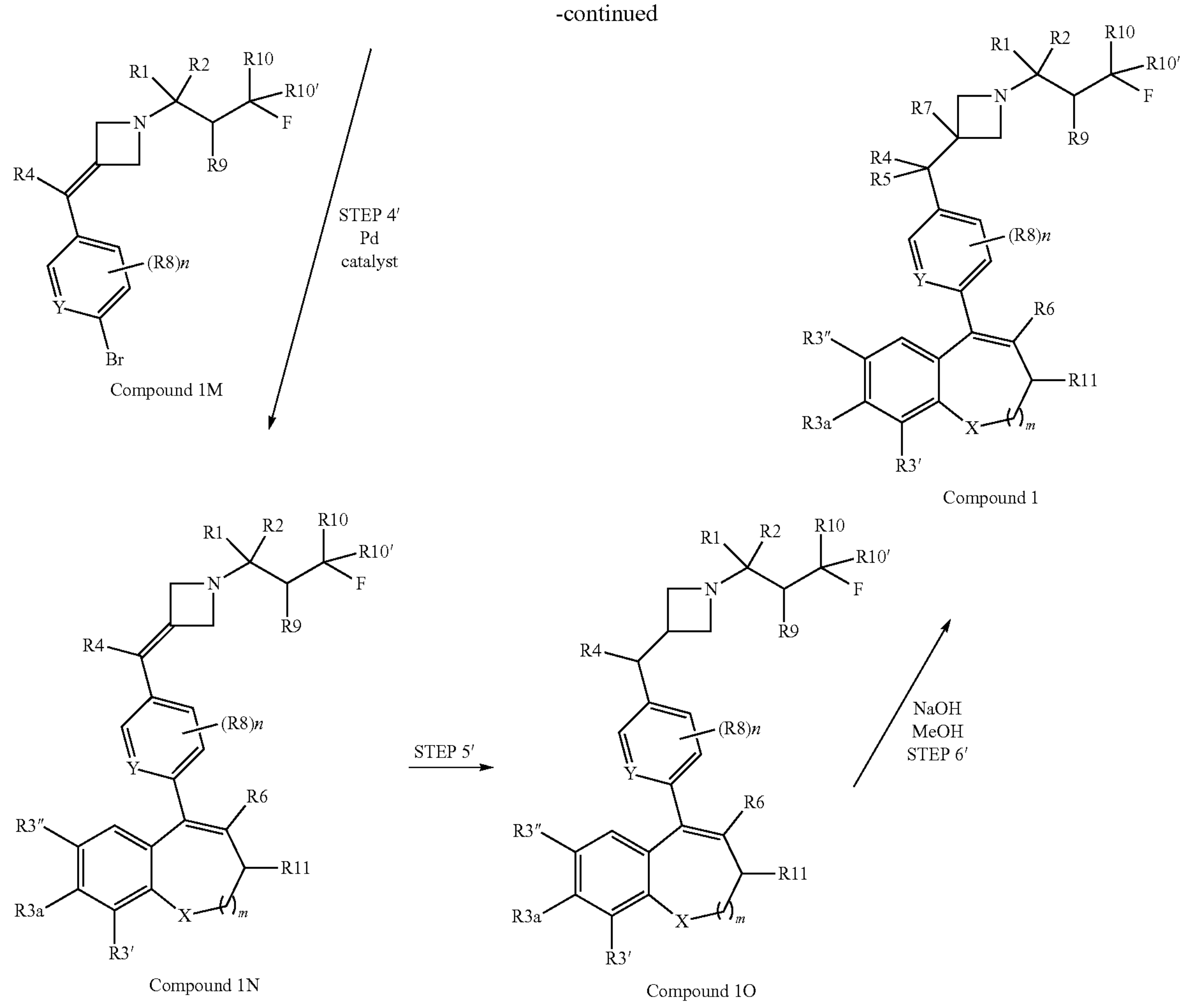

Compound 1M

Compound 1

Compound 1N

Compound 1O

According to SCHEME 1b, in which R3a is H, a carboxylic ester such as COOMe, COOEt or protected OH with O-pivaloyl for example, and R11 is a hydrogen atom, R1, R2, R3, R3', R3", R4, R5, R6, R7, R8, R9, R10, R10', n, m, X and Y are defined as described above, compound 1I can be converted in STEP 1 to compound 1J by treatment with aryl bromide or iodide in the presence of a palladium catalyst, for example tris(dibenzylideneacetone)dipalladium (0) ($Pd_2(dba)_3$), in solution in toluene by heating up to reflux of solvent, in presence of a base such as $K_2CO_3$ or $Cs_2CO_3$.

Compound 1J can be converted in STEP 2 to compound 1K by treatment with N,N-bis(trifluoromethylsulfonyl)aniline in the presence of base such as DBU or NaH or KHMDS at −50° C. in a solvent such as MeTHF.

Compound 1K can be converted in STEP 3 to compound 1L by treatment for example with bis(pinacolato)diboron (compound 1B), and with a palladium catalyst, for example bis (triphenylphosphine) palladium(II) dichloride $Pd(PPh_3)_2Cl_2$, and a phosphine such as triphenylphosphine in solution in toluene by heating up to reflux of solvent, in presence of a base such as KOPh.

Compound 1G can be prepared in a Suzuki coupling reaction between compounds 1L and 1D in STEP 4 using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

When R3a is COOMe, COOEt, or a protected OH such as O-pivaloyl, compound 1G can be converted in STEP 5 to compound of formula (I) in presence of a source of hydroxide ions such as NaOH in solution in methanol (MeOH). When R3 represents a —COOH group, extraction of the product could give the sodium salt of compound I. The acidification with an aqueous solution of HCl 2N to pH 6-7 could give the neutral form of compound I. The acidification with an aqueous solution of HCl 2N to pH 1-2 could give the hydrochloride salt of compound I. The purification using HPLC in presence of formic acid or trifluoroacetic acid in the eluent could give the formate or trifluoroacetate salt of compound I.

Alternatively, compound 1L can be converted in STEP 4' to compound 1N in a Suzuki coupling reaction with compound 1 M using for example [1,1'-bis(diphenylphosphino) ferrocene]dichloropalladium(II) ($Pd(dppf)Cl_2$), complex with DCM, as catalyst, in a mixture of dioxane and water and in the presence of a base, for example cesium carbonate ($Cs_2CO_3$), by heating up to reflux of solvent.

Compound 1N can be reduced to compound 10 in STEP 5' by hydrogenation with a catalyst, such as $PtO_2$ under hydrogen ($H_2$) pressure, around 2 bars for example, at room temperature.

When R3a is COOMe, COOEt, or a protected OH such as O-pivaloyl, compound 1O can be converted in STEP 6' to compound of formula (I) in presence of a source of hydroxide ions such as NaOH in solution in methanol (MeOH). When R3 represents a —COOH group, extraction of the product could give the sodium salt of compound I. The acidification with an aqueous solution of HCl 2N to pH 6-7 could give the neutral form of compound I. The acidification with an aqueous solution of HCl 2N to pH 1-2 could give the hydrochloride salt of compound I. The purification using HPLC in presence of formic acid or trifluoroacetic acid in the eluent could give the formate or trifluoroacetate salt of compound I.

Herein is further provided the intermediate compound of formula 1L, or any of its pharmaceutically acceptable salt

1L

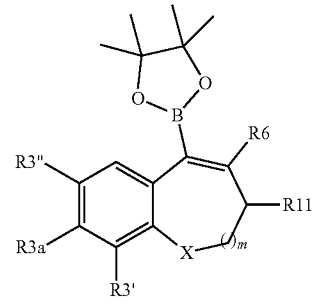

wherein R3a, R3', R3", X, m and R6 are as described above and R11 is a hydrogen atom.

-continued

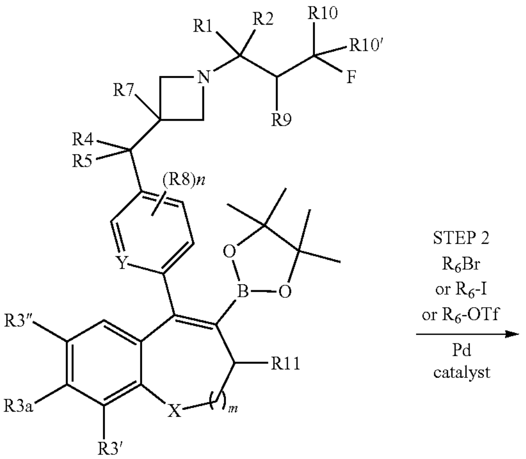

Compound 1H

SCHEME 1c: Preparation of compounds of the formula (I) - General process

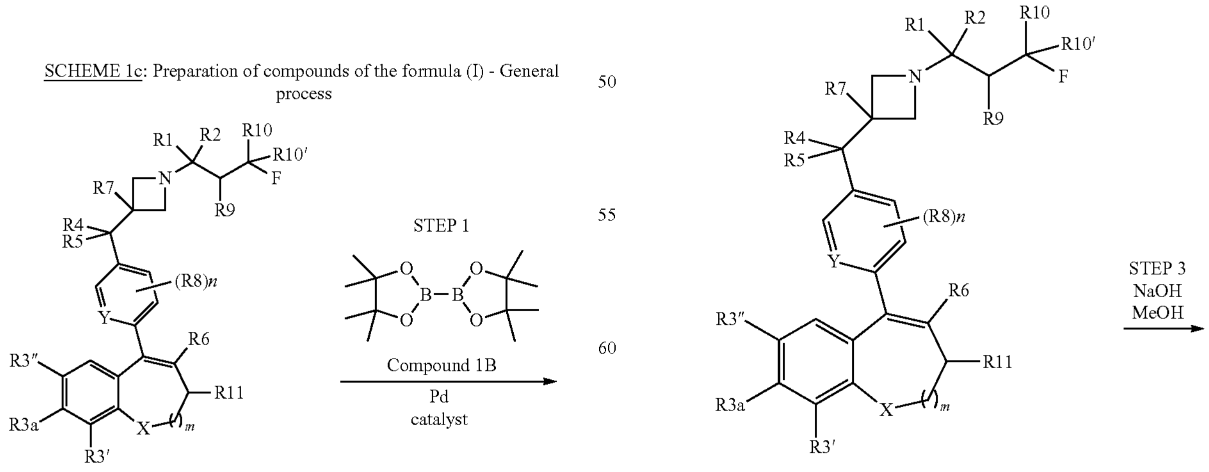

Compound 1F

Compound 1G

-continued

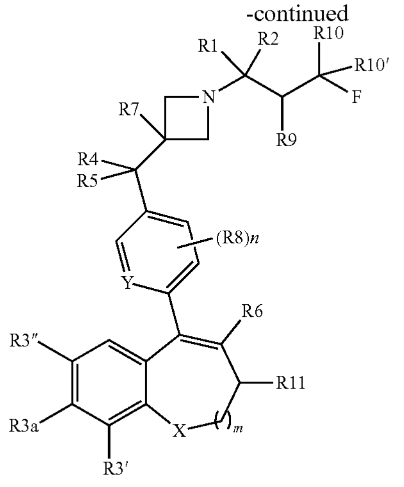

Compound I

According to SCHEME 1c, in which R3a is H, a carboxylic ester such as COOMe, COOEt, or protected OH with O-pivaloyl for example, and R11 is a hydrogen atom R1, R2, R3, R3', R3", R4, R5, R6, R7, R8, R9, R10, R10', R11, n, m, X and Y are defined as described above, compound 1F can be converted in STEP 1 to compound 1H by treatment for example with bis(pinacolato)diboron (compound 1B) and with a palladium catalyst, for example bis(triphenylphosphine)palladium(II) dichloride $Pd(PPh_3)_2Cl_2$, and a phosphine such as triphenylphosphine in toluene by heating up to reflux of solvent in presence of a base such as KOPh.

Compound 1G wherein R6 is phenyl or heteroaryl can be prepared in a Suzuki coupling reaction between compounds 1H and either R6Br or R6I or R6OTf in STEP 2 using for example [1,1'-bis(diphenylphosphino) ferrocene]dichloropalladium(II) ($Pd(dppf)Cl_2$), complex with DCM as catalyst, in a mixture of dioxane and water and in the presence of a base, for example cesium carbonate ($Cs_2CO_3$), by heating up to reflux of solvent.

When R3a is COOMe, COOEt, or a protected OH such as O-pivaloyl, compound 1G can be converted in STEP 3 to compound of formula (I) in presence of a source of hydroxide ions such as NaOH in solution in methanol (MeOH). When R3 represents a —COOH group, extraction of the product could give the sodium salt of compound I. The acidification with an aqueous solution of HCl 2N to pH 6-7 could give the neutral form of compound I. The acidification with an aqueous solution of HCl 2N to pH 1-2 could give the hydrochloride salt of compound I. The purification using HPLC in presence of formic acid or trifluoroacetic acid in the eluent could give the formate or trifluoroacetate salt of compound I.

SCHEME 1d: Preparation of compounds of the formula (1A) wherin R3a = $CO_2Me$ - General process

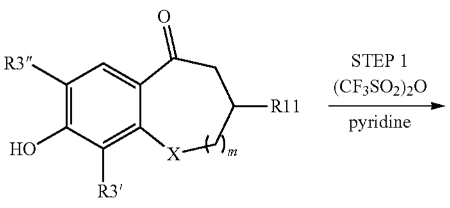

Compound 1Aa

-continued

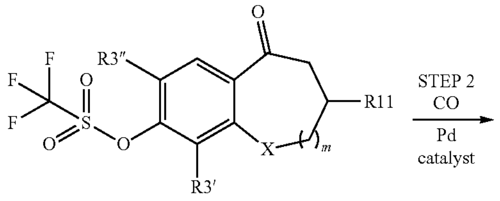

Compound 1Ab

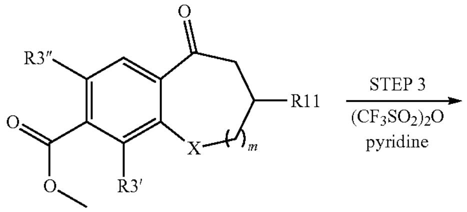

Compound 1Ac

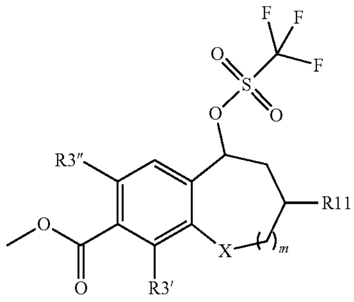

Compound 1A

According to SCHEME 1d, in which X, m, R3', R3" and R11 are defined as described above, compound 1A could be commercially available or prepared as follows: compound 1Aa (commercially available or prepared according to WO2017140669 and WO2018091153), can be converted in STEP 1 to compound 1Ab by treatment with trifluoromethanesulfonic anhydride, in solution in DCM, in the presence of pyridine as a base.

Compound 1Ab can be converted in STEP 2 to compound 1Ac by carbonylation with carbon monoxide, in solution in DMF and MeOH, in the presence of a palladium catalyst, for example [1,1'-bis(diphenylphosphino)ferrocene]dichloropalladium(II) ($Pd(dppf)Cl_2$), complex with DCM.

Compound 1Ac can be converted in STEP 3 to compound 1A wherein R3a $=CO_2Me$ by treatment with trifluoromethanesulfonic anhydride, in solution in DCM, in the presence of pyridine as a base.

SCHEME 1e: Preparation of compounds of the formula (I) - General process

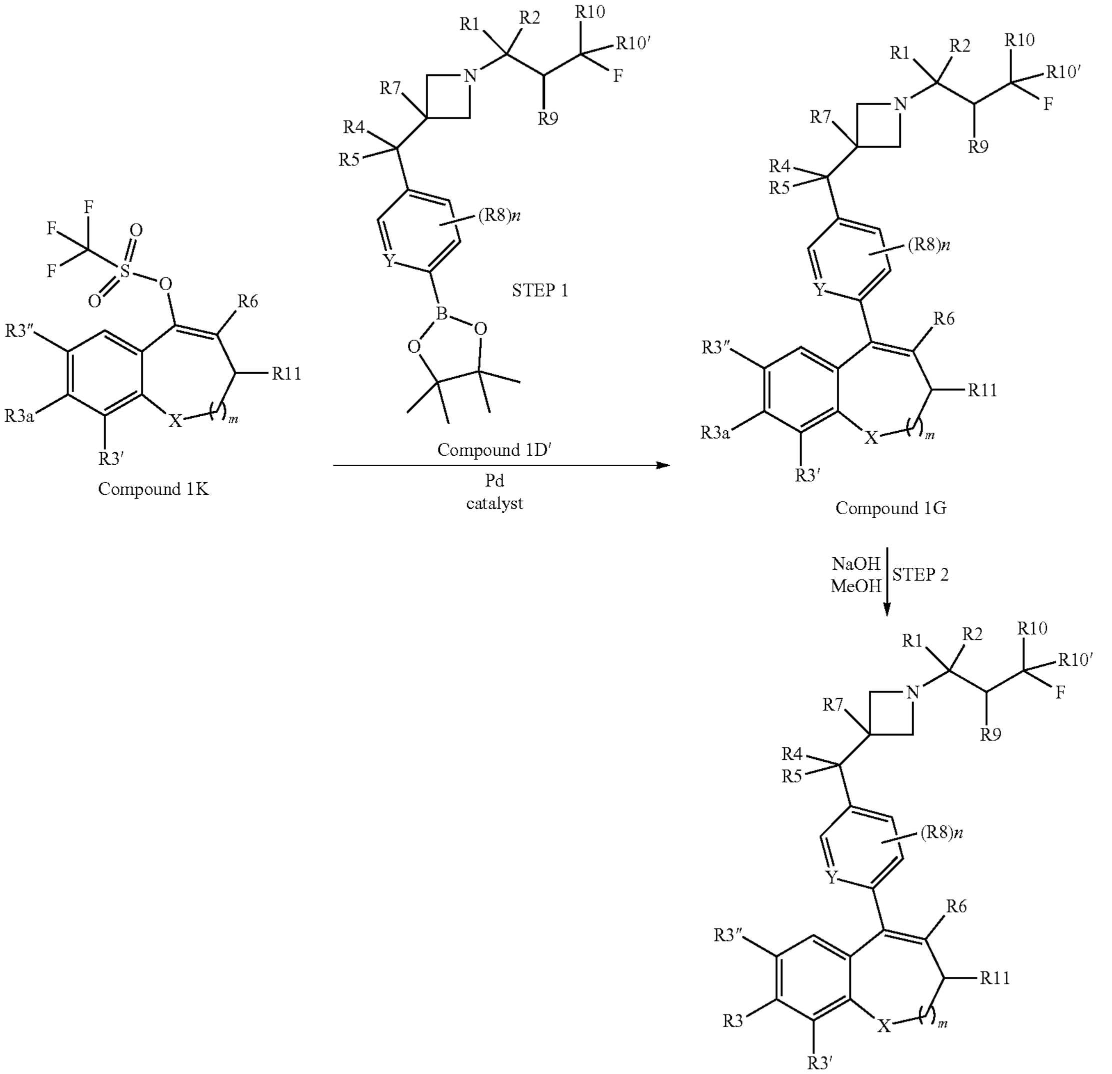

Compound 1K

Compound 1G

Compound I

According to SCHEME 1e, in which R3a is H, a carboxylic ester such as COOMe, COOEt or protected OH with O-pivaloyl for example, and R11 is a hydrogen atom R1, R2, R3, R3', R3", R4, R5, R6, R7, R8, R9, R10, R10', R11, n, m, X and Y are defined as described above, compound 1K can be converted in STEP 1 to compound 1G by treatment with compound 1D' in the presence of a palladium catalyst, for example [1,1'-bis(diphenylphosphino)ferrocene]dichloropalladium(II) ($Pd(dppf)Cl_2$), complex with DCM, in a mixture of dioxane and water and in the presence of a base, for example cesium carbonate ($Cs_2CO_3$), by heating up to reflux of solvent.

When R3a is COOMe, COOEt, or a protected OH such as O-pivaloyl, compound 1G can be converted in STEP 2 to compound of formula (I) in presence of a source of hydroxide ions such as NaOH in solution in methanol (MeOH). When R3 represents a —COOH group, extraction of the product could give the sodium salt of compound I. The acidification with an aqueous solution of HCl 2N to pH 6-7 could give the neutral form of compound I. The acidification with an aqueous solution of HCl 2N to pH 1-2 could give the hydrochloride salt of compound I. The purification using HPLC in presence of formic acid or trifluoroacetic acid in the eluent could give the formate or trifluoroacetate salt of compound I.

SCHEME 1f: Alternative preparation of compounds of the formula (1J) - General process

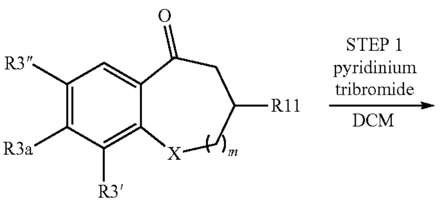

Compound 1I

-continued

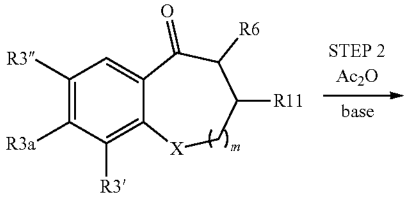

Compound 1Ia

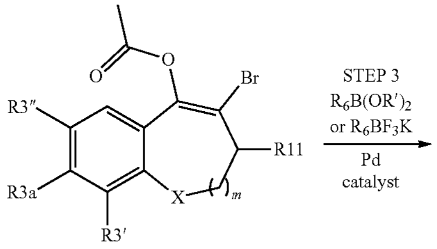

Compound 1Ib

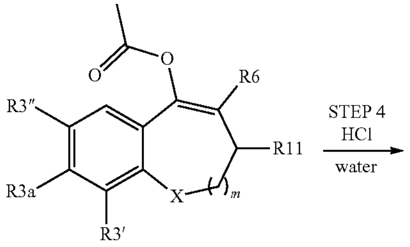

Compound 1Ic

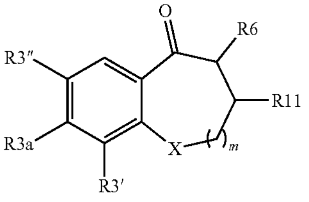

Compound 1J

According to SCHEME 1f, in which R3a is H, a carboxylic ester such as COOMe, COOEt, or protected OH with O-pivaloyl for example, R3', R3", R11, X and m are defined as described above, compound 1J could alternatively be prepared as follows: compound 1I can be converted in STEP 1 to compound 1Ia by treatment with pyridinium tribromide in DCM or THF at room temperature for example.

Compound 1Ia can be converted in STEP 2 to compound 1Ib by deprotonation with a base such as LiHMDS in THF followed by treatment with acetic anhydride.

Compound 1Ic can be prepared in STEP 3 in a Suzuki coupling reaction between compounds 1Ib and $R_6B(OR')_2$ or $R_6BF_3K$ using for example [1,1'-bis(diphenylphosphino) ferrocene]dichloropalladium(I) ($Pd(dppf)Cl_2$), complex with DCM, as catalyst, in a mixture of toluene and water and in the presence of a base, for example cesium carbonate ($Cs_2CO_3$), by heating up to reflux of solvent.

Compound 1Ic can be converted in STEP 4 to compound 1J by hydrolysis with aqueous HCl solution by heating in methanol and DCM for example.

The $^{1}H$ NMR Spectra at 400 and 500 MHz were performed on a Bruker Avance DRX-400 and Bruker Avance DPX-500 spectrometer, respectively, with the chemical shifts (δ in ppm) in the solvent dimethyl sulfoxide-d6 (d6-DMSO) referenced at 2.5 ppm at a temperature of 303 K. Coupling constants (J) are given in Hertz.

The liquid chromatography/mass spectra (LC/MS) were obtained on a UPLC Acquity Waters instrument, light scattering detector Sedere and SQD Waters mass spectrometer using UV detection DAD 210-400 nm and flash Acquity UPLC CSH C18 1.7 μm, dimension 2.1×30 mm, mobile phase $H_2O$+0.1% $HCO_2H/CH_3CN$+0.1% $HCO_2H$.

The following tables 1a and 1b comprise respectively specific compounds of formula (I) (name and structure) in accordance with the present disclosure as well their characterization ($^{1}H$ NMR and liquid chromatography/mass).

TABLE 1a

| Example or compound | Structure | Name |
|---|---|---|
| 1 | 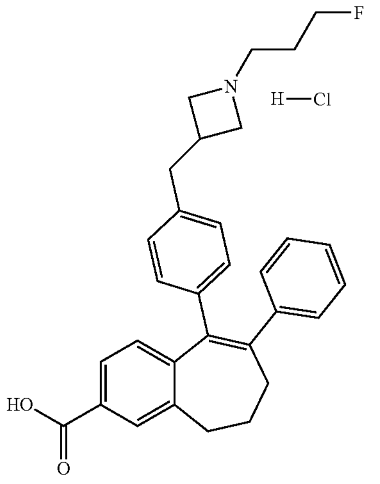 | 9-(4-((1-(3-fluoropropyl)azetidin-3-yl)methyl)phenyl)-8-phenyl-6,7-dihydro-5H-benzo[7]annulene-3-carboxylic acid hydrochloride |

TABLE 1a-continued

| Example or compound | Structure | Name |
| --- | --- | --- |
| 2 | 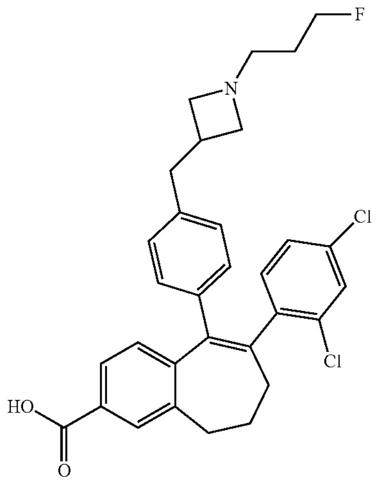 [SMILES: O=C(O)c1ccc2c(c1)CCCC(c1ccc(Cl)cc1Cl)=C2c1ccc(CC2CN(CCCF)C2)cc1] | 8-(2,4-dichlorophenyl)-9-(4-((1-(3-fluoropropyl)azetidin-3-yl)methyl)phenyl)-6,7-dihydro-5H-benzo[7]annulene-3-carboxylic acid |
| 3 | 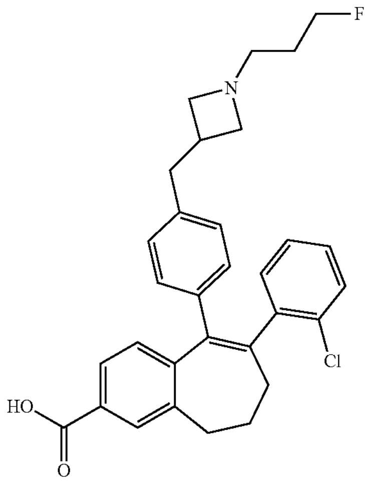 [SMILES: O=C(O)c1ccc2c(c1)CCCC(c1ccccc1Cl)=C2c1ccc(CC2CN(CCCF)C2)cc1] | 8-(2-chlorophenyl)-9-(4-((1-(3-fluoropropyl)azetidin-3-yl)methyl)phenyl)-6,7-dihydro-5H-benzo[7]annulene-3-carboxylic acid |
| 4 | 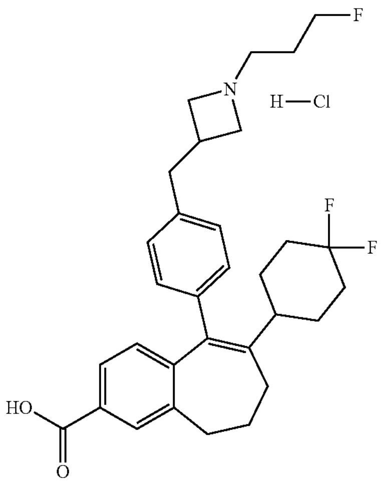 | 8-(4,4-difluorocyclohexyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 5 | 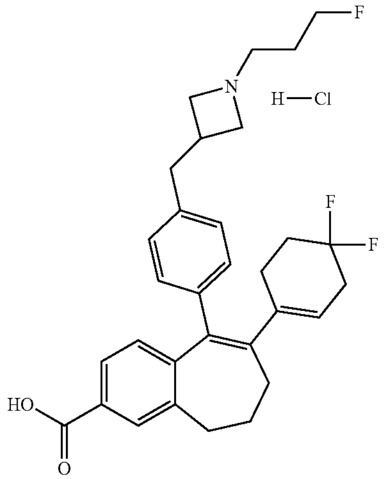 | 8-(4,4-difluorocylcohex-1-en-1-yl)-9-(4-((1-(3-fluoropropyl)azetidin-3-yl)methyl)phenyl)-6,7-dihydro-5H-benzo[7]annulene-3-carboxylic acid hydrochloride |
| 6 | 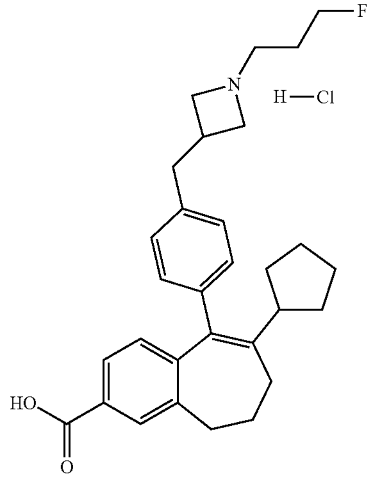 | 8-cyclopentyl-9-(4-((1-(3-fluoropropyl)azetidin-3-yl)methyl)phenyl)-6,7-dihydro-5H-benzo[7]annulene-3-carboxylic acid hydrochloride |
| 7 | 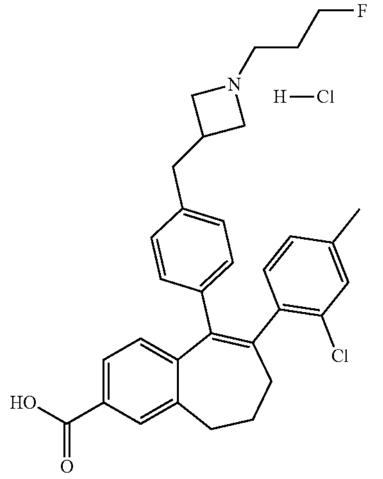 | 8-(2-chloro-4-methylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 8 | 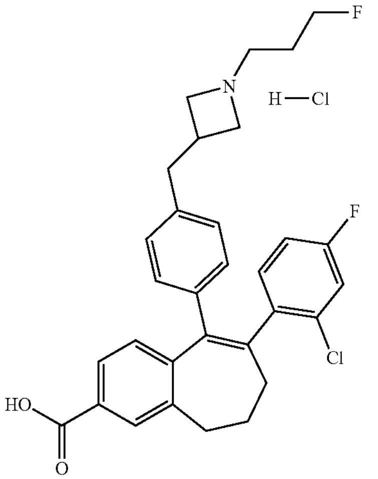 | 8-(2-chloro-4-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 9 | 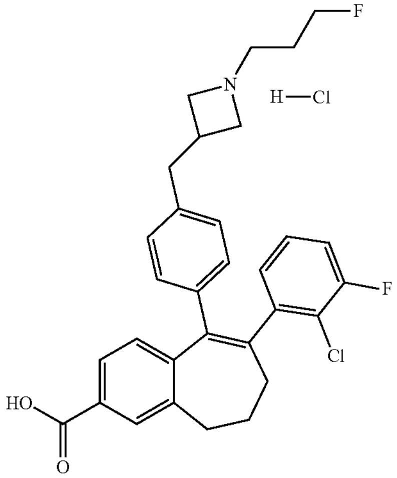 | 8-(2-chloro-3-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 10 | 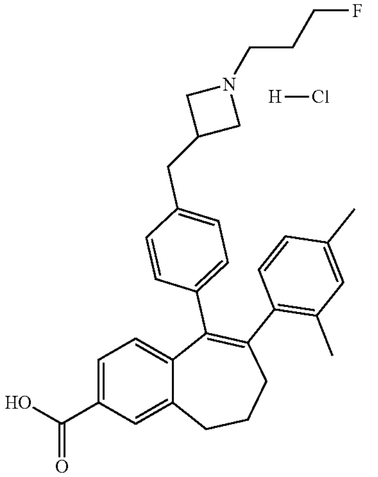 | 8-(2,4-dimethylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 11 | 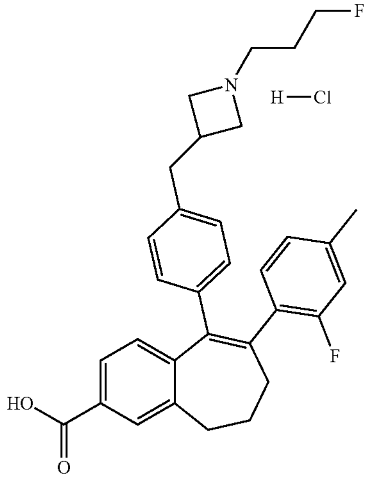 | 8-(2-fluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride |
| 12 | 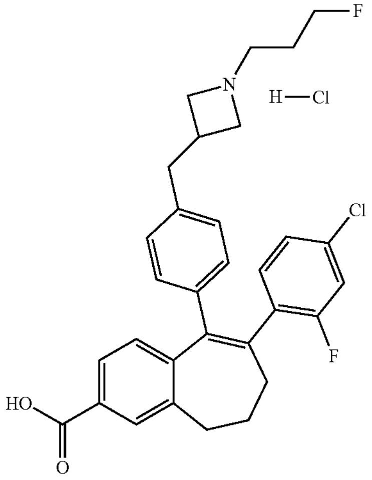 | 8-(4-chloro-2-fluorophenyl)-9-(4-((1-(3-fluoropropyl)azetidin-3-yl)methyl)phenyl)-6,7-dihydro-5H-benzo[7]annulene-3-carboxylic acid hydrochlrodie |
| 13 | 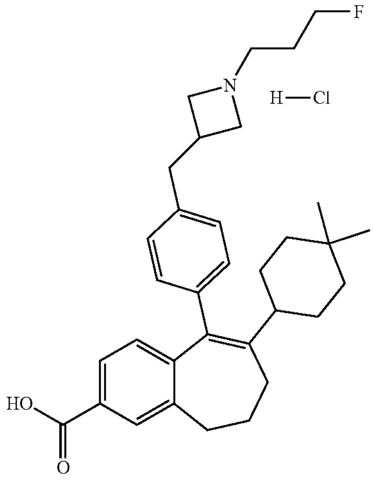 | 8-(4,4-dimethylcyclohexyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 14 | 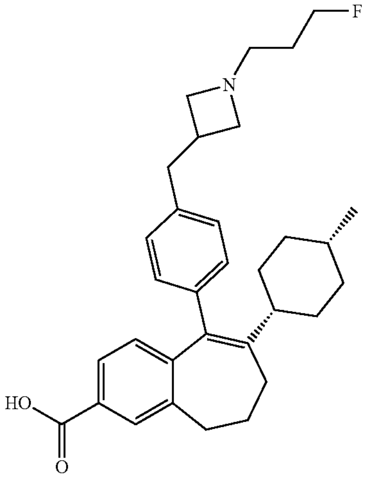 [SMILES: C[C@H]1CC[C@@H](C2=C(c3ccc(CC4CN(CCCF)C4)cc3)c3ccc(C(=O)O)cc3CCC2)CC1] | 9-(4-((1-(3-fluoropropyl)azetidin-3-yl)methyl)phenyl)-8-(cis-4-methylcyclohexyl)-6,7-dihydro-5H-benzo[7]annulene-3-carboxylic acid |
| 15 | 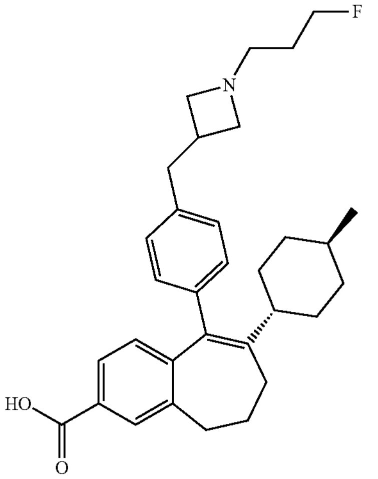 [SMILES: C[C@H]1CC[C@H](C2=C(c3ccc(CC4CN(CCCF)C4)cc3)c3ccc(C(=O)O)cc3CCC2)CC1] | 9-(4-((1-(3-fluoropropyl)azetidin-3-yl)methyl)phenyl)-8-(trans-4-methylcyclohexyl)-6,7-dihydro-5H-benzo[7]annilene-3-carboxylic acid |
| 16 | 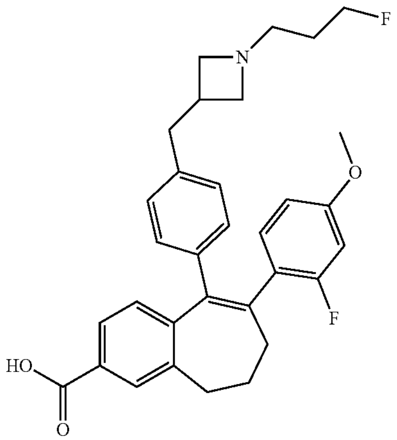 [SMILES: COc1ccc(C2=C(c3ccc(CC4CN(CCCF)C4)cc3)c3ccc(C(=O)O)cc3CCC2)c(F)c1] | 8-(2-fluoro-4-methoxyphenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 17 | 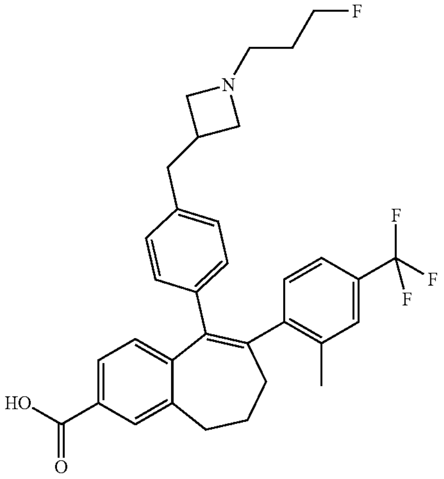 [SMILES: Cc1cc(C(F)(F)F)ccc1C1=C(c2ccc(CC3CN(CCCF)C3)cc2)c2ccc(C(=O)O)cc2CCC1] | 9-(4-((1-(3-fluoropropyl)azetidin-3-yl)methyl)phenyl)-8-(2-methyl-4-(trifluoromethyl)phenyl)-6,7-dihydro-5H-benzo[7]annulene-3-carboxylic acid |
| 18 | 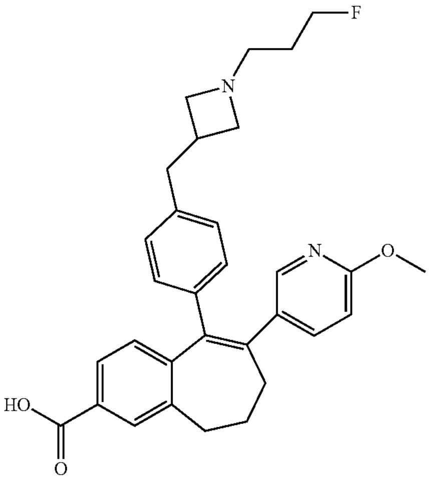 [SMILES: COc1ccc(C2=C(c3ccc(CC4CN(CCCF)C4)cc3)c3ccc(C(=O)O)cc3CCC2)cn1] | 9-(4-((1-(3-fluoropropyl)azetidin-3-yl)methyl)phenyl)-8-(6-methoxypyridin-3-yl)-6,7-dihydro-5H-benzo[7]annulene-3-carboxylic acid |
| 19 | 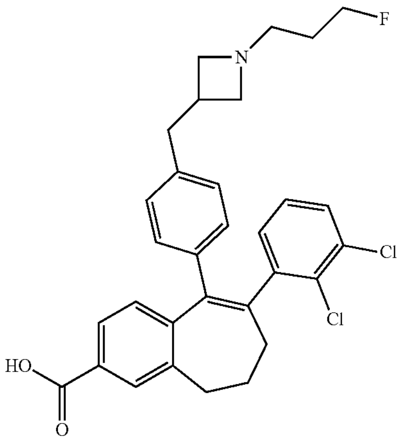 [SMILES: O=C(O)c1ccc2c(c1)CCCC(c1cccc(Cl)c1Cl)=C2c1ccc(CC2CN(CCCF)C2)cc1] | 8-(2,3-dichlorophenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 20 | 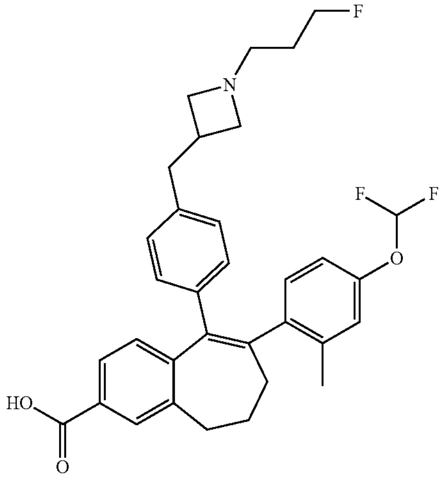 [SMILES: Cc1cc(OC(F)F)ccc1C1=C(c2ccc(CC3CN(CCCF)C3)cc2)c2ccc(C(=O)O)cc2CCC1] | 8-(4-(difluoromethoxy)-2-methylphenyl)-9-(4-((1-(3-fluoropropyl)azetidin-3-yl)methyl)phenyl)-6,7-dihydro-5H-benzo[7]annulene-3-carboxylic acid |
| 21 | 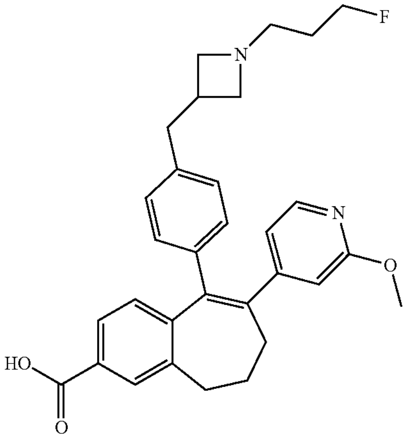 [SMILES: COc1cc(C2=C(c3ccc(CC4CN(CCCF)C4)cc3)c3ccc(C(=O)O)cc3CCC2)ccn1] | 9-(4-((1-(3-fluoropropyl)azetidin-3-yl)methyl)phenyl)-8-(2-methoxypyridin-4-yl)-6,7-dihydro-5H-benzo[7]annulene-3-carboxylic acid |
| 22 | 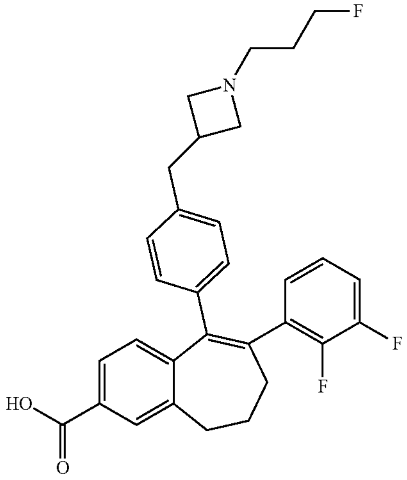 | 8-(2,3-difluorophenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 23 | 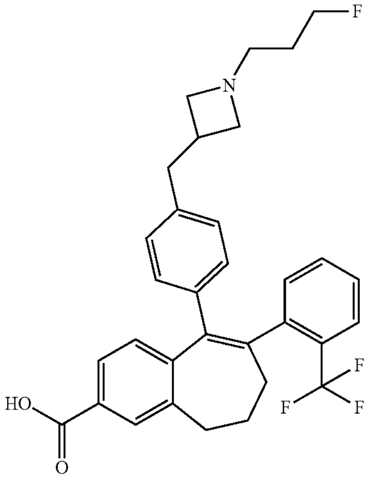 [SMILES: O=C(O)c1ccc2c(c1)CCCC(c1ccccc1C(F)(F)F)=C2c1ccc(CC2CN(CCCF)C2)cc1] | 9-(4-((1-(3-fluoropropyl)azetidin-3-yl)methyl)phenyl)-8-(2-(trifluoromethyl)phenyl)-6,7-dihydro-5H-benzo[7]annulene-3-carboxylic acid |
| 24 | 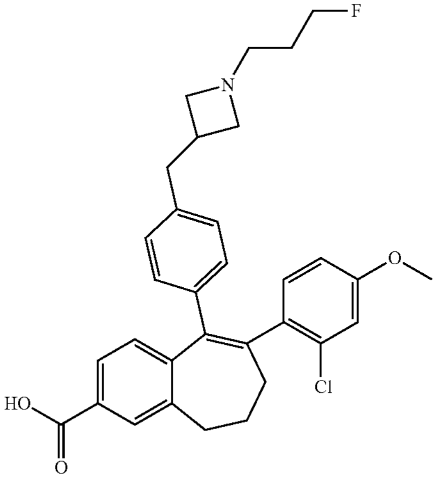 [SMILES: COc1ccc(C2=C(c3ccc(CC4CN(CCCF)C4)cc3)c3ccc(C(=O)O)cc3CCC2)c(Cl)c1] | 8-(2-chloro-4-methoxyphenyl)-9-(4-((1-(3-fluoropropyl)azetidin-3-yl)methyl)phenyl)-6,7-dihydro-5H-benzo[7]annulene-3-carboxylic acid |
| 25 | 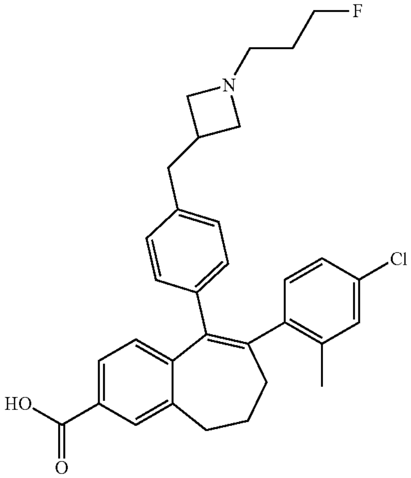 [SMILES: Cc1cc(Cl)ccc1C1=C(c2ccc(CC3CN(CCCF)C3)cc2)c2ccc(C(=O)O)cc2CCC1] | 8-(4-chloro-2-methylphenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 26 | 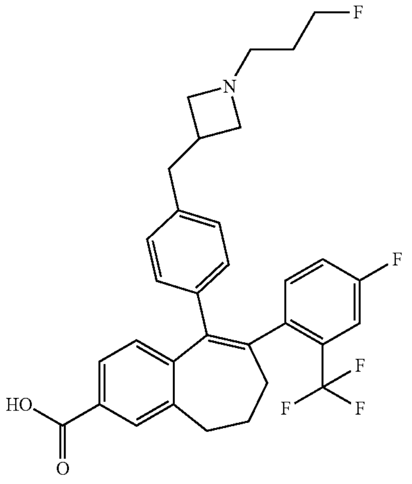 [SMILES: O=C(O)c1ccc2c(c1)CCCC(c1ccc(F)cc1C(F)(F)F)=C2c1ccc(CC2CN(CCCF)C2)cc1] | 8-(4-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid |
| 27 | 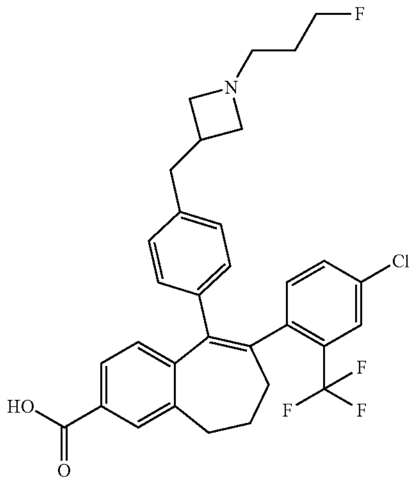 [SMILES: O=C(O)c1ccc2c(c1)CCCC(c1ccc(Cl)cc1C(F)(F)F)=C2c1ccc(CC2CN(CCCF)C2)cc1] | 8-(4-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid |
| 28 | 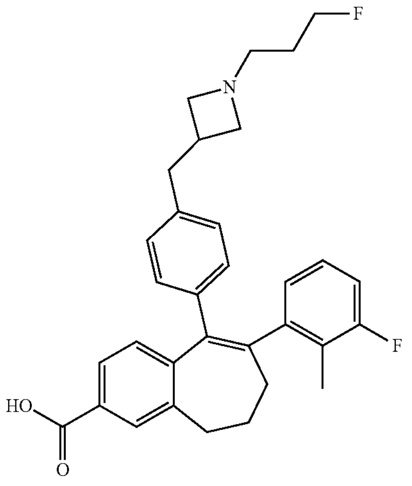 [SMILES: Cc1c(F)cccc1C1=C(c2ccc(CC3CN(CCCF)C3)cc2)c2ccc(C(=O)O)cc2CCC1] | 8-(3-fluoro-2-methylphenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 29 | 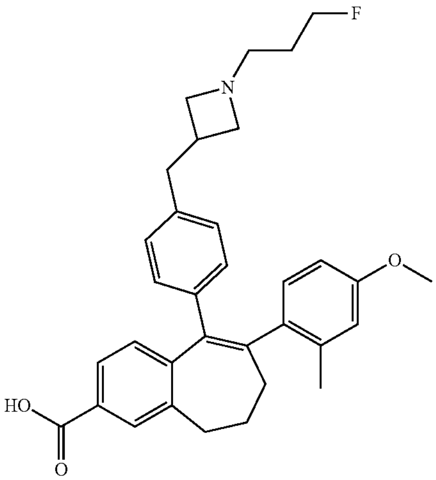 [SMILES: COc1ccc(C2=C(c3ccc(CC4CN(CCCF)C4)cc3)c3ccc(C(=O)O)cc3CCC2)c(C)c1] | 9-(4-((1-(3-fluoropropyl)azetidin-3-yl)methyl)phenyl)-8-(4-methoxy-2-methylphenyl)-6,7-dihydro-5H-benzo[7]annulene-3-carboxylic acid |
| 30 | 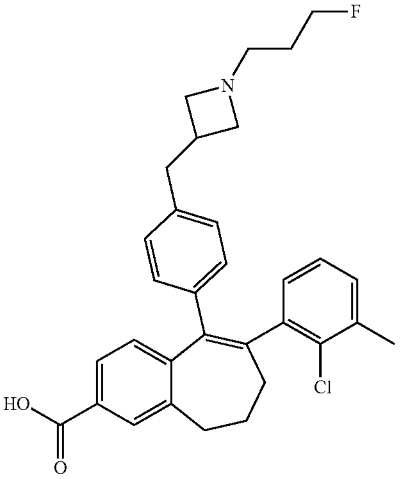 [SMILES: Cc1cccc(C2=C(c3ccc(CC4CN(CCCF)C4)cc3)c3ccc(C(=O)O)cc3CCC2)c1Cl] | 8-(2-chloro-3-methylphenyl)-9-(4-((1-(3-fluoropropyl)azetidin-3-yl)methyl)phenyl)-6,7-dihydro-5H-benzo[7]annulene-3-carboxylic acid |
| 31 | 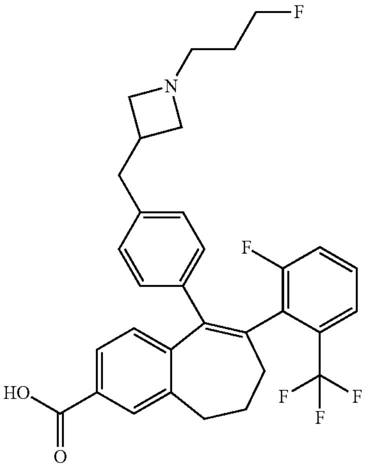 [SMILES: O=C(O)c1ccc2c(c1)CCCC(c1c(F)cccc1C(F)(F)F)=C2c1ccc(CC2CN(CCCF)C2)cc1] | 8-(2-fluoro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 32 | 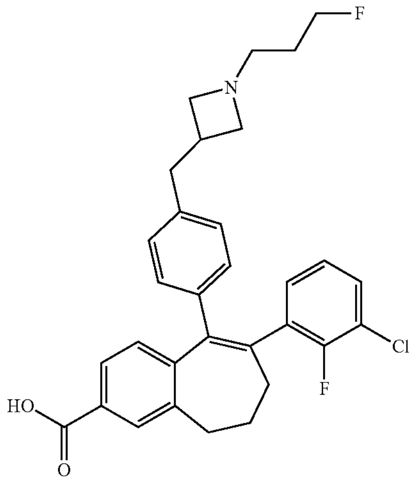 [SMILES: O=C(O)c1ccc2c(c1)CCCC(c1cccc(Cl)c1F)=C2c1ccc(CC2CN(CCCF)C2)cc1] | 8-(3-chloro-2-fluorophenyl)-9-(4-((1-(3-fluoropropyl)azetidin-3-yl)methyl)phenyl)-6,7-dihydro-5H-benzo[7]annulene-3-carboxylic acid |
| 33 | 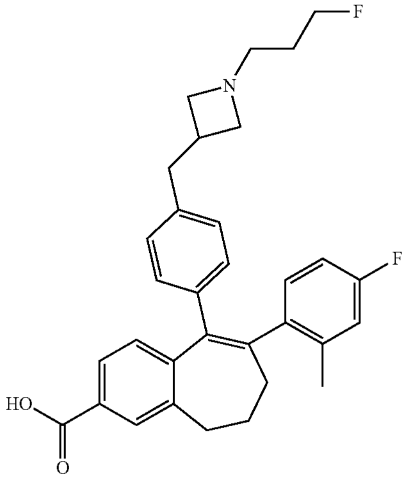 [SMILES: Cc1cc(F)ccc1C1=C(c2ccc(CC3CN(CCCF)C3)cc2)c2ccc(C(=O)O)cc2CCC1] | 8-(4-fluoro-2-methylphenyl)-9-(4-((1-(3-fluoropropyl)azetidin-3-yl)methyl)phenyl)-6,7-dihydro-5H-benzo[7]annulene-3-carboxylic acid |
| 34 | 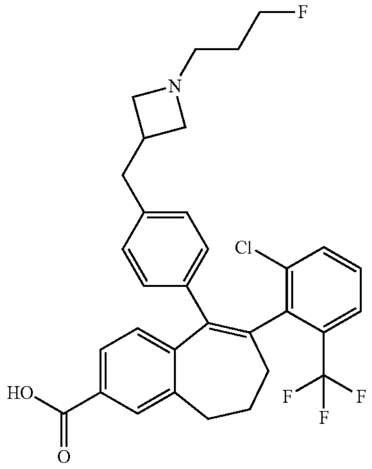 [SMILES: O=C(O)c1ccc2c(c1)CCCC(c1c(Cl)cccc1C(F)(F)F)=C2c1ccc(CC2CN(CCCF)C2)cc1] | 8-(2-chloro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid |

TABLE 1a-continued
| Example or compound | Structure | Name |
|---|---|---|
| 35 | 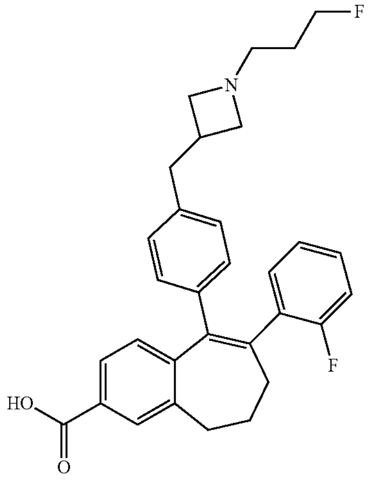 [SMILES: O=C(O)c1ccc2c(c1)CCCC(c1ccccc1F)=C2c1ccc(CC2CN(CCCF)C2)cc1] | 8-(2-fluorophenyl)-9-(4-((1-(3-fluoropropyl)azetidin-3-yl)methyl)phenyl)-6,7-dihydro-5H-benzo[7]annulene-3-carboxylic acid |
| 36 | 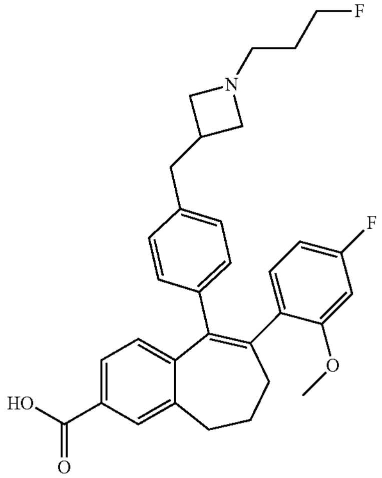 [SMILES: COc1cc(F)ccc1C1=C(c2ccc(CC3CN(CCCF)C3)cc2)c2ccc(C(=O)O)cc2CCC1] | 8-(4-fluoro-2-methoxyphenyl)-9-(4-((1-(3-fluoropropyl)azetidin-3-yl)methyl)phenyl)-6,7-dihydro-5H-benzo[7]annulene-3-carboxylic acid |
| 37 | 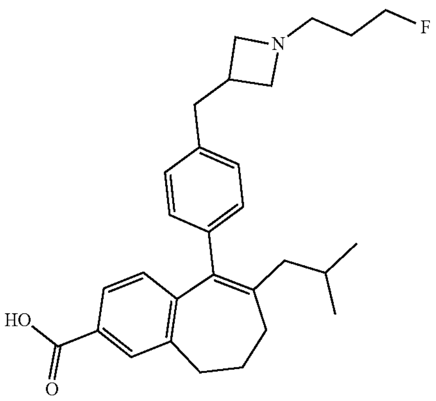 [SMILES: CC(C)CC1=C(c2ccc(CC3CN(CCCF)C3)cc2)c2ccc(C(=O)O)cc2CCC1] | 9-(4-((1-(3-fluoropropyl)azetidin-3-yl)methyl)phenyl)-8-isobutyl-6,7-dihydro-5H-benzo[7]annulene-3-carboxylic acid |

TABLE 1a-continued

| Example or compound | Structure | Name |
|---|---|---|
| 38 | 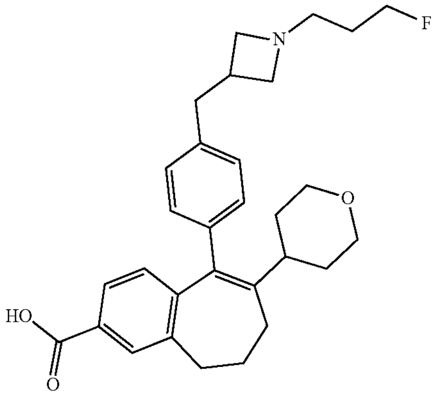 [SMILES: O=C(O)c1ccc2c(c1)CCCC(C1CCOCC1)=C2c1ccc(CC2CN(CCCF)C2)cc1] | 9-(4-((1-(3-fluoropropyl)azetidin-3-yl)methyl)phenyl)-8-(tetrahydro-2H-pyran-4-yl)-6,7-dihydro-5H-benzo[7]annulene-3-carboxylic acid |
| 39 | 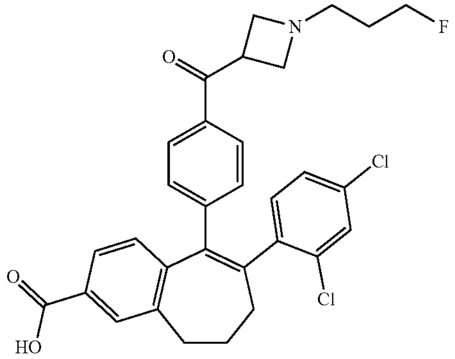 [SMILES: O=C(O)c1ccc2c(c1)CCCC(c1ccc(Cl)cc1Cl)=C2c1ccc(C(=O)C2CN(CCCF)C2)cc1] | 8-(2,4-dichlorophenyl)-9-(4-(1-(3-fluoropropyl)azetidine-3-carbonyl)phenyl)-6,7-dihydro-5H-benzo[7]annulene-3-carboxylic acid |
| 40 | 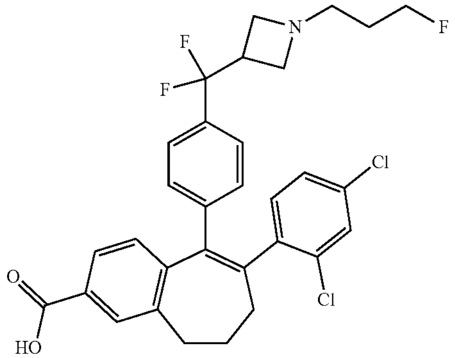 [SMILES: O=C(O)c1ccc2c(c1)CCCC(c1ccc(Cl)cc1Cl)=C2c1ccc(C(F)(F)C2CN(CCCF)C2)cc1] | 8-(2,4-dichlorophenyl)-9-(4-(difluoro(1-(3-fluoropropyl)azetidin-3-yl)methyl)phenyl)-6,7-dihydro-5H-benzo[7]annulene-3-carboxylic acid |
| 41 | 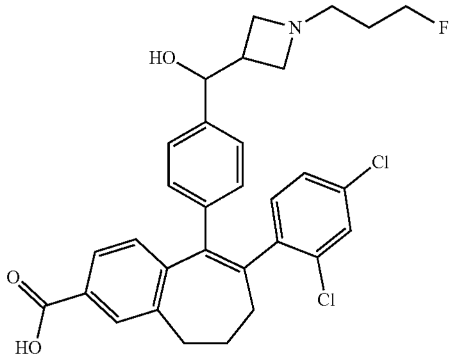<br>Isomer 1 | 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylic acid, Isomer 1 |

TABLE 1a-continued

| Example or compound | Structure | Name |
| --- | --- | --- |
| 42 | 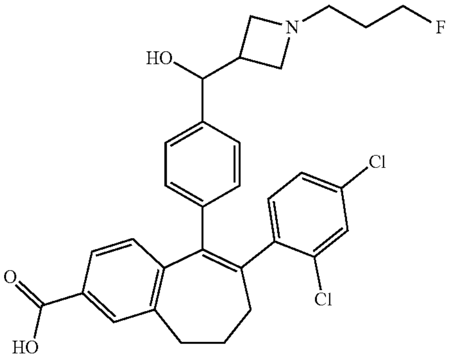 Isomer 2 | 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylic acid, Isomer 2 |
| 43 | 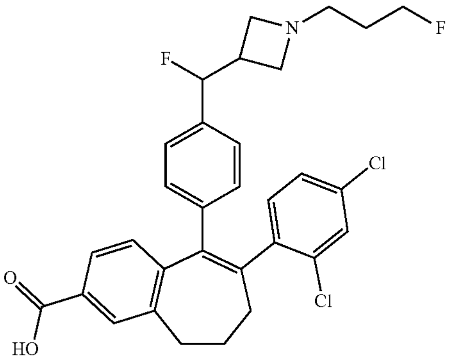 Isomer 1 | 8-(2,4-dichlorophenyl)-9-(4-(fluoro(1-(3-fluoroproyl)azetidin-3-yl)methyl)phenyl)-6,7-dihydro-5H-benzo[7]annulene-3-carboxylic acid, Isomer 1 |
| 44 | 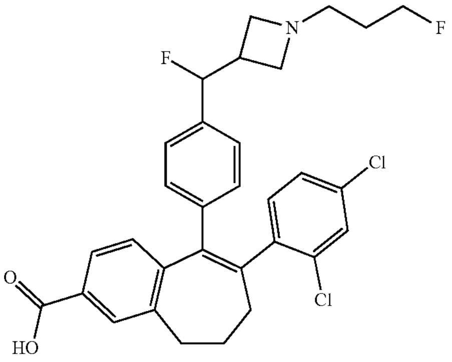 Isomer 2 | 8-(2,4-dichlorophenyl)-9-(4-(fluoro(1-(3-fluoropropyl)azetidin-3-yl)methyl)phenyl)-6,7-dihydro-5H-benzo[7]annulene-3-carboxylic acid, Isomer 2 |

TABLE 1a-continued

| Example or compound | Structure | Name |
|---|---|---|
| 45 | 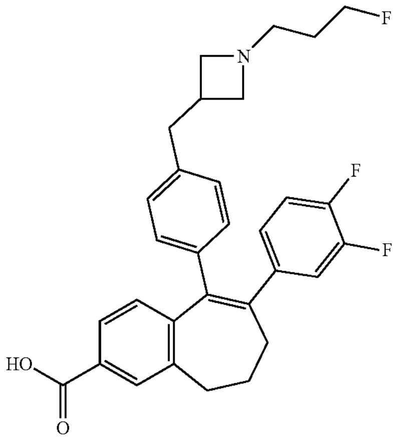 [SMILES: O=C(O)c1ccc2c(c1)CCCC(c1ccc(F)c(F)c1)=C2c1ccc(CC2CN(CCCF)C2)cc1] | 8-(3,4-difluorophenyl)-9-(4-((1-(3-fluoropropyl)azetidin-3-yl)methyl)phenyl)-6,7-dihydro-5H-benzo[7]annulene-3-carboxylic acid |
| 46 | 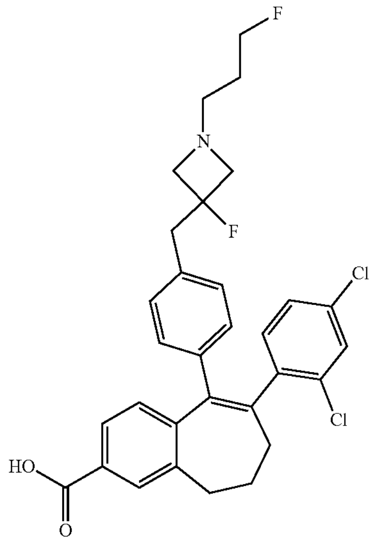 [SMILES: O=C(O)c1ccc2c(c1)CCCC(c1ccc(Cl)cc1Cl)=C2c1ccc(CC2(F)CN(CCCF)C2)cc1] | 8-(2,4-dichlorophenyl)-9-(4-((3-fluoro-1-(3-fluoropropyl)azetidin-3-yl)methyl)phenyl)-6,7-dihydro-5H-benzo[7]annulene-3-carboxylic acid |
| 47 | 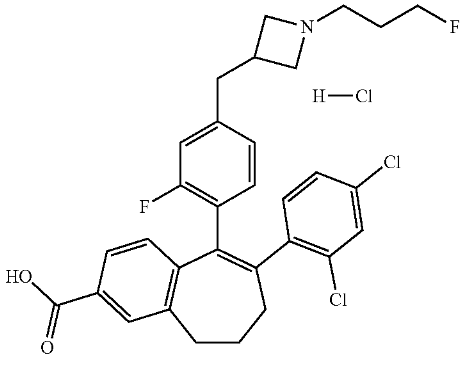 | 8-(2,4-dichlorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 48 | 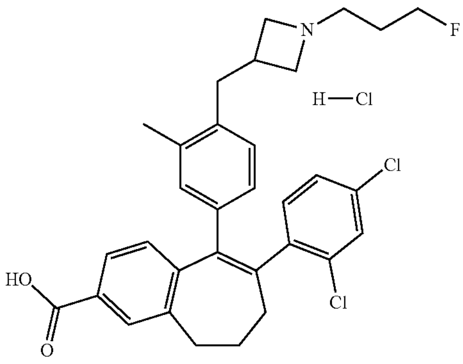 | 8-(2,4-dichlorophenyl)-9-(4-((1-(3-fluoropropyl)azetidin-3-yl)methyl)-3-methylphenyl)-6,7-dihydro-5H-benzo[7]annulene-3-carboxylic acid hydrochloride |
| 49 | 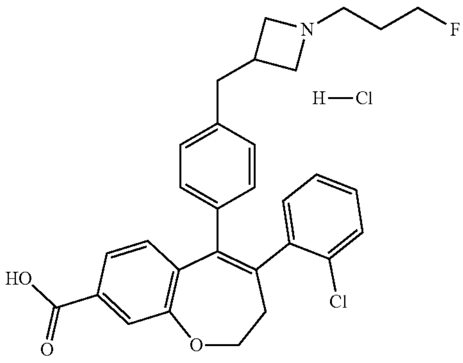 | 4-(2-chlorophenyl)-5-(4-((1-(3-fluoropropyl)azetidin-3-yl)methyl)phenyl)-2,3-dihydrobenzo[b]oxepine-8-carboxylic acid, hydrochloride |
| 50 | 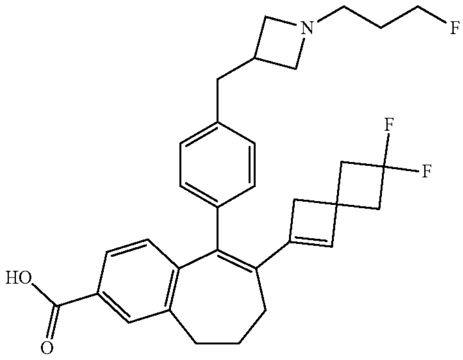 [SMILES: O=C(O)c1ccc2c(c1)CCCC(C1=CC3(C1)CC(F)(F)C3)=C2c1ccc(CC2CN(CCCF)C2)cc1] | 8-(6,6-difluorospiro[3.3]hept-1-en-2-yl)-9-(4-((1-(3-fluoropropyl)azetidin-3-yl)methyl)phenyl)-6,7-dihydro-5H-benzo[7]annulene-3-carboxylic acid |
| 51 | 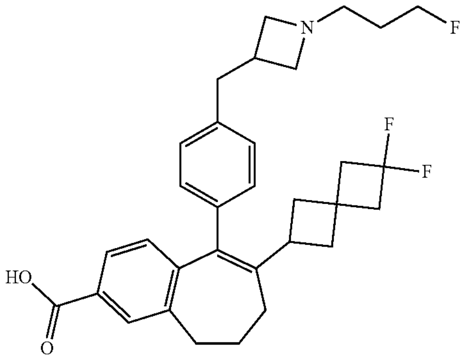 [SMILES: O=C(O)c1ccc2c(c1)CCCC(C1CC3(C1)CC(F)(F)C3)=C2c1ccc(CC2CN(CCCF)C2)cc1] | 8-(6,6-difluorospiro[3.3]heptan-2-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 52 | 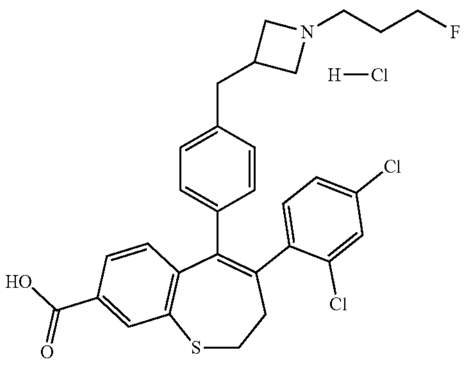 | 4-(2,4-dichlorophenyl)-5-(4-((1-(3-fluoropropyl)azetidin-3-yl)methyl)phenyl)-2,3-dihydrobenzo[b]thiepine-8-carboxylic acid hydrochloride |
| 53 | 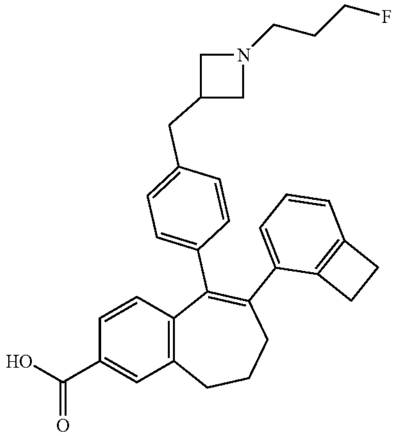 [SMILES: O=C(O)c1ccc2c(c1)CCCC(c1cccc3c1CC3)=C2c1ccc(CC2CN(CCCF)C2)cc1] | 8-(bicyclo[4.2.0]octa-1(6),2,4-trien-2-yl)-9-(4-((1-(3-fluoropropyl)azetidin-3-yl)methyl)phenyl)-6,7-dihydro-5H-benzo[7]annulene-3-carboxylic acid |
| 54 | 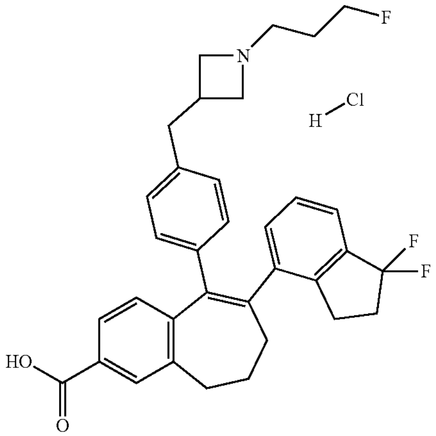 [SMILES: O=C(O)c1ccc2c(c1)CCCC(c1cccc3c1CCC3(F)F)=C2c1ccc(CC2CN(CCCF)C2)cc1 ; Cl] | 8-(1,1-difluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 55 | 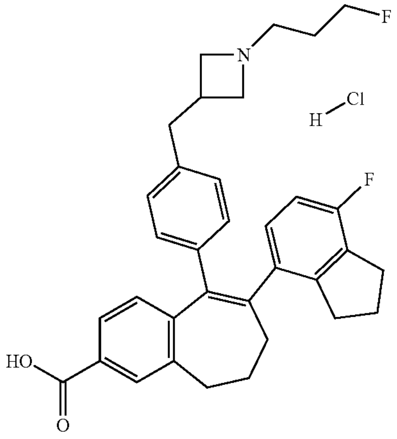 [SMILES: O=C(O)c1ccc2c(c1)CCCC(c1ccc(F)c3c1CCC3)=C2c1ccc(CC2CN(CCCF)C2)cc1 ; Cl] | 8-(7-fluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride |
| 56 | 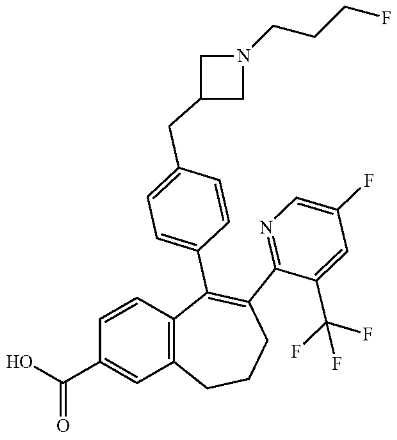 [SMILES: O=C(O)c1ccc2c(c1)CCCC(c1ncc(F)cc1C(F)(F)F)=C2c1ccc(CC2CN(CCCF)C2)cc1] | 8-(5-fluoro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid |
| 57 | 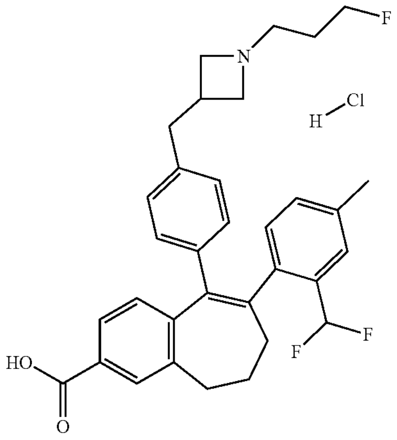 [SMILES: Cc1ccc(C2=C(c3ccc(CC4CN(CCCF)C4)cc3)c3ccc(C(=O)O)cc3CCC2)c(C(F)F)c1 ; Cl] | 8-(2-(difluoromethyl)-4-methylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 58 | 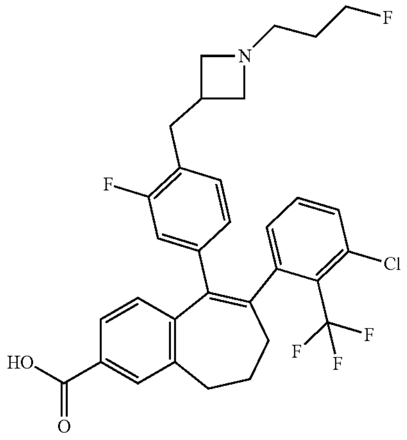 [SMILES: O=C(O)c1ccc2c(c1)CCCC(c1cccc(Cl)c1C(F)(F)F)=C2c1ccc(CC2CN(CCCF)C2)c(F)c1] | 8-(3-chloro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid |
| 59 | 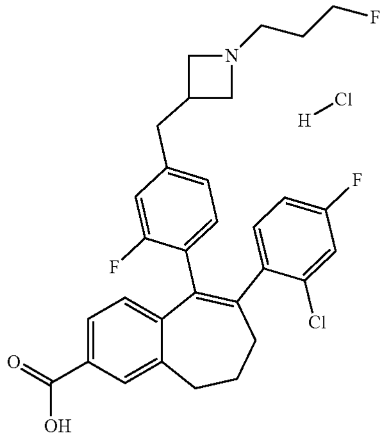 [SMILES: O=C(O)c1ccc2c(c1)CCCC(c1ccc(F)cc1Cl)=C2c1ccc(CC2CN(CCCF)C2)cc1F ; Cl] | 8-(2-chloro-4-fluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride |
| 60 | 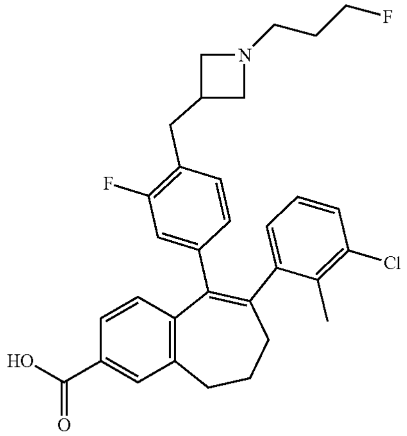 [SMILES: Cc1c(Cl)cccc1C1=C(c2ccc(CC3CN(CCCF)C3)c(F)c2)c2ccc(C(=O)O)cc2CCC1] | 8-(3-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 61 | 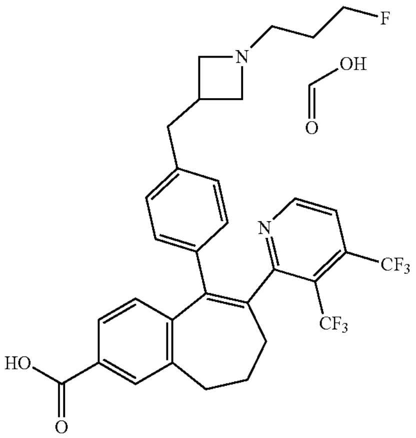 | 8-(3,4-bis(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid |
| 62 | 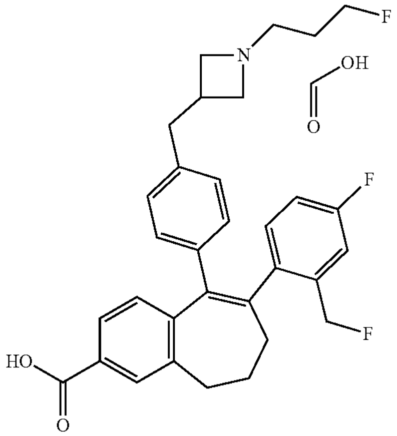 | 8-(4-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid, formic acid |
| 63 | 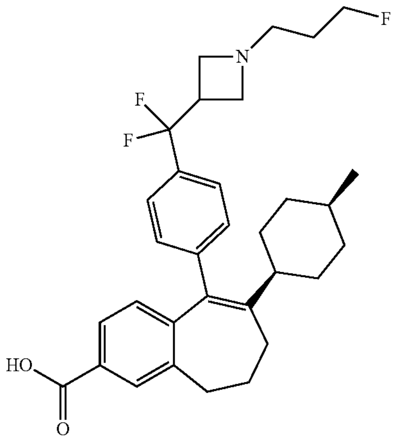 [SMILES: C[C@H]1CC[C@@H](C2=C(c3ccc(C(F)(F)C4CN(CCCF)C4)cc3)c3ccc(C(=O)O)cc3CCC2)CC1] | 9-(4-(difluoro(1-(3-fluoropropyl)azetidin-3-yl)methyl)phenyl)-8-(cis-4-methylcyclohexyl)-6,7-dihydro-5H-benzo[7]annulene-3-carboxylic acid |

TABLE 1a-continued

| Example or compound | Structure | Name |
|---|---|---|
| 64 | 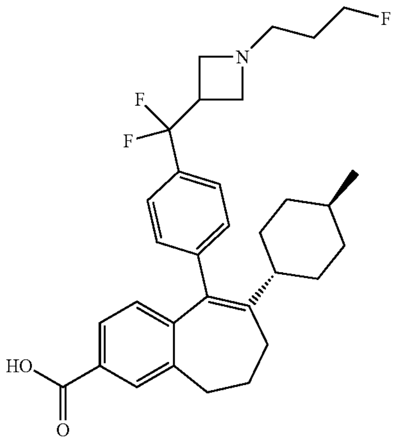 [SMILES: C[C@H]1CC[C@H](C2=C(c3ccc(C(F)(F)C4CN(CCCF)C4)cc3)c3ccc(C(=O)O)cc3CCC2)CC1] | 9-(4-(difluoro(1-(3-fluoropropyl)azetidin-3-yl)methyl)phenyl)-8-(trans-4-methylcyclohexyl)-6,7-dihydro-5H-benzo[7]annulene-3-carboxylic acid |
| 65 | 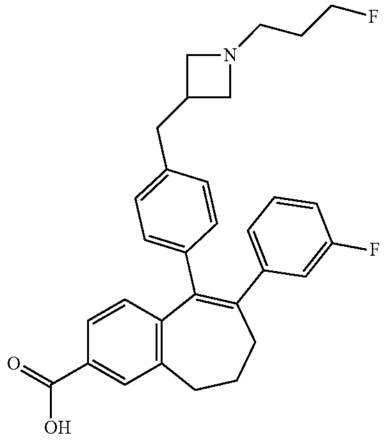 [SMILES: O=C(O)c1ccc2c(c1)CCCC(c1cccc(F)c1)=C2c1ccc(CC2CN(CCCF)C2)cc1] | 8-(3-fluorophenyl)-9-(4-((1-(3-fluoropropyl)azetidin-3-yl)methyl)phenyl)-6,7-dihydro-5H-benzo[7]annulene-3-carboxylic acid |
| 66 | 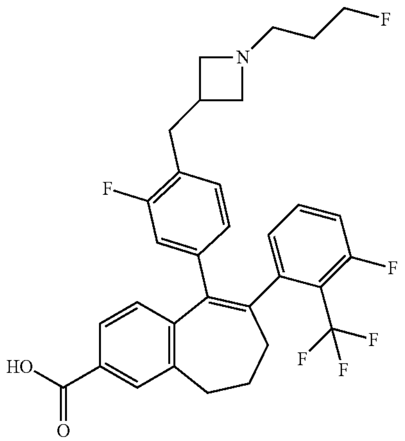 [SMILES: O=C(O)c1ccc2c(c1)CCCC(c1cccc(F)c1C(F)(F)F)=C2c1ccc(CC2CN(CCCF)C2)c(F)c1] | 8-(3-fluoro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 67 | 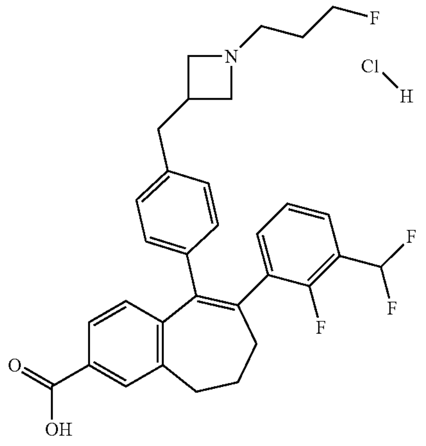 | 8-(3-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 68 | 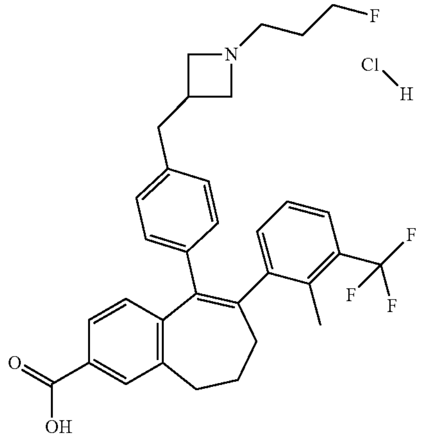 | 9-(4-((1-(3-fluoropropyl)azetidin-3-yl)methyl)phenyl)-8-(2-methyl-3-(trifluoromethyl)phenyl)-6,7-dihydro-5H-benzo[7]annulene-3-carboxylic acid hydrochloride |
| 69 | 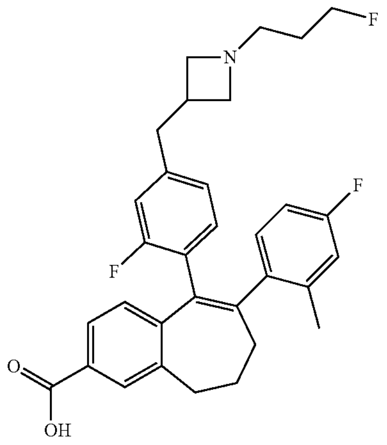 [SMILES: Cc1cc(F)ccc1C1=C(c2ccc(CC3CN(CCCF)C3)cc2F)c2ccc(C(=O)O)cc2CCC1] | 8-(4-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 70 | 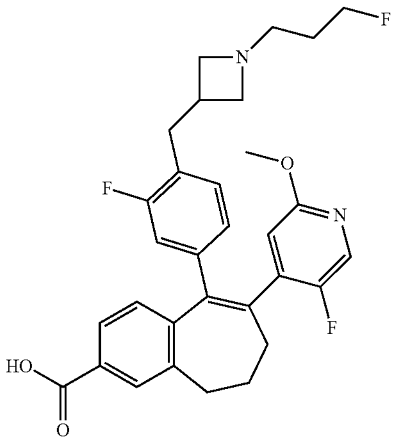 [SMILES: COc1cc(C2=C(c3ccc(CC4CN(CCCF)C4)c(F)c3)c3ccc(C(=O)O)cc3CCC2)c(F)cn1] | 8-(5-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid |
| 71 | 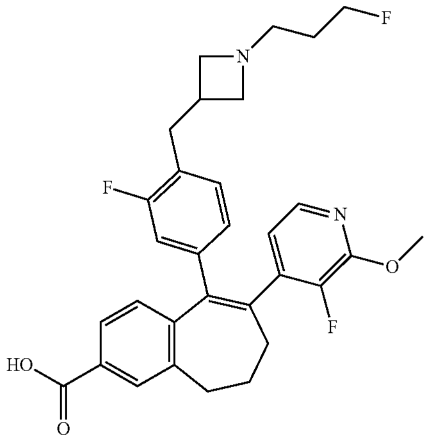 [SMILES: COc1nccc(C2=C(c3ccc(CC4CN(CCCF)C4)c(F)c3)c3ccc(C(=O)O)cc3CCC2)c1F] | 8-(3-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid |
| 72 | 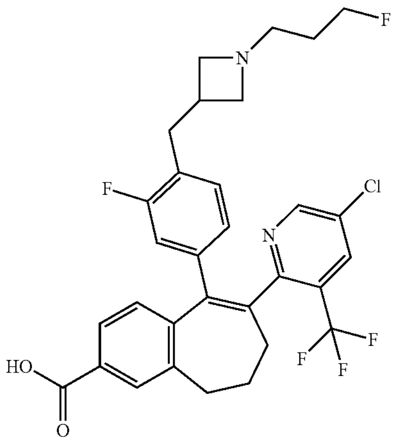 [SMILES: O=C(O)c1ccc2c(c1)CCCC(c1ncc(Cl)cc1C(F)(F)F)=C2c1ccc(CC2CN(CCCF)C2)c(F)c1] | 8-(5-chloro-3-(trifluoromethyl)pyridin-2-yl)-9-(3-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 73 | 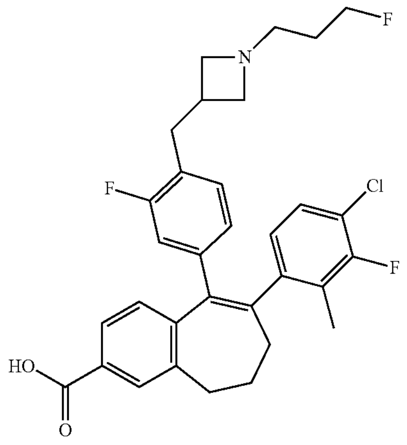 [SMILES: Cc1c(C2=C(c3ccc(CC4CN(CCCF)C4)c(F)c3)c3ccc(C(=O)O)cc3CCC2)ccc(Cl)c1F] | 8-(4-chloro-3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid |
| 74 | 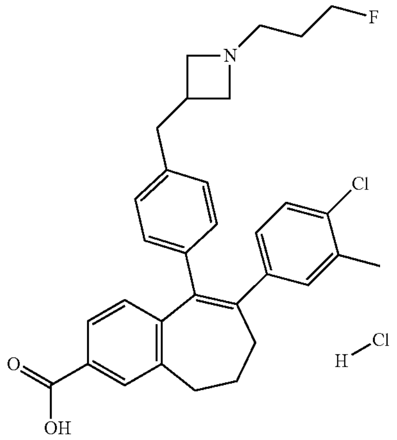 [SMILES: Cc1cc(C2=C(c3ccc(CC4CN(CCCF)C4)cc3)c3ccc(C(=O)O)cc3CCC2)ccc1Cl ; Cl] | 8-(4-chloro-3-methylphenyl)-9-(4-((1-(3-fluoropropyl)azetidin-3-yl)methyl)phenyl)-6,7-dihydro-5H-benzo[7]annulene-3-carboxylic acid hydrochloride |
| 75 | 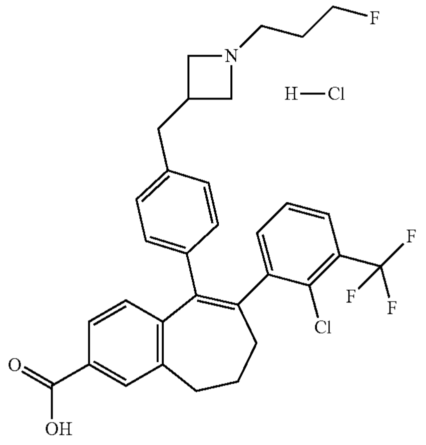 | 8-(2-chloro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 76 | 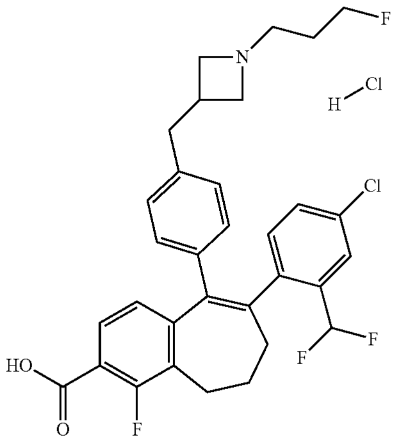 [SMILES: O=C(O)c1ccc2c(c1F)CCCC(c1ccc(Cl)cc1C(F)F)=C2c1ccc(CC2CN(CCCF)C2)cc1 ; Cl] | 8-(4-chloro-2-(difluoromethyl)phenyl)-4-fluoro-9-(4-((1-(3-fluoropropyl)azetidin-3-yl)methyl)phenyl)-6,7-dihydro-5H-benzo[7]annulene-3-carboxylic acid hydrochloride |
| 77 | 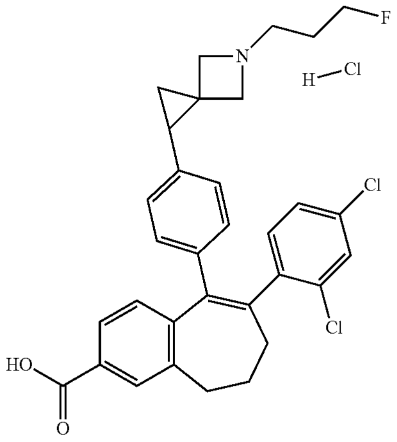 Isomer 1 | 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid, hydrochloride isomer 1 |
| 78 | 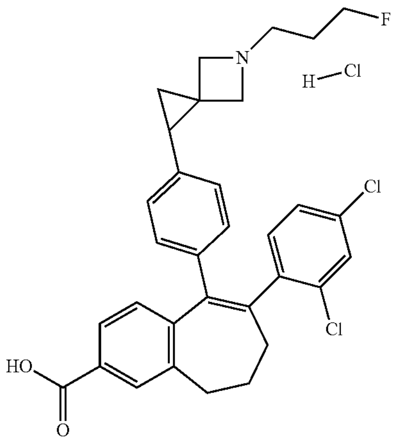 Isomer 2 | 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid, hydrochloride isomer 2 |

TABLE 1a-continued

| Example or compound | Structure | Name |
|---|---|---|
| 79 | 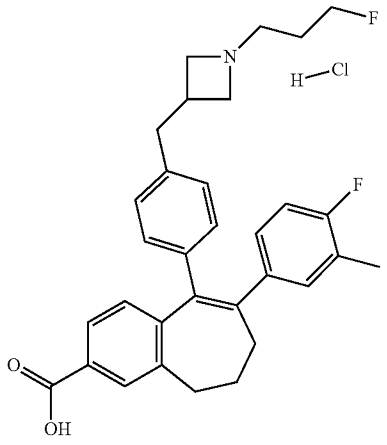 | 8-(4-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride |
| 80 | 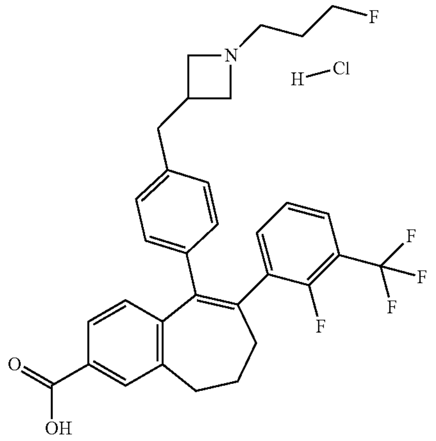 | 8-(2-fluoro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |
| 81 | 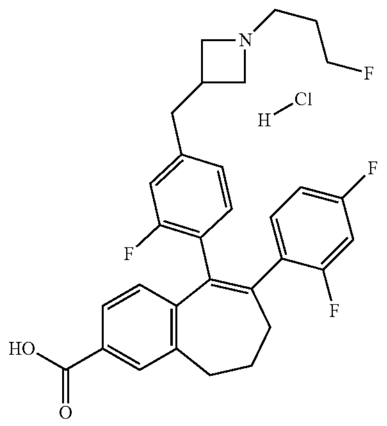 | 8-(2,4-difluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 82 | 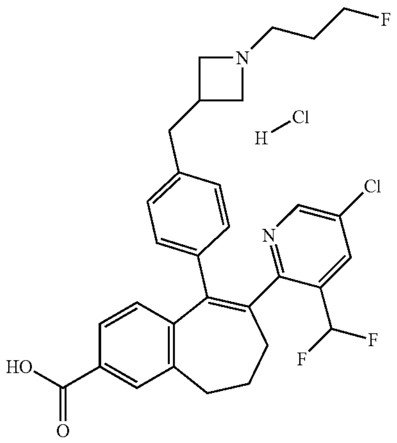 | 8-(5-chloro-3-(difluoromethyl)pyridin-2-yl)-9-(4-((1-(3-fluoropropyl)azetidin-3-yl)methyl)phenyl)-6,7-dihydro-5H-benzo[7]annulene-3-carboxylic acid hydrochloride |
| 83 | 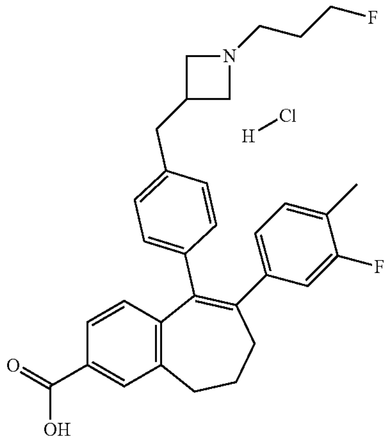 | 8-(3-fluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride |
| 84 | 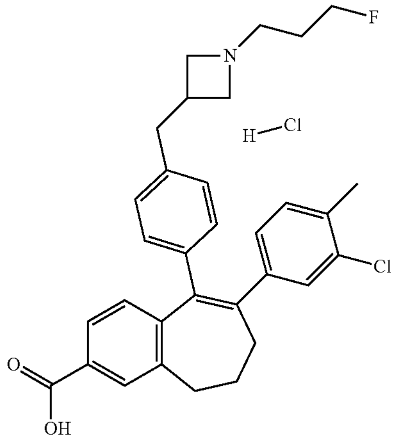 | 8-(3-chloro-4-methylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 85 | 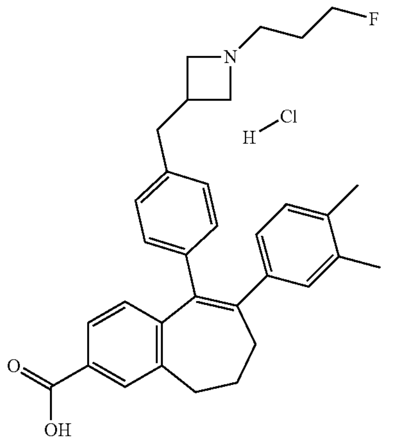 | 8-(3,4-dimethylphenyl)-9-(4-((1-(3-fluoropropyl)azetidin-3-yl)methyl)phenyl)-6,7-dihydro-5H-benzo[7]annulene-3-carboxylic acid hydrochloride |
| 86 | 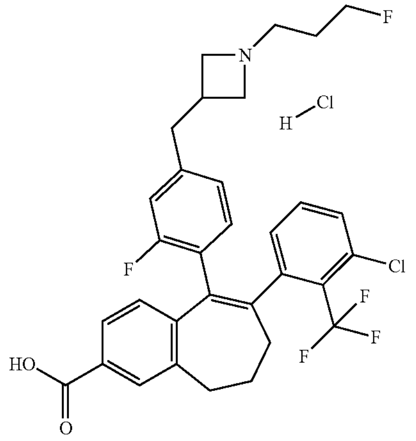 | 8-(3-chloro-2-(trifluoromethyl)phenyl)-9-(2-fluoro-4-((1-(3-fluoropropyl)azetidin-3-yl)methyl)phenyl)-6,7-dihydro-5H-benzo[7]annulene-3-carboxylic acid hydrochloride |
| 87 | 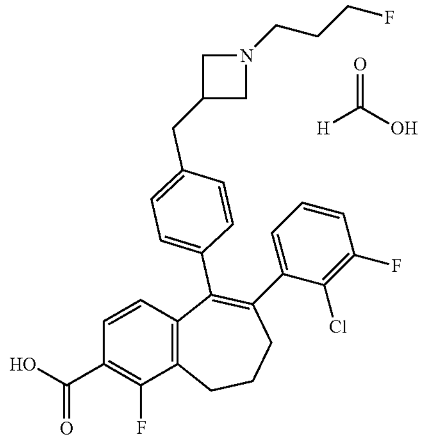 | 8-(2-chloro-3-fluorophenyl)-4-fluoro-9-(4-((1-(3-fluoropropyl)azetidin-3-yl)methyl)phenyl)-6,7-dihydro-5H-benzo[7]annulene-3-carboxylic acid, formic acid |

TABLE 1a-continued

| Example or compound | Structure | Name |
|---|---|---|
| 88 | 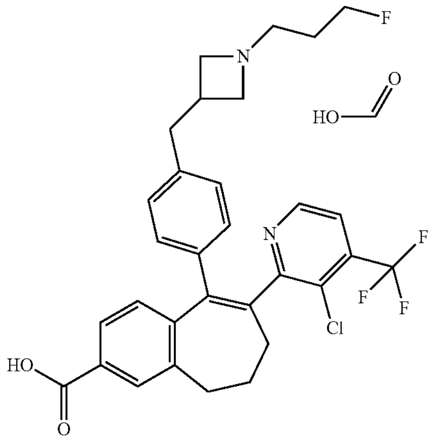 [SMILES: O=C(O)c1ccc2c(c1)CCCC(c1nccc(C(F)(F)F)c1Cl)=C2c1ccc(CC2CN(CCCF)C2)cc1 ; O=CO] | 8-(3-chloro-4-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid |
| 89 | 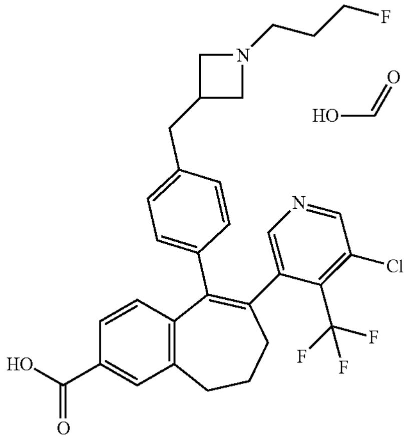 [SMILES: O=C(O)c1ccc2c(c1)CCCC(c1cncc(Cl)c1C(F)(F)F)=C2c1ccc(CC2CN(CCCF)C2)cc1 ; O=CO] | 8-(5-chloro-4-(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid, formic acid |
| 90 | 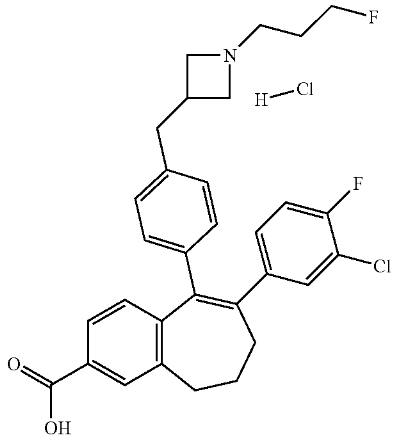 | 8-(3-chloro-4-fluorophenyl)-9-(4-((1-(3-fluoropropyl)azetidin-3-yl)methyl)phenyl)-6,7-dihydro-5H-benzo[7]annulene--3-carboxylic acid hydrochloride |

TABLE 1a-continued

| Example or compound | Structure | Name |
|---|---|---|
| 91 | 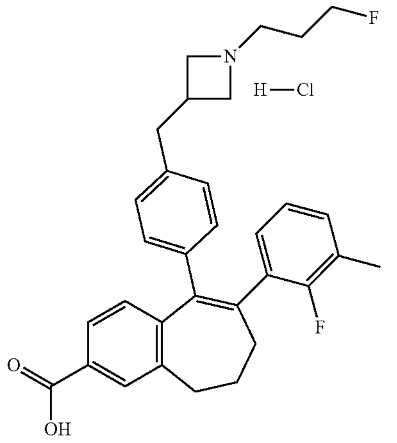 | 8-(2-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride |
| 92 | 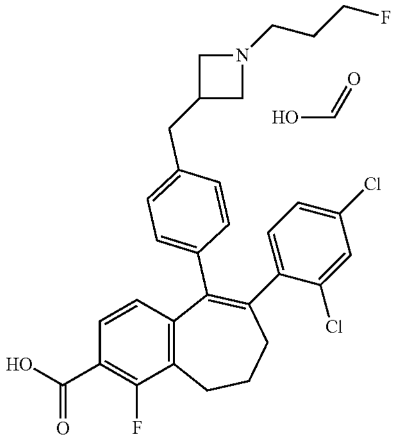 | 8-(2,4-dichlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid |
| 93 | 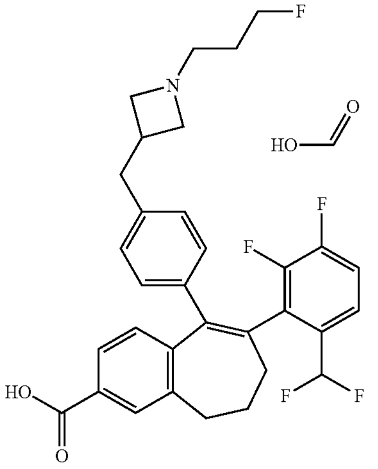 [SMILES: O=C(O)c1ccc2c(c1)CCCC(c1c(C(F)F)ccc(F)c1F)=C2c1ccc(CC2CN(CCCF)C2)cc1 ; O=CO] | 8-(6-(difluoromethyl)-2,3-difluorophenyl)-9-(4-((1-(3-fluoropropyl)azetidin-3-yl)methyl)phenyl)-6,7-dihydro-5H-benzo[7]annulene-3-carboxylic, acid formic acid |

TABLE 1a-continued

| Example or compound | Structure | Name |
|---|---|---|
| 94 | 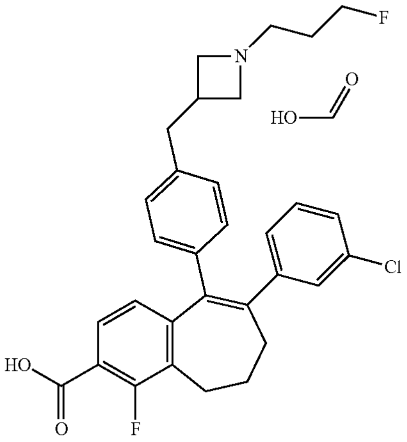 | 8-(3-chlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid |
| 95 | 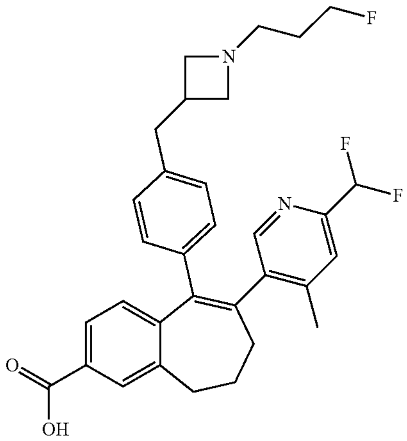 [SMILES: Cc1cc(C(F)F)ncc1C1=C(c2ccc(CC3CN(CCCF)C3)cc2)c2ccc(C(=O)O)cc2CCC1] | 8-(6-(difluoromethyl)-4-methylpyridin-3-yl)-9-(4-((1-(3-fluoropropyl)azetidin-3-yl)methyl)phenyl)-6,7-dihydro-5H-benzo[7]annulene-3-carboxylic acid |
| 96 | 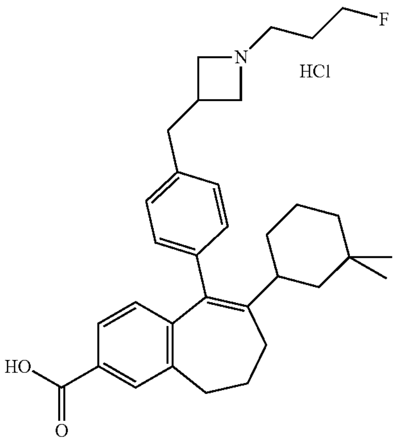 Isomer 1 | 8-(3,3-dimethylcyclohexyl)-9-(4-((1-(3-fluoropropyl)azetidin-3-yl)methyl)phenyl)-6,7-dihydro-5H-benzo[7]annulene-3-carboyxlic acid hydrochloride Isomer 1 |

TABLE 1a-continued

| Example or compound | Structure | Name |
|---|---|---|
| 97 | 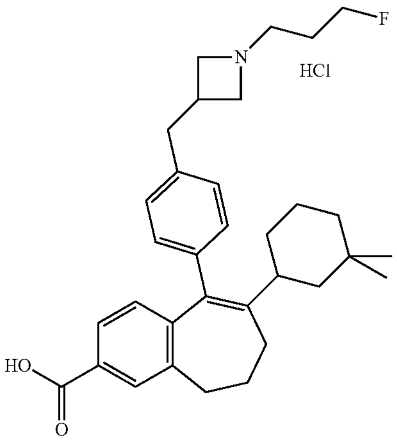 Isomer 2 | 8-(3,3-dimethylcyclohexyl)-9-(4-((1-(3-fluoropropyl)azetidin-3-yl)methyl)phenyl)-6,7-dihydro-5H-benzo[7]annulene-3-carboxylic acid hydrochloride Isomer 2 |
| 98 | 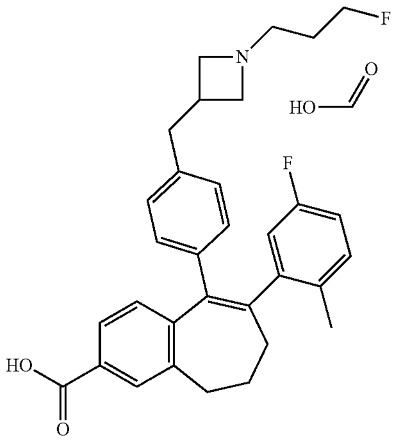 | 8-(5-fluoro-2-methylphenyl)-9-(4-((1-(3-fluoropropyl)azetidin-3-yl)methyl)phenyl)-6,7-dihydro-5H-benzo[7]annulene-3-carboxylic acid, formic acid |
| 99 | 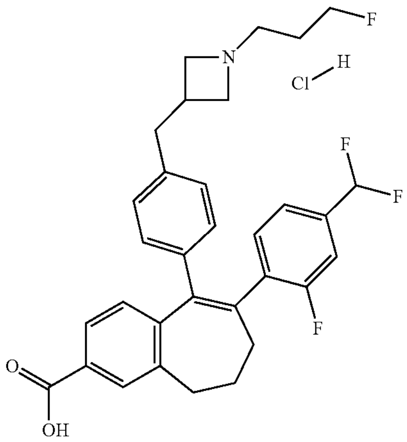 | 8-(4-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 100 | 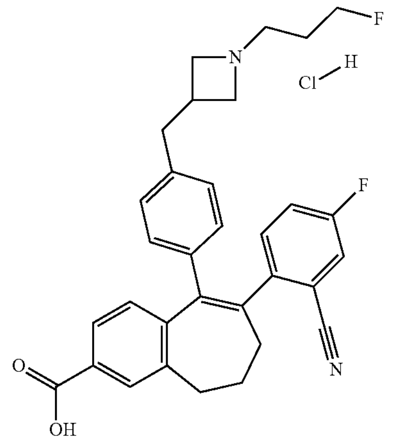 | 8-(2-cyano-4-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 101 | 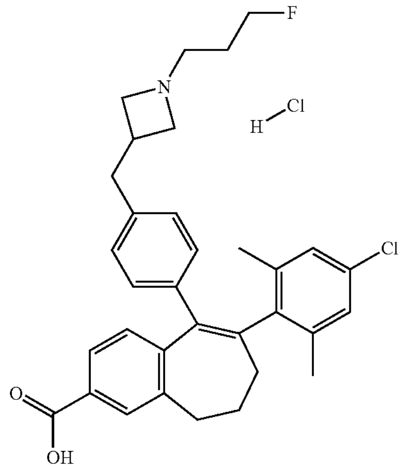 [SMILES: Cc1cc(Cl)cc(C)c1C1=C(c2ccc(CC3CN(CCCF)C3)cc2)c2ccc(C(=O)O)cc2CCC1 ; Cl] | 8-(4-chloro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride |
| 102 | 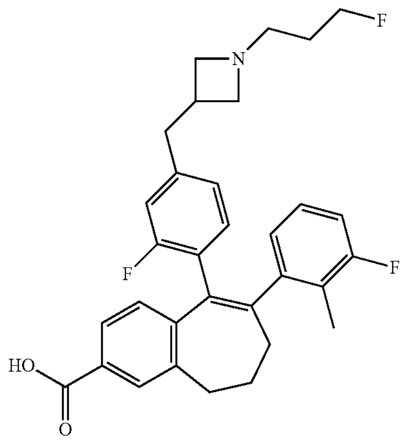 [SMILES: Cc1c(F)cccc1C1=C(c2ccc(CC3CN(CCCF)C3)cc2F)c2ccc(C(=O)O)cc2CCC1] | 8-(3-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 103 | 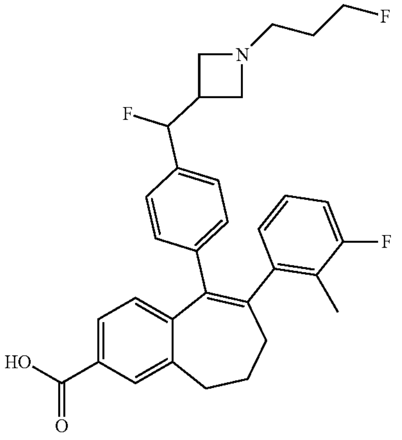 Isomer 1 | ® 9-(4-(fluoro(1-(3-fluoropropyl)azetidin-3-yl)methyl)phenyl)-8-(3-fluoro-2-methylphenyl)-6,7-dihydro-5H-benzo[7]annulene-3-carboxylic acid Isomer 1 |
| 104 | 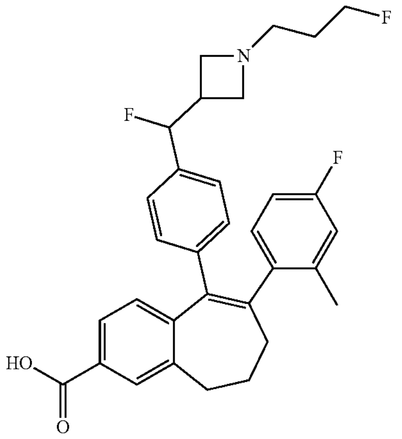 Isomer 2 | 9-(4-(fluoro(1-(3-fluoropropyl)azetidin-3-yl)methyl)phenyl)-8-(4-fluoro-2-methylphenyl)-6,7-dihydro-5H-benzo[7]annulene-3-carboxylic acid Isomer 2 |
| 105 | 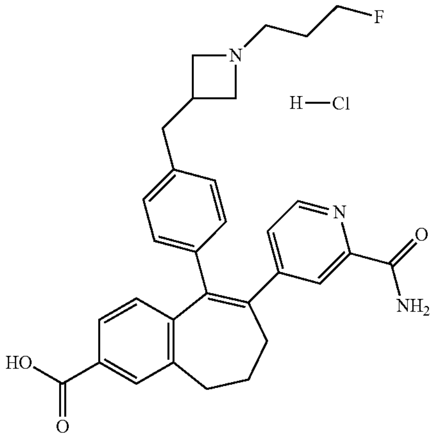 [SMILES: NC(=O)c1cc(C2=C(c3ccc(CC4CN(CCCF)C4)cc3)c3ccc(C(=O)O)cc3CCC2)ccn1 ; Cl] | 8-(2-carbamoylpyridin-4-yl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 106 | 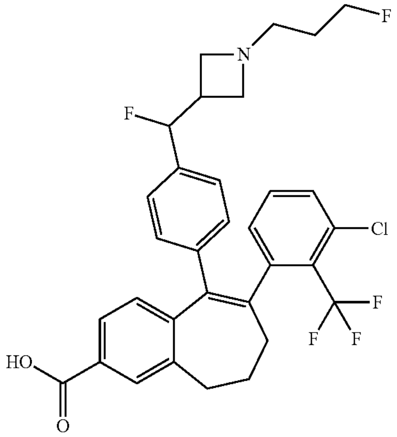 Isomer 2 | 8-(3-chloro-2-(trifluoromethyl)phenyl)-9-(4-(fluoro(1-(3-fluoropropyl)azetidin-3-yl)methyl)phenyl)-6,7-dihydro-5H-benzo[7]annulene-3-carboxylic acid Isomer 2 |
| 107 | 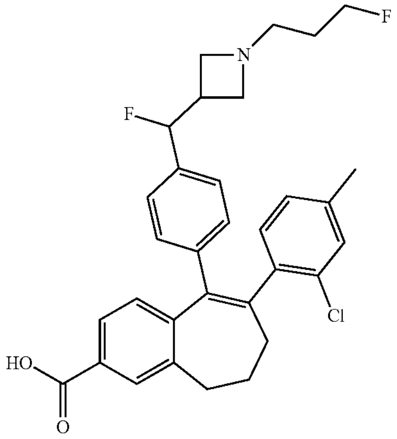 Isomer 2 | 8-(2-chloro-4-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 |
| 108 | 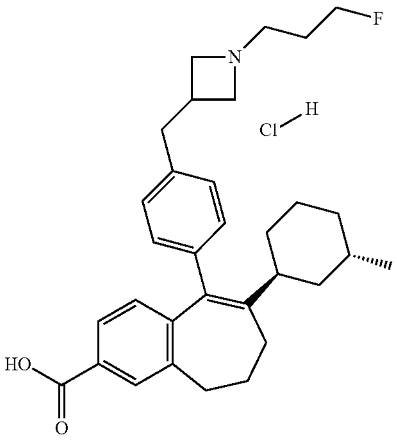 | 9-(4-((1-(3-fluoropropyl)azetidin-3-yl)methyl)phenyl)-8-(trans-3-methylcyclohexyl)-6,7-dihydro-5H-benzo[7]annulene-3-carboxylic acid hydrochloride |

TABLE 1a-continued

| Example or compound | Structure | Name |
|---|---|---|
| 109 | 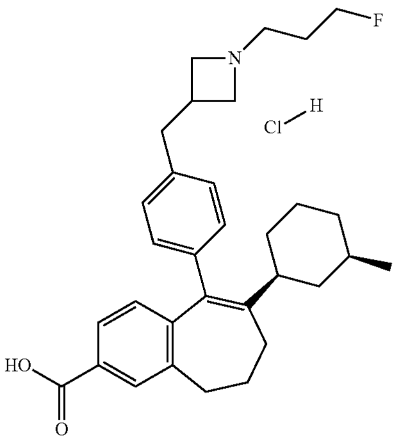 | 9-(4-((1-(3-fluoropropyl)azetidin-3-yl)methyl)phenyl)-8-(cis-3-methylcyclohexyl)-6,7-dihydro-5H-benzo[7]annulene-3-carboxylic acid hydrochloride |
| 110 | 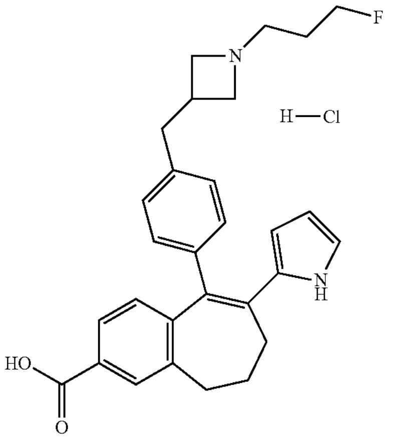 | 9-(4-((1-(3-fluoropropyl)azetidin-3-yl)methyl)phenyl)-8-(1H-pyrrol-2-yl)-6,7-dihydro-5H-benzo[7]annulene-3-carboxylic, hydrochloride acid |
| 111 | 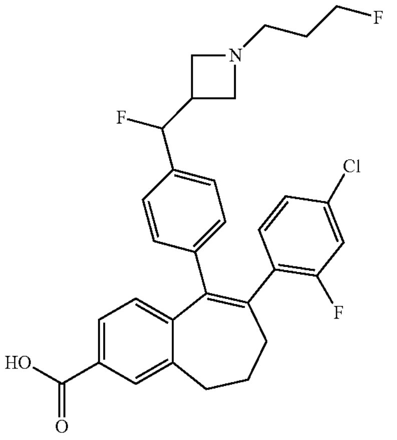 Isomer 2 | 8-(4-chloro-2-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 2 |

TABLE 1a-continued

| Example or compound | Structure | Name |
|---|---|---|
| 112 | 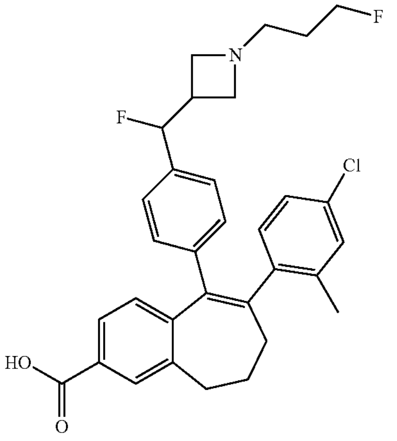 Isomer 2 | 8-(4-chloro-2-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 |
| 113 | 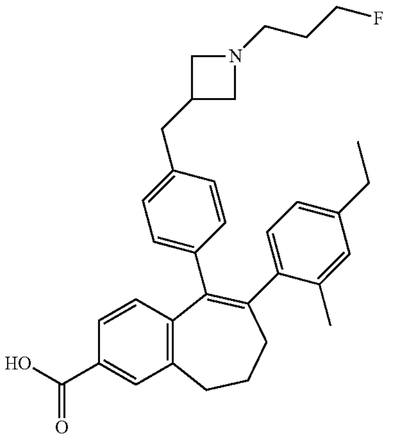 [SMILES: CCc1ccc(C2=C(c3ccc(CC4CN(CCCF)C4)cc3)c3ccc(C(=O)O)cc3CCC2)c(C)c1] | 8-(4-ethyl-2-methylphenyl)-9-(4-((1-(3-fluoropropyl)azetidin-3-yl)methyl)phenyl)-6,7-dihydro-5H-benzo[7]annulene-3-carboxylic acid |
| 114 | 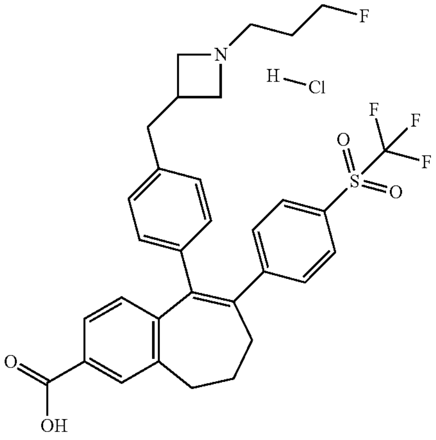 | 9-(4-((1-(3-fluoropropyl)azetidin-3-yl)methyl)phenyl)-8-(4-((trifluoromethyl)sulfonyl)phenyl)-6,7-dihydro-5H-benzo[7]annulene-3-carboxylic acid hydrochloride |

TABLE 1a-continued

| Example or compound | Structure | Name |
|---|---|---|
| 115 | 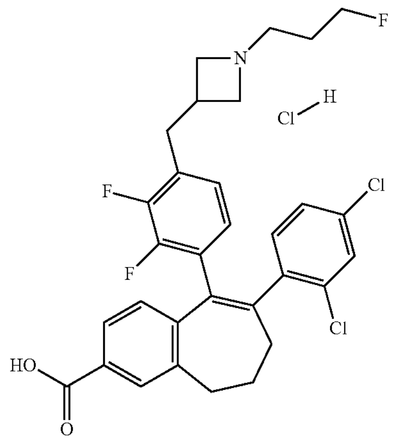 | 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylic acid hydrochloride |
| 116 | 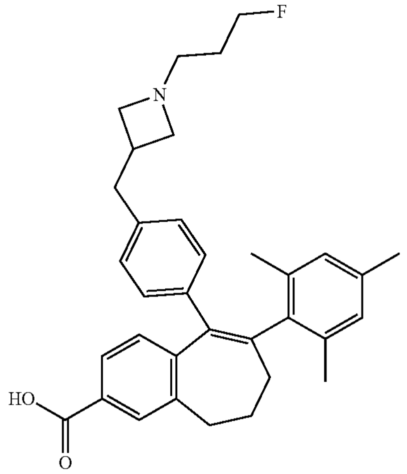 [SMILES: Cc1cc(C)c(C2=C(c3ccc(CC4CN(CCCF)C4)cc3)c3ccc(C(=O)O)cc3CCC2)c(C)c1] | 9-(4-((1-(3-fluoropropyl)azetidin-3-yl)methyl)phenyl)-8-mesityl-6,7-dihydro-5H-benzo[7]annulene-3-carboxylic acid |
| 117 | 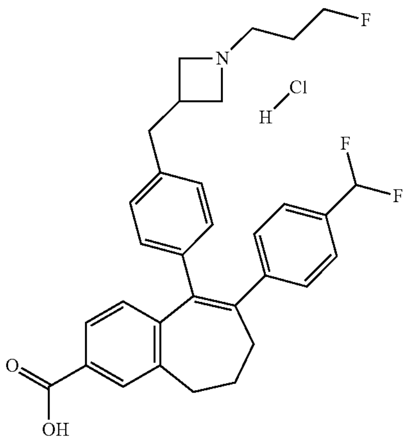 | 8-(4-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 118 | 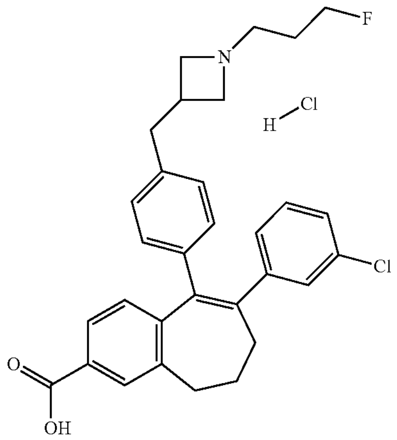 | 8-(3-chlorophenyl)-9-(4-((1-(3-fluoropropyl)azetidin-3-yl)methyl)phenyl)-6,7-dihydro-5H-benzo[7]annulene-3-carboxylic acid hydrochloride |
| 119 | 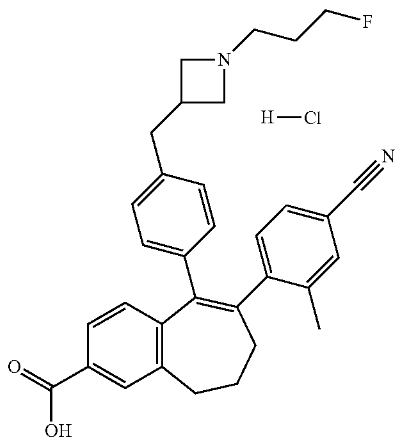 | 8-(4-cyano-2-methylphenyl)-9-(4-((1-(3-fluoropropyl)azetidin-3-yl)methyl)phenyl)-6,7-dihydro-5H-benzo[7]annulene-3-carboxylic acid hydrochloride |
| 120 | 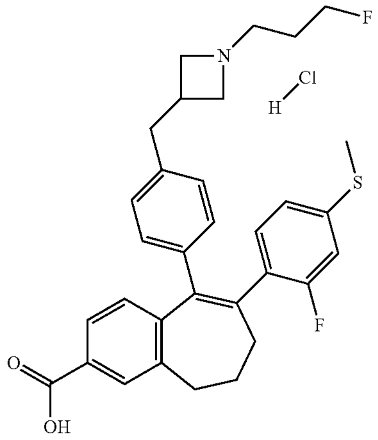 | 8-(2-fluoro-4-(methylthio)phenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 121 | 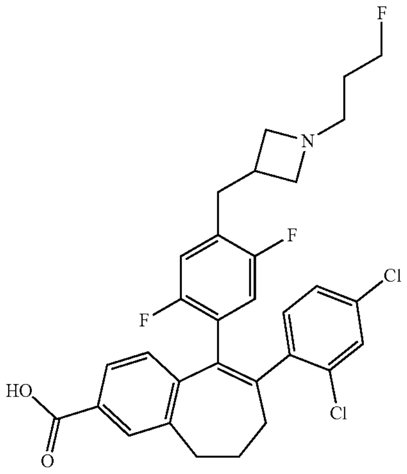 [SMILES: O=C(O)c1ccc2c(c1)CCCC(c1ccc(Cl)cc1Cl)=C2c1cc(F)c(CC2CN(CCCF)C2)cc1F] | 8-(2,4-dichlorophenyl)-9-(2,5-difluoro-4-((1-(3-fluoropropyl)azetidin-3-yl)methyl)phenyl)-6,7-dihydro-5H-benzo[7]annulene-3-carboxylic acid |
| 122 | 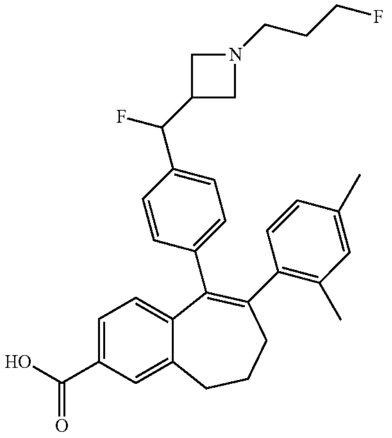 Isomer 2 | 8-(2,4-dimethylphenyl)-9-(4-(fluoro(1-(3-fluoropropyl)azetidin-3-yl)methyl)phenyl)-6,7-dihydro-5H-benzo[7]annulene-3-carboxylic acid Isomer 2 |
| 123 | 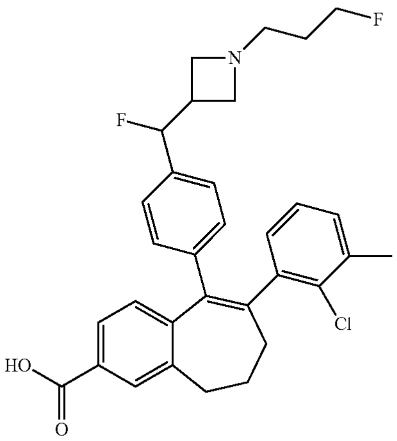 Isomer 2 | 8-(2-chloro-3-methylphenyl)-9-(4-(fluoro(1-(3-fluoropropyl)azetidin-3-yl)methyl)phenyl)-6,7-dihydro-5H-benzo[7]annulene-3-carboxylic acid Isomer 2 |

TABLE 1a-continued

| Example or compound | Structure | Name |
|---|---|---|
| 124 | 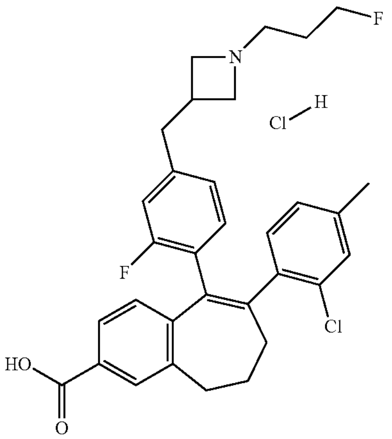 | 8-(2-chloro-4-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride |
| 125 | 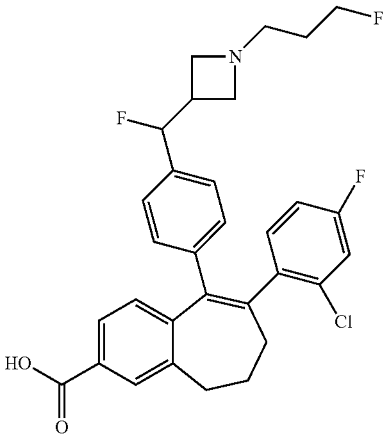 Isomer 2 | 8-(2-chloro-4-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 2 |
| 126 | 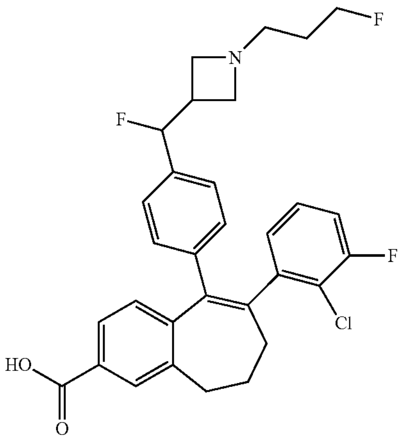 Isomer 2 | 8-(2-chloro-3-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 2 |

TABLE 1a-continued

| Example or compound | Structure | Name |
|---|---|---|
| 127 | 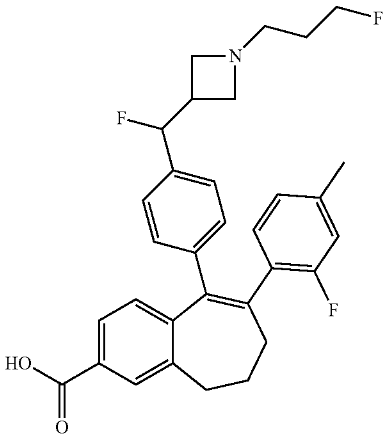 Isomer 2 | 9-(4-(fluoro(1-(3-fluoropropyl)azetidin-3-yl)methyl)phenyl)-8-(2-fluoro-4-methylphenyl)-6,7-dihydro-5H-benzo[7]annulene-3-carboxylic acid Isomer 2 |
| 128 | 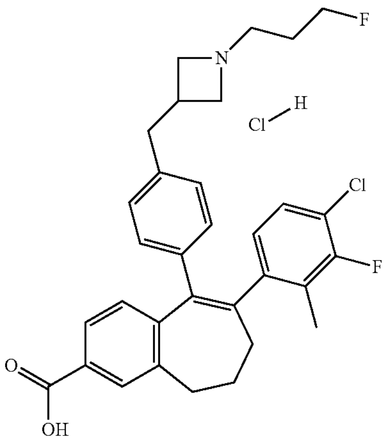 | 8-(4-chloro-3-fluoro-2-methylphenyl)-9-(4-((1-(3-fluoropropyl)azetidin-3-yl)methyl)phenyl)-6,7-dihydro-5H-benzo[7]annulene-3-carboxylic acid hydrochloride |
| 129 | 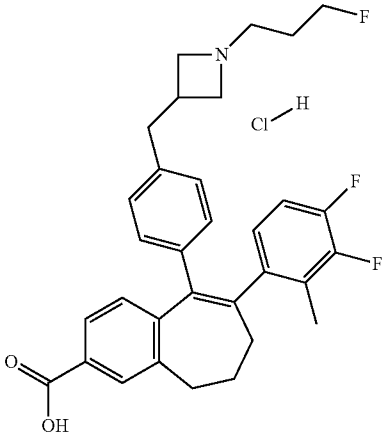 | 8-(3,4-difluoro-2-methylphenyl)-9-(4-((1-(3-fluoropropyl)azetidin-3-yl)methyl)phenyl)-6,7-dihydro-5H-benoz[7]annulene-3-carboxylic acid hydrochloride |

TABLE 1a-continued

| Example or compound | Structure | Name |
| --- | --- | --- |
| 130 | 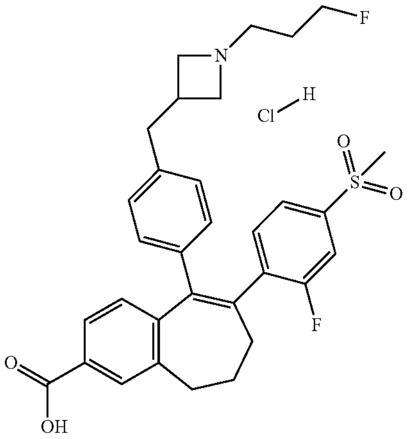 | 8-(2-fluoro-4-(methylsulfonyl)phenyl)-9-(4-((1-(3-fluoropropyl)azetidin-3-yl)methyl)phenyl)-6,7-dihydro-5H-benzo[7]annulene-3-carboxylic acid hydrochloride |
| 131 | 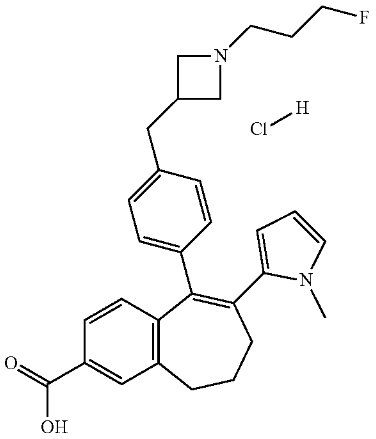 | 9-(4-((1-(3-fluoropropyl)azetidin-3-yl)methyl)phenyl)-8-(1-methyl-1H-pyrrol-2-yl)-6,7-dihydro-5H-benzo[7]annulene-3-carboxylic acid hydrochloride |
| 132 | 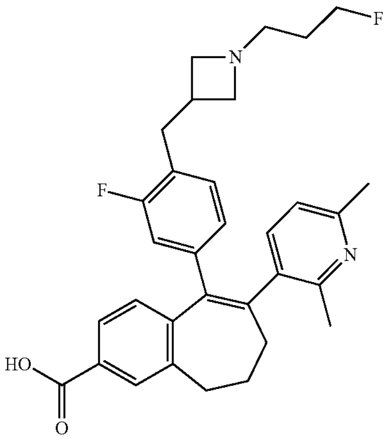 [SMILES: Cc1ccc(C2=C(c3ccc(CC4CN(CCCF)C4)c(F)c3)c3ccc(C(=O)O)cc3CCC2)c(C)n1] | 8-(2,6-dimethylpyridin-3-yl)-9-(3-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 133 | 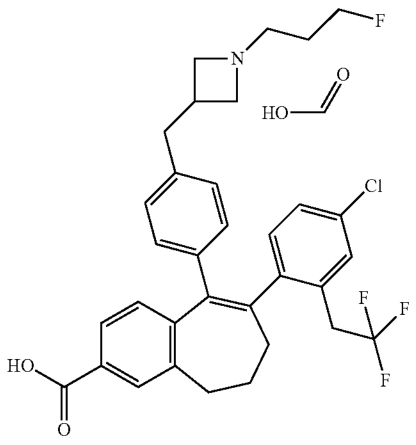 | 8-(4-chloro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, formic acid |
| 134 | 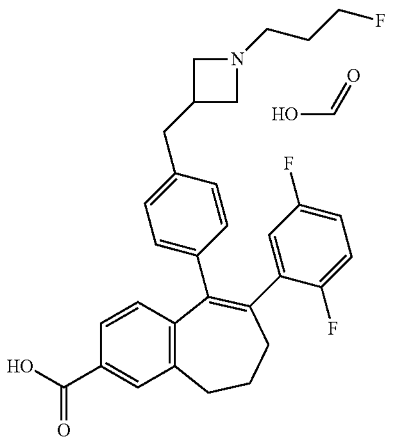 | 8-(2,5-difluorophenyl)-9-(4-((1-(3-fluoropropyl)azetidin-3-yl)methyl)phenyl)-6,7-dihydro-5H-benoz[7]annulene-3-carboxylic acid, formic acid |
| 135 | 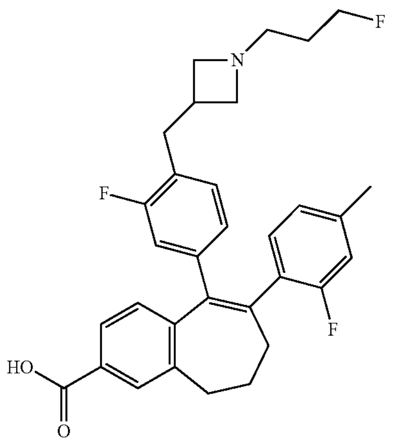 [SMILES: Cc1ccc(C2=C(c3ccc(CC4CN(CCCF)C4)c(F)c3)c3ccc(C(=O)O)cc3CCC2)c(F)c1] | 9-(3-fluoro-4-((1-(3-fluoropropyl)azetidin-3-yl)methyl)phenyl)-8-(2-fluoro-4-methylphenyl)-6,7-dihydro-5H-benzo[7]annulene-3-carboxylic acid |

TABLE 1a-continued

| Example or compound | Structure | Name |
| --- | --- | --- |
| 136 | 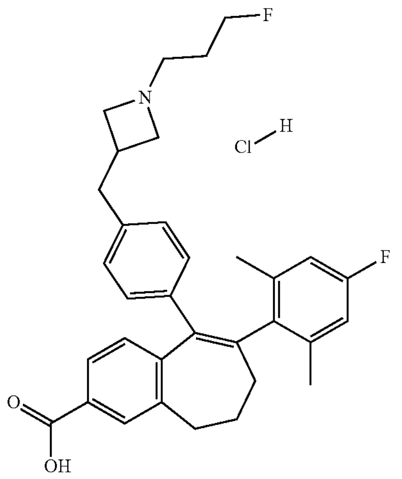 [SMILES: Cc1cc(F)cc(C)c1C1=C(c2ccc(CC3CN(CCCF)C3)cc2)c2ccc(C(=O)O)cc2CCC1 ; Cl] | 8-(4-fluoro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride |
| 137 | 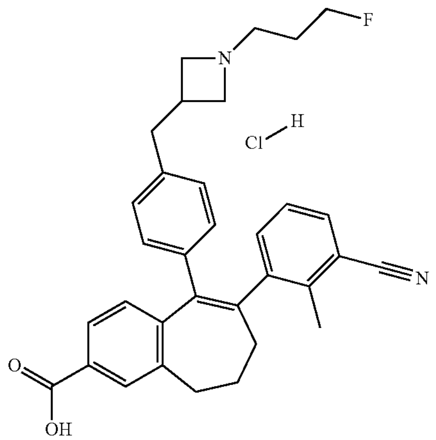 | 8-(3-cyano-2-methylphenyl)-9-(4-((1-(3-fluoropropyl)azetidin-3-yl)methyl)phenyl)-6,7-dihydro-5H-benzo[7]annulene-3-carboxylic acid hydrochloride |
| 138 | 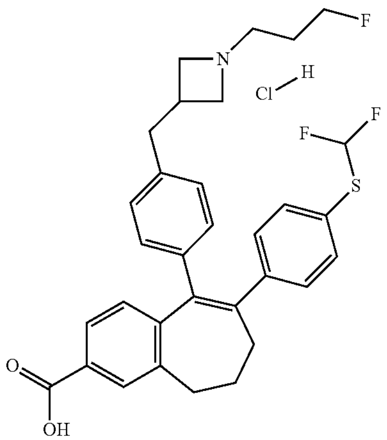 | 8-(4-((difluoromethylthio)phenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 139 | 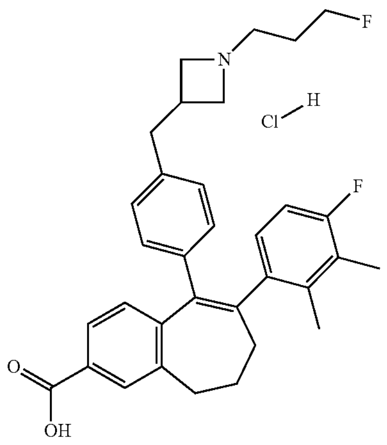 | 8-(4-fluoro-2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride |
| 140 | 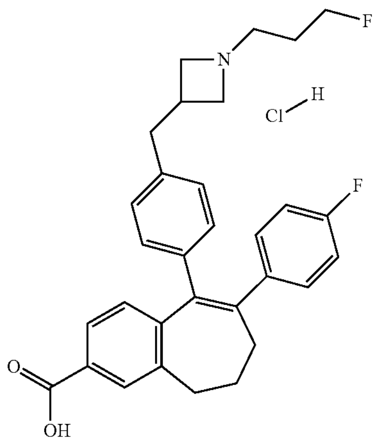 | 8-(4-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 141 | 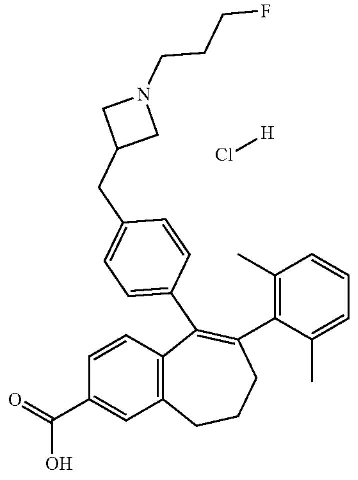 [SMILES: Cc1cccc(C)c1C1=C(c2ccc(CC3CN(CCCF)C3)cc2)c2ccc(C(=O)O)cc2CCC1 ; Cl] | 8-(2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 142 | 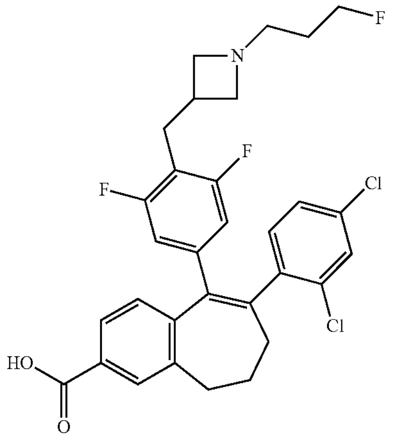 [SMILES: O=C(O)c1ccc2c(c1)CCCC(c1ccc(Cl)cc1Cl)=C2c1cc(F)c(CC2CN(CCCF)C2)c(F)c1] | 8-(2,4-dichlorophenyl)-9-(3,5-difluoro-4-((1-(3-fluoropropyl)azetidin-3-yl)methyl)phenyl)-6,7-dihydro-5H-benzo[7]annulene-3-carboxylic acid |
| 143 | 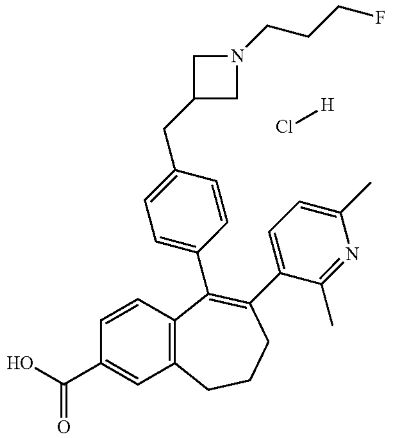 [SMILES: Cc1ccc(C2=C(c3ccc(CC4CN(CCCF)C4)cc3)c3ccc(C(=O)O)cc3CCC2)c(C)n1 ; Cl] | 8-(2,6-dimethylpyridin-3-yl)-9-(4-((1-(3-fluoropropyl)azetidin-3-yl)methyl)phenyl)-6,7-dihydro-5H-benzo[7]annulene-3-carboxylic acid hydrochloride |
| 144 | 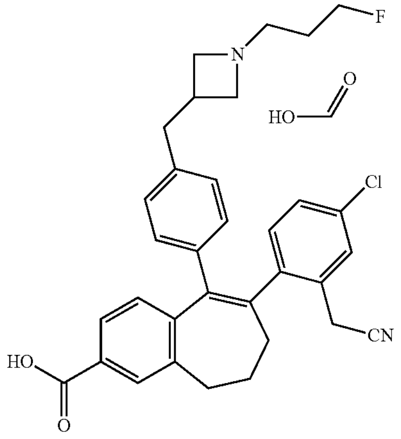 | 8-(4-chloro-2-(cyanomethyl)phenyl)-9-(4-((1-(3-fluoropropyl)azetidin-3-yl)methyl)phenyl)-6,7-dihydro-5H-benzo[7]annulene-3-carboxylic acid, formic acid |

TABLE 1a-continued

| Example or compound | Structure | Name |
| --- | --- | --- |
| 145 | 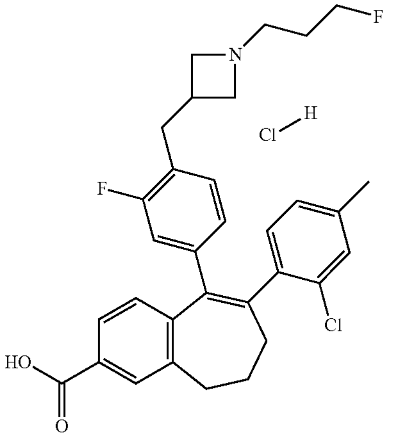 | 8-(2-chloro-4-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride |
| 146 | 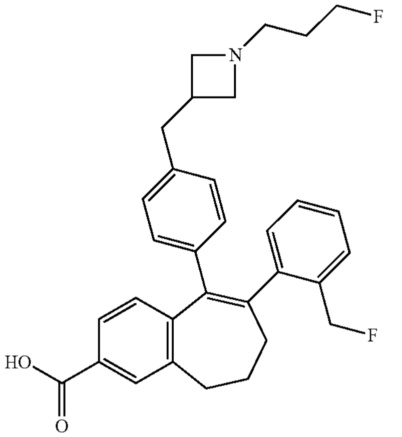 [SMILES: O=C(O)c1ccc2c(c1)CCCC(c1ccccc1CF)=C2c1ccc(CC2CN(CCCF)C2)cc1] | 8-(2-(fluoromethyl)phenyl)-9-(4-((1-(3-fluoropropyl)azetidin-3-yl)methyl)phenyl)-6,7-dihydro-5H-benzo[7]annulene-3-carboxylic acid |
| 147 | 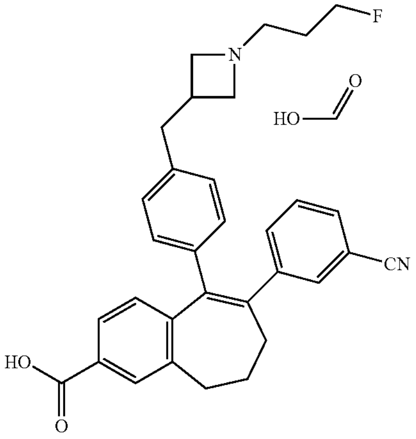 [SMILES: N#Cc1cccc(C2=C(c3ccc(CC4CN(CCCF)C4)cc3)c3ccc(C(=O)O)cc3CCC2)c1 ; O=CO] | 8-(3-cyanophenyl)-9-(4-((1-(3-fluoropropyl)azetidin-3-yl)methyl)phenyl)-6,7-dihydro-5H-benzo[7]annulene-3-carboxylic acid, formic acid |

TABLE 1a-continued

| Example or compound | Structure | Name |
|---|---|---|
| 148 | 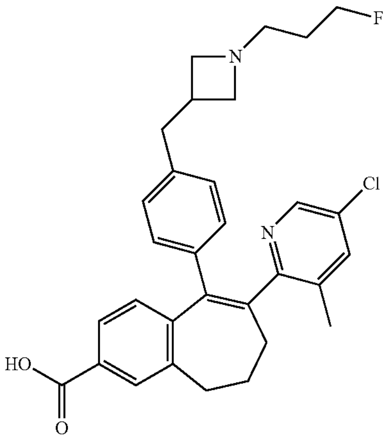 [SMILES: Cc1cc(Cl)cnc1C1=C(c2ccc(CC3CN(CCCF)C3)cc2)c2ccc(C(=O)O)cc2CCC1] | 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylic acid |
| 149 | 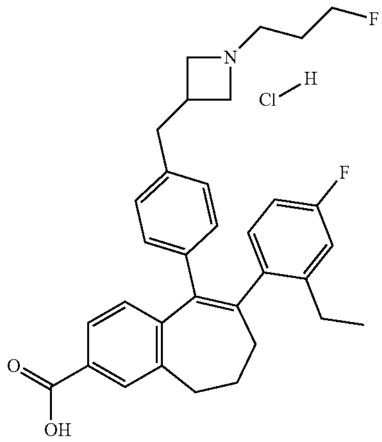 | 8-(2-ethyl-4-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 150 | 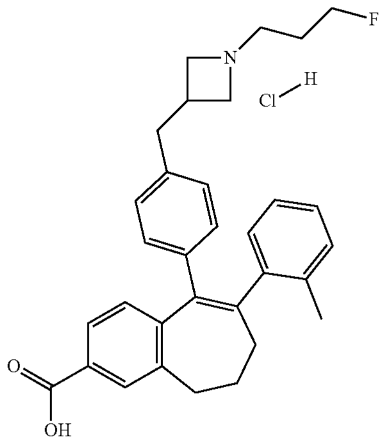 | 9-(4-((1-(3-fluoropropyl)azetidin-3-yl)methyl)phenyl)-8-(o-tolyl)-6,7-dihydro-5H-benzo[7]annulene-3-carboxylic acid hydrochloride |

TABLE 1a-continued

| Example or compound | Structure | Name |
|---|---|---|
| 151 | 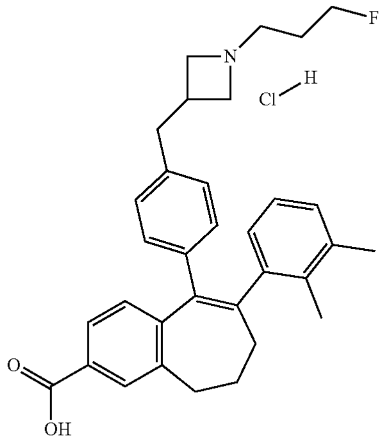 | 8-(2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride |
| 152 | 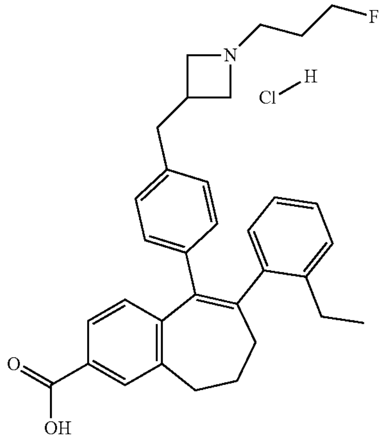 | 8-(2-ethylphenyl)-9-(4-((1-(3-fluoropropyl)azetidin-3-yl)methyl)phenyl)-6,7-dihydro-5H-benzo[7]annulene-3-carboxylic acid hydrochloride |
| 153 | 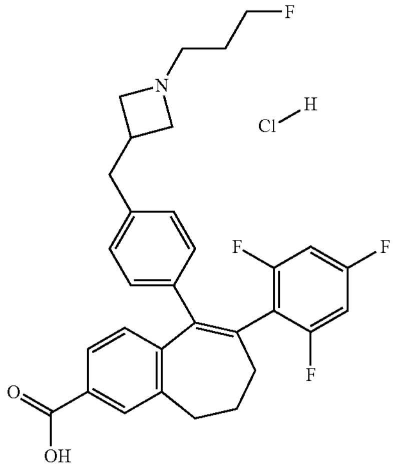 [SMILES: O=C(O)c1ccc2c(c1)CCCC(c1c(F)cc(F)cc1F)=C2c1ccc(CC2CN(CCCF)C2)cc1 ; Cl] | 9-(4-((1-(3-fluoropropyl)azetidin-3-yl)methyl)phenyl)-8-(2,4,6-trifluorophenyl)-6,7-dihydro-5H-benzo[7]annulene-3-carboxylic acid hydrochloride |

TABLE 1a-continued

| Example or compound | Structure | Name |
|---|---|---|
| 154 | 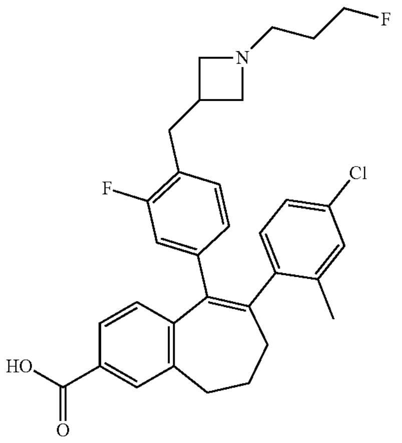 [SMILES: Cc1cc(Cl)ccc1C1=C(c2ccc(CC3CN(CCCF)C3)c(F)c2)c2ccc(C(=O)O)cc2CCC1] | 8-(4-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid |
| 155 | 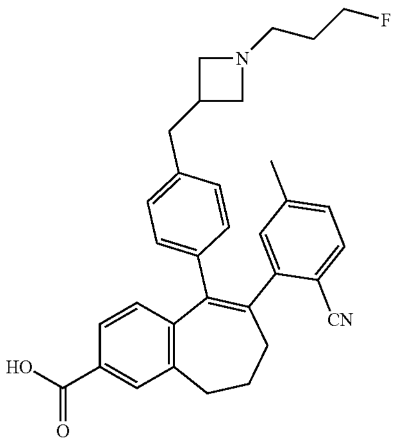 [SMILES: Cc1ccc(C#N)c(C2=C(c3ccc(CC4CN(CCCF)C4)cc3)c3ccc(C(=O)O)cc3CCC2)c1] | 8-(2-cyano-5-methylphenyl)-9-(4-((1-(3-fluoropropyl)azetidin-3-yl)methyl)phenyl)-6,7-dihydro-5H-benzo[7]annulene-3-carboxylic acid |
| 156 | 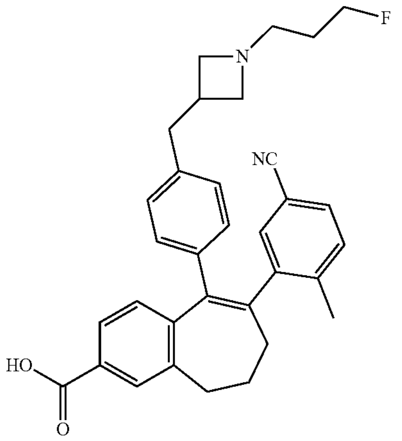 [SMILES: Cc1ccc(C#N)cc1C1=C(c2ccc(CC3CN(CCCF)C3)cc2)c2ccc(C(=O)O)cc2CCC1] | 8-(5-cyano-2-methylphenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 157 | 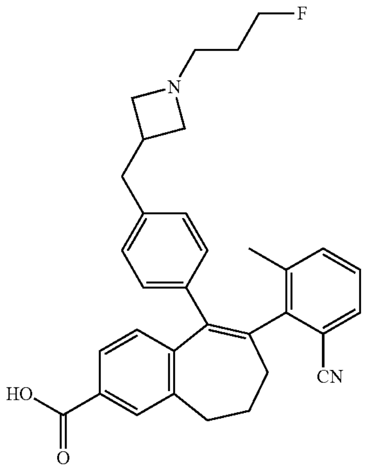 [SMILES: Cc1cccc(C#N)c1C1=C(c2ccc(CC3CN(CCCF)C3)cc2)c2ccc(C(=O)O)cc2CCC1] | 8-(2-cyano-6-methylphenyl)-9-(4-((1-(3-fluoropropyl)azetidin-3-yl)methyl)phenyl)-6,7-dihydro-5H-benzo[7]annulene-3-carboxylic acid |
| 158 | 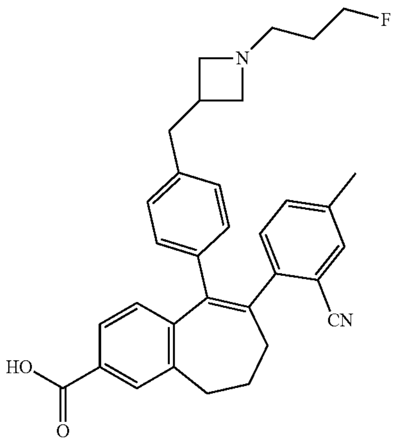 [SMILES: Cc1ccc(C2=C(c3ccc(CC4CN(CCCF)C4)cc3)c3ccc(C(=O)O)cc3CCC2)c(C#N)c1] | 8-(2-cyano-4-methylphenyl)-9-(4-((1-(3-fluoropropyl)azetidin-3-yl)methyl)phenyl)-6,7-dihydro-5H-benzo[7]annulene-3-carboxylic acid |
| 159 | 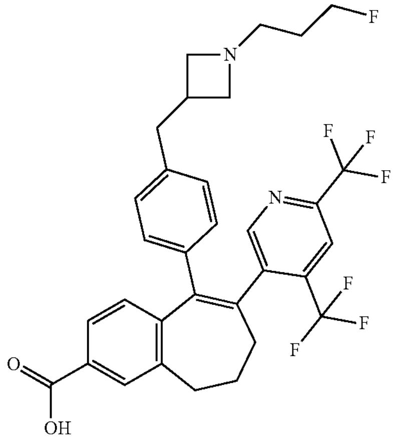 [SMILES: O=C(O)c1ccc2c(c1)CCCC(c1cnc(C(F)(F)F)cc1C(F)(F)F)=C2c1ccc(CC2CN(CCCF)C2)cc1] | 8-(4,6-bis(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 160 | 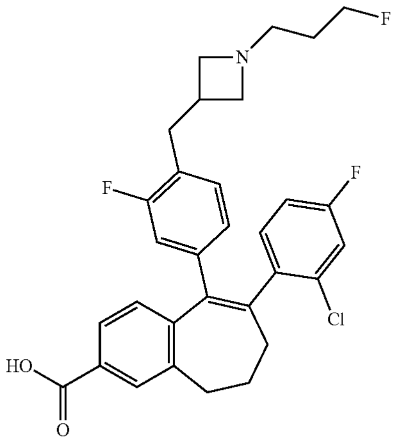 [SMILES: O=C(O)c1ccc2c(c1)CCCC(c1ccc(F)cc1Cl)=C2c1ccc(CC2CN(CCCF)C2)c(F)c1] | 8-(2-chloro-4-fluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride |
| 161 | 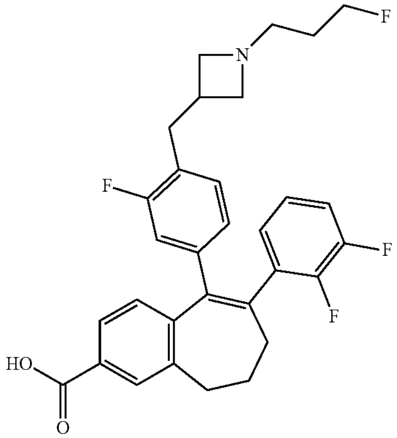 [SMILES: O=C(O)c1ccc2c(c1)CCCC(c1cccc(F)c1F)=C2c1ccc(CC2CN(CCCF)C2)c(F)c1] | 8-(2,3-difluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride |
| 162 | 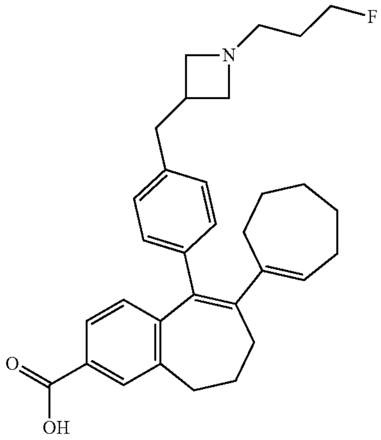 [SMILES: O=C(O)c1ccc2c(c1)CCCC(C1=CCCCCC1)=C2c1ccc(CC2CN(CCCF)C2)cc1] | 8-(cyclohept-1-en-1-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 163 | 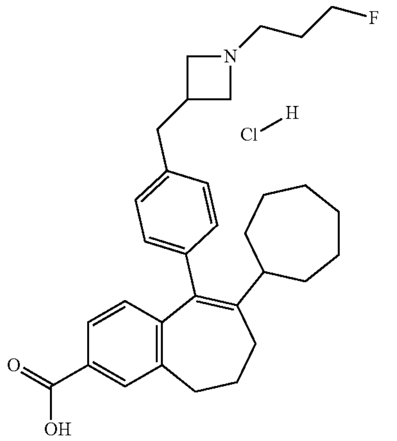 | 8-cycloheptyl-9-(4-((1-(3-fluoropropyl)azetidin-3-yl)methyl)phenyl)-6,7-dihydro-5H-benzo[7]annulene-3-carboxylic acid hydrochloride |
| 164 | 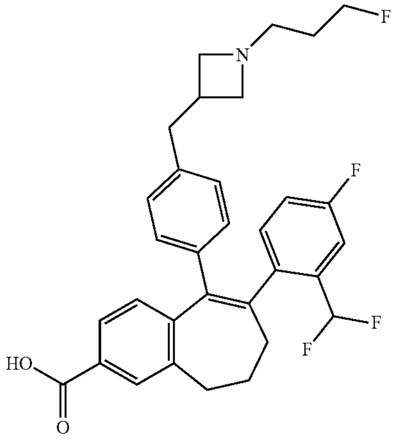 [SMILES: O=C(O)c1ccc2c(c1)CCCC(c1ccc(F)cc1C(F)F)=C2c1ccc(CC2CN(CCCF)C2)cc1] | 8-(2-(difluoromethyl)-4-fluorophenyl)-9-(4-((1-(3-fluoropropyl)azetidin-3-yl)methyl)phenyl)-6,7-dihydro-5H-benzo[7]annulene-3-carboxylic acid |
| 165 | 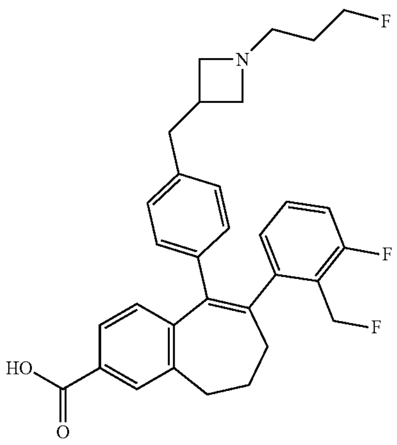 [SMILES: O=C(O)c1ccc2c(c1)CCCC(c1cccc(F)c1CF)=C2c1ccc(CC2CN(CCCF)C2)cc1] | 8-(3-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 166 | 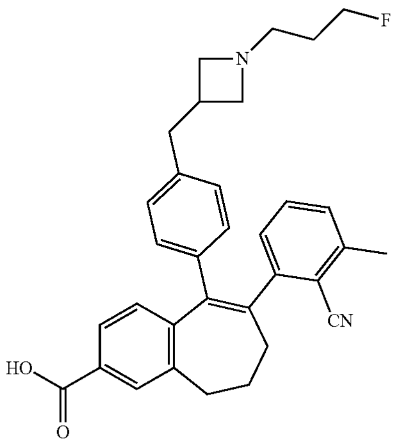 [SMILES: Cc1cccc(C2=C(c3ccc(CC4CN(CCCF)C4)cc3)c3ccc(C(=O)O)cc3CCC2)c1C#N] | 8-(2-cyano-3-methylphenyl)-9-(4-((1-(3-fluoropropyl)azetidin-3-yl)methyl)phenyl)-6,7-dihydro-5H-benzo[7]annulene-3-carboxylic acid |
| 167 | 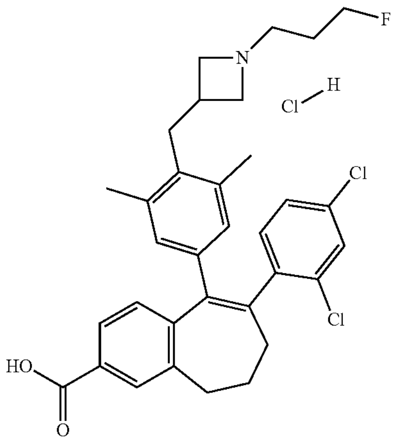 | 8-(2,4-dichlorophenyl)-9-(4-((1-(3-fluoropropyl)azetidin-3-yl)methyl)-3,5-dimethylphenyl)-6,7-dihydro-5H-benzo[7]annulene-3-carboxylic acid hydrochloride |
| 168 | 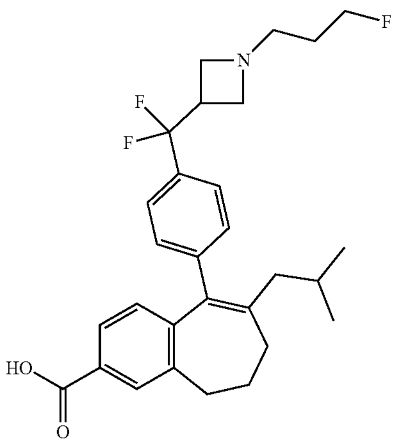 [SMILES: CC(C)CC1=C(c2ccc(C(F)(F)C3CN(CCCF)C3)cc2)c2ccc(C(=O)O)cc2CCC1] | 9-(4-(difluoro(1-(3-fluoropropyl)azetidin-3-yl)methyl)phenyl)-8-isobutyl-6,7-dihydro-5H-benzo[7]annulene-3-carboxylic acid |

TABLE 1a-continued

| Example or compound | Structure | Name |
|---|---|---|
| 169 | 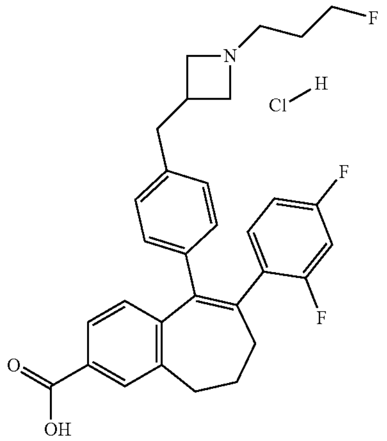 | 8-(2,4-difluorophenyl)-9-(4-((1-(3-fluoropropyl)azetidin-3-yl)methyl)phenyl)-6,7-dihydro-5H-benzo[7]annulene-3-carboxylic acid hydrochloride |
| 170 | 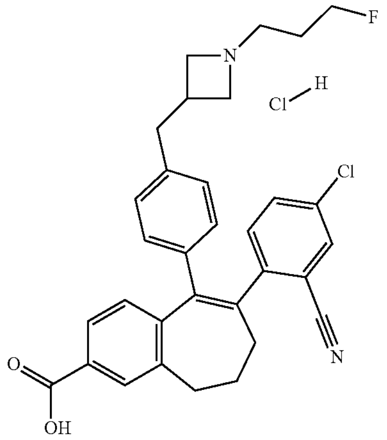 | 8-(4-chloro-2-cyanophenyl)-9-(4-((1-(3-fluoropropyl)azetidin-3-yl)methyl)phenyl)-6,7-dihydro-5H-benzo[7]annulene-3-carboxylic acid hydrochloride |
| 171 | 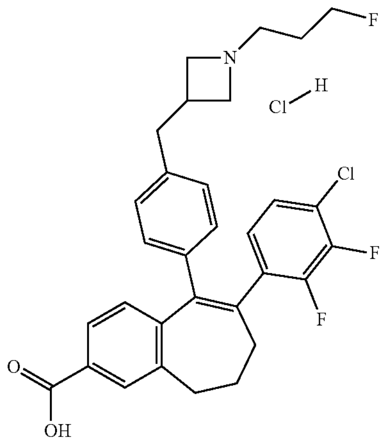 | 8-(4-chloro-2,3-difluorophenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 172 | 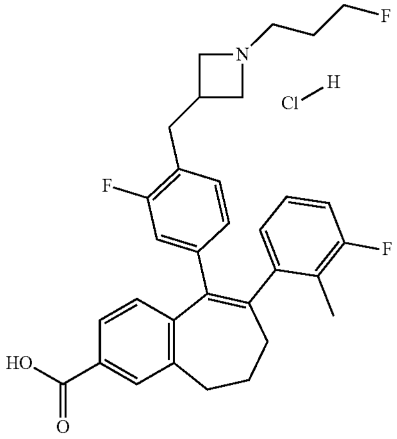 | 8-(3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride |
| 173 | 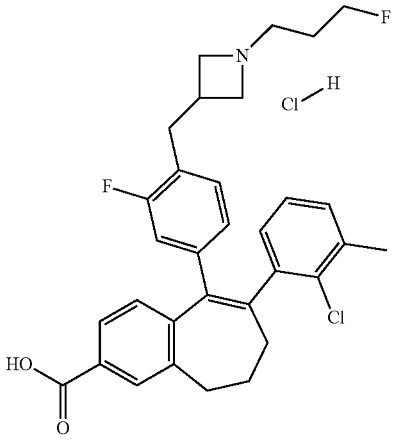 | 8-(2-chlroo-3-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride |
| 174 | 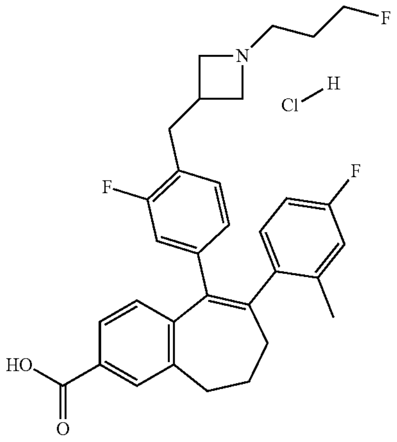 | 8-(4-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride |

TABLE 1a-continued
| Example or compound | Structure | Name |
| --- | --- | --- |
| 175 | 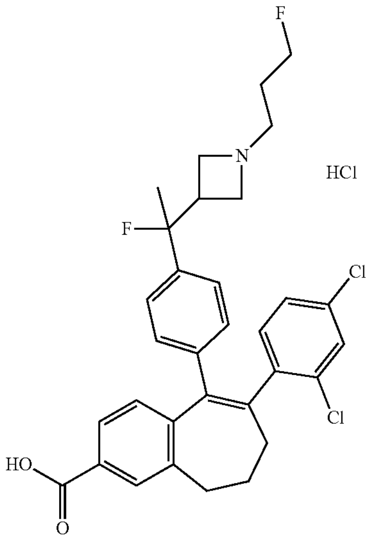 Isomer 1 | 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 1 |
| 176 | 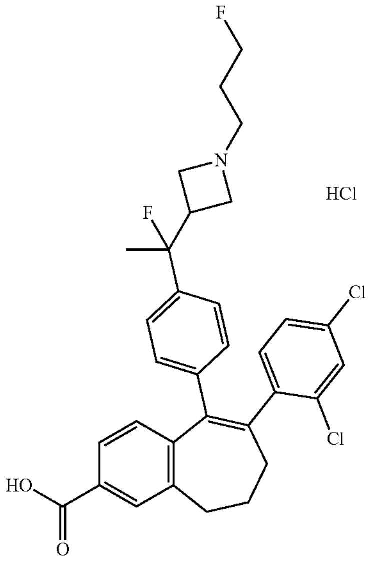 Isomer 2 | 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 2 |

TABLE 1a-continued

| Example or compound | Structure | Name |
|---|---|---|
| 177 | 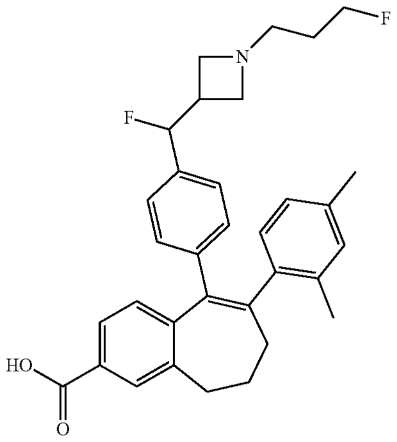 Isomer 1 | 9-(4-(fluoro(1-(3-fluoropropyl)azetidin-3-yl)methyl)phenyl)-8-(2-fluoro-4-methylphenyl)-6,7-dihydro-5H-benzo[7]annulene-3-carboxylic acid Isomer 1 |
| 178 | 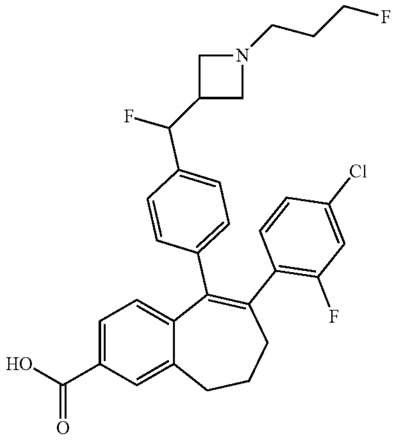 Isomer 1 | 8-(4-chloro-2-fluorophenyl)-9-(4-(fluoro(1-(3-fluoropropyl)azetidin-3-yl)methyl)phenyl)-6,7-dihydro-5H-benzo[7]annulene-3-carboxylic acid Isomer 1 |
| 179 | 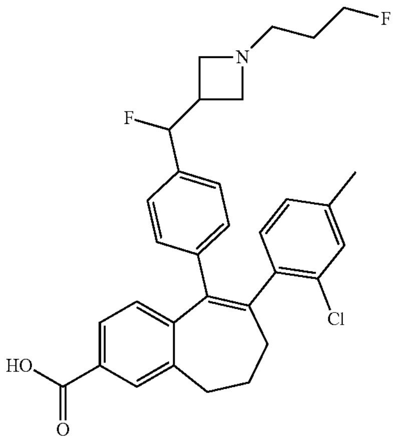 Isomer 1 | 8-(2-chloro-4-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 |

TABLE 1a-continued

| Example or compound | Structure | Name |
|---|---|---|
| 180 | 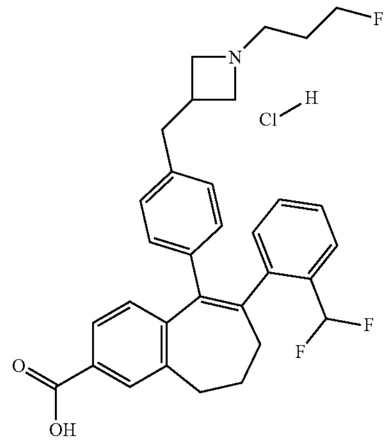 | 8-(2-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |
| 181 | 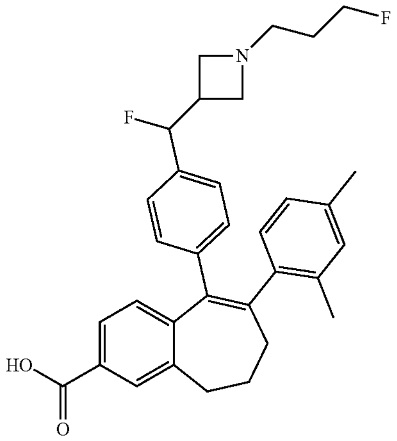 Isomer 1 | 8-(2,4-dimethylphenyl)-9-(4-(fluoro(1-(3-fluoropropyl)azetidin-3-yl)methyl)phenyl)-6,7-dihydro-5H-benzo[7]annulene-3-carboxylic acid Isomer 1 |
| 182 | 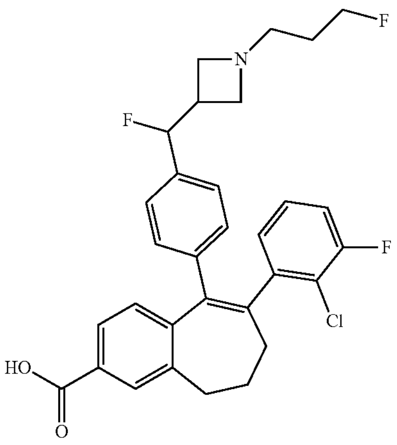 Isomer 1 | 8-(2-chloro-3-fluorophenyl)-9-(4-fluoro(1-(3-fluoropropyl)azetidin-3-yl)methyl)phenyl)-6,7-dihydro-5H-benzo[7]annulene-3-carboxylic acid Isomer 1 |

TABLE 1a-continued

| Example or compound | Structure | Name |
|---|---|---|
| 183 | 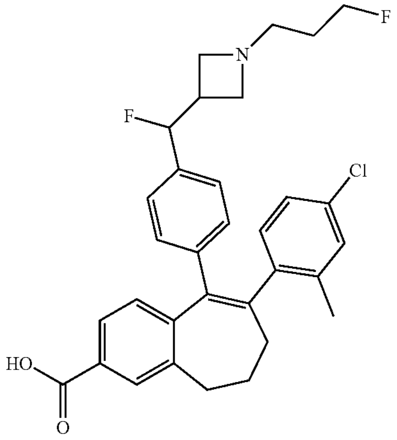 Isomer 1 | 8-(4-chloro-2-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 |
| 184 | 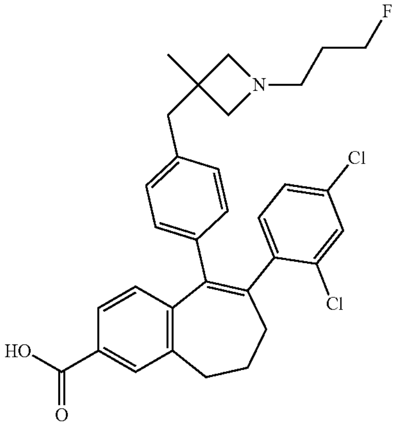 [SMILES: CC1(Cc2ccc(C3=C(c4ccc(Cl)cc4Cl)CCCc4cc(C(=O)O)ccc43)cc2)CN(CCCF)C1] | 8-(2,4-dichlorophenyl)-9-(4-((1-(3-fluoropropyl)-3-methylazetidin-3-yl)methyl)phenyl)-6,7-dihydro-5H-benzo[7]annulene-3-carboxylic acid |
| 185 | 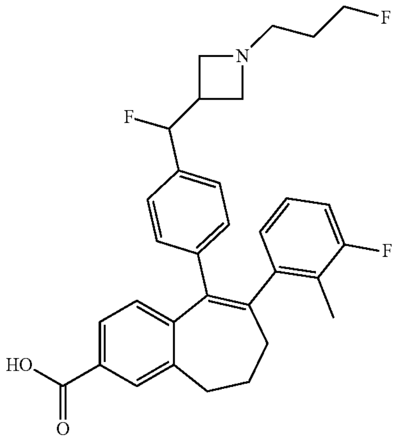 Isomer 1 | 9-(4-(fluoro(1-(3-fluoropropyl)azetidin-3-yl)methyl)phenyl)-8-(3-fluoro-2-methylphenyl)-6,7-dihydro-5H-benzo[7]annulene-3-carboxylic acid Isomer 1 |

TABLE 1a-continued

| Example or compound | Structure | Name |
| --- | --- | --- |
| 186 | 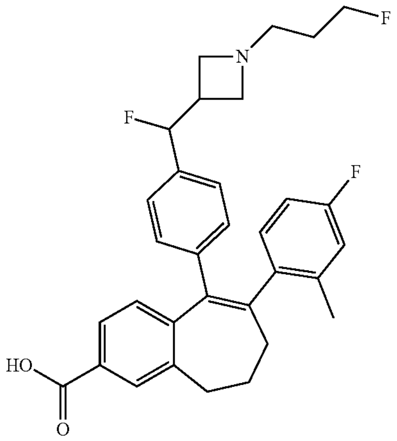 Isomer 1 | 9-(4-(fluoro(1-(3-fluoropropyl)azetidin-3-yl)methyl)phenyl)-8-(4-fluoro-2-methylphenyl)-6,7-dihydro-5H-benzo[7]annulene-3-carboxylic acid Isomer 1 |
| 187 | 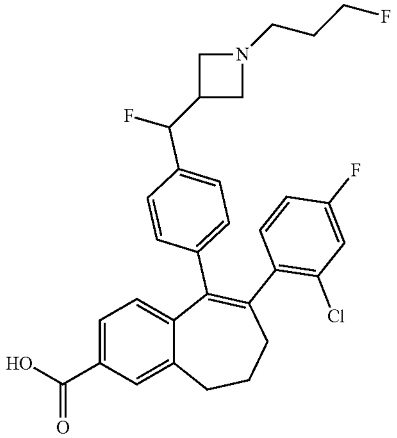 Isomer 1 | 8-(2-chloro-4-fluorophenyl)-9-(4-(fluoro(1-(3-fluoropropyl)azetiidn-3-yl)methyl)phenyl)-6,7-dihydro-5H-benzo[7]annulene-3-carboxylic acid Isomer 1 |
| 188 | 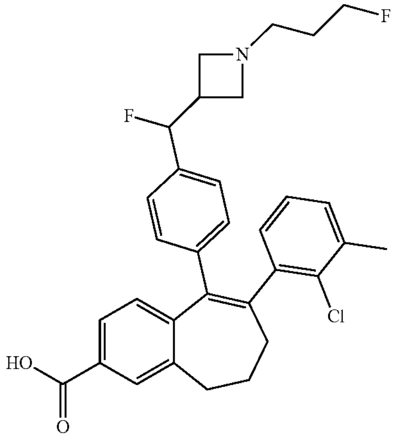 Isomer 1 | 8-(2-chloro-3-methylphenyl)-9-(4-(fluoro(1-(3-fluoropropyl)azetidin-3-yl)methyl)phenyl)-6,7-dihydro-5H-benzo[7]annulene-3-carboxylic acid Isomer 1 |

TABLE 1a-continued

| Example or compound | Structure | Name |
|---|---|---|
| 189 | 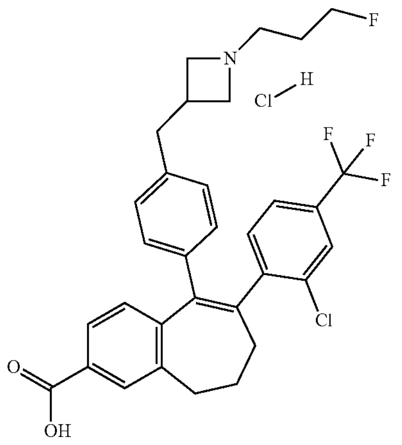 | 8-(2-chloro-4-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |
| 190 | 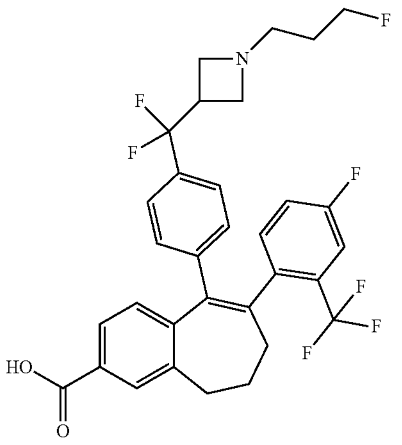 [SMILES: O=C(O)c1ccc2c(c1)CCCC(c1ccc(F)cc1C(F)(F)F)=C2c1ccc(C(F)(F)C2CN(CCCF)C2)cc1] | 9-(4-(difluoro(1-(3-fluoropropyl)azetidin-3-yl)methyl)phenyl)-8-(4-fluoro-2-(trifluoromethyl)phenyl)-6,7-dihydro-5H-benzo[7]annulene-3-carboxylic acid |
| 191 | 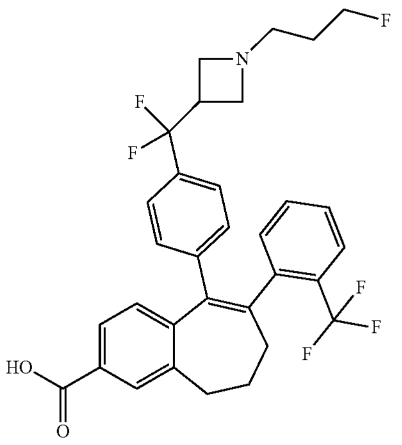 [SMILES: O=C(O)c1ccc2c(c1)CCCC(c1ccccc1C(F)(F)F)=C2c1ccc(C(F)(F)C2CN(CCCF)C2)cc1] | 9-(4-(difluoro(1-(3-fluoropropyl)azetidin-3-yl)methyl)phenyl)-8-(2-(trifluoromethyl)phenyl)-6,7-dihydro-5H-benzo[7]annulene-3-carboxylic acid |

TABLE 1a-continued

| Example or compound | Structure | Name |
|---|---|---|
| 192 | 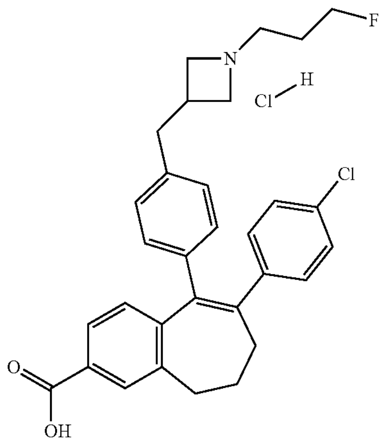 | 8-(4-chlorophenyl)-9-(4-((1-(3-fluoropropyl)azetidin-3-yl)methyl)phenyl)-6,7-dihydro-5H-benzo[7]annulene-3-carboxylic acid hydrochloride |
| 193 | 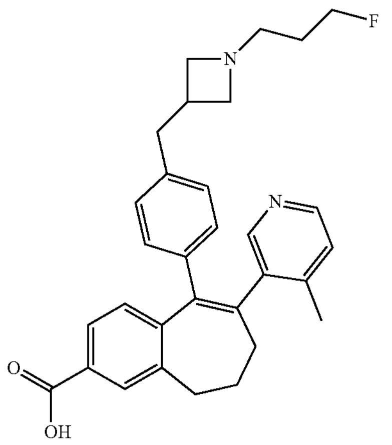 [SMILES: Cc1ccncc1C1=C(c2ccc(CC3CN(CCCF)C3)cc2)c2ccc(C(=O)O)cc2CCC1] | 9-(4-((1-(3-fluoropropyl)azetidin-3-yl)methyl)phenyl)-8-(4-methylpyridin-3-yl)-6,7-dihydro-5H-benzo[7]annulene-3-carboxylic acid |
| 194 | 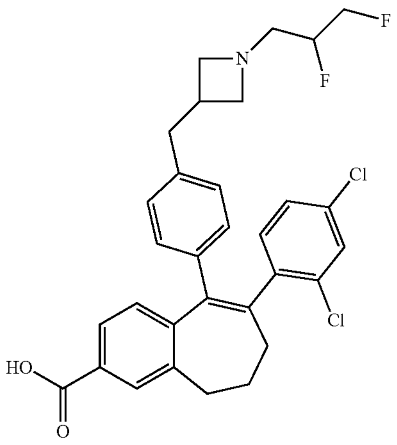 Isomer 1 | 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 1 |

TABLE 1a-continued

| Example or compound | Structure | Name |
|---|---|---|
| 195 | 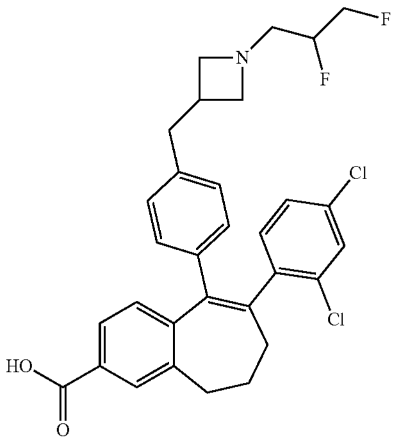 Isomer 2 | 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 2 |
| 196 | 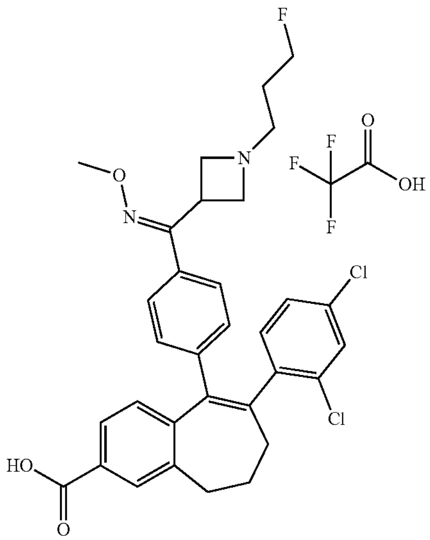 | (E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid |
| 197 | 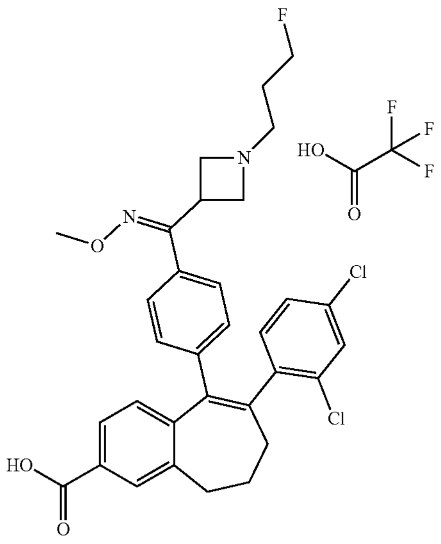 | (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid |

TABLE 1a-continued

| Example or compound | Structure | Name |
|---|---|---|
| 198 | 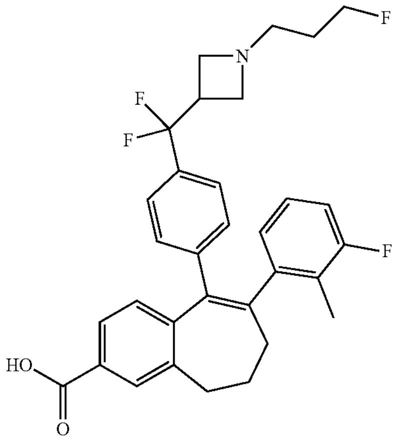 [SMILES: Cc1c(F)cccc1C1=C(c2ccc(C(F)(F)C3CN(CCCF)C3)cc2)c2ccc(C(=O)O)cc2CCC1] | 9-(4-(difluoro(1-(3-fluoropropyl)azetidin-3-yl)methyl)phenyl)-8-(3-fluoro-2-methylphenyl)-6,7-dihydro-5H-benzo[7]annulene-3-carboxylic acid |
| 199 | 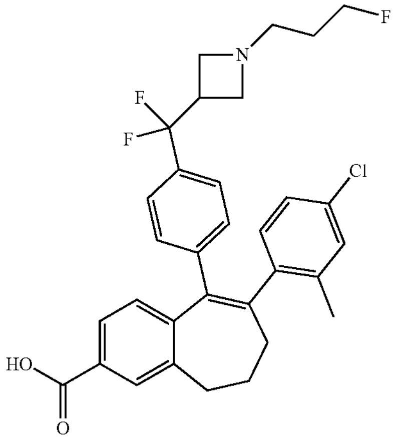 [SMILES: Cc1cc(Cl)ccc1C1=C(c2ccc(C(F)(F)C3CN(CCCF)C3)cc2)c2ccc(C(=O)O)cc2CCC1] | 8-(4-chloro-2-methylphenyl)-9-(4-(difluoro(1-(3-fluoropropyl)azetidin-3-yl)methyl)phenyl)-6,7-dihydro-5H-benzo[7]annulene-3-carboxylic acid |
| 200 | 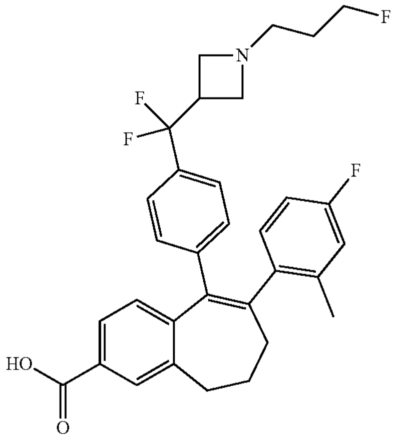 [SMILES: Cc1cc(F)ccc1C1=C(c2ccc(C(F)(F)C3CN(CCCF)C3)cc2)c2ccc(C(=O)O)cc2CCC1] | 9-(4-(difluoro(1-(3-fluoropropyl)azetidin-3-y)methyl)phenyl)-8-(4-fluoro-2-methylphenyl)-6,7-dihydro-5H-benzo[7]annulene-3-carboxylic acid |

TABLE 1a-continued

| Example or compound | Structure | Name |
| --- | --- | --- |
| 201 | 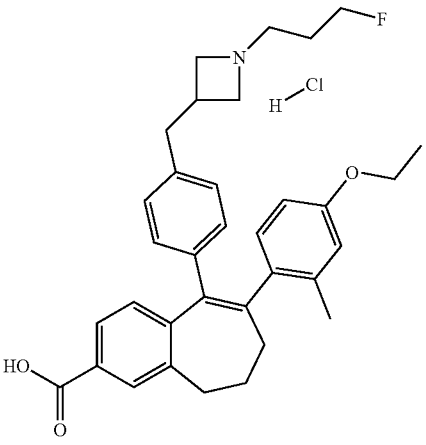 | 8-(4-ethoxy-2-methylphenyl)-9-(4-((1-(3-fluoropropyl)azetidin-3-yl)methyl)phenyl)-6,7-dihydro-5H-benzo[7]annulene-3-carboxylic acid hydrochloride |
| 202 | 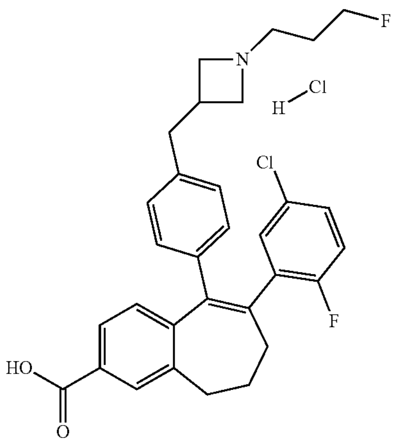 | 8-(5-chloro-2-fluorophenyl)-9-(4-((1-(3-fluoropropyl)azetidin-3-yl)methyl)phenyl)-6,7-dihydro-5H-benzo[7]annulene-3-carobxylic acid hydrochloride |
| 203 | 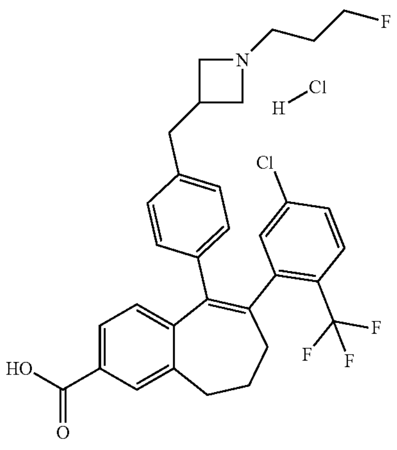 | 8-(5-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
|---|---|---|
| 204 | 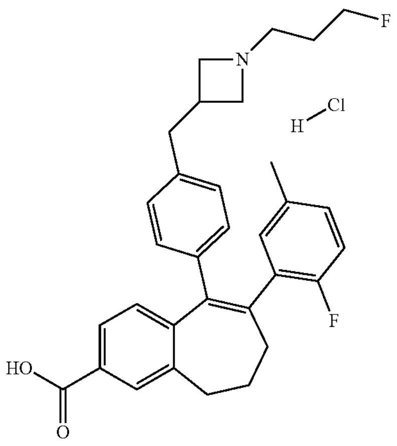 | 8-(2-fluoro-5-methylphenyl)-9-(4-((1-(3-fluoropropyl)azetidin-3-yl)methyl)phenyl)-6,7-dihydro-5H-benzo[7]annulene-3-carboxylic acid hydrochloride |
| 205 | 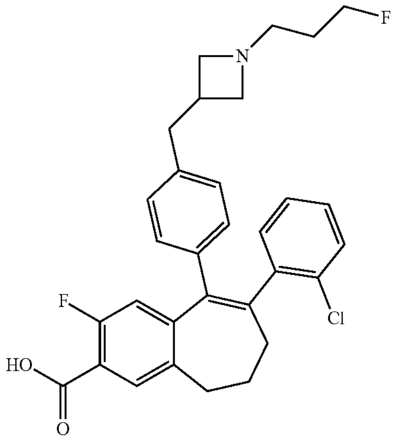 [SMILES: O=C(O)c1cc2c(cc1F)C(c1ccc(CC3CN(CCCF)C3)cc1)=C(c1ccccc1Cl)CCC2] | 8-(2-chlorophenyl)-2-fluoro-9-(4-((1-(3-fluoropropyl)azetidin-3-yl)methyl)phenyl)-6,7-dihydro-5H-benzo[7]annulene-3-carboxylic acid |
| 206 | 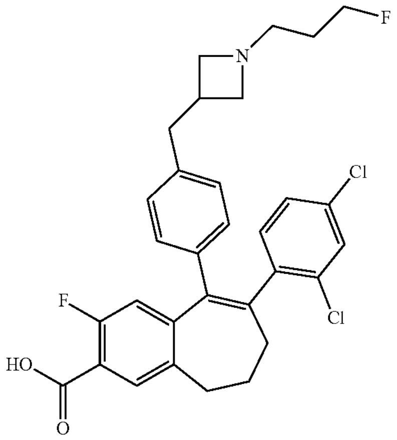 [SMILES: O=C(O)c1cc2c(cc1F)C(c1ccc(CC3CN(CCCF)C3)cc1)=C(c1ccc(Cl)cc1Cl)CCC2] | 8-(2,4-dichlorophenyl)-2-fluoro-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 207 | 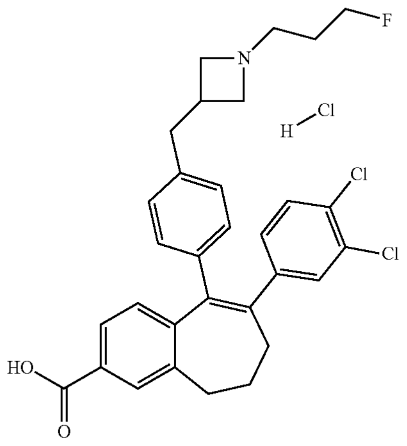 | 8-(3,4-dichlorophenyl)-9-(4-((1-(3-fluoropropyl)azetidin-3-yl)methyl)phenyl)-6,7-dihydro-5H-benzo[7]annulene-3-carboxylic acid hydrochloride |
| 208 | 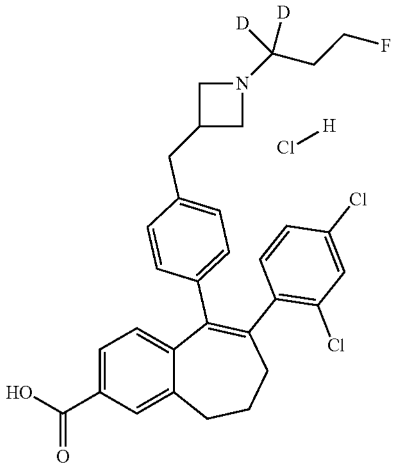 | 8-(2,4-dichlorophenyl)-9-(4-((1-(3-fluoropropyl-1,1-d2)azetidin-3-yl)methyl)phenyl)-6,7-dihydro-5H-benzo[7]annulene-3-carboxylic acid hydrochloride |
| 209 | 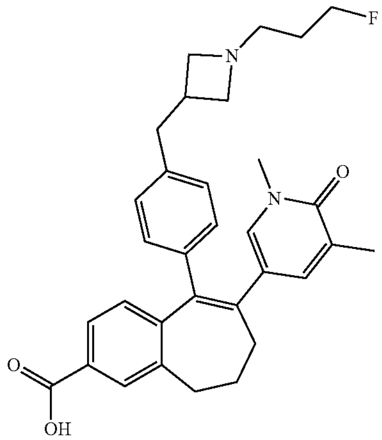 [SMILES: Cc1cc(C2=C(c3ccc(CC4CN(CCCF)C4)cc3)c3ccc(C(=O)O)cc3CCC2)cn(C)c1=O] | 8-(1,5-dimethyl-6-oxo-1,6-dihydropyridin-3-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 210 | 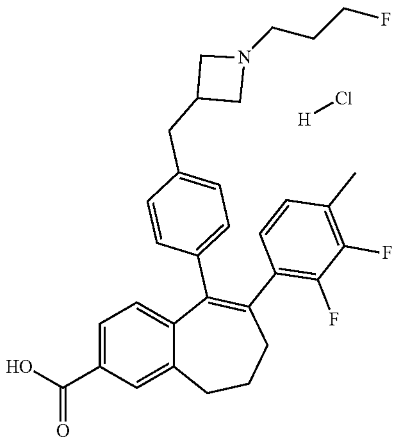 [SMILES: Cc1ccc(C2=C(c3ccc(CC4CN(CCCF)C4)cc3)c3ccc(C(=O)O)cc3CCC2)c(F)c1F ; Cl] | 8-(2,3-difluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride |
| 211 | 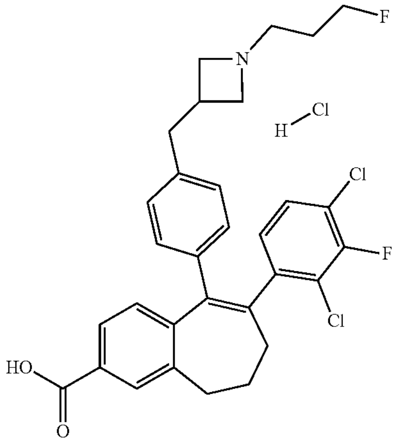 | 8-(2,4-dichloro-3-fluorophenyl)-9-(4-((1-(3-fluoropropyl)azetidin-3-yl)methyl)phenyl)-6,7-dihydro-5H-benzo[7]annulene-3-carboxylic acid hydrochloride |
| 212 | 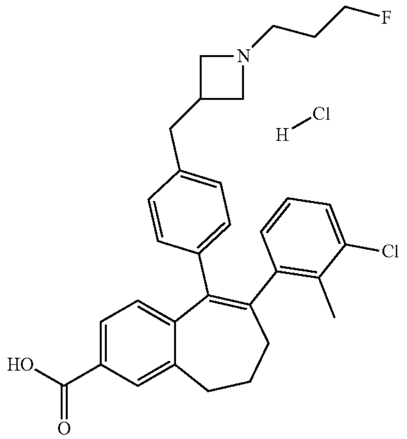 | 8-(3-chloro-2-methylphenyl)-9-(4-((1-(3-fluoropropyl)azetidin-3-yl)methyl)phenyl)-6,7-dihydro-5H-benzo[7]annulene-3-carboxylic acid hydrochloride |

TABLE 1a-continued

| Example or compound | Structure | Name |
| --- | --- | --- |
| 213 | 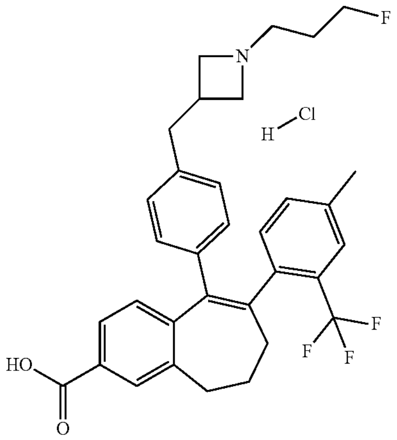 | 9-(4-((1-(3-fluoropropyl)azetidin-3-yl)methyl)phenyl)-8-(4-methyl-2-(trifluoromethyl)phenyl)-6,7-dihydro-5H-benzo[7]annulene-3-carboxylic acid hydrochloride |
| 214 | 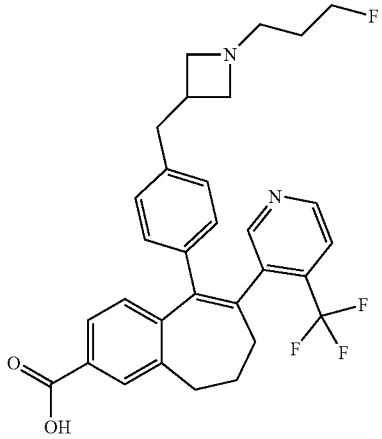 [SMILES: O=C(O)c1ccc2c(c1)CCCC(c1cnccc1C(F)(F)F)=C2c1ccc(CC2CN(CCCF)C2)cc1] | 9-(4-((1-(3-fluoropropyl)azetidin-3-yl)methyl)phenyl)-8-(4-(trifluoromethyl)pyridin-3-yl)-6,7-dihydro-5H-benzo[7]annulene-3-carboxylic acid |
| 215 | 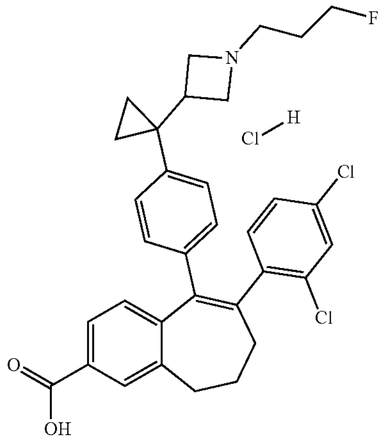 | 8-(2,4-dichlorophenyl)-9-(4-(1-(1-(3-fluoropropyl)azetidin-3-yl)cyclopropyl)phenyl)-6,7-dihydro-5H-benzo[7]annulene-3-carboxylic acid hydrochloride |

TABLE 1a-continued

| Example or compound | Structure | Name |
| --- | --- | --- |
| 216 | 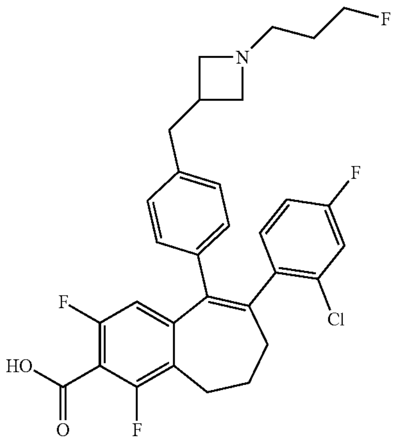 [SMILES: O=C(O)c1c(F)cc2c(c1F)CCCC(c1ccc(F)cc1Cl)=C2c1ccc(CC2CN(CCCF)C2)cc1] | 8-(2-chloro-4-fluorophenyl)-2,4-difluoro-9-(4-((1-(3-fluoropropyl)azetidin-3-yl)methyl)phenyl)-6,7-dihydro-5H-benzo[7]annulene-3-carboxylic acid |
| 217 | 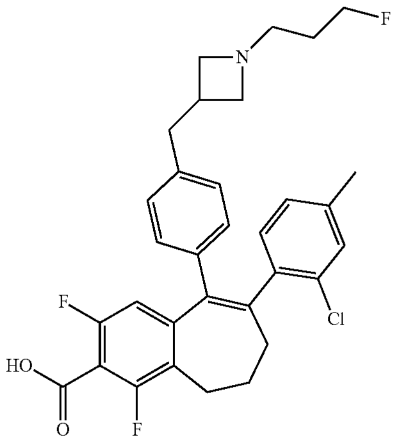 [SMILES: Cc1ccc(C2=C(c3ccc(CC4CN(CCCF)C4)cc3)c3cc(F)c(C(=O)O)c(F)c3CCC2)c(Cl)c1] | 8-(2-chloro-4-methylphenyl)-2,4-difluoro-9-(4-((1-(3-fluoropropyl)azetidin-3-yl)methyl)phenyl)-6,7-dihydro-5H-benzo[7]annulene-3-carboxylic acid |
| 218 | 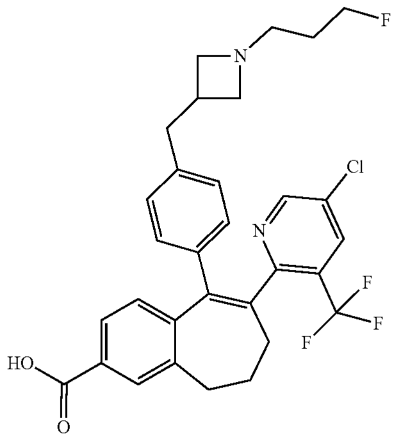 [SMILES: O=C(O)c1ccc2c(c1)CCCC(c1ncc(Cl)cc1C(F)(F)F)=C2c1ccc(CC2CN(CCCF)C2)cc1] | 8-(5-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 219 | 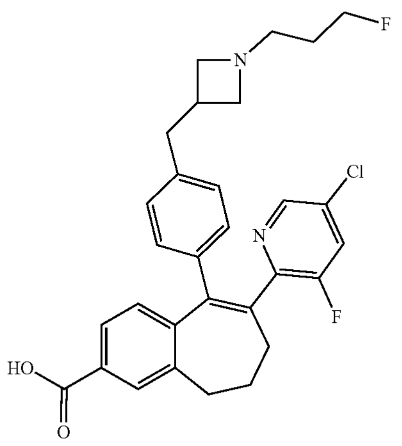 [SMILES: O=C(O)c1ccc2c(c1)CCCC(c1ncc(Cl)cc1F)=C2c1ccc(CC2CN(CCCF)C2)cc1] | 8-(5-chloro-3-fluoropyridin-2-yl)-9-(4-((1-(3-fluoropropyl)azetidin-3-yl)methyl)phenyl)-6,7-dihydro-5H-benzo[7]annulene-3-carboxylic acid |
| 220 | 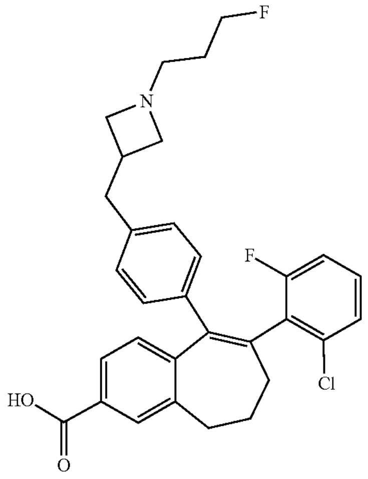 [SMILES: O=C(O)c1ccc2c(c1)CCCC(c1c(F)cccc1Cl)=C2c1ccc(CC2CN(CCCF)C2)cc1] | 8-(2-chloro-6-fluorophenyl)-9-(4-((1-(3-fluoropropyl)azetidin-3-yl)methyl)phenyl)-6,7-dihydro-5H-benzo[7]annulene-3-carboxylic acid |
| 221 | 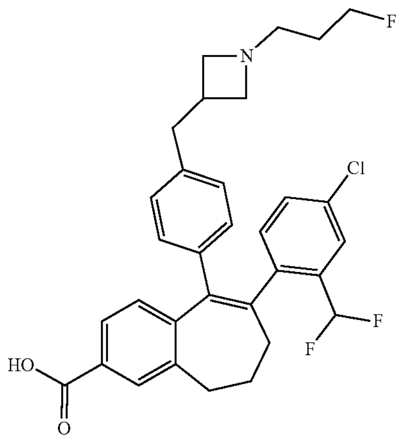 [SMILES: O=C(O)c1ccc2c(c1)CCCC(c1ccc(Cl)cc1C(F)F)=C2c1ccc(CC2CN(CCCF)C2)cc1] | 8-(4-chloro-2-(difluoromethyl)phenyl)-9-(4-((1-(3-fluoropropyl)azetidin-3-yl)methyl)phenyl)-6,7-dihydro-5H-benzo[7]annulene-3-carboxylic acid |

TABLE 1a-continued
| Example or compound | Structure | Name |
|---|---|---|
| 222 | 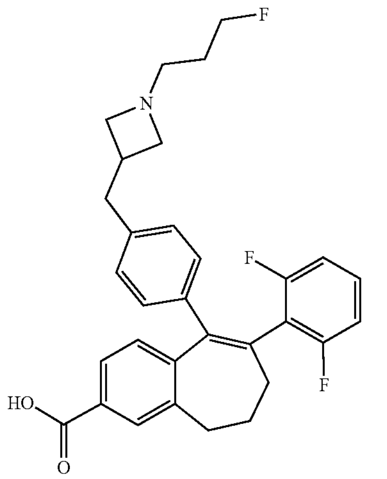 [SMILES: O=C(O)c1ccc2c(c1)CCCC(c1c(F)cccc1F)=C2c1ccc(CC2CN(CCCF)C2)cc1] | 8-(2,6-difluorophenyl)-9-(4-((1-(3-fluoropropyl)azetidin-3-yl)methyl)phenyl)-6,7-dihydro-5H-benzo[7]annulene-3-carboxylic acid |
| 223 | 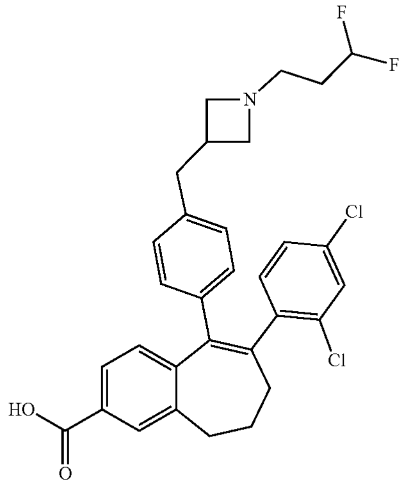 [SMILES: O=C(O)c1ccc2c(c1)CCCC(c1ccc(Cl)cc1Cl)=C2c1ccc(CC2CN(CCC(F)F)C2)cc1] | 8-(2,4-dichlorophenyl)-9-(4-((1-(3,3-difluoropropyl)azetidin-3-yl)methyl)phenyl)-6,7-dihydro-5H-benzo[7]annulene-3-carboxylic acid |
| 224 | 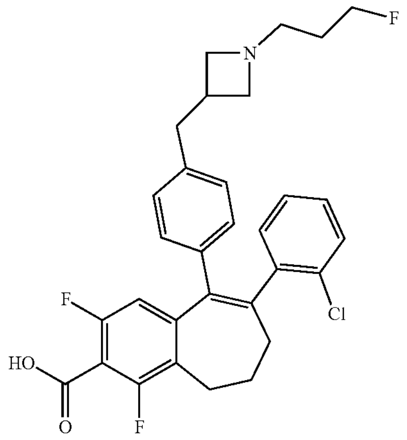 [SMILES: O=C(O)c1c(F)cc2c(c1F)CCCC(c1ccccc1Cl)=C2c1ccc(CC2CN(CCCF)C2)cc1] | 8-(2-chlorophenyl)-2,4-difluoro-9-(4-((1-(3-fluoropropyl)azetidin-3-yl)oxy)phenyl)-6,7-dihydro-5H-benzo[7]annulene-3-carboxylic acid |

TABLE 1a-continued

| Example or compound | Structure | Name |
| --- | --- | --- |
| 225 | 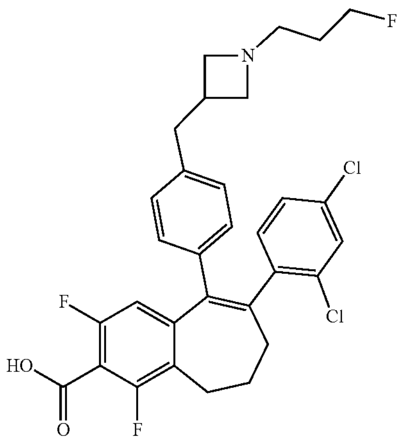 [SMILES: O=C(O)c1c(F)cc2c(c1F)CCCC(c1ccc(Cl)cc1Cl)=C2c1ccc(CC2CN(CCCF)C2)cc1] | 8-(2,4-dichlorophenyl)-2,4-difluoro-9-(4-((1-(3-fluoropropyl)azetidin-3-yl)methyl)phenyl)-6,7-dihydro-5H-benzo[7]annulene-3-carboxylic acid |
| 226 | 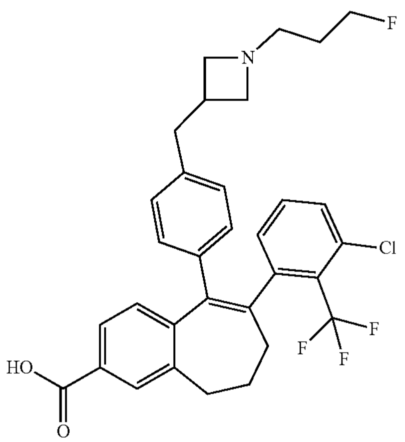 [SMILES: O=C(O)c1ccc2c(c1)CCCC(c1cccc(Cl)c1C(F)(F)F)=C2c1ccc(CC2CN(CCCF)C2)cc1] | 8-(3-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid |
| 227 | 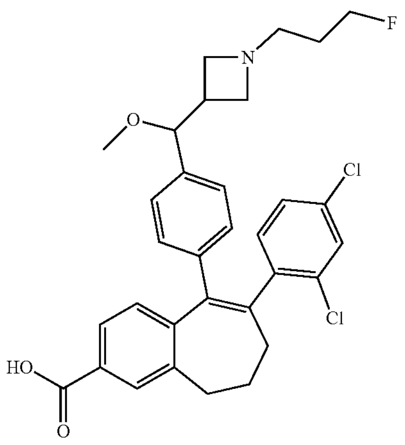 Isomer 1 | 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 1 |

TABLE 1a-continued

| Example or compound | Structure | Name |
|---|---|---|
| 228 | 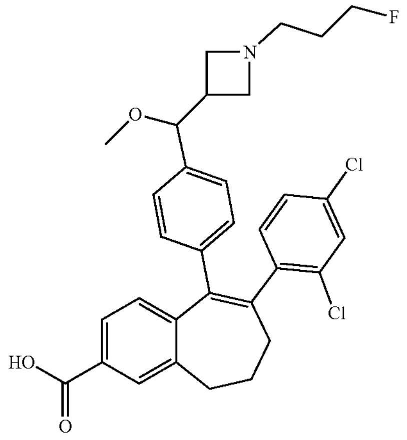 Isomer 2 | 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 2 |
| 229 | 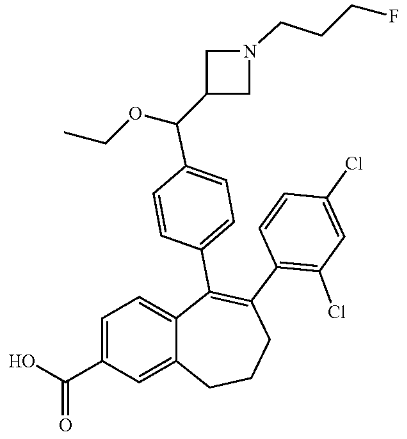 Isomer 1 | 8-(2,4-dichlorophenyl)-9-(4-(ethoxy(1-(3-fluoropropyl)azetidin-3-y)methyl)phenyl)-6,7-dihydro-5H-benzo[7]annulene-3-carboxylic acid Isomer 1 |
| 230 | 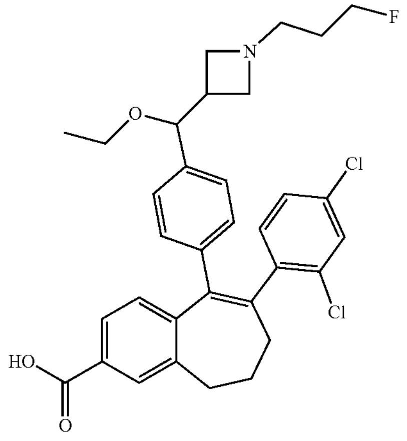 Isomer 2 | 8-(2,4-dichlorophenyl)-9-(4-(ethoxy(1-(3-fluropropyl)azetidin-3-yl)methyl)phenyl)-6,7-dihydro-5H-benzo[7]annulene-3-carboxylic acid Isomer 2 |

TABLE 1a-continued

| Example or compound | Structure | Name |
|---|---|---|
| 231 | 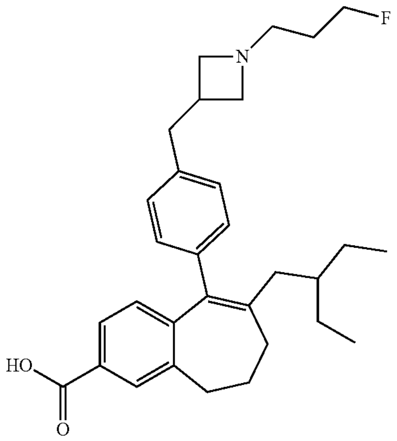 [SMILES: CCC(CC)CC1=C(c2ccc(CC3CN(CCCF)C3)cc2)c2ccc(C(=O)O)cc2CCC1] | 8-(2-ethylbutyl)-9-(4-((1-(3-fluoropropyl)azetidin-3-yl)methyl)phenyl)-6,7-dihydro-5H-benzo[7]annulene-3-carboxylic acid |
| 232 | 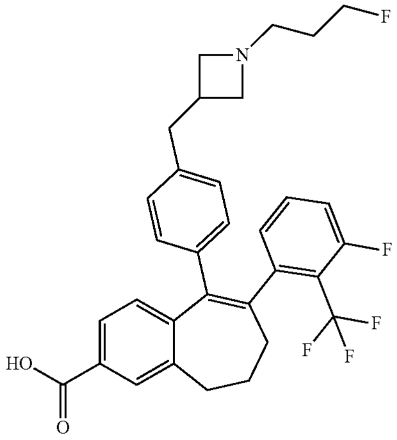 [SMILES: O=C(O)c1ccc2c(c1)CCCC(c1cccc(F)c1C(F)(F)F)=C2c1ccc(CC2CN(CCCF)C2)cc1] | 8-(3-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid |
| 233 | 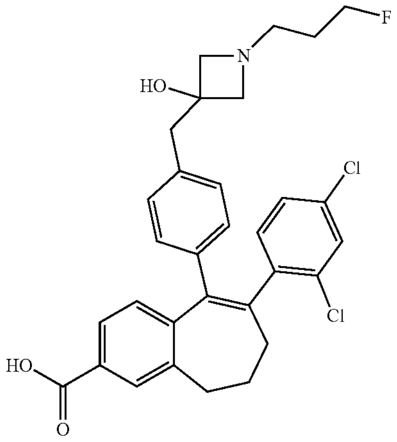 [SMILES: O=C(O)c1ccc2c(c1)CCCC(c1ccc(Cl)cc1Cl)=C2c1ccc(CC2(O)CN(CCCF)C2)cc1] | 8-(2,4-dichlorophenyl)-9-(4-((1-(3-fluoropropyl)-3-hydroxyazetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 234 | 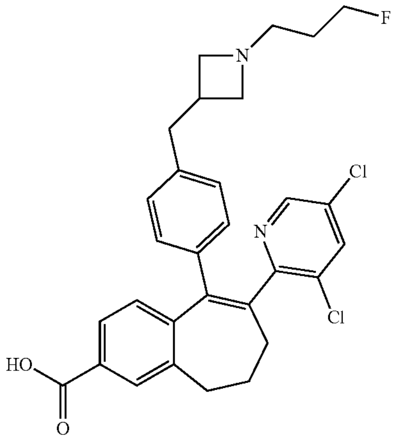 [SMILES: O=C(O)c1ccc2c(c1)CCCC(c1ncc(Cl)cc1Cl)=C2c1ccc(CC2CN(CCCF)C2)cc1] | 8-(3,5-dichloropyridin-2-yl)-9-(4-((1-(3-fluoropropyl)azetidin-3-yl)methyl)phenyl)-6,7-dihydro-5H-benzo[7]annulene-3-carboxylic acid |
| 235 | 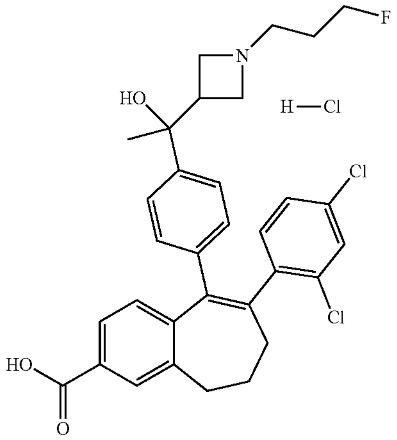 Isomer 1 | 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, hydrochloride Isomer 1 |
| 236 | 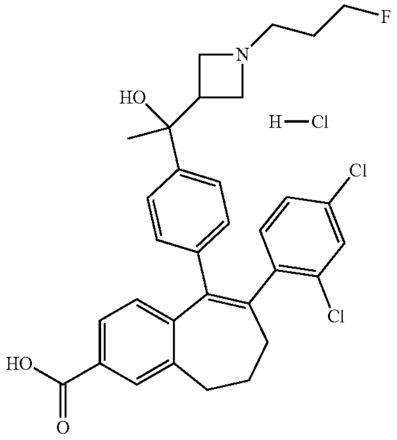 Isomer 2 | 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, hydrochloride Isomer 2 |

TABLE 1a-continued

| Example or compound | Structure | Name |
|---|---|---|
| 237 | 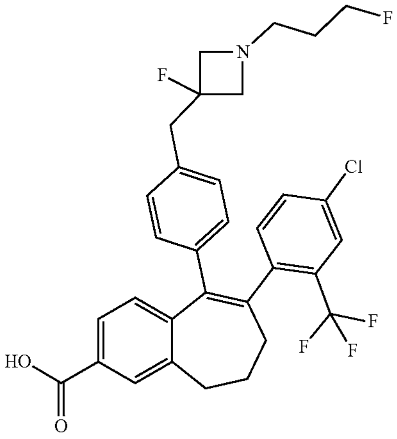 [SMILES: O=C(O)c1ccc2c(c1)CCCC(c1ccc(Cl)cc1C(F)(F)F)=C2c1ccc(CC2(F)CN(CCCF)C2)cc1] | 8-(4-chloro-2-(trifluoromethyl)phenyl)-9-(4-((3-fluoro-1-(3-fluoropropyl)azetidin-3-yl)methyl)phenyl)-6,7-dihydro-5H-benzo[7]annulene-3-carboxylic acid |
| 238 | 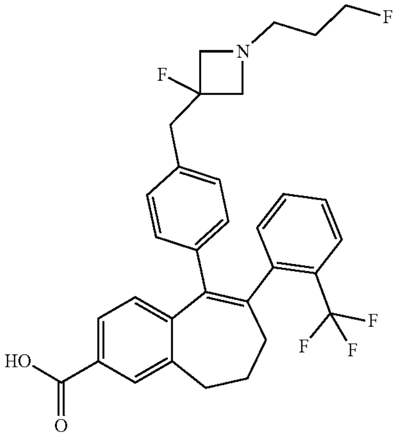 [SMILES: O=C(O)c1ccc2c(c1)CCCC(c1ccccc1C(F)(F)F)=C2c1ccc(CC2(F)CN(CCCF)C2)cc1] | 9-(4-((3-fluoro-1-(3-fluoropropyl)azetidin-3-yl)methyl)phenyl)-8-(2-(trifluoromethyl)phenyl)-6,7-dihydro-5H-benzo[7]annulene-3-carboxylic acid |
| 239 | 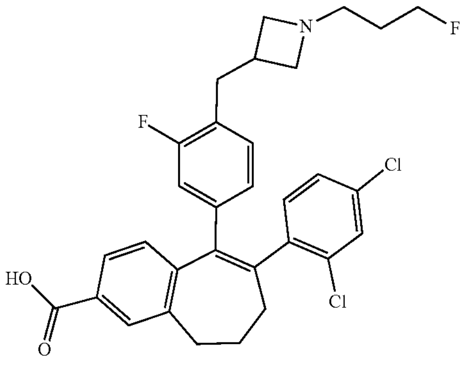 [SMILES: O=C(O)c1ccc2c(c1)CCCC(c1ccc(Cl)cc1Cl)=C2c1ccc(CC2CN(CCCF)C2)c(F)c1] | 8-(2,4-dichlorophenyl)-9-(3-fluoro-4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 240 | 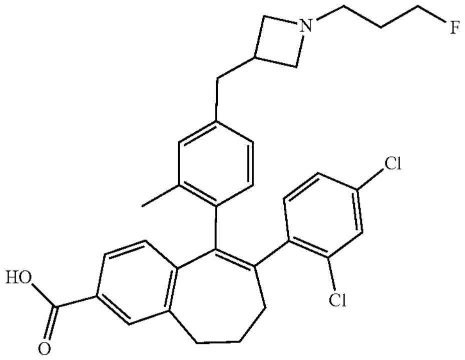 [SMILES: Cc1cc(CC2CN(CCCF)C2)ccc1C1=C(c2ccc(Cl)cc2Cl)CCCc2cc(C(=O)O)ccc21] | 8-(2,4-dichlorophenyl)-9-(4-((1-(3-fluoropropyl)azetidin-3-yl)methyl)-2-methylphenyl)-6,7-dihydro-5H-benzo[7]annulene-3-carboxylic acid |
| 241 | 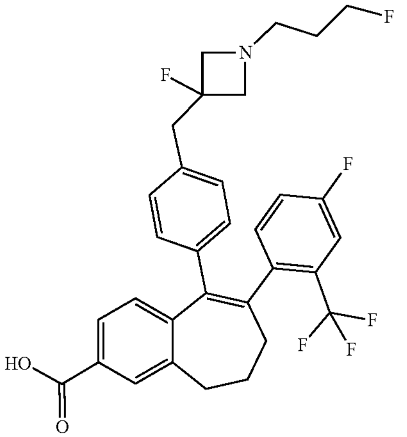 [SMILES: O=C(O)c1ccc2c(c1)CCCC(c1ccc(F)cc1C(F)(F)F)=C2c1ccc(CC2(F)CN(CCCF)C2)cc1] | 9-(4-((3-fluoro-1-(3-fluoropropyl)azetidin-3-yl)methyl)phenyl)-8-(4-fluoro-2-(tifluoromethyl)phenyl)-6,7-dihydro-5H-benzo[7]annulene-3-carboxylic acid |
| 242 | 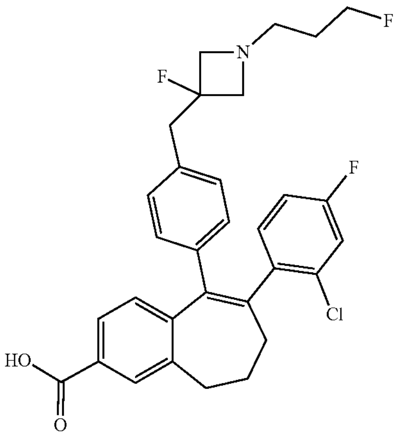 [SMILES: O=C(O)c1ccc2c(c1)CCCC(c1ccc(F)cc1Cl)=C2c1ccc(CC2(F)CN(CCCF)C2)cc1] | 8-(2-chloro-4-fluorophenyl)-9-(4-((3-fluoro-1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 243 | 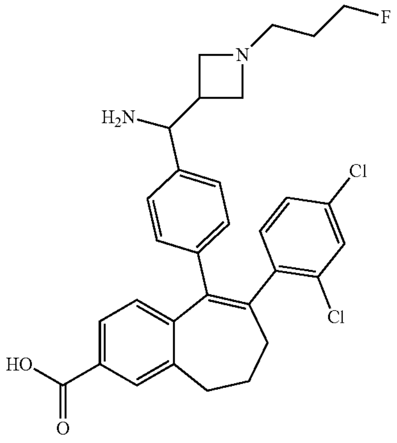 Isomer 1 | 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 1 |
| 244 | 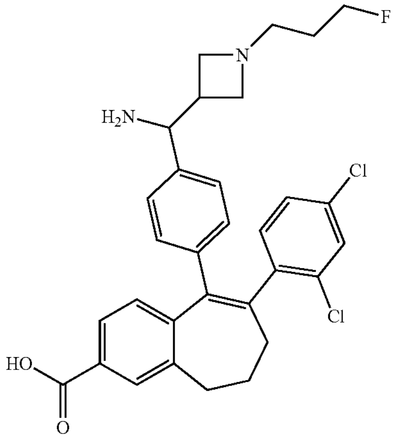 Isomer 2 | 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 2 |
| 245 | 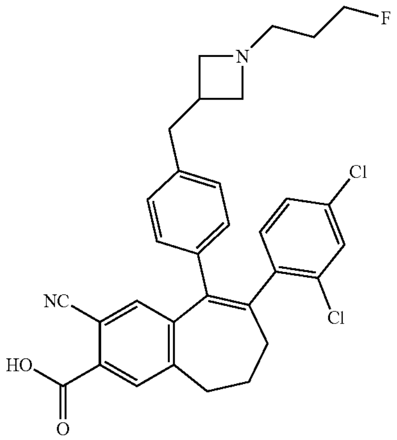 [SMILES: N#Cc1cc2c(cc1C(=O)O)CCCC(c1ccc(Cl)cc1Cl)=C2c1ccc(CC2CN(CCCF)C2)cc1] | 2-cyano-8-(2,4-dichlorophenyl)-9-(4-((1-(3-flurooropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 246 | 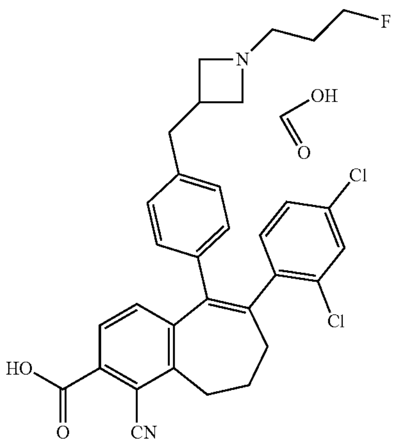 | 4-cyano-8-(2,4-dichlorophenyl)-9-(4-((1-(3-fluoropropyl)azetidin-3-yl)methyl)phenyl)-6,7-dihydro-5H-benzo[7]annulene-3-carboxylic acid, formic acid |
| 247 | 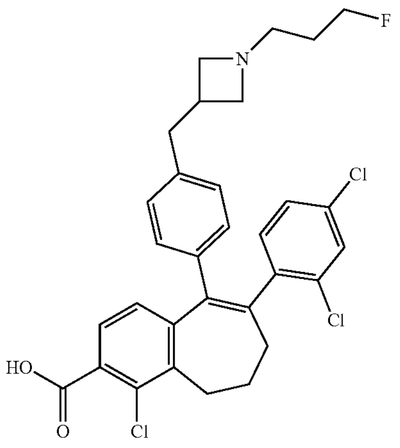 [SMILES: O=C(O)c1ccc2c(c1Cl)CCCC(c1ccc(Cl)cc1Cl)=C2c1ccc(CC2CN(CCCF)C2)cc1] | 4-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid |
| 248 | 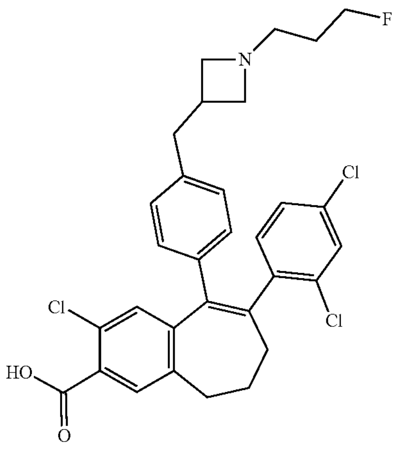 [SMILES: O=C(O)c1cc2c(cc1Cl)C(c1ccc(CC3CN(CCCF)C3)cc1)=C(c1ccc(Cl)cc1Cl)CCC2] | 2-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 249 | 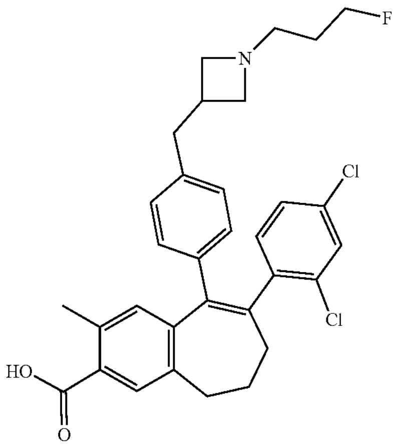 [SMILES: Cc1cc2c(cc1C(=O)O)CCCC(c1ccc(Cl)cc1Cl)=C2c1ccc(CC2CN(CCCF)C2)cc1] | 8-(2,4-dichlorophenyl)-9-(4-((1-(3-fluoropropyl)azetidin-3-yl)methyl)phenyl)-2-methyl-6,7-dihydro-5H-benzo[7]annulene-3-carboxylic acid |
| 250 | 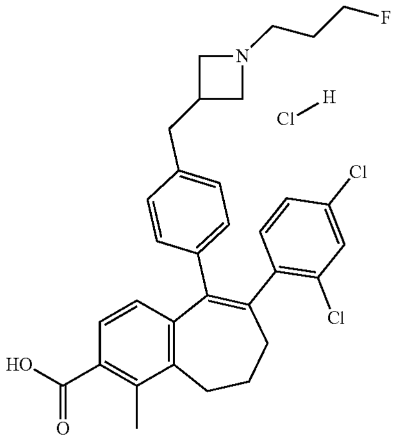 | 8-(2,4-dichlorophenyl)-9-(4-((1-(3-fluoropropyl)azetidin-3-yl)methyl)phenyl)-4-methyl-6,7-dihydro-5H-benzo[7]annulene-3-carboxylic acid hydrochlroide |
| 251 | 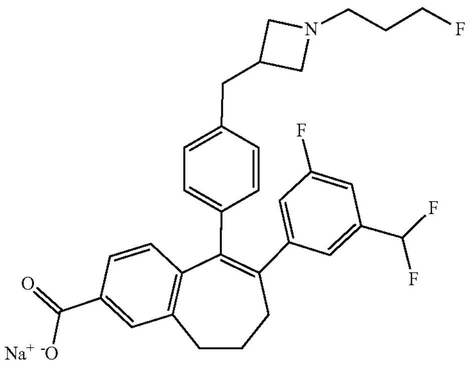 | sodium 8-(3-(difluoromethyl)-5-fluorophenyl)-9-(4-((1-(3-fluoropropyl)azetidin-3-yl)methyl)phenyl)-6,7-dihydro-5H-benzo[7]annulene-3-carboxylate |

TABLE 1a-continued
| Example or compound | Structure | Name |
|---|---|---|
| 252 | 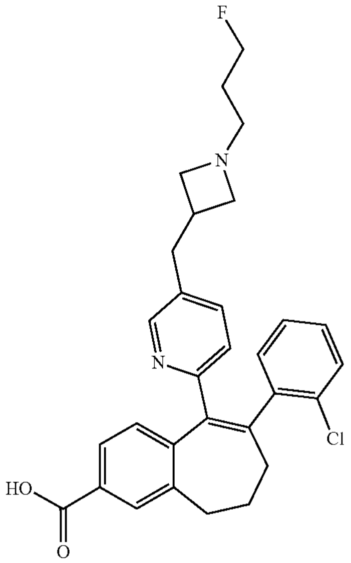 [SMILES: O=C(O)c1ccc2c(c1)CCCC(c1ccccc1Cl)=C2c1ccc(CC2CN(CCCF)C2)cn1] | 8-(2-chlorophenyl)-9-(5-((1-(3-fluoropropyl)azetidin-3-yl)methyl)pyridin-2-yl)-6,7-dihydro-5H-benzo[7]annulene-3-carboxylic acid |
| 253 | 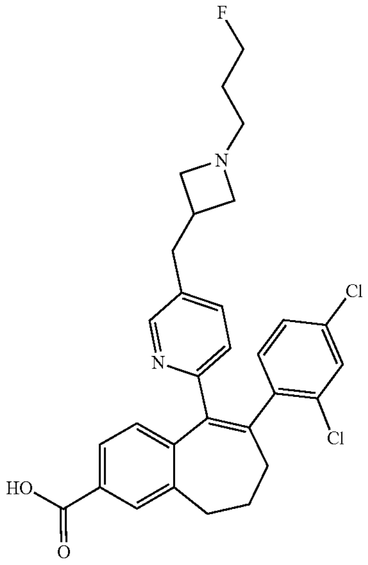 [SMILES: O=C(O)c1ccc2c(c1)CCCC(c1ccc(Cl)cc1Cl)=C2c1ccc(CC2CN(CCCF)C2)cn1] | 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic acid |
| 254 | 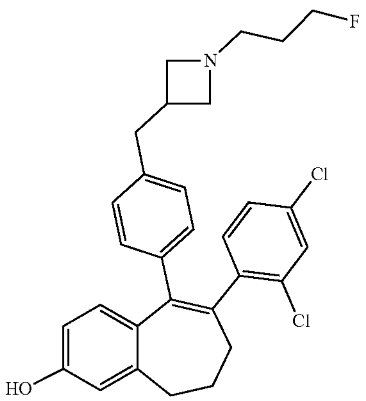 [SMILES: Oc1ccc2c(c1)CCCC(c1ccc(Cl)cc1Cl)=C2c1ccc(CC2CN(CCCF)C2)cc1] | 8-(2,4-dichlorophenyl)-9-(4-((1-(3-fluoropropyl)azetidin-3-yl)methyl)phenyl)-6,7-dihydro-5H-benzo[7]annulen-3-ol |

TABLE 1a-continued

| Example or compound | Structure | Name |
| --- | --- | --- |
| 255 | 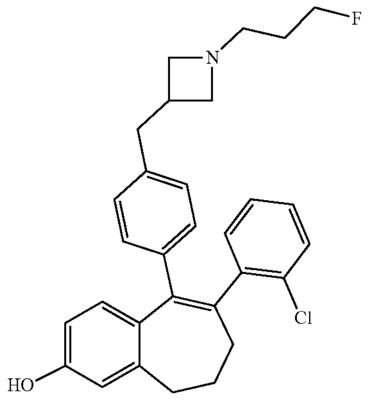 [SMILES: Oc1ccc2c(c1)CCCC(c1ccccc1Cl)=C2c1ccc(CC2CN(CCCF)C2)cc1] | 8-(2-chlorophenyl)-9-(4-((1-(3-fluoropropyl)azetidin-3-yl)methyl)phenyl)-6,7-dihydro-5H-benzo[7]annulen-3-ol |
| 256 | 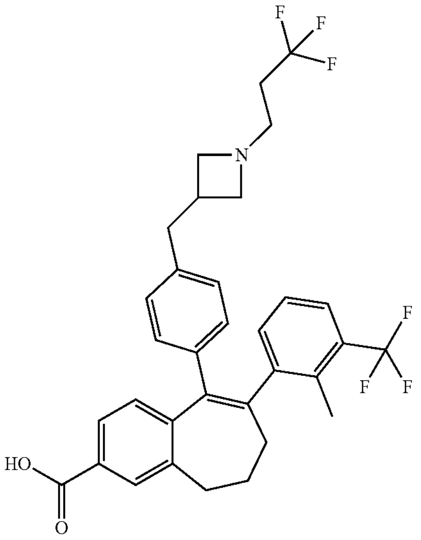 [SMILES: Cc1c(C2=C(c3ccc(CC4CN(CCC(F)(F)F)C4)cc3)c3ccc(C(=O)O)cc3CCC2)cccc1C(F)(F)F] | 8-(2-methyl-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid |
| 257 | 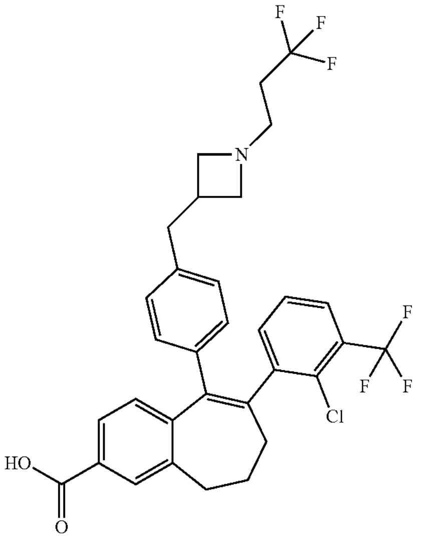 [SMILES: O=C(O)c1ccc2c(c1)CCCC(c1cccc(C(F)(F)F)c1Cl)=C2c1ccc(CC2CN(CCC(F)(F)F)C2)cc1] | 8-(2-chloro-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid |

TABLE 1a-continued
| Example or compound | Structure | Name |
| --- | --- | --- |
| 258 | 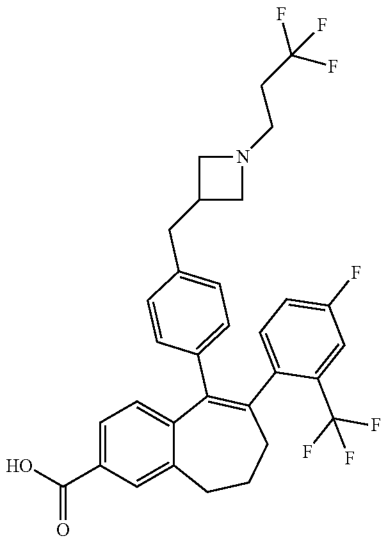 [SMILES: O=C(O)c1ccc2c(c1)CCCC(c1ccc(F)cc1C(F)(F)F)=C2c1ccc(CC2CN(CCC(F)(F)F)C2)cc1] | 8-(4-fluoro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid |
| 259 | 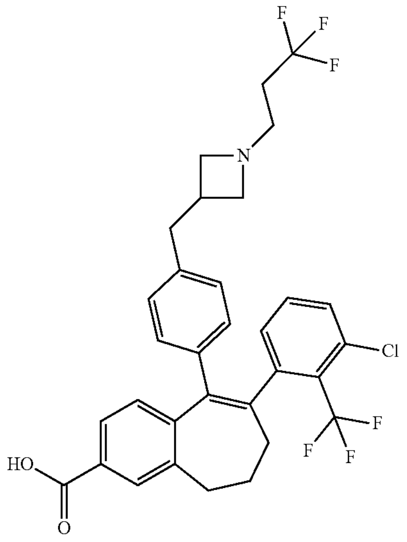 [SMILES: O=C(O)c1ccc2c(c1)CCCC(c1cccc(Cl)c1C(F)(F)F)=C2c1ccc(CC2CN(CCC(F)(F)F)C2)cc1] | 8-(3-chloro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 260 | 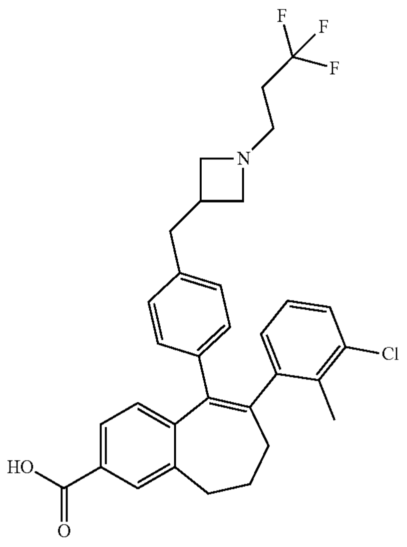 [SMILES: Cc1c(Cl)cccc1C1=C(c2ccc(CC3CN(CCC(F)(F)F)C3)cc2)c2ccc(C(=O)O)cc2CCC1] | 8-(3-chloro-2-methylphenyl)-9-(4-((1-(3,3,3-trifluoropropyl)azetidin-3-yl)methyl)phenyl)-6,7-dihydro-5H-benzo[7]annulene-3-carboxylic acid |
| 261 | 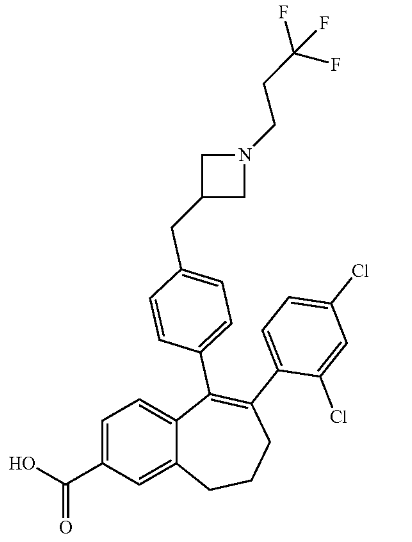 [SMILES: O=C(O)c1ccc2c(c1)CCCC(c1ccc(Cl)cc1Cl)=C2c1ccc(CC2CN(CCC(F)(F)F)C2)cc1] | 8-(2,4-dichloropehnyl)-9-(4-((1-(3,3,3-trifluoropropyl)azetidin-3-yl)methyl)phenyl)-6,7-dihydro-5H-benzo[7]annulene-3-carboxylic acid |
| 262 | 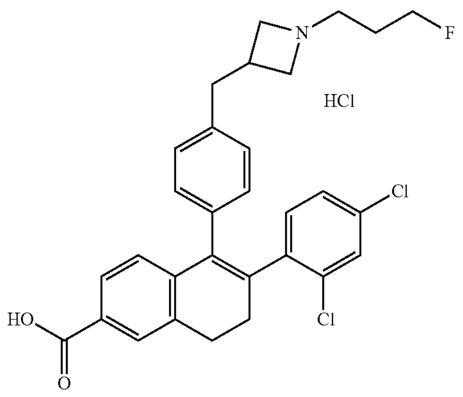 [SMILES: O=C(O)c1ccc2c(c1)CCC(c1ccc(Cl)cc1Cl)=C2c1ccc(CC2CN(CCCF)C2)cc1 ; Cl] | 6-(2,4-dichlorophenyl)-5-(4-((1-(3-fluoropropyl)azetidin-3-yl)methyl)phenyl)-7,8-dihydronaphthalene-2-carboxylic acid hydrochloride |

TABLE 1a-continued

| Example or compound | Structure | Name |
| --- | --- | --- |
| 263 | 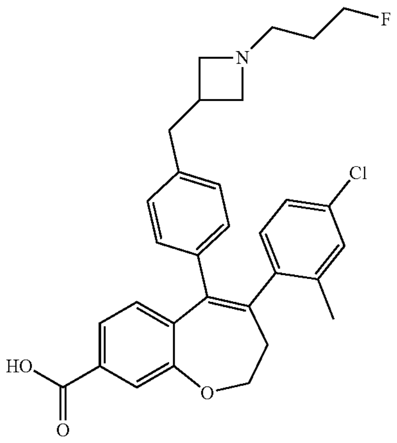 [SMILES: Cc1cc(Cl)ccc1C1=C(c2ccc(CC3CN(CCCF)C3)cc2)c2ccc(C(=O)O)cc2OCC1] | 4-(4-chloro-2-methylphenyl)-5-(4-((1-(3-fluoropropyl)azetidin-3-yl)methyl)phenyl)-2,3-dihydrobenzo[b]oxepine-8-carboxylic acid |
| 264 | 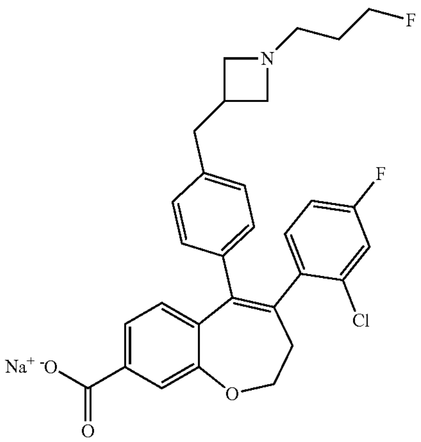 | sodium 4-(2-chloro-4-fluorophenyl)-5-(4-((1-(3-fluoropropyl)azetidin-3-yl)methyl)phenyl)-2,3-dihydrobenzo[b]oxepine-8-carboxylate |
| 265 | 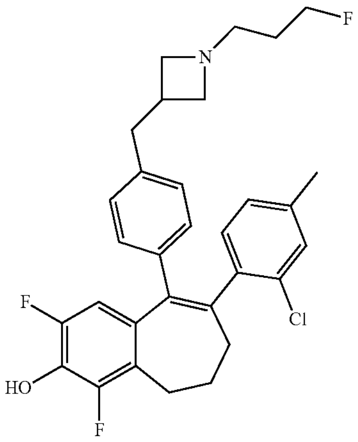 [SMILES: Cc1ccc(C2=C(c3ccc(CC4CN(CCCF)C4)cc3)c3cc(F)c(O)c(F)c3CCC2)c(Cl)c1] | 8-(2-chloro-4-methylphenyl)-2,4-difluoro-9-(4-((1-(3-fluoropropyl)azetidin-3-yl)methyl)phenyl)-6,7-dihydro-5H-benzo[7]annulen-3-ol |

TABLE 1a-continued

| Example or compound | Structure | Name |
| --- | --- | --- |
| 266 | 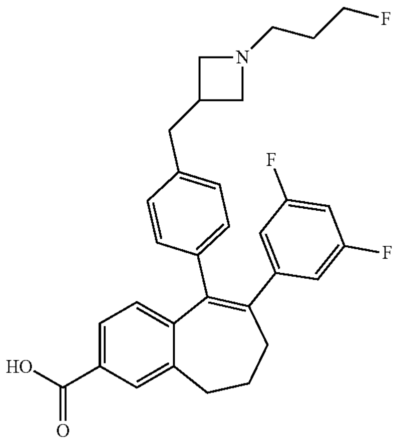 [SMILES: O=C(O)c1ccc2c(c1)CCCC(c1cc(F)cc(F)c1)=C2c1ccc(CC2CN(CCCF)C2)cc1] | 8-(3,5-difluorophenyl)-9-(4-((1-(3-fluoropropyl)azetidin-3-yl)methyl)phenyl)-6,7-dihydro-5H-benzo[7]annulene-3-carboxylic acid |
| 267 | 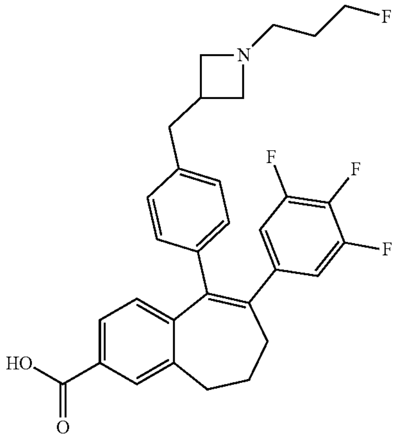 [SMILES: O=C(O)c1ccc2c(c1)CCCC(c1cc(F)c(F)c(F)c1)=C2c1ccc(CC2CN(CCCF)C2)cc1] | 9-(4-((1-(3-fluoropropyl)azetidin-3-yl)methyl)phenyl)-8-(3,4,5-trifluorophenyl)-6,7-dihydro-5H-benzo[7]annulene-3-carboxylic acid |
| 268 | 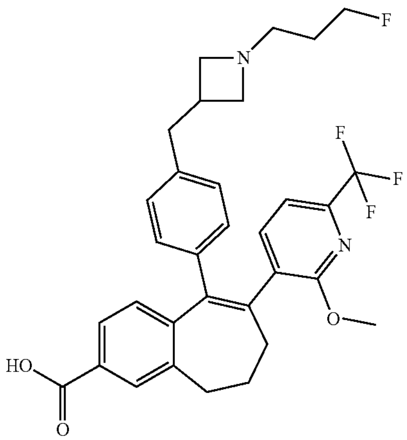 [SMILES: COc1nc(C(F)(F)F)ccc1C1=C(c2ccc(CC3CN(CCCF)C3)cc2)c2ccc(C(=O)O)cc2CCC1] | 9-(4-((1-(3-fluoropropyl)azetidin-3-yl)methyl)phenyl)-8-(2-methoxy-6-(trifluoromethyl)pyridin-3-yl)-6,7-dihydro-5H-benzo[7]annulene-3-carboxylic acid |

TABLE 1a-continued

| Example or compound | Structure | Name |
|---|---|---|
| 269 | 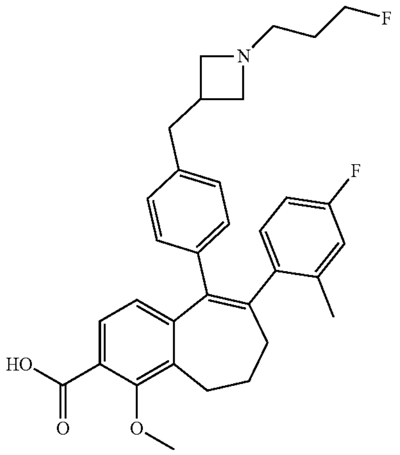 [SMILES: COc1c(C(=O)O)ccc2c1CCCC(c1ccc(F)cc1C)=C2c1ccc(CC2CN(CCCF)C2)cc1] | 8-(4-fluoro-2-methylphenyl)-9-(4-((1-(3-fluoropropyl)azetidin-3-yl)methyl)phenyl)-4-methoxy-6,7-dihydro-5H-benzo[7]annulene-3-carboxylic acid |
| 270 | 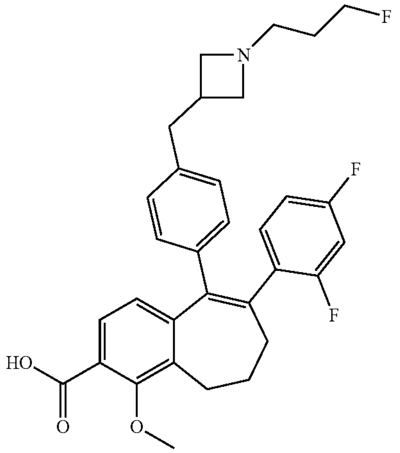 | 8-(2,4-difluorophenyl)-9-(4-((1-(3-fluoropropyl)azetidin-3-yl)methyl)phenyl)-4-methoxy-6,7-dihydro-5H-benzo[7]annulene-3-carboxylic acid |
| 271 | 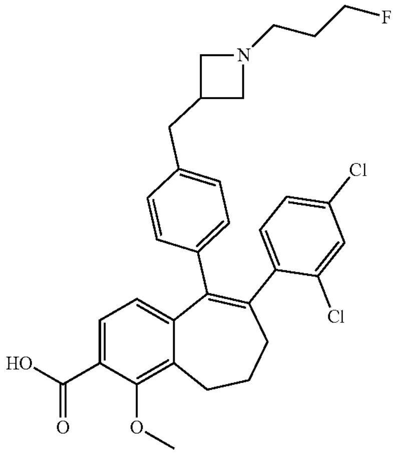 [SMILES: COc1c(C(=O)O)ccc2c1CCCC(c1ccc(Cl)cc1Cl)=C2c1ccc(CC2CN(CCCF)C2)cc1] | 8-(2,4-dichlorophenyl)-9-(4-((1-(3-fluoropropyl)azetidin-3-yl)methyl)phenyl)-4-methoxy-6,7-dihydro-5H-benzo[7]annulene-3-carboxylic acid |

TABLE 1a-continued

| Example or compound | Structure | Name |
|---|---|---|
| 272 | 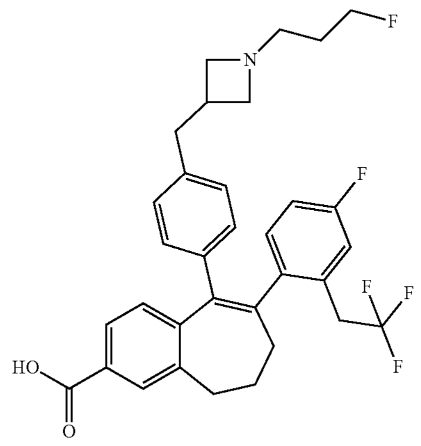 [SMILES: O=C(O)c1ccc2c(c1)CCCC(c1ccc(F)cc1CC(F)(F)F)=C2c1ccc(CC2CN(CCCF)C2)cc1] | 8-(4-fluoro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid |
| 273 | 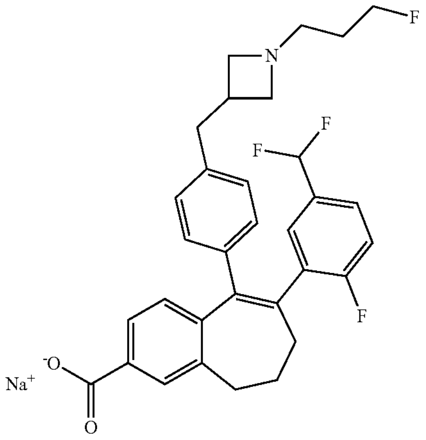 | sodium 8-(5-(difluoromethyl)-2-fluorophenyl)-9-(4-((1-(3-fluoropropyl)azetidin-3-yl)methyl)phenyl)-6,7-dihydro-5H-benzo[7]annulene-3-carboxylate |
| 274 | 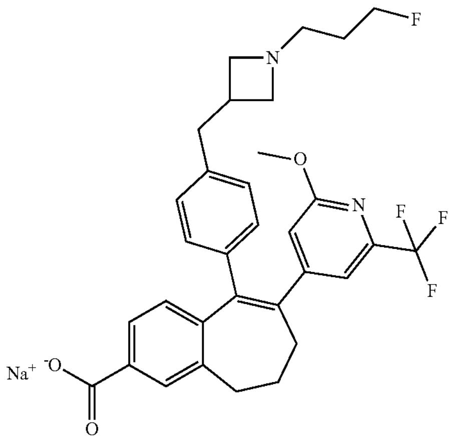 | sodium 9-(4-((1-(3-fluoropropyl)azetidin-3-y)methyl)phenyl)-8-(2-methoxy-6-(trifluoromethyl)pyridin-4-yl)-6,7-dihydro-5H-benzo[7]annulene-3-carboxylate |

TABLE 1a-continued

| Example or compound | Structure | Name |
| --- | --- | --- |
| 275 | 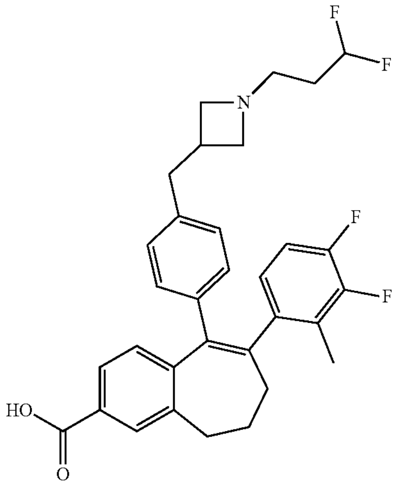 [SMILES: Cc1c(C2=C(c3ccc(CC4CN(CCC(F)F)C4)cc3)c3ccc(C(=O)O)cc3CCC2)ccc(F)c1F] | 8-(3,4-difluoro-2-methylphenyl)-9-(4-((1-(3,3-difluoropropyl)azetidin-3-yl)methyl)phenyl)-6,7-dihydro-5H-benzo[7]annulene-3-carboxylic acid |
| 276 | 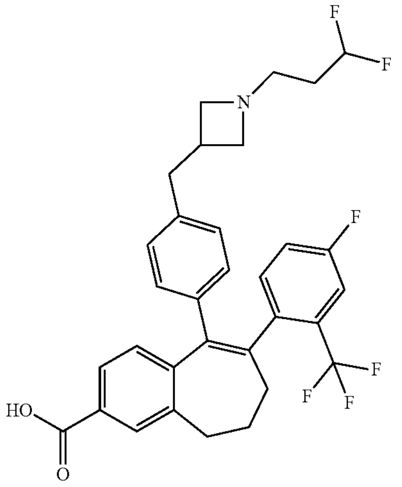 [SMILES: O=C(O)c1ccc2c(c1)CCCC(c1ccc(F)cc1C(F)(F)F)=C2c1ccc(CC2CN(CCC(F)F)C2)cc1] | 9-(4-((1-(3,3-difluoropropyl)azetidin-3-yl)methyl)phenyl)-8-(4-fluoro-2-(trifluoromethyl)phenyl)-6,7-dihydro-5H-benzo[7]annulene-3-carboxylic acid |
| 277 | 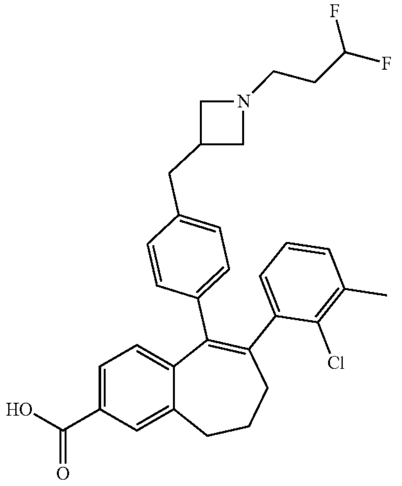 [SMILES: Cc1cccc(C2=C(c3ccc(CC4CN(CCC(F)F)C4)cc3)c3ccc(C(=O)O)cc3CCC2)c1Cl] | 8-(2-chloro-3-methylphenyl)-9-(4-((1-(3,3-difluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 278 | 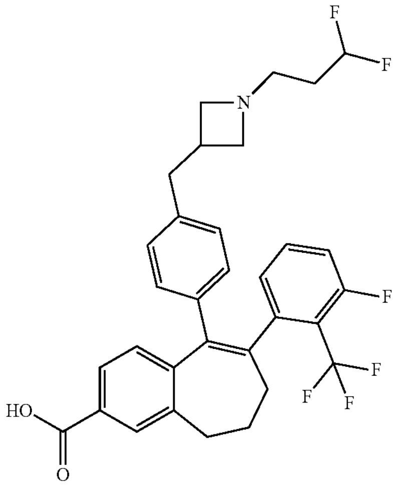 [SMILES: O=C(O)c1ccc2c(c1)CCCC(c1cccc(F)c1C(F)(F)F)=C2c1ccc(CC2CN(CCC(F)F)C2)cc1] | 9-(4-((1-(3,3-difluoropropyl)azetidin-3-yl)methyl)phenyl)-8-(3-fluoro-2-(trifluoromethyl)phenyl)-6,7-dihydro-5H-benzo[7]annulene-3-carboxylic acid |
| 279 | 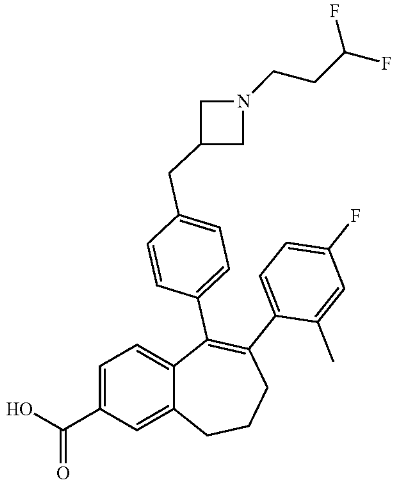 [SMILES: Cc1cc(F)ccc1C1=C(c2ccc(CC3CN(CCC(F)F)C3)cc2)c2ccc(C(=O)O)cc2CCC1] | 9-(4-((1-(3,3-difluoropropyl)azetidin-3-yl)methyl)phenyl)-8-(4-fluoro-2-methylphenyl)-6,7-dihydro-5H-benzo[7]annulene-3-carboxylic acid |
| 280 | 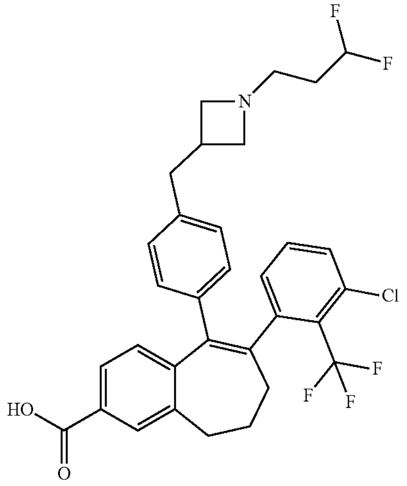 [SMILES: O=C(O)c1ccc2c(c1)CCCC(c1cccc(Cl)c1C(F)(F)F)=C2c1ccc(CC2CN(CCC(F)F)C2)cc1] | 8-(3-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 281 | 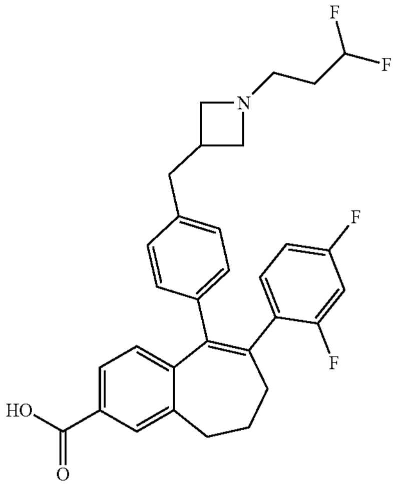 | 8-(2,4-difluorophenyl)-9-(4-((1-(3,3-difluoropropyl)azetidin-3-yl)methyl)phenyl)-6,7-dihydro-5H-benzo[7]annulene-3-carboxylic acid |
| 282 | 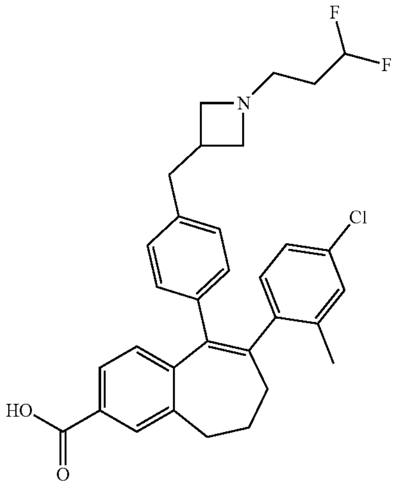 [SMILES: Cc1cc(Cl)ccc1C1=C(c2ccc(CC3CN(CCC(F)F)C3)cc2)c2ccc(C(=O)O)cc2CCC1] | 8-(4-chloro-2-methylphenyl)-9-(4-((1-(3,3-difluoropropyl)azetidin-3-yl)methyl)phenyl)-6,7-dihydro-5H-benzo[7]annulene-3-carboxylic acid |
| 283 | 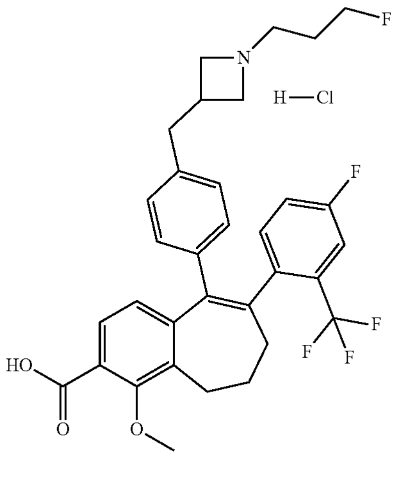 | 8-(4-fluoro-2-(trifluoromethyl)phenyl)-9-(4-((1-(3-fluoropropyl)azetidin-3-yl)methyl)phenyl)-4-methoxy-6,7-dihydro-5H-benzo[7]annulene-3-carboxylic acid hydrochloride |

TABLE 1a-continued

| Example or compound | Structure | Name |
|---|---|---|
| 284 | 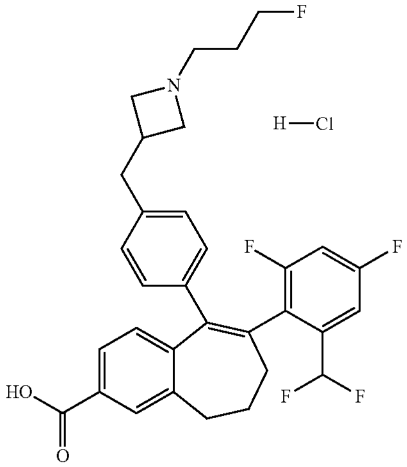 [SMILES: O=C(O)c1ccc2c(c1)CCCC(c1c(F)cc(F)cc1C(F)F)=C2c1ccc(CC2CN(CCCF)C2)cc1 ; Cl] | 8-(2-(difluoromethyl)-4,6-difluorophenyl)-9-(4-((1-(3-fluoropropyl)azetidin-3-yl)methyl)phenyl)-6,7-dihydro-5H-benzo[7]annulene-3-carboxylic acid hydrochloride |
| 285 | 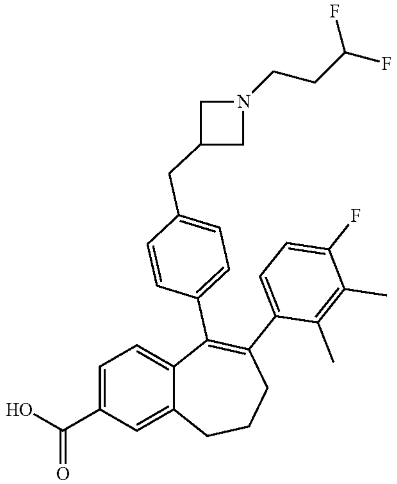 | 9-(4-((1-(3,3-difluoropropyl)azetidin-3-yl)methyl)phenyl)-8-(4-fluoro-2,3-dimethylphenyl)-6,7-dihydro-5H-benzo[7]annulene-3-carboxylic acid |
| 286 | 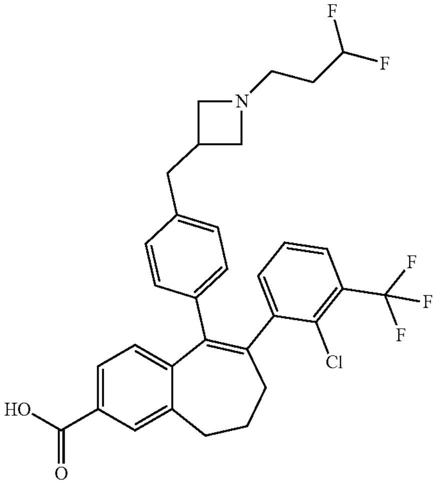 [SMILES: O=C(O)c1ccc2c(c1)CCCC(c1cccc(C(F)(F)F)c1Cl)=C2c1ccc(CC2CN(CCC(F)F)C2)cc1] | 8-(2-chloro-3-(trifluoromethyl)phenyl)-9-(4-((1-(3,3-difluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 287 | 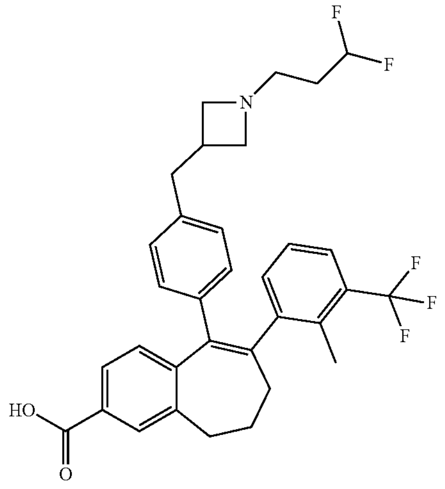 [SMILES: Cc1c(C2=C(c3ccc(CC4CN(CCC(F)F)C4)cc3)c3ccc(C(=O)O)cc3CCC2)cccc1C(F)(F)F] | 9-(4-((1-(3,3-difluoropropyl)azetidin-3-yl)methyl)phenyl)-8-(2-methyl-3-(trifluoromethyl)phenyl)-6,7-dihydro-5H-benzo[7]annulene-3-carboxylic acid |
| 288 | 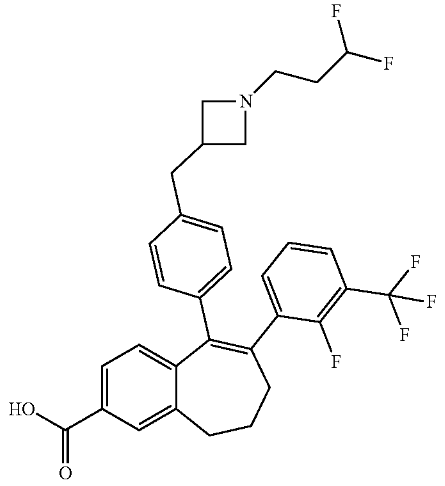 [SMILES: O=C(O)c1ccc2c(c1)CCCC(c1cccc(C(F)(F)F)c1F)=C2c1ccc(CC2CN(CCC(F)F)C2)cc1] | 9-(4-((1-(3,3-difluoropropyl)azetidin-3-yl)methyl)phenyl)-8-(2-fluoro-3-(trifluoromethyl)phenyl)-6,7-dihydro-5H-benzo[7]annulene-3-carboxylic acid |
| 289 | 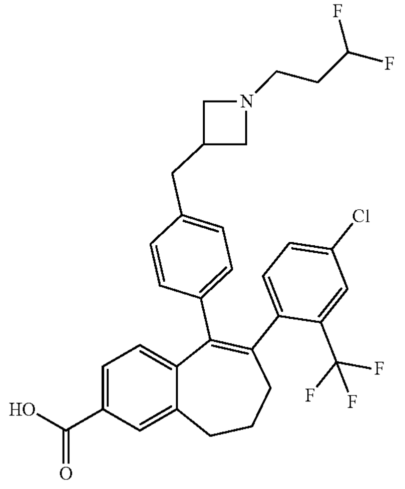 [SMILES: O=C(O)c1ccc2c(c1)CCCC(c1ccc(Cl)cc1C(F)(F)F)=C2c1ccc(CC2CN(CCC(F)F)C2)cc1] | 8-(4-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 290 | 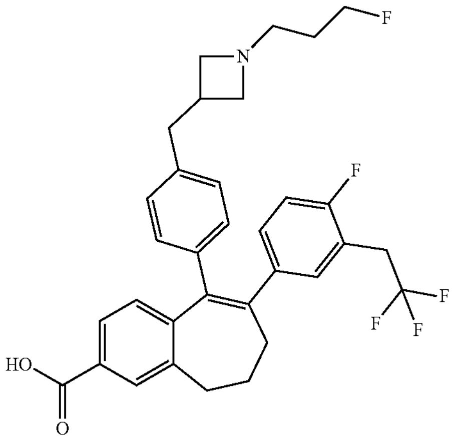 [SMILES: O=C(O)c1ccc2c(c1)CCCC(c1ccc(F)c(CC(F)(F)F)c1)=C2c1ccc(CC2CN(CCCF)C2)cc1] | 8-(4-fluoro-3-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid |
| 291 | 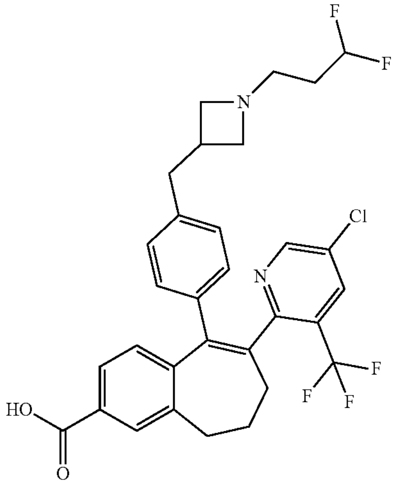 [SMILES: O=C(O)c1ccc2c(c1)CCCC(c1ncc(Cl)cc1C(F)(F)F)=C2c1ccc(CC2CN(CCC(F)F)C2)cc1] | 8-(5-chloro-3-(trifluoromethyl)pyridin-2-yl)-9-(4-((1-(3,3-difluoropropyl)azetidin-3-yl)methyl)phenyl)-6,7-dihydro-5H-benzo[7]annulene-3-carboxylic acid |
| 292 | 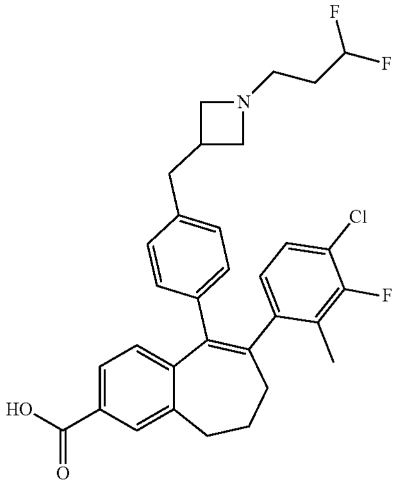 | 8-(4-chloro-3-fluoro-2-methylphenyl)-9-(4-((1-(3,3-difluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 293 | 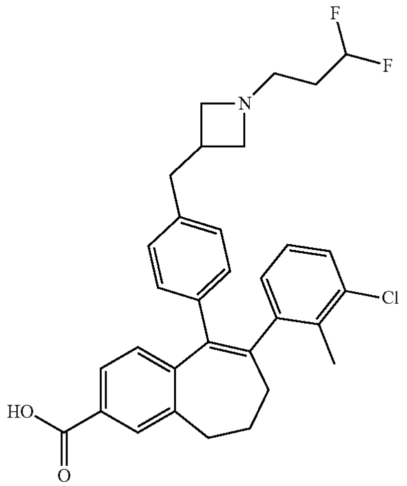 [SMILES: Cc1c(Cl)cccc1C1=C(c2ccc(CC3CN(CCC(F)F)C3)cc2)c2ccc(C(=O)O)cc2CCC1] | 8-(3-chloro-2-methylphenyl)-9-(4-((1-(3,3-difluoropropyl)azetidin-3-yl)methyl)phenyl)-6,7-dihydro-5H-benzo[7]annulene-3-carboxylic acid |
| 294 | 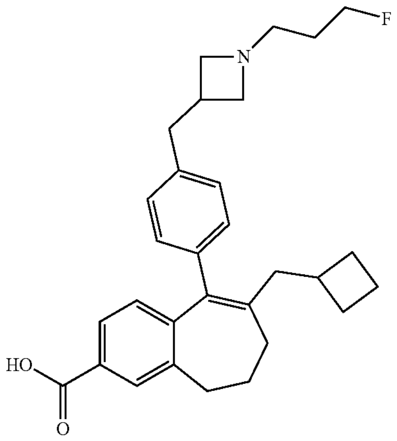 [SMILES: O=C(O)c1ccc2c(c1)CCCC(CC1CCC1)=C2c1ccc(CC2CN(CCCF)C2)cc1] | 8-(cyclobutylmethyl)-9-(4-((1-(3-fluoropropyl)azetidin-3-yl)methyl)phenyl)-6,7-dihydro-5H-benzo[7]annulene-3-carboxylic acid |
| 295 | 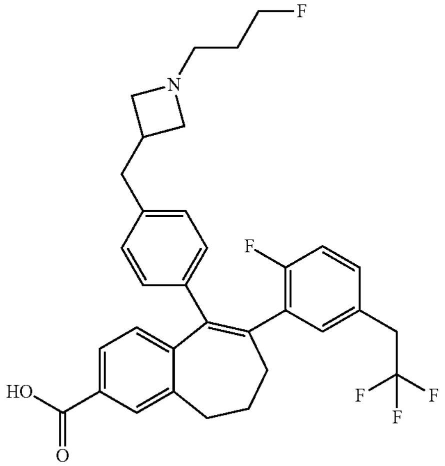 [SMILES: O=C(O)c1ccc2c(c1)CCCC(c1cc(CC(F)(F)F)ccc1F)=C2c1ccc(CC2CN(CCCF)C2)cc1] | 8-(2-fluoro-5-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 296 | 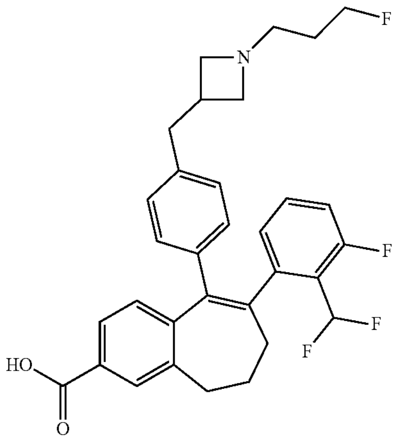 [SMILES: O=C(O)c1ccc2c(c1)CCCC(c1cccc(F)c1C(F)F)=C2c1ccc(CC2CN(CCCF)C2)cc1] | 8-(2-(difluoromethyl)-3-fluorophenyl)-9-(4-((1-(3-fluoropropyl)azetidin-3-yl)methyl)phenyl)-6,7-dihydro-5H-benzo[7]annulene-3-carboxylic acid |
| 297 | 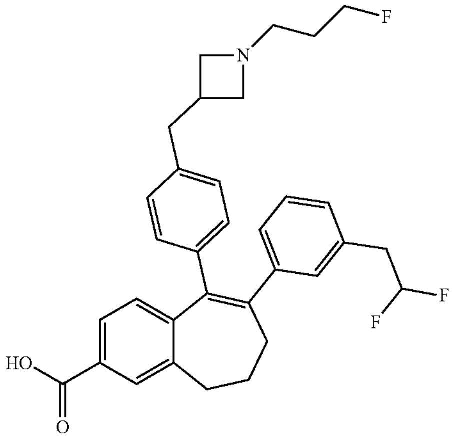 [SMILES: O=C(O)c1ccc2c(c1)CCCC(c1cccc(CC(F)F)c1)=C2c1ccc(CC2CN(CCCF)C2)cc1] | 8-(3-(2,2-difluoroethyl)phenyl)-9-(4-((1-(3-fluoropropyl)azetidin-3-yl)methyl)phenyl)-6,7-dihydro-5H-benzo[7]annulene-3-carboxylic acid |
| 298 | 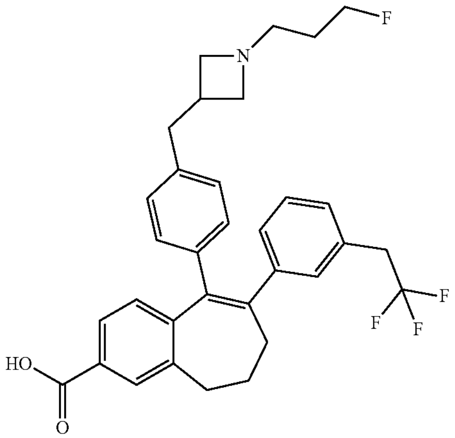 [SMILES: O=C(O)c1ccc2c(c1)CCCC(c1cccc(CC(F)(F)F)c1)=C2c1ccc(CC2CN(CCCF)C2)cc1] | 9-(4-((1-(3-fluoropropyl)azetidin-3-yl)methyl)phenyl)-8-(3-(2,2,2-trifluoroethyl)phenyl)-6,7-dihydro-5H-benzo[7]annulene-3-carboxylic acid |

TABLE 1a-continued

| Example or compound | Structure | Name |
|---|---|---|
| 299 | 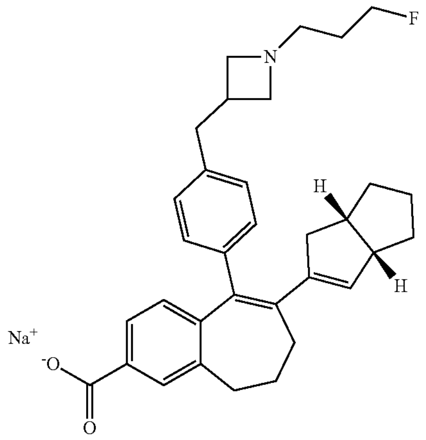 | sodium 9-(4-((1-(3-fluoropropyl)azetidin-3-yl)methyl)phenyl)-8-(cis-1,3a,4,5,6,6a-hexahydropentalen-2-yl)-6,7-dihydro-5H-benzo[7]annulene-3-carboxylate |
| 300 | 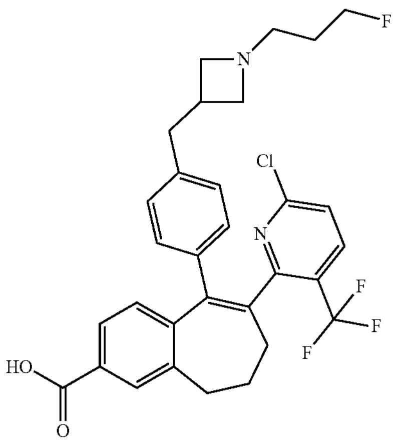 [SMILES: O=C(O)c1ccc2c(c1)CCCC(c1nc(Cl)ccc1C(F)(F)F)=C2c1ccc(CC2CN(CCCF)C2)cc1] | 8-(6-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid |
| 301 | 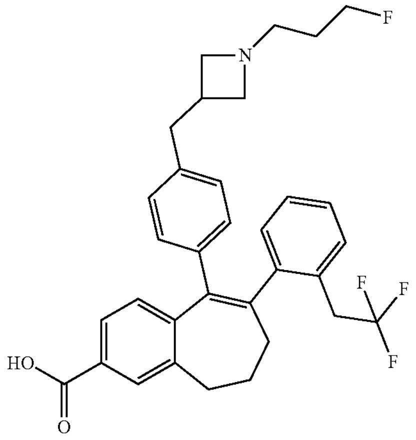 [SMILES: O=C(O)c1ccc2c(c1)CCCC(c1ccccc1CC(F)(F)F)=C2c1ccc(CC2CN(CCCF)C2)cc1] | 9-(4-((1-(3-fluoropropyl)azetidin-3-yl)methyl)phenyl)-8-(2-(2,2,2-trifluoroethyl)phenyl)-6,7-dihydro-5H-benzo[7]annulene-3-carboxylic acid |

TABLE 1a-continued

| Example or compound | Structure | Name |
|---|---|---|
| 302 | 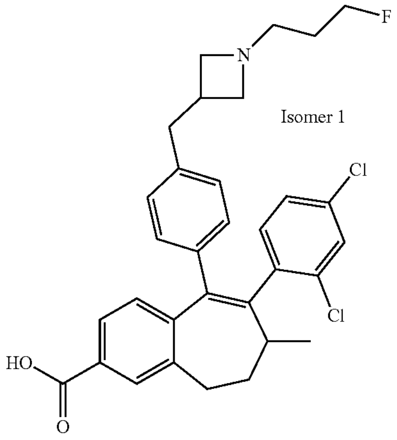 [SMILES: CC1CCc2cc(C(=O)O)ccc2C(c2ccc(CC3CN(CCCF)C3)cc2)=C1c1ccc(Cl)cc1Cl] Isomer 1 | 8-(2,4-dichlorophenyl)-9-(4-((1-(3-fluoropropyl)azetidin-3-yl)methyl)phenyl)-7-methyl-6,7-dihydro-5H-benzo[7]annulene-3-carboxylic acid Isomer 1 (50/50 mixture of atropoisomers) |
| 303 | 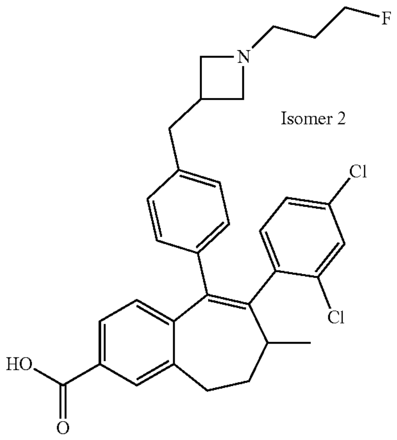 [SMILES: CC1CCc2cc(C(=O)O)ccc2C(c2ccc(CC3CN(CCCF)C3)cc2)=C1c1ccc(Cl)cc1Cl] Isomer 2 | 8-(2,4-dichlorophenyl)-9-(4-((1-(3-fluoropropyl)azetidin-3-yl)methyl)phenyl)-7-methyl-6,7-dihydro-5H-benzo[7]annulene-3-carboxylic acid Isomer 2 (50/50 mixture of atropoisomers) |
| 304 | 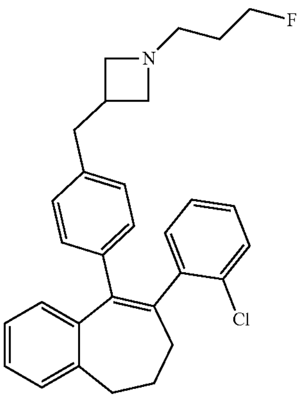 [SMILES: FCCCN1CC(Cc2ccc(C3=C(c4ccccc4Cl)CCCc4ccccc43)cc2)C1] | 3-(4-(8-(2-chlorophenyl)-6,7-dihydro-5H-benzo[7]annulen-9-yl)benzyl)-1-(3-fluoropropyl)azetidine |

TABLE 1a-continued

| Example or compound | Structure | Name |
| --- | --- | --- |
| 305 | 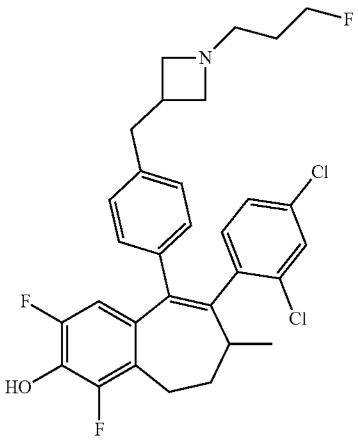 [SMILES: CC1CCc2c(cc(F)c(O)c2F)C(c2ccc(CC3CN(CCCF)C3)cc2)=C1c1ccc(Cl)cc1Cl] | 8-(2,4-dichlorophenyl)-2,4-difluoro-9-(4-((1-(3-fluoropropyl)azetidin-3-yl)methyl)phenyl)-6,7-dihydro-5H-benzo[7]annulen-3-ol |
| 306 | 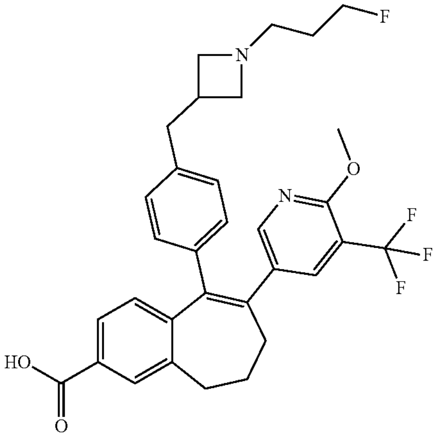 [SMILES: COc1ncc(C2=C(c3ccc(CC4CN(CCCF)C4)cc3)c3ccc(C(=O)O)cc3CCC2)cc1C(F)(F)F] | 9-(4-((1-(3-fluoropropyl)azetidin-3-yl)methyl)phenyl)-8-(6-methoxy-5-(trifluoromethyl)pyridin-3-yl)-6,7-dihydro-5H-benzo[7]annulene-3-carboxylic acid |
| 307 | 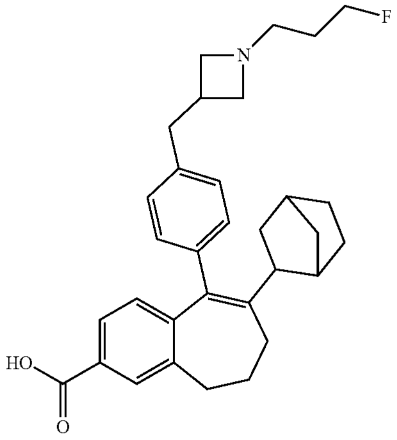 [SMILES: O=C(O)c1ccc2c(c1)CCCC(C1CC3CCC1C3)=C2c1ccc(CC2CN(CCCF)C2)cc1] | 8-(bicyclo[2.2.1]heptan-2-yl)-9-(4-((1-(3-fluoropropyl)azetidin-3-yl)methyl)phenyl)-6,7-dihydro-5H-benzo[7]annulene-3-carboxylic acid, mixture of isomers |

TABLE 1a-continued

| Example or compound | Structure | Name |
| --- | --- | --- |
| 308 | 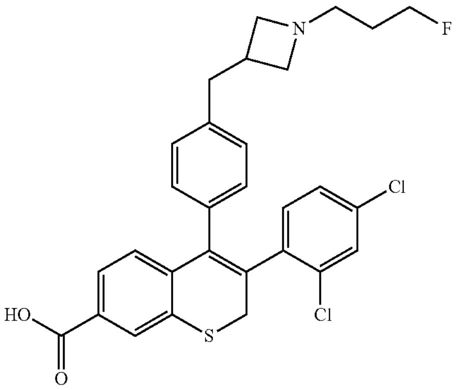 [SMILES: O=C(O)c1ccc2c(c1)SCC(c1ccc(Cl)cc1Cl)=C2c1ccc(CC2CN(CCCF)C2)cc1] | 3-(2,4-dichlorophenyl)-4-(4-((1-(3-fluoropropyl)azetidin-3-yl)methyl)phenyl)-2H-thiochromene-7-carboxylic acid |
| 309 | 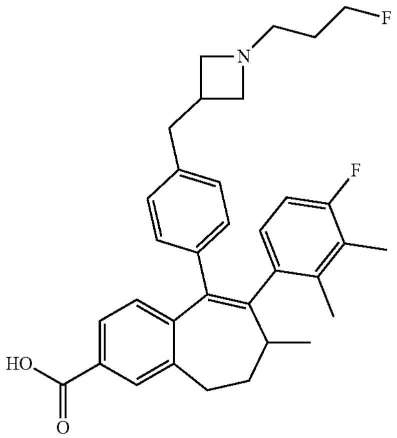 [SMILES: Cc1c(F)ccc(C2=C(c3ccc(CC4CN(CCCF)C4)cc3)c3ccc(C(=O)O)cc3CCC2C)c1C] | 8-(4-fluoro-2,3-dimethylphenyl)-9-(4-((1-(3-fluoropropyl)azetidin-3-yl)methyl)phenyl)-7-methyl-6,7-dihydro-5H-benzo[7]annulene-3-carboxylic acid, racemic mixture |
| 310 | 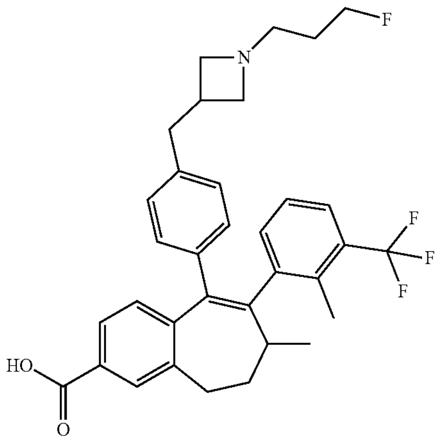 [SMILES: Cc1c(C2=C(c3ccc(CC4CN(CCCF)C4)cc3)c3ccc(C(=O)O)cc3CCC2C)cccc1C(F)(F)F] | 9-(4-((1-(3-fluoropropyl)azetidin-3-yl)methyl)phenyl)-7-methyl-8-(2-methyl-3-(trifluoromethyl)phenyl)-6,7-dihydro-5H-benzo[7]annulene-3-carboxylic acid, racemic mixture |

TABLE 1a-continued

| Example or compound | Structure | Name |
|---|---|---|
| 311 | 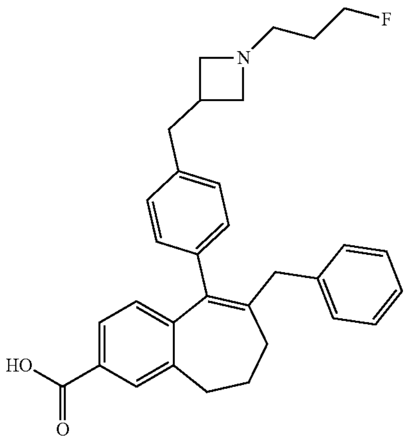 [SMILES: O=C(O)c1ccc2c(c1)CCCC(Cc1ccccc1)=C2c1ccc(CC2CN(CCCF)C2)cc1] | 8-benzyl-9-(4-((1-(3-fluoropropyl)azetidin-3-yl)methyl)phenyl)-6,7-dihydro-5H-benzo[7]annulene-3-carboxylic acid |
| 312 | 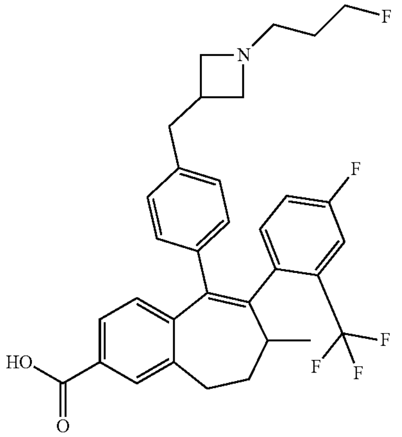 [SMILES: CC1CCc2cc(C(=O)O)ccc2C(c2ccc(CC3CN(CCCF)C3)cc2)=C1c1ccc(F)cc1C(F)(F)F] | 8-(4-fluoro-2-(trifluoromethyl)phenyl)-9-(4-((1-(3-fluoropropyl)azetidin-3-yl)methyl)phenyl)-7-methyl-6,7-dihydro-5H-benzo[7]annulene-3-carboxylic acid, racemic mixture |
| 313 | 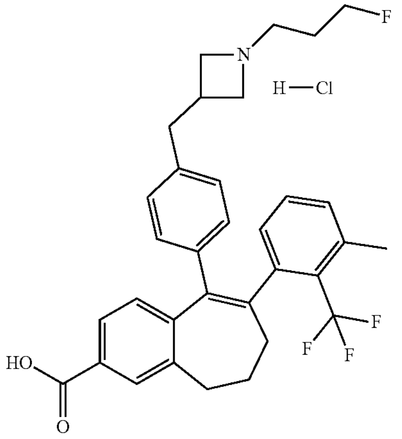 | 9-(4-((1-(3-fluoropropyl)azetidin-3-yl)methyl)phenyl)-8-(3-methyl-2-(trifluoromethyl)phenyl)-6,7-dihydro-5H-benzo[7]annulene-3-carboxylic acid hydrochloride |

TABLE 1a-continued

| Example or compound | Structure | Name |
|---|---|---|
| 314 | 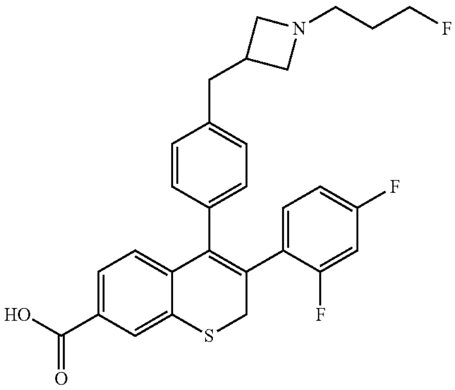 [SMILES: O=C(O)c1ccc2c(c1)SCC(c1ccc(F)cc1F)=C2c1ccc(CC2CN(CCCF)C2)cc1] | 3-(2,4-difluorophenyl)-4-(4-((1-(3-fluoropropyl)azetidin-3-yl)methyl)phenyl)-2H-thiochromene-7-carboxylic acid |
| 315 | 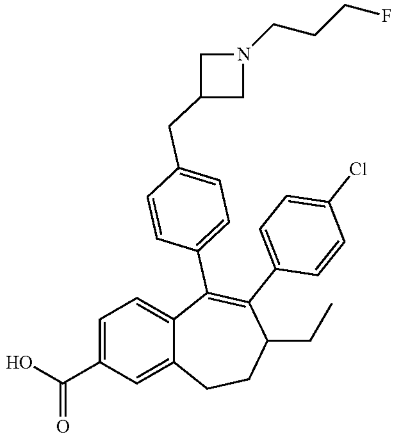 [SMILES: CCC1CCc2cc(C(=O)O)ccc2C(c2ccc(CC3CN(CCCF)C3)cc2)=C1c1ccc(Cl)cc1] | 8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, racemic mixture |
| 316 | 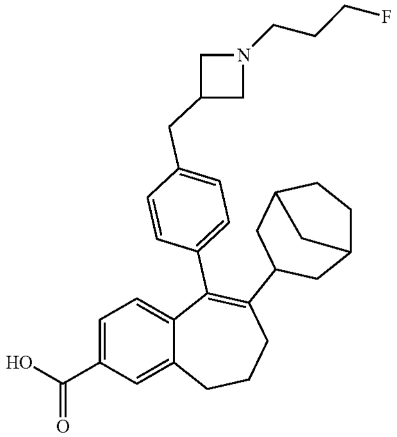 [SMILES: O=C(O)c1ccc2c(c1)CCCC(C1CC3CCC(C3)C1)=C2c1ccc(CC2CN(CCCF)C2)cc1] | 8-(bicyclo[3.2.1]octan-3-yl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 317 | 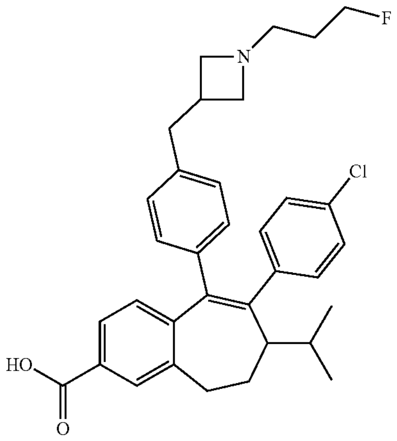 [SMILES: CC(C)C1CCc2cc(C(=O)O)ccc2C(c2ccc(CC3CN(CCCF)C3)cc2)=C1c1ccc(Cl)cc1] | 8-(4-chloropehnyl)-9-(4-((1-(3-fluoropropyl)azetidin-3-yl)methyl)phenyl)-7-isopropyl-6,7-dihydro-5H-benzo[7]annulene-3-carboxylic acid, racemic mixture |
| 318 | 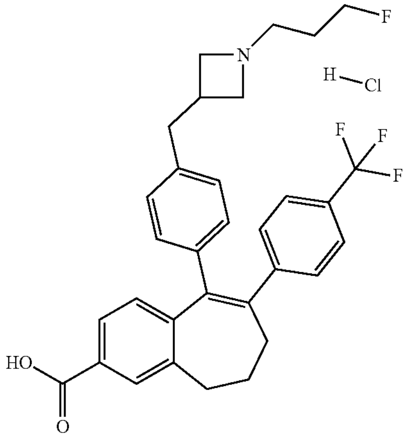 | 9-(4-((1-(3-fluoropropyl)azetidin-3-yl)methyl)phenyl)-8-(4-(trifluoromethyl)phenyl)-6,7-dihydro-5H-benzo[7]annulene-3-carboxylic acid hydrochloride |
| 319 | 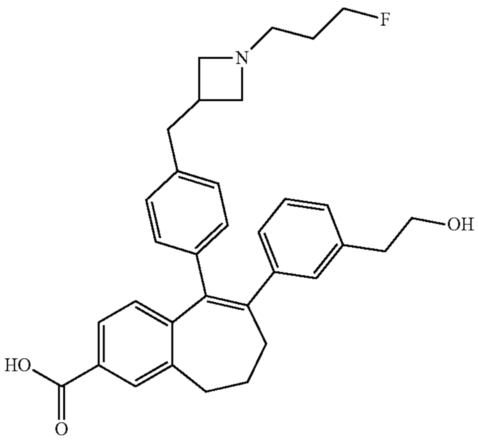 [SMILES: O=C(O)c1ccc2c(c1)CCCC(c1cccc(CCO)c1)=C2c1ccc(CC2CN(CCCF)C2)cc1] | 9-(4-((1-(3-fluoropropyl)azetidin-3-yl)methyl)phenyl)-8-(3-(2-hydroxyethyl)phenyl)-6,7-dihydro-5H-benzo[7]annulene-3-carboxylic acid |

TABLE 1a-continued

| Example or compound | Structure | Name |
|---|---|---|
| 320 | 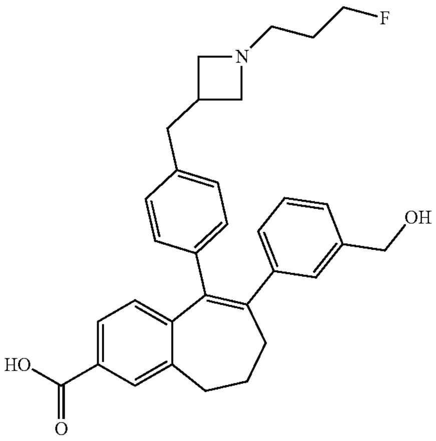 [SMILES: O=C(O)c1ccc2c(c1)CCCC(c1cccc(CO)c1)=C2c1ccc(CC2CN(CCCF)C2)cc1] | 9-(4-((1-(3-fluoropropyl)azetidin-3-yl)methyl)phenyl)-8-(3-(hydroxymethyl)phenyl)-6,7-dihydro-5H-benzo[7]annulene-3-carboxylic acid |
| 321 | 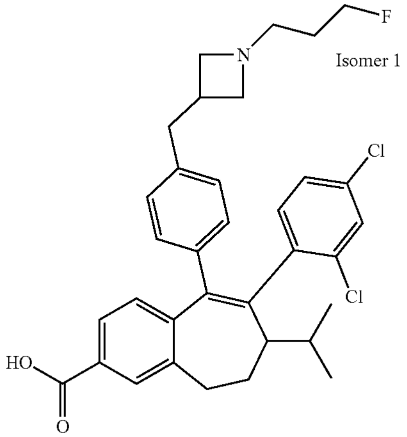 [SMILES: CC(C)C1CCc2cc(C(=O)O)ccc2C(c2ccc(CC3CN(CCCF)C3)cc2)=C1c1ccc(Cl)cc1Cl] | 8-(2,4-dichlorophenyl)-9-(4-((1-(3-fluoropropyl)azetidin-3-yl)methyl)phenyl)-7-isopropyl-6,7-dihydro-5H-benzo[7]annulene-3-carboxylic acid, Isomer 1 |
| 322 | 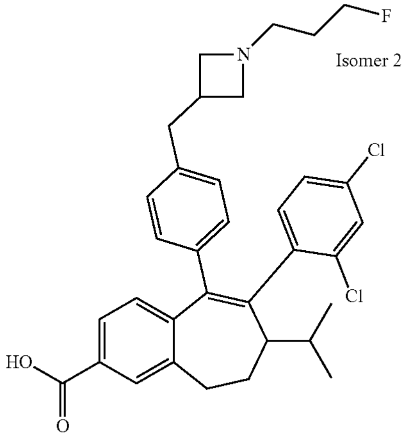 [SMILES: CC(C)C1CCc2cc(C(=O)O)ccc2C(c2ccc(CC3CN(CCCF)C3)cc2)=C1c1ccc(Cl)cc1Cl] | 8-(2,4-dichlorophenyl)-9-(4-((1-(3-fluoropropyl)azetidin-3-yl)methyl)phenyl)-7-isopropyl-6,7-dihydro-5H-benzo[7]annulene-3-carboxylic acid, Isomer 2 |

TABLE 1a-continued

| Example or compound | Structure | Name |
| --- | --- | --- |
| 323 | 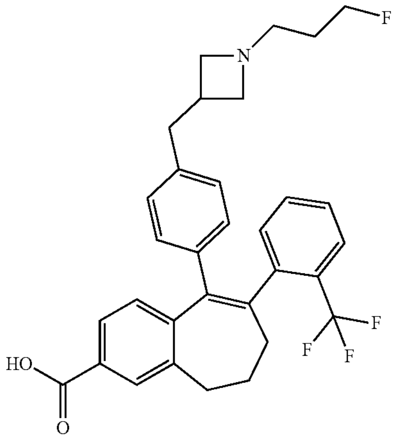 [SMILES: O=C(O)c1ccc2c(c1)CCCC(c1ccccc1C(F)(F)F)=C2c1ccc(CC2CN(CCCF)C2)cc1] | 9-(4-((1-(3-fluoropropyl)azetidin-3-yl)methyl)phenyl)-8-(3-(trifluoromethyl)phenyl)-6,7-dihydro-5H-benzo[7]annulene-3-carboxylic acid |
| 324 | 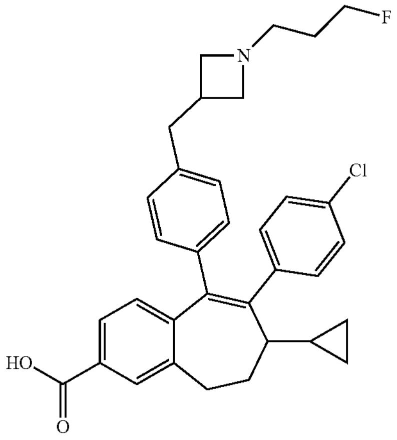 [SMILES: O=C(O)c1ccc2c(c1)CCC(C1CC1)C(c1ccc(Cl)cc1)=C2c1ccc(CC2CN(CCCF)C2)cc1] | 8-(4-chlorophenyl)-7-cyclopropyl-9-(4-((1-(3-fluoropropyl)azetidin-3-yl)methyl)phenyl)-6,7-dihydro-5H-benzo[7]annulene-3-carboxylic acid, racemic mixture |
| 325 | 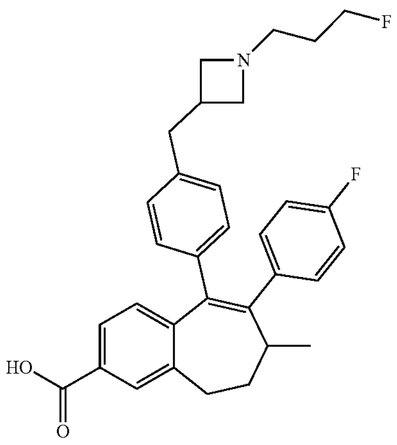 [SMILES: CC1CCc2cc(C(=O)O)ccc2C(c2ccc(CC3CN(CCCF)C3)cc2)=C1c1ccc(F)cc1] | 8-(4-fluorophenyl)-9-(4-((1-(3-fluoropropyl)azetidin-3-yl)methyl)phenyl)-7-methyl-6,7-dihydro-5H-benzo[7]annulene-3-carboxylic acid, racemic mixture |

TABLE 1a-continued

| Example or compound | Structure | Name |
|---|---|---|
| 326 | 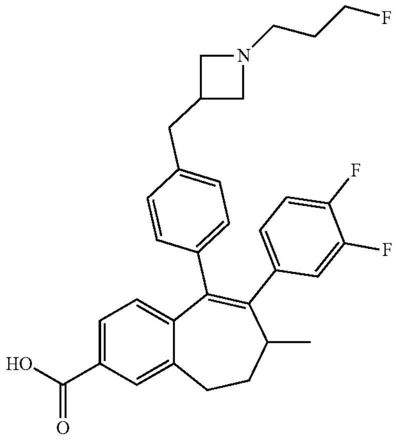 [SMILES: CC1CCc2cc(C(=O)O)ccc2C(c2ccc(CC3CN(CCCF)C3)cc2)=C1c1ccc(F)c(F)c1] | 8-(3,4-difluorophenyl)-9-(4-((1-(3-fluoropropyl)azetidin-3-yl)methyl)phenyl)-7-methyl-6,7-dihydro-5H-benzo[7]annulene-3-carboxylic acid, racemic mixture |
| 327 | 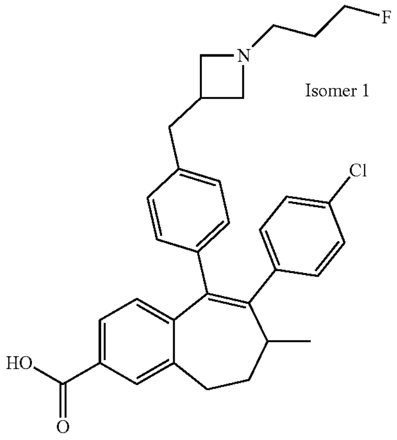 [SMILES: CC1CCc2cc(C(=O)O)ccc2C(c2ccc(CC3CN(CCCF)C3)cc2)=C1c1ccc(Cl)cc1] | 8-(4-chlorophenyl)-9-(4-((1-(3-fluoropropyl)azetidin-3-yl)methyl)phenyl)-7-methyl-6,7-dihydro-5H-benzo[7]annulene-3-carboxylic acid, Isomer 1 |
| 328 | 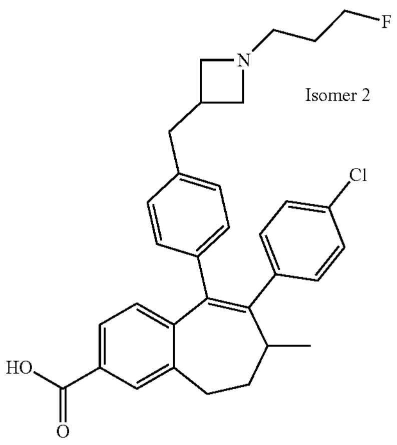 [SMILES: CC1CCc2cc(C(=O)O)ccc2C(c2ccc(CC3CN(CCCF)C3)cc2)=C1c1ccc(Cl)cc1] | 8-(4-chlorophenyl)-9-(4-((1-(3-fluoropropyl)azetidin-3-yl)methyl)phenyl)-7-methyl-6,7-dihydro-5H-benzo[7]annulene-3-carboxylic acid, Isomer 2 |

TABLE 1a-continued

| Example or compound | Structure | Name |
|---|---|---|
| 329 | 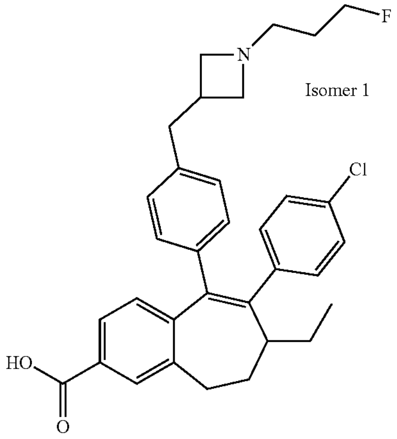 [SMILES: CCC1CCc2cc(C(=O)O)ccc2C(c2ccc(CC3CN(CCCF)C3)cc2)=C1c1ccc(Cl)cc1] Isomer 1 | 8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, Isomer 1 |
| 330 | 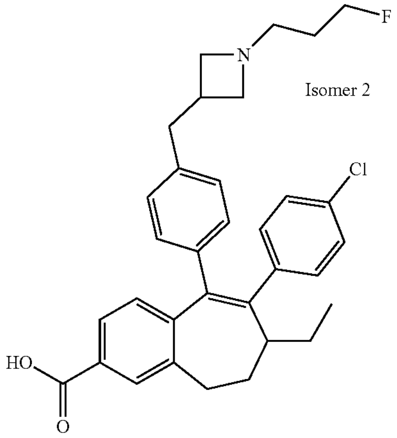 [SMILES: CCC1CCc2cc(C(=O)O)ccc2C(c2ccc(CC3CN(CCCF)C3)cc2)=C1c1ccc(Cl)cc1] Isomer 2 | 8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, Isomer 2 |
| 331 | 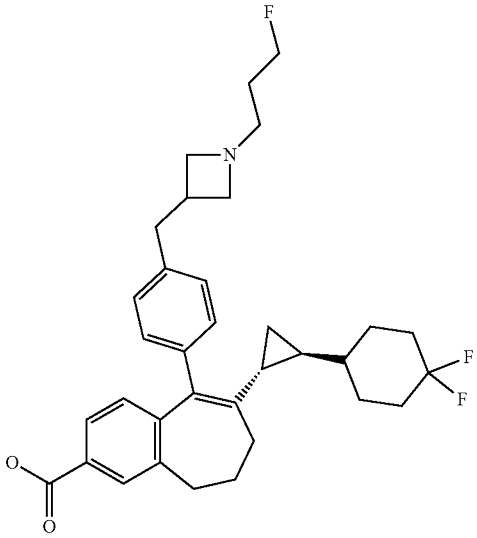 [SMILES: O=C(O)c1ccc2c(c1)CCCC([C@@H]1C[C@H]1C1CCC(F)(F)CC1)=C2c1ccc(CC2CN(CCCF)C2)cc1] | 8-((1R,2S)-2-(4,4-difluorocyclohexyl)cyclopropyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
| --- | --- | --- |
| 332 | 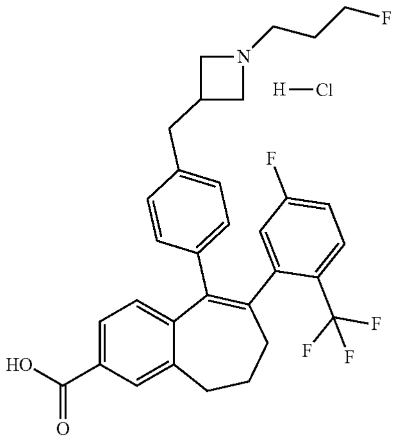 | 8-(5-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride |
| 333 | 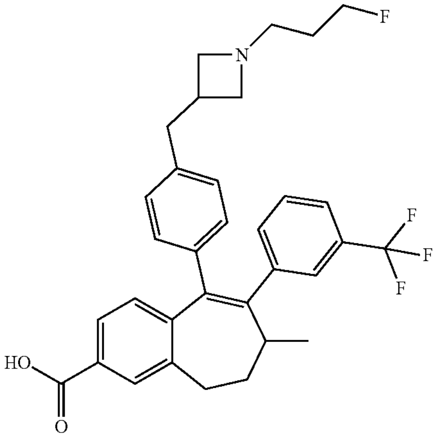 [SMILES: CC1CCc2cc(C(=O)O)ccc2C(c2ccc(CC3CN(CCCF)C3)cc2)=C1c1cccc(C(F)(F)F)c1] | 9-(4-((1-(3-fluoroproypl)azetidin-3-yl)methyl)phenyl)-7-methyl-8-(3-(trifluoromethyl)phenyl)-6,7-dihydro-5H-benzo[7]annulene-3-carboxylic acid, Mixture of isomers |
| 334 | 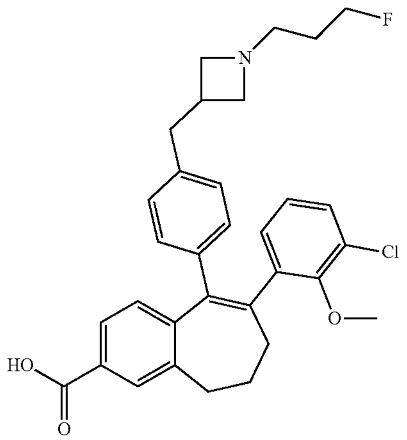 [SMILES: COc1c(Cl)cccc1C1=C(c2ccc(CC3CN(CCCF)C3)cc2)c2ccc(C(=O)O)cc2CCC1] | 8-(3-chloro-2-methoxyphenyl)-9-(4-((1-(3-fluoropropyl)azetidin-3-yl)methyl)phenyl)-6,7-dihydro-5H-benzo[7]annulene-3-carboxylic acid |

TABLE 1a-continued

| Example or compound | Structure | Name |
|---|---|---|
| 335 | 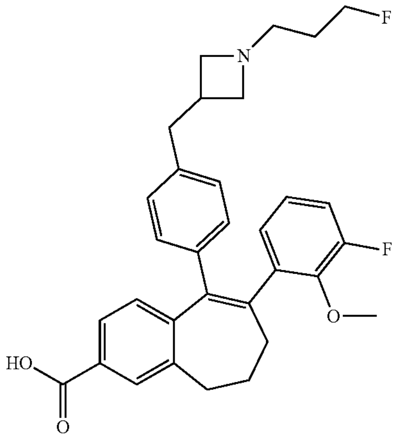 [SMILES: COc1c(F)cccc1C1=C(c2ccc(CC3CN(CCCF)C3)cc2)c2ccc(C(=O)O)cc2CCC1] | 8-(3-fluoro-2-methoxyphenyl)-9-(4-((1-(3-fluoropropyl)azetidin-3-yl)methyl)phenyl)-6,7-dihydro-5H-benzo[7]annulene-3-carboxylic acid |
| 336 | 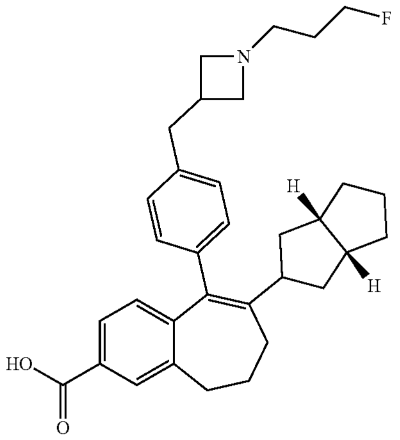 [SMILES: O=C(O)c1ccc2c(c1)CCCC(C1C[C@H]3CCC[C@H]3C1)=C2c1ccc(CC2CN(CCCF)C2)cc1] | 9-(4-((1-(3-fluoropropyl)azetidin-3-yl)methyl)phenyl)-8-(octahydropentalen-2-yl)-6,7-dihydro-5H-benzo[7]annulene-3-carboxylic acid, Isomer 1 |

TABLE 1b

| Example or compound | Preparation Method | NMR | MASS: LC/MS (m/z, MH+): |
|---|---|---|---|
| 1 | A | 1H NMR (400 MHz, DMSO-d6) δ ppm 1.78-1.93 (m, 2 H); 2.13 (m, 2 H); 2.28 (t, J = 7 Hz, 2 H); 2.77-2.98 (m, 5 H); 3.18 (br m, 2 H); 3.75 (br m, 2 H); 4.01 (br m, 2 H); 4.50 (td, J = 6, 47 Hz, 2 H); 6.79 (d, J = 8 Hz, 2 H); 6.83 (d, J = 8 Hz, 1 H); 6.94 (d, J = 8 Hz, 2 H); 7.11-7.22 (m, 5 H); 7.74 (dd, J = 8, 2 Hz, 1 H); 7.90 (d, J = 2 Hz, 1 H); 10.29 (br m, 1 H); 12.76 (br m, 1 H) | 470 |
| 2 | A | 1H NMR (400 MHz, DMSO-d6) δ ppm 1.77-1.93 (m, 2 H); 2.10-2.25 (m, 4 H); 2.77-2.98 (br m, 5 H); 3.16 (br m, 2 H); 3.72 (br m, 2 H); 3.98 (br m, 2 H); 4.50 (td, J = 6, 47 Hz, 2 H); 6.80 (d, J = 8 Hz, 2 H); 6.84 (d, J = 8 Hz, 1 H); 6.97 (d, J = 8 Hz, 2 H); 7.19 (d, J = 8 Hz, 1 H); 7.27 (dd, J = 8, 2 Hz, 1 H); 7.59 (d, J = 2 Hz, 1 H); 7.75 (dd, J = 8, 2 Hz, 1 H); 7.92 (d, J = 2 Hz, 1 H); 10.49 (br m, 1 H); 12.87 (br m, 1 H) | 538 |
| 3 | A | 1H NMR (400 MHz, DMSO-d6) δ ppm 1.53-1.68 (m, 2 H); 2.10-2.25 (m, 4 H); 2.42 (t, J = 7 Hz, 2 H); 2.54 (m, 1 H); 2.68 (d, J = 7 Hz, 2 H); 2.74 (m, 2 H); 2.94 (m, 2 H); 3.25 (m, 2 H); 4.41 (td, J = 6, 47 Hz, 2 H); 6.75 (d, J = 8 Hz, 2 H); 6.85 (d, J = 8 Hz, 1 H); 6.89 (d, J = 8 Hz, 2 H); 7.13-7.24 (m, 3 H); 7.41 (br d, J = 8 Hz, 1 H); 7.74 (dd, J = 8, 2 Hz, 1 H); 7.91 (d, J = 2 Hz, 1 H); 12.80 (br m, 1 H) | 504 |

TABLE 1b-continued

| Example or compound | Preparation Method | NMR | MASS: LC/MS (m/z, MH+): |
|---|---|---|---|
| 4 | C | 1H NMR (400 MHz, DMSO-d6) δ ppm 1.52-1.74 (m, 7 H); 1.79-1.94 (m, 4 H); 2.04 (m, 2 H); 2.12 (m, 2 H); 2.73 (t, J = 7 Hz, 2 H); 2.86-3.07 (br m, 3 H); 3.21 (br m, 2 H); 3.82 (br m, 2 H); 4.07 (br m, 2 H); 4.51 (td, J = 6, 47 Hz, 2 H); 6.72 (d, J = 8 Hz, 1 H); 7.03 (d, J = 8 Hz, 2 H); 7.18 (d, J = 8 Hz, 2 H); 7.66 (dd, J = 8, 2 Hz, 1 H); 7.83 (d, J = 2 Hz, 1 H); 10.32 (br m, 1 H); 12.81 (br m, 1 H) | 512 |
| 5 | A | 1H NMR (400 MHz, DMSO-d6) δ ppm 1.76-1.96 (m, 4 H); 2.01 (t, J = 7 Hz, 2 H); 2.13 (m, 2 H); 2.18 (m, 2 H); 2.37-2.57 (m partially hidden, 2 H); 2.73 (t, J = 7 Hz, 2 H); 2.84-2.99 (m, 3 H); 3.13 (br m, 2 H); 3.69 (br m, 2 H); 3.96 (br m, 2 H); 4.50 (td, J = 6, 47 Hz, 2 H); 5.38 (br s, 1 H); 6.81 (d, J = 8 Hz, 1 H); 6.98 (d, J = 8 Hz, 2 H); 7.10 (d, J = 8 Hz, 2 H); 7.71 (dd, J = 8, 2 Hz, 1 H); 7.85 (d, J = 2 Hz, 1 H); 10.09 (br m, 1 H); 12.84 (br m, 1 H) | 510 |
| 6 | C | 1H NMR (400 MHz, DMSO-d6) δ ppm 1.47 (m, 4 H); 1.67 (m, 4 H); 1.81-1.94 (m, 4 H); 2.15 (m, 2 H); 2.69-2.78 (m, 3 H); 2.88-3.06 (br m, 3 H); 3.21 (br m, 2 H); 3.82 (br m, 2 H); 4.07 (br m, 2 H); 4.51 (td, J = 47, 6 Hz, 2 H); 6.69 (d, J = 8 Hz, 1 H); 7.00 (d, J = 8 Hz, 2 H); 7.17 (d, J = 8 Hz, 2 H); 7.65 (dd, J = 8, 2 Hz, 1 H); 7.83 (d, J = 2 Hz, 1 H); 10.35 (br m, 1 H); 12.78 (br m, 1 H) | 462 |
| 7 | A | 1H NMR (400 MHz, DMSO-d6) δ ppm 1.77-1.92 (m, 2 H); 2.08-2.21 (m, 4 H); 2.25 (s, 3 H); 2.75-2.95 (br m, 5 H); 3.16 (br m, 2 H); 3.74 (br m, 2 H); 4.00 (br m, 2 H); 4.49 (td, J = 6, 47 Hz, 2 H); 6.80 (d, J = 8 Hz, 2 H); 6.83 (d, J = 8 Hz, 1 H); 6.94 (d, J = 8 Hz, 2 H); 6.97 (m, 1 H); 7.03 (d, J = 8 Hz, 1 H); 7.25 (br s, 1 H); 7.74 (dd, J = 8, 2 Hz, 1 H); 7.91 (d, J = 2 Hz, 1 H); 10.29 (br m, 1 H); 12.89 (br m, 1 H) | 518 |
| 8 | A | 1H NMR (400 MHz, DMSO-d6) δ ppm 1.77-1.92 (m, 2 H); 2.13-2.23 (m, 4 H); 2.76-2.97 (br m, 5 H); 3.17 (br m, 2 H); 3.72 (br m, 2 H); 3.99 (br m, 2 H); 4.50 (td, J = 6, 47 Hz, 2 H); 6.79 (d, J = 8 Hz, 2 H); 6.84 (d, J = 8 Hz, 1 H); 6.96 (d, J = 8 Hz, 2 H); 7.07 (dt, J = 9, 3 Hz, 1 H); 7.21 (dd, J = 9, 6 Hz, 1 H); 7.42 (dd, J = 9, 3 Hz, 1 H); 7.75 (dd, J = 8, 2 Hz, 1 H); 7.92 (d, J = 2 Hz, 1 H); 10.29 (br m, 1 H); 12.90 (br m, 1 H) | 522 |
| 9 | A | 1H NMR (400 MHz, DMSO-d6) δ ppm 1.76-1.93 (m, 2 H); 2.11-2.25 (m, 4 H); 2.75-2.98 (br m, 5 H); 3.17 (br m, 2 H); 3.74 (br m, 2 H); 4.00 (br m, 2 H); 4.49 (td, J = 6, 47 Hz, 2 H); 6.80 (d, J = 8 Hz, 2 H); 6.85 (d, J = 8 Hz, 1 H); 6.97 (d, J = 8 Hz, 2 H); 7.03 (br d, J = 8 Hz, 1 H); 7.18-7.28 (m, 2 H); 7.76 (br d, J = 8 Hz, 1 H); 7.93 (br s, 1 H); 10.25 (br m, 1 H); 12.91 (br m, 1 H) | 522 |
| 10 | A | 1H NMR (400 MHz, DMSO-d6) δ ppm 1.76-1.93 (m, 2 H); 2.11 (m, 7 H); 2.20 (s, 3 H); 2.75-2.98 (m, 5 H); 3.17 (m, 2 H); 3.73 (m, 2 H); 4.00 (m, 2 H); 4.50 (td, J = 6, 47 Hz, 2 H); 6.73 (d, J = 8 Hz, 2 H); 6.80-6.96 (m, 6 H); 7.74 (d, J = 8 Hz, 1 H); 7.91 (s, 1 H); 10.30 (s, 1 H); 12.86 (s, 1 H) | 498 |
| 11 | A | 1H NMR (400 MHz, DMSO-d6) δ ppm 1.77-1.93 (m, 2 H); 2.08-2.21 (m, 4 H); 2.25 (s, 3 H); 2.76-2.98 (br m, 5 H); 3.18 (br m, 2 H); 3.75 (br m, 2 H); 4.02 (br m, 2 H); 4.50 (td, J = 6, 47 Hz, 2 H); 6.79 (d, J = 8 Hz, 2 H); 6.83 (d, J = 8 Hz, 1 H); 6.86 (br d, J = 8 Hz, 1 H); 6.90 (d, J = 11 Hz, 1 H); 6.96 (d, J = 8 Hz, 2 H); 7.04 (t, J = 8 Hz, 1 H); 7.74 (dd, J = 8, 2 Hz, 1 H); 7.94 (d, J = 2 Hz, 1 H); 10.32 (br m, 1 H); 12.88 (br m, 1 H) | 502 |
| 12 | A | 1H NMR (400 MHz, DMSO-d6) δ ppm 1.76-1.94 (m, 2 H); 2.09-2.23 (m, 4 H); 2.77-2.99 (m, 5 H); 3.19 (m, 2 H); 3.76 (m, 2 H); 4.02 (m, 2 H); 4.50 (td, J = 6, 47 Hz, 2 H); 6.79 (d, J = 8 Hz, 2 H); 6.84 (d, J = 8 Hz, 1 H); 6.98 (d, J = 8 Hz, 2 H); 7.15 (d, J = 8 Hz, 1 H); 7.24 (t, J = 8 Hz, 1 H); 7.31 (d, J = 10 Hz, 1 H); 7.75 (d, J = 8 Hz, 1 H); 7.92 (s, 1 H); 10.24 (s, 1 H); 12.91 (s, 1 H) | 522 |
| 13 | C | 1H NMR (400 MHz, DMSO-d6) δ ppm 0.84 (s, 3 H); 0.91 (s, 3 H); 1.00 (m, 2 H); 1.33-1.44 (m, 4 H); 1.60 (m, 2 H); 1.77-1.96 (m, 4 H); 2.14 (m, 2 H); 2.28 (tt, J = 12, 3 Hz, 1 H); 2.72 (t, J = 7 Hz, 2 H); 2.85-3.07 (br m, 3 H); 3.21 (br m, 2 H); 3.82 (br m, 2 | 504 |

TABLE 1b-continued

| Example or compound | Preparation Method | NMR | MASS: LC/MS (m/z, MH+): |
|---|---|---|---|
| | | H); 4.07 (br m, 2 H); 4.51 (td, J = 6, 47 Hz, 2 H); 6.71 (d, J = 8 Hz, 1 H); 6.99 (d, J = 8 Hz, 2 H); 7.17 (d, J = 8 Hz, 2 H); 7.65 (dd, J = 8, 2 Hz, 1 H); 7.82 (d, J = 2 Hz, 1 H); 10.33 (br m, 1 H); 12.88 (br m, 1 H) | |
| 14 | C | 1H NMR (400 MHz, DMSO-d6) δ ppm 0.98 (d, J = 7 Hz, 3 H); 1.27-1.39 (m, 3 H); 1.47 (m, 2 H); 1.64 (m, 2 H); 1.79-1.95 (m, 6 H); 2.14 (m, 2 H); 2.33 (m partially hidden, 1 H); 2.72 (t, J = 7 Hz, 2 H); 2.81-3.05 (br m, 3 H); 3.19 (br m, 2 H); 3.80 (br m, 2 H); 4.05 (br m, 2 H); 4.50 (td, J = 6, 47 Hz, 2 H); 6.72 (d, J = 8 Hz, 1 H); 6.99 (d, J = 8 Hz, 2 H); 7.17 (d, J = 8 Hz, 2 H); 7.65 (dd, J = 8, 2 Hz, 1 H); 7.82 (d, J = 2 Hz, 1 H); 10.46 (br m, 1 H); 12.80 (br m, 1 H) | 490 |
| 15 | C | 1H NMR (400 MHz, DMSO-d6) δ ppm 0.74 (m, 2 H); 0.81 (d, J = 7 Hz, 3 H); 1.32 (m, 1 H); 1.45 (m, 2 H); 1.54-1.72 (m, 6 H); 1.85 (t, J = 7 Hz, 2 H); 2.11 (m, 2 H); 2.32 (m partially hidden, 1 H); 2.45-2.58 (m partially hidden, 3 H); 2.71 (t, J = 7 Hz, 2 H); 2.78 (m, 2 H); 2.82 (d, J = 8 Hz, 2 H); 2.88 (m, 2 H); 4.43 (td, J = 6, 47 Hz, 2 H); 6.72 (d, J = 8 Hz, 1 H); 6.95 (d, J = 8 Hz, 2 H); 7.13 (d, J = 8 Hz, 2 H); 7.64 (dd, J = 8, 2 Hz, 1 H); 7.81 (d, J = 2 Hz, 1 H) | 490 |
| 16 | A | 1H NMR (400 MHz, DMSO-d6) δ ppm 1.60 (dquin, J = 25, 7 Hz, 2 H); 2.18 (m, 4 H); 2, 40 (t, J = 7 Hz, 2 H); 2.52 (m, partially hidden, 3 H); 2.72 (m, 2 H); 2.85 (t, J = 6 Hz, 2 H); 3.23 (t, J = 7 Hz, 2 H); 3.71 (s, 3 H); 4.42 (dt, J = 47, 6 Hz, 2 H); 6.62 (dd, J = 8, 3 Hz, 1 H); 6.69 (dd, J = 12, 3 Hz, 1 H); 6.75 (d, J = 8 Hz, 2 H); 6.82 (d, J = 8 Hz, 1 H); 6.92 (d, J = 8 Hz, 2 H); 7.05 (t, J = 9 Hz, 1 H); 7.72 (dd, J = 8, 2 Hz, 1 H); 7.89 (d, J = 2 Hz, 1 H) | 518 |
| 17 | A | 1H NMR (400 MHz, DMSO-d6) δ ppm 1.60 (m, 2 H); 2.17 (m, 4 H); 2.25 (s, 3 H); 2.37 (t, J = 7 Hz, 2 H); 2.56 (m, 1 H); 2.68 (m, 4 H); 2.80-3.02 (m, 2 H); 3.19 (m, 2 H); 4.41 (dt, J = 47, 6 Hz, 2 H); 6.70 (d, J = 8 Hz, 2 H); 6.85 (d, J = 8 Hz, 1 H); 6.89 (d, J = 8 Hz, 2 H hidden); 7.24 (d, J = 8 Hz, 1 H); 7.37 (d, J = 9 Hz, 1 H); 7.49 (d, J = 2 Hz, 1 H); 7.74 (dd, J = 8, 2 Hz, 1 H); 7.91 (d, J = 2 Hz, 1 H) | 552 |
| 18 | A | 1H NMR (400 MHz, DMSO-d6) δ ppm 1.60 (m, 2 H); 2.18 (m, 2 H); 2.25 (t, J = 7 Hz, 2 H); 2.46 (t, J = 7 Hz, 2 H); 2.59 (m, 1 H); 2.73 (d, J = 8 Hz, 2 H); 2.79 (t, J = 6 Hz, 2 H); 2.84 (t, J = 7 Hz, 2 H); 3.21 (m hidden, 2 H); 3.77 (s, 3 H); 4.42 (dt, J = 47, 6 Hz, 2 H); 6.65 (dd, J = 9, 1 Hz, 1 H); 6.80 (d, J = 8 Hz, 2 H); 6.83 (d, J = 8 Hz, 1 H); 6.97 (d, J = 8 Hz, 2 H); 7.47 (dd, J = 9, 3 Hz, 1 H); 7.73 (dd, J = 8, 2 Hz, 1 H); 7.89 (d, J = 2 Hz, 1 H); 7.91 (dd, J = 3, 1 Hz, 1 H) | 501 |
| 19 | A | 1H NMR (400 MHz, DMSO-d6) δ ppm 1.60 (m, 2 H); 2.18 (m, 4 H); 2.43 (t, J = 7 Hz, 2 H); 2.57 (m, 1 H); 2.65-2.79 (m, 4 H); 2.94 (m, 2 H); 3.26 (t, J = 7 Hz, 2 H); 4.42 (dt, J = 47, 6 Hz, 2 H); 6.76 (d, J = 8 Hz, 2 H); 6.85 (d, J = 8 Hz, 1 H); 6.93 (d, J = 8 Hz, 2 H); 7.13 (dd, J = 8, 2 Hz, 1 H); 7.17 (t, J = 8 Hz, 1 H); 7.46 (dd, J = 8, 2 Hz, 1 H); 7.74 (dd, J = 8, 2 Hz, 1 H); 7.91 (d, J = 2 Hz, 1 H) | 538 |
| 20 | A | 1H NMR (400 MHz, DMSO-d6) δ ppm 1.60 (m, 2 H); 2.12 (m, 4 H); 2.16 (s, 3 H); 2.38 (t, J = 7 Hz, 2 H); 2.57 (m partially hidden, 1 H); 2.64-2.74 (m, 4 H); 2.89 (m, 2 H); 3.01 (m, 2 H); 4.41 (dt, J = 47, 6 Hz, 2 H); 6.69 (d, J = 8 Hz, 2 H); 6.81-6.87 (m, 2 H); 6.89 (d, J = 8 Hz, 2 H); 6, 94 (d, J = 3 Hz, 1 H); 7.17 (t, J = 74 Hz, 1 H); 7.07 (d, J = 8 Hz, 1 H); 7.73 (dd, J = 8, 2 Hz, 1 H); 7.90 (d, J = 2 Hz, 1 H) | 550 |
| 21 | A | 1H NMR (400 MHz, DMSO-d6) δ ppm 1.60 (m, 2 H); 2.11 (m, 2 H); 2.23 (m, 2 H); 2.42 (t, J = 7 Hz, 2 H); 2.59 (m, 1 H); 2.69-2.77 (m, 4 H); 2.84 (t, J = 7 Hz, 2 H); 3.25 (m, partially hidden, 2 H); 3.75 (s, 3 H); 4.42 (dt, J = 47, 6 Hz, 2 H); 6.55 (m, 1 H); 6.71 (dd, J = 5, 1 Hz, 1 H); 6.81 (d, J = 8 Hz, 2 H); 6.83 (d, J = 8 Hz, 1 H); 6.97 (d, J = 8 Hz, 2 H); 7.74 (dd, J = 8, 2 Hz, 1 H); 7.90 (d, J = 2 Hz, 1 H); 7.94 (dd, J = 5, 1 Hz, 1 H) | 501 |
| 22 | A | RMN 1H (400 MHz, DMSO-d6) δ ppm 1.60 (m, 2 H); 2.18 (m, 4 H); 2.42 (t, J = 7 Hz, 2 H); 2.57 (m partially hidden, 1 H); 2.68-2.77 (m, 4 H); 2.87 (t, J = 6 Hz, 2 H); 3.25 (t, J = 7 Hz, 2 H); 4.42 (dt, J = 47, 6 Hz, 2 H); | 506 |

TABLE 1b-continued

| Example or compound | Preparation Method | NMR | MASS: LC/MS (m/z, MH+): |
|---|---|---|---|
| | | 6.76 (d, J = 8 Hz, 2 H); 6.85 (d, J = 8 Hz, 1 H); 6.93 (d, J = 8 Hz, 2 H); 6.99-7.13 (m, 2 H); 7.16-7.31 (m, 1 H); 7.75 (dd, J = 8, 2 Hz, 1 H); 7.92 (d, J = 2 Hz, 1 H) | |
| 23 | A | 1H NMR 400 MHz, DMSO-d6) δ ppm 1.60 (m, 2 H); 2.17 (m, 4 H); 2.38 (t, J = 7 Hz, 2 H); 2.54 (m partially hidden, 1 H); 2.62-2.71 (m, 4 H); 2.85 (m, 1 H); 2.99 (m, 1 H); 3.00 (m, 2 H); 4.41 (dt, J = 47, 6 Hz, 2 H); 6.73 (d, J = 8 Hz, 2 H); 6.84 (d, J = 8 Hz, 1 H); 6.89 (d, J = 8 Hz, 2 H); 7.18 (dd, J = 7, 2 Hz, 1 H); 7.42 (m, 2 H); 7.71 (dd, J = 8, 2 Hz, 1 H); 7.74 (dd, J = 8, 2 Hz, 1 H); 7.90 (d, J = 2 Hz, 1 H) | 538 |
| 24 | A | 1H NMR (400 MHz, DMSO-d6) δ ppm 1.59 (m, 2 H); 2.14 (m, 4 H); 2.39 (t, J = 7 Hz, 2 H); 2.57 (m, 1 H); 2.69 (m, 4 H); 2.91 (t, J = 6 Hz, 2 H); 3.22 (m, 2 H); 3.72 (s, 3 H); 4.41 (dt, J = 47, 6 Hz, 2 H); 6.70-6.77 (m, 3 H); 6.82 (d, J = 8 Hz, 1 H); 6.91 (d, J = 8 Hz, 2 H); 6.99 (d, J = 3 Hz, 1 H); 7.04 (d, J = 8 Hz, 1 H); 7.73 (dd, J = 8, 2 Hz, 1 H); 7.89 (d, J = 2 Hz, 1 H) | 534 |
| 25 | A | 1H NMR (400 MHz, DMSO-d6) δ ppm 1.60 (m, 2 H); 2.13 (m, 4 H); 2.16 (s, 3 H); 2.39 (t, J = 7 Hz, 2 H); 2.56 (m hidden, 1 H); 2.64-2.74 (m, 4 H); 2.82-2.98 (m, 2 H); 3.22 (m partially hidden, 2 H); 4.42 (dt, J = 47, 6 Hz, 2 H); 6.71 (d, J = 8 Hz, 2 H); 6.84 (d, J = 8 Hz, 1 H); 6.90 (d, J = 8 Hz, 2 H); 7.05 (d, J = 8 Hz, 1 H); 7.10 (dd, J = 8, 2 Hz, 1 H); 7.20 (d, J = 2 Hz, 1 H); 7.74 (dd, J = 8, 2 Hz, 1 H); 7.90 (d, J = 2 Hz, 1 H) | 518 |
| 26 | A | 1H NMR (400 MHz, DMSO-d6) δ ppm 1.59 (m, 2 H); 2.18 (m, 4 H); 2.38 (t, J = 7 Hz, 2 H); 2.56 (m hidden, 1 H); 2.62-2.73 (m, 4 H); 2.84 (m, 1 H); 2.98 (m, 1 H); 3.22 (m partially hidden, 2 H); 4.42 (dt, J = 47, 6 Hz, 2 H); 6.74 (d, J = 8 Hz, 2 H); 6.84 (d, J = 8 Hz, 1 H); 6.92 (d, J = 8 Hz, 2 H); 7.25 (dd, J = 9, 6 Hz, 1 H); 7.34 (td, J = 8, 3 Hz, 1 H); 7.62 (dd, J = 9, 3 Hz, 1 H); 7.74 (dd, J = 8, 2 Hz, 1 H); 7.90 (d, J = 2 Hz, 1 H) | 556 |
| 27 | A | 1H NMR (400 MHz, DMSO-d6) δ ppm 1.60 (dquin, J = 25, 6 Hz, 2 H); 2.17 (m, 4 H); 2.38 (t, J = 7 Hz, 2 H); 2.56 (m hidden, 1 H); 2.63-2.74 (m, 4 H); 2.85 (m, 1 H); 2.99 (m, 1 H); 3.22 (m partially hidden, 2 H); 4.42 (dt, J = 47, 6 Hz, 2 H); 6.75 (d, J = 8 Hz, 2 H); 6.84 (d, J = 8 Hz, 1 H); 6.93 (d, J = 8 Hz, 2 H); 7.23 (d, J = 8 Hz, 1 H); 7.54 (dd, J = 8, 2 Hz, 1 H); 7.74 (dd, J = 8, 2 Hz, 1 H); 7.80 (d, J = 2 Hz, 1 H); 7.90 (d, J = 2 Hz, 1 H) | 572 |
| 28 | A | 1H NMR (400 MHz, DMSO-d6) δ ppm 1.60 (dquin, J = 25, 6 Hz, 2 H); 2.06 (d, J = 2 Hz, 3 H); 2.17 (m, 4 H); 2.38 (t, J = 7 Hz, 2 H); 2.55 (m hidden, 1 H); 2.65-2.72 (m, 4 H); 2.91 (m, 2 H); 3.21 (m partially hidden, 2 H); 4.42 (dt, J = 47, 6 Hz, 2 H); 6.70 (d, J = 8 Hz, 2 H); 6.84 (d, J = 8 Hz, 1 H); 6.87-6.92 (m, 3 H); 6.96 (t, J = 9 Hz, 1 H); 7.09 (m, 1 H); 7.74 (dd, J = 8, 2 Hz, 1 H); 7.91 (d, J = 2 Hz, 1 H) | 502 |
| 29 | A | 1H NMR (400 MHz, DMSO-d6) δ ppm 1.59 (m, 2 H); 2.11 (s, 3 H); 2.14 (m, 4 H); 2.38 (t, J = 7 Hz, 2 H); 2.56 (m partially hidden, 1 H); 2.64-2.73 (m, 4 H); 2.87 (m, 2 H); 3.01 (t, J = 7 Hz, 2 H); 3.68 (s, 3 H); 4.41 (dt, J = 47, 6 Hz, 2 H); 6.61 (dd, J = 8, 2 Hz, 1 H); 6.65-6.72 (m, 3 H); 6.82 (d, J = 8 Hz, 1 H); 6.87 (d, J = 8 Hz, 2 H); 6.94 (d, J = 8 Hz, 1 H); 7.72 (dd, J = 8, 2 Hz, 1 H); 7.89 (d, J = 2 Hz, 1 H) | 514 |
| 30 | A | 1H NMR (400 MHz, DMSO-d6) δ ppm 1, 60 (dquin, J = 25, 7 Hz, 2 H); 2.16 (m, 4 H); 2.33 (s, 3 H); 2.39 (t, J = 7 Hz, 2 H); 2.57 (m partially hidden, 1 H); 2.62-2.74 (m, 4 H); 2.93 (m, 2 H); 3.02 (t, J = 7 Hz, 2 H); 4.41 (dt, J = 47, 6 Hz, 2 H); 6.76 (d, J = 8 Hz, 2 H); 6.83 (d, J = 8 Hz, 1 H); 6.89 (d, J = 8 Hz, 2 H); 6.94 (dd, J = 8, 2 Hz, 1 H); 7.02 (t, J = 8 Hz, 1 H); 7.16 (d, J = 6 Hz, 1 H); 7.73 (dd, J = 8, 2 Hz, 1 H); 7.90 (d, J = 2 Hz, 1 H) | 518 |
| 31 | A | 1H NMR (400 MHz, DMSO-d6) δ ppm 1.60 (m, 2 H); 2.18 (m, 4 H); 2.39 (t, J = 7 Hz, 2 H); 2.55 (m hidden, 1 H); 2.58-2.74 (m, 4 H); 2.82-3.05 (m, 2 H); 3.21 (m partially hidden, 2 H); 4.41 (dt, J = 47, 6 Hz, 2 H); 6.75 (d, J = 8 Hz, 2 H); 6.85 (d, J = 8 Hz, 1 H); 6.91 (d, J = 8 Hz, 2 H); 7.41 (t, J = 8 Hz, 1 H); 7.45(m, 1 H); 7.56 (d, J = 8 Hz, 1 H); 7.74 (dd, J = 8, 2 Hz, 1 H); 7.91 (d, J = 2 Hz, 1 H) | 556 |

TABLE 1b-continued

| Example or compound | Preparation Method | NMR | MASS: LC/MS (m/z, MH+): |
|---|---|---|---|
| 32 | A | 1H NMR (400 MHz, DMSO-d6) δ ppm 1.60 (dquin, J = 25, 7 Hz, 2 H); 2.18 (dd, J = 15, 6 Hz, 4 H); 2.39 (t, J = 7 Hz, 2 H); 2.57 (m hidden, 1 H); 2.67-2.75 (m, 4 H); 2.87 (t, J = 7 Hz, 2 H); 3.21 (m partially hidden, 2 H); 4.41 (dt, J = 47, 6 Hz, 2 H); 6.75 (d, J = 8 Hz, 2 H); 6.85 (d, J = 8 Hz, 1 H); 6.93 (d, J = 8 Hz, 2 H); 7.07 (t, J = 8 Hz, 1 H); 7.18 (ddd, J = 8, 6, 2 Hz, 1 H); 7.39 (td, J = 8, 2 Hz, 1 H); 7.74 (dd, J = 8, 2 Hz, 1 H); 7.91 (d, J = 2 Hz, 1 H) | 522 |
| 33 | A | 1H NMR (400 MHz, DMSO-d6) δ ppm 1.60 (m, 2 H); 2, 09-2, 22 (m, 7 H); 2.38 (t, J = 7 Hz, 2 H); 2.55 (m hidden, 1 H); 2.64-2.73 (m, 4 H); 2.89 (m, 2 H); 3.22 (m partially hidden, 2 H); 4.41 (dt, J = 47, 6 Hz, 2 H); 6.69 (d, J = 8 Hz, 2 H); 6.80-6.91 (m, 4 H); 6.96 (dd, J = 10, 3 Hz, 1 H); 7.05 (dd, J = 8, 6 Hz, 1 H); 7.73 (dd, J = 8, 2 Hz, 1 H); 7.89 (d, J = 2 Hz, 1 H) | 502 |
| 34 | A | 1H NMR (400 MHz, DMSO-d6) δ ppm 1.59 (dquin, J = 25, 7 Hz, 2 H); 2.20 (m, 4 H); 2.38 (t, J = 7 Hz, 2 H); 2.54 (m hidden, 1 H); 2.64-2.73 (m, 4 H); 2.92 (m, 2 H); 3.02 (m partially hidden, 2 H); 4.41 (dt, J = 47, 6 Hz, 2 H); 6.73 (d, J = 8 Hz, 2 H); 6.79 (d, J = 8 Hz, 1 H); 6.89 (d, J = 8 Hz, 2 H); 7.47 (t, J = 8 Hz, 1 H); 7.69 (dd, J = 8, 1 Hz, 1 H); 7.71-7.78 (m, 2 H); 7.91 (d, J = 2 Hz, 1 H) | 572 |
| 35 | A | 1H NMR (400 MHz, DMSO-d6) δ ppm 1.60 (dquin, J = 25, 7 Hz, 2 H); 2.16 (m, 4 H); 2.39 (t, J = 7 Hz, 2 H); 2.55 (m hidden, 1 H); 2.64-2.75 (m, 4 H); 2.88 (t, J = 7 Hz, 2 H); 3.01 (m partially hidden, 2 H); 4.41 (dt, J = 47, 6 Hz, 2 H); 6.75 (d, J = 7 Hz, 2 H); 6.84 (d, J = 8 Hz, 1 H); 6.90 (d, J = 8 Hz, 2 H); 6.99-7.10 (m, 2 H); 7.16 (td, J = 8, 2 Hz, 1 H); 7.23 (m, 1 H); 7.74 (dd, J = 8, 2 Hz, 1 H); 7.90 (d, J = 2 Hz, 1 H) | 488 |
| 36 | A | 1H NMR (400 MHz, DMSO-d6) δ ppm 1.60 (dquin, J = 25, 7 Hz, 2 H); 2.10 (m, 4 H); 2.39 (t, J = 7 Hz, 2 H); 2.55 (m hidden, 1 H); 2.64-2.73 (m, 4 H); 2.86 (t, J = 5 Hz, 2 H); 3.21 (m partially hidden, 2 H); 3.70 (s, 3 H); 4.41 (dt, J = 47, 6 Hz, 2 H); 6.54 (td, J = 8, 2 Hz, 1 H); 6.71 (d, J = 8 Hz, 2 H); 6.78-6.96 (m, 5 H); 7.72 (dd, J = 8, 2 Hz, 1 H); 7.87 (d, J = 2 Hz, 1 H) | 518 |
| 37 | C | 1H NMR (400 MHz, DMSO-d6) δ ppm 0.78 (d, J = 7 Hz, 6 H); 1.62 (m, 2 H); 1.83 (m, 1 H); 1.91 (t, J = 5 Hz, 2 H); 2.09 (d, J = 7 Hz, 2 H); 2.16 (m, 2 H); 2.45 (t, J = 6 Hz, 2 H); 2.64 (m, 1 H); 2.75-2.85 (m, 6 H); 3.32 (m, 2 H); 4.45 (td, J = 6, 47 Hz, 2 H); 6.75 (d, J = 8 Hz, 1 H); 6.97 (d, J = 7 Hz, 2 H); 7.15 (d, J = 7 Hz, 2 H); 7.65 (dd, J = 8, 2 Hz, 1 H); 7.83 (d, J = 2 Hz, 1 H) | 450 |
| 38 | C | 1H NMR (400 MHz, DMSO-d6) δ ppm 1.45 (d, J = 7 Hz, 2 H); 1.70 (m, 2 H); 1.80-1.95 (m, 4 H); 2.14 (m, 2 H); 2, 61 (m, 1 H); 2.72 (t, J = 7 Hz, 2 H); 2.95-3.25 (m, 7 H); 3.75-4.10 (m, 6 H); 4.50 (td, J = 6, 47 Hz, 2 H); 6.72 (d, J = 8 Hz, 1 H); 7.02 (d, J = 7 Hz, 2 H); 7.18 (d, J = 7 Hz, 2 H); 7.67 (dd, J = 8, 2 Hz, 1 H); 7.83 (d, J = 2 Hz, 1 H); 10.40 (br s, 1 H); 12.80 (br s, 1 H) | 478 |
| 39 | D | 1H NMR (400 MHz, DMSO-d6) δ ppm 1.62 (m, 2 H); 2.19 (m, 4 H); 2.42 (m hidden, 2 H); 2.97 (t, J = 6 Hz, 2 H); 3.21 (m, 2 H); 3.57 (m, 2 H); 4.13 (quin, J = 8 Hz, 1 H); 4.42 (dt, J = 47, 6 Hz, 2 H); 6.83 (d, J = 8 Hz, 1 H); 7.00 (d, J = 9 Hz, 2 H); 7.19-7.34 (m, 2 H); 7.60 (d, J = 2 Hz, 1 H); 7.67 (d, J = 9 Hz, 2 H); 7.76 (dd, J = 8, 2 Hz, 1 H); 7.94 (d, J = 2 Hz, 1 H); 13.8 (br s, 1 H) | 552 |
| 40 | D | 1H NMR (400 MHz, DMSO-d6) δ ppm 1.60 (dquin, J = 25, 6 Hz, 2 H); 2.19 (m, 4 H); 2.39 (t, J = 7 Hz, 2 H); 2.95 (m, 4 H); 3.24 (m hidden, 3 H); 4.40 (dt, J = 47, 6 Hz, 2 H); 6.84 (d, J = 8 Hz, 1 H); 6.96 (d, J = 9 Hz, 2 H); 7.19 (m, 1 H); 7.24-7.36 (m, 3 H); 7.59 (d, J = 2 Hz, 1 H); 7.75 (dd, J = 8, 2 Hz, 1 H); 7.93 (d, J = 2 Hz, 1 H); 12, 90 (br s, 1 H) | 574 |
| 41 | D | 1H NMR (400 MHz, DMSO-d6) δ ppm 1.60 (dquin, J = 25, 6 Hz, 2 H); 2.18 (m, 4 H); 2.39 (t, J = 7 Hz, 2 H); 2.72 (m, 1 H); 2.93 (m, 4 H); 3.19 (m hidden, 2 H); 4.29-4.52 (m, 3 H); 5.26 (br s, 1 H); 6.81 (m, 3 H); 7.07 (d, J = 8 Hz, 2 H); 7.19 (m, 1 H); 7.23 (m, 1 H); 7.58 (t, J = 2 Hz, 1 H); 7.74 (dd, J = 8, 2 Hz, 1 H); 7.91 (d, J = 2 Hz, 1 H) | 554 |
| 42 | D | 1H NMR (400 MHz, DMSO-d6) δ ppm 1.60 (dquin, J = 25, 6 Hz, 2 H); 2.18 (m, 4 H); 2.39 (t, J = 7 Hz, 2 | 554 |

TABLE 1b-continued

| Example or compound | Preparation Method | NMR | MASS: LC/MS (m/z, MH+): |
|---|---|---|---|
| | | H); 2.72 (m, 1 H); 2.93 (m, 4 H); 3.19 (m hidden, 2 H); 4.29-4.52 (m, 3 H); 5.26 (br s, 1 H); 6.81 (m, 3 H); 7.07 (d, J = 8 Hz, 2 H); 7.19 (m, 1 H); 7.23 (m, 1 H); 7.58 (t, J = 2 Hz, 1 H); 7.74 (dd, J = 8, 2 Hz, 1 H); 7.91 (d, J = 2 Hz, 1 H) | |
| 43 | D | 1H NMR (400 MHz, DMSO-d6) δ ppm 1.61 (m, 2 H); 2.19 (m, 4 H); 2.40 (t, J = 7 Hz, 2 H); 2.70-3.12 (m, 7 H); 4.42 (dt, J = 47, 6 Hz, 2 H); 5.53 (dd, J = 48, 7 Hz, 1 H); 6.84 (d, J = 8 Hz, 1 H); 6.88 (d, J = 8 Hz, 2 H); 7.15 (d, J = 8 Hz, 2 H); 7.20 (d, J = 8 Hz, 1 H); 7.26 (dd, J = 8, 2 Hz, 1 H); 7.58 (d, J = 2 Hz, 1 H); 7.75 (dd, J = 8, 2 Hz, 1 H); 7.92 (d, J = 2 Hz, 1 H) | 556 |
| 44 | D | 1H NMR (400 MHz, DMSO-d6) δ ppm 1.60 (m, 2 H); 2.18 (m, 4 H); 2.40 (t, J = 7 Hz, 2 H); 2.70-3.12 (m, 7 H); 4.42 (dt, J = 47, 6 Hz, 2 H); 5.52 (dd, J = 48, 7 Hz, 1 H); 6.80 (d, J = 8 Hz, 1 H); 6.88 (d, J = 8 Hz, 2 H); 7.14 (d, J = 8 Hz, 2 H); 7.19 (d, J = 8 Hz, 1 H); 7.25 (dd, J = 8, 2 Hz, 1 H); 7.58 (d, J = 2 Hz, 1 H); 7.72 (dd, J = 8, 2 Hz, 1 H); 7.90 (d, J = 2 Hz, 1 H) | 556 |
| 45 | A | 1H NMR (400 MHz, DMSO-d6) δ ppm 1.60 (dquin, J = 25, 7 Hz, 2 H), 2.06-2.20 (m, 2 H), 2.22-2.29 (m, 2 H), 2.39 (t, J = 7 Hz, 2 H), 2.58 (m, 1 H), 2.68-2.76 (m, 4 H), 2.84 (t, J = 7 Hz, 2 H), 3.23 (t, J = 7 Hz, 2 H), 4.42 (dt, J = 47, 6 Hz, 2 H), 6.78 (d, J = 8 Hz, 2 H), 6.81 (d, J = 8 Hz, 1 H), 6.93-7.01 (m, 3 H), 7.12-7.28 (m, 2 H), 7.71 (dd, J = 8, 2 Hz, 1 H), 7.88 (d, J = 2 Hz, 1 H) | |
| 46 | A | 1H NMR (400 MHz, DMSO-d6) δ ppm 1.63 (dquin, J = 25, 6 Hz, 2 H); 2.18 (m, 4 H); 2.44-2.61 (m hidden, 2 H); 2.94 (t, J = 6 Hz, 2 H); 2.97-3.10 (m, 4 H); 3.22-3.29 (m hidden, 2 H); 4, 43 (dt, J = 47, 6 Hz, 2 H); 6.80 (d, J = 8 Hz, 2 H); 6.84 (d, J = 8 Hz, 1 H); 7.03 (d, J = 8 Hz, 2 H); 7.20 (d, J = 8 Hz, 1 H); 7.25 (dd, J = 8, 2 Hz, 1 H); 7.58 (d, J = 2 Hz, 1 H); 7.74 (dd, J = 8, 2 Hz, 1 H); 7.91 (d, J = 2 Hz, 1 H) | 556 |
| 47 | D | 1H NMR (400 MHz, DMSO-d6) δ ppm 1.76-1.97 (m, 2 H); 2.12-2.29 (m, 4 H); 2.79-3.05 (m, 5 H); 3.10-3.21 (m, 2 H); 3.63-3.81 (m, 2 H); 3.92-4.08 (m, 2 H); 4.50 (td, J = 6, 47 Hz, 2 H); 6.76-7.00 (m, 4 H); 7.14-7, 35 (m, 2 H); 7.56 (d, J = 1 Hz, 1 H); 7.75 (dd, J = 8, 2 Hz, 1 H); 7.92 (d, J = 2 Hz, 1 H); 10.37 (br s, 1 H); 12.37 (br s, 1 H) | 556 |
| 48 | D | 1H NMR (400 MHz, DMSO-d6) δ ppm 1.72-1.91 (m, 2 H); 2.06 (s, 3 H); 2.11-2, 23 (m, 4 H); 2.76-2.84 (m, 2 H); 2.85-2.98 (m, 3 H); 3.00-3.13 (m, 2 H); 3.48-3.65 (m, 2 H); 3.81-4.00 (m, 2 H); 4.49 (td, J = 6, 48 Hz, 2 H); 6.60-6.70 (m, 2 H); 6.79-6.87 (m, 2 H); 7.19 (d, J = 8 Hz, 1 H); 7.27 (dd, J = 8, 2 Hz, 1 H); 7.59 (d, J = 2 Hz, 1 H); 7.75 (dd, J = 8, 2 Hz, 1 H); 7.92 (d, J = 2 Hz, 1 H) | 552 |
| 49 | A | 1H NMR (400 MHz, DMSO-d6) δ ppm 1.58 (m, 2 H); 1.83 (m, 1 H); 2.36 (t, J = 6 Hz, 2 H); 2.50 (m, 3H); 2.60-2.80 (m, 5 H); 3.20 (t, J = 6 Hz, 2 H); 3.86 (s, 3 H); 4.42 (td, J = 6, 47 Hz, 2 H); 4.55-4.65 (m, 3 H); 6.80 (d, J = 7 Hz, 2 H); 6.87 (d, J = 8 Hz, 1 H); 6.93 (d, J = 7 Hz, 2 H); 7.03 (dd, J = 8, 2 Hz, 1 H); 7.12 (t, J = 8 Hz, 1 H); 7.21 (dt, J = 8, 2 Hz, 1 H); 7.43 (d, J = 8 Hz, 1 H); 7.60-7.70 (m, 2H) | 506 |
| 50 | A | 1H NMR (400 MHz, DMSO-d6) δ ppm 1.55-1.71 (m, 2 H); 2.01 (s, 2 H); 2.06-2.12 (m, 2 H); 2.13-2.23 (m, 2 H); 2.42 (t, J = 7 Hz, 2 H); 2.54-2.69 (m, 5 H); 2.70-2.87 (m, 6 H); 3.28 (br t, J = 7 Hz, 2 H); 4.43 (td, J = 6, 48 Hz, 2 H); 6.22 (s, 1 H); 6.80 (d, J = 8 Hz, 1 H); 7.02 (d, J = 8 Hz, 2 H); 7.13 (d, J = 8 Hz, 2 H); 7.67 (dd, J = 8, 2 Hz, 1 H); 7.82 (d, J = 2 Hz, 1 H); 12.78 (br s, 1 H) | 522 |
| 51 | C | 1H NMR (400 MHz, DMSO-d6) δ ppm 1.56-1.69 (m, 2 H); 1.94 (br t, J = 7 Hz, 2 H); 2.04-2.20 (m, 6 H); 2.42 (t, J = 7 Hz, 2 H); 2.45-2.48 (m, 2 H); 2.53-2.71 (m, 5 H); 2.75-2.87 (m, 4 H); 3.33-3.38 (m, 3 H); 4.43 (td, J = 6, 48 Hz, 2 H); 6.66 (d, J = 9 Hz, 1 H); 6.89 (d, J = 8 Hz, 2 H); 7.12 (d, J = 8 Hz, 2 H); 7.64 (dd, J = 9, 2 Hz, 1 H); 7.82 (d, J = 2 Hz, 1 H) | 524 |
| 52 | A | 1H NMR (400 MHz, DMSO-d6) δ ppm 1.82 (m, 2 H); 2.55 (m, 2 H); 2.84 (m, 2 H); 2.92 (m, 1 H); 3, 12 (m, 2 H); 3.55-3.75 (m, 4 H); 3.96 (m, 2 H); 4.49 (td, J = 6, 47 Hz, 2 H); 6.78 (d, J = 7 Hz, 2 H); 6.98 (d, J = 7 | 556 |

TABLE 1b-continued

| Example or compound | Preparation Method | NMR | MASS: LC/MS (m/z, MH+): |
|---|---|---|---|
| | | Hz, 2 H); 7.10 (d, J = 8 Hz, 1 H); 7.28 (dd, J = 8, 2 Hz, 1 H); 7.39 (d, J = 2 Hz, 1 H); 7.68 (d, J = 2 Hz, 1 H); 7.78 (d, J = 8 Hz, 1 H); 7.83 (dd, J = 8, 2 Hz, 1 H); 10.40 (br s, 1 H); 13.00 (br s, 1 H) | |
| 53 | B | 1H NMR (500 MHz, DMSO-d6) δ ppm 1.68-1.85 (m, 2 H), 2.06-2.16 (m, 2 H), 2.25 (t, J = 7 Hz, 2 H), 2.77-2.88 (m, 5 H), 2.89-2.99 (m, 2 H), 3.05 (m, 4 H), 3.37-3.52 (m, 2 H), 3.70-3.83 (m, 2 H), 4.48 (dt, J = 47, 6 Hz, 2 H), 6.79 (d, J = 8 Hz, 2 H), 6.82 (d, J = 8 Hz, 1 H), 6.84-6.90 (m, 2 H), 6.92-6.98 (m, 3 H), 7.72 (dd, J = 8, 2 Hz, 1 H), 7.88 (d, J = 2 Hz, 1 H), 12.57 (br s, 1 H) | 496 |
| 54 | B | 1H NMR (400 MHz, DMSO-d6) δ ppm 1.72-1.94 (m, 2 H), 2.09-2.29 (m, 4 H), 2.33-2.48 (m, 4 H), 2.73-2.97 (m, 5 H), 3.13-3.22 (m, 2 H), 3.62-3.80 (m, 2 H), 3.88-4.02 (m, 2 H), 4.50 (dt, J = 47, 6 Hz, 2 H), 6.72 (d, J = 8 Hz, 2 H), 6.87 (d, J = 8 Hz, 1 H), 6.93 (d, J = 8 Hz, 2 H), 7.30-7.44 (m, 3 H), 7.76 (dd, J = 8, 2 Hz, 1 H), 7.93 (d, J = 2 Hz, 1 H), 10.23 (br s, 1 H), 12.88 (br s, 1 H) | 546 |
| 55 | B | 1H NMR (400 MHz, DMSO-d6) δ ppm 1.73-1.90 (m, 4 H), 2.06-2.23 (m, 4 H), 2.69-2.96 (m, 9 H), 3.03-3.19 (m, 2 H), 3.55-3.73 (m, 2 H), 3.85-3.99 (m, 2 H), 4.49 (dt, J = 47, 6 Hz, 2 H), 6.72 (d, J = 8 Hz, 2 H), 6.81-6.90 (m, 2 H), 6.93 (d, J = 8 Hz, 2 H), 7.00 (dd, J = 8, 5 Hz, 1 H), 7.74 (dd, J = 8, 2 Hz, 1 H), 7.91 (d, J = 2 Hz, 1 H), 10.15 (br s, 1 H), 12.84 (br s, 1 H) | 528 |
| 56 | B | 1H NMR (400 MHz, DMSO-d6) δ ppm 1.59 (dquin, J = 25, 7 Hz, 2 H), 2.13-2.31 (m, 4 H), 2.37 (t, J = 7 Hz, 2 H), 2.52-2.54 (m hidden, 2 H), 2.62-2.72 (m, 3 H), 2.86-2.95 (m, 2 H), 3.20 (t, J = 7 Hz, 2 H), 4.41 (dt, J = 47, 6 Hz, 2 H), 6.60 (d, J = 8 Hz, 2 H), 6.81 (d, J = 8 Hz, 1 H), 6.88 (d, J = 8 Hz, 2 H), 7.73 (dd, J = 8, 2 Hz, 1 H), 7.90 (d, J = 2 Hz, 1 H), 8.15 (dd, J = 9, 3 Hz, 1 H), 8.87 (d, J = 3 Hz, 1 H) | 557 |
| 57 | B | 1H NMR (400 MHz, DMSO-d6) δ ppm 1.73-1.91 (m, 2 H), 2.10-2.26 (m, 4 H), 2.31 (s, 3 H), 2.73-3.00 (m, 5 H), 3.05-3.17 (m, 2 H), 3.59-3.73 (m, 2 H), 3.93 (d, J = 7 Hz, 2 H), 4.49 (dt, J = 47, 6 Hz, 2 H), 6.90 (t, J = 55 Hz, 1 H), 6.79 (d, J = 8 Hz, 2 H), 6.84 (d, J = 8 Hz, 1 H), 6.93 (d, J = 8 Hz, 2 H), 7.09 (d, J = 8 Hz, 1 H), 7.21 (d, J = 8 Hz, 1 H), 7.33 (s, 1 H), 7.75 (dd, J = 8, 2 Hz, 1 H), 7.91 (d, J = 2 Hz, 1 H), 10.46 (br s, 1 H), 12.78 (br s, 1 H) | 534 |
| 58 | A | 1H NMR (400 MHz, DMSO-d6) δ ppm 1.65 (dquin, J = 26, 6 Hz, 2 H), 2.02-2.29 (m, 4 H), 2.52-2.65 (m partially hidden, 3 H), 2.74 (d, J = 8 Hz, 2 H), 2.79-3.11 (m, 4 H), 3.32-3.45 (m, 2 H), 4.43 (dt, J = 47, 6 Hz, 2 H), 6.60 (ddd, J = 17, 9, 2 Hz, 2 H), 6.88 (d, J = 8 Hz, 1 H), 7.06 (t, J = 8 Hz, 1 H), 7.18 (d, J = 8 Hz, 1 H), 7.44 (t, J = 8 Hz, 1 H), 7.57 (d, J = 8 Hz, 1 H), 7.76 (dd, J = 8, 2 Hz, 1 H), 7.92 (d, J = 2 Hz, 1 H), 12.44 (br s, 1 H) | 590 |
| 59 | A | 1H NMR (400 MHz, DMSO-d6) δ ppm 1.73-1.95 (m, 2 H), 2.11-2.31 (m, 4 H), 2.73-3.03 (m, 5 H), 3.10-3.22 (m, 2 H), 3.60-3.87 (m, 2 H), 3.89-4.05 (m, 2 H), 4.50 (dt, J = 47, 6 Hz, 2 H), 6.78-6.91 (m, 3 H), 6.94 (m, 1 H), 7.07 (td, J = 9, 3 Hz, 1 H), 7.21 (m, 1 H), 7.38 (dd, J = 9, 2 Hz, 1 H), 7.74 (dd, J = 8, 2 Hz, 1 H), 7.92 (d, J = 2 Hz, 1 H), 10.15 (br s, 1 H), 12.91 (br s, 1 H) | 540 |
| 60 | A | 1H NMR (400 MHz, DMSO-d6) δ ppm 1.68 (dquin, J = 25, 7 Hz, 2 H), 2.11-2.22 (m, 4 H), 2.23 (s, 3 H), 2.60-2.70 (m, 3 H), 2.76 (d, J = 8 Hz, 2 H), 2.82-2.99 (m, 3 H), 3.05 (m, 1 H), 3.50 (m partially hidden, 2 H), 4.44 (dt, J = 47, 6 Hz, 2 H), 6.52 (dd, J = 11, 2 Hz, 1 H), 6.57 (dd, J = 8, 2 Hz, 1 H), 6.89 (d, J = 8 Hz, 1 H), 6.96-7.05 (m, 2 H), 7.07 (t, J = 9 Hz, 1 H), 7.28 (dd, J = 8, 2 Hz, 1 H), 7.76 (dd, J = 8, 2 Hz, 1 H), 7.92 (d, J = 2 Hz, 1 H), 10.61-13.16 (m, 1 H) | 536 |
| 61 | B | 1H NMR (400 MHz, DMSO-d6) δ ppm 1.60 (dquin, J = 25, 6 Hz, 2 H), 2.09-2.29 (m, 4 H), 2.39-2.44 (m, 2 H), 2.67-2.76 (m, 3 H), 2.81-2.91 (m, 2 H), 2.97-3.08 (m, 2 H), 3.23 (m, hidden, 2 H), 4.41 (dt, J = 47, 6 Hz, 2 H), 6.76 (d, J = 8 Hz, 2 H), 6.87 (d, J = 8 Hz, 1 H), 6.98 (d, J = 8 Hz, 2 H), 7.59 (d, J = 5 Hz, 1 H), 7.76 (dd, J = 8, 2 Hz, 1 H), 7.92 (d, J = 2 Hz, 1 H), 8.17 (s, 1 H), 8.71 (d, J = 5 Hz, 1 H) | 607 |
| 62 | B | 1H NMR (400 MHz, DMSO-d6) δ ppm 1.59 (dquin, J = 25, 7 Hz, 2 H), 2.08-2.25 (m, 4 H), 2.37 (br t, J = 7 | 520 |

TABLE 1b-continued

| Example or compound | Preparation Method | NMR | MASS: LC/MS (m/z, MH+): |
|---|---|---|---|
| | | Hz, 2 H), 2.77-3.22 (m partially hidden, 9 H), 4.41 (dt, J = 48, 6 Hz, 2 H), 5.07 (dd, J = 47, 11 Hz, 1 H), 5.41 (dd, J = 47, 11 Hz, 1 H), 6.71 (d, J = 8 Hz, 2 H), 6.79 (br d, J = 8 Hz, 1 H), 6.89 (d, J = 8 Hz, 2 H), 7.06-7.25 (m, 3 H), 7.62-7.77 (m, 1 H), 7.87 (br s, 1 H), 8.25-8.40 (m, 3 H) | |
| 63 | C | 1H NMR (400 MHz, DMSO-d6) δ ppm 0.98 (d, J = 7 Hz, 3 H), 1.25-1.41 (m, 4 H), 1.47 (d, J = 11 Hz, 2 H), 1.54-1.72 (m, 4 H), 1.85 (m, 1 H), 1.92 (br t, J = 7 Hz, 2 H), 2.15 (quin, J = 7 Hz, 2 H), 2.27 (m, 1 H), 2.43 (t, J = 7 Hz, 2 H), 2.74 (t, J = 7 Hz, 2 H), 3.06 (t, J = 6 Hz, 2 H), 3.31-3.42 (m, 3 H), 4.42 (dt, J = 47, 6 Hz, 2 H), 6.71 (d, J = 8 Hz, 1 H), 7.17 (d, J = 8 Hz, 2 H), 7.48 (d, J = 8 Hz, 2 H), 7.66 (dd, J = 8, 2 Hz, 1 H), 7.83 (d, J = 2 Hz, 1 H), 12.68 (br s, 1 H) | 526 |
| 64 | C | 1H NMR (400 MHz, DMSO-d6) δ ppm 0.98 (d, J = 7 Hz, 3 H), 1.27-1.40 (m, 4 H), 1.47 (br d, J = 11 Hz, 2 H), 1.53-1.74 (m, 4 H), 1.85 (br s, 1 H), 1.92 ( t, J = 7 Hz, 2 H), 2.15 (quin, J = 7 Hz, 2 H), 2.28 (m, 1 H), 2.43 (t, J = 7 Hz, 2 H), 2.74 ( t, J = 7 Hz, 2 H), 3.06 (t, J = 6 Hz, 2 H), 3.31-3.45 (m, 3 H), 4.42 (dt, J = 47, 6 Hz, 2 H), 6.71 (d, J = 8 Hz, 1 H), 7.17 (d, J = 8 Hz, 2 H), 7.48 (d, J = 8 Hz, 2 H), 7.66 (dd, J = 8, 2 Hz, 1 H), 7.83 (d, J = 2 Hz, 1 H), 12.77 (s, 1 H) | 520 |
| 65 | A | 1H NMR (400 MHz, DMSO-d6) δ ppm 1.60 (dquin, J = 25, 7 Hz, 2 H), 2.07-2.19 (m, 2 H), 2.27 (t, J = 7 Hz, 2 H), 2.40 (t, J = 7 Hz, 2 H), 2.57 (m, 1 H), 2.68-2.75 (m, 4 H), 2.85 (t, J = 7 Hz, 2 H), 3.20-3.25 (m, 2 H), 4.42 (dt, J = 47, 6 Hz, 2 H), 6.78 (d, J = 8 Hz, 2 H), 6.84 (d, J = 8 Hz, 1 H), 6.89-7.01 (m, 5 H), 7.21 (q, J = 8 Hz, 1 H), 7.73 (dd, J = 8, 2 Hz, 1 H), 7.89 (d, J = 2 Hz, 1 H), 12.77 (br s, 1 H) | 488 |
| 66 | A | 1H NMR (400 MHz, DMSO-d6) δ ppm 1.59 (dquin, J = 26, 7 Hz, 2 H), 2.07-2.26 (m, 4 H), 2.37 (t, J = 7 Hz, 2 H), 2.55 (m hidden, 1 H), 2.67-2.73 (m, 4 H), 2.80-2.88 (m, 1 H), 2.95-3.07 (m, 1 H), 3.21 (dt, J = 7, 5 Hz, 2 H), 4.41 (dt, J = 47, 6 Hz, 2 H), 6.57 (dd, J = 11, 2 Hz, 1 H), 6.61 (dd, J = 8, 2 Hz, 1 H), 6.88 (d, J = 8 Hz, 1 H), 7.04 (dt, J = 8, 4 Hz, 2 H), 7.34 (dd, J = 11, 8 Hz, 1 H), 7.51 (td, J = 8, 6 Hz, 1 H), 7.76 (dd, J = 8, 2 Hz, 1 H), 7.91 (d, J = 2 Hz, 1 H), 12.70 (br s, 1 H) | 574 |
| 67 | A | 1H NMR (400 MHz, DMSO-d6) δ ppm 1.71-1.93 (m, 2 H), 2.09-2.29 (m, 4 H), 2.74-3.00 (m, 5 H), 3.05-3.21 (m, 2 H), 3.57-3.72 (m, 2 H), 3.85-3.99 (m, 2 H), 4.49 (dt, J = 47, 6 Hz, 2 H), 6.78 (d, J = 8 Hz, 2 H), 6.87 (d, J = 8 Hz, 1 H), 6.96 (d, J = 8 Hz, 2 H), 7.08 (t, J = 55 Hz, 1 H), 7.21 (d, J = 7 Hz, 1 H), 7.41 (t, J = 8 Hz, 1 H), 7.45 (t, J = 7 Hz, 1 H), 7.76 (dd, J = 8, 2 Hz, 1 H), 7.93 (d, J = 2 Hz, 1 H), 10.32 (br s, 1 H), 12.84 (br s, 1 H) | 538 |
| 68 | A | 1H NMR (400 MHz, DMSO-d6) δ ppm 1.79 (dquin, J = 26, 7 Hz, 2 H), 2.09-2.26 (m, 4 H), 2.31 (s, 3 H), 2.72-3.05 (m, 7 H), 3.33-3.50 (m, 2 H), 3.67-3.81 (m, 2 H), 4.48 (dt, J = 47, 6 Hz, 2 H), 6.70 (d, J = 8 Hz, 2 H), 6.88 (d, J = 8 Hz, 1 H), 6.92 (d, J = 8 Hz, 2 H), 7.24 (t, J = 8 Hz, 1 H), 7.33 (d, J = 7 Hz, 1 H), 7.52 (d, J = 7 Hz, 1 H), 7.76 (dd, J = 8, 2 Hz, 1 H), 7.93 (d, J = 2 Hz, 1 H), 11.94 (br s, 2 H) | 552 |
| 69 | A | 1H NMR (400 MHz, DMSO-d6) δ ppm 1.62-1.81 (m, 2 H), 2.15-2.21 (m, 4 H), 2.22 (s, 3 H), 2.68-3.17 (m, 9 H), 3.53-3.67 (m, 2 H), 4.45 (dt, J = 47, 6 Hz, 2 H), 6.73-6.91 (m, 5 H), 6.96 (dd, J = 10, 3 Hz, 1 H), 7.02 (t, J = 7 Hz, 1 H), 7.73 (dd, J = 8, 2 Hz, 1 H), 7.90 (d, J = 2 Hz, 1 H) | 520 |
| 70 | A | 1H NMR (400 MHz, DMSO-d6) δ ppm 1.61 (dquin, J = 26, 6 Hz, 2 H), 2.08-2.25 (m, 4 H), 2.43 (t, J = 7 Hz, 2 H), 2.59 (m, 1 H), 2.71-2.79 (m, 4 H), 2.87 (t, J = 6 Hz, 2 H), 3.27 (t, J = 7 Hz, 2 H), 3.77 (s, 3 H), 4.42 (dt, J = 47, 6 Hz, 2 H), 6.66 (ddd, J = 9, 8, 2 Hz, 2 H), 6.73 (d, J = 5 Hz, 1 H), 6.88 (d, J = 8 Hz, 1 H), 7.07 (t, J = 8 Hz, 1 H), 7.77 (dd, J = 8, 2 Hz, 1 H), 7.92 (d, J = 2 Hz, 1 H), 8.00 (d, J = 2 Hz, 1 H) | 537 |
| 71 | A | 1H NMR (400 MHz, DMSO-d6) δ ppm 1.62 (dquin, J = 25, 7 Hz, 2 H), 2.09-2.26 (m, 4 H), 2.44-2.46 (m, 2 H), 2.59 (m, 1 H), 2.75 (d, J = 8 Hz, 2 H), 2.80 (t, J = 7 Hz, 2 H), 2.87 (t, J = 7 Hz, 2 H), 3.29-3.30 (m hidden, 2 H), 3.87 (s, 3 H), 4.42 (dt, J = 47, 6 Hz, 2 H), 6.65 (ddd, | 537 |

TABLE 1b-continued

| Example or compound | Preparation Method | NMR | MASS: LC/MS (m/z, MH+): |
|---|---|---|---|
| | | J = 9, 8, 2 Hz, 2 H), 6.86 (m, 1 H), 6.89 (d, J = 8 Hz, 1 H), 7.06 (t, J = 8 Hz, 1 H), 7.77 (dd, J = 8, 2 Hz, 1 H), 7.82 (d, J = 5 Hz, 1 H), 7.93 (d, J = 2 Hz, 1 H) | |
| 72 | B | 1H NMR (400 MHz, DMSO-d6) δ ppm 1.59 (ddq, J = 25, 7, 6 Hz, 2 H), 2.12-2.32 (m, 4 H), 2.36 (t, J = 7 Hz, 2 H), 2.40-2.57 (m hidden, 3 H), 2.65 (d, J = 6 Hz, 1 H), 2.70 (d, J = 8 Hz, 1 H), 2.87-2.95 (m, 2 H), 3.20 (m, 2 H), 4.41 (dt, J = 47, 6 Hz, 2 H), 6.42 (dd, J = 11, 2 Hz, 1 H), 6.48 (dd, J = 8, 2 Hz, 1 H), 6.87 (d, J = 8 Hz, 1 H), 7.00 (t, J = 8 Hz, 1 H), 7.76 (dd, J = 8, 2 Hz, 1 H), 7.92 (d, J = 2 Hz, 1 H), 8.33 (d, J = 3 Hz, 1 H), 8.92 (d, J = 2 Hz, 1 H), 13.06 (br s, 1 H) | 591 |
| 73 | A | 1H NMR (400 MHz, DMSO-d6) δ ppm 1.62 (dquin, J = 25, 7 Hz, 2 H), 2.13 (d, J = 3 Hz, 3 H), 2.14-2.21 (m, 4 H), 2.45 (t, J = 7 Hz, 2 H), 2.58 (m, 1 H), 2.73 (d, J = 8 Hz, 2 H), 2.75-2.81 (m, 2 H), 2.81-3.01 (m, 2 H), 3.24-3.27 (m, 2 H), 4.42 (dt, J = 47, 6 Hz, 2 H), 6.54 (dd, J = 11, 2 Hz, 1 H), 6.58 (dd, J = 8, 2 Hz, 1 H), 6.89 (d, J = 8 Hz, 1 H), 6.93 (dd, J = 8, 1 Hz, 1 H), 7.02 (t, J = 8 Hz, 1 H), 7.27 (t, J = 8 Hz, 1 H), 7.76 (dd, J = 8, 2 Hz, 1 H), 7.92 (d, J = 2 Hz, 1 H) | 554 |
| 74 | A | 1H NMR (400 MHz, DMSO-d6) δ ppm 1.74-1.92 (m, 2 H), 2.08-2.17 (m, 2 H), 2.19 (s, 3 H), 2.22-2.30 (m, 2 H), 2.75-2.99 (m, 5 H), 3.02-3.19 (m, 2 H), 3.53-3.76 (m, 2 H), 3.84-3.98 (m, 2 H), 4.49 (dt, J = 47, 6 Hz, 2 H), 6.81 (d, J = 8 Hz, 2 H), 6.83 (d, J = 8 Hz, 1 H), 6.94 (dd, J = 8, 2 Hz, 1 H), 6.98 (d, J = 8 Hz, 2 H), 7.16 (d, J = 2 Hz, 1 H), 7.18 (d, J = 8 Hz, 1 H), 7.73 (dd, J = 8, 2 Hz, 1 H), 7.90 (d, J = 2 Hz, 1 H), 10.51 (br s, 1 H), 12.70 (br s, 1 H) | 518 |
| 75 | A | 1H NMR (400 MHz, DMSO-d6) δ ppm 1.73-1.93 (m, 2 H), 2.12-2.28 (m, 4 H), 2.73-3.03 (m, 5 H), 3.03-3.19 (m, 2 H), 3.52-3.76 (m, 2 H), 3.82-3.98 (m, 2 H), 4.49 (dt, J = 47, 6 Hz, 2 H), 6.80 (d, J = 8 Hz, 2 H), 6.87 (d, J = 8 Hz, 1 H), 6.96 (d, J = 8 Hz, 2 H), 7.39 (t, J = 8 Hz, 1 H), 7.50 (d, J = 7 Hz, 1 H), 7.70 (dd, J = 8, 1 Hz, 1 H), 7.77 (dd, J = 8, 2 Hz, 1 H), 7.95 (d, J = 2 Hz, 1 H), 10.10 (br s, 1 H), 12.85 (br s, 1 H) | 572 |
| 76 | A | 1H NMR (400 MHz, DMSO-d6) δ ppm 1.73-1.90 (m, 2 H), 2.09-2.30 (m, 4 H), 2.77-3.03 (m, 5 H), 3.14 (t, J = 7 Hz, 2 H), 3.63-3.74 (m, 2 H), 3.96 (t, J = 8 Hz, 2 H), 4.49 (dt, J = 47, 6 Hz, 2 H), 6.66 (d, J = 8 Hz, 1 H), 6.82 (d, J = 8 Hz, 2 H), 6.95 (t, J = 55 Hz, 1 H), 6.97 (d, J = 8 Hz, 2 H), 7.25 (d, J = 8 Hz, 1 H), 7.48 (dd, J = 8, 2 Hz, 1 H), 7.55 (d, J = 2 Hz, 1 H), 7.65 (t, J = 8 Hz, 1 H), 10.52 (br s, 1 H), 12.99 (br s, 1 H) | 572 |
| 77 | H | 1H NMR (500 MHz, DMSO-d6) δ ppm 0.96 (t, J = 5 Hz, 1 H), 1.12 (dd, J = 9, 6 Hz, 1 H), 1.66 (dquin, J = 26, 6 Hz, 2 H), 1.94 (t, J = 8 Hz, 1 H), 2.05-2.30 (m, 4 H), 2.63-2.68 (m, 2 H), 2.92 (m, J = 6 Hz, 3 H), 3.23-3.53 (m, 3 H), 4.43 (dt, J = 47, 6 Hz, 2 H), 6.74 (d, J = 6 Hz, 4 H), 6.86 (d, J = 8 Hz, 1 H), 7.17 (m, 1 H), 7.25 (ddd, J = 8, 6, 2 Hz, 1 H), 7.57 (d, J = 2 Hz, 1 H), 7.75 (dd, J = 8, 2 Hz, 1 H), 7.92 (d, J = 2 Hz, 1 H), 12.37 (br s, 1 H) | 550 |
| 78 | H | 1H NMR (500 MHz, DMSO-d6) δ ppm 0.97 (m, 1 H), 1.12 (dd, J = 9, 6 Hz, 1 H), 1.66 (dquin, J = 26, 6 Hz, 2 H), 1.95 (t, J = 7 Hz, 1 H), 2.08-2.26 (m, 4 H), 2.65-2.71 (m, 2 H), 2.92 (m, 3 H), 3.38-3.50 (m, 3 H), 4.43 (dt, J = 47, 6 Hz, 2 H), 6.72-6.76 (m, 4 H), 6.87 (dd, J = 8, 1 Hz, 1 H), 7.17 (m, 1 H), 7.25 (m, 1 H), 7.57 (d, J = 2 Hz, 1 H), 7.75 (dd, J = 8, 2 Hz, 1 H), 7.92 (d, J = 2 Hz, 1 H) | 550 |
| 79 | A | 1H NMR (400 MHz, DMSO-d6) δ ppm 1.66-1.86 (m, 2 H), 2.05-2.19 (m, 5 H), 2.26 (t, J = 7 Hz, 2 H), 2.72-2.99 (m, 7 H), 3.32-3.46 (m, 2 H), 3.60-3.79 (m, 2 H), 4.47 (dt, J = 47, 6 Hz, 2 H), 6.78 (d, J = 8 Hz, 2 H), 6.83 (d, J = 8 Hz, 1 H), 6.87-6.99 (m, 4 H), 7.07 (d, J = 8 Hz, 1 H), 7.73 (dd, J = 8, 2 Hz, 1 H), 7.89 (d, J = 2 Hz, 1 H), 12.63 (br s, 1 H) | 502 |
| 80 | A | 1H NMR (400 MHz, DMSO-d6) δ ppm 1.84 (dquin, J = 27, 7 Hz, 2 H), 2.12-2.30 (m, 4 H), 2.73-2.97 (m, 5 H), 3.16 (t, J = 6 Hz, 2 H), 3.61-3.80 (m, 2 H), 3.94 (t, J = 8 Hz, 2 H), 4.50 (dt, J = 47, 6 Hz, 2 H), 6.77 (d, J = 8 Hz, 2 H), 6.87 (d, J = 8 Hz, 1 H), 6.97 (d, J = 8 Hz, 2 H), | 556 |

TABLE 1b-continued

| Example or compound | Preparation Method | NMR | MASS: LC/MS (m/z, MH+): |
|---|---|---|---|
| | | 7.29 (t, J = 8 Hz, 1 H), 7.60 (q, J = 7 Hz, 2 H), 7.76 (dd, J = 8, 2 Hz, 1 H), 7.94 (d, J = 2 Hz, 1 H), 10.36 (br s, 1 H), 12.87 (br s, 1 H) | |
| 81 | A | 1H NMR (400 MHz, DMSO-d6) δ ppm 1.87 (dqd, J = 27, 7 6 Hz, 2 H), 2.15-2.30 (m, 4 H), 2.61 (m, 1 H), 2.80-3.02 (m, 4 H), 3.18 (t, J = 8 Hz, 2 H), 3.65-3.83 (m, 2 H), 4.00 (t, J = 8 Hz, 2 H), 4.51 (dt, J = 47, 6 Hz, 2 H), 6.77-7.00 (m, 5 H), 7.11 (td, J = 10, 3 Hz, 1 H), 7.23 (td, J = 9, 7 Hz, 1 H), 7.75 (dd, J = 8, 2 Hz, 1 H), 7.92 (d, J = 2 Hz, 1 H) | 524 |
| 82 | B | 1H NMR (400 MHz, DMSO-d6) δ ppm 1.75-1.95 (m, 2 H), 2.13-2.25 (m, 4 H), 2.76-3.01 (m, 5 H), 3.10-3.19 (m, 2 H), 3.63-3.79 (m, 2 H), 3.91-4.03 (m, 2 H), 4.49 (dt, J = 47, 6 Hz, 2 H), 6.76 (t, J = 53 Hz, 1 H), 6.74 (d, J = 8 Hz, 2 H), 6.84 (d, J = 8 Hz, 1 H), 6.98 (d, J = 8 Hz, 2 H), 7.76 (dd, J = 8, 2 Hz, 1 H), 7.95 (d, J = 2 Hz, 1 H), 7.98 (d, J = 2 Hz, 1 H), 8.85 (d, J = 2 Hz, 1 H), 9.91 (br s, 1 H), 12.88 (br s, 1 H) | 555 |
| 83 | A | 1H NMR (400 MHz, DMSO-d6) δ ppm 1.76-1.95 (m, 2 H), 2.06-2.19 (m, 5 H), 2.25 (t, J = 8 Hz, 2 H), 2.76-3.03 (m, 5 H), 3.13-3.25 (m, 2 H), 3.70-3.81 (m, 2 H), 3.94-4.06 (m, 2 H), 4.51 (dt, J = 47, 6 Hz, 2 H), 6.79-6.92 (m, 5 H), 6.99 (d, J = 8 Hz, 2 H), 7.08 (t, J = 8 Hz, 1 H), 7.73 (dd, J = 8, 2 Hz, 1 H), 7.90 (d, J = 1 Hz, 1 H), 10.51 (br s, 1 H), 12.82 (br s, 1 H) | 502 |
| 84 | A | 1H NMR (400 MHz, DMSO-d6) δ ppm 1.72-1.91 (m, 2 H), 2.10-2.17 (m, 5 H), 2.25 (t, J = 8 Hz, 2 H), 2.73-2.93 (m, 5 H), 2.94-3.13 (m, 2 H), 3.46-3.64 (m, 2 H), 3.78-3.91 (m, 2 H), 4.49 (dt, J = 47, 6 Hz, 2 H), 6.76-6.87 (m, 4 H), 6.91 (d, J = 8 Hz, 1 H), 6.93-6.99 (m, 3 H), 7.72 (dd, J = 8, 2 Hz, 1 H), 7.88 (d, J = 2 Hz, 1 H), 10.63 (br s, 1 H), 12.56 (br s, 1 H) | 518 |
| 85 | A | 1H NMR (400 MHz, DMSO-d6) δ ppm1.71-1.92 (m, 2 H), 2.07-2.19 (m, 2 H), 2.25 (s, 8 H), 2.75-2.97 (m, 5 H), 3.00-3.16 (m, 2 H), 3.52-3.69 (m, 2 H), 3.82-3.94 (m, 2 H), 4.49 (dt, J = 47, 6 Hz, 2 H), 6.78-6.87 (m, 3 H), 7.00 (d, J = 8 Hz, 2 H), 7.03 (d, J = 8 Hz, 1 H), 7.12 (s, 1 H), 7.16 (d, J = 8 Hz, 1 H), 7.73 (d, J = 8 Hz, 1 H), 7.90 (s, 1 H), 10.41 (br s, 1 H), 12.70 (br s, 1 H) | 498 |
| 86 | A | 1H NMR (500 MHz, DMSO-d6) δ ppm 1.76-1.90 (m, 2 H), 2.05-2.32 (m, 4 H), 2.75-2.97 (m, 4 H), 3.02 (dt, J = 13, 10 Hz, 1 H), 3.11-3.24 (m, 2 H), 3.62-4.12 (m, 4 H), 4.49 (dt, J = 47, 6 Hz, 2 H), 6.78-6.98 (m, 4 H), 7.15 (d, J = 8 Hz, 1 H), 7.44 (t, J = 8 Hz, 1 H), 7.55 (d, J = 8 Hz, 1 H), 7.75 (dd, J = 8, 2 Hz, 1 H), 7.91 (d, J = 2 Hz, 1 H), 10.24 (br s, 1 H), 12.88 (br s, 1 H) | 590 |
| 87 | A | 1H NMR (500 MHz, DMSO-d6) δ ppm 1.63 (dquin, J = 25, 7 Hz, 2 H), 2.08-2.29 (m, 4 H), 2.51 (m hidden, 2 H), 2.58 (m, 1 H), 2.70 (d, J = 8 Hz, 2 H), 2.79-2.92 (m, 3 H), 3.07 (m, 1 H), 3.32-3.35 (m, 2 H), 4.42 (dt, J = 47, 6 Hz, 2 H), 6.64 (d, J = 8 Hz, 1 H), 6.77 (d, J = 8 Hz, 2 H), 6.93 (d, J = 8 Hz, 2 H), 7.04 (m, 1 H), 7.14-7.30 (m, 2 H), 7.59 (t, J = 8 Hz, 1 H), 8.17 (s, 1 H) | 540 |
| 88 | B | 1H NMR (500 MHz, DMSO-d6) δ ppm 1.59 (dquin, J = 24, 8 Hz, 2 H), 2.14-2.29 (m, 4 H), 2.39 (t, J = 7 Hz, 2 H), 2.65-2.71 (m, 3 H), 2.93 (m, 1 H), 3.05 (m, 1 H), 3.18 (t, J = 7 Hz, 2 H), 3.49-3.53 (m hidden, 2 H), 4.41 (dt, J = 47, 6 Hz, 2 H), 6.63 (d, J = 8 Hz, 2 H), 6.85-6.94 (m, 3 H), 7.73 (d, J = 5 Hz, 1 H), 7.77 (d, J = 8 Hz, 1 H), 7.94 (s, 1 H), 8.21 (br s, 1 H), 8.78 (d, J = 5 Hz, 1 H) | 573 |
| 89 | B | 1H NMR (500 MHz, DMSO-d6) δ ppm 1.61 (dquin, J = 25, 7 Hz, 2 H), 2.09-2.30 (m, 4 H), 2.45 (t, J = 7 Hz, 2 H), 2.57 (m, 1 H), 2.70 (d, J = 8 Hz, 2 H), 2.78 (q, J = 7 Hz, 2 H), 2.84 (dd, J = 13, 6 Hz, 1 H), 3.08 (m, 1 H), 3.28 (m, 2 H), 4.42 (dt, J = 47, 6 Hz, 2 H), 6.76 (d, J = 8 Hz, 2 H), 6.86 (d, J = 8 Hz, 1 H), 6.99 (d, J = 8 Hz, 2 H), 7.76 (dd, J = 8, 2 Hz, 1 H), 7.92 (d, J = 2 Hz, 1 H), 8.17 (s, 1 H), 8.37 (s, 1 H), 8.73 (s, 1 H) | 573 |
| 90 | A | 1H NMR (400 MHz, DMSO-d6) δ ppm 1.76-1.94 (m, 2 H), 2.10-2.20 (m, 2 H), 2.27 (t, J = 7 Hz, 2 H), 2.79-2.98 (m, 5 H), 3.07-3.22 (m, 2 H), 3.65-3.78 (m, 2 H), 3.90-4.03 (m, 2 H), 4.50 (dt, J = 47, 6 Hz, 2 H), 6.82 (d, J = 7 Hz, 2 H), 6.84 (d, J = 7 Hz, 1 H), 7.01 (d, J = 8 Hz, 2 H), 7.12-7.19 (m, 1 H), 7.21-7.27 (m, 1 H), 7.29 (dd, J = 7, 2 Hz, 1 H), 7.74 (dd, J = 8, 2 Hz, 1 H), 7.91 (d, J = 2 Hz, 1 H), 10.16 (br s, 1 H), 12.74 (br s, 1 H) | 522 |

TABLE 1b-continued

| Example or compound | Preparation Method | NMR | MASS: LC/MS (m/z, MH+): |
|---|---|---|---|
| 91 | A | 1H NMR (400 MHz, DMSO-d6) δ ppm 1.84 (dquin, J = 26, 8 Hz, 2 H), 2.11-2.24 (m, 4 H), 2.15 (d, J = 2 Hz, 3 H), 2.74-2.97 (m, 5 H), 3.07-3.18 (m, 2 H), 3.59-3.74 (m, 2 H), 3.94 (t, J = 9 Hz, 2 H), 4.49 (dt, J = 47, 6 Hz, 2 H), 6.79 (d, J = 8 Hz, 2 H), 6.85 (d, J = 8 Hz, 1 H), 6.88-6.98 (m, 4 H), 7.09 (tdd, J = 7, 2, 1 Hz, 1 H), 7.75 (dd, J = 8, 2 Hz, 1 H), 7.91 (d, J = 2 Hz, 1 H), 10.62 (br s, 1 H), 12.68 (br s, 1 H) | 502 |
| 92 | A | 1H NMR (400 MHz, DMSO-d6) δ ppm 1.64 (dq, J = 32, 7 Hz, 2 H), 2.08-2.27 (m, 4 H), 2.51 (m hidden, 2 H), 2.60 (dt, J = 15, 7 Hz, 1 H), 2.71 (d, J = 8 Hz, 2 H), 2.76-2.91 (m, 3 H), 3.05 (m, 1 H), 3.32-3.38 (m, 2 H), 4.43 (dt, J = 47, 6 Hz, 2 H), 6.63 (d, J = 8 Hz, 1 H), 6.78 (d, J = 8 Hz, 2 H), 6.94 (d, J = 8 Hz, 2 H), 7.19 (d, J = 9 Hz, 1 H), 7.25 (dd, J = 9, 3 Hz, 1 H), 7.58 (d, J = 2 Hz, 1 H), 7.61 (d, J = 8 Hz, 1 H), 8.16 (s, 1 H) | 556 |
| 93 | B | 1H NMR (400 MHz, DMSO-d6) δ ppm 1.63 (dquin, J = 26, 7 Hz, 2 H), 2.14-2.29 (m, 4 H), 2.51 (m hidden, 2 H), 2.59 (m, 1 H), 2.70 (d, J = 8 Hz, 2 H), 2.83 (t, J = 7 Hz, 2 H), 2.89-2.99 (m, 2 H), 3.30-3.35 (m, 2 H), 4.42 (dt, J = 47, 6 Hz, 2 H), 6.80 (d, J = 8 Hz, 2 H), 6.95 (t, J = 56 Hz, 1 H), 6.88 (br d, J = 8 Hz, 1 H), 6.95 (br d, J = 8 Hz, 2 H), 7.37-7.51 (m, 2 H), 7.77 (br d, J = 8 Hz, 1 H), 7.94 (br s, 1 H), 8.17 (br s, 1 H) | 556 |
| 94 | A | 1H NMR (400 MHz, DMSO-d6) δ ppm 1.67 (dquin, J = 25, 8 Hz, 2 H), 2.06-2.18 (m, 2 H), 2.29 (t, J = 7 Hz, 2 H), 2.62 (t, J = 7 Hz, 2 H), 2.66 (m, 1 H), 2.75 (d, J = 7 Hz, 2 H), 2.87 (t, J = 7 Hz, 2 H), 3.00 (t, J = 7 Hz, 2 H), 3.44 (t, J = 8 Hz, 2 H), 4.44 (dt, J = 47, 6 Hz, 2 H), 6.63 (d, J = 8 Hz, 1 H), 6.80 (d, J = 8 Hz, 2 H), 6.97 (d, J = 8 Hz, 2 H), 7.09-7.27 (m, 4 H), 7.60 (t, J = 8 Hz, 1 H), 8.16 (s, 1 H) | 522 |
| 95 | B | 1H NMR (500 MHz, DMSO-d6) δ ppm 1.59 (dquin, J = 25, 6 Hz, 2 H), 2.12-2.24 (m, 4 H), 2.27 (s, 3 H), 2.37 (t, J = 7 Hz, 2 H), 2.54 (m hidden, 1 H), 2.64-2.70 (m, 4 H), 2.87 (m, 1 H), 2.98 (m, 1 H), 3.20 (m, 4 Hz, 2 H), 4.41 (dt, J = 47, 6 Hz, 2 H), 6.72 (d, J = 8 Hz, 2 H), 6.82 (t, J = 56 Hz, 1 H), 6.81 (d, J = 8 Hz, 1 H), 6.90 (d, J = 8 Hz, 2 H), 7.47 (s, 1 H), 7.72 (dd, J = 8, 2 Hz, 1 H), 7.90 (d, J = 1 Hz, 1 H), 8.26 (s, 1 H) | 535 |
| 96 | C | 1H NMR (500 MHz, DMSO-d6) δ ppm 0.66 (s, 3 H), 0.89 (s, 3 H), 1.04-1.39 (m, 6 H), 1.45-1.56 (m, 2 H), 1.70-1.99 (m, 4 H), 2.11 (quin, J = 7 Hz, 2 H), 2.59 (m, 1 H), 2.71 (t, J = 7 Hz, 2 H), 2.89-3.03 (m, 3 H), 3.09-3.19 (m, 2 H), 3.71 (s, 2 H), 3.97 (s, 2 H), 4.50 (dt, J = 47, 6 Hz, 2 H), 6.76 (d, J = 8 Hz, 1 H), 7.00 (d, J = 8 Hz, 2 H), 7.17 (d, J = 8 Hz, 2 H), 7.66 (dd, J = 8, 2 Hz, 1 H), 7.82 (d, J = 2 Hz, 1 H), 10.33 (br s, 1 H), 12.69 (br s, 1 H) | 504 |
| 97 | C | 1H NMR (500 MHz, DMSO-d6) δ ppm 0.66 (s, 3 H), 0.89 (s, 3 H), 1.01-1.35 (m, 6 H), 1.51 (m, 2 H), 1.71-1.98 (m, 6 H), 2.11 (quin, J = 7 Hz, 2 H), 2.45 (m, 1 H), 2.59 (m, 1 H), 2.71 (t, J = 7 Hz, 2 H), 2.83-3.13 (m, 4 H), 3.72-4.04 (m, 2 H), 4.49 (dt, J = 47, 6 Hz, 2 H), 6.76 (d, J = 8 Hz, 1 H), 7.00 (d, J = 8 Hz, 2 H), 7.16 (d, J = 8 Hz, 2 H), 7.66 (dd, J = 8, 2 Hz, 1 H), 7.82 (d, J = 2 Hz, 1 H), 9.89 (br s, 1 H), 12.73 (br s, 1 H) | 504 |
| 98 | B | 1H NMR (400 MHz, DMSO-d6) δ ppm 1.60 (dquin, J = 25, 7 Hz, 2 H), 2.12 (s, 3 H), 2.13-2.22 (m, 4 H), 2.40 (t, J = 7 Hz, 2 H), 2.64-2.76 (m, 5 H), 2.83-3.02 (m, 2 H), 3.20-3.25 (m, 2 H), 4.41 (dt, J = 47, 6 Hz, 2 H), 6.71 (d, J = 8 Hz, 2 H), 6.80-6.96 (m, 5 H), 7.13 (dd, J = 8, 6 Hz, 1 H), 7.74 (dd, J = 8, 2 Hz, 1 H), 7.91 (d, J = 2 Hz, 1 H), 8.18 (s, 1 H) | 502 |
| 99 | A | 1H NMR (500 MHz, DMSO-d6) δ ppm 1.84 (dquin, J = 26, 8 Hz, 2 H), 2.10-2.26 (m, 4 H), 2.81-2.95 (m, 5 H), 3.06-3.18 (m, 2 H), 3.59-3.72 (m, 2 H), 3.88-3.99 (m, 2 H), 4.50 (dt, J = 47, 6 Hz, 2 H), 6.81 (d, J = 8 Hz, 2 H), 6.86 (d, J = 8 Hz, 1 H), 6.99 (t, J = 56 Hz, 1 H), 6.97 (d, J = 8 Hz, 2 H), 7.28 (d, J = 8 Hz, 1 H), 7.32 (d, J = 10 Hz, 1 H), 7.36 (t, J = 7 Hz, 1 H), 7.76 (dd, J = 8, 2 Hz, 1 H), 7.94 (d, J = 1 Hz, 1 H), 10.70 (br s, 1 H), 12.72 (br s, 1 H) | 538 |
| 100 | A | 1H NMR (500 MHz, DMSO-d6) δ ppm 1.84 (dquin, J = 26, 8 Hz, 2 H), 2.17-2.31 (m, 4 H), 2.82-3.08 (m, 5 H), 3.09-3.17 (m, 2 H), 3.67 (br s, 2 H), 3.90-4.00 (m, 2 H), 4.50 (dt, J = 47, 6 Hz, 2 H), 6.78 (d, J = 8 Hz, 2 | 513 |

TABLE 1b-continued

| Example or compound | Preparation Method | NMR | MASS: LC/MS (m/z, MH+): |
|---|---|---|---|
| | | H), 6.85 (d, J = 8 Hz, 1 H), 6.98 (d, J = 8 Hz, 2 H), 7.50-7.60 (m, 2 H), 7.70 (dd, J = 9, 3 Hz, 1 H), 7.77 (dd, J = 8, 2 Hz, 1 H), 7.94 (d, J = 2 Hz, 1 H), 10.80 (br s, 1 H), 12.74 (br s, 1 H) | |
| 101 | A | 1H NMR (500 MHz, DMSO-d6) δ ppm 1.84 (dquin, J = 26, 8 Hz, 2 H), 2.08 (t, J = 9 Hz, 2 H), 2.16 (s, 6 H), 2.17-2.24 (m, 2 H), 2.78-3.03 (m, 5 H), 3.10-3.22 (m, 2 H), 3.71 (m, 2 H), 3.99 (m, 2 H), 4.50 (dt, J = 47, 6 Hz, 2 H), 6.71 (d, J = 8 Hz, 2 H), 6.82 (d, J = 8 Hz, 1 H), 6.94 (d, J = 8 Hz, 2 H), 7.07 (s, 2 H), 7.75 (dd, J = 8, 2 Hz, 1 H), 7.94 (d, J = 2 Hz, 1 H), 10.39 (br s, 1 H), 12.87 (br s, 1 H) | 532 |
| 102 | A | 1H NMR (500 MHz, DMSO-d6) δ ppm 1.60-1.78 (m, 2 H), 2.14-2.32 (m, 4 H), 2.59-2.71 (m, 3 H), 2.75 (d, J = 8 Hz, 2 H), 2.84-3.09 (m, 4 H), 3.40-3.57 (m, 2 H), 4.44 (dt, J = 47, 6 Hz, 2 H), 6.77 (dd, J = 8, 2 Hz, 1 H), 6.80-6.90 (m, 3 H), 6.94 (t, J = 9 Hz, 1 H), 7.04 (q, J = 8 Hz, 1 H), 7.74 (dd, J = 8, 2 Hz, 1 H), 7.91 (d, J = 2 Hz, 1 H), 12.28 (br s, 1 H) | 520 |
| 103 | A | 1H NMR (500 MHz, DMSO-d6) δ ppm 1.60 (dquin, J = 25, 7 Hz, 2 H), 2.06 (t, J = 2 Hz, 3 H), 2.12-2.24 (m, 4 H), 2.40 (t, J = 7 Hz, 2 H), 2.74 (td, J = 7, 3 Hz, 1 H), 2.77-2.98 (m, 3 H), 3.01 (t, J = 7 Hz, 1 H), 3.08 (t, J = 7 Hz, 1 H), 3.23 (t, J = 8 Hz, 1 H), 4.41 (dt, J = 47, 6 Hz, 2 H), 5.51 (dd, J = 48, 7 Hz, 1 H), 6.82 (d, J = 8 Hz, 2 H), 6.85 (d, J = 8 Hz, 1 H), 6.89 (m, 1 H), 6.97 (t, J = 8 Hz, 1 H), 7.05 (m, 1 H), 7.10 (dd, J = 8, 1 Hz, 2 H), 7.75 (dd, J = 8, 2 Hz, 1 H), 7.92 (d, J = 2 Hz, 1 H) | 520 |
| 104 | A | 1H NMR (500 MHz, DMSO-d6) δ ppm 1.54-1.69 (m, 2 H), 2.41 (t, J = 7 Hz, 2 H), 2.71-3.14 (m, 10 H), 3.20-3.25 (m hidden, 2 H), 3.39-3.41 (m hidden, 2 H), 4.42 (dt, J = 47, 6 Hz, 2 H), 5.52 (dd, J = 48, 7 Hz, 1 H), 6.81 (d, J = 8 Hz, 2 H), 6.84-6.90 (m, 2 H), 6.98 (d, J = 10 Hz, 1 H), 7.05 (t, J = 7 Hz, 1 H), 7.10 (d, J = 8 Hz, 2 H), 7.75 (d, J = 11 Hz, 1 H), 7.92 (s, 1 H) | 520 |
| 105 | No general method; described in example section | 1H NMR (500 MHz, DMSO-d6) δ ppm 1.60 (dquin, J = 25, 7 Hz, 2 H), 2.09-2.22 (m, 2 H), 2.31 (t, J = 7 Hz, 2 H), 2.38 (t, J = 7 Hz, 2 H), 2.55 (m hidden, 1 H), 2.65-2.73 (m, 4 H), 2.87 (t, J = 7 Hz, 2 H), 3.21 (t, J = 7 Hz, 2 H), 4.42 (dt, J = 47, 6 Hz, 2 H), 6.79 (d, J = 8 Hz, 2 H), 6.84 (d, J = 8 Hz, 1 H), 6.96 (d, J = 8 Hz, 2 H), 7.32 (dd, J = 5, 2 Hz, 1 H), 7.56 (br s, 1 H), 7.70-7.78 (m, 2 H), 7.91 (s, 1 H), 8.01 (d, J = 3 Hz, 1 H), 8.41 (d, J = 5 Hz, 1 H), 12.91 (br s, 1 H) | 514 |
| 106 | A | 1H NMR (400 MHz, DMSO-d6) δ ppm 1.60 (dquin, J = 25, 7 Hz, 2 H), 1.99-2.29 (m, 4 H), 2.40 (t, J = 7 Hz, 2 H), 2.69-2.93 (m, 3 H), 2.94-3.12 (m, 3 H), 3.23 (dd, J = 12, 7 Hz, 1 H), 4.41 (dt, J = 47, 6 Hz, 2 H), 5.51 (dd, J = 48, 7 Hz, 1 H), 6.76-6.94 (m, 3 H), 7.06-7.21 (m, 3 H), 7.38 (m, 1 H), 7.54 (d, J = 8 Hz, 1 H), 7.75 (dd, J = 8, 2 Hz, 1 H), 7.92 (d, J = 2 Hz, 1 H) | 590 |
| 107 | A | 1H NMR (400 MHz, DMSO-d6) δ ppm 1.60 (dquin, J = 25, 7 Hz, 2 H), 2.06-2.21 (m, 4 H), 2.24 (s, 3 H), 2.40 (t, J = 7 Hz, 2 H), 2.69-2.89 (m, 2 H), 2.93 (t, J = 6 Hz, 2 H), 2.98-3.13 (m, 2 H), 3.24 (m, 1 H), 4.41 (dt, J = 47, 6 Hz, 2 H), 5.51 (dd, J = 48, 7 Hz, 1 H), 6.83 (d, J = 8 Hz, 1 H), 6.88 (d, J = 8 Hz, 2 H), 6.96(m, 1 H), 7.02 (m, 1 H), 7.11 (dd, J = 8, 1 Hz, 2 H), 7.24 (d, J = 1 Hz, 1 H), 7.74 (dd, J = 8, 2 Hz, 1 H), 7.91 (d, J = 2 Hz, 1 H) | 536 |
| 108 | C | 1H NMR (500 MHz, DMSO-d6) δ ppm 0.80-0.89 (m, 4 H), 1.02-1.50 (m, 4 H), 1.52-1.61 (m, 3 H), 1.71 (m, 1 H), 1.78-1.97 (m, 4 H), 2.12 (quin, J = 7 Hz, 2 H), 2.41 (m, 1 H), 2.72 (t, J = 7 Hz, 2 H), 2.87-3.09 (m, 3 H), 3.16-3.24 (m, 2 H), 3.71-3.94 (m, 2 H), 3.95-4.21 (m, 2 H), 4.51 (dt, J = 47, 6 Hz, 2 H), 6.72 (d, J = 8 Hz, 1 H), 7.00 (d, J = 8 Hz, 2 H), 7.17 (d, J = 8 Hz, 2 H), 7.65 (dd, J = 8, 2 Hz, 1 H), 7.82 (d, J = 2 Hz, 1 H), 9.80-10.40 (m, 1 H), 12.78 (br s, 1 H) | 490 |
| 109 | C | 1H NMR (500 MHz, DMSO-d6) δ ppm 0.76 (d, J = 7 Hz, 3 H), 1.12-1.60 (m, 7 H), 1.65 (td, J = 13, 5 Hz, 1 H), 1.73-2.05 (m, 5 H), 2.05-2.20 (m, 2 H), 2.67 (br t, J = 3 Hz, 1 H), 2.71 (br t, J = 7 Hz, 2 H), 2.81-3.09 (m, 3 H), 3.16-3.26 (m, 2 H), 3.74-3.93 (m, 2 H), 3.96-4.16 (m, 2 H), 4.51 (dt, J = 47, 6 Hz, 2 H), 6.75 (d, J = 8 | 490 |

TABLE 1b-continued

| Example or compound | Preparation Method | NMR | MASS: LC/MS (m/z, MH+): |
|---|---|---|---|
| | | Hz, 1 H), 7.01 (d, J = 8 Hz, 2 H), 7.18 (d, J = 8 Hz, 2 H), 7.66 (dd, J = 8, 2 Hz, 1 H), 7.82 (d, J = 2 Hz, 1 H), 10.11 (m, 1 H), 12.74 (br s, 1 H) | |
| 110 | No general method; described in example section | 1H NMR (500 MHz, DMSO-d6) δ ppm 1.62 (dquin, J = 25, 7 Hz, 2 H), 2.08-2.21 (m, 2 H), 2.31 (t, J = 7 Hz, 2 H), 2.42 (t, J = 7 Hz, 2 H), 2.55 (m hidden, 1 H), 2.72-2.82 (m, 6 H), 3.28 (t, J = 7 Hz, 2 H), 4.43 (dt, J = 47, 6 Hz, 2 H), 5.54 (br s, 1 H), 5.86 (q, J = 2 Hz, 1 H), 6.59-6.63 (m, 1 H), 6.80 (d, J = 8 Hz, 1 H), 6.93 (d, J = 8 Hz, 2 H), 7.07 (d, J = 8 Hz, 2 H), 7.67 (dd, J = 8, 2 Hz, 1 H), 7.82 (d, J = 2 Hz, 1 H), 10.25 (br d, J = 2 Hz, 1 H), 12.81 (br s, 1 H) | 459 |
| 111 | A | 1H NMR (500 MHz, DMSO-d6) δ ppm 1.61 (dquin, J = 25, 7 Hz, 2 H), 2.10-2.24 (m, 4 H), 2.40 (t, J = 7 Hz, 2 H), 2.75 (t, J = 8 Hz, 1 H), 2.78-2.92 (m, 3 H), 3.02 (t, J = 7 Hz, 1 H), 3.10 (t, J = 7 Hz, 1 H), 3.24 (t, J = 7 Hz, 1 H), 4.42 (dt, J = 47, 6 Hz, 2 H), 5.54 (dd, J = 48, 7 Hz, 1 H), 6.84 (d, J = 8 Hz, 1 H), 6.88 (d, J = 8 Hz, 2 H), 7.11-7.17 (m, 3 H), 7.23 (t, J = 8 Hz, 1 H), 7.29 (dd, J = 10, 2 Hz, 1 H), 7.75 (dd, J = 8, 2 Hz, 1 H), 7.92 (d, J = 2 Hz, 1 H) | 540 |
| 112 | A | 1H NMR (500 MHz, DMSO-d6) δ ppm 1.60 (dquin, J = 25, 7 Hz, 2 H), 2.10-2.23 (m, 7 H), 2.40 (t, J = 7 Hz, 2 H), 2.75 (q, J = 7 Hz, 1 H), 2.78-2.99 (m, 3 H), 3.01 (t, J = 7 Hz, 1 H), 3.09 (t, J = 7 Hz, 1 H), 3.21-3.27 (m, 1 H), 4.42 (dt, J = 47, 6 Hz, 2 H), 5.51 (dd, J = 48, 7 Hz, 1 H), 6.82 (d, J = 8 Hz, 2 H), 6.84 (d, J = 8 Hz, 1 H), 7.04 (m, 1 H), 7.07-7.14 (m, 3 H), 7.21 (d, J = 2 Hz, 1 H), 7.75 (dd, J = 8, 2 Hz, 1 H), 7.92 (d, J = 2 Hz, 1 H) | 536 |
| 113 | B | 1H NMR (500 MHz, DMSO-d6) δ ppm 1.14 (t, J = 8 Hz, 3 H), 1.77-1.90 (m, 2 H), 2.09-2.18 (m, 7 H), 2.50-2.54 (m hidden, 2 H), 2.74-2.98 (m, 5 H), 3.09-3.20 (m, 2 H), 3.64-3.77 (m, 2 H), 3.92-4.04 (m, 2 H), 4.49 (dt, J = 47, 6 Hz, 2 H), 6.73 (d, J = 8 Hz, 2 H), 6.83 (d, J = 8 Hz, 1 H), 6.86-6.98 (m, 5 H), 7.74 (dd, J = 8, 2 Hz, 1 H), 7.91 (d, J = 2 Hz, 1 H), 10.27 (br s, 1 H), 12.82 (br s, 1 H) | 512 |
| 114 | A | 1H NMR (400 MHz, DMSO-d6) δ ppm 1.68-1.89 (m, 2 H), 2.18 (quin, J = 7 Hz, 2 H), 2.30-2.40 (m, 2 H), 2.73-3.07 (m, 7 H), 3.38-3.88 (m, 4 H), 4.48 (dt, J = 47, 6 Hz, 2 H), 6.79 (d, J = 8 Hz, 2 H), 6.87 (d, J = 8 Hz, 1 H), 6.97 (d, J = 8 Hz, 2 H), 7.59 (d, J = 9 Hz, 2 H), 7.77 (dd, J = 8, 2 Hz, 1 H), 7.93 (d, J = 9 Hz, 2 H), 7.95 (d, J = 2 Hz, 1 H), 10.37 (br s, 1 H), 12.70 (br s, 1 H) | 602 |
| 115 | F | 1H NMR (500 MHz, DMSO-d6) δ ppm 1.76-1.90 (m, 2 H), 2.14-2.33 (m, 4 H), 2.86-3.03 (m, 5 H), 3.10-3.20 (m, 2 H), 3.70 (br s, 2 H), 3.99 (br s, 2 H), 4.49 (dt, J = 47, 6 Hz, 2 H), 6.77 ( t, J = 7 Hz, 1 H), 6.89 (d, J = 8 Hz, 2 H), 7.20-7.36 (m, 2 H), 7.58 (d, J = 2 Hz, 1 H), 7.76 (dd, J = 8, 2 Hz, 1 H), 7.93 (d, J = 2 Hz, 1 H), 10.40 (br s, 1 H), 12.90 (br s, 1 H) | 574 |
| 116 | B | 1H NMR (500 MHz, DMSO-d6) δ ppm 1.78-1.90 (m, 2 H), 2.06 (t, J = 8 Hz, 2 H), 2.11 (s, 6 H), 2.14-2.22 (m, 5 H), 2.72-2.92 (m, 3 H), 2.95 (t, J = 7 Hz, 2 H), 3.06-3.19 (m, 2 H), 3.57-3.78 (m, 2 H), 3.88-4.04 (m, 2 H), 4.49 (dt, J = 47, 6 Hz, 2 H), 6.71 (d, J = 8 Hz, 2 H), 6.77 (s, 2 H), 6.81 (d, J = 8 Hz, 1 H), 6.90 (d, J = 8 Hz, 2 H), 7.73 (dd, J = 8, 2 Hz, 1 H), 7.92 (d, J = 2 Hz, 1 H), 10.62 (br s, 1 H), 12.80 (br s, 1 H) | 512 |
| 117 | A | 1H NMR (400 MHz, DMSO-d6) δ ppm 1.75-1.96 (m, 2 H), 2.07-2.22 (m, 2 H), 2.29 (t, J = 10 Hz, 2 H), 2.78-3.02 (m, 4 H), 3.11-3.23 (m, 2 H), 3.73 (m, 2 H), 3.91-4.10 (m, 2 H), 4.50 (dt, J = 47, 6 Hz, 2 H), 6.81 (d, J = 1 Hz, 3 H), 6.95 (t, J = 58 Hz, 1 H), 6.92-7.01 (m, 3 H), 7.29 (d, J = 8 Hz, 2 H), 7.38 (d, J = 9 Hz, 2 H), 7.74 (dd, J = 8, 2 Hz, 1 H), 7.91 (d, J = 2 Hz, 1 H), 10.21 (br s, 1 H), 12.86 (br s, 1 H) | 520 |
| 118 | A | 1H NMR (400 MHz, DMSO-d6) δ ppm 1.84 (dquin, J = 25, 7 Hz, 2 H), 2.08-2.20 (m, 2 H), 2.27 (t, J = 7 Hz, 2 H), 2.78-2.95 (m, 5 H), 3.02-3.17 (m, 2 H), 3.56-3.72 (m, 2 H), 3.87-3.97 (m, 2 H), 4.50 (dt, J = 47, 6 Hz, 2 H), 6.81 (d, J = 8 Hz, 2 H), 6.84 (d, J = 8 Hz, 1 H), 6.99 (d, J = 8 Hz, 2 H), 7.09-7.16 (m, 2 H), 7.17-7.27 (m, 2 H), 7.74 (dd, J = 8, 2 Hz, 1 H), 7.91 (d, J = 2 Hz, 1 H), 10.80 (br s, 1 H), 12.49 (br s, 1 H) | 502 |
| 119 | A | 1H NMR (400 MHz, DMSO-d6) δ ppm 1.73-1.89 (m, 2 H), 2.08-2.19 (m, 4 H), 2.21 (s, 3 H), 2.76-3.12 (m, | 509 |

TABLE 1b-continued

| Example or compound | Preparation Method | NMR | MASS: LC/MS (m/z, MH+): |
|---|---|---|---|
| | | 7 H), 3.49-3.63 (m, 2 H), 3.81-3.95 (m, 2 H), 4.48 (dt, J = 47, 6 Hz, 2 H), 6.72 (d, J = 8 Hz, 2 H), 6.85 (d, J = 8 Hz, 1 H), 6.93 (d, J = 8 Hz, 2 H), 7.24 (d, J = 8 Hz, 1 H), 7.51 (d, J = 8 Hz, 1 H), 7.62 (s, 1 H), 7.75 (d, J = 8 Hz, 1 H), 7.93 (s, 1 H), 10.48 (br s, 1 H), 12.49 (br s, 1 H) | |
| 120 | A | 1H NMR (400 MHz, DMSO-d6) δ ppm 1.70-1.90 (m, 2 H), 2.03-2.24 (m, 5 H), 2.39(m hidden, 1 H), 2.77-3.07 (m, 8 H), 3.46-4.01 (m, 4 H), 4.48 (dt, J = 47, 6 Hz, 2 H), 6.80 (d, J = 8 Hz, 2 H), 6.83 (d, J = 8 Hz, 1 H), 6.89-7.02 (m, 4 H), 7.10 (t, J = 8 Hz, 1 H), 7.74 (d, J = 9 Hz, 1 H), 7.91 (s, 1 H), 9.89 (br s, 1 H), 12.78 (br s, 1 H) | 534 |
| 121 | F | 1H NMR (500 MHz, DMSO-d6) δ ppm 1.59 (dquin, J = 25, 7 Hz, 2 H), 2.13-2.31 (m, 4 H), 2.36 (t, J = 7 Hz, 2 H), 2.57 (m, 1 H), 2.66 (t, J = 7 Hz, 2 H), 2.71 (d, J = 7 Hz, 2 H), 2.94 (t, J = 6 Hz, 2 H), 3.21 (t, J = 6 Hz, 2 H), 4.41 (dt, J = 47, 6 Hz, 2 H), 6.76 (dd, J = 10, 6 Hz, 1 H), 6.89 (d, J = 8 Hz, 1 H), 6.96 (dd, J = 10, 6 Hz, 1 H), 7.22 (m, 1 H), 7.30 (m, 1 H), 7.57 (br s, 1 H), 7.74 (dd, J = 8, 2 Hz, 1 H), 7.90 (d, J = 2 Hz, 1 H) | 574 |
| 122 | A | 1H NMR (500 MHz, DMSO-d6) δ ppm 1.60 (dquin, J = 25, 7 Hz, 2 H), 2.12 (s, 3 H), 2.14 (m, 4 H), 2.20 (s, 3 H), 2.39 (t, J = 7 Hz, 2 H), 2.73 (td, J = 7, 4 Hz, 1 H), 2.77-2.97 (m, 3 H), 3.01 (t, J = 7 Hz, 1 H), 3.08 (t, J = 7 Hz, 1 H), 3.22-3.24 (m, 1 H), 4.41 (dt, J = 47, 6 Hz, 2 H), 5.50 (dd, J = 48, 7 Hz, 1 H), 6.77-6.86 (m, 4 H), 6.88-6.95 (m, 2 H), 7.08 (dd, J = 8, 1 Hz, 2 H), 7.73 (dd, J = 8, 2 Hz, 1 H), 7.90 (d, J = 2 Hz, 1 H) | 516 |
| 123 | A | 1H NMR (500 MHz, DMSO-d6) δ ppm 1.60 (dquin, J = 25, 7 Hz, 2 H), 2.09-2.26 (m, 4 H), 2.32 (s, 3 H), 2.39 (t, J = 7 Hz, 2 H), 2.73 (dt, J = 10, 7 Hz, 1 H), 2.83 (m, 1 H), 2.89-3.04 (m, 3 H), 3.07 (t, J = 7 Hz, 1 H), 3.22 (m hidden, 1 H), 4.41 (dt, J = 47, 6 Hz, 2 H), 5.50 (dd, J = 48, 8 Hz, 1 H), 6.84 (d, J = 8 Hz, 1 H), 6.87 (d, J = 8 Hz, 2 H), 6.96 (ddd, J = 8, 3, 2 Hz, 1 H), 7.03 (td, J = 8, 2 Hz, 1 H), 7.10 (d, J = 8 Hz, 2 H), 7.17 (d, J = 8 Hz, 1 H), 7.74 (dd, J = 8, 2 Hz, 1 H), 7.92 (d, J = 2 Hz, 1 H) | 536 |
| 124 | A | 1H NMR (500 MHz, DMSO-d6) δ ppm 1.77-1.90 (m, 2 H), 2.07-2.30 (m, 7 H), 2.78-3.03 (m, 5 H), 3.08-3.18 (m, 2 H), 3.61-3.79 (m, 2 H), 3.90-4.02 (m, 2 H), 4.49 (dt, J = 47, 6 Hz, 2 H), 6.81 (dd, J = 8, 1 Hz, 1 H), 6.83-6.90 (m, 2 H), 6.94 (d, J = 8 Hz, 1 H), 6.97 (d, J = 8 Hz, 1 H), 7.06 (m, 1 H), 7.21 (s, 1 H), 7.74 (dd, J = 8, 2 Hz, 1 H), 7.91 (d, J = 2 Hz, 1 H), 10.34 (br s, 1 H), 12.73 (br s, 1 H) | 536 |
| 125 | A | 1H NMR (500 MHz, DMSO-d6) δ ppm 1.60 (dquin, J = 26, 6 Hz, 2 H), 2.09-2.27 (m, 4 H), 2.40 (t, J = 7 Hz, 2 H), 2.74 (q, J = 7 Hz, 1 H), 2.83 (m, 1 H), 2.90-2.98 (m, 2 H), 3.01 (td, J = 7, 2 Hz, 1 H), 3.08 (t, J = 7 Hz, 1 H), 3.23 (m, 1 H), 4.41 (dt, J = 47, 6 Hz, 2 H), 5.52 (dd, J = 48, 7 Hz, 1 H), 6.84 (d, J = 8 Hz, 1 H), 6.87 (d, J = 8 Hz, 2 H), 7.05 (td, J = 8, 3 Hz, 1 H), 7.13 (d, J = 8 Hz, 2 H), 7.21 (t, J = 7 Hz, 1 H), 7.40 (dd, J = 9, 3 Hz, 1 H), 7.74 (dd, J = 8, 2 Hz, 1 H), 7.92 (d, J = 2 Hz, 1 H) | 540 |
| 126 | A | 1H NMR (500 MHz, DMSO-d6) δ ppm 1.60 (dquin, J = 25, 7 Hz, 2 H), 2.10-2.30 (m, 4 H), 2.39 (t, J = 7 Hz, 2 H), 2.74 (q, J = 6 Hz, 1 H), 2.82 (m, 1 H), 2.95 (t, J = 7 Hz, 2 H), 3.00 (t, J = 7 Hz, 1 H), 3.08 (t, J = 7 Hz, 1 H), 3.23 (t, J = 7 Hz, 1 H), 4.41 (dt, J = 47, 6 Hz, 2 H), 5.51 (dd, J = 48, 7 Hz, 1 H), 6.85 (d, J = 8 Hz, 1 H), 6.88 (d, J = 8 Hz, 2 H), 7.04 (d, J = 7 Hz, 1 H), 7.13 (dd, J = 8, 1 Hz, 2 H), 7.17-7.27 (m, 2 H), 7.75 (dd, J = 8, 2 Hz, 1 H), 7.93 (d, J = 2 Hz, 1 H) | 540 |
| 127 | A | 1H NMR (500 MHz, DMSO-d6) δ ppm 1.61 (dquin, J = 25, 7 Hz, 2 H), 2.08-2.22 (m, 4 H), 2.24 (s, 3 H), 2.41 (t, J = 7 Hz, 2 H), 2.76 (t, J = 8 Hz, 1 H), 2.78-2.91 (m, 3 H), 3.03 (t, J = 7 Hz, 1 H), 3.10 (t, J = 7 Hz, 1 H), 3.25 (t, J = 7 Hz, 1 H), 4.42 (dt, J = 47, 6 Hz, 2 H), 5.53 (dd, J = 48, 7 Hz, 1 H), 6.83 (d, J = 8 Hz, 1 H), 6.84-6.92 (m, 4 H), 7.04 (t, J = 8 Hz, 1 H), 7.12 (dd, J = 8, 1 Hz, 2 H), 7.74 (dd, J = 8, 2 Hz, 1 H), 7.91 (d, J = 2 Hz, 1 H) | 520 |
| 128 | A | 1H NMR (400 MHz, DMSO-d6) δ ppm 1.80 (dquin, J = 26, 7 Hz, 2 H), 2.11 (d, J = 3 Hz, 3 H), 2.13-2.21 (m, 4 H), 2.73-3.11 (m, 7 H), 3.41-3.59 (m, 2 H), 3.76-3.89 (m, 2 H), 4.48 (dt, J = 47, 6 Hz, 2 H), 6.74 (d, J = 8 Hz, 2 H), 6.85 (d, J = 8 Hz, 1 H), 6.91 (m, 1 H), 6.96 (d, J = 8 Hz, 2 H), 7.25 (t, J = 8 Hz, 1 H), 7.75 (dd, J = 8, 2 Hz, | 536 |

TABLE 1b-continued

| Example or compound | Preparation Method | NMR | MASS: LC/MS (m/z, MH+): |
|---|---|---|---|
| | | 1 H), 7.92 (d, J = 2 Hz, 1 H), 11.82 (br s, 2 H) | |
| 129 | A | 1H NMR (400 MHz, DMSO-d6) δ ppm 1.80 (dquin, J = 26, 7 Hz, 2 H), 2.11 (d, J = 3 Hz, 3 H), 2.13-2.21 (m, 4 H), 2.73-3.11 (m, 7 H), 3.41-3.59 (m, 2 H), 3.76-3.89 (m, 2 H), 4.48 (dt, J = 47, 6 Hz, 2 H), 6.74 (d, J = 8 Hz, 2 H), 6.85 (d, J = 8 Hz, 1 H), 6.91 (m, 1 H), 6.96 (d, J = 8 Hz, 2 H), 7.25 (t, J = 8 Hz, 1 H), 7.75 (dd, J = 8, 2 Hz, 1 H), 7.92 (d, J = 2 Hz, 1 H), 11.82 (br s, 2 H) | 520 |
| 130 | A | 1H NMR (400 MHz, DMSO-d6) δ ppm 1.83 (dquin, J = 25, 7 Hz, 2 H), 2.10-2.29 (m, 4 H), 2.77-2.95 (m, 5 H), 3.10 (br s, 2 H), 3.24 (s, 3 H), 3.56-3.70 (m, 2 H), 3.85-3.98 (m, 2 H), 4.49 (dt, J = 47, 6 Hz, 2 H), 6.81 (d, J = 8 Hz, 2 H), 6.86 (d, J = 8 Hz, 1 H), 6.98 (d, J = 8 Hz, 2 H), 7.51 (t, J = 8 Hz, 1 H), 7.62 (dd, J = 8, 3 Hz, 1 H), 7.65 (dd, J = 9, 2 Hz, 1 H), 7.77 (dd, J = 8, 2 Hz, 1 H), 7.94 (d, J = 2 Hz, 1 H), 10.44 (br s, 1 H), 12.78 (br s, 1 H) | 566 |
| 131 | A | 1H NMR (400 MHz, DMSO-d6) δ ppm 1.82 (dquin, J = 25, 7 Hz, 2 H), 2.09-2.28 (m, 4 H), 2.76-2.93 (m, 5 H), 2.98 (s, 3 H), 3.00-3.09 (m, 2 H), 3.46-3.61 (m, 2 H), 3.86 (br s, 2 H), 4.49 (dt, J = 47, 6 Hz, 2 H), 5.92-6.04 (m, 2 H), 6.57 (t, J = 2 Hz, 1 H), 6.70 (d, J = 8 Hz, 2 H), 6.86 (d, J = 8 Hz, 1 H), 6.98 (d, J = 8 Hz, 2 H), 7.74 (dd, J = 8, 2 Hz, 1 H), 7.90 (d, J = 2 Hz, 1 H), 11.82 (br s, 2 H) | 473 |
| 132 | A | 1H NMR (400 MHz, DMSO-d6) δ ppm 1.59 (dquin, J = 25, 6 Hz, 2 H), 2.08-2.22 (m, 4 H), 2.29 (s, 3 H), 2.34-2.39 (m, 5 H), 2.59 (m, 1 H), 2.63-2.73 (m, 4 H), 2.81-2.96 (m, 2 H), 3.21 (t, J = 7 Hz, 2 H), 4.41 (dt, J = 47, 6 Hz, 2 H), 6.52 (dd, J = 11, 2 Hz, 1 H), 6.57 (dd, J = 8, 2 Hz, 1 H), 6.82 (d, J = 8 Hz, 1 H), 6.95 (d, J = 8 Hz, 1 H), 7.00 (t, J = 8 Hz, 1 H), 7.33 (d, J = 8 Hz, 1 H), 7.72 (dd, J = 8, 2 Hz, 1 H), 7.88 (d, J = 2 Hz, 1 H) | 517 |
| 133 | B | 1H NMR (500 MHz, DMSO-d6) δ ppm 1.62 (dquin, J = 25, 7 Hz, 2 H), 2.09-2.30 (m, 4 H), 2.45 (t, J = 7 Hz, 2 H), 2.57 (m, 1 H), 2.69 (d, J = 8 Hz, 2 H), 2.78 (t, J = 7 Hz, 2 H), 2.83 (m, 1 H), 2.93 (dd, J = 13, 6 Hz, 1 H), 3.28 (t, J = 7 Hz, 2 H), 3.34 (m, 1 H), 3.63 (m, 1 H), 4.42 (dt, J = 47, 6 Hz, 2 H), 6.70 (d, J = 8 Hz, 2 H), 6.84 (d, J = 8 Hz, 1 H), 6.91 (d, J = 8 Hz, 2 H), 7.24 (d, J = 8 Hz, 1 H), 7.28-7.41 (m, 2 H), 7.74 (dd, J = 8, 2 Hz, 1 H), 7.91 (d, J = 2 Hz, 1 H), 8.18 (s, 1 H) | 586 |
| 134 | B | 1H NMR (500 MHz, DMSO-d6) δ ppm 1.63 (dquin, J = 26, 7 Hz, 2 H), 2.10-2.25 (m, 4 H), 2.51-2.53 (m partially hidden, 2 H), 2.55-2.62 (m, 1 H), 2.72 (d, J = 8 Hz, 2 H), 2.87 (dt, J = 13, 7 Hz, 4 H), 3.33 (t, J = 7 Hz, 2 H), 4.43 (dt, J = 47, 6 Hz, 2 H), 6.78 (d, J = 8 Hz, 2 H), 6.85 (d, J = 8 Hz, 1 H), 6.95 (d, J = 8 Hz, 2 H), 7.02-7.17 (m, 3 H), 7.75 (dd, J = 8, 2 Hz, 1 H), 7.91 (d, J = 2 Hz, 1 H), 8.17 (s, 1 H) | 506 |
| 135 | A | 1H NMR (500 MHz, DMSO-d6) δ ppm 1.59-1.76 (m, 2 H), 2.08-2.22 (m, 4 H), 2.26 (s, 3 H), 2.64-2.74 (m, 3 H), 2.78 (d, J = 7 Hz, 2 H), 2.86 (t, J = 7 Hz, 2 H), 3.02-3.14 (m, 2 H), 3.45-3.58 (m, 2 H), 4.45 (dt, J = 47, 6 Hz, 2 H), 6.58 (dd, J = 11, 2 Hz, 1 H), 6.62 (dd, J = 8, 2 Hz, 1 H), 6.85-6.95 (m, 3 H), 7.02 (t, J = 8 Hz, 1 H), 7.08 (t, J = 8 Hz, 1 H), 7.75 (dd, J = 8, 2 Hz, 1 H), 7.91 (d, J = 2 Hz, 1 H), 12.12 (br s, 1 H) | 520 |
| 136 | A | 1H NMR (400 MHz, DMSO-d6) δ ppm 1.72-1.93 (m, 2 H), 2.01-2.27 (m, 10 H), 2.73-2.93 (m, 3 H), 2.96 (t, J = 7 Hz, 2 H), 3.05-3.21 (m, 2 H), 3.56-3.82 (m, 2 H), 3.87-4.09 (m, 2 H), 4.49 (dt, J = 47, 6 Hz, 2 H), 6.70 (d, J = 8 Hz, 2 H), 6.78-6.86 (m, 3 H), 6.92 (d, J = 8 Hz, 2 H), 7.74 (dd, J = 8, 2 Hz, 1 H), 7.93 (d, J = 2 Hz, 1 H), 10.05 (br s, 1 H), 12.84 (br s, 1 H) | 516 |
| 137 | A | 1H NMR (400 MHz, DMSO-d6) δ ppm 1.64-1.99 (m, 2 H), 2.14-2.21 (m, 4 H), 2.35 (s, 3 H), 2.71-3.04 (m, 5 H), 3.09-3.21 (m, 2 H), 3.56-4.17 (m, 4 H), 4.48 (dt, J = 46, 6 Hz, 2 H), 6.72 (d, J = 8 Hz, 2 H), 6.86 (d, J = 8 Hz, 1 H), 6.94 (d, J = 8 Hz, 2 H), 7.24 (t, J = 8 Hz, 1 H), 7.38 (dd, J = 8, 1 Hz, 1 H), 7.62 (dd, J = 8, 1 Hz, 1 H), 7.76 (dd, J = 8, 2 Hz, 1 H), 7.93 (d, J = 2 Hz, 1 H), 9.70 (br s, 1 H), 12.88 (br s, 1 H) | 509 |
| 138 | A | 1H NMR (400 MHz, DMSO-d6) δ ppm 1.86 (dquin, J = 26, 7 Hz, 2 H), 2.14 (quin, J = 7 Hz, 2 H), 2.28 (t, J = 7 Hz, 2 H), 2.79-2.99 (m, 5 H), 3.17 (t, J = 7 Hz, 2 H), 3.66-3.79 (m, 2 H), 3.99 (t, J = 8 Hz, 2 H), 4.50 (dt, J = 47, 6 Hz, 2 H), 6.80 (d, J = 8 Hz, 2 H), 6.83 (d, J = 8 | 552 |

TABLE 1b-continued

| Example or compound | Preparation Method | NMR | MASS: LC/MS (m/z, MH+): |
|---|---|---|---|
| | | Hz, 1 H), 6.97 (d, J = 8 Hz, 2 H), 7.23 (d, J = 9 Hz, 2 H), 7.45 (t, J = 55 Hz, 1 H), 7.39 (d, J = 8 Hz, 2 H), 7.74 (dd, J = 8, 2 Hz, 1 H), 7.91 (d, J = 2 Hz, 1 H), 10.55 (br s, 1 H), 12.83 (br s, 1 H) | |
| 139 | A | 1H NMR (400 MHz, DMSO-d6) δ ppm 1.76-1.94 (m, 2 H), 2.04-2.22 (m, 10 H), 2.72-3.03 (m, 5 H), 3.08-3.24 (m, 2 H), 3.62-3.84 (m, 2 H), 3.89-4.07 (m, 2 H), 4.49 (dt, J = 47, 6 Hz, 2 H), 6.72 (d, J = 8 Hz, 2 H), 6.77-6.83 (m, 2 H), 6.84 (d, J = 8 Hz, 2 H), 7.74 (dd, J = 8, 2 Hz, 1 H), 7.91 (d, J = 2 Hz, 1 H), 10.16 (br s, 1 H), 12.84 (br s, 1 H) | 516 |
| 140 | A | 1H NMR (400 MHz, DMSO-d6) δ ppm 1.72-1.97 (m, 2 H), 2.10-2.19 (m, 2 H), 2.23-2.29 (m, 2 H), 2.80-2.91 (m, 5 H), 3.09-3.19 (m, 2 H), 3.70 (br s, 2 H), 3.97 (br s, 2 H), 4.50 (dt, J = 47, 6 Hz, 2 H), 6.77-6.84 (m, 3 H), 6.94-7.04 (m, 4 H), 7.14-7.21 (m, 2 H), 7.73 (d, J = 7 Hz, 1 H), 7.90 (s, 1 H), 10.32 (br s, 1 H), 12.76 (br s, 1 H) | 488 |
| 141 | A | 1H NMR (400 MHz, DMSO-d6) δ ppm 1.83 (dquin, J = 27, 8 Hz, 2 H), 2.10 (m, 2 H), 2.15 (s, 6 H), 2.17-2.26 (m, 2 H), 2.74-2.92 (m, 3 H), 2.97 ( t, J = 7 Hz, 2 H), 3.03-3.18 (m, 2 H), 3.54-3.75 (m, 2 H), 3.92 (t, J = 8 Hz, 2 H), 4.49 (dt, J = 47, 6 Hz, 2 H), 6.69 (d, J = 8 Hz, 2 H), 6.82 (d, J = 8 Hz, 1 H), 6.89 (d, J = 8 Hz, 2 H), 6.93-7.04 (m, 3 H), 7.74 (dd, J = 8, 2 Hz, 1 H), 7.93 (d, J = 2 Hz, 1 H), 10.62 (br s, 1 H), 12.63 (br s, 1 H) | 498 |
| 142 | F | 1H NMR (500 MHz, DMSO-d6) δ ppm 1.60 (dquin, J = 25, 6 Hz, 2 H), 2.11-2.26 (m, 4 H), 2.39 (t, J = 7 Hz, 2 H), 2.56 (m, 1 H), 2.65-2.71 (m, 2 H), 2.73 (d, J = 7 Hz, 2 H), 2.86-3.02 (m, 2 H), 3.18-3.27 (m, 2 H), 4.41 (dt, J = 47, 6 Hz, 2 H), 6.50-6.57 (m, 2 H), 6.93 (d, J = 8 Hz, 1 H), 7.27 (m, 1 H), 7.33 (m, 1 H), 7.62 (d, J = 2 Hz, 1 H), 7.77 (dd, J = 8, 2 Hz, 1 H), 7.93 (d, J = 2 Hz, 1 H) | 574 |
| 143 | A | 1H NMR (400 MHz, DMSO-d6) δ ppm 1.73-1.90 (m, 2 H), 2.08-2.24 (m, 4 H), 2.27 (s, 3 H), 2.36 (s, 3 H), 2.74-3.01 (m, 5 H), 3.05-3.22 (m, 2 H), 3.57-3.80 (m, 2 H), 3.96 (t, J = 6 Hz, 2 H), 4.50 (dt, J = 47, 6 Hz, 2 H), 6.75 (d, J = 8 Hz, 2 H), 6.84 (d, J = 8 Hz, 1 H), 6.90-7.01 (m, 3 H), 7.32 (d, J = 8 Hz, 1 H), 7.74 (dd, J = 8, 2 Hz, 1 H), 7.92 (d, J = 2 Hz, 1 H), 10.42 (br s, 1 H), 12.76 (br s, 1 H) | 499 |
| 144 | B | 1H NMR (500 MHz, DMSO-d6) δ ppm 1.61 (dquin, J = 26, 7 Hz, 2 H), 2.07-2.26 (m, 4 H), 2.40-2.45 (m, 2 H), 2.56 (d, J = 7 Hz, 1 H), 2.69 (d, J = 8 Hz, 2 H), 2.75 (t, J = 7 Hz, 2 H), 2.82-3.00 (m, 2 H), 3.26 (br t, J = 7 Hz, 2 H), 3.84 (m, 2 H), 4.42 (dt, J = 47, 6 Hz, 2 H), 6.74 (d, J = 8 Hz, 2 H), 6.84 (d, J = 8 Hz, 1 H), 6.92 (d, J = 8 Hz, 2 H), 7.17 (d, J = 8 Hz, 1 H), 7.29 (dd, J = 8, 2 Hz, 1 H), 7.39 (d, J = 2 Hz, 1 H), 7.74 (dd, J = 8, 2 Hz, 1 H), 7.91 (d, J = 2 Hz, 1 H), 8.18 (s, 1 H) | 543 |
| 145 | A | 1H NMR (500 MHz, DMSO-d6) δ ppm 1.85 (dquin, J = 28, 7 Hz, 2 H), 2.08-2.22 (m, 4 H), 2.26 (s, 3 H), 2.80-3.02 (m, 5 H), 3.12-3.22 (m, 2 H), 3.62-3.83 (m, 2 H), 3.96-4.11 (m, 2 H), 4.50 (dt, J = 47, 6 Hz, 2 H), 6.61 (dd, J = 11, 2 Hz, 1 H), 6.66 (dd, J = 8, 2 Hz, 1 H), 6.87 (d, J = 8 Hz, 1 H), 6.98-7.05 (m, 2 H), 7.08 (m, 1 H), 7.27 (d, J = 1 Hz, 1 H), 7.76 (dd, J = 8, 2 Hz, 1 H), 7.92 (d, J = 2 Hz, 1 H), 10.41 (br s, 1 H), 12.86 (br s, 1 H) | 536 |
| 146 | B | 1H NMR (400 MHz, DMSO-d6) δ ppm 1.73-1.90 (m, 2 H), 2.08-2.29 (m, 4 H), 2.75-2.99 (m, 5 H), 3.09-3.20 (m, 2 H), 3.63-3.78 (m, 2 H), 3.89-4.04 (m, 2 H), 4.49 (dt, J = 47, 6 Hz, 2 H), 5.13 (dd, J = 48, 11 Hz, 1 H), 5.42 (dd, J = 48, 11 Hz, 1 H), 6.76 (d, J = 8 Hz, 2 H), 6.84 (d, J = 8 Hz, 1 H), 6.91 (d, J = 8 Hz, 2 H), 7.16 (m, 1 H), 7.23-7.31 (m, 2 H), 7.37 (m, 1 H), 7.75 (dd, J = 8, 2 Hz, 1 H), 7.92 (d, J = 2 Hz, 1 H), 10.03 (br s, 1 H), 12.80 (br s, 1 H) | 502 |
| 147 | B | 1H NMR (500 MHz, DMSO-d6) δ ppm 1.60 (dquin, J = 26, 6 Hz, 2 H), 2.15-2.24 (m, 2 H), 2.24-2.32 (m, 2 H), 2.41 (t, J = 7 Hz, 2 H), 2.55 (d, J = 7 Hz, 1 H), 2.69 (d, J = 8 Hz, 2 H), 2.73 (t, J = 7 Hz, 2 H), 2.93-3.08 (m, 2 H), 3.24 (t, J = 7 Hz, 2 H), 4.41 (dt, J = 47, 6 Hz, 2 H), 6.74 (d, J = 8 Hz, 2 H), 6.85 (d, J = 8 Hz, 1 H), 6.90 (d, J = 8 Hz, 2 H), 7.37 (td, J = 8, 1 Hz, 1 H), 7.47 (dd, J = 8, 1 | 495 |

TABLE 1b-continued

| Example or compound | Preparation Method | NMR | MASS: LC/MS (m/z, MH+): |
|---|---|---|---|
| | | Hz, 1 H), 7.61 (td, J = 8, 1 Hz, 1 H), 7.66 (dd, J = 8, 1 Hz, 1 H), 7.75 (dd, J = 8, 2 Hz, 1 H), 7.93 (d, J = 2 Hz, 1 H), 8.18 (s, 1 H) | |
| 148 | B | 1H NMR (500 MHz, DMSO-d6) δ ppm 1.76-1.90 (m, 2 H), 1.93 (s, 3 H), 2.17 (m, J = 9, 4 Hz, 3 H), 2.41-2.48 (m hidden, 1 H), 2.72-3.01 (m, 5 H), 3.05-3.25 (m, 2 H), 3.61-3.88 (m, 2 H), 3.92-4.09 (m, 2 H), 4.50 (dt, J = 47, 6 Hz, 2 H), 6.68 (d, J = 8 Hz, 2 H), 6.84 (d, J = 8 Hz, 1 H), 6.96 (d, J = 8 Hz, 2 H), 7.61 (dd, J = 2, 1 Hz, 1 H), 7.76 (dd, J = 8, 2 Hz, 1 H), 7.94 (d, J = 2 Hz, 1 H), 8.48 (d, J = 2 Hz, 1 H), 10.19 (br s, 1 H), 12.88 (br s, 1 H) | 519 |
| 149 | A | 1H NMR (400 MHz, DMSO-d6) δ ppm 1.08 (t, J = 8 Hz, 3 H), 1.69-1.92 (m, 2 H), 2.07-2.23 (m, 4 H), 2.41-2.45 (m hidden, 1 H), 2.57-2.66 (m, 1 H), 2.74-3.17 (m, 7 H), 3.47-3.76 (m, 2 H), 3.76-4.09 (m, 2 H), 4.48 (dt, J = 47, 6 Hz, 2 H), 6.72 (d, J = 8 Hz, 2 H), 6.81-6.90 (m, 2 H), 6.92 (d, J = 8 Hz, 2 H), 6.98-7.09 (m, 2 H), 7.74 (dd, J = 8, 2 Hz, 1 H), 7.91 (d, J = 2 Hz, 1 H), 9.90 (br s, 1 H), 12.83 (br s, 1 H) | 516 |
| 150 | A | 1H NMR (400 MHz, DMSO-d6) δ ppm 1.67-1.89 (m, 2 H), 2.06-2.25 (m, 7 H), 2.72-3.11 (m, 7 H), 3.40-3.68 (m, 2 H), 3.74-3.98 (m, 2 H), 4.47 (dt, J = 47, 6 Hz, 2 H), 6.72 (d, J = 8 Hz, 2 H), 6.84 (d, J = 8 Hz, 1 H), 6.89 (d, J = 8 Hz, 2 H), 6.99-7.14 (m, 4 H), 7.74 (dd, J = 8, 2 Hz, 1 H), 7.92 (d, J = 2 Hz, 1 H), 10.08 (br s, 1 H), 12.78 (br s, 1 H) | 484 |
| 151 | A | 1H NMR (400 MHz, DMSO-d6) δ ppm 1.75-1.95 (m, 2 H), 2.08-2.18 (m, 7 H), 2.20 (s, 3 H), 2.73-3.02 (m, 5 H), 3.11-3.22 (m, 2 H), 3.66-3.79 (m, 2 H), 3.92-4.04 (m, 2 H), 4.50 (dt, J = 47, 6 Hz, 2 H), 6.73 (d, J = 8 Hz, 2 H), 6.78-6.94 (m, 5 H), 6.98 (d, J = 8 Hz, 1 H), 7.75 (dd, J = 8, 2 Hz, 1 H), 7.92 (d, J = 2 Hz, 1 H), 10.54 (br s, 1 H), 12.77 (br s, 1 H) | 498 |
| 152 | A | 1H NMR (400 MHz, DMSO-d6) δ ppm 1.08 (t, J = 8 Hz, 3 H), 1.65-1.88 (m, 2 H), 2.08-2.25 (m, 4 H), 2.43 (m, 1 H), 2.61 (m, 1 H), 2.73-3.03 (m, 7 H), 3.41-3.93 (m, 4 H), 4.47 (dt, J = 47, 6 Hz, 2 H), 6.72 (d, J = 8 Hz, 2 H), 6.85 (d, J = 8 Hz, 1 H), 6.89 (d, J = 8 Hz, 2 H), 6.98-7.08 (m, 2 H), 7.11-7.21 (m, 2 H), 7.74 (dd, J = 8, 2 Hz, 1 H), 7.91 (d, J = 2 Hz, 1 H), 9.94 (br s, 1 H), 12.81 (br s, 1 H) | 498 |
| 153 | A | 1H NMR (400 MHz, DMSO-d6) δ ppm 1.70-1.89 (m, 2 H), 2.07-2.24 (m, 4 H), 2.76-2.93 (m, 5 H), 2.94-3.10 (m, 2 H), 3.40-3.65 (m, 2 H), 3.71-3.94 (m, 2 H), 4.48 (dt, J = 47, 6 Hz, 2 H), 6.80 (d, J = 8 Hz, 2 H), 6.86 (d, J = 8 Hz, 1 H), 6.99 (d, J = 8 Hz, 2 H), 7.09 (dd, J = 9, 8 Hz, 2 H), 7.76 (dd, J = 8, 2 Hz, 1 H), 7.93 (d, J = 2 Hz, 1 H), 10.49 (br s, 1 H), 12.68 (br s, 1 H) | 524 |
| 154 | A | 1H NMR (500 MHz, DMSO-d6) δ ppm 1.66 (dquin, J = 26, 6 Hz, 2 H), 2.12-2.17 (m, 4 H), 2.18 (s, 3 H), 2.55-2.62 (m, 2 H), 2.66 (m, 1 H), 2.75 (d, J = 7 Hz, 2 H), 2.83-3.01 (m, 4 H), 3.45 (m hidden, 2 H), 4.43 (dt, J = 47, 6 Hz, 2 H), 6.52 (dd, J = 11, 2 Hz, 1 H), 6.57 (dd, J = 8, 2 Hz, 1 H), 6.88 (d, J = 8 Hz, 1 H), 7.00 (t, J = 8 Hz, 1 H), 7.05-7.09 (m, 1 H), 7.09-7.14 (m, 1 H), 7.23 (d, J = 2 Hz, 1 H), 7.76 (dd, J = 8, 2 Hz, 1 H), 7.92 (d, J = 2 Hz, 1 H) | 536 |
| 155 | B | 1H NMR (500 MHz, DMSO-d6) δ ppm 1.60 (dquin, J = 25, 7 Hz, 2 H), 2.10-2.21 (m, 4 H), 2.25 (s, 3 H), 2.41 (t, J = 7 Hz, 2 H), 2.55 (m, 1 H), 2.66-2.74 (m, 4 H), 2.86 (m, 1 H), 3.00 (m, 1 H), 3.20-3.25 (m, 2 H), 4.41 (dt, J = 47, 6 Hz, 2 H), 6.70 (d, J = 8 Hz, 2 H), 6.86 (d, J = 8 Hz, 1 H), 6.90 (d, J = 8 Hz, 2 H), 7.33 (d, J = 8 Hz, 1 H), 7.47 (d, J = 2 Hz, 1 H), 7.53 (dd, J = 8, 2 Hz, 1 H), 7.74 (dd, J = 8, 2 Hz, 1 H), 7.91 (d, J = 2 Hz, 1 H), 8.20 (s, 1 H) | 509 |
| 156 | B | 1H NMR (500 MHz, DMSO-d6) δ ppm 1.62 (dquin, J = 25, 7 Hz, 2 H), 2.10-2.22 (m, 4 H), 2.25 (s, 3 H), 2.45 (t, J = 7 Hz, 2 H), 2.57 (m, 1 H), 2.69 (d, J = 8 Hz, 2 H), 2.77 (td, J = 7, 3 Hz, 2 H), 2.87 (m, 1 H), 2.99(m, 1 H), 3.28 (t, J = 7 Hz, 2 H), 4.42 (dt, J = 47, 6 Hz, 2 H), 6.70 (d, J = 8 Hz, 2 H), 6.86 (d, J = 8 Hz, 1 H), 6.91 (d, J = 8 Hz, 2 H), 7.33 (d, J = 8 Hz, 1 H), 7.47 (d, J = 2 Hz, 1 H), 7.53 (dd, J = 8, 2 Hz, 1 H), 7.74 (dd, J = 8, 2 Hz, 1 H), 7.91 (d, J = 2 Hz, 1 H), 8.19 (s, 1 H) | 509 |
| 157 | B | 1H NMR (500 MHz, DMSO-d6) δ ppm 1.61 (dquin, J = 26, 6 Hz, 2 H), 2.13-2.28 (m, 4 H), 2.30 (s, 3 H), | 509 |

TABLE 1b-continued

| Example or compound | Preparation Method | NMR | MASS: LC/MS (m/z, MH+): |
|---|---|---|---|
| | | 2.43 (t, J = 7 Hz, 2 H), 2.57 (m, 1 H), 2.69 (d, J = 8 Hz, 2 H), 2.75 (t, J = 7 Hz, 2 H), 2.88 (m, 1 H), 3.26 (t, J = 7 Hz, 2 H), 3.30 (m, 1 H), 4.42 (dt, J = 47, 6 Hz, 2 H), 6.72 (d, J = 8 Hz, 2 H), 6.84 (d, J = 8 Hz, 1 H), 6.90 (d, J = 8 Hz, 2 H), 7.29 (t, J = 8 Hz, 1 H), 7.43-7.60 (m, 2 H), 7.75 (dd, J = 8, 1 Hz, 1 H), 7.93 (d, J = 1 Hz, 1 H), 8.20 (s, 1 H) | |
| 158 | B | 1H NMR (500 MHz, DMSO-d6) δ ppm 1.62 (dquin, J = 26, 6 Hz, 2 H), 2.12-2.26 (m, 4 H), 2.28 (s, 3 H), 2.45 (t, J = 7 Hz, 1 H), 2.57 (dt, J = 15, 7 Hz, 1 H), 2.70 (d, J = 8 Hz, 2 H), 2.78 (t, J = 7 Hz, 2 H), 2.98 (m, 2 H), 3.29 (t, J = 7 Hz, 2 H), 4.42 (dt, J = 47, 6 Hz, 2 H), 6.74 (d, J = 8 Hz, 2 H), 6.83 (d, J = 8 Hz, 1 H), 6.91 (d, J = 8 Hz, 2 H), 7.35 (d, J = 8 Hz, 1 H), 7.42 (dd, J = 8, 2 Hz, 1 H), 7.48 (d, J = 1 Hz, 1 H), 7.74 (dd, J = 8, 2 Hz, 1 H), 7.91 (d, J = 2 Hz, 1 H), 8.20 (s, 1 H), 12.71 (br s, 1 H) | 509 |
| 159 | B | 1H NMR (500 MHz, DMSO-d6) δ ppm 1.59 (dquin, J = 25, 7 Hz, 2 H), 2.10-2.29 (m, 4 H), 2.41 (t, J = 7 Hz, 2 H), 2.57 (m, 1 H), 2.65-2.74 (m, 4 H), 2.87 (m, 1 H), 3.09 (m, 1 H), 3.16-3.24 (m, 2 H), 4.41 (dt, J = 47, 6 Hz, 2 H), 6.76 (d, J = 8 Hz, 2 H), 6.89 (d, J = 8 Hz, 1 H), 6.96 (d, J = 8 Hz, 2 H), 7.77 (dd, J = 8, 2 Hz, 1 H), 7.94 (d, J = 2 Hz, 1 H), 8.22 (s, 1 H), 8.68 (s, 1 H) | 607 |
| 160 | A | 1H NMR (500 MHz, DMSO-d6) δ ppm 1.65 (dquin, J = 26, 7 Hz, 2 H), 2.11-2.26 (m, 4 H), 2.53-2.59 (m, 2 H), 2.60 (m, 1 H), 2.75 (r d, J = 7 Hz, 2 H), 2.88-2.99 (m, 4 H), 3.34 (m hidden, 2 H), 4.43 (dt, J = 47, 6 Hz, 2 H), 6.58 (dd, J = 11, 2 Hz, 1 H), 6.62 (dd, J = 8, 2 Hz, 1 H), 6.88 (d, J = 8 Hz, 1 H), 7.02 (t, J = 8 Hz, 1 H), 7.09 (td, J = 9, 3 Hz, 1 H), 7.26 (dd, J = 9, 6 Hz, 1 H), 7.42 (dd, J = 9, 3 Hz, 1 H), 7.76 (dd, J = 8, 2 Hz, 1 H), 7.92 (d, J = 2 Hz, 1 H) | 540 |
| 161 | A | 1H NMR (500 MHz, DMSO-d6) δ ppm 1.66 (dquin, J = 26, 6 Hz, 2 H), 2.13-2.27 (m, 4 H), 2.55-2.61 (m, 2 H), 2.66 (m, 1 H), 2.76 (d, J = 8 Hz, 2 H), 2.88 (t, J = 7 Hz, 2 H), 2.92-3.00 (m, 2 H), 3.42-3.45 (m hidden, 2 H), 4.43 (dt, J = 47, 6 Hz, 2 H), 6.60 (dd, J = 11, 2 Hz, 1 H), 6.63 (dd, J = 8, 2 Hz, 1 H), 6.90 (d, J = 8 Hz, 1 H), 7.01-7.14 (m, 3 H), 7.26 (m, 1 H), 7.77 (dd, J = 8, 2 Hz, 1 H), 7.93 (d, J = 2 Hz, 1 H) | 524 |
| 162 | A | 1H NMR (500 MHz, DMSO-d6) δ ppm 1.25-1.32 (m, 2 H), 1.33-1.43 (m, 2 H), 1.51-1.72 (m, 4 H), 1.90-2.02 (m, 4 H), 2.07-2.22 (m, 4 H), 2.42 (t, J = 7 Hz, 2 H), 2.51-2.62 (m, 1 H), 2.72 (t, J = 7 Hz, 2 H), 2.76 (t, J = 7 Hz, 4 H), 3.26 (t, J = 6 Hz, 2 H), 4.42 (dt, J = 47, 6 Hz, 2 H), 5.60 (t, J = 6 Hz, 1 H), 6.78 (d, J = 8 Hz, 1 H), 6.93 (d, J = 8 Hz, 2 H), 7.05 (d, J = 8 Hz, 2 H), 7.68 (dd, J = 8, 2 Hz, 1 H), 7.82 (d, J = 2 Hz, 1 H), 12.67 (br s, 1 H) | 488 |
| 163 | C | 1H NMR (500 MHz, DMSO-d6) δ ppm 1.24-1.32 (m, 2 H), 1.44 (m, 4 H), 1.51-1.72 (m, 6 H), 1.75-1.95 (m, 4 H), 2.15 (spt, J = 7 Hz, 2 H), 2.45 (m hidden, 1 H), 2.73 (t, J = 7 Hz, 2 H), 2.80-3.08 (m, 3 H), 3.09-3.25 (m, 2 H), 3.63-3.91 (m, 2 H), 3.92-4.15 (m, 2 H), 4.50 (dt, J = 47, 6 Hz, 2 H), 6.72 (d, J = 8 Hz, 1 H), 7.00 (d, J = 8 Hz, 2 H), 7.18 (d, J = 8 Hz, 2 H), 7.64 (dd, J = 8, 2 Hz, 1 H), 7.82 (d, J = 2 Hz, 1 H), 9.98 (br s, 1 H), 12.76 (br s, 1 H) | 490 |
| 164 | B | 1H NMR (500 MHz, DMSO-d6) δ ppm 1.76-1.90 (m, 2 H), 2.13-2.30 (m, 4 H), 2.75-3.02 (m, 5 H), 3.08-3.19 (m, 2 H), 3.62-3.85 (m, 2 H), 3.87-4.08 (m, 2 H), 4.49 (dt, J = 47, 6 Hz, 2 H), 6.79 (d, J = 8 Hz, 2 H), 6.96 (t, J = 54 Hz, 1 H), 6.85 (d, J = 8 Hz, 1 H), 6.95 (d, J = 8 Hz, 2 H), 7.27 (dd, J = 7, 2 Hz, 2 H), 7.33 (d, J = 9 Hz, 1 H), 7.75 (dd, J = 8, 2 Hz, 1 H), 7.92 (d, J = 2 Hz, 1 H), 10.14 (br s, 1 H), 12.84 (br s, 1 H) | 538 |
| 165 | B | 1H NMR (400 MHz, DMSO-d6) δ ppm 1.69-1.89 (m, 2 H), 2.11-2.30 (m, 4 H), 2.59 (m, 1 H), 2.74-3.15 (m, 8 H), 3.77-3.98 (m, 2 H), 4.48 (dt, J = 47, 6 Hz, 2 H), 5.30 (dd, J = 39, 10 Hz, 1 H), 5.43 (dd, J = 40, 11 Hz, 1 H), 6.77 (d, J = 8 Hz, 2 H), 6.85 (d, J = 8 Hz, 1 H), 6.93 (d, J = 8 Hz, 2 H), 6.99 (d, J = 8 Hz, 1 H), 7.12 (t, J = 9 Hz, 1 H), 7.33 (tdd, J = 8, 6, 2 Hz, 1 H), 7.76 (dd, J = 8, 2 Hz, 1 H), 7.93 (d, J = 2 Hz, 1 H), 9.96 (br s, 1 H), 12.89 (br s, 1 H) | 520 |
| 166 | B | 1H NMR (500 MHz, DMSO-d6) δ ppm 1.61 (dquin, J = 25, 7 Hz, 2 H), 2.13-2.31 (m, 4 H), 2.36 (s, 3 H), 2.43 (t, J = 7 Hz, 2 H), 2.57 (m, 1 H), 2.69 (d, J = 8 Hz, 2 H), 2.75 (t, J = 7 Hz, 2 H), 2.85-3.00 (m, 2 H), 3.22- | 509 |

TABLE 1b-continued

| Example or compound | Preparation Method | NMR | MASS: LC/MS (m/z, MH+): |
|---|---|---|---|
| | | 3.27 (m, 2 H), 4.42 (dt, J = 47, 6 Hz, 2 H), 6.74 (d, J = 8 Hz, 2 H), 6.85 (d, J = 8 Hz, 1 H), 6.91 (d, J = 8 Hz, 2 H), 7.25 (dd, J = 11, 8 Hz, 2 H), 7.46 (t, J = 10 Hz, 1 H), 7.75 (dd, J = 8, 2 Hz, 1 H), 7.92 (s, 1 H), 8.18 (s, 1 H) | |
| 167 | F | 1H NMR (500 MHz, DMSO-d6) δ ppm 1.75-1.90 (m, 2 H), 2.09 (s, 6 H), 2.12-2.21 (m, 4 H), 2.76-2.99 (m, 5 H), 3.08-3.21 (m, 2 H), 3.59-3.77 (m, 2 H), 3.94-4.00 (m, 2 H), 4.49 (dt, J = 47, 6 Hz, 2 H), 6.52 (s, 2 H), 6.87 (d, J = 8 Hz, 1 H), 7.18 (d, J = 8 Hz, 1 H), 7.26 (m, 1 H), 7.59 (d, J = 2 Hz, 1 H), 7.75 (dd, J = 8, 2 Hz, 1 H), 7.91 (d, J = 2 Hz, 1 H), 10.27 (br s, 1 H), 12.85 (br s, 1 H) | 566 |
| 168 | C | 1H NMR (500 MHz, DMSO-d6) δ ppm 0.80 (d, J = 6 Hz, 6 H), 1.62 (dquin, J = 25, 7 Hz, 2 H), 1.77-1.89 (m, 1 H), 1.95 (t, J = 7 Hz, 2 H), 2.08 (d, J = 7 Hz, 2 H), 2.18 (quin, J = 7 Hz, 2 H), 2.42 (t, J = 7 Hz, 2 H), 2.80 (t, J = 7 Hz, 2 H), 3.05 (t, J = 6 Hz, 2 H), 3.25-3.28 (m, 3 H), 4.41 (dt, J = 47, 6 Hz, 2 H), 6.74 (d, J = 8 Hz, 1 H), 7.19 (d, J = 8 Hz, 2 H), 7.48 (d, J = 8 Hz, 2 H), 7.66 (dd, J = 8, 2 Hz, 1 H), 7.84 (s, 1 H) | 486 |
| 169 | A | 1H NMR (400 MHz, DMSO-d6) δ ppm 1.84 (dquin, J = 27, 7 Hz, 2 H), 2.10-2.25 (m, 4 H), 2.78-2.97 (m, 5 H), 3.14 (br s, 2 H), 3.69 (br s, 2 H), 3.89-4.04 (m, 2 H), 4.50 (dt, J = 47, 6 Hz, 2 H), 6.79 (d, J = 8 Hz, 2 H), 6.84 (d, J = 8 Hz, 1 H), 6.94-7.02 (m, 3 H), 7.11 (td, J = 10, 3 Hz, 1 H), 7.25 (td, J = 9, 7 Hz, 1 H), 7.75 (dd, J = 8, 2 Hz, 1 H), 7.92 (d, J = 2 Hz, 1 H), 10.36 (br s, 1 H), 12.88 (br s, 1 H) | 506 |
| 170 | B | 1H NMR (400 MHz, DMSO-d6) δ ppm 1.71-1.90 (m, 2 H), 2.08-2.30 (m, 4 H), 2.75-3.14 (m, 7 H), 3.45-3.72 (m, 2 H), 3.76-4.05 (m, 2 H), 4.48 (dt, J = 47, 6 Hz, 2 H), 6.78 (d, J = 8 Hz, 2 H), 6.84 (d, J = 8 Hz, 1 H), 6.98 (d, J = 8 Hz, 2 H), 7.54 (d, J = 9 Hz, 1 H), 7.72 (dd, J = 8, 2 Hz, 1 H), 7.76 (dd, J = 8, 2 Hz, 1 H), 7.88 (d, J = 2 Hz, 1 H), 7.94 (d, J = 2 Hz, 1 H), 10.53 (br s, 1 H), 12.60 (br s, 1 H) | 529 |
| 171 | A | 1H NMR (400 MHz, DMSO-d6) δ ppm 1.79 (dquin, J = 25, 7 Hz, 2 H), 2.12-2.26 (m, 4 H), 2.74-2.93 (m, 5 H), 2.93-3.07 (m, 2 H), 3.45-3.57 (m, 2 H), 3.74-3.89 (m, 2 H), 4.48 (dt, J = 47, 6 Hz, 2 H), 6.80 (d, J = 8 Hz, 2 H), 6.86 (d, J = 8 Hz, 1 H), 7.00 (d, J = 8 Hz, 2 H), 7.11 (td, J = 8, 2 Hz, 1 H), 7.32 (ddd, J = 9, 7, 2 Hz, 1 H), 7.76 (dd, J = 8, 2 Hz, 1 H), 7.93 (d, J = 2 Hz, 1 H), 10.45 (br s, 1 H), 12.74 (br s, 1 H) | 540 |
| 172 | A | 1H NMR (400 MHz, DMSO-d6) δ ppm 1.75-1.91 (m, 2 H), 2.05-2.11 (m, 3 H), 2.13-2.24 (m, 4 H), 2.79-3.00 (m, 5 H), 3.10-3.19 (m, 2 H), 3.60-3.77 (m, 2 H), 3.93-4.03 (m, 2 H), 4.49 (dt, J = 47, 6 Hz, 2 H), 6.55 (dd, J = 11, 2 Hz, 1 H), 6.60 (dd, J = 8, 2 Hz, 1 H), 6.84-6.94 (m, 2 H), 6.97-7.05 (m, 2 H), 7.11 (m, 1 H), 7.77 (dd, J = 8, 2 Hz, 1 H), 7.93 (d, J = 2 Hz, 1 H), 10.28 (br s, 1 H), 12.88 (br s, 1 H) | 520 |
| 173 | A | 1H NMR (400 MHz, DMSO-d6) δ ppm 1.75-1.93 (m, 2 H), 2.10-2.26 (m, 4 H), 2.34 (s, 3 H), 2.81-3.01 (m, 5 H), 3.12-3.20 (m, 2 H), 3.65-3.76 (m, 2 H), 3.95-4.04 (m, 2 H), 4.49 (dt, J = 47, 6 Hz, 2 H), 6.60 (dd, J = 11, 2 Hz, 1 H), 6.65 (dd, J = 8, 2 Hz, 1 H), 6.88 (d, J = 8 Hz, 1 H), 6.97-7.05 (m, 2 H), 7.07 (t, J = 8 Hz, 1 H), 7.20 (m, 1 H), 7.76 (dd, J = 8, 2 Hz, 1 H), 7.93 (d, J = 2 Hz, 1 H), 10.48 (br s, 1 H), 12.84 (br s, 1 H) | 536 |
| 174 | A | 1H NMR (400 MHz, DMSO-d6) δ ppm 1.72-1.92 (m, 2 H), 2.12-2.18 (m, 4 H), 2.19 (s, 3 H), 2.78-3.01 (m, 5 H), 3.11-3.19 (m, 2 H), 3.61-3.76 (m, 2 H), 3.94-4.04 (m, 2 H), 4.49 (dt, J = 47, 6 Hz, 2 H), 6.54 (dd, J = 11, 2 Hz, 1 H), 6.58 (dd, J = 8, 2 Hz, 1 H), 6.85-6.93 (m, 2 H), 6.97-7.04 (m, 2 H), 7.07 (dd, J = 9, 6 Hz, 1 H), 7.76 (dd, J = 8, 2 Hz, 1 H), 7.92 (d, J = 2 Hz, 1 H), 10.31 (br s, 1 H), 12.85 (br s, 1 H) | 520 |
| 175 | No general method; described in example section | 1H NMR (400 MHz, DMSO-d6) δ ppm 1.57 (d, J = 23 Hz, 3 H), 1.81-2.02 (m, 2 H), 2.10-2.35 (m, 4 H), 2.65 (m, 1 H), 2.93-3.08 (m, 2 H), 3.41 (m hidden, 6 H), 4.56 (dt, J = 47, 6 Hz, 2 H), 6.91 (d, J = 8 Hz, 1 H), 6.96 (d, J = 8 Hz, 2 H), 7.18-7.28 (m, 3 H), 7.34 (m, 1 H), 7.66 (d, J = 2 Hz, 1 H), 7.82 (dd, J = 8, 2 Hz, 1 H), 8.00 (d, J = 2 Hz, 1 H), 9.80 (br s, 1 H), 10.27 (br s, 1 H) | 570 |
| 176 | No general method; | 1H NMR (500 MHz, DMSO-d6) δ ppm 1.51 (d, J = 22 Hz, 3 H), 1.77-1.91 (m, 2 H), 2.09-2.29 (m, 4 H), | 570 |

TABLE 1b-continued

| Example or compound | Preparation Method | NMR | MASS: LC/MS (m/z, MH+): |
|---|---|---|---|
| | described in example section | 2.46 (m, 1 H), 2.94 (t, J = 7 Hz, 2 H), 3.00-3.20 (m, 2 H), 3.53-3.80 (m, 2 H), 4.04-4.25 (m, 2 H), 4.49 (dt, J = 47, 6 Hz, 2 H), 6.85 (d, J = 8 Hz, 1 H), 6.90 (d, J = 8 Hz, 2 H), 7.19 (dd, J = 8, 4 Hz, 3 H), 7.26 (dd, J = 8, 2 Hz, 1 H), 7.60 (d, J = 2 Hz, 1 H), 7.76 (dd, J = 8, 2 Hz, 1 H), 7.93 (d, J = 2 Hz, 1 H), 9.46-10.76 (m, 1 H), 12.87 (br s, 1 H) | |
| 177 | A | 1H NMR (400 MHz, DMSO-d6) δ ppm 1.60 (dquin, J = 25, 7 Hz, 2 H), 2.09-2.22 (m, 4 H), 2.24 (s, 3 H), 2.40 (t, J = 7 Hz, 2 H), 2.76 (q, J = 7 Hz, 1 H), 2.80-2.92 (m, 3 H), 3.02 (t, J = 7 Hz, 1 H), 3.10 (t, J = 7 Hz, 1 H), 3.24 (t, J = 7 Hz, 1 H), 4.42 (dt, J = 47, 6 Hz, 2 H), 5.52 (dd, J = 48, 7 Hz, 1 H), 6.83 (d, J = 8 Hz, 2 H), 6.85-6.92 (m, 3 H), 7.04 (t, J = 8 Hz, 1 H), 7.12 (dd, J = 8, 1 Hz, 2 H), 7.74 (dd, J = 8, 2 Hz, 1 H), 7.91 (d, J = 2 Hz, 1 H) | 520 |
| 178 | A | 1H NMR (400 MHz, DMSO-d6) δ ppm 1.53-1.69 (m, 2 H), 2.18 (br dd, J = 14, 6 Hz, 4 H), 2.38-2.44 (m, 2 H), 2.72-2.92 (m, 3 H), 2.96-3.16 (m, 2 H), 3.20-3.29 (m, 2 H), 4.42 (dt, J = 47, 6 Hz, 2 H), 5.51 (dd, J = 48, 7 Hz, 1 H), 6.82-6.90 (m, 3 H), 7.12-7.18 (m, 3 H), 7.20-7.32 (m, 2 H), 7.75 (dd, J = 8, 2 Hz, 1 H), 7.92 (d, J = 2 Hz, 1 H) | 540 |
| 179 | A | 1H NMR (400 MHz, DMSO-d6) δ ppm 1.56-1.70 (m, 2 H), 2.13-2.22 (m, 4 H), 2.24 (s, 3 H), 2.50-2.58 (m, 2 H), 2.80-2.99 (m, 4 H), 3.10-3.22 (m, 2 H), 3.38-3.47 (m, 1 H), 4.42 (dt, J = 47, 6 Hz, 2 H), 5.51 (dd, J = 48, 7 Hz, 1 H), 6.81-6.91 (m, 3 H), 6.96 (d, J = 8 Hz, 1 H), 7.03 (d, J = 8 Hz, 1 H), 7.12 (d, J = 8 Hz, 2 H), 7.24 (s, 1 H), 7.74 (dd, J = 8, 2 Hz, 1 H), 7.92 (d, J = 2 Hz, 1 H) | 536 |
| 180 | A | 1H NMR (400 MHz, DMSO-d6) δ ppm 1.82 (dquin, J = 25, 7 Hz, 2 H), 2.11-2.31 (m, 4 H), 2.75-3.01 (m, 5 H), 3.02-3.13 (m, 2 H), 3.59 (br s, 2 H), 3.88 (br s, 2 H), 4.49 (dt, J = 47, 6 Hz, 2 H), 6.78 (d, J = 8 Hz, 2 H), 6.95 (t, J = 55 Hz, 1 H), 6.86 (d, J = 8 Hz, 1 H), 6.92 (d, J = 8 Hz, 2 H), 7.21 (d, J = 7 Hz, 1 H), 7.32-7.45 (m, 2 H), 7.52 (d, J = 7 Hz, 1 H), 7.75 (dd, J = 8, 2 Hz, 1 H), 7.92 (d, J = 2 Hz, 1 H), 10.97 (br s, 1 H), 12.48 (br s, 1 H) | 520 |
| 181 | A | 1H NMR (500 MHz, DMSO-d6) δ ppm 1.62-1.74 (m, 2 H), 2.09-2.17 (m, 7 H), 2.21 (s, 3 H), 2.59-2.68 (m, 2 H), 2.82-3.02 (m, 3 H), 3.35-3.54 (m, 4 H), 4.44 (dt, J = 47, 6 Hz, 2 H), 5.51 (dd, J = 48, 7 Hz, 1 H), 6.81-6.86 (m, 4 H), 6.89-6.96 (m, 2 H), 7.09 (d, J = 8 Hz, 2 H), 7.74 (dd, J = 8, 2 Hz, 1 H), 7.91 (d, J = 2 Hz, 1 H) | 516 |
| 182 | A | 1H NMR (500 MHz, DMSO-d6) δ ppm 1.55-1.65 (m, 2 H), 2.12-2.26 (m, 4 H), 2.36-2.46 (m, 2 H), 2.72-2.88 (m, 2 H), 2.94-3.04 (m, 3 H), 3.08 (br t, J = 7 Hz, 1 H), 3.20-3.26 (m, 1 H), 4.41 (dt, J = 47, 6 Hz, 2 H), 5.51 (dd, J = 48, 7 Hz, 1 H), 6.84-6.89 (m, 3 H), 7.04 (br d, J = 7 Hz, 1 H), 7.13 (d, J = 8 Hz, 2 H), 7.18-7.26 (m, 2 H), 7.76 (dd, J = 8, 2 Hz, 1 H), 7.93 (d, J = 2 Hz, 1 H) | 540 |
| 183 | A | 1H NMR (500 MHz, DMSO-d6) δ ppm 1.55-1.65 (m, 2 H), 2.17 (s, 7 H), 2.36-2.43 (m, 2 H), 2.72-2.90 (m, 3 H), 2.91-3.04 (m, 2 H), 3.09 (br t, J = 7 Hz, 1 H), 3.23 (br dd, J = 10, 7 Hz, 1 H), 4.41 (dt, J = 47, 6 Hz, 2 H), 5.51 (dd, J = 48, 7 Hz, 1 H), 6.80-6.86 (m, 3 H), 7.02-7.13 (m, 4 H), 7.21 (d, J = 2 Hz, 1 H), 7.74 (dd, J = 8, 2 Hz, 1 H), 7.92 (d, J = 2 Hz, 1 H) | 536 |
| 184 | A | 1H NMR (500 MHz, DMSO-d6) δ ppm 1.02 (s, 3 H), 1.60 (dquin, J = 25, 7 Hz, 2 H), 2.09-2.27 (m, 4 H), 2.38 (t, J = 7 Hz, 2 H), 2.65 (m, 2 H), 2.77-2.85 (m, 2 H), 2.88-2.97 (m, 4 H), 4.42 (dt, J = 47, 6 Hz, 2 H), 6.77 (d, J = 8 Hz, 2 H), 6.84 (d, J = 8 Hz, 1 H), 6.91 (d, J = 8 Hz, 2 H), 7.17 (d, J = 8 Hz, 1 H), 7.22 (dd, J = 8, 2 Hz, 1 H), 7.55 (d, J = 2 Hz, 1 H), 7.73 (dd, J = 8, 2 Hz, 1 H), 7.90 (d, J = 2 Hz, 1 H) | 552 |
| 185 | A | 1H NMR (500 MHz, DMSO-d6) δ ppm 1.55-1.65 (m, 2 H), 2.06 (s, 3 H), 2.13-2.23 (m, 4 H), 2.37-2.42 (m, 2 H), 2.71-2.92 (m, 3 H), 2.93-3.04 (m, 2 H), 3.08 (br t, J = 7 Hz, 1 H), 3.20-3.27 (m, 1 H), 4.41 (dt, J = 47, 6 Hz, 2 H), 5.51 (dd, J = 48, 7 Hz, 1 H), 6.78-6.91 (m, 4 H), 6.94-7.00 (m, 1 H), 7.04-7.12 (m, 3 H), 7.75 (dd, J = 8, 2 Hz, 1 H), 7.92 (d, J = 2 Hz, 1 H) | 520 |
| 186 | A | 1H NMR (500 MHz, DMSO-d6) δ ppm 1.55-1.65 (m, 2 H), 2.13-2.21 (m, 7 H), 2.37-2.44 (m, 2 H), 2.73-2.90 (m, 3 H), 2.92-3.04 (m, 2 H), 3.09 (t, J = 7 Hz, 1 H), 3.24 (m, 1 H), 4.41 (dt, J = 47, 6 Hz, 2 H), 5.51 (dd, | 520 |

TABLE 1b-continued

| Example or compound | Preparation Method | NMR | MASS: LC/MS (m/z, MH+): |
|---|---|---|---|
| | | J = 48, 7 Hz, 1 H), 6.79-6.88 (m, 4 H), 6.97 (dd, J = 10, 2 Hz, 1 H), 7.03-7.13 (m, 3 H), 7.74 (dd, J = 8, 2 Hz, 1 H), 7.92 (d, J = 2 Hz, 1 H) | |
| 187 | A | 1H NMR (500 MHz, DMSO-d6) δ ppm 1.55-1.65 (m, 2 H), 2.15-2.24 (m, 4 H), 2.37-2.46 (m, 2 H), 2.72-2.87 (m, 2 H), 2.95 (br s, 2 H), 3.01 (br t, J = 6 Hz, 1 H), 3.09 (br t, J = 7 Hz, 1 H), 3.24 (br s, 1 H), 4.42 (dt, J = 47, 6 Hz, 2 H), 5.51 (dd, J = 48, 7 Hz, 1 H), 6.84 (br d, J = 8 Hz, 1 H), 6.87 (d, J = 8 Hz, 2 H), 7.05 (td, J = 8, 3 Hz, 1 H), 7.13 (d, J = 8 Hz, 2 H), 7.22 (t, J = 7 Hz, 1 H), 7.40 (dd, J = 9, 3 Hz, 1 H), 7.75 (dd, J = 8, 2 Hz, 1 H), 7.92 (d, J = 2 Hz, 1 H) | 540 |
| 188 | A | 1H NMR (500 MHz, DMSO-d6) δ ppm 1.54-1.65 (m, 2 H), 2.10-2.27 (m, 4 H), 2.30-2.35 (m, 3 H), 2.71-2.90 (m, 3 H), 2.91-3.03 (m, 3 H), 3.07 (t, J = 7 Hz, 2 H), 3.23 (m, 1 H), 4.41 (dt, J = 47, 6 Hz, 2 H), 5.41-5.59 (m, 1 H), 6.84 (d, J = 8 Hz, 1 H), 6.87 (d, J = 8 Hz, 2 H), 6.96 (m, 1 H), 7.03 (td, J = 8, 2 Hz, 1 H), 7.10 (d, J = 8 Hz, 2 H), 7.17 (d, J = 8 Hz, 1 H), 7.75 (dd, J = 8, 2 Hz, 1 H), 7.92 (d, J = 2 Hz, 1 H) | 536 |
| 189 | A | 1H NMR (400 MHz, DMSO-d6) δ ppm 1.84 (dquin, J = 25, 7 Hz, 2 H), 2.12-2.30 (m, 4 H), 2.76-3.03 (m, 5 H), 3.08-3.20 (m, 2 H), 3.62-3.75 (m, 2 H), 3.89-4.02 (m, 2 H), 4.50 (dt, J = 47, 6 Hz, 2 H), 6.81 (d, J = 8 Hz, 2 H), 6.86 (d, J = 8 Hz, 1 H), 6.98 (d, J = 8 Hz, 2 H), 7.42 (d, J = 8 Hz, 1 H), 7.57 (d, J = 7 Hz, 1 H), 7.77 (dd, J = 8, 2 Hz, 1 H), 7.86 (s, 1 H), 7.95 (d, J = 2 Hz, 1 H), 10.39 (br s, 1 H), 12.91 (br s, 1 H) | 572 |
| 190 | A | 1H NMR (400 MHz, DMSO-d6) δ ppm 1.59 (dquin, J = 25, 7 Hz, 2 H), 2.10-2.27 (m, 4 H), 2.38 (t, J = 7 Hz, 2 H), 2.82-3.09 (m, 3 H), 3.24 (m, 2 H), 3.41 (m hidden, 2 H), 4.40 (dt, J = 47, 6 Hz, 2 H), 6.82 (d, J = 8 Hz, 1 H), 6.94 (d, J = 8 Hz, 2 H), 7.24-7.30 (m, 3 H), 7.35 (td, J = 8, 3 Hz, 1 H), 7.64 (dd, J = 9, 3 Hz, 1 H), 7.74 (dd, J = 8, 2 Hz, 1 H), 7.91 (d, J = 2 Hz, 1 H) | 592 |
| 191 | A | 1H NMR (500 MHz, DMSO-d6) δ ppm 1.59 (dquin, J = 25, 7 Hz, 2 H), 2.11-2.27 (m, 4 H), 2.37 (t, J = 7 Hz, 2 H), 2.84-3.07 (m, 3 H), 3.20-3.25 (m, 2 H), 3.39 (m hidden, 2 H), 4.40 (dt, J = 47, 6 Hz, 2 H), 6.83 (d, J = 8 Hz, 1 H), 6.94 (d, J = 8 Hz, 2 H), 7.21 (dd, J = 7, 2 Hz, 1 H), 7.24 (d, J = 8 Hz, 2 H), 7.39-7.49 (m, 2 H), 7.72 (dd, J = 6, 2 Hz, 1 H), 7.75 (dd, J = 8, 2 Hz, 1 H), 7.92 (d, J = 2 Hz, 1 H) | 574 |
| 192 | A | 1H NMR (400 MHz, DMSO-d6) δ ppm 1.76-1.94 (m, 2 H), 2.07-2.20 (m, 2 H), 2.27 (t, J = 7 Hz, 2 H), 2.75-3.01 (m, 5 H), 3.07-3.23 (m, 2 H), 3.52-4.09 (m, 4 H), 4.50 (dt, J = 47, 6 Hz, 2 H), 6.77-6.86 (m, 3 H), 6.99 (d, J = 8 Hz, 2 H), 7.17 (d, J = 9 Hz, 2 H), 7.25 (d, J = 9 Hz, 2 H), 7.74 (dd, J = 8, 2 Hz, 1 H), 7.91 (d, J = 2 Hz, 1 H), 9.92 (br s, 1 H), 12.88 (br s, 1 H) | 504 |
| 193 | B | 1H NMR (400 MHz, DMSO-d6) δ ppm 1.62 (dquin, J = 25, 7 Hz, 2 H), 2.12-2.19 (m, 4 H), 2.45 (t, J = 8 Hz, 2 H), 2.56 (m, 1 H), 2.69 (d, J = 8 Hz, 2 H), 2.78 (t, J = 7 Hz, 2 H), 2.83-3.02 (m, 4 H), 3.28 (t, J = 7 Hz, 2 H), 4.42 (dt, J = 47, 6 Hz, 3 H), 6.71 (d, J = 8 Hz, 2 H), 6.85 (d, J = 8 Hz, 1 H), 6.90 (d, J = 8 Hz, 2 H), 7.14 (d, J = 5 Hz, 1 H), 7.74 (dd, J = 8, 2 Hz, 1 H), 7.92 (d, J = 2 Hz, 1 H), 8.15 (s, 1 H), 8.22 (d, J = 5 Hz, 1 H) | 485 |
| 194 | No general method; described in example section | 1H NMR (400 MHz, DMSO-d6) δ ppm 2.09-2.25 (m, 4 H), 2.55 (m, 1 H), 2.62 (m, 2 H), 2.68-2.71 (m, 2 H), 2.80 (t, J = 7 Hz, 2 H), 2.93 (t, J = 5 Hz, 2 H), 3.22 (m hidden, 2 H), 4.36-4.79 (m, 3 H), 6.76 (d, J = 8 Hz, 2 H), 6.85 (d, J = 8 Hz, 1 H), 6.93 (d, J = 8 Hz, 2 H), 7.18 (d, J = 8 Hz, 1 H), 7.25 (dd, J = 9, 2 Hz, 1 H), 7.57 (d, J = 2 Hz, 1 H), 7.74 (dd, J = 8, 2 Hz, 1 H), 7.91 (d, J = 2 Hz, 1 H), 12.87 (br s, 1 H) | 556 |
| 195 | No general method; described in example section | 1H NMR (400 MHz, DMSO-d6) δ ppm 2.09-2.25 (m, 4 H), 2.54-2.65 (m, 3 H), 2.69 (m, 2 H), 2.76-2.83 (m, 2 H), 2.90-2.96 (m, 2 H), 3.25 (m hidden, 2 H), 4.34-4.80 (m, 3 H), 6.76 (d, J = 8 Hz, 2 H), 6.85 (d, J = 8 Hz, 1 H), 6.93 (d, J = 8 Hz, 2 H), 7.18 (d, J = 9 Hz, 1 H), 7.25 (dd, J = 8, 3 Hz, 1 H), 7.57 (d, J = 2 Hz, 1 H), 7.74 (dd, J = 8, 2 Hz, 1 H), 7.91 (d, J = 2 Hz, 1 H), 12.86 (br s, 1 H) | 556 |
| 196 | No general method; described in | 1H NMR (400 MHz, DMSO-d6) δ ppm 1.73-1.93 (m, 2 H), 2.11-2.30 (m, 4 H), 2.91-3.03 (m, 2 H), 3.10-3.23 (m, 2 H), 3.86 (s, 3 H), 3.90-3.93 (m, 1 H), 4.02- | 581 |

TABLE 1b-continued

| Example or compound | Preparation Method | NMR | MASS: LC/MS (m/z, MH+): |
|---|---|---|---|
| | example section | 4.22 (m, 2 H), 4.27-4.38 (m, 2 H), 4.46 (dt, J = 47, 6 Hz, 2 H), 6.86 (d, J = 8 Hz, 1 H), 6.91 (d, J = 9 Hz, 2 H), 7.20 (d, J = 8 Hz, 2 H), 7.22-7.35 (m, 2 H), 7.60 (d, J = 2 Hz, 1 H), 7.77 (dd, J = 8, 2 Hz, 1 H), 7.95 (d, J = 2 Hz, 1 H), 9.96 (br s, 1 H), 10.78 (br s, 1 H), 12.94 (br s, 1 H) | |
| 197 | No general method; described in example section | 1H NMR (400 MHz, DMSO-d6) δ ppm 1.80-1.96 (m, 2 H), 2.10-2.28 (m, 4 H), 2.89-3.04 (m, 2 H), 3.15-3.23 (m, 2 H), 3.83 (s, 3 H), 3.95-4.32 (m, 5 H), 4.51 (dt, J = 47, 6 Hz, 2 H), 6.85 (d, J = 8 Hz, 1 H), 6.93 (d, J = 9 Hz, 2 H), 7.23 (d, J = 8 Hz, 1 H), 7.28 (dd, J = 8, 3 Hz, 1 H), 7.34 (d, J = 9 Hz, 2 H), 7.61 (d, J = 2 Hz, 1 H), 7.77 (dd, J = 8, 2 Hz, 1 H), 7.94 (d, J = 2 Hz, 1 H), 10.10 (br s, 1 H), 10.62 (br s, 1 H), 12.73 (m, 1 H) | 581 |
| 198 | A | 1H NMR (400 MHz, DMSO-d6) δ ppm 1.59 (dquin, J = 25, 6 Hz, 2 H), 2.08 (d, J = 2 Hz, 3 H), 2.13-2.26 (m, 4 H), 2.38 (t, J = 7 Hz, 2 H), 2.95 (m, 3 H), 3.21-3.27 (m, 2 H), 3.35 (m hidden, 2 H), 4.40 (dt, J = 47, 6 Hz, 2 H), 6.84 (d, J = 8 Hz, 1 H), 6.86-6.92 (m, 3 H), 6.98 (m, 1 H), 7.07 (m, 1 H), 7.24 (d, J = 9 Hz, 2 H), 7.75 (dd, J = 8, 2 Hz, 1 H), 7.93 (d, J = 2 Hz, 1 H) | 538 |
| 199 | A | 1H NMR (400 MHz, DMSO-d6) δ ppm 1.60 (dquin, J = 25, 6 Hz, 2 H), 2.12-2.22 (m, 7 H), 2.39 (t, J = 7 Hz, 2 H), 2.82-3.02 (m, 3 H), 3.23-3.27 (m, 2 H), 3.345 (m hidden, 2 H), 4.40 (dt, J = 47, 6 Hz, 2 H), 6.84 (d, J = 8 Hz, 1 H), 6.91 (d, J = 9 Hz, 2 H), 7.03 (m, 1 H), 7.09 (dd, J = 8, 2 Hz, 1 H), 7.22 (d, J = 2 Hz, 1 H), 7.25 (d, J = 9 Hz, 2 H), 7.75 (dd, J = 8, 2 Hz, 1 H), 7.93 (d, J = 2 Hz, 1 H) | 554 |
| 200 | A | 1H NMR (400 MHz, DMSO-d6) δ ppm 1.59 (dquin, J = 25, 6 Hz, 2 H), 2.11-2.24 (m, 7 H), 2.38 (t, J = 7 Hz, 2 H), 2.83-3.01 (m, 5 H), 3.24 (m hidden, 2 H), 4.40 (dt, J = 47, 6 Hz, 2 H), 6.83 (d, J = 8 Hz, 1 H), 6.84-6.87 (m, 1 H), 6.89 (d, J = 8 Hz, 2 H), 6.99 (dd, J = 10, 3 Hz, 1 H), 7.05 (dd, J = 9, 6 Hz, 1 H), 7.24 (d, J = 8 Hz, 2 H), 7.75 (dd, J = 8, 2 Hz, 1 H), 7.92 (d, J = 2 Hz, 1 H) | 538 |
| 201 | A | 1H NMR (400 MHz, DMSO-d6) δ ppm 1.29 (t, J = 7 Hz, 3 H), 1.71-1.91 (m, 2 H), 2.11 (s, 3 H), 2.12-2.18 (m, 4 H), 2.74-2.97 (m, 5 H), 2.98-3.20 (m, 2 H), 3.52-3.73 (m, 2 H), 3.84-3.94 (m, 2 H), 3.94 (q, J = 7 Hz, 2 H), 4.48 (dt, J = 47, 6 Hz, 2 H), 6.60 (dd, J = 8, 3 Hz, 1 H), 6.67 (d, J = 2 Hz, 1 H), 6.72 (d, J = 8 Hz, 2 H), 6.82 (d, J = 8 Hz, 1 H), 6.88-6.94 (m, 3 H), 7.73 (dd, J = 8, 2 Hz, 1 H), 7.90 (d, J = 2 Hz, 1 H), 10.12 (br s, 1 H), 12.82 (br s, 1 H) | 528 |
| 202 | A | 1H NMR (400 MHz, DMSO-d6) δ ppm 1.73-1.92 (m, 2 H), 2.09-2.27 (m, 4 H), 2.77-2.98 (m, 5 H), 3.02-3.25 (m, 2 H), 3.54-3.78 (m, 2 H), 3.80-4.05 (m, 2 H), 4.49 (dt, J = 47, 6 Hz, 2 H), 6.81 (d, J = 8 Hz, 2 H), 6.85 (d, J = 8 Hz, 1 H), 6.99 (d, J = 8 Hz, 2 H), 7.13 (t, J = 9 Hz, 1 H), 7.23-7.33 (m, 2 H), 7.75 (dd, J = 8, 2 Hz, 1 H), 7.92 (d, J = 2 Hz, 1 H), 10.01 (br s, 1 H), 12.92 (br s, 1 H) | 522 |
| 203 | A | 1H NMR (400 MHz, DMSO-d6) δ ppm 1.70-1.91 (m, 2 H), 2.11-2.26 (m, 4 H), 2.75-2.92 (m, 4 H), 2.97-3.14 (m, 3 H), 3.50-3.70 (m, 2 H), 3.80-3.93 (m, 2 H), 4.48 (dt, J = 47, 6 Hz, 2 H), 6.79 (d, J = 8 Hz, 2 H), 6.85 (d, J = 8 Hz, 1 H), 6.98 (d, J = 8 Hz, 2 H), 7.27 (d, J = 2 Hz, 1 H), 7.46-7.55 (m, 1 H), 7.75 (d, J = 8 Hz, 1 H), 7.75 (d, J = 8 Hz, 1 H), 7.92 (d, J = 2 Hz, 1 H), 10.20 (br s, 1 H), 12.51 (br s, 1 H) | 572 |
| 204 | A | 1H NMR (400 MHz, DMSO-d6) δ ppm 1.74-1.92 (m, 2 H), 2.07-2.25 (m, 7 H), 2.76-2.99 (m, 5 H), 3.06-3.23 (m, 2 H), 3.60-3.82 (m, 2 H), 3.86-4.06 (m, 2 H), 4.49 (dt, J = 47, 6 Hz, 2 H), 6.79 (d, J = 8 Hz, 2 H), 6.84 (d, J = 8 Hz, 1 H), 6.88-7.05 (m, 5 H), 7.74 (dd, J = 8, 2 Hz, 1 H), 7.91 (d, J = 2 Hz, 1 H), 10.02 (br s, 1 H), 12.84 (br s, 1 H) | 502 |
| 205 | A | 1H NMR (400 MHz, DMSO-d6) δ ppm 1.65 (dquin, J = 25, 7 Hz, 2 H), 2.04-2.30 (m, 4 H), 2.51 (m hidden, 2 H), 2.61 (m, 1 H), 2.68-2.75 (m, 2 H), 2.90 (t, J = 6 Hz, 4 H), 3.37 (t, J = 7 Hz, 2 H), 4.43 (dt, J = 47, 6 Hz, 2 H), 6.51 (d, J = 12 Hz, 1 H), 6.78 (d, J = 8 Hz, 2 H), 6.92 (d, J = 8 Hz, 2 H), 7.12-7.17 (m, 2 H), 7.17-7.25 (m, 1 H), 7.40 (d, J = 8 Hz, 1 H), 7.79 (d, J = 8 Hz, 1 H) | 522 |
| 206 | A | 1H NMR (400 MHz, DMSO-d6) δ ppm 1.64 (dquin, J = 26, 7 Hz, 2 H), 2.08-2.26 (m, 4 H), 2.51 (m hidden, 2 H), 2.60 (m, 1 H), 2.72 (d, J = 8 Hz, 2 H), 2.87 (q, J = 6 | 555 |

TABLE 1b-continued

| Example or compound | Preparation Method | NMR | MASS: LC/MS (m/z, MH+): |
|---|---|---|---|
| | | Hz, 4 H), 3.35 (t, J = 7 Hz, 2 H), 4.43 (dt, J = 47, 6 Hz, 2 H), 6.49 (d, J = 12 Hz, 1 H), 6.78 (d, J = 8 Hz, 2 H), 6.95 (d, J = 8 Hz, 2 H), 7.18 (d, J = 8 Hz, 1 H), 7.25 (dd, J = 9, 3 Hz, 1 H), 7.57 (d, J = 2 Hz, 1 H), 7.77 (d, J = 8 Hz, 1 H) | |
| 207 | A | 1H NMR (400 MHz, DMSO-d6) δ ppm 1.71-1.95 (m, 2 H), 2.09-2.21 (m, 2 H), 2.27 (t, J = 7 Hz, 2 H), 2.78-2.98 (m, 5 H), 3.02-3.22 (m, 2 H), 3.52-3.81 (m, 2 H), 3.84-4.01 (m, 2 H), 4.49 (dt, J = 47, 6 Hz, 2 H), 6.83 (dd, J = 8, 3 Hz, 3 H), 7.02 (d, J = 8 Hz, 2 H), 7.15 (dd, J = 8, 2 Hz, 1 H), 7.35 (d, J = 2 Hz, 1 H), 7.45 (d, J = 8 Hz, 1 H), 7.74 (dd, J = 8, 2 Hz, 1 H), 7.91 (d, J = 2 Hz, 1 H), 10.11 (br s, 1 H), 12.88 (br s, 1 H) | 538 |
| 208 | D | 1H NMR (400 MHz, DMSO-d6) δ ppm 1.83 (dt, J = 27, 5 Hz, 2 H), 2.09-2.24 (m, 4 H), 2.76-3.00 (m, 5 H), 3.66-3.79 (m, 2 H), 3.92-4.07 (m, 2 H), 4.49 (dt, J = 47, 6 Hz, 2 H), 6.80 (d, J = 8 Hz, 2 H), 6.84 (d, J = 8 Hz, 1 H), 6.97 (d, J = 8 Hz, 2 H), 7.19 (m, 1 H), 7.29 (m, 1 H), 7.59 (d, J = 2 Hz, 1 H), 7.75 (dd, J = 8, 2 Hz, 1 H), 7.93 (d, J = 2 Hz, 1 H), 10.03 (br s, 1 H), 12.90 (br s, 1 H) | 540 |
| 209 | B | 1H NMR (400 MHz, DMSO-d6) δ ppm 1.59-1.75 (m, 2 H), 1.78 (s, 3 H), 2.09-2.26 (m, 4 H), 2.54(m hidden, 2 H), 2.66 (m, 1 H), 2.76-2.84 (m, 2 H), 2.98-3.11 (m, 2 H), 3.19-3.34 (m hidden, 7 H), 4.45 (dt, J = 47, 6 Hz, 2 H), 6.82 (d, J = 8 Hz, 1 H), 6.87 (d, J = 8 Hz, 2 H), 6.90-6.94 (m, 1 H), 7.04 (d, J = 8 Hz, 2 H), 7.45 (d, J = 3 Hz, 1 H), 7.71 (dd, J = 8, 2 Hz, 1 H), 7.87 (d, J = 2 Hz, 1 H) | 515 |
| 210 | A | 1H NMR (400 MHz, DMSO-d6) δ ppm 1.75-1.94 (m, 2 H), 2.09-2.20 (m, 4 H), 2.21 (d, J = 2 Hz, 3 H), 2.76-3.03 (m, 5 H), 3.09-3.26 (m, 2 H), 3.65-3.84 (m, 2 H), 3.92-4.09 (m, 2 H), 4.50 (dt, J = 47, 6 Hz, 2 H), 6.81 (d, J = 8 Hz, 2 H), 6.84 (d, J = 8 Hz, 1 H), 6.89-7.02 (m, 4 H), 7.75 (dd, J = 8, 2 Hz, 1 H), 7.92 (d, J = 2 Hz, 1 H), 10.18 (br s, 1 H), 12.90 (br s, 1 H) | 520 |
| 211 | A | 1H NMR (400 MHz, DMSO-d6) δ ppm 1.75-1.94 (m, 2 H), 2.06-2.28 (m, 4 H), 2.76-3.00 (m, 5 H), 3.09-3.22 (m, 2 H), 3.64-3.77 (m, 2 H), 3.91-4.04 (m, 2 H), 4.50 (dt, J = 47, 6 Hz, 2 H), 6.80 (d, J = 8 Hz, 2 H), 6.85 (d, J = 8 Hz, 1 H), 6.99 (d, J = 8 Hz, 2 H), 7.09 (dd, J = 8, 2 Hz, 1 H), 7.45 (dd, J = 8, 7 Hz, 1 H), 7.76 (dd, J = 8, 2 Hz, 1 H), 7.93 (d, J = 2 Hz, 1 H), 10.37 (br s, 1 H), 12.87 (br s, 1 H) | 556 |
| 212 | A | 1H NMR (400 MHz, DMSO-d6) δ ppm 1.69-1.92 (m, 2 H), 2.09-2.21 (m, 4 H), 2.23 (s, 3 H), 2.76-3.02 (m, 5 H), 3.04-3.20 (m, 2 H), 3.54-3.78 (m, 2 H), 3.81-4.04 (m, 2 H), 4.49 (dt, J = 47, 6 Hz, 2 H), 6.74 (d, J = 8 Hz, 2 H), 6.86 (d, J = 8 Hz, 1 H), 6.94 (d, J = 8 Hz, 2 H), 7.00 (dd, J = 8, 1 Hz, 1 H), 7.06 (t, J = 8 Hz, 1 H), 7.26 (dd, J = 8, 1 Hz, 1 H), 7.76 (dd, J = 8, 2 Hz, 1 H), 7.93 (d, J = 2 Hz, 1 H), 10.01 (br s, 1 H), 12.87 (br s, 1 H) | 518 |
| 213 | A | 1H NMR (400 MHz, DMSO-d6) δ ppm 1.73-1.94 (m, 2 H), 2.13-2.30 (m, 4 H), 2.38 (s, 3 H), 2.76-3.17 (m, 7 H), 3.47-3.71 (m, 2 H), 3.75-4.01 (m, 2 H), 4.53 (dt, J = 47, 6 Hz, 2 H), 6.84 (d, J = 8 Hz, 2 H), 6.90 (d, J = 8 Hz, 1 H), 6.99 (d, J = 8 Hz, 2 H), 7.13 (d, J = 8 Hz, 1 H), 7.31 (d, J = 8 Hz, 1 H), 7.59 (s, 1 H), 7.81 (dd, J = 8, 2 Hz, 1 H), 7.97 (d, J = 2 Hz, 1 H), 9.98 (br s, 1 H), 12.93 (br s, 1 H) | 552 |
| 214 | B | 1H NMR (400 MHz, DMSO-d6) δ ppm 1.75-1.93 (m, 2 H), 2.11-2.28 (m, 4 H), 2.73-2.99 (m, 5 H), 3.00-3.26 (m, 2 H), 3.68-4.09 (m, 4 H), 4.49 (dt, J = 47, 5 Hz, 2 H), 6.74-6.82 (m, 2 H), 6.87 (d, J = 8 Hz, 1 H), 6.93-7.01 (m, 2 H), 7.74 (d, J = 5 Hz, 1 H), 7.76 (dd, J = 8, 2 Hz, 1 H), 7.94 (d, J = 2 Hz, 1 H), 8.46 (d, J = 2 Hz, 1 H), 8.65 (d, J = 5 Hz, 1 H), 10.50 (m, 1 H), 12.87 (br s, 1 H) | 539 |
| 215 | D | 1H NMR (500 MHz, DMSO-d6) δ ppm 0.65-0.82 (m, 2 H), 0.83-1.03 (m, 2 H), 1.71-1.89 (m, 2 H), 2.07-2.27 (m, 4 H), 2.56 (m partially hidden, 1 H), 2.73-3.17 (m, 6 H), 3.66-4.05 (m, 2 H), 4.47 (dt, J = 47, 6 Hz, 2 H), 6.81 (d, J = 8 Hz, 2 H), 6.83 (d, J = 8 Hz, 1 H), 7.00 (d, J = 8 Hz, 2 H), 7.20 (d, J = 8 Hz, 1 H), 7.27 (dd, J = 9, 2 Hz, 1 H), 7.60 (d, J = 2 Hz, 1 H), 7.75 (dd, J = 8, 2 Hz, 1 H), 7.92 (d, J = 2 Hz, 1 H), 9.96 (br s, 1 H), 12.82 (br s, 1 H) | 564 |
| 216 | A | 1H NMR (400 MHz, DMSO-d6) δ ppm 1.82 (dquin, J = 27, 6 Hz, 2 H), 2.01-2.30 (m, 4 H), 2.71-2.91 (m, 4 H), 2.91-3.18 (m, 3 H), 3.49-3.70 (m, 2 H), 3.76- | 558 |

TABLE 1b-continued

| Example or compound | Preparation Method | NMR | MASS: LC/MS (m/z, MH+): |
|---|---|---|---|
| | | 3.99 (m, 2 H), 4.48 (dt, J = 47, 6 Hz, 2 H), 6.27 (d, J = 10 Hz, 1 H), 6.79 (d, J = 8 Hz, 2 H), 6.95 (d, J = 8 Hz, 2 H), 7.05 (td, J = 8, 3 Hz, 1 H), 7.22 (dd, J = 9, 6 Hz, 1 H), 7.40 (dd, J = 9, 3 Hz, 1 H), 11.74 (br s, 1 H) | |
| 217 | A | 1H NMR (400 MHz, DMSO-d6) δ ppm 1.82 (dquin, J = 26, 8 Hz, 2 H), 2.01-2.23 (m, 4 H), 2.24 (s, 3 H), 2.69-2.91 (m, 4 H), 2.93-3.10 (m, 3 H), 3.49-3.68 (m, 2 H), 3.78-3.95 (m, 2 H), 4.48 (dt, J = 47, 6 Hz, 2 H), 6.28 (d, J = 10 Hz, 1 H), 6.80 (d, J = 8 Hz, 2 H), 6.94 (d, J = 8 Hz, 2 H), 6.97 (dd, J = 9, 1 Hz, 1 H), 7.03 (d, J = 8 Hz, 1 H), 7.24 (s, 1 H), 11.61 (br s, 1 H) | 554 |
| 218 | B | 1H NMR (400 MHz, DMSO-d6) δ ppm 1.60 (dquin, J = 26, 6 Hz, 2 H), 2.21 (m, 2 H), 2.33 (dt, J = 4, 2 Hz, 2 H), 2.40 (t, J = 7 Hz, 2 H), 2.68-2.75 (m, 3 H), 2.91 (m, 2 H), 3.15-3.26 (m hidden, 4 H), 4.41 (dt, J = 47, 6 Hz, 2 H), 6.62 (d, J = 8 Hz, 2 H), 6.84 (d, J = 8 Hz, 1 H), 6.90 (d, J = 8 Hz, 2 H), 7.75 (dd, J = 8, 2 Hz, 1 H), 7.92 (d, J = 2 Hz, 1 H), 8.17 (s, 1 H), 8.29 (d, J = 2 Hz, 1 H), 8.89 (d, J = 2 Hz, 1 H) | 573 |
| 219 | B | 1H NMR (500 MHz, DMSO-d6) δ ppm 1.61 (dquin, J = 26, 7 Hz, 2 H), 2.11-2.34 (m, 4 H), 2.42 (t, J = 7 Hz, 2 H), 2.55(m, 1 H), 2.68 (d, J = 8 Hz, 2 H), 2.73 (t, J = 7 Hz, 2 H), 2.87-2.94 (m, 2 H), 3.24 (t, J = 7 Hz, 2 H), 4.41 (dt, J = 47, 6 Hz, 2 H), 6.62 (d, J = 8 Hz, 2 H), 6.83 (d, J = 8 Hz, 1 H), 6.90 (d, J = 8 Hz, 2 H), 7.74 (br d, J = 8 Hz, 1 H), 7.92 (s, 1 H), 8.29 (d, J = 2 Hz, 1 H), 8.89 (d, J = 2 Hz, 1 H) | 523 |
| 220 | B | 1H NMR (500 MHz, DMSO-d6) δ ppm 1.61 (dquin, J = 26, 6 Hz, 2 H), 2.08-2.25 (m, 4 H), 2.45 (t, J = 7 Hz, 2 H), 2.57(m, 1 H), 2.69 (d, J = 8 Hz, 2 H), 2.78 (t, J = 6 Hz, 2 H), 2.90-3.03 (m, 2 H), 3.28 (m hidden, 2 H), 4.42 (dt, J = 47, 6 Hz, 2 H), 6.78 (d, J = 8 Hz, 2 H), 6.85 (d, J = 8 Hz, 1 H), 6.92 (d, J = 8 Hz, 2 H), 7.05-7.13 (m, 1 H), 7.23-7.31 (m, 2 H), 7.75 (dd, J = 8, 2 Hz, 1 H), 7.93 (d, J = 1 Hz, 1 H) | 522 |
| 221 | A | 1H NMR (500 MHz, DMSO-d6) δ ppm 1.62 (dquin, J = 26, 6 Hz, 2 H), 2.10-2.31 (m, 4 H), 2.46 (t, J = 7 Hz, 2 H), 2.58 (m, 1 H), 2.69 (d, J = 8 Hz, 2 H), 2.78 (t, J = 7 Hz, 2 H), 2.83-3.00 (m, 2 H), 3.25-3.30 (m, 2 H), 4.42 (dt, J = 47, 6 Hz, 2 H), 6.73-6.80 (m, 2 H), 6.95 (t, J = 55 Hz, 1 H), 6.86 (d, J = 8 Hz, 1 H), 6.93 (d, J = 8 Hz, 2 H), 7.25 (d, J = 8 Hz, 1 H), 7.47 (dd, J = 8, 2 Hz, 1 H), 7.53 (d, J = 2 Hz, 1 H), 7.75 (dd, J = 8, 2 Hz, 1 H), 7.91 (d, J = 2 Hz, 1 H), 8.18 (s, 1 H) | 524 |
| 222 | B | 1H NMR (500 MHz, DMSO-d6) δ ppm 1.61 (dquin, J = 25, 7 Hz, 2 H), 2.07-2.24 (m, 4 H), 2.44 (t, J = 7 Hz, 2 H), 2.57 (m, 1 H), 2.70 (d, J = 8 Hz, 2 H), 2.77 (t, J = 7 Hz, 2 H), 2.85-2.92 (m, 2 H), 3.27 (t, J = 7 Hz, 2 H), 4.42 (dt, J = 47, 6 Hz, 2 H), 6.77 (d, J = 8 Hz, 2 H), 6.86 (d, J = 8 Hz, 1 H), 6.93 (d, J = 8 Hz, 2 H), 6.97 (t, J = 8 Hz, 2 H), 7.24-7.34 (m, 1 H), 7.75 (dd, J = 8, 1 Hz, 1 H), 7.92 (s, 1 H) | 506 |
| 223 | D | 1H NMR (400 MHz, DMSO-d6) δ ppm 1.68-1.86 (m, 2 H), 2.08-2.27 (m, 4 H), 2.42 (t, J = 7 Hz, 2 H), 2.56 (m, 1 H), 2.68-2.72 (m, 2 H), 2.88-2.96 (m, 2 H), 3.19-3.25 (m, 4 H), 6.03 (tt, J = 57, 5 Hz, 1 H), 6.76 (d, J = 8 Hz, 2 H), 6.85 (d, J = 8 Hz, 1 H), 6.93 (d, J = 8 Hz, 2 H), 7.18 (d, J = 8 Hz, 1 H), 7.25 (dd, J = 8, 3 Hz, 1 H), 7.57 (d, J = 2 Hz, 1 H), 7.74 (dd, J = 8, 2 Hz, 1 H), 7.91 (d, J = 2 Hz, 1 H) | 556 |
| 224 | A | 1H NMR (400 MHz, DMSO-d6) δ ppm 1.74-1.90 (m, 2 H), 2.03-2.30 (m, 4 H), 2.70-2.90 (m, 4 H), 2.93-3.08 (m, 3 H), 3.54-3.66 (m, 2 H), 3.82-3.93 (m, 2 H), 4.48 (dt, J = 47, 6 Hz, 2 H), 6.29 (d, J = 10 Hz, 1 H), 6.80 (d, J = 8 Hz, 2 H), 6.93 (d, J = 8 Hz, 2 H), 7.16 (d, J = 4 Hz, 2 H), 7.21 (dtd, J = 6, 5, 4 Hz, 1 H), 7.41 (d, J = 8 Hz, 1 H), 11.70 (br s, 1 H) | 540 |
| 225 | A | 1H NMR (500 MHz, DMSO-d6) δ ppm 1.72-1.90 (m, 2 H), 2.04-2.31 (m, 4 H), 2.71-2.92 (m, 4 H), 2.93-3.01 (m, 1 H), 3.09 (t, J = 10 Hz, 2 H), 3.57-3.73 (m, 2 H), 3.87-3.99 (m, 2 H), 4.49 (dt, J = 47, 6 Hz, 2 H), 6.30 (d, J = 10 Hz, 1 H), 6.80 (d, J = 8 Hz, 2 H), 6.97 (d, J = 8 Hz, 2 H), 7.17-7.21 (m, 1 H), 7.26 (dd, J = 9, 2 Hz, 1 H), 7.58 (d, J = 2 Hz, 1 H), 11.21 (br s, 1 H) | 574 |
| 226 | A | 1H NMR (400 MHz, DMSO-d6) δ ppm 1.59 (dquin, J = 25, 6 Hz, 2 H), 2.01-2.28 (m, 4 H), 2.37 (t, J = 7 Hz, | 572 |

TABLE 1b-continued

| Example or compound | Preparation Method | NMR | MASS: LC/MS (m/z, MH+): |
| --- | --- | --- | --- |
| | | 2 H), 2.54 (m hidden, 3 H), 2.63-2.68 (m, 2 H), 2.82 (m, 1 H), 2.99 (m, 1 H), 3.16-3.23 (m, 2 H), 4.41 (dt, J = 47, 6 Hz, 2 H), 6.75 (d, J = 8 Hz, 2 H), 6.84 (d, J = 8 Hz, 1 H), 6.95 (d, J = 8 Hz, 2 H), 7.12 (d, J = 7 Hz, 1 H), 7.40 (t, J = 8 Hz, 1 H), 7.54 (d, J = 8 Hz, 1 H), 7.74 (dd, J = 8, 2 Hz, 1 H), 7.90 (d, J = 2 Hz, 1 H), 12.87 (br s, 1 H) | |
| 227 | No general method; described in example section | 1H NMR (400 MHz, DMSO-d6) δ ppm 1.62-1.89 (m, 2 H), 2.08-2.29 (m, 4 H), 2.45-2.49 (m hidden, 2 H), 2.77 (m, 1 H), 2.86-3.01 (m, 4 H), 3.04-3.13 (m, 3 H), 3.45-3.80 (m, 2 H), 4.32 (m, 1 H), 4.48 (dt, J = 47, 6 Hz, 2 H), 6.82-6.94 (m, 3 H), 7.08 (d, J = 8 Hz, 2 H), 7.12-7.30 (m, 2 H), 7.57 (br s, 1 H), 7.76 (dd, J = 8, 2 Hz, 1 H), 7.93 (d, J = 2 Hz, 1 H), 10.31-13.80 (m, 1 H) | 568 |
| 228 | No general method; described in example section | 1H NMR (400 MHz, DMSO-d6) δ ppm 1.69 (dquin, J = 25, 7 Hz, 2 H), 2.13-2.36 (m, 4 H), 2.57-3.28 (m partially hidden, 9 H), 3.10 (s, 3 H), 4.24 (d, J = 8 Hz, 1 H), 4.48 (dt, J = 47, 6 Hz, 2 H), 6.91 (d, J = 8 Hz, 2 H), 6.95 (dd, J = 8, 3 Hz, 1 H), 7.11 (d, J = 8 Hz, 2 H), 7.16-7.33 (m, 2 H), 7.64 (m, 1 H), 7.82 (dd, J = 8, 2 Hz, 1 H), 7.99 (d, J = 2 Hz, 1 H) | 568 |
| 229 | No general method; described in example section | 1H NMR (400 MHz, DMSO-d6) δ ppm 1.01 (td, J = 7, 4 Hz, 3 H), 1.58 (dquin, J = 25, 7 Hz, 2 H), 2.08-2.28 (m, 4 H), 2.37 (t, J = 7 Hz, 2 H), 2.58 (m, 1 H), 2.78-3.00 (m, 4 H), 3.10-3.29 (m partially hidden, 4 H), 4.24 (d, J = 9 Hz, 1 H), 4.40 (dt, J = 47, 6 Hz, 2 H), 6.82 (d, J = 7 Hz, 2 H), 6.88 (dd, J = 8, 5 Hz, 1 H), 7.04 (d, J = 8 Hz, 2 H), 7.08-7.25 (m, 2 H), 7.55 (m, 1 H), 7.75 (dd, J = 8, 2 Hz, 1 H), 7.91 (d, J = 2 Hz, 1 H), 13.06 (br s, 1 H) | 582 |
| 230 | No general method; described in example section | 1H NMR (400 MHz, DMSO-d6) δ ppm 0.96-1.06 (m, 3 H), 1.59 (dquin, J = 25, 7 Hz, 2 H), 2.09-2.29 (m, 4 H), 2.37 (t, J = 7 Hz, 2 H), 2.59 (m, 1 H), 2.77-3.01 (m, 4 H), 3.08-3.41 (m partially hidden, 4 H), 4.24 (d, J = 9 Hz, 1 H), 4.41 (dt, J = 47, 6 Hz, 2 H), 6.82 (d, J = 7 Hz, 2 H), 6.88 (dd, J = 8, 5 Hz, 1 H), 7.04 (d, J = 8 Hz, 2 H), 7.07-7.26 (m, 2 H), 7.55 (dd, J = 6, 2 Hz, 1 H), 7.75 (dd, J = 8, 2 Hz, 1 H), 7.91 (d, J = 2 Hz, 1 H), 12.82 (br s, 1 H) | 582 |
| 231 | E | 1H NMR (400 MHz, DMSO-d6) δ ppm 0.81 (t, J = 7 Hz, 6 H), 1.21-1.45 (m, 4 H), 1.57 (dt, J = 12, 6 Hz, 1 H), 1.74-1.97 (m, 2 H), 2.05 (t, J = 7 Hz, 2 H), 2.22-2.36 (m, 4 H), 2.84-3.06 (m, 7 H), 3.79 (m partially hidden, 4 H), 4.59 (dt, J = 47, 6 Hz, 2 H), 6.88 (d, J = 8 Hz, 1 H), 7.13 (d, J = 8 Hz, 2 H), 7.28 (d, J = 8 Hz, 2 H), 7.78 (dd, J = 8, 2 Hz, 1 H), 7.96 (d, J = 2 Hz, 1 H) | 478 |
| 232 | A | 1H NMR (400 MHz, DMSO-d6) δ ppm 1.61 (dquin, J = 25, 7 Hz, 2 H), 2.02-2.28 (m, 4 H), 2.45 (t, J = 7 Hz, 2 H), 2.57 (m, 1 H), 2.66-2.72 (m, 2 H), 2.73-2.90 (m, 3 H), 3.01 (m, 1 H), 3.23-3.31 (m, 2 H), 4.42 (dt, J = 47, 6 Hz, 2 H), 6.75 (d, J = 8 Hz, 2 H), 6.85 (d, J = 8 Hz, 1 H), 6.95 (d, J = 8 Hz, 2 H), 6.99 (d, J = 8 Hz, 1 H), 7.31 (dd, J = 11, 9 Hz, 1 H), 7.47 (td, J = 8, 6 Hz, 1 H), 7.75 (dd, J = 8, 2 Hz, 1 H), 7.91 (d, J = 2 Hz, 1 H), 12.86 (br s, 1 H) | 556 |
| 233 | D | 1H NMR (400 MHz, DMSO-d6) δ ppm 1.57-1.82 (m, 2 H), 1.98-2.26 (m, 4 H), 2.69-3.05 (m, 6 H), 3.34 (m hidden, 2 H), 3.49-3.65 (m, 2 H), 4.45 (dt, J = 47, 6 Hz, 2 H), 5.41-5.79 (m, 1 H), 6.78 (d, J = 8 Hz, 2 H), 6.86 (d, J = 8 Hz, 1 H), 7.04 (d, J = 8 Hz, 2 H), 7.19 (d, J = 8 Hz, 1 H), 7.26 (dd, J = 8, 2 Hz, 1 H), 7.58 (d, J = 2 Hz, 1 H), 7.75 (dd, J = 8, 2 Hz, 1 H), 7.92 (d, J = 2 Hz, 1 H), 11.39 (br s, 1 H) | 554 |
| 234 | B | 1H NMR (500 MHz, DMSO-d6) δ ppm 1.60 (dquin, J = 25, 7 Hz, 2 H), 2.10-2.32 (m, 4 H), 2.40 (t, J = 7 Hz, 2 H), 2.57 (m, 1 H), 2.67-2.73 (m, 4 H), 2.91-3.01 (m, 2 H), 3.17-3.25 (m, 2 H), 4.42 (dt, J = 47, 6 Hz, 2 H), 6.68 (d, J = 8 Hz, 2 H), 6.85 (d, J = 8 Hz, 1 H), 6.92 (d, J = 8 Hz, 2 H), 7.76 (dd, J = 8, 2 Hz, 1 H), 7.93 (d, J = 2 Hz, 1 H), 8.05 (d, J = 2 Hz, 1 H), 8.60 (d, J = 2 Hz, 1 H) | 539 |
| 235 | No general method; described in example section | 1H NMR (500 MHz, DMSO-d6) δ ppm 1.26 (s, 3 H), 1.57 (dquin, J = 25, 7 Hz, 2 H), 2.04-2.24 (m, 4 H), 2.25-2.34 (m, 2 H), 2.60 (m, 1 H), 2.69 (t, J = 7 Hz, 1 H), 2.78 (t, J = 7 Hz, 1 H), 2.83-2.96 (m, 3 H), 3.15 (m, 1 H), 4.40 (dt, J = 47, 6 Hz, 2 H), 4.91 (m, 1 H), 6.71 (d, J = 8 Hz, 1 H), 6.77 (d, J = 8 Hz, 2 H), 7.11-7.18 (m, 3 H), 7.21 (d, J = 8 Hz, 1 H), 7.55 (s, 1 H), 7.67 (d, J = 8 Hz, 1 H), 7.84 (s, 1 H) | 568 |

TABLE 1b-continued

| Example or compound | Preparation Method | NMR | MASS: LC/MS (m/z, MH+): |
|---|---|---|---|
| 236 | No general method; described in example section | 1H NMR (500 MHz, DMSO-d6) δ ppm 1.26 (s, 3 H), 1.60 (dquin, J = 25, 6 Hz, 2 H), 2.08-2.25 (m, 4 H), 2.38-2.44 (m, 2 H), 2.68 (m, 1 H), 2.76-3.07 (m, 6 H), 4.41 (dt, J = 47, 6 Hz, 2 H), 5.03 (m, 1 H), 6.78 (d, J = 8 Hz, 2 H), 6.83 (d, J = 8 Hz, 1 H), 7.11-7.30 (m, 4 H), 7.57 (br s, 1 H), 7.74 (dd, J = 8, 2 Hz, 1 H), 7.91 (d, J = 2 Hz, 1 H) | 568 |
| 237 | A | 1H NMR (400 MHz, DMSO-d6) δ ppm 1.62 (dquin, J = 25, 7 Hz, 2 H), 2.10-2.23 (m, 4 H), 2.43-2.47 (m, 2 H), 2.79-3.07 (m, 6 H), 3.20-3.28 (m, 2 H), 4.41 (dt, J = 47, 6 Hz, 2 H), 6.78 (d, J = 8 Hz, 2 H), 6.85 (d, J = 8 Hz, 1 H), 7.02 (d, J = 8 Hz, 2 H), 7.24 (d, J = 8 Hz, 1 H), 7.53 (dd, J = 8, 2 Hz, 1 H), 7.74 (d, J = 8 Hz, 1 H), 7.80 (d, J = 2 Hz, 1 H), 7.90 (d, J = 1 Hz, 1 H), 12.91 (br s, 1 H) | 590 |
| 238 | A | 1H NMR (400 MHz, DMSO-d6) δ ppm 1.61 (dquin, J = 25, 7 Hz, 2 H), 2.10-2.23 (m, 4 H), 2.45 (t, J = 7 Hz, 2 H), 2.80-3.07 (m, 6 H), 3.21-3.28 (m, 2 H), 4.41 (dt, J = 47, 6 Hz, 2 H), 6.77 (d, J = 8 Hz, 2 H), 6.84 (d, J = 8 Hz, 1 H), 6.97 (d, J = 8 Hz, 2 H), 7.20 (d, J = 8 Hz, 1 H), 7.37-7.47 (m, 2 H), 7.72 (t, J = 9 Hz, 2 H), 7.90 (d, J = 1 Hz, 1 H), 12.85 (br s, 1 H) | 556 |
| 239 | D | 1H NMR (400 MHz, DMSO-d6) δ ppm 1.84 (dqd, J = 27, 7, 6 Hz, 2 H), 2.08-2.27 (m, 4 H), 2.82-3.02 (m, 5 H), 3.06-3.18 (m, 2 H), 3.57-3.75 (m, 2 H), 3.87-4.04 (m, 2 H), 4.49 (dt, J = 47, 6 Hz, 2 H), 6.62 (dd, J = 11, 2 Hz, 1 H), 6.66 (dd, J = 8, 2 Hz, 1 H), 6.88 (d, J = 8 Hz, 1 H), 7.06 (t, J = 8 Hz, 1 H), 7.25 (d, J = 9 Hz, 1 H), 7.30 (dd, J = 7, 2 Hz, 1 H), 7.61 (d, J = 2 Hz, 1 H), 7.77 (dd, J = 8, 2 Hz, 1 H), 7.93 (d, J = 2 Hz, 1 H), 10.80 (br s, 1 H) | 556 |
| 240 | D | 1H NMR (400 MHz, DMSO-d6) δ ppm 1.69-1.98 (m, 5 H), 2.08-2.28 (m, 4 H), 2.72-3.17 (m, 7 H), 3.52-3.73 (m, 2 H), 3.90 (br s, 2 H), 4.49 (dt, J = 47, 6 Hz, 2 H), 6.75 (d, J = 8 Hz, 1 H), 6.80 (d, J = 6 Hz, 1 H), 6.87 (s, 1 H), 6.92 (d, J = 7 Hz, 1 H), 7.08 (d, J = 8 Hz, 1 H), 7.17 (d, J = 8 Hz, 1 H), 7.59 (br s, 1 H), 7.72 (dd, J = 8, 2 Hz, 1 H), 7.92 (d, J = 2 Hz, 1 H), 10.92 (br s, 1 H) | 552 |
| 241 | A | 1H NMR (400 MHz, DMSO-d6) δ ppm 1.62 (dquin, J = 25, 6 Hz, 2 H), 2.09-2.24 (m, 4 H), 2.45 (t, J = 7 Hz, 2 H), 2.81-3.07 (m, 6 H), 3.20-3.28 (m, 2 H), 4.41 (dt, J = 47, 6 Hz, 2 H), 6.77 (d, J = 8 Hz, 2 H), 6.86 (d, J = 8 Hz, 1 H), 7.01 (d, J = 8 Hz, 2 H), 7.26 (dd, J = 9, 6 Hz, 1 H), 7.34 (td, J = 9, 3 Hz, 1 H), 7.63 (dd, J = 9, 3 Hz, 1 H), 7.75 (dd, J = 8, 2 Hz, 1 H), 7.91 (d, J = 2 Hz, 1 H), 12.94 (br s, 1 H) | 574 |
| 242 | A | 1H NMR (400 MHz, DMSO-d6) δ ppm 1.62 (dquin, J = 25, 7 Hz, 2 H), 2.08-2.26 (m, 4 H), 2.46 (t, J = 7 Hz, 2 H), 2.87-3.09 (m, 6 H), 3.21-3.29 (m, 2 H), 4.42 (dt, J = 47, 6 Hz, 2 H), 6.79 (d, J = 8 Hz, 2 H), 6.84 (d, J = 8 Hz, 1 H), 7.01 (d, J = 8 Hz, 2 H), 7.06 (m, 1 H), 7.21 (dd, J = 9, 6 Hz, 1 H), 7.40 (dd, J = 9, 3 Hz, 1 H), 7.74 (dd, J = 8, 2 Hz, 1 H), 7.91 (d, J = 2 Hz, 1 H), 12.96 (br s, 1 H) | 540 |
| 243 | No general method; described in example section | 1H NMR (500 MHz, DMSO-d6) δ ppm 1.59 (dquin, J = 25, 6 Hz, 2 H), 2.10-2.27 (m, 4 H), 2.36-2.41 (m, 2 H), 2.44 (m, 1 H), 2.58 (m, 1 H), 2.84-2.97 (m, 4 H), 3.26 (m, 1 H), 3.79 (br d, J = 9 Hz, 1 H), 4.41 (dt, J = 47, 6 Hz, 2 H), 6.79 (br d, J = 8 Hz, 3 H), 7.09 (d, J = 8 Hz, 2 H), 7.16 (dd, J = 12, 7 Hz, 1 H), 7.20-7.26 (m, 1 H), 7.56 (s, 1 H), 7.71 (dd, J = 8, 2 Hz, 1 H), 7.88 (d, J = 2 Hz, 1 H) | 553 |
| 244 | No general method; described in example section | 1H NMR (500 MHz, DMSO-d6) δ ppm 1.59 (dquin, J = 25, 7 Hz, 2 H), 2.06-2.25 (m, 4 H), 2.36-2.40 (m, 2 H), 2.43 (m, 1 H), 2.58 (m, 1 H), 2.83-2.97 (m, 4 H), 3.25 (m, 1 H), 3.80 (d, J = 9 Hz, 1 H), 4.41 (dt, J = 47, 6 Hz, 2 H), 6.75-6.84 (m, 3 H), 7.09 (d, J = 8 Hz, 2 H), 7.16 (dd, J = 11, 8 Hz, 1 H), 7.21-7.25 (m, 1 H), 7.56 (s, 1 H), 7.72 (dd, J = 8, 2 Hz, 1 H), 7.89 (d, J = 2 Hz, 1 H) | 553 |
| 245 | A | 1H NMR (400 MHz, DMSO-d6) δ ppm 1.57 (t, J = 6 Hz, 1H), 1.63 (br t, J = 6 Hz, 1H), 2.18 (br d, J = 3 Hz, 4H), 2.67-2.71 (m, 5H), 3.22 (br d, J = 3 Hz, 2H), 4.35-4.38 (m, 1H), 3.41-3.50 (m, 4H), 4.48 (t, J = 6 Hz, 1H), 6.78 (d, J = 8 Hz, 2H), 6.89 (s, 1H), 6.95 (d, J = 8 Hz, 2H), 7.21-7.18 (m, 1H), 7.25 (br d, J = 2 Hz, 1H), 7.58 (d, J = 2 Hz, 1H), 7.88 (s, 1H) | 563 |
| 246 | A | 1H NMR (400 MHz, DMSO-d6) δ ppm 1.89-2.08 (m, 2H), 2.15-2.41 (m, 4H), 2.88 (d, J = 8 Hz, 2H), 3.04-3.22 (m, 2H), 3.28 (br s, 1H), 3.35 (s, 2H), 3.87 (br t, | 563 |

TABLE 1b-continued

| Example or compound | Preparation Method | NMR | MASS: LC/MS (m/z, MH+): |
|---|---|---|---|
| | | J = 9 Hz, 2H), 4.13 (br t, J = 9 Hz, 2H), 4.43-4.64 (m, 2H), 6.85 (d, J = 8 Hz, 2H), 6.97 (d, J = 8 Hz, 2H), 7.02 (d, J = 8 Hz, 1H), 7.09-7.18 (m, 2H), 7.41 (s, 1H), 7.69 (d, J = 8 Hz, 1H) | |
| 247 | A | 1H NMR (400 MHz, DMSO-d6) δ ppm 1.87-2.06 (m, 2H), 2.16-2.36 (m, 4H), 2.99-2.80 (m, 2H), 3.02-3.19 (m, 2H), 3.24-3.29 (m, 1H), 3.33-3.47 (m, 2H), 3.83 (br t, J = 9 Hz, 1H), 3.91-4.13 (m, 2H), 4.19 (br s, 1H), 4.43-4.64 (m, 2H), 6.80 (d, J = 8 Hz, 1H), 6.89 (d, J = 8 Hz, 2H), 7.00 (br d, J = 8 Hz, 2H), 7.09-7.18 (m, 2H), 7.42 (d, J = 2 Hz, 1H), 7.51 (d, J = 8 Hz, 1H) | 572 |
| 248 | A | 1H NMR (400 MHz, DMSO-d6) δ ppm 1.79-1.86 (m, 1H), 1.87-1.94 (m, 1H), 2.18 (br dd, J = 8, 13 Hz, 4H), 2.84-2.96 (m, 5H), 3.17 (br t, J = 8 Hz, 2H), 3.74 (br t, J = 8 Hz, 2H), 4.00 (br s, 2H), 4.44 (t, J = 6 Hz, 1H), 4.56 (t, J = 6 Hz, 1H), 6.77 (s, 1H), 6.82 (d, J = 8 Hz, 2H), 7.00 (d, J = 8 Hz, 2H), 7.18-7.22 (m, 1H), 7.30-7.26 (m, 1H), 7.80 (s, 1H), 7.60 (s, 1H) | 572 |
| 249 | A | 1H NMR (400 MHz, DMSO-d6) δ ppm 1.77-1.94 (m, 2H), 2.13 (br d, J = 4 Hz, 2H), 2.17 (br d, J = 6 Hz, 2H), 2.81 (br s, 1H), 2.37 (s, 3H), 2.88 (br d, J = 6 Hz, 2H), 2.92 (br d, J = 5 Hz, 2H), 3.13-3.24 (m, 2H), 3.68-3.89 (m, 2H), 3.93-4.13 (m, 2H), 4.41-4.47 (m, 1H), 4.56 (br t, J = 5 Hz, 1H), 6.64 (s, 1H), 6.79 (d, J = 8 Hz, 2H), 6.97 (br d, J = 8 Hz, 2H), 7.16 (d, J = 8 Hz, 1H), 7.22-7.30 (m, 1H), 7.59 (d, J = 2 Hz, 1H), 7.80 (s, 1H), 12.69-12.88 (m, 1H) | 552 |
| 250 | A | 1H NMR (500 MHz, DMSO-d6) δ ppm 1.78-1.96 (m, 2H), 2.06-2.20 (m, 4H), 2.57 (s, 3H), 2.80 (br d, J = 8 Hz, 1H), 2.83-2.98 (m, 3H), 3.01-3.08 (m, 1H), 3.15-3.25 (m, 2H), 3.70-3.82 (m, 2H), 3.93-4.09 (m, 2H), 4.41-4.50 (m, 1H), 4.53-4.62 (m, 1H), 6.63 (d, J = 8 Hz, 1H), 6.80 (dd, J = 2, 8 Hz, 2H), 6.94-7.01 (m, 2H), 7.17 (d, J = 8 Hz, 1H), 7.27 (dd, J = 8, 2 Hz, 1H), 7.48 (d, J = 8 Hz, 1H), 7.60 (d, J = 2 Hz, 1H), 10.83 (br dd, J = 5, 3 Hz, 1H), 12.42-13.18 (m, 1H), | 552 |
| 251 | A | 1H NMR (500 MHz, DMSO-d6) δ ppm 1.59 (dquin, J = 25, 7 Hz, 2 H), 2.08-2.19 (m, 2 H), 2.29 (t, J = 8 Hz, 2 H), 2.38 (t, J = 7 Hz, 2 H), 2.55 (m, 1 H), 2.66-2.73 (m, 4 H), 2.83 (t, J = 7 Hz, 2 H), 3.20 (t, J = 7 Hz, 2 H), 4.41 (dt, J = 47, 6 Hz, 2 H), 6.86 (t, J = 56 Hz, 1 H), 6.77 (d, J = 8 Hz, 2 H), 6.80 (d, J = 8 Hz, 1 H), 6.95 (d, J = 8 Hz, 2 H), 7.09-7.22 (m, 3 H), 7.72 (br d, J = 8 Hz, 1 H), 7.89 (br s, 1 H) | 538 |
| 252 | No general method; described in example section | 1H NMR (400 MHz, DMSO-d6) δ ppm 1.65 (dquin, J = 25, 7 Hz, 2 H), 2.11-2.29 (m, 4 H), 2.56 (m hidden, 1 H), 2.73 (d, J = 8 Hz, 2 H), 2.93 (m, 4 H), 3.41-3.46 (m hidden, 4 H), 4.43 (dt, J = 47, 5 Hz, 2 H), 6.82 (d, J = 8 Hz, 1 H), 6.83 (d, J = 8 Hz, 1 H), 7.10 (dd, J = 8, 2 Hz, 1 H), 7.15 (td, J = 7, 2 Hz, 1 H), 7.22 (td, J = 8, 2 Hz, 1 H), 7.30 (dd, J = 8, 2 Hz, 1 H), 7.42 (dd, J = 8, 1 Hz, 1 H), 7.73 (dd, J = 8, 2 Hz, 1 H), 7.91 (d, J = 2 Hz, 1 H), 8.18 (d, J = 2 Hz, 1 H) | 505 |
| 253 | No general method; described in example section | 1H NMR (400 MHz, DMSO-d6) δ ppm 1.61 (dquin, J = 25, 7 Hz, 2 H), 2.13-2.29 (m, 4 H), 2.61 (m, 1 H), 2.69-2.81 (m, 4 H), 2.87-2.97 (m, 2 H), 3.22-3.26 (m hidden, 4 H), 4.42 (dt, J = 47, 6 Hz, 2 H), 6.82 (dd, J = 8, 1 Hz, 1 H), 6.85 (d, J = 8 Hz, 1 H), 7.13 (d, J = 8 Hz, 1 H), 7.24 (dd, J = 8, 2 Hz, 1 H), 7.36 (dd, J = 8, 2 Hz, 1 H), 7.57 (d, J = 2 Hz, 1 H), 7.74 (dd, J = 8, 2 Hz, 1 H), 7.91 (d, J = 2 Hz, 1 H), 8.18 (d, J = 2 Hz, 1 H), 12.62 (br s, 1 H) | 539 |
| 254 | A | 1H NMR (400 MHz, DMSO-d6) δ ppm 1.59 (dquin, J = 25, 6 Hz, 2 H), 2.01-2.22 (m, 4 H), 2.36 (t, J = 7 Hz, 2 H), 2.54-2.87 (m partially hidden, 7 H), 3.15-3.22 (m, 2 H), 4.41 (dt, J = 47, 6 Hz, 2 H), 6.49-6.60 (m, 2 H), 6.72 (d, J = 2 Hz, 1 H), 6.74 (d, J = 8 Hz, 2 H), 6.89 (d, J = 8 Hz, 2 H), 7.11 (m, 1 H), 7.20 (m, 1 H), 7.53 (d, J = 2 Hz, 1 H), 9.39 (s, 1 H) | 510 |
| 255 | A | 1H NMR (500 MHz, DMSO-d6) δ ppm 1.58 (dquin, J = 25, 6 Hz, 2 H), 2.07 (dq, J = 14, 7 Hz, 2 H), 2.19 (t, J = 7 Hz, 2 H), 2.35 (t, J = 7 Hz, 2 H), 2.50 (m hidden, 1 H), 2.61-2.68 (m, 4 H), 2.70-2.88 (m, 2 H), 3.18 (t, J = 7 Hz, 2 H), 4.41 (dt, J = 47, 6 Hz, 2 H), 6.51-6.59 (m, | 476 |

TABLE 1b-continued

| Example or compound | Preparation Method | NMR | MASS: LC/MS (m/z, MH+): |
|---|---|---|---|
| | | 2 H), 6.72 (d, J = 2 Hz, 1 H), 6.74 (d, J = 8 Hz, 2 H), 6.85 (d, J = 8 Hz, 2 H), 7.06-7.19 (m, 3 H), 7.37 (dd, J = 8, 1 Hz, 1 H), 9.40 (s, 1 H) | |
| 256 | A | 1H NMR (400 MHz, DMSO-d6) δ ppm 2.12-2.27 (m, 6 H), 2.29 (d, J = 2 Hz, 3 H), 2.45-2.49 (m hidden, 3 H), 2.62-2.75 (m, 4 H), 2.89 (m, 1 H), 2.97(m, 1 H), 3.20 (t, J = 7 Hz, 2 H), 6.67 (d, J = 8 Hz, 2 H), 6.85-6.91 (m, 3 H), 7.24 (t, J = 7 Hz, 1 H), 7.34 (d, J = 7 Hz, 1 H), 7.51 (d, J = 7 Hz, 1 H), 7.75 (dd, J = 8, 2 Hz, 1 H), 7.92 (d, J = 2 Hz, 1 H) | 588 |
| 257 | A | 1H NMR (400 MHz, DMSO-d6) δ ppm 2.10-2.30 (m, 6 H), 2.44-2.50 (m hidden, 3 H), 2.64-2.74 (m, 4 H), 2.87-3.06 (m, 2 H), 3.17-3.23 (m, 2 H), 6.75 (d, J = 7 Hz, 2 H), 6.88 (d, J = 8 Hz, 1 H), 6.91 (d, J = 8 Hz, 2 H), 7.37 (t, J = 8 Hz, 1 H), 7.49 (dd, J = 8, 2 Hz, 1 H), 7.68 (dd, J = 8, 2 Hz, 1 H), 7.76 (dd, J = 8, 2 Hz, 1 H), 7.93 (d, J = 2 Hz, 1 H) | 608 |
| 258 | A | 1H NMR (400 MHz, DMSO-d6) δ ppm 2.10-2.30 (m, 6 H), 2.52-2.57 (m hidden, 3 H), 2.63-2.73 (m, 4 H), 2.85 (s, 1 H), 2.98 (m, 1 H), 3.18-3.24 (m, 2 H), 6.73 (d, J = 8 Hz, 2 H), 6.86 (d, J = 8 Hz, 1 H), 6.91 (d, J = 8 Hz, 2 H), 7.26 (m, 1 H), 7.33 (td, J = 8, 2 Hz, 1 H), 7.62 (dd, J = 9, 3 Hz, 1 H), 7.75 (dd, J = 8, 2 Hz, 1 H), 7.91 (d, J = 2 Hz, 1 H) | 592 |
| 259 | A | 1H NMR (400 MHz, DMSO-d6) δ ppm 1.97-2.29 (m, 6 H), 2.41-2.48 (m hidden, 3 H), 2.64-2.77 (m, 4 H), 2.85 (m, 1 H), 2.99 (m, 1 H), 3.15-3.25 (m, 2 H), 6.76 (d, J = 8 Hz, 2 H), 6.85 (d, J = 8 Hz, 1 H), 6.95 (d, J = 8 Hz, 2 H), 7.12 (d, J = 8 Hz, 1 H), 7.40 (t, J = 8 Hz, 1 H), 7.53 (d, J = 8 Hz, 1 H), 7.75 (dd, J = 8, 2 Hz, 1 H), 7.91 (d, J = 2 Hz, 1 H) | 608 |
| 260 | A | 1H NMR (400 MHz, DMSO-d6) δ ppm 2.09-2.28 (m, 9 H), 2.21 (s, 2 H), 2.52-2.57 (m hidden, 3 H), 2.63-2.75 (m, 4 H), 2.81-3.00 (m, 2 H), 3.18-3.25 (m, 2 H), 6.69 (d, J = 8 Hz, 1 H), 6.86 (d, J = 8 Hz, 1 H), 6.90 (d, J = 8 Hz, 1 H), 7.00 (dd, J = 8, 3 Hz, 1 H), 7.05 (t, J = 7 Hz, 1 H), 7.24 (dd, J = 8, 1 Hz, 1 H), 7.75 (dd, J = 8, 2 Hz, 1 H), 7.91 (d, J = 2 Hz, 1 H) | 554 |
| 261 | A | 1H NMR (400 MHz, DMSO-d6) δ ppm 2.12-2.29 (m, 6 H), 2.51-2.59 (m hidden, 3 H), 2.66-2.75 (m, 4 H), 2.85-3.02 (m, 2 H), 3.19-3.26 (m, 2 H), 6.76 (d, J = 7 Hz, 2 H), 6.85 (d, J = 8 Hz, 1 H), 6.93 (d, J = 8 Hz, 2 H), 7.18 (d, J = 9 Hz, 1 H), 7.25 (dd, J = 7, 2 Hz, 1 H), 7.57 (d, J = 2 Hz, 1 H), 7.74 (dd, J = 8, 2 Hz, 1 H), 7.91 (d, J = 2 Hz, 1 H) | 574 |
| 262 | G | 1H NMR (400 MHz, DMSO-d6) δ ppm 1.60 (dquin, J = 25, 6, 6, 6, 6 Hz, 2 H), 2.37 (t, J = 7 Hz, 2 H), 2.43 (m, 1 H), 2.52-2.69 (m, 4 H), 2.71 (d, J = 8 Hz, 2 H), 2.88-3.05 (m, 2 H), 3.21 (t, J = 7 Hz, 2 H), 4.42 (dt, J = 47, 6 Hz, 2 H), 6.55 (d, J = 8 Hz, 1 H), 6.91-6.96 (m, 2 H), 6.98-7.04 (m, 2 H), 7.07 (d, J = 8 Hz, 1 H), 7.16 (dd, J = 8, 2 Hz, 1 H), 7.50 (d, J = 2 Hz, 1 H), 7.55 (d, J = 8 Hz, 1 H), 7.73 (s, 1 H) | 524 |
| 263 | A | 1H NMR (400 MHz, DMSO-d6) δ ppm 1.61 (dquin, J = 25, 6 Hz, 2 H), 2.12 (s, 3 H), 2.42 (t, J = 7 Hz, 2 H), 2.54-2.60 (m hidden, 3 H), 2.68-2.78 (m, 4 H), 3.23-3.28 (m, 2 H), 4.43 (dt, J = 47, 6 Hz, 2 H), 4.53-4.59 (m, 2 H), 6.74 (d, J = 8 Hz, 2 H), 6.83 (d, J = 9 Hz, 1 H), 6.93 (d, J = 8 Hz, 2 H), 7.07 (d, J = 8 Hz, 1 H), 7.13 (dd, J = 9, 2 Hz, 1 H), 7.19 (d, J = 2 Hz, 1 H), 7.54-7.73 (m, 2 H) | 520 |
| 264 | A | 1H NMR (400 MHz, DMSO-d6) δ ppm 1.41-1.90 (m, 2 H), 2.23-3.58 (m hidden, 11 H), 4.28-4.68 (m, 4 H), 6.66-7.17 (m, 7 H), 7.43 (br d, J = 7 Hz, 1 H), 7.48-7.77 (m, 2 H) | 524 |
| 265 | A | 1H NMR (500 MHz, DMSO-d6) δ ppm 1.59 (dquin, J = 25, 6 Hz, 2 H), 2.01-2.10 (m, 2 H), 2.20 (t, J = 7 Hz, 2 H), 2.23 (s, 3 H), 2.34-2.39 (m, 2 H), 2.54 (m, 1 H), 2.64-2.70 (m, 4 H), 2.78 (t, J = 7 Hz, 2 H), 3.20 (t, J = 7 Hz, 2 H), 4.41 (dt, J = 47, 6 Hz, 2 H), 6.29 (dd, J = 11, 1 Hz, 1 H), 6.76 (d, J = 8 Hz, 2 H), 6.82 (dt, J = 7, 1 Hz, 1 H), 6.87 (d, J = 11 Hz, 1 H), 6.90 (d, J = 8 Hz, 2 H), 6.99 (t, J = 8 Hz, 1 H), 10.18 (br s, 1 H) | 510 |
| 266 | A | 1H NMR (400 MHz, DMSO-d6) δ ppm 1.60 (dquin, J = 25, 7 Hz, 2 H), 2.14 (quin, J = 7 Hz, 2 H), 2.26 (t, J = 8 Hz, 2 H), 2.39 (t, J = 7 Hz, 2 H), 2.57 (m, 1 H), 2.68-2.76 (m, 4 H), 2.85 (t, J = 7 Hz, 2 H), 3.18-3.24 (m, 2 | 506 |

TABLE 1b-continued

| Example or compound | Preparation Method | NMR | MASS: LC/MS (m/z, MH+): |
|---|---|---|---|
| | | H), 4.42 (dt, J = 47, 6 Hz, 2 H), 6.74-6.88 (m, 5 H), 6.94-7.04 (m, 3 H), 7.73 (dd, J = 8, 2 Hz, 1 H), 7.89 (d, J = 2 Hz, 1 H) | |
| 267 | A | 1H NMR (400 MHz, DMSO-d6) δ ppm 1.50-1.68 (m, 2 H), 2.06-2.19 (m, 2 H), 2.20-2.29 (m, 2 H), 2.38 (t, J = 7 Hz, 2 H), 2.57 (m, 1 H), 2.66-2.76 (m, 4 H), 2.83 (t, J = 7 Hz, 2 H), 3.21 (t, J = 7 Hz, 2 H), 4.42 (dt, J = 47, 6 Hz, 2 H), 6.74-6.83 (m, 3 H), 6.99 (d, J = 8 Hz, 2 H), 7.06 (dd, J = 9, 7 Hz, 2 H), 7.72 (d, J = 8 Hz, 1 H), 7.88 (s, 1 H), 9.66 (br s, 1 H) | 524 |
| 268 | A | 1H NMR (400 MHz, DMSO-d6) δ ppm 1.59 (dquin, J = 25, 7 Hz, 2 H), 2.05-2.27 (m, 4 H), 2.37 (t, J = 7 Hz, 2 H), 2.56 (m hidden, 1 H), 2.63-2.73 (m, 4 H), 2.88 (t, J = 6 Hz, 2 H), 3.19 (t, J = 7 Hz, 2 H), 3.82 (s, 3 H), 4.41 (dt, J = 47, 6 Hz, 2 H), 6.74 (d, J = 8 Hz, 2 H), 6.81 (d, J = 8 Hz, 1 H), 6.93 (d, J = 8 Hz, 2 H), 7.29 (d, J = 8 Hz, 1 H), 7.58 (d, J = 7 Hz, 1 H), 7.74 (br d, J = 8 Hz, 1 H), 7.90 (s, 1 H) | 569 |
| 269 | A | 1H NMR (500 MHz, DMSO-d6) δ ppm 1.61 (dquin, J = 25, 7 Hz, 2 H), 2.16 (m, 7 H), 2.42 (t, J = 7 Hz, 2 H), 2.55 (m, 1 H), 2.68 (d, J = 8 Hz, 2 H), 2.74 (t, J = 7 Hz, 2 H), 2.85-2.99 (m, 2 H), 3.25 (br t, J = 7 Hz, 2 H), 3.83 (s, 3 H), 4.41 (dt, J = 47, 6 Hz, 2 H), 6.56 (d, J = 8 Hz, 1 H), 6.69 (d, J = 8 Hz, 2 H), 6.85 (td, J = 8, 4 Hz, 1 H), 6.88 (d, J = 8 Hz, 2 H), 6.96 (dd, J = 10, 3 Hz, 1 H), 7.03 (dd, J = 9, 6 Hz, 1 H), 7.45 (d, J = 8 Hz, 1 H) | 532 |
| 270 | A | 1H NMR (500 MHz, DMSO-d6) δ ppm 1.62 (dquin, J = 26, 8 Hz, 2 H), 2.09-2.25 (m, 4 H), 2.43 (t, J = 7 Hz, 2 H), 2.56 (m, 1 H), 2.70 (d, J = 8 Hz, 2 H), 2.75 (t, J = 7 Hz, 2 H), 2.89 (t, J = 7 Hz, 2 H), 3.26 (t, J = 7 Hz, 2 H), 3.83 (s, 3 H), 4.42 (dt, J = 47, 6 Hz, 2 H), 6.55 (d, J = 8 Hz, 1 H), 6.75 (d, J = 8 Hz, 2 H), 6.92 (d, J = 8 Hz, 2 H), 6.93-6.97 (m, 1 H), 7.09 (td, J = 10, 3 Hz, 1 H), 7.22 (td, J = 9, 7 Hz, 1 H), 7.45 (d, J = 8 Hz, 1 H) | 536 |
| 271 | A | 1H NMR (500 MHz, DMSO-d6) δ ppm 1.61 (dquin, J = 26, 7 Hz, 2 H), 2.10-2.27 (m, 4 H), 2.42 (t, J = 7 Hz, 2 H), 2.57 (m, 1 H), 2.69 (d, J = 8 Hz, 2 H), 2.72-2.77 (m, 2 H), 2.78-2.86 (m, 1 H), 3.06-3.12 (m, 1 H), 3.22-3.28 (m, 2 H), 3.84 (s, 3 H), 4.42 (dt, J = 47, 6 Hz, 2 H), 6.55 (d, J = 8 Hz, 1 H), 6.76 (d, J = 8 Hz, 2 H), 6.92 (d, J = 8 Hz, 2 H), 7.16 (d, J = 8 Hz, 1 H), 7.24 (dd, J = 8, 2 Hz, 1 H), 7.45 (d, J = 8 Hz, 1 H), 7.57 (d, J = 2 Hz, 1 H) | 568 |
| 272 | B | 1H NMR (400 MHz, DMSO-d6) δ ppm 1.65-1.84 (m, 2 H), 2.07-2.26 (m, 4 H), 2.54-2.60 (m hidden, 3 H), 2.69-2.89 (m, 7 H), 2.90-3.00 (m, 1 H), 3.60-3.74 (m, 2 H), 4.46 (dt, J = 47, 6 Hz, 2 H), 6.70 (d, J = 8 Hz, 2 H), 6.85 (d, J = 8 Hz, 1 H), 6.92 (d, J = 8 Hz, 2 H), 7.03-7.17 (m, 2 H), 7.25 (br dd, J = 9, 6 Hz, 1 H), 7.74 (dd, J = 8, 2 Hz, 1 H), 7.92 (d, J = 2 Hz, 1 H) | 570 |
| 273 | A | 1H NMR (400 MHz, DMSO-d6) δ ppm 1.58 (dquin, J = 25, 7 Hz, 2 H), 2.04-2.27 (m, 4 H), 2.36 (t, J = 7 Hz, 2 H), 2.55 (m hidden, 1 H), 2.61-2.70 (m, 4 H), 2.83 (t, J = 7 Hz, 2 H), 3.17 (t, J = 7 Hz, 2 H), 4.41 (dt, J = 47, 6 Hz, 2 H), 6.65-6.80 (m, 3 H), 6.81-6.98 (m, 2 H), 7.21 (t, J = 9 Hz, 1 H), 7.35 (br d, J = 7 Hz, 1 H), 7.40-7.49 (m, 1 H), 7.67-7.82 (m, 1 H), 7.89 (br s, 1 H) | 538 |
| 274 | A | 1H NMR (400 MHz, DMSO-d6) δ ppm 1.47-1.74 (m, 2 H), 2.04-2.18 (m, 2 H), 2.23-2.31 (m, 2 H), 2.38 (t, J = 7 Hz, 2 H), 2.55 (m hidden, 1 H), 2.66-2.85 (m, 6 H), 3.18 (t, J = 7 Hz, 2 H), 3.83 (s, 3 H), 4.42 (dt, J = 47, 6 Hz, 2 H), 6.75 (br d, J = 8 Hz, 1 H), 6.81 (d, J = 8 Hz, 2 H), 6.91-7.08 (m, 4 H), 7.59-7.79 (m, 1 H), 7.81-8.04 (m, 1 H) | 569 |
| 275 | A | 1H NMR (400 MHz, DMSO-d6) δ ppm 1.65-1.89 (m, 2 H), 2.10 (d, J = 2 Hz, 3 H), 2.12-2.24 (m, 4 H), 2.42 (t, J = 7 Hz, 2 H), 2.57 (m hidden, 1 H), 2.67-2.72 (m, 4 H), 2.82-2.98 (m, 2 H), 3.23 (t, J = 6 Hz, 2 H), 6.03 (tt, J = 57, 5 Hz, 1 H), 6.70 (d, J = 8 Hz, 2 H), 6.85 (d, J = 8 Hz, 1 H), 6.86-6.90 (m, 1 H), 6.92 (d, J = 8 Hz, 2 H), 7.10 (q, J = 8 Hz, 1 H), 7.74 (dd, J = 8, 2 Hz, 1 H), 7.91 (d, J = 2 Hz, 1 H) | 538 |
| 276 | A | 1H NMR (400 MHz, DMSO-d6) δ ppm 1.61-1.89 (m, 2 H), 2.06-2.25 (m, 4 H), 2.43 (t, J = 7 Hz, 2 H), 2.55 (m hidden, 1 H), 2.64-2.75 (m, 4 H), 2.79-2.91 (m, 1 H), 2.93-3.05 (m, 1 H), 3.23 (q, J = 1 Hz, 2 H), 6.03 (tt, J = 57, 5 Hz, 1 H), 6.73 (d, J = 8 Hz, 2 H), 6.85 (d, J = 8 | 574 |

TABLE 1b-continued

| Example or compound | Preparation Method | NMR | MASS: LC/MS (m/z, MH+): |
|---|---|---|---|
| | | Hz, 1 H), 6.92 (d, J = 8 Hz, 2 H), 7.25 (dd, J = 9, 6 Hz, 1 H), 7.33 (td, J = 8, 3 Hz, 1 H), 7.62 (dd, J = 9, 3 Hz, 1 H), 7.74 (dd, J = 8, 2 Hz, 1 H), 7.91 (d, J = 2 Hz, 1 H) | |
| 277 | A | 1H NMR (400 MHz, DMSO-d6) δ ppm 1.66-1.86 (m, 2 H), 2.03-2.27 (m, 4 H), 2.33 (s, 3 H), 2.42 (t, J = 7 Hz, 2 H), 2.55 (m, 1 H), 2.63-2.75 (m, 4 H), 2.87-2.98 (m, 2 H), 3.18-3.25 (m, 2 H), 6.02 (tt, J = 57, 5 Hz, 1 H), 6.76 (d, J = 8 Hz, 2 H), 6.84 (d, J = 8 Hz, 1 H), 6.89 (d, J = 8 Hz, 2 H), 6.94 (dd, J = 8, 2 Hz, 1 H), 7.02 (t, J = 8 Hz, 1 H), 7.16 (d, J = 7 Hz, 1 H), 7.74 (dd, J = 8, 2 Hz, 1 H), 7.90 (d, J = 2 Hz, 1 H) | 536 |
| 278 | A | 1H NMR (400 MHz, DMSO-d6) δ ppm 1.64-1.88 (m, 2 H), 2.01-2.27 (m, 4 H), 2.42 (t, J = 7 Hz, 2 H), 2.58 (m hidden, 1 H), 2.64-2.76 (m, 4 H), 2.79-2.91 (m, 1 H), 2.94-3.06 (m, 1 H), 3.22 (m, 2 H), 6.03 (tt, J = 57, 5 Hz, 1 H), 6.76 (d, J = 8 Hz, 2 H), 6.85 (d, J = 8 Hz, 1 H), 6.95 (d, J = 8 Hz, 2 H), 6.99 (d, J = 8 Hz, 1 H), 7.31 (dd, J = 11, 8 Hz, 1 H), 7.47 (td, J = 8, 6 Hz, 1 H), 7.75 (dd, J = 8, 2 Hz, 1 H), 7.91 (d, J = 2 Hz, 1 H) | 574 |
| 279 | A | 1H NMR (400 MHz, DMSO-d6) δ ppm 1.64-1.86 (m, 2 H), 2.10-2.19 (m, 7 H), 2.42 (t, J = 7 Hz, 2 H), 2.56 (m, 1 H), 2.63-2.74 (m, 4 H), 2.80-2.99 (m, 2 H), 3.22 (t, J = 9 Hz, 2 H), 6.03 (tt, J = 57, 5 Hz, 1 H), 6.69 (d, J = 8 Hz, 2 H), 6.80-6.92 (m, 4 H), 6.96 (dd, J = 10, 3 Hz, 1 H), 7.05 (dd, J = 9, 6 Hz, 1 H), 7.73 (dd, J = 8, 2 Hz, 1 H), 7.90 (d, J = 2 Hz, 1 H) | 520 |
| 280 | A | 1H NMR (400 MHz, DMSO-d6) δ ppm 1.66-1.87 (m, 2 H), 2.03-2.28 (m, 4 H), 2.41 (t, J = 7 Hz, 2 H), 2.56 (m hidden, 1 H), 2.64-2.75 (m, 4 H), 2.78-2.88 (m, 1 H), 2.94-3.07 (m, 1 H), 3.18-3.24 (m, 2 H), 6.02 (tt, J = 57, 5 Hz, 1 H), 6.75 (d, J = 8 Hz, 2 H), 6.84 (d, J = 8 Hz, 1 H), 6.95 (d, J = 8 Hz, 2 H), 7.12 (d, J = 8 Hz, 1 H), 7.40 (t, J = 8 Hz, 1 H), 7.53 (d, J = 8 Hz, 1 H), 7.74 (dd, J = 8, 2 Hz, 1 H), 7.90 (d, J = 2 Hz, 1 H) | 590 |
| 281 | A | 1H NMR (400 MHz, DMSO-d6) δ ppm 1.67-1.86 (m, 2 H), 2.06-2.23 (m, 4 H), 2.42 (t, J = 7 Hz, 2 H), 2.56 (m, 1 H), 2.67-2.76 (m, 4 H), 2.87 (t, J = 6 Hz, 2 H), 3.20-3.26 (m, 2 H), 6.03 (tt, J = 57, 5 Hz, 1 H), 6.75 (d, J = 8 Hz, 2 H), 6.84 (d, J = 8 Hz, 1 H), 6.91-6.98 (m, 3 H), 7.10 (td, J = 10, 3 Hz, 1 H), 7.22 (td, J = 9, 7 Hz, 1 H), 7.74 (dd, J = 8, 2 Hz, 1 H), 7.90 (d, J = 2 Hz, 1 H) | 524 |
| 282 | A | 1H NMR (400 MHz, DMSO-d6) δ ppm 1.66-1.86 (m, 2 H), 2.05-2.22 (m, 7 H), 2.42 (t, J = 7 Hz, 2 H), 2.56 (m, 1 H), 2.66-2.75 (m, 4 H), 2.82-2.99 (m, 2 H), 3.23 (t, J = 8 Hz, 2 H), 6.03 (tt, J = 57, 5 Hz, 1 H), 6.70 (d, J = 8 Hz, 2 H), 6.84 (d, J = 8 Hz, 1 H), 6.90 (d, J = 8 Hz, 2 H), 7.04 (d, J = 9 Hz, 1 H), 7.09 (dd, J = 9, 3 Hz, 1 H), 7.20 (d, J = 2 Hz, 1 H), 7.74 (dd, J = 8, 2 Hz, 1 H), 7.90 (d, J = 2 Hz, 1 H) | 536 |
| 283 | B | 1H NMR (400 MHz, DMSO-d6) δ ppm 1.69-1.89 (m, 2 H), 2.05-2.27 (m, 4 H), 2.70-2.93 (m, 4 H), 2.98-3.17 (m, 4 H), 3.50-3.65 (m, 2 H), 3.78-3.98 (m, 5 H), 4.48 (dt, J = 47, 6 Hz, 2 H), 6.57 (d, J = 8 Hz, 1 H), 6.77 (d, J = 8 Hz, 2 H), 6.95 (d, J = 8 Hz, 2 H), 7.23 (dd, J = 9, 6 Hz, 1 H), 7.34 (td, J = 8, 3 Hz, 1 H), 7.49 (d, J = 8 Hz, 1 H), 7.64 (dd, J = 9, 3 Hz, 1 H) | 586 |
| 284 | B | 1H NMR (400 MHz, DMSO-d6) δ ppm 1.71-1.95 (m, 2 H), 2.12-2.31 (m, 4 H), 2.76-3.04 (m, 5 H), 3.08-3.19 (m, 2 H), 3.60-3.76 (m, 2 H), 3.95 (t, J = 8 Hz, 2 H), 4.49 (dt, J = 47, 6 Hz, 2 H), 6.94 (t, J = 55 Hz, 1 H), 6.82 (d, J = 8 Hz, 2 H), 6.85 (d, J = 8 Hz, 1 H), 6.97 (d, J = 8 Hz, 2 H), 7.10 (dd, J = 10, 3 Hz, 1 H), 7.21 (td, J = 9, 3 Hz, 1 H), 7.58 (dd, J = 9, 6 Hz, 1 H), 7.75 (dd, J = 8, 2 Hz, 1 H), 7.92 (d, J = 2 Hz, 1 H) | 538 |
| 285 | A | 1H NMR (400 MHz, DMSO-d6) δ ppm 1.62-1.91 (m, 2 H), 2.00-2.23 (m, 10 H), 2.43 (t, J = 7 Hz, 2 H), 2.56 (m, 1 H), 2.61-2.75 (m, 4 H), 2.82-2.99 (m, 2 H), 3.23 (t, J = 7 Hz, 2 H), 6.03 (tt, J = 57, 5 Hz, 1 H), 6.68 (d, J = 8 Hz, 2 H), 6.76-6.86 (m, 3 H), 6.89 (d, J = 8 Hz, 2 H), 7.74 (dd, J = 8, 2 Hz, 1 H), 7.90 (d, J = 2 Hz, 1 H) | 534 |
| 286 | A | 1H NMR (400 MHz, DMSO-d6) δ ppm 1.66-1.87 (m, 2 H), 2.09-2.28 (m, 4 H), 2.42 (t, J = 7 Hz, 2 H), 2.56 (m, 1 H), 2.63-2.72 (m, 4 H), 2.92-3.05 (m, 2 H), 3.18-3.23 (m, 2 H), 6.03 (tt, J = 57, 5 Hz, 1 H), 6.76 (d, J = 8 Hz, 2 H), 6.88 (d, J = 8 Hz, 1 H), 6.92 (d, J = 8 Hz, 2 H), 7.38 (t, J = 8 Hz, 1 H), 7.49 (dd, J = 8, 2 Hz, 1 H), | 590 |

TABLE 1b-continued

| Example or compound | Preparation Method | NMR | MASS: LC/MS (m/z, MH+): |
|---|---|---|---|
| | | 7.69 (dd, J = 8, 2 Hz, 1 H), 7.76 (dd, J = 8, 2 Hz, 1 H), 7.93 (d, J = 2 Hz, 1 H) | |
| 287 | A | 1H NMR (400 MHz, DMSO-d6) δ ppm 1.65-1.86 (m, 2 H), 2.08-2.26 (m, 4 H), 2.29 (d, J = 2 Hz, 3 H), 2.41 (t, J = 7 Hz, 2 H), 2.55 (m, 1 H), 2.63-2.72 (m, 4 H), 2.81-3.04 (m, 2 H), 3.19 (t, J = 7 Hz, 2 H), 6.02 (tt, J = 57, 5 Hz, 1 H), 6.67 (d, J = 8 Hz, 2 H), 6.84-6.94 (m, 3 H), 7.24 (t, J = 8 Hz, 1 H), 7.33 (d, J = 7 Hz, 1 H), 7.51 (d, J = 7 Hz, 1 H), 7.75 (dd, J = 8, 2 Hz, 1 H), 7.92 (d, J = 2 Hz, 1 H) | 570 |
| 288 | A | 1H NMR (400 MHz, DMSO-d6) δ ppm 1.64-1.87 (m, 2 H), 2.10-2.29 (m, 4 H), 2.42 (t, J = 7 Hz, 2 H), 2.56 (m, 1 H), 2.64-2.74 (m, 4 H), 2.89 (t, J = 7 Hz, 2 H), 3.20 (t, J = 7 Hz, 2 H), 6.03 (tt, J = 57, 5 Hz, 1 H), 6.73 (d, J = 8 Hz, 2 H), 6.87 (d, J = 8 Hz, 1 H), 6.92 (d, J = 8 Hz, 2 H), 7.28 (t, J = 8 Hz, 1 H), 7.59 (q, J = 7 Hz, 2 H), 7.75 (dd, J = 8, 2 Hz, 1 H), 7.93 (d, J = 2 Hz, 1 H) | 574 |
| 289 | A | 1H NMR (400 MHz, DMSO-d6) δ ppm 1.66-1.86 (m, 2 H), 2.09-2.25 (m, 4 H), 2.42 (t, J = 7 Hz, 2 H), 2.56 (m, 1 H), 2.63-2.74 (m, 4 H), 2.81-3.06 (m, 2 H), 3.17-3.25 (m, 2 H), 6.02 (tt, J = 57, 5 Hz, 1 H), 6.74 (d, J = 8 Hz, 2 H), 6.85 (d, J = 8 Hz, 1 H), 6.93 (d, J = 8 Hz, 2 H), 7.22 (d, J = 8 Hz, 1 H), 7.53 (dd, J = 8, 2 Hz, 1 H), 7.74 (dd, J = 8, 2 Hz, 1 H), 7.79 (d, J = 2 Hz, 1 H), 7.90 (d, J = 2 Hz, 1 H) | 590 |
| 290 | B | 1H NMR (500 MHz, DMSO-d6) δ ppm 1.53-1.68 (m, 2 H), 2.14 (quin, J = 7 Hz, 2 H), 2.26 (t, J = 7 Hz, 2 H), 2.42 (t, J = 7 Hz, 2 H), 2.55 (m, 1 H), 2.70 (d, J = 8 Hz, 2 H), 2.75 (t, J = 7 Hz, 2 H), 2.85 (t, J = 7 Hz, 2 H), 3.25 (t, J = 7 Hz, 2 H), 3.53 (q, J = 11 Hz, 2 H), 4.42 (dt, J = 47, 6 Hz, 2 H), 6.73 (d, J = 8 Hz, 2 H), 6.82 (d, J = 8 Hz, 1 H), 6.92 (d, J = 8 Hz, 2 H), 7.09 (t, J = 10 Hz, 1 H), 7.18-7.25 (m, 2 H), 7.72 (dd, J = 8, 2 Hz, 1 H), 7.89 (d, J = 2 Hz, 1 H) | 570 |
| 291 | B | 1H NMR (400 MHz, DMSO-d6) δ ppm 1.78 (ttd, J = 18, 7, 5 Hz, 2 H), 2.10-2.37 (m, 4 H), 2.43 (t, J = 7 Hz, 2 H), 2.58 (m, 1 H), 2.64-2.75 (m, 4 H), 2.91 (t, J = 7 Hz, 2 H), 3.23 (t, J = 7 Hz, 2 H), 6.03 (tt, J = 57, 5 Hz, 1 H), 6.63 (d, J = 8 Hz, 2 H), 6.84 (d, J = 8 Hz, 1 H), 6.91 (d, J = 8 Hz, 2 H), 7.75 (dd, J = 8, 2 Hz, 1 H), 7.92 (d, J = 2 Hz, 1 H), 8.30 (d, J = 2 Hz, 1 H), 8.90 (d, J = 2 Hz, 1 H) | 591 |
| 292 | A | 1H NMR (400 MHz, DMSO-d6) δ ppm 1.69-1.86 (m, 2 H), 2.10 (d, J = 3 Hz, 3 H), 2.13-2.23 (m, 4 H), 2.42 (t, J = 7 Hz, 2 H), 2.56 (m, 1 H), 2.65-2.75 (m, 4 H), 2.82-2.98 (m, 2 H), 3.23 (t, J = 7 Hz, 2 H), 6.03 (tt, J = 57, 5 Hz, 1 H), 6.71 (d, J = 8 Hz, 2 H), 6.85 (d, J = 8 Hz, 1 H), 6.89-6.96 (m, 3 H), 7.24 (t, J = 8 Hz, 1 H), 7.74 (dd, J = 8, 2 Hz, 1 H), 7.91 (d, J = 2 Hz, 1 H) | 554 |
| 293 | A | 1H NMR (400 MHz, DMSO-d6) δ ppm 1.67-1.87 (m, 2 H), 2.09-2.19 (m, 4 H), 2.21 (s, 3 H), 2.42 (t, J = 7 Hz, 2 H), 2.56 (m, 1 H), 2.64-2.76 (m, 4 H), 2.80-3.01 (m, 2 H), 3.22 (t, J = 7 Hz, 2 H), 6.02 (tt, J = 57, 5 Hz, 1 H), 6.69 (d, J = 8 Hz, 2 H), 6.86 (d, J = 8 Hz, 1 H), 6.90 (d, J = 8 Hz, 2 H), 6.99 (dd, J = 9, 3 Hz, 1 H), 7.05 (t, J = 8 Hz, 1 H), 7.24 (dd, J = 8, 1 Hz, 1 H), 7.74 (dd, J = 8, 2 Hz, 1 H), 7.91 (d, J = 2 Hz, 1 H) | 536 |
| 294 | A | 1H NMR (400 MHz, DMSO-d6) δ ppm 1.38-1.53 (m, 2 H), 1.53-1.72 (m, 3 H), 1.77 (m, 1 H), 1.86 (t, J = 7 Hz, 2 H), 1.93-2.06 (m, 2 H), 2.13 (dt, J = 14, 7 Hz, 2 H), 2.24-2.38 (m, 2 H), 2.45 (m hidden, 1 H), 2.56 (m hidden, 1 H), 2.61-2.74 (m, 4 H), 2.77-2.91 (m, 4 H), 3.30-3.33 (m hidden, 2 H), 4.43 (dt, J = 47, 6 Hz, 2 H), 6.74 (d, J = 8 Hz, 1 H), 6.97 (d, J = 8 Hz, 2 H), 7.14 (d, J = 8 Hz, 2 H), 7.65 (dd, J = 8, 2 Hz, 1 H), 7.81 (d, J = 2 Hz, 1 H) | 462 |
| 295 | B | 1H NMR (400 MHz, DMSO-d6) δ ppm 1.64-1.82 (m, 2 H), 2.06-2.27 (m, 4 H), 2.56 (m, 1 H), 2.69-2.97 (m, 6 H), 3.20-3.24 (m hidden, 2 H), 3.51 (q, J = 12 Hz, 2 H), 3.58-3.72 (m, 2 H), 4.46 (dt, J = 47, 6 Hz, 2 H), 6.75 (d, J = 8 Hz, 2 H), 6.86 (d, J = 8 Hz, 1 H), 6.92 (d, J = 8 Hz, 2 H), 7.09 (dd, J = 11, 9 Hz, 1 H), 7.13-7.26 (m, 2 H), 7.75 (dd, J = 8, 2 Hz, 1 H), 7.92 (d, J = 2 Hz, 1 H) | 570 |
| 296 | B | 1H NMR (400 MHz, DMSO-d6) δ ppm 1.49-1.72 (m, 2 H), 2.09-2.31 (m, 4 H), 2.41 (t, J = 7 Hz, 2 H), 2.56 (m, 1 H), 2.63-2.77 (m, 4 H), 2.78-3.01 (m, 2 H), 3.20-3.26 (m, 2 H), 4.41 (dt, J = 47, 6 Hz, 2 H), 6.75 (d, | 538 |

TABLE 1b-continued

| Example or compound | Preparation Method | NMR | MASS: LC/MS (m/z, MH+): |
|---|---|---|---|
| | | J = 8 Hz, 2 H), 6.86 (d, J = 8 Hz, 1 H), 6.92 (d, J = 8 Hz, 2 H), 6.96-7.24 (m, 3 H), 7.34-7.45 (m, 1 H), 7.75 (dd, J = 8, 2 Hz, 1 H), 7.91 (d, J = 2 Hz, 1 H) | |
| 297 | B | 1H NMR (400 MHz, DMSO-d6) δ ppm 1.75-1.94 (m, 2 H), 2.05-2.20 (m, 2 H), 2.28 (t, J = 8 Hz, 2 H), 2.56 (m, 1 H), 2.76-3.28 (m, 8 H), 3.70-3.82 (m, 2 H), 3.94-4.06 (m, 2 H), 4.50 (dt, J = 47, 6 Hz, 2 H), 5.97 (tt, J = 56, 5 Hz, 1 H), 6.78 (d, J = 8 Hz, 2 H), 6.83 (d, J = 8 Hz, 1 H), 6.95 (d, J = 8 Hz, 2 H), 7.03-7.12 (m, 3 H), 7.13-7.19 (m, 1 H), 7.73 (dd, J = 8, 2 Hz, 1 H), 7.90 (d, J = 2 Hz, 1 H) | 534 |
| 298 | B | 1H NMR (400 MHz, DMSO-d6) δ ppm 1.52-1.70 (m, 2 H), 2.09-2.19 (m, 2 H), 2.27 (t, J = 8 Hz, 2 H), 2.42 (t, J = 7 Hz, 2 H), 2.56 (m, 1 H), 2.69 (d, J = 8 Hz, 2 H), 2.75 (t, J = 7 Hz, 2 H), 2.85 (t, J = 7 Hz, 2 H), 3.20-3.52 (m hidden, 4 H), 4.42 (dt, J = 47, 6 Hz, 2 H), 6.73 (d, J = 8 Hz, 2 H), 6.83 (d, J = 8 Hz, 1 H), 6.89 (d, J = 8 Hz, 2 H), 7.09-7.23 (m, 4 H), 7.72 (dd, J = 8, 2 Hz, 1 H), 7.89 (d, J = 2 Hz, 1 H) | 552 |
| 299 | A | 1H NMR (400 MHz, DMSO-d6) δ ppm 0.97-1.76 (m, 8 H), 1.92-2.19 (m, 4 H), 2.30-2.45 (m, 4 H), 2.59 (m, 1 H), 2.65-2.88 (m, 6 H), 3.07 (m, 1 H), 3.20-3.27 (m, 2 H), 4.42 (dt, J = 47, 6 Hz, 2 H), 5.38 (br s, 1 H), 6.71 (d, J = 8 Hz, 1 H), 6.93 (d, J = 8 Hz, 2 H), 7.06 (d, J = 8 Hz, 2 H), 7.64 (m, 1 H), 7.80 (br s, 1 H) | 500 |
| 300 | B | 1H NMR (400 MHz, DMSO-d6) δ ppm 1.52-1.71 (m, 2 H), 2.15 (dt, J = 14, 7 Hz, 2 H), 2.42 (q, J = 7 Hz, 2 H), 2.55-2.65 (m hidden, 1 H), 2.69-2.80 (m, 4 H), 2.86 (t, J = 7 Hz, 2 H), 3.18-3.28 (m, 4 H), 4.43 (dt, J = 47, 6 Hz, 2 H), 6.79-6.90 (m, 3 H), 7.03 (d, J = 8 Hz, 2 H), 7.08 (d, J = 8 Hz, 1 H), 7.75 (dd, J = 8, 2 Hz, 1 H), 7.92 (d, J = 2 Hz, 1 H), 7.98 (d, J = 9 Hz, 1 H) | 573 |
| 301 | B | 1H NMR (400 MHz, DMSO-d6) δ ppm 1.52-1.68 (m, 2 H), 2.11-2.31 (m, 4 H), 2.40 (t, J = 7 Hz, 2 H), 2.52 (m hidden 1 H), 2.62-2.75 (m, 4 H), 2.76-3.00 (m, 2 H), 3.20-3.26 (m, 2 H), 3.53-3.75 (m, 2 H), 4.41 (dt, J = 47, 6 Hz, 2 H), 6.67 (d, J = 7 Hz, 2 H), 6.80-6.92 (m, 3 H), 7.12-7.37 (m, 4 H), 7.74 (dd, J = 8, 2 Hz, 1 H), 7.91 (d, J = 2 Hz, 1 H) | 552 |
| 302 | A | 1H NMR (400 MHz, DMSO-d6) δ ppm 0.61-0.82 (m, 3 H), 1.43-1.71 (m, 2 H), 1.87-2.47 (m, 4 H), 2.51-3.24 (m, 10 H), 4.41 (dtd, J = 47, 6, 1 Hz, 2 H), 6.72-6.99 (m, 5 H), 7.13 (d, J = 8 Hz, 0.5 H), 7.27 (m, 1 H), 7.37-7.48 (m, 1 H), 7.58 (d, J = 2 Hz, 0.5 H), 7.72 (td, J = 8, 2 Hz, 1 H), 7.89 (t, J = 2 Hz, 1 H) | 552 |
| 303 | A | 1H NMR (400 MHz, DMSO-d6) δ ppm 0.65-0.79 (m, 3 H), 1.47-1.72 (m, 2 H), 1.87-2.45 (m, 4 H), 2.52-3.25 (m, 10 H), 4.41 (dtd, J = 47, 6, 2 Hz, 2 H), 6.82-7.00 (m, 5 H), 7.13 (d, J = 8 Hz, 0.5 H), 7.28 (m, 1 H), 7.36-7.48 (m, 1 H), 7.58 (d, J = 2 Hz, 0.5 H), 7.73 (td, J = 8, 2 Hz, 1 H), 7.89 (t, J = 2 Hz, 1 H) | 552 |
| 304 | A | 1H NMR (400 MHz, DMSO-d6) δ ppm 1.47-1.67 (m, 2 H), 2.16 (br dd, J = 17, 3 Hz, 4 H), 2.33-2.39 (m, 2 H), 2.53-2.58 (m hidden, 1 H), 2.64-2.72 (m, 4 H), 2.79-2.99 (m, 2 H), 3.12-3.23 (m, 2 H), 4.41 (dt, J = 47, 6 Hz, 2 H), 6.71-6.79 (m, 3 H), 6.87 (d, J = 8 Hz, 2 H), 7.07-7.27 (m, 5 H), 7.32 (m, 1 H), 7.41 (m, 1 H) | 460 |
| 305 | A | 1H NMR (400 MHz, DMSO-d6) δ ppm 1.59 (dquin, J = 25, 7 Hz, 2 H), 2.02-2.15 (m, 2 H), 2.16-2.27 (m, 2 H), 2.36 (t, J = 7 Hz, 2 H), 2.56 (m, 1 H), 2.61-2.79 (m, 5 H), 2.91-3.01 (m, 1 H), 3.14-3.22 (m, 2 H), 4.41 (dt, J = 47, 6 Hz, 2 H), 6.30 (dd, J = 11, 1 Hz, 1 H), 6.76 (d, J = 8 Hz, 2 H), 6.92 (d, J = 8 Hz, 2 H), 7.14 (d, J = 6 Hz, 1 H), 7.22 (dd, J = 8, 2 Hz, 1 H), 7.55 (d, J = 2 Hz, 1 H), 10.27 (br s, 1 H) | 546 |
| 306 | A | 1H NMR (400 MHz, DMSO-d6) δ ppm 1.59 (dquin, J = 25, 7 Hz, 2 H), 2.11-2.23 (m, 2 H), 2.28-2.32 (m, 2 H), 2.39 (t, J = 7 Hz, 2 H), 2.59 (m hidden, 1 H), 2.68-2.74 (m, 4 H), 2.86 (t, J = 7 Hz, 2 H), 3.20 (t, J = 7 Hz, 2 H), 3.92 (s, 3 H), 4.42 (dt, J = 47, 6 Hz, 2 H), 6.82 (d, J = 8 Hz, 2 H), 6.84 (d, J = 8 Hz, 1 H), 7.00 (d, J = 8 Hz, 2 H), 7.67 (d, J = 2 Hz, 1 H), 7.73 (dd, J = 8, 2 Hz, 1 H), 7.89 (d, J = 2 Hz, 1 H), 8.26 (d, J = 2 Hz, 1 H), 12.76 (br s, 1 H) | 569 |
| 307 | E | 1H NMR (400 MHz, DMSO-d6) δ ppm 0.88 (m, 1 H), 0.98 (m, 1 H), 1.16 (m, 1 H), 1.30-1.54 (m, 4 H), 1.54- | 488 |

TABLE 1b-continued

| Example or compound | Preparation Method | NMR | MASS: LC/MS (m/z, MH+): |
|---|---|---|---|
| | | 1.72 (m, 3 H), 1.83-2.02 (m, 2 H), 2.04-2.21 (m, 3 H), 2.25 (br s, 1 H), 2.43 (t, J = 7 Hz, 2 H), 2.52-2.87 (m, 8 H), 3.28 (m hidden, 2 H), 4.43 (dt, J = 47, 6 Hz, 2 H), 6.73 (d, J = 8 Hz, 1 H), 6.96 (d, J = 8 Hz, 2 H), 7.13 (d, J = 8 Hz, 2 H), 7.64 (dd, J = 8, 2 Hz, 1 H), 7.80 (d, J = 2 Hz, 1 H) | |
| 308 | A | 1H NMR (400 MHz, DMSO-d6) δ ppm 1.76-1.96 (m, 2 H), 2.80-3.02 (m, 3 H), 3.15-3.21 (m, 2 H), 3.64 (d, J = 15 Hz, 1 H), 3.74 (t, J = 8 Hz, 2 H), 3.85 (d, J = 15 Hz, 1 H), 4.01 (t, J = 8 Hz, 2 H), 4.51 (dt, J = 47, 6 Hz, 2 H), 6.81 (d, J = 8 Hz, 1 H), 6.94 (d, J = 8 Hz, 2 H), 7.03-7.14 (m, 3 H), 7.20 (dd, J = 8, 2 Hz, 1 H), 7.52-7.66 (m, 2 H), 7.93 (d, J = 2 Hz, 1 H), 9.53-13.23 (m, 1 H) | 542 |
| 309 | A | 1H NMR (400 MHz, DMSO-d6) δ ppm 0.54-0.69 (m, 3 H), 1.49-1.68 (m, 2 H), 1.88-2.29 (m, 8 H), 2.35-2.46 (m, 2 H), 2.57-2.92 (m, 6 H), 2.98-3.23 (m partially hidden, 4 H), 4.29-4.50 (m, 2 H), 6.70-7.06 (m, 7 H), 7.66-7.76 (m, 1 H), 7.86-7.91 (m, 1 H) | 530 |
| 310 | A | 1H NMR (400 MHz, DMSO-d6) δ ppm 0.46-0.81 (m, 3 H), 1.58 (dquin, J = 25, 7 Hz, 2 H), 2.20-2.72 (m, 13 H), 2.78-3.21 (m, 4 H), 4.40 (dt, J = 47, 6 Hz, 2 H), 6.66-7.05 (m, 5 H), 7.13-7.57 (m, 3 H), 7.67-7.79 (m, 1 H), 7.83-7.97 (m, 1 H) | 566 |
| 311 | G | 1H NMR (400 MHz, DMSO-d6) δ ppm 1.52-1.78 (m, 4 H), 1.86 (t, J = 8 Hz, 2 H), 2.43 (t, J = 7 Hz, 2 H), 2.59-2.68 (m, 3 H), 2.77-2.86 (m, 4 H), 3.26-3.33 (m, 2 H), 3.54 (s, 2 H), 4.42 (dt, J = 47, 6 Hz, 2 H), 6.82 (d, J = 8 Hz, 1 H), 7.04-7.12 (m, 2 H), 7.14-7.25 (m, 5 H), 7.26-7.34 (m, 2 H), 7.68 (dd, J = 8, 2 Hz, 1 H), 7.79 (d, J = 2 Hz, 1 H) | 484 |
| 312 | A | 1H NMR (400 MHz, DMSO-d6) δ ppm 0.60-0.71 (m, 3 H), 1.51-1.68 (m, 2 H), 1.94-2.32 (m, 3 H), 2.34-2.72 (m, 7 H), 2.77-3.24 (m, 4 H), 4.29-4.50 (m, 2 H), 6.71-7.02 (m, 5 H), 7.24-7.50 (m, 2 H), 7.57 (m, 1 H), 7.72 (m, 1 H), 7.88 (d, J = 2 Hz, 1 H) | 570 |
| 313 | A | 1H NMR (400 MHz, DMSO-d6) δ ppm 1.76-1.94 (m, 2 H), 1.99-2.29 (m, 4 H), 2.43-2.49 (m, 3 H), 2.76-3.06 (m, 5 H), 3.12 (t, J = 7 Hz, 2 H), 3.60-3.74 (m, 2 H), 3.86-4.00 (m, 2 H), 4.50 (dt, J = 47, 6 Hz, 2 H), 6.79 (d, J = 8 Hz, 2 H), 6.84 (d, J = 8 Hz, 1 H), 6.90-6.99 (m, 3 H), 7.22-7.31 (m, 2 H), 7.75 (dd, J = 8, 2 Hz, 1 H), 7.90 (d, J = 2 Hz, 1 H), 10.22-13.49 (m, 1 H) | 552 |
| 314 | A | 1H NMR (400 MHz, DMSO-d6) δ ppm 1.78-1.95 (m, 2 H), 2.80-3.04 (m, 3 H), 3.15-3.24 (m, 2 H), 3.68-3.83 (m, 4 H), 4.01 ( t, J = 8 Hz, 2 H), 4.51 (dt, J = 47, 6 Hz, 2 H), 6.79 (d, J = 8 Hz, 1 H), 6.84-6.96 (m, 3 H), 7.05-7.18 (m, 4 H), 7.60 (dd, J = 8, 2 Hz, 1 H), 7.92 (d, J = 2 Hz, 1 H), 10.26 (br s, 1 H), 13.04 (br s, 1 H) | 510 |
| 315 | A | 1H NMR (400 MHz, DMSO-d6) δ ppm 0.73 (t, J = 8 Hz, 4 H), 0.85 (m, 1 H), 1.20 (m, 1 H), 1.60 (dquin, J = 25, 7 Hz, 2 H), 1.96 (m, 1 H), 2.24 (m, 1 H), 2.35 (m, 1 H), 2.40 (t, J = 7 Hz, 2 H), 2.55 (m, 1 H), 2.62-2.74 (m, 3 H), 2.85-3.03 (m, 2 H), 3.18-3.25 (m, 2 H), 4.41 (dt, J = 47, 6 Hz, 2 H), 6.81-6.95 (m, 5 H), 7.13-7.18 (m, 2 H), 7.19-7.26 (m, 2 H), 7.73 (dd, J = 8, 2 Hz, 1 H), 7.87 (d, J = 2 Hz, 1 H) | 532 |
| 316 | G | 1H NMR (500 MHz, DMSO-d6) δ ppm 0.76-1.53 (m, 9 H), 1.54-1.74 (m, 3 H), 1.78-1.93 (m, 4 H), 2.03-2.17 (m, 4 H), 2.38-2.47 (m, 2 H), 2.60-2.87 (m, 8 H), 3.22-3.27 (m, 2 H), 4.30-4.53 (m, 2 H), 6.66-6.81 (m, 1 H), 6.91-7.03 (m, 2 H), 7.05-7.22 (m, 2 H), 7.55-7.68 (m, 1 H), 7.72-7.93 (m, 1 H) | 502 |
| 317 | A | 1H NMR (400 MHz, DMSO-d6) δ ppm 0.70 (d, J = 7 Hz, 3 H), 0.81 (d, J = 7 Hz, 3 H), 1.03 (m, 1 H), 1.49-1.72 (m, 2 H), 2.08 (m, 1 H), 2.15-2.32 (m, 2 H), 2.40 (t, J = 7 Hz, 2 H), 2.56 (m, 1 H), 2.64-2.74 (m, 4 H), 2.77-3.05 (m, 2 H), 3.22 (t, J = 8 Hz, 2 H), 4.41 (dt, J = 47, 6 Hz, 2 H), 6.79-7.00 (m, 5 H), 7.12-7.27 (m, 4 H), 7.72 (dd, J = 8, 2 Hz, 1 H), 7.85 (d, J = 2 Hz, 1 H), 10.58-15.32 (m, 1 H) | 546 |
| 318 | A | 1H NMR (400 MHz, DMSO-d6) δ ppm 1.77-1.97 (m, 2 H), 2.04-2.21 (m, 2 H), 2.30 (t, J = 7 Hz, 2 H), 2.74-3.06 (m, 5 H), 3.14-3.25 (m, 2 H), 3.65-3.82 (m, 2 H), 4.01 (br s, 2 H), 4.50 (dt, J = 47, 6 Hz, 2 H), 6.77- | 574 |

TABLE 1b-continued

| Example or compound | Preparation Method | NMR | MASS: LC/MS (m/z, MH+): |
|---|---|---|---|
| | | 6.89 (m, 3 H), 6.98 (d, J = 8 Hz, 2 H), 7.37 (d, J = 8 Hz, 2 H), 7.55 (d, J = 8 Hz, 2 H), 7.75 (d, J = 8 Hz, 1 H), 7.92 (s, 1 H), 10.13-10.91 (m, 1 H), 12.60-13.17 (m, 1 H) | |
| 319 | A | 1H NMR (400 MHz, DMSO-d6) δ ppm 1.75-1.93 (m, 2 H), 2.07-2.19 (m, 2 H), 2.22-2.31 (m, 2 H), 2.52-2.59 (m, 2 H), 2.75-2.93 (m, 5 H), 3.06-3.16 (m, 2 H), 3.32-3.35 (m hidden, 2 H), 3.60-3.72 (m, 2 H), 3.87-3.99 (m, 2 H), 4.50 (dt, J = 47, 6 Hz, 2 H), 6.77 (d, J = 8 Hz, 2 H), 6.83 (d, J = 8 Hz, 1 H), 6.90-7.03 (m, 5 H), 7.10 (m, 1 H), 7.73 (dd, J = 8, 2 Hz, 1 H), 7.90 (d, J = 2 Hz, 1 H), 9.74-11.40 (m, 1 H), 12.00-13.30 (m, 1 H) | 514 |
| 320 | A | 1H NMR (400 MHz, DMSO-d6) δ ppm 1.62 (dquin, J = 26, 6 Hz, 2 H), 2.06-2.18 (m, 2 H), 2.28 (t, J = 6 Hz, 2 H), 2.44 (t, J = 7 Hz, 2 H), 2.57 (m, 1 H), 2.70 (d, J = 8 Hz, 2 H), 2.77 (t, J = 7 Hz, 2 H), 2.85 (t, J = 7 Hz, 2 H), 3.23-3.30 (m, 2 H), 4.31-4.51 (dt, J = 47, 6 Hz, 2 H), 4.36 (m, 2 H), 4.99-5.19 (m, 1 H), 6.75 (d, J = 8 Hz, 2 H), 6.83 (d, J = 8 Hz, 1 H), 6.91 (d, J = 8 Hz, 2 H), 6.96 (m, 1 H), 7.09 (d, J = 5 Hz, 2 H), 7.13 (s, 1 H), 7.72 (dd, J = 8, 2 Hz, 1 H), 7.89 (d, J = 2 Hz, 1 H) | 500 |
| 321 | A | 1H NMR (400 MHz, DMSO-d6) δ ppm 0.34-0.68 (m, 3 H), 0.71-0.92 (m, 3 H), 1.25 (m, 1 H), 1.51-1.80 (m, 2 H), 1.98-2.44 (m, 3 H), 2.52-2.76 (m, 5 H), 2.78-2.97 (m, 3 H), 3.22-3.34 (m, 3 H), 4.43 (dt, J = 47, 6 Hz, 2 H), 6.79-7.00 (m, 5 H), 7.17-7.56 (m, 3 H), 7.59-7.77 (m, 1 H), 7.88 (m, 1 H) | 580 |
| 322 | A | 1H NMR (400 MHz, DMSO-d6) δ ppm 0.36-0.67 (m, 3 H), 0.73-0.88 (m, 3 H), 1.19-1.73 (m, 1 H), 1.73-1.90 (m, 2 H), 2.04-2.41 (m, 4 H), 2.74-2.93 (m, 4 H), 3.06-3.16 (m, 2 H), 3.58-3.70 (m, 2 H), 3.87-3.97 (m, 2 H), 4.48 (dt, J = 47, 6 Hz, 2 H), 6.87-7.01 (m, 5 H), 7.25-7.54 (m, 3 H), 7.67-7.76 (m, 1 H), 7.83-7.91 (m, 1 H), 9.46-10.67 (m, 1 H), 11.87-13.19 (m, 1 H) | 580 |
| 323 | A | 1H NMR (400 MHz, DMSO-d6) δ ppm 1.60 (dquin, J = 25, 7 Hz, 2 H), 2.15 (quin, J = 7 Hz, 2 H), 2.27-2.37 (m, 2 H), 2.41 (t, J = 7 Hz, 2 H), 2.55 (m hidden, 1 H), 2.68-2.77 (m, 4 H), 2.87 (t, J = 7 Hz, 1 H), 3.22 (t, J = 7 Hz, 3 H), 4.42 (dt, J = 47, 6 Hz, 2 H), 6.75 (d, J = 8 Hz, 2 H), 6.85 (d, J = 8 Hz, 1 H), 6.94 (d, J = 8 Hz, 2 H), 7.34 (s, 1 H), 7.40-7.56 (m, 3 H), 7.74 (dd, J = 8, 2 Hz, 1 H), 7.90 (d, J = 2 Hz, 1 H) | 538 |
| 324 | A | 1H NMR (400 MHz, DMSO-d6) δ ppm-0.05 (m, 1 H), 0.04-0.19 (m, 2 H), 0.31 (m, 2 H), 1.43 (m, 1 H), 1.52-1.71 (m, 2 H), 2.13 (m, 1 H), 2.30 (dd, J = 10, 5 Hz, 1 H), 2.40 (t, J = 7 Hz, 2 H), 2.55 (m, 1 H), 2.66 (m, 4 H), 2.85 (m, 1 H), 3.02 (m, 1 H), 3.18-3.26 (m, 2 H), 4.41 (dt, J = 47, 6 Hz, 2 H), 6.76-6.83 (m, 2 H), 6.84-6.98 (m, 3 H), 7.24 (s, 4 H), 7.71 (dd, J = 8, 2 Hz, 1 H), 7.87 (d, J = 2 Hz, 1 H), 11.66-13.34 (m, 1 H) | 544 |
| 325 | A | 1H NMR (400 MHz, DMSO-d6) δ ppm 0.72 (d, J = 7 Hz, 3 H), 1.50-1.68 (m, 2 H), 1.95 (m, 1 H), 2.12 (m, 1 H), 2.39 (t, J = 7 Hz, 2 H), 2.45 (m, 1 H), 2.56 (m, 1 H), 2.62-2.74 (m, 4 H), 2.82 (m, 1 H), 3.02 (m, 1 H), 3.18-3.25 (m, 2 H), 4.41 (dt, J = 48, 7 Hz, 2 H), 6.77-6.92 (m, 5 H), 7.01 (t, J = 9 Hz, 2 H), 7.15 (dd, J = 9, 6 Hz, 2 H), 7.72 (dd, J = 8, 2 Hz, 1 H), 7.88 (d, J = 2 Hz, 1 H) | 502 |
| 326 | A | 1H NMR (400 MHz, DMSO-d6) δ ppm 0.74 (d, J = 7 Hz, 3 H), 1.50-1.68 (m, 2 H), 1.98 (m, 1 H), 2.21 (m, 1 H), 2.39 (t, J = 7 Hz, 2 H), 2.45 (m, 1 H), 2.56 (m, 1 H), 2.63-2.73 (m, 4 H), 2.80 (m, 1 H), 3.03 (m, 1 H), 3.18-3.25 (m, 2 H), 4.41 (dt, J = 47, 6 Hz, 2 H), 6.78-7.00 (m, 6 H), 7.15-7.33 (m, 2 H), 7.73 (dd, J = 8, 2 Hz, 1 H), 7.88 (d, J = 2 Hz, 1 H) | 520 |
| 327 | A | 1H NMR (400 MHz, DMSO-d6) δ ppm 0.72 (d, J = 7 Hz, 3 H), 1.60 (dquin, J = 25, 7 Hz, 2 H), 1.96 (m, 1 H), 2.21 (m, 1 H), 2.39 (t, J = 7 Hz, 2 H), 2.44 (m, 1 H), 2.55 (m, 1 H), 2.63-2.74 (m, 4 H), 2.82 (m, 1 H), 3.01(m, 1 H), 3.18-3.25 (m, 2 H), 4.41 (dt, J = 48, 6 Hz, 2 H), 6.82 (d, J = 8 Hz, 2 H), 6.86-6.92 (m, 3 H), 7.14 (d, J = 9 Hz, 2 H), 7.24 (d, J = 8 Hz, 2 H), 7.73 (dd, J = 8, 2 Hz, 1 H), 7.88 (d, J = 2 Hz, 1 H) | 518 |
| 328 | A | 1H NMR (400 MHz, DMSO-d6) δ ppm 0.72 (d, J = 7 Hz, 3 H), 1.52-1.68 (m, 2 H), 1.96 (m, 1 H), 2.21 (m, 1 H), 2.40 (t, J = 7 Hz, 2 H), 2.46 (m, 1 H), 2.57 (m, 1 H), 2.66 (d, J = 7 Hz, 2 H), 2.68-2.75 (m, 2 H), 2.82 (m, 1 | 518 |

TABLE 1b-continued

| Example or compound | Preparation Method | NMR | MASS: LC/MS (m/z, MH+): |
|---|---|---|---|
| | | H), 3.01 (m, 1 H), 3.19-3.26 (m, 2 H), 4.41 (dt, J = 47, 7 Hz, 2 H), 6.81 (d, J = 8 Hz, 2 H), 6.85-6.93 (m, 3 H), 7.14 (d, J = 9 Hz, 2 H), 7.24 (d, J = 8 Hz, 2 H), 7.73 (dd, J = 8, 2 Hz, 1 H), 7.88 (d, J = 2 Hz, 1 H) | |
| 329 | A | 1H NMR (400 MHz, DMSO-d6) δ ppm 0.73 (t, J = 8 Hz, 3 H), 0.85 (m, 1 H), 1.20 (m, 1 H), 1.50-1.69 (m, 2 H), 1.97 (m, 1 H), 2.24 (m, 1 H), 2.36 (m, 1 H), 2.40 (t, J = 7 Hz, 2 H), 2.54 (m, 1 H), 2.67 (d, J = 8 Hz, 2 H), 2.71 (t, J = 7 Hz, 2 H), 2.85-3.02 (m, 2 H), 3.23 (br d, J = 14 Hz, 2 H), 4.41 (dt, J = 47, 6 Hz, 2 H), 6.76-6.99 (m, 5 H), 7.14 (d, J = 8 Hz, 2 H), 7.23 (d, J = 8 Hz, 2 H), 7.72 (dd, J = 8, 2 Hz, 1 H), 7.87 (d, J = 2 Hz, 1 H) | 532 |
| 330 | A | 1H NMR (400 MHz, DMSO-d6) δ ppm 0.73 (t, J = 8 Hz, 3 H), 0.85 (m, 1 H), 1.20 (m, 1 H), 1.50-1.69 (m, 2 H), 1.97 (m, 1 H), 2.25 (quin, J = 8 Hz, 1 H), 2.33-2.38 (m, 1 H), 2.41 (t, J = 7 Hz, 2 H), 2.56 (m, 1 H), 2.67 (d, J = 8 Hz, 2 H), 2.71 (t, J = 7 Hz, 2 H), 2.84-3.03 (m, 2 H), 3.20-3.25 (m, 2 H), 4.41 (dt, J = 47, 7 Hz, 2 H), 6.82-6.94 (m, 5 H), 7.11-7.18 (m, 2 H), 7.20-7.26 (m, 2 H), 7.72 (dd, J = 8, 2 Hz, 1 H), 7.87 (d, J = 2 Hz, 1 H) | 532 |
| 331 | A | 1H NMR (400 MHz, DMSO-d6) δ ppm 0.54-0.73 (m, 2 H), 0.80-0.92 (m, 2 H), 1.09 (t, J = 7 Hz, 1 H), 1.18-1.36 (m, 2 H), 1.42-1.81 (m, 9 H), 1.89-1.99 (m, 2 H), 2.00-2.09 (m, 2 H), 2.44 (br t, J = 7 Hz, 2 H), 2.61-2.71 (m, 3 H), 2.77-2.84 (m, 4 H), 3.26-3.34 (m, 2 H), 4.43 (dt, J = 47, 6 Hz, 1 H), 6.72 (d, J = 8 Hz, 1 H), 7.05 (d, J = 8 Hz, 2 H), 7.11-7.16 (m, 2 H), 7.65 (dd, J = 8, 2 Hz, 1 H), 7.80 (d, J = 2 Hz, 1 H) | 552 |
| 332 | A | 1H NMR (400 MHz, DMSO-d6) δ ppm 1.63-1.88 (m, 2 H), 2.09-2.30 (m, 4 H), 2.39-3.53 (m, 9 H), 3.75 (m, 2 H), 4.47 (dt, J = 47, 6 Hz, 2 H), 6.79 (br d, J = 8 Hz, 2 H), 6.85 (d, J = 8 Hz, 1 H), 6.96 (br d, J = 8 Hz, 2 H), 7.10 (br d, J = 9 Hz, 1 H), 7.27 (t, J = 12 Hz, 1 H), 7.75 (br d, J = 8 Hz, 1 H), 7.80 (dd, J = 9, 5 Hz, 1 H), 7.92 (s, 1 H), 10.30 (s, 1 H), 12.77 (s, 1 H) | 226 |
| 333 | A | 1H NMR (400 MHz, DMSO-d6) δ ppm 0.75 (d, J = 7 Hz, 3 H), 1.52-1.65 (m, 2 H), 1.99 (m, 1 H), 2.20-2.49 (m, 5 H), 2.61-3.22 (m, 8 H), 4.41 (dt, J = 47, 6 Hz, 2 H), 6.81 (d, J = 8 Hz, 2 H), 6.87 (d, J = 8 Hz, 2 H), 6.92 (d, J = 8 Hz, 1 H), 7.37 (s, 1 H), 7.39-7.53 (m, 3 H), 7.74 (dd, J = 8, 2 Hz, 1 H), 7.90 (d, J = 2 Hz, 1 H) | 552 |
| 334 | A | 1H NMR (400 MHz, DMSO-d6) δ ppm 1.60 (dquin, J = 25, 7 Hz, 2 H), 2.05-2.31 (m, 4 H), 2.39 (t, J = 7 Hz, 2 H), 2.56 (m, 1 H), 2.63-2.75 (m, 4 H), 2.88 (t, J = 7 Hz, 2 H), 3.22 (t, J = 7 Hz, 2 H), 3.79 (s, 3 H), 4.41 (dt, J = 47, 7 Hz, 2 H), 6.80 (d, J = 8 Hz, 2 H), 6.85 (d, J = 8 Hz, 1 H), 6.88-7.01 (m, 4 H), 7.29 (dd, J = 8, 2 Hz, 1 H), 7.74 (dd, J = 8, 2 Hz, 1 H), 7.90 (d, J = 2 Hz, 1 H) | 534 |
| 335 | A | 1H NMR (400 MHz, DMSO-d6) δ ppm 1.54-1.67 (m, 2 H), 2.10-2.22 (m, 4 H), 2.41 (t, J = 7 Hz, 2 H), 2.55(m partially hidden, 1 H), 2.65-2.76 (m, 4 H), 2.88 ( t, J = 6 Hz, 2 H), 3.23 (t, J = 7 Hz, 2 H), 3.74 (d, J = 2 Hz, 3 H), 4.42 (dt, J = 47, 6 Hz, 2 H), 6.78 (d, J = 8 Hz, 2 H), 6.80-6.90 (m, 3 H), 6.92 (d, J = 8 Hz, 2 H), 7.07 (m, 1 H), 7.74 (dd, J = 8, 2 Hz, 1 H), 7.90 (d, J = 2 Hz, 1 H) | 518 |
| 336 | C | 1H NMR (500 MHz, DMSO-d6) δ ppm 1.10-1.22 (m, 2 H), 1.32-1.63 (m, 6 H), 1.66-1.79 (m, 2 H), 1.80-1.92 (m, 4 H), 2.11 (quin, J = 7 Hz, 2 H), 2.26-2.34 (m, 2 H), 2.61-2.98 (m, 8 H), 3.19 (br s, 2 H), 3.61 (m hidden, 2 H), 4.46 (dt, J = 47, 6 Hz, 2 H), 6.69 (d, J = 8 Hz, 1 H), 6.97 (d, J = 8 Hz, 2 H), 7.14 (d, J = 8 Hz, 2 H), 7.64 (dd, J = 8, 2 Hz, 1 H), 7.82 (d, J = 2 Hz, 1 H) | 502 |

The examples which follow describe the preparation of some compounds of formula (I) described herein. The numbers of the compounds exemplified below match those given in the Table 1a above. All reactions are performed under inert atmosphere, unless otherwise stated.

In the following examples, when the source of the starting products is not specified, it should be understood that said products are known compounds.

Intermediates

Intermediate 1: 3-(4-bromobenzyl)-1-(3-fluoropropyl)azetidine

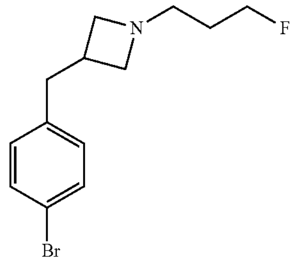 [SMILES: FCCCN1CC(Cc2ccc(Br)cc2)C1]

Method 1:

A suspension of 3-(4-bromobenzyl)azetidine, trifluoroacetic acid (4.5 g, 13.23 mmol) in DMF (45 ml), $K_2CO_3$ (5.67 g, 41.01 mmol) and 1-fluoro-3-iodopropane (2.49 g, 13.32 mmol) was heated to 70° C. for 2 hours. After cooling to room temperature, water (500 ml) was added and the reaction mixture was extracted three times with 200 ml of EtOAc. The organic phases were gathered, washed with water (150 ml), dried over $MgSO_4$, filtered and concentrated under reduced pressure. The residue obtained was purified by flash chromatography, eluting with a gradient of DCM/MeOH: from 100/00 to 95/05 to give 2.3 g (61%) of 3-(4-bromobenzyl)-1-(3-fluoropropyl)azetidine as a viscous oil.

LC/MS (m/z, MH+): 286

Method 2:

A mixture of 3-(4-bromobenzyl)azetidine, trifluoroacetic acid (4 g, 11.76 mmol) in THF (20 ml), 1-fluoro-3-iodopropane (2.21 g, 11.76 mmol) and NaOH 5N (7.06 ml, 35.28 mmol) was stirred at room temperature for 18 hours. The reaction mixture was concentrated under reduced pressure. To the resulting residue was added water (150 ml) and the reaction mixture was extracted three times with 150 ml of EtOAc. The organic phases were gathered, washed with water (150 ml), dried over $MgSO_4$, filtered and concentrated under reduced pressure. The residue obtained was purified by flash chromatography, eluting with a gradient of DCM/MeOH: from 100/00 to 95/05 to give 1.58 g (47%) of 3-(4-bromobenzyl)-1-(3-fluoropropyl)azetidine as a viscous oil.

Intermediate 2: 1-(3-fluoropropyl)-3-(4-(4,4,5,5-tetramethyl-1,3,2-dioxaborolan-2-yl)benzyl)azetidine

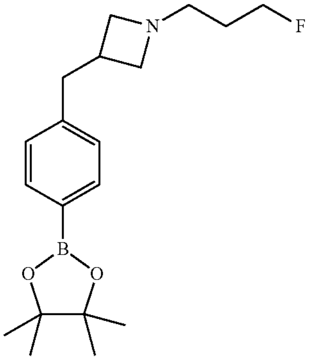 [SMILES: CC1(C)OB(c2ccc(CC3CN(CCCF)C3)cc2)OC1(C)C]

A mixture of Intermediate 1 (5 g, 17.47 mmol), bis(pinacolato)diboron (6.65 g, 26.21 mmol), KOAc (5.14 g, 52.41 mmol) and Pd(dppf)$Cl_2$ (1.28 g, 1.75 mmol) in dioxane (50 mL) was degassed and purged 3 times with Ar and then the mixture was stirred at 80° C. for 12 hours under Ar atmosphere. The reaction mixture was filtered through celite and washed with EtOAc (50 mL). The filtrate was concentrated under reduced pressure and the residue was purified by flash chromatography, eluting with a gradient of DCM/MeOH: from 100/00 to 90/10, to give 4 g (69% yield) of 1-(3-fluoropropyl)-3-(4-(4,4,5,5-tetramethyl-1,3,2-dioxaborolan-2-yl)benzyl)azetidine as a brown oil.

LC/MS (m/z, MH+): 334

Intermediate 3: 3-(4-bromobenzyl)-1-(1,1-dideuterio-3-fluoro-propyl)azetidine

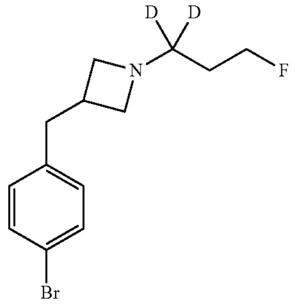 [SMILES: [2H]C([2H])(CCF)N1CC(Cc2ccc(Br)cc2)C1]

Step 1: 1-(3-(4-bromobenzyl)azetidin-1-yl)-3-fluoropropan-1-one

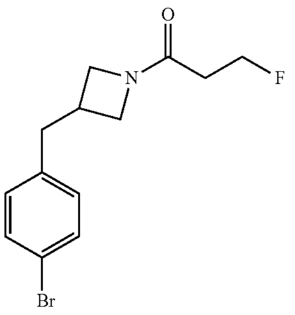 [SMILES: O=C(CCF)N1CC(Cc2ccc(Br)cc2)C1]

A mixture of 3-(4-bromobenzyl)azetidine 4-methylbenzenesulfonate (19.39 g, 48.68 mmol), DMAP (17.98 g, 145.70 mmol), N-(3-dimethylaminopropyl)-N'-ethylcarbodiimide hydrochloride (11.29 g, 58.30 mmol) and 3-fluoropropanoic acid (4.7 g, 48.50 mmol) in DMF (120 ml) was stirred at room temperature for 18 hours. The solvent was concentrated under reduced pressure. To the resulting residue obtained were added water (150 ml) and EtOAc (300 ml). After decantation, the organic phase was washed successively with NaOH 1N (50 ml), water (100 ml), HCl 1N (50 ml) and water (200 ml). The organic phase was dried over $MgSO_4$, filtered and concentrated under reduced pressure to give 8.5 g (58%) of 1-(3-(4-bromobenzyl)azetidin-1-yl)-3-fluoropropan-1-one.

LC/MS (m/z, MH+): 299

Step 2: 3-(4-bromobenzyl)-1-(1,1-dideuterio-3-fluoro-propyl)azetidine

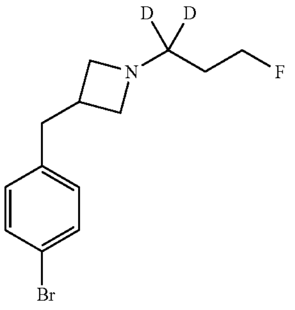 [SMILES: [2H]C([2H])(CCF)N1CC(Cc2ccc(Br)cc2)C1]

To a mixture of 1-(3-(4-bromobenzyl)azetidin-1-yl)-3-fluoropropan-1-one (510 mg, 1.70 mmol) in diethyl ether (10 ml) at room temperature was added lithium aluminium deuteride (147 mg, 3.43 mmol). After 30 minutes, the reaction mixture was cooled to 4° C. After addition successively of EtOAc (1 ml), water (150 µl), NaOH 15% (150 µl) and water (450 µl), the white precipitate was filtered. The filtrate was concentrated under reduced pressure. The residue obtained was purified by flash chromatography, eluting with a gradient of DCM/MeOH: from 100/00 to 95/05 to give 214 mg (44%) of 3-(4-bromobenzyl)-1-(1,1-dideuterio-3-fluoro-propyl)azetidine.

LC/MS (m/z, MH+): 287

Intermediate 4: Methyl 9-(4,4,5,5-tetramethyl-1,3,2-dioxaborolan-2-yl)-6,7-dihydro-5H-benzo[7]annulene-3-carboxylate

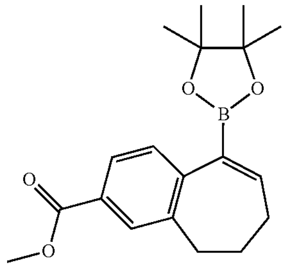

A mixture of methyl 9-(((trifluoromethyl)sulfonyl)oxy)-6,7-dihydro-5H-benzo[7]annulene-3-carboxylate (15 g, 42.82 mmol) (prepared according to WO2017140669), in toluene (150 ml), $Pd(PPh_3)_2Cl_2$ (1.53 g, 2.14 mmol), $PPh_3$ (673.87 mg, 2.57 mmol), bis(pinacolato)diboron (144.08 g, 52.67 mmol) and PhOK (8.04 g, 60.80 mmol) was heated to 75° C. during 1.5 hours. The yellow suspension becomes orange then brown. After cooling to room temperature, DCM (150 ml) and water (150 ml) were added, and decantation was done by hydrophobic column. The organic phase was concentrated under reduced pressure. The residue obtained was purified by flash chromatography, eluting with a gradient of heptane/DCM: from 85/15 to 20/80 to give 10.1 g (72%) of methyl 9-(4,4,5,5-tetramethyl-1,3,2-dioxaborolan-2-yl)-6,7-dihydro-5H-benzo[7]annulene-3-carboxylate as a white solid.

LC/MS (m/z, MH+): 329

Intermediate 5: Methyl 8-(2,4-dichlorophenyl)-9-(4,4,5,5-tetramethyl-1,3,2-dioxaborolan-2-yl)-6,7-dihydro-5H-benzo[7]annulene-3-carboxylate

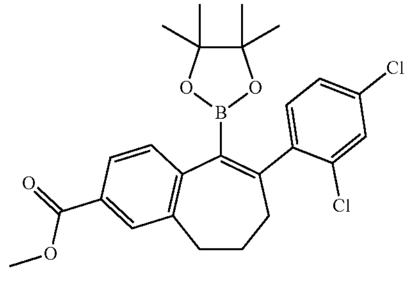 [SMILES: COC(=O)c1ccc2c(c1)CCCC(c1ccc(Cl)cc1Cl)=C2B1OC(C)(C)C(C)(C)O1]

Intermediate 5 was prepared following a similar procedure to that of Intermediate 4 from methyl 8-(2,4-dichlorophenyl)-9-(((trifluoromethyl)sulfonyl)oxy)-6,7-dihydro-5H-benzo[7]annulene-3-carboxylate (prepared according to WO2020/049153) to give 3.9 g (82%) of methyl 8-(2,4-dichlorophenyl)-9-(4,4,5,5-tetramethyl-1,3,2-dioxaborolan-2-yl)-6,7-dihydro-5H-benzo[7]annulene-3-carboxylate as a white solid.

LC/MS (m/z, MH+): 473

Intermediate 6: Methyl 8-(2,4-difluorophenyl)-9-(4,4,5,5-tetramethyl-1,3,2-dioxaborolan-2-yl)-6,7-dihydro-5H-benzo[7]annulene-3-carboxylate

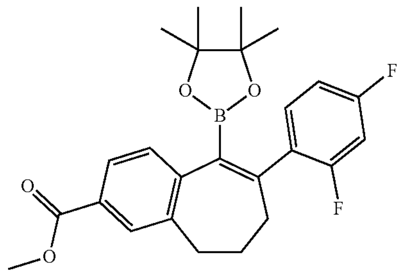 [SMILES: COC(=O)c1ccc2c(c1)CCCC(c1ccc(F)cc1F)=C2B1OC(C)(C)C(C)(C)O1]

Step 1: Methyl 6-(2,4-difluorophenyl)-5-oxo-6,7,8,9-tetrahydro-5H-benzo[7]annulene-2-carboxylate

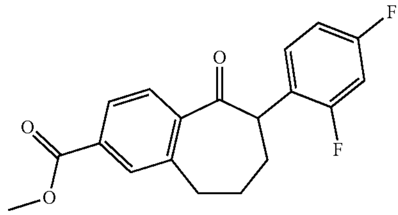 [SMILES: COC(=O)c1ccc2c(c1)CCCC(c1ccc(F)cc1F)C2=O]

Argon is bubbled for 10 minutes in a mixture of 1-bromo-2,4-difluoro-benzene (6.63 g, 34.37 mmol), methyl 5-oxo-6,7,8,9-tetrahydro-5H-benzo[7]annulene-2-carboxylate (5 g; 22.91 mmol), $K_2CO_3$ (12.67 g, 91.66 mmol) in toluene (40 ml). After addition of 4,5-bis(diphenylphosphino)-9,9-dimethylxanthene (1.32 g, 2.91 mmol) and tris(dibenzylideneacetone)dipalladium(0) (1.05 g, 1.15 mmol), the reaction mixture was heated to reflux for 72 hours. After cooling to room temperature, water (40 ml) and DCM (40 ml) were added. After decantation, the aqueous phase was washed three times with 40 ml of DCM. The combined organic phases were dried over $MgSO_4$, filtered and concentrated under reduced pressure. The residue obtained was purified by flash chromatography, eluting with a gradient of Heptane/EtOAc from 100/00 to 90/10 to give 2.55 g (34%) of methyl 6-(2,4-difluorophenyl)-5-oxo-6,7,8,9-tetrahydro-5H-benzo[7]annulene-2-carboxylate.

LC/MS (m/z, MH+): 331

Step 2: Methyl 8-(2,4-difluorophenyl)-9-(((trifluoromethyl)sulfonyl)oxy)-6,7-dihydro-5H-benzo[7]annulene-3-carboxylate

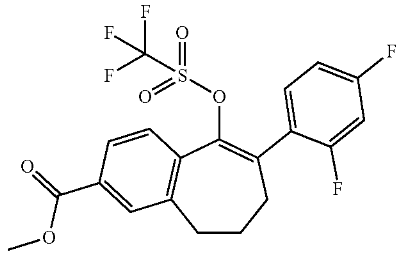 [SMILES: COC(=O)c1ccc2c(c1)CCCC(c1ccc(F)cc1F)=C2OS(=O)(=O)C(F)(F)F]

To a suspension of sodium hydride (545 mg, 13.62 mmol) in Me-THF (22 ml) cooled at 5° C. was added DBU (277 mg, 0.27 ml, 1.82 mmol) followed by a solution of methyl 6-(2,4-difluorophenyl)-5-oxo-6,7,8,9-tetrahydrobenzo[7]annulene-2-carboxylate (3 g, 9.08 mmol) and N,N-bis(trifluoromethylsulfonyl)aniline (4.2 g, 11.81 mmol) in THF. The cooling bath was removed to allow the temperature to warm up to room temperature. A mixture of acetic acid (0.4 ml) and water (32 ml) was dropwise added, followed by water (100 ml) and EtOAc (150 ml). After decantation, the organic phase was dried over $MgSO_4$, filtered and concentrated under reduced pressure The residue obtained was purified by flash chromatography, eluting with DCM/heptane 50/50 to give 2.77 g (66%) of methyl 8-(2,4-difluorophenyl)-9-(((trifluoromethyl)sulfonyl)oxy)-6,7-dihydro-5H-benzo[7]annulene-3-carboxylate.

LC/MS (m/z, MH+): 463

Step 3: Methyl 8-(2,4-difluorophenyl)-9-(4,4,5,5-tetramethyl-1,3,2-dioxaborolan-2-yl)-6,7-dihydro-5H-benzo[7]annulene-3-carboxylate

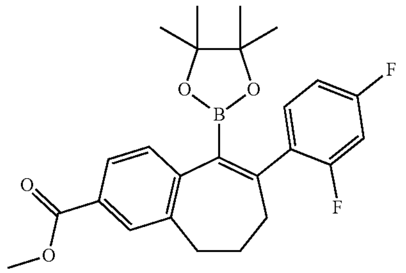 [SMILES: COC(=O)c1ccc2c(c1)CCCC(c1ccc(F)cc1F)=C2B1OC(C)(C)C(C)(C)O1]

Intermediate 6 was prepared following a similar procedure to that of Intermediate 4 from methyl 8-(2,4-difluorophenyl)-9-(((trifluoromethyl)sulfonyl)oxy)-6,7-dihydro-5H-benzo[7]annulene-3-carboxylate, to give 1.89 g (72%) of methyl 8-(2,4-difluorophenyl)-9-(4,4,5,5-tetramethyl-1,3,2-dioxaborolan-2-yl)-6,7-dihydro-5H-benzo[7]annulene-3-carboxylate.

LC/MS (m/z, MH+): 473

Intermediate 7: Methyl 8-bromo-9-(4-((1-(3-fluoropropyl)azetidin-3-yl)methyl)phenyl)-6,7-dihydro-5H-benzo[7]annulene-3-carboxylate

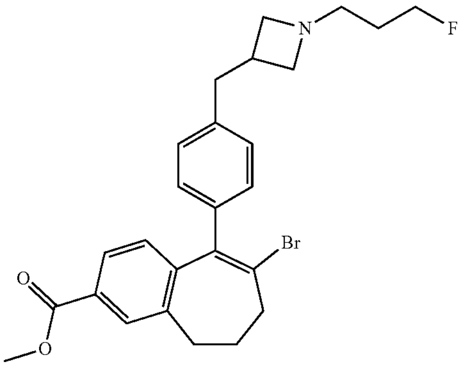 [SMILES: COC(=O)c1ccc2c(c1)CCCC(Br)=C2c1ccc(CC2CN(CCCF)C2)cc1]

Step 1: Methyl 9-(4-((1-(3-fluoropropyl)azetidin-3-yl)methyl)phenyl)-6,7-dihydro-5H-benzo[7]annulene-3-carboxylate

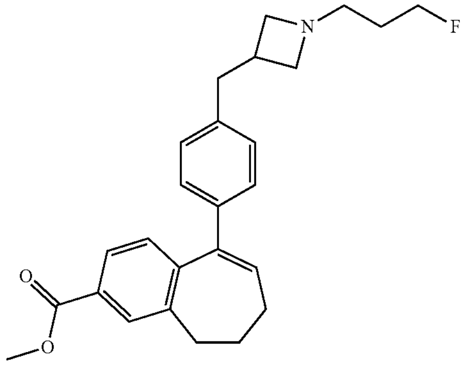

A mixture of methyl 9-(4,4,5,5-tetramethyl-1,3,2-dioxaborolan-2-yl)-6,7-dihydro-5H-benzo[7]annulene-3-carboxylate (Intermediate 4) (17 g, 52.41 mmol), 3-(4-bromobenzyl)-1-(3-fluoropropyl)azetidine (Intermediate 1) (15 g, 52.41 mmol), Pd(dppf)$Cl_2$ complex with DCM (2.42 g, 3.14 mmol), $Cs_2CO_3$ (43.56 g, 134 mmol) in dioxane (120 ml) and water (50 ml) was heated to reflux for 1 hour. After cooling to room temperature, DCM (500 ml) and water (300 ml) were added, and decantation was done by hydrophobic column. The organic phase was concentrated under reduced pressure. The residue obtained was purified by flash chromatography, eluting with a gradient of DCM/MeOH: from 100/00 to 98/02 to give 16.19 g (90%) of methyl 9-(4-((1-(3-fluoropropyl)azetidin-3-yl)methyl)phenyl)-6,7-dihydro-5H-benzo[7]annulene-3-carboxylate as an orange viscous oil.

LC/MS (m/z, MH+): 408

Step 2: Methyl 8-bromo-9-(4-((1-(3-fluoropropyl)azetidin-3-yl)methyl)phenyl)-6,7-dihydro-5H-benzo[7]annulene-3-carboxylate

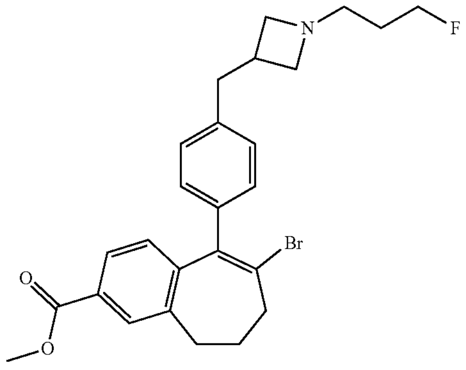 [SMILES: COC(=O)c1ccc2c(c1)CCCC(Br)=C2c1ccc(CC2CN(CCCF)C2)cc1]

To a mixture of methyl 9-(4-((1-(3-fluoropropyl)azetidin-3-yl)methyl)phenyl)-6,7-dihydro-5H-benzo[7]annulene-3-carboxylate (19 g, 46.62 mmol) in DCM (150 ml) was added pyridinium tribromide (21.54 g, 60.61 mmol). The reaction mixture was stirred for 2 hours at room temperature. Water (100 ml) and DCM (150 ml) were added and pH was adjusted to 8 with concentrated solution of $NaHCO_3$. The aqueous phase was washed 3 times with DCM and the gathered organic phases were dried over $MgSO_4$, filtered and concentrated under reduced pressure. The residue obtained was purified by flash chromatography eluting with a gradient of DCM/MeOH: from 100/00 to 95/05 to give 7.48 g (33%) of methyl 8-bromo-9-(4-((1-(3-fluoropropyl)azetidin-3-yl)methyl)phenyl)-6,7-dihydro-5H-benzo[7]annulene-3-carboxylate as a brown viscous oil.

LC/MS (m/z, MH+): 486

Intermediate 8: Methyl 9-(4-((1-(3-fluoropropyl)azetidin-3-yl)methyl)phenyl)-8-(4,4,5,5-tetramethyl-1,3,2-dioxaborolan-2-yl)-6,7-dihydro-5H-benzo[7]annulene-3-carboxylate

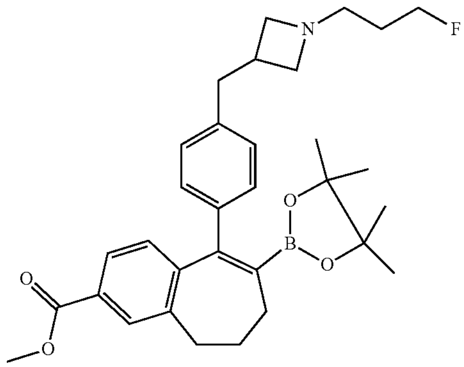 [SMILES: COC(=O)c1ccc2c(c1)CCCC(B1OC(C)(C)C(C)(C)O1)=C2c1ccc(CC2CN(CCCF)C2)cc1]

A mixture of methyl 8-bromo-9-(4-((1-(3-fluoropropyl)azetidin-3-yl)methyl)phenyl)-6,7-dihydro-5H-benzo[7]annulene-3-carboxylate (Intermediate 7) (9.7 g, 20 mmol) in toluene (150 ml), $Pd(PPh_3)_2Cl_2$ (1.5 g, 2 mmol), $PPh_3$ (1 g, 4 mmol), bis(pinacolato)diboron (13 g, 50 mmol) and PhOK (7.9 g, 60 mmol) was heated to 100° C. for 3 hours. After cooling to room temperature, a saturated solution of $Na_2CO_3$ (50 ml) was added. After decantation, the organic phase was washed with water (25 ml), dried over $MgSO_4$, filtered and concentrated under reduced pressure. The residue obtained was purified by flash chromatography, eluting with a gradient of DCM/MeOH: from 100/00 to 95/05 to give 8.2 g (75%) of methyl 9-(4-((1-(3-fluoropropyl)azetidin-3-yl)methyl)phenyl)-8-(4,4,5,5-tetramethyl-1,3,2-dioxaborolan-2-yl)-6,7-dihydro-5H-benzo[7]annulene-3-carboxylate.

LC/MS (m/z, MH+): 534

Intermediate 9: Methyl 4-bromo-5-(4-((1-(3-fluoropropyl)azetidin-3-yl)methyl)phenyl)-2,3-dihydrobenzo[b]oxepine-8-carboxylate

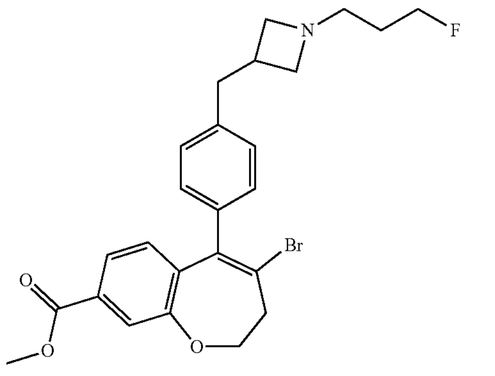 [SMILES: COC(=O)c1ccc2c(c1)OCCC(Br)=C2c1ccc(CC2CN(CCCF)C2)cc1]

Step 1: 5-oxo-2,3,4,5-tetrahydrobenzo[b]oxepine-8-yl trifluoromethanesulfonate

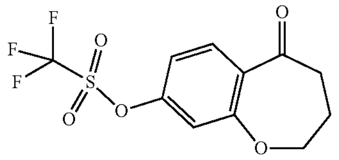 [SMILES: O=C1CCCOc2cc(OS(=O)(=O)C(F)(F)F)ccc21]

To a mixture of 8-hydroxy-3,4-dihydrobenzo[b]oxepine-5(2H)-one (4.2 g, 23.57 mmol) (prepared according to WO2018091153) and pyridine (2.82 g, 2.89 ml, 35.36 mmol) in DCM (120 ml) cooled at −20° C. was dropwise added trifluoromethanesulfonic anhydride (8.14 g, 6 ml, 28.28 mmol). The reaction mixture was stirred at 0° C. for 30 minutes. Water (50 ml) was added. The organic phase was separated and washed with saturated solution of $NaHCO_3$ (50 ml). The organic phase was dried over $MgSO_4$, filtered and concentrated under reduced pressure to give 7.30 g (100%) of 5-oxo-2,3,4,5-tetrahydrobenzo[b]oxepine-8-yl trifluoromethanesulfonate.

LC/MS (m/z, MH+): 311

Step 2: Methyl 5-oxo-2,3,4,5-tetrahydrobenzo[b]oxepine-8-carboxylate

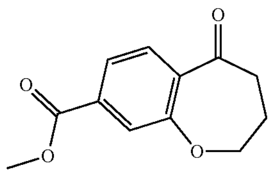 [SMILES: COC(=O)c1ccc2c(c1)OCCCC2=O]

To a solution of compound 5-oxo-2,3,4,5-tetrahydrobenzo[b]oxepine-8-yl trifluoromethanesulfonate (7.4 g, 23.85 mmol) in DMF (30 mL) and MeOH (15 mL) was added DIEA (3.15 g, 4.16 ml, 23.85 mmol) and Pd(dppf)$Cl_2$ complex with DCM (1.10 g, 1.43 mmol), the suspension was degassed and purged with CO 3 times. The mixture was stirred under CO (5 bars) at 75° C. for 2 hours. The reaction was filtered through celite. The filtrate was diluted with water (400 ml) and extracted with EtOAc (three times 300 mL). The combined organic layers were dried over $Na_2SO_4$, filtered and concentrated under reduced pressure to give a residue. The residue was purified by flash chromatography eluting with a gradient of heptane/ethyl acetate: from 85/15 to 80/20 to give 4.6 g (87.6%) methyl 5-oxo-2,3,4,5-tetrahydrobenzo[b]oxepine-8-carboxylate.

LC/MS (m/z, MH+): 221

Step 3: Methyl 5-(((trifluoromethyl)sulfonyl)oxy)-2,3-dihydrobenzo[b]oxepine-8-carboxylate

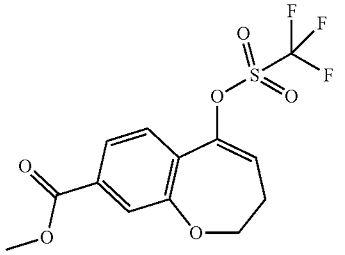 [SMILES: COC(=O)c1ccc2c(c1)OCCC=C2OS(=O)(=O)C(F)(F)F]

To a mixture of methyl-5-oxo-2,3,4,5-tetrahydrobenzo[b]oxepine-8-carboxylate (1.5 g, 6.811 mmol) and pyridine (812 mg, 0.826 ml, 10.22 mmol) in DCM (60 ml) cooled at 1.5° C., was dropwise added trifluoromethanesulfonic anhydride (3.92 g, 2.31 ml, 13.62 mmol). The reaction mixture was stirred at room temperature for 18 hours. Ice (25 g) and water (25 ml) were added. The organic phase was separated and washed with water (35 ml) and saturated solution of $NaHCO_3$ (35 ml). The organic phase was dried over $MgSO_4$, filtered and concentrated under reduced pressure. The residue obtained was purified by flash chromatography, eluting with a gradient of DCM/heptane: from 50/50 to 100/00 to give 2.06 g (86%) of methyl 5-(((trifluoromethyl)sulfonyl)oxy)-2,3-dihydrobenzo[b]oxepine-8-carboxylate.

LC/MS (m/z, MH+): 353

Step 4: Methyl 5-(4,4,5,5-tetramethyl-1,3,2-dioxaborolan-2-yl)-2,3-dihydrobenzo[b]oxepine-8-carboxylate

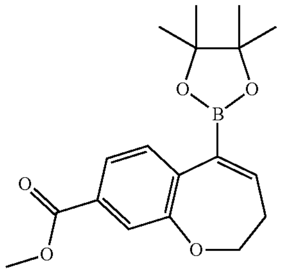

Step 4 of Intermediate 9 was prepared following a similar procedure to that of Intermediate 4 from methyl 5-(((trifluoromethyl)sulfonyl)oxy)-2,3-dihydrobenzo[b]oxepine-8-carboxylate to give 1.34 g (73%) of methyl 5-(4,4,5,5-tetramethyl-1,3,2-dioxaborolan-2-yl)-2,3-dihydrobenzo[b]oxepine-8-carboxylate.

LC/MS (m/z, MH+): 331

Step 5: Methyl 5-(4-((1-(3-fluoropropyl)azetidin-3-yl)methyl)phenyl)-2,3-dihydrobenzo[b]oxepine-8-carboxylate

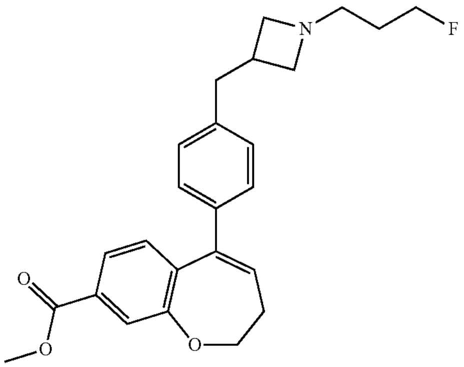

Step 5 of Intermediate 9 was prepared following a similar procedure to that of step 1 of Intermediate 7 from methyl 5-(4,4,5,5-tetramethyl-1,3,2-dioxaborolan-2-yl)-2,3-dihydrobenzo[b]oxepine-8-carboxylate and 3-(4-bromobenzyl)-1-(3-fluoropropyl)azetidine to give 230 mg (55%) methyl 5-(4-((1-(3-fluoropropyl)azetidin-3-yl)methyl)phenyl)-2,3-dihydrobenzo[b]oxepine-8-carboxylate.

LC/MS (m/z, MH+): 410

Step 6: Methyl 4-bromo-5-(4-((1-(3-fluoropropyl) azetidin-3-yl)methyl)phenyl)-2,3-dihydrobenzo[b] oxepine-8-carboxylate

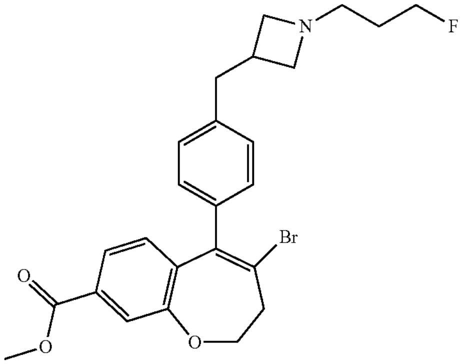 [SMILES: COC(=O)c1ccc2c(c1)OCCC(Br)=C2c1ccc(CC2CN(CCCF)C2)cc1]

Step 6 of Intermediate 9 was prepared following a similar procedure to that of step 2 of Intermediate 7 from methyl 5-(4-((1-(3-fluoropropyl)azetidin-3-yl)methyl)phenyl)-2,3-dihydrobenzo[b]oxepine-8-carboxylate to give 111 mg (40.5%) of methyl 4-bromo-5-(4-((1-(3-fluoropropyl)azetidin-3-yl)methyl)phenyl)-2,3-dihydrobenzo[b]oxepine-8-carboxylate.

Intermediate 10: Methyl 4-bromo-5-(4-((1-(3-fluoropropyl)azetidin-3-yl)methyl)phenyl)-2,3-dihydrobenzo[b]thiepine-8-carboxylate

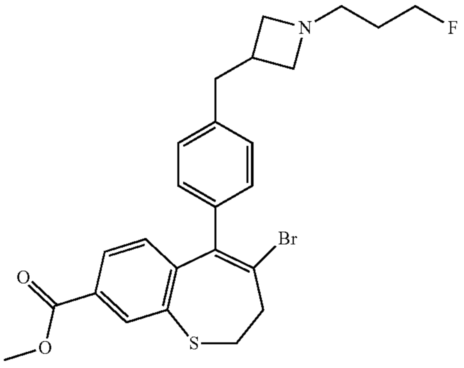 [SMILES: COC(=O)c1ccc2c(c1)SCCC(Br)=C2c1ccc(CC2CN(CCCF)C2)cc1]

Step 1: 5-oxo-2,3,4,5-tetrahydrobenzo[b]thiepine-8-yl trifluoromethanesulfonate

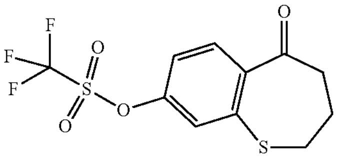 [SMILES: O=C1CCCSc2cc(OS(=O)(=O)C(F)(F)F)ccc21]

Step 1 of Intermediate 10 was prepared following a similar procedure to that of step 1 of Intermediate 9 from 8-hydroxy-3,4-dihydrobenzo[b]thiepine-5(2H)-one (prepared according to WO2018091153) to give 6.3 g (48%) of 5-oxo-2,3,4,5-tetrahydrobenzo[b]thiepine-8-yl trifluoromethanesulfonate.

LC/MS (m/z, MH+): 327

Step 2: Methyl 5-oxo-2,3,4,5-tetrahydrobenzo[b] thiepine-8-carboxylate

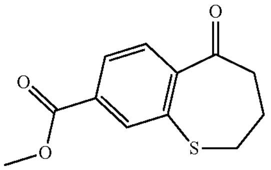

Step 2 of Intermediate 10 was prepared following a similar procedure to that of step 2 Intermediate 9 from 5-oxo-2,3,4,5-tetrahydrobenzo[b]thiepine-8-yl trifluoromethanesulfonate to give 6.36 g (94%) of methyl 5-oxo-2,3,4,5-tetrahydrobenzo[b]thiepine-8-carboxylate.

LC/MS (m/z, MH+): 237

Step 3: Methyl 5-(((trifluoromethyl)sulfonyl)oxy)-2,3-dihydrobenzo[b]thiepine-8-carboxylate

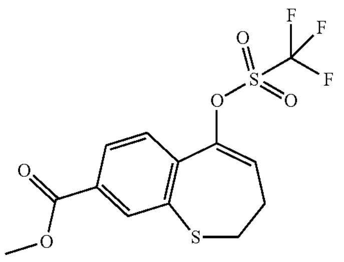

Step 3 of Intermediate 10 was prepared following a similar procedure to that of step 3 of Intermediate 9 from methyl-5-oxo-2,3,4,5-tetrahydrobenzo[b]thiepine-8-carboxylate to give 1.84 g (79%) of methyl 5-(((trifluoromethyl)sulfonyl)oxy)-2,3-dihydrobenzo[b]thiepine-8-carboxylate.

LC/MS (m/z, MH+): 369

Step 4: Methyl 5-(4,4,5,5-tetramethyl-1,3,2-dioxaborolan-2-yl)-2,3-dihydrobenzo[b]thiepine-8-carboxylate

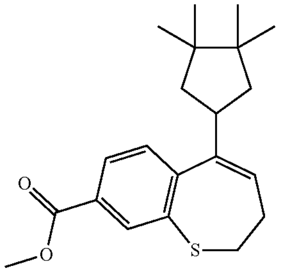

Step 4 of Intermediate 10 was prepared following a similar procedure to that of Intermediate 4 from methyl 5-(((trifluoromethyl)sulfonyl)oxy)-2,3-dihydrobenzo[b]thiepine-8-carboxylate to give 867 mg (50%) of methyl 5-(4,4,5,5-tetramethyl-1,3,2-dioxaborolan-2-yl)-2,3-dihydrobenzo[b]thiepine-8-carboxylate.

LC/MS (m/z, MH+): 347

Step 5: Methyl 5-(4-((1-(3-fluoropropyl)azetidin-3-yl)methyl)phenyl)-2,3-dihydrobenzo[b]thiepine-8-carboxylate

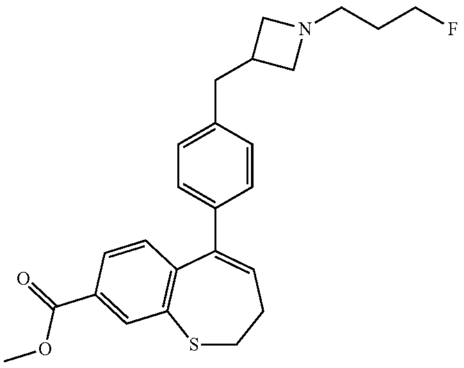 [SMILES: COC(=O)c1ccc2c(c1)SCCC=C2c1ccc(CC2CN(CCCF)C2)cc1]

Step 5 of Intermediate 10 was prepared following a similar procedure to that of step 1 Intermediate 7 from methyl 5-(4,4,5,5-tetramethyl-1,3,2-dioxaborolan-2-yl)-2,3-dihydrobenzo[b]thiepine-8-carboxylate and 3-(4-bromobenzyl)-1-(3-fluoropropyl)azetidine to give 650 mg (86%) of methyl 5-(4-((1-(3-fluoropropyl)azetidin-3-yl)methyl)phenyl)-2,3-dihydrobenzo[b]thiepine-8-carboxylate.

LC/MS (m/z, MH+): 410

Step 6: Methyl 4-bromo-5-(4-((1-(3-fluoropropyl)azetidin-3-yl)methyl)phenyl)-2,3-dihydrobenzo[b]thiepine-8-carboxylate

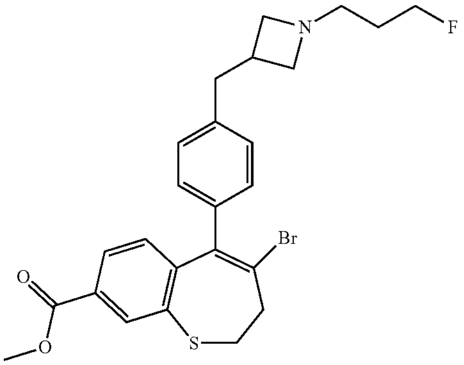

Step 6 of Intermediate 10 was prepared following a similar procedure to that of step 2 Intermediate 7 from methyl 5-(4-((1-(3-fluoropropyl)azetidin-3-yl)methyl)phenyl)-2,3-dihydrobenzo[b]thiepine-8-carboxylate to give 445 mg (84%) of methyl 4-bromo-5-(4-((1-(3-fluoropropyl)azetidin-3-yl)methyl)phenyl)-2,3-dihydrobenzo[b]thiepine-8-carboxylate.

LC/MS (m/z, MH+): 504

Intermediate 11: (4-bromophenyl)(3-fluoropropyl) azetidin-3-ylmethanone

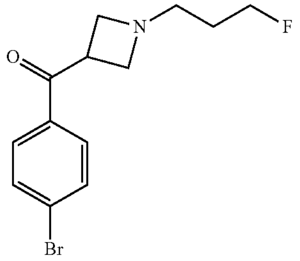 [SMILES: O=C(c1ccc(Br)cc1)C1CN(CCCF)C1]

Step 1: Tert-butyl 3-(4-bromobenzoyl)azetidine-1-carboxylate

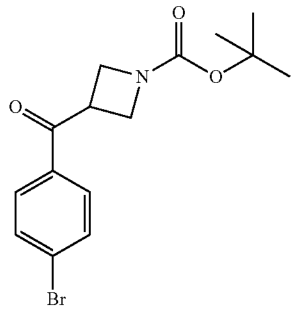 [SMILES: CC(C)(C)OC(=O)N1CC(C(=O)c2ccc(Br)cc2)C1]

To a solution of 1,4-dibromobenzene (290 g, 1.23 mol, 157 mL, 1.50 eq) in THF (1050 ml) was added n-BuLi (2.5 M, 491 ml, 1.50 eq) at −70° C. The mixture was stirred for 30 minutes before addition of 1-azetidinecarboxylic acid, 3-[(methoxymethylamino)carbonyl]-1,1-dimethylethyl ester (200 g, 819 mmol, 1.00 eq) in THF (420 mL) at −70° C. The mixture was stirred for 1.5 hours. The solution was warmed up to −25° C. and slowly quenched by aqueous saturated $NH_4Cl$ (2000 ml). The mixture was extracted twice with MTBE (800 ml), dried over $Na_2SO_4$, filtered, and concentrated under reduced pressure. The obtained residue was purified by flash chromatography eluting with a gradient of petroleum ether/EtOAc from 10/1 to 0/1 to give 180 g (65%) of tert-butyl 3-(4-bromobenzoyl)azetidine-1-carboxylate as a white solid.

LC/MS (m/z, MH+): 340

Step 2: 3-Azetidinyl(4-bromophenyl)-methanone, trifluoroacetic Acid

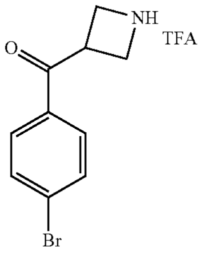 [SMILES: O=C(c1ccc(Br)cc1)C1CNC1]

To a solution of tert-butyl 3-(4-bromobenzoyl)azetidine-1-carboxylate (40 g, 117 mmol) in DCM (200 ml) was added TFA (88.6 g, 777 mmol, 57.5 ml). The mixture was stirred at 15° C. for 2 hours. The reaction mixture was concentrated under reduced pressure to give 41.6 g (100%) of 3-azetidinyl (4-bromophenyl)-methanone, trifluoroacetic acid.

LC/MS (m/z, MH+): 240

Step 3: (4-bromophenyl)(3-fluoropropyl)azetidin-3-ylmethanone

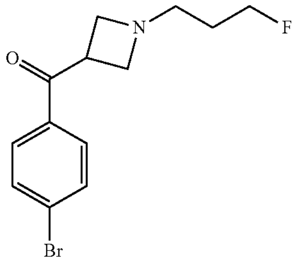 [SMILES: O=C(c1ccc(Br)cc1)C1CN(CCCF)C1]

Step 3 of Intermediate 11 was prepared following a similar procedure to that of Method 2 of Intermediate 1 from 3-azetidinyl(4-bromophenyl)-methanone, trifluoroacetic acid to give 20 g (54%) of (4-bromophenyl)(3-fluoropropyl) azetidin-3-ylmethanone.

LC/MS (m/z, MH+): 300

Intermediate 12: 3-((4-bromophenyl)difluoromethyl)-1-(3-fluoropropyl)azetidine

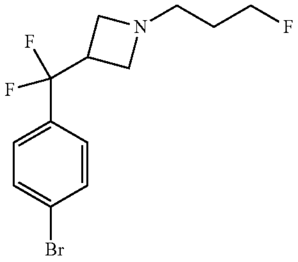 [SMILES: FCCCN1CC(C(F)(F)c2ccc(Br)cc2)C1]

Step 1: Tert-butyl 3-((4-bromophenyl)difluoromethyl)azetidine-1-carboxylate

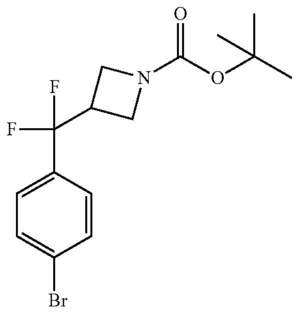 [SMILES: CC(C)(C)OC(=O)N1CC(C(F)(F)c2ccc(Br)cc2)C1]

To a solution of tert-butyl 3-(4-bromobenzoyl)azetidine-1-carboxylate (40 g, 117 mmol) in DCM (200 ml) was added Deoxo-Fluor (260 g, 1.18 mol, 257 ml). The mixture was stirred at 40° C. for 48 hours. The mixture was poured into ice and aqueous saturated solution of $NaHCO_3$ (1000 ml) and extracted with DCM (300 ml), the organic layer was dried over $Na_2SO_4$, filtered, and concentrated under reduced pressure. The residue obtained was purified by flash chromatography eluting with a gradient of petroleum ether/EtOAc from 98/02 to 00/100 to give 36 g (85%) of tert-butyl 3-((4-bromophenyl)difluoromethyl)azetidine-1-carboxylate as a yellow oil.

LC/MS (m/z, MH+): 362

Step 2: 3-[(4-bromophenyl)difluoromethyl]-azetidine, trifluoroacetic Acid

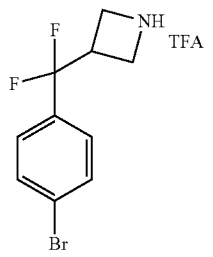

Step 2 of Intermediate 12 was prepared following a similar procedure to that of step 2 of Intermediate 11 from tert-butyl 3-((4-bromophenyl)difluoromethyl)azetidine-1-carboxylate to give 37.4 g (100%) of 3-[(4-bromophenyl)difluoromethyl]-azetidine, trifluoroacetic acid as a yellow solid.

LC/MS (m/z, MH+): 262

Step 3: 3-((4-bromophenyl)difluoromethyl)-1-(3-fluoropropyl)azetidine

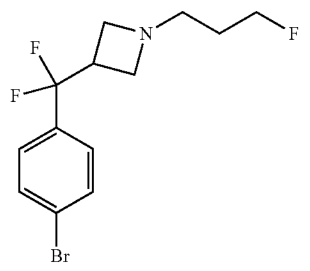 [SMILES: FCCCN1CC(C(F)(F)c2ccc(Br)cc2)C1]

Step 3 of Intermediate 12 was prepared following a similar procedure to that of Intermediate 1 Method 2 from 3-[(4-bromophenyl)difluoromethyl]-azetidine, trifluoroacetic acid to give 13.3 g (41%) of 3-((4-bromophenyl)difluoromethyl)-1-(3-fluoropropyl)azetidine as a yellow oil.

LC/MS (m/z, MH+): 322

Intermediate 13: Methyl 8-bromo-9-(4-(difluoro(1-(3-fluoropropyl)azetidin-3-yl)methyl)phenyl)-6,7-dihydro-5H-benzo[7]annulene-3-carboxylate

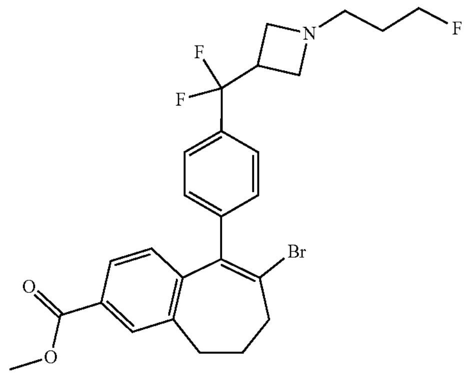 [SMILES: COC(=O)c1ccc2c(c1)CCCC(Br)=C2c1ccc(C(F)(F)C2CN(CCCF)C2)cc1]

Step 1: Methyl 9-(4-(difluoro(1-(3-fluoropropyl)azetidin-3-yl)methyl)phenyl)-6,7-dihydro-5H-benzo[7]annulene-3-carboxylate

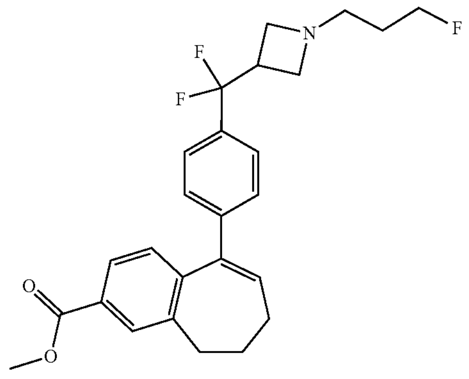 [SMILES: COC(=O)c1ccc2c(c1)CCCC=C2c1ccc(C(F)(F)C2CN(CCCF)C2)cc1]

Step 1 of Intermediate 13 was prepared following a similar procedure to that of step 1 of Intermediate 7 from 3-((4-bromophenyl)difluoromethyl)-1-(3-fluoropropyl)azetidine (Intermediate 12) to give 3.5 g (99%) of methyl 9-(4-(difluoro(1-(3-fluoropropyl)azetidin-3-yl)methyl)phenyl)-6,7-dihydro-5H-benzo[7]annulene-3-carboxylate as a yellow oil.

LC/MS (m/z, MH+): 444

Step 2: Methyl 8-bromo-9-(4-(difluoro(1-(3-fluoropropyl)azetidin-3-yl)methyl)phenyl)-6,7-dihydro-5H-benzo[7]annulene-3-carboxylate

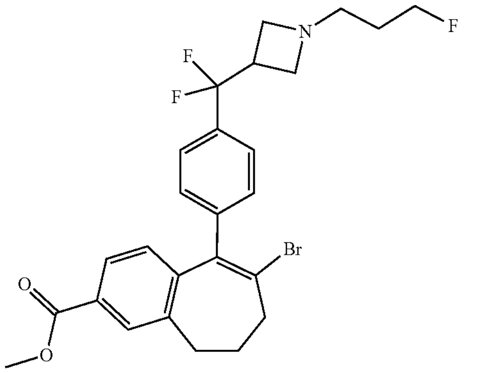 [SMILES: COC(=O)c1ccc2c(c1)CCCC(Br)=C2c1ccc(C(F)(F)C2CN(CCCF)C2)cc1]

Step 2 of Intermediate 13 was prepared following a similar procedure to that of step 2 of Intermediate 7 from methyl 9-(4-(difluoro(1-(3-fluoropropyl)azetidin-3-yl)methyl)phenyl)-6,7-dihydro-5H-benzo[7]annulene-3-carboxylate to give 3.48 g (84%) of methyl 8-bromo-9-(4-(difluoro(1-(3-fluoropropyl)azetidin-3-yl)methyl)phenyl)-6,7-dihydro-5H-benzo[7]annulene-3-carboxylate as a brown oil.

LC/MS (m/z, MH+): 522

Intermediates 14 and 15: (4-bromophenyl)(1-(3-fluoropropyl)azetidin-3-yl)methanol Isomer 1 and Isomer 2

Isomer 1

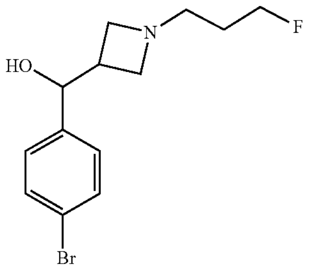

and

Isomer 2

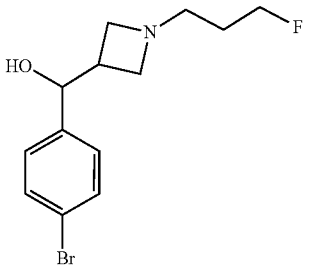

To a solution of (4-bromophenyl)(3-fluoropropyl)azetidin-3-ylmethanone Intermediate 11 (20.0 g, 66.6 mmol) in MeOH (100 ml) was added $NaBH_4$ (5.04 g, 133 mmol) at 0° C. The mixture was stirred at 15° C. for 1 hour. The reaction mixture was slowly quenched by water (100 mL) and concentrated to remove MeOH. The aqueous layer was extracted three times with EtOAc (80 ml). After decantation, the organic layer was dried over $Na_2SO_4$, filtered, and concentrated under reduced pressure. The residue was purified by flash chromatography eluting with a gradient of DCM:MeOH from 98/02 to 90/10 to give 16.0 g (77%) of (4-bromophenyl)(1-(3-fluoropropyl)azetidin-3-yl)methanol as mixture of two isomers.

LC/MS (m/z, MH+): 302

The mixture of two isomers of (4-bromophenyl)(1-(3-fluoropropyl)azetidin-3-yl)methanol was separated by SFC (condition: flash DAICEL CHIRALPAK AD (250×50 mm, 10 μm); supercritical $CO_2$ 80%/MeOH 20%/[0.1% $NH_4OH$ MeOH] to give 5.3 g of isomer 1 and 5.2 g of isomer 2.

Intermediates 16 and 17: 3-((4-bromophenyl)fluoromethyl)-1-(3-fluoropropyl)azetidine Isomer 1 and Isomer 2

Isomer 1

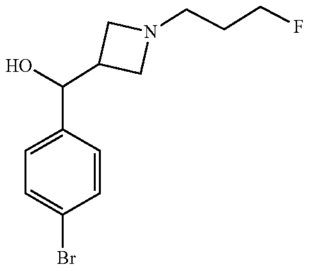

and

Isomer 2

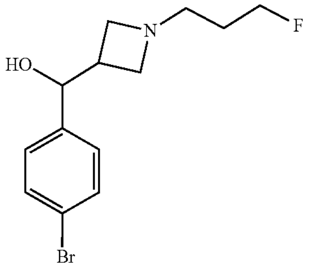

To a solution of racemic (4-bromophenyl)(1-(3-fluoropropyl)azetidin-3-yl)methanol (Intermediates 14 and 15) (30.0 g, 99.3 mmol) in DCM (150 ml) was added Deoxo-Fluor (26.4 g, 119 mmol, 26.1 ml) at −70° C. The mixture was stirred at 15° C. for 0.5 hour. The mixture was quenched by aqueous saturated solution of $NaHCO_3$ (500 ml) and extracted with DCM (200 ml). After decantation, the organic layer was dried over $Na_2SO_4$, filtered, concentrated under reduced pressure and the residue obtained was purified by flash chromatography eluting with a gradient of petroleum ether/EtOAc from 98/02 to 00/100 to give 10.5 g (32%) of 3-((4-bromophenyl)fluoromethyl)-1-(3-fluoropropyl)azetidine as mixture of two isomers.

LC/MS (m/z, MH+): 304

The mixture of two isomers of 3-((4-bromophenyl)fluoromethyl)-1-(3-fluoropropyl)azetidine was separated by SFC (condition: flash DAICEL CHIRALPAK AD (250×50 mm, 10 μm); supercritical $CO_2$ 60%/MeOH 40%/[0.1% $NH_4OH$ MeOH] to give 5.9 g of Isomer 1 and 6.3 g of Isomer 2.

Intermediate 18: Methyl 8-bromo-9-(4-(fluoro(1-(3-fluoropropyl)azetidin-3-yl)methyl)phenyl)-6,7-dihydro-5H-benzo[7]annulene-3-carboxylate, Isomer 1

Isomer 1

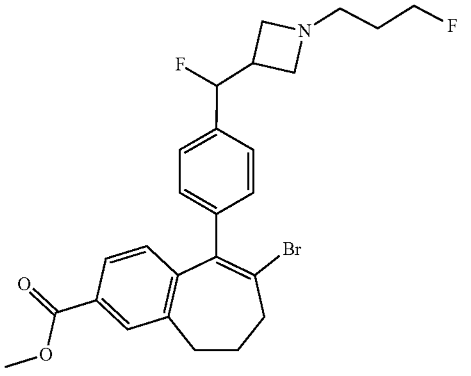

Step 1: Methyl 9-(4-(fluoro(1-(3-fluoropropyl)azetidin-3-yl)methyl)phenyl)-6,7-dihydro-5H-benzo[7]annulene-3-carboxylate, Isomer 1

Isomer 1

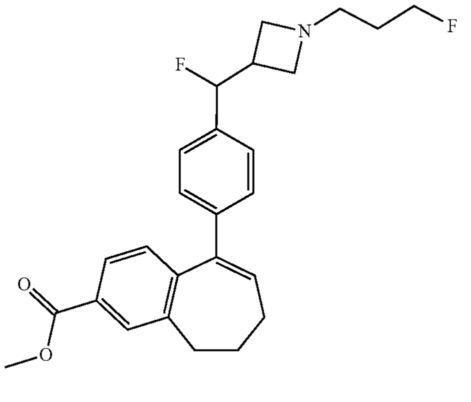

Step 1 of Intermediate 18 was prepared following a similar procedure to that of Step 1 of Intermediate 7 from methyl 9-(4,4,5,5-tetramethyl-1,3,2-dioxaborolan-2-yl)-6,7-dihydro-5H-benzo[7]annulene-3-carboxylate and 3-((4-bromophenyl)fluoromethyl)-1-(3-fluoropropyl)azetidine Isomer 1 to give 1.18 g (84%) of methyl 9-(4-(fluoro(1-(3-fluoropropyl)azetidin-3-yl)methyl)phenyl)-6,7-dihydro-5H-benzo[7]annulene-3-carboxylate, Isomer 1.

LC/MS (m/z, MH+): 426

Step 2: Methyl 8-bromo-9-(4-(fluoro(1-(3-fluoropropyl)azetidin-3-yl)methyl)phenyl)-6,7-dihydro-5H-benzo[7]annulene-3-carboxylate, Isomer 1

Isomer 1

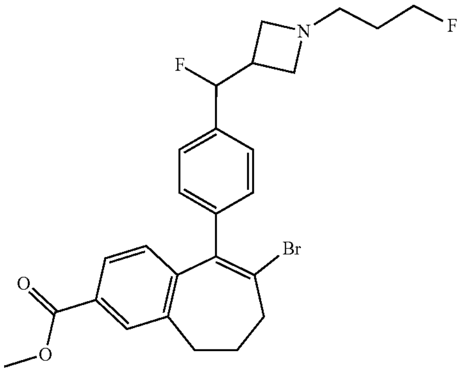

Step 2 of Intermediate 18 was prepared following a similar procedure to that of Step 2 of Intermediate 7 from methyl 9-(4-(fluoro(1-(3-fluoropropyl)azetidin-3-yl)methyl)phenyl)-6,7-dihydro-5H-benzo[7]annulene-3-carboxylate, Isomer 1 to give 833 mg (60%) of methyl 8-bromo-9-(4-(fluoro(1-(3-fluoropropyl)azetidin-3-yl)methyl)phenyl)-6,7-dihydro-5H-benzo[7]annulene-3-carboxylate, Isomer 1.

LC/MS (m/z, MH+): 504

Intermediate 19: Methyl 8-bromo-9-(4-(fluoro(1-(3-fluoropropyl)azetidin-3-yl)methyl)phenyl)-6,7-dihydro-5H-benzo[7]annulene-3-carboxylate, Isomer 2

Isomer 2

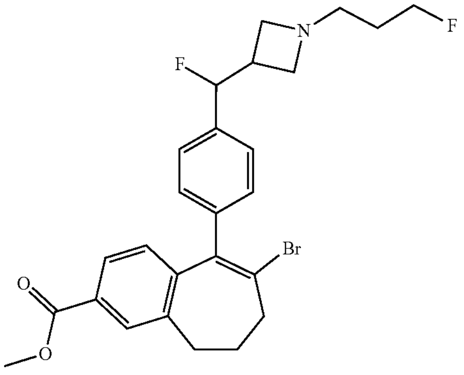

Step 1: Methyl 9-(4-(fluoro(1-(3-fluoropropyl)azetidin-3-yl)methyl)phenyl)-6,7-dihydro-5H-benzo[7]annulene-3-carboxylate, Isomer 2

Isomer 2

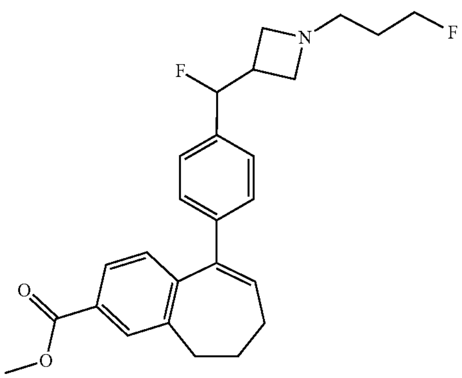

Step 1 of Intermediate 19 was prepared following a similar procedure to that of Step 1 of Intermediate 7 from 3-((4-bromophenyl)fluoromethyl)-1-(3-fluoropropyl)azetidine Isomer 2 to give 2.59 g (92%) of methyl 9-(4-(fluoro(1-(3-fluoropropyl)azetidin-3-yl)methyl)phenyl)-6,7-dihydro-5H-benzo[7]annulene-3-carboxylate, Isomer 2.

LC/MS (m/z, MH+): 426

Step 2: Methyl 8-bromo-9-(4-(fluoro(1-(3-fluoropropyl)azetidin-3-yl)methyl)phenyl)-6,7-dihydro-5H-benzo[7]annulene-3-carboxylate, Isomer 2

Isomer 2

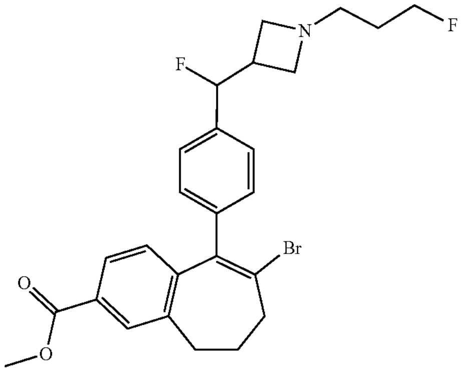

Step 2 of Intermediate 19 was prepared following a similar procedure to that of Step 2 of Intermediate 7 from methyl 9-(4-(fluoro(1-(3-fluoropropyl)azetidin-3-yl)methyl)phenyl)-6,7-dihydro-5H-benzo[7]annulene-3-carboxylate, Isomer 2 to give 1.03 g (36%) of methyl 8-bromo-9-(4-(fluoro(1-(3-fluoropropyl)azetidin-3-yl)methyl)phenyl)-6,7-dihydro-5H-benzo[7]annulene-3-carboxylate, Isomer 2.

LC/MS (m/z, MH+): 504

Intermediate 20: 3-(4-bromobenzyl)-3-fluoro-1-(3-fluoropropyl)azetidine

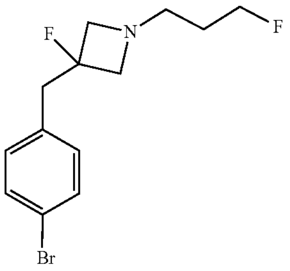 [SMILES: FCCCN1CC(F)(Cc2ccc(Br)cc2)C1]

Step 1: Tert-butyl 3-(4-bromobenzylidene)azetidine-1-carboxylate

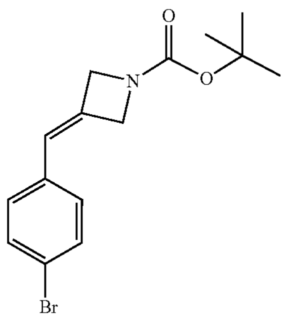 [SMILES: CC(C)(C)OC(=O)N1CC(=Cc2ccc(Br)cc2)C1]

To a solution of (4-bromobenzyl)triphenylphosphonium bromide (79.2 g, 155 mmol) in DMF (400 ml) was added NaH (6.18 g, 155 mmol) at 0° C. The mixture was stirred at 0° C. for 15 min. To this reaction mixture, a solution of tert-butyl 3-oxoazetidine-1-carboxylate (24.1 g, 141 mmol) in DMF (160 ml) was added. The mixture was stirred at 20° C. for 9 hours. The reaction mixture was quenched by addition of $NH_4Cl$ (100 ml) at 0° C. The reaction mixture was filtered and the filtrate was concentrated under reduced pressure to give 60.0 g (crude) of tert-butyl 3-(4-bromobenzylidene)azetidine-1-carboxylate as a yellow solid.

LC/MS (m/z, MH+): 324

Step 2: Tert-butyl 2-(4-bromophenyl)-1-oxa-5-azaspiro[2.3]hexane-5-carboxylate

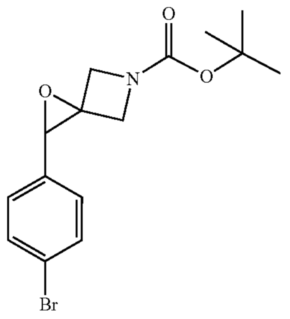 [SMILES: CC(C)(C)OC(=O)N1CC2(C1)OC2c1ccc(Br)cc1]

To a solution of tert-butyl 3-(4-bromobenzylidene)azetidine-1-carboxylate (72.0 g, 222 mmol) in DCM (500 ml) was added m-CPBA (57.5 g, 266 mmol, 80% purity). The mixture was stirred at 50° C. for 12 hours. The reaction mixture was quenched by addition of $NaHSO_3$ aqueous solution (650 ml) at 0° C., and then diluted with EtOAc (500 ml) and extracted with EtOAc (300 ml×2). The combined organic layers were dried over $Na_2SO_4$, filtered and concentrated under reduced pressure. The residue obtained was purified by flash chromatography eluting with a gradient of Petroleum ether/EtOAc from 00/100 to 90/10 to give 35.0 g (46.3%) of tert-butyl 2-(4-bromophenyl)-1-oxa-5-azaspiro[2.3]hexane-5-carboxylate as a yellow solid.

LC/MS (m/z, MH+): 340

Step 3: Tert-butyl 3-(4-bromobenzyl)-3-hydroxyazetidine-1-carboxylate

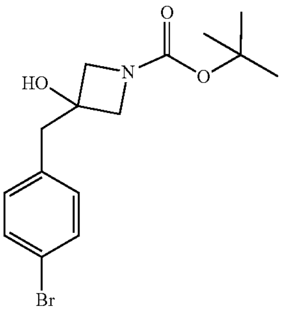 [SMILES: CC(C)(C)OC(=O)N1CC(O)(Cc2ccc(Br)cc2)C1]

To a solution of tert-butyl 2-(4-bromophenyl)-1-oxa-5-azaspiro[2.3]hexane-5-carboxylate (35.0 g, 103 mmol) in THF (200 ml) was added $LiAlH_4$ (4.30 g, 113 mmol) at −70° C. The mixture was stirred at −70° C. for 2 hours. The reaction mixture was quenched by water (100 ml), and then extracted with EtOAc (100 ml). After decantation, the organic phase was dried over $MgSO_4$, filtered, concentrated under reduced pressure and the residue obtained was purified by flash chromatography eluting with a gradient of petroleum ether/EtOAc from 99/01 to 90/10 to give 28 g (79.5%) of tert-butyl 3-(4-bromobenzyl)-3-hydroxyazetidine-1-carboxylate as a white solid.

LC/MS (m/z, MH+): 342

Step 4: tert-butyl 3-(4-bromobenzyl)-3-fluoroazetidine-1-carboxylate

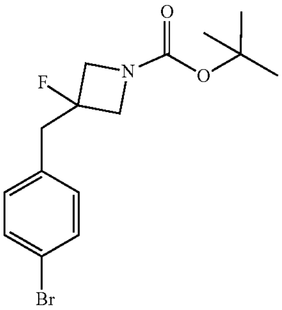 [SMILES: CC(C)(C)OC(=O)N1CC(F)(Cc2ccc(Br)cc2)C1]

To a solution of tert-butyl 3-(4-bromobenzyl)-3-hydroxyazetidine-1-carboxylate (10.0 g, 29.2 mmol) in DCM (60.0 ml) was added deoxo fluor (5.65 g, 35.1 mmol, 4.63 ml) at −70° C. The mixture was stirred at −60° C. for 2 hours. The reaction mixture was quenched by water (60 ml). After decantation, the organic layer was dried over $MgSO_4$, filtered, concentrated under reduced pressure and the residue obtained was purified by flash chromatography eluting with a gradient of petroleum ether/EtOAc from 99/01 to 95/05 to give 10 g (50%) of tert-butyl 3-(4-bromobenzyl)-3-fluoroazetidine-1-carboxylate as a white solid.

LC/MS (m/z, MH+): 344

Step 5: 3-(4-Bromobenzyl)-3-fluoroazetidine, trifluoroacetic Acid

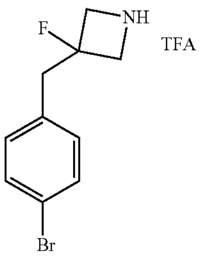 [SMILES: FC1(Cc2ccc(Br)cc2)CNC1]

Step 5 of Intermediate 20 was prepared following a similar procedure to that of step 2 of Intermediate 11 from 1-azetidinecarboxylic acid, 3-[(4-bromophenyl)methyl]-3-fluoro-1,1-dimethylethyl ester to give 9.80 g (94%) of 3-(4-bromobenzyl)-3-fluoroazetidine, trifluoroacetic acid as a crude product which was used into the next step without further purification.

LC/MS (m/z, MH+): 244

Step 6: 3-(4-Bromobenzyl)-3-fluoro-1-(3-fluoropropyl)azetidine

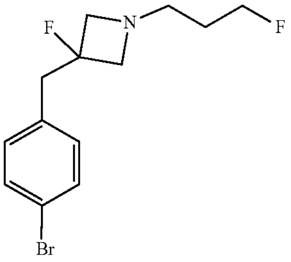 [SMILES: FCCCN1CC(F)(Cc2ccc(Br)cc2)C1]

Step 6 of Intermediate 20 was prepared following a similar procedure to that of Method 2 of Intermediate 1 from 3-(4-bromobenzyl)-3-fluoroazetidine, trifluoroacetic acid to give 5.10 g (61.3%) of 3-(4-bromobenzyl)-3-fluoro-1-(3-fluoropropyl)azetidine.

LC/MS (m/z, MH+): 304

Intermediate 21: Methyl 8-bromo-9-(4-((3-fluoro-1-(3-fluoropropyl)azetidin-3-yl)methyl)phenyl)-6,7-dihydro-5H-benzo[7]annulene-3-carboxylate

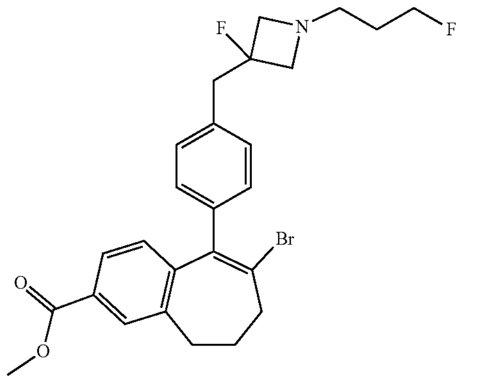 [SMILES: COC(=O)c1ccc2c(c1)CCCC(Br)=C2c1ccc(CC2(F)CN(CCCF)C2)cc1]

Step 1: Methyl 9-(4-((3-fluoro-1-(3-fluoropropyl)azetidin-3-yl)methyl)phenyl)-6,7-dihydro-5H-benzo[7]annulene-3-carboxylate

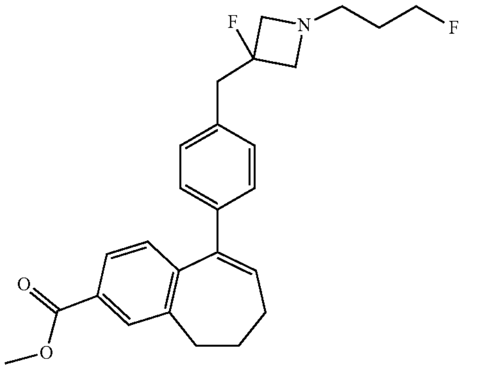 [SMILES: COC(=O)c1ccc2c(c1)CCCC=C2c1ccc(CC2(F)CN(CCCF)C2)cc1]

Step 1 of Intermediate 21 was prepared following a similar procedure to that of Step 1 of Intermediate 7 from methyl 9-(4,4,5,5-tetramethyl-1,3,2-dioxaborolan-2-yl)-6,7-dihydro-5H-benzo[7]annulene-3-carboxylate and 3-(4-bromobenzyl)-3-fluoro-1-(3-fluoropropyl)azetidine to give 0.93 g (71%) of methyl 9-(4-((3-fluoro-1-(3-fluoropropyl)azetidin-3-yl)methyl)phenyl)-6,7-dihydro-5H-benzo[7]annulene-3-carboxylate.

LC/MS (m/z, MH+): 426

Step 2: Methyl 8-bromo-9-(4-((3-fluoro-1-(3-fluoropropyl)azetidin-3-yl)methyl)phenyl)-6,7-dihydro-5H-benzo[7]annulene-3-carboxylate

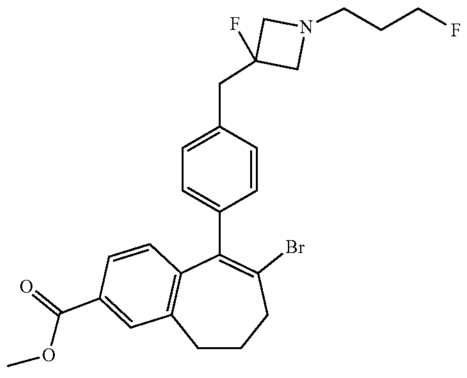 [SMILES: COC(=O)c1ccc2c(c1)CCCC(Br)=C2c1ccc(CC2(F)CN(CCCF)C2)cc1]

Step 2 of Intermediate 21 was prepared following a similar procedure to that of Step 2 of Intermediate 7 from methyl 9-(4-((3-fluoro-1-(3-fluoropropyl)azetidin-3-yl)methyl)phenyl)-6,7-dihydro-5H-benzo[7]annulene-3-carboxylate to give 404 mg (59%) of methyl 8-bromo-9-(4-((3-fluoro-1-(3-fluoropropyl)azetidin-3-yl)methyl)phenyl)-6,7-dihydro-5H-benzo[7]annulene-3-carboxylate.

LC/MS (m/z, MH+): 504

Intermediate 22: 3-(4-Bromobenzyl)-1-(3-fluoropropyl)azetidin-3-ol

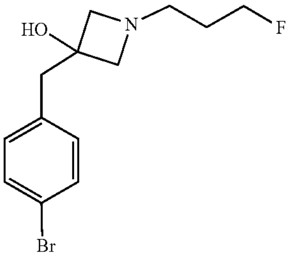 [SMILES: OC1(Cc2ccc(Br)cc2)CN(CCCF)C1]

Step 1: 3-(4-Bromobenzyl)azetidin-3-ol, trifluoroacetic Acid

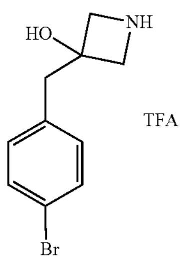 [SMILES: OC1(Cc2ccc(Br)cc2)CNC1]

Step 1 of Intermediate 22 was prepared following a similar procedure to that of Step 2 of Intermediate 11 from tert-butyl 3-(4-bromobenzyl)-3-hydroxyazetidine-1-carboxylate to give 36.8 g (76%) of 3-(4-bromobenzyl)azetidin-3-ol, trifluoroacetic acid as a yellow solid.

LC/MS (m/z, MH+): 242

Step 2: 3-(4-Bromobenzyl)-1-(3-fluoropropyl)azetidin-3-ol

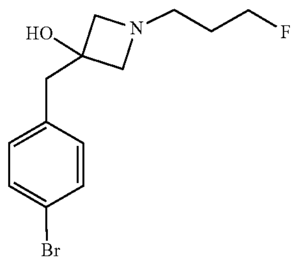 [SMILES: OC1(Cc2ccc(Br)cc2)CN(CCCF)C1]

Step 2 of Intermediate 22 was prepared following a similar procedure to that of Method 1 of Intermediate 1 from 3-(4-bromobenzyl)azetidin-3-ol, trifluoroacetic acid to give 10 g (31%) of 3-(4-bromobenzyl)-1-(3-fluoropropyl)azetidin-3-ol.

LC/MS (m/z, MH+): 302

Intermediate 23: 3-(4-Bromobenzyl)-1-(3-fluoropropyl)azetidin-3-ol

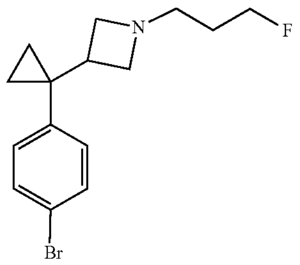 [SMILES: FCCCN1CC(C2(c3ccc(Br)cc3)CC2)C1]

A mixture of commercially available 3-(1-(4-bromophenyl)cyclopropyl)azetidine hydrochloride (0.3 g, 1.04 mmol), $K_2CO_3$ (0.36 g, 2.6 mmol) and 1-fluoro-3-iodopropane (108.5 μL, 1.06 mmol) in acetonitrile (20 mL) was stirred overnight at room temperature. It was then concentrated under reduced pressure. The residue was taken into EtOAc and water. The organic layer was separated and dried over $Na_2SO_4$, filtered and concentrated under reduced pressure. The residue obtained was purified by flash chromatography, eluting with a gradient of DCM/MeOH: from 95/5 to 90/10 to give 0.1 g (31%) of 3-(4-bromobenzyl)-1-(3-fluoropropyl)azetidin-3-ol as a brown oil.

LC/MS (m/z, MH+): 312

Intermediate 24: 3-(4-Bromobenzyl)-1-(3-fluoropropyl)-3-methylazetidine

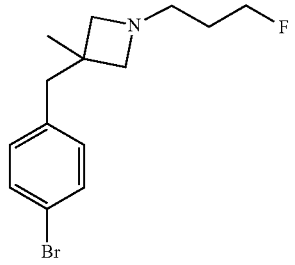 [SMILES: CC1(Cc2ccc(Br)cc2)CN(CCCF)C1]

Intermediate 24 was prepared following a similar procedure to that of Intermediate 23 from commercially available 3-(4-bromobenzyl)-3-methylazetidine hydrochloride to give 295 mg (90%) of 3-(4-bromobenzyl)-1-(3-fluoropropyl)-3-methylazetidine as a yellow oil.

LC/MS (m/z, MH+): 300

Intermediate 25: 3-(Azido(4-bromophenyl)methyl)-1-(3-fluoropropyl)azetidine Isomer 1

Isomer 1

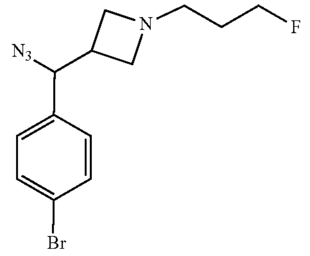

Step 1: 3-((4-Bromophenyl)chloromethyl)-1-(3-fluoropropyl)azetidine Isomer 1

Isomer 1

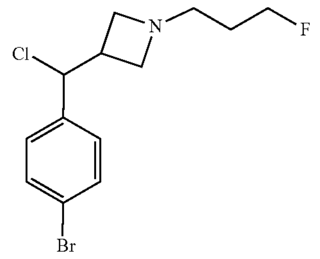

To a solution of (4-bromophenyl)(1-(3-fluoropropyl)azetidin-3-yl)methanol Isomer 1 (1 g, 3.31 mmol) in DCM (40 mL) at 0° C. was slowly added thionyl chloride (0.48 mL, 6.62 mmol). The mixture was stirred at room temperature for 3 hours. DCM (75 mL) and saturated aqueous $NaHCO_3$ (200 mL) were added. The organic layer was separated, dried over $Na_2SO_4$, filtered and concentrated under reduced pressure to give 1 g (94%) of 3-((4-bromophenyl)chloromethyl)-1-(3-fluoropropyl)azetidine Isomer 1 as a yellow oil.

LC/MS (m/z, MH+): 320

Step 2: 3-(Azido(4-bromophenyl)methyl)-1-(3-fluoropropyl)azetidine Isomer 1

Isomer 1

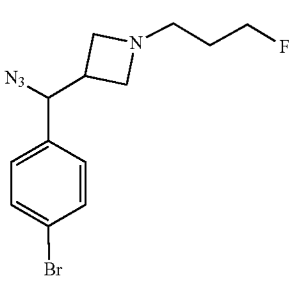

To a solution of 3-((4-bromophenyl)chloromethyl)-1-(3-fluoropropyl)azetidine Isomer 1 (0.65 g, 2.03 mmol) in DMF (20 mL) was added sodium azide (269 mg, 4.05 mmol). The mixture was stirred at 78° C. for 4 hours. Ether (100 mL) and water (100 mL) were added. The aqueous layer was separated and extracted three times with ether (100 mL). The combined organic layers were dried over $Na_2SO_4$, filtered and concentrated under reduced pressure. The residue was purified by flash chromatography, eluting with a gradient of DCM/MeOH: from 100/0 to 95/5 to give 0.55 g (83%) of 3-(azido(4-bromophenyl)methyl)-1-(3-fluoropropyl)azetidine Isomer 1 as a colorless oil.

LC/MS (m/z, MH+): 327

Intermediate 26: 3-(Azido(4-bromophenyl)methyl)-1-(3-fluoropropyl)azetidine Isomer 2

Isomer 2

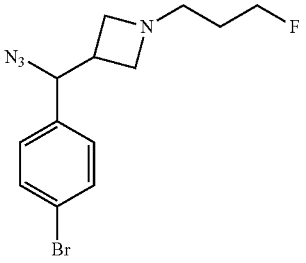

Step 1: 3-((4-Bromophenyl)chloromethyl)-1-(3-fluoropropyl)azetidine Isomer 2

Isomer 1

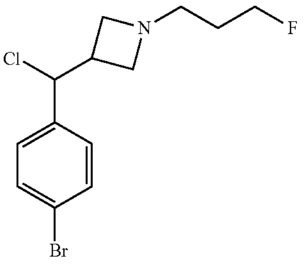

Step 1 of Intermediate 26 was prepared following a similar procedure to that of step 1 of Intermediate 25 from (4-bromophenyl)(1-(3-fluoropropyl)azetidin-3-yl)methanol Isomer 2 to give 1.1 g (95%) of 3-((4-bromophenyl)chloromethyl)-1-(3-fluoropropyl)azetidine Isomer 2 as a yellow oil.

LC/MS (m/z, MH+): 320

Step 2: 3-(Azido(4-bromophenyl)methyl)-1-(3-fluoropropyl)azetidine Isomer 2

Isomer 2

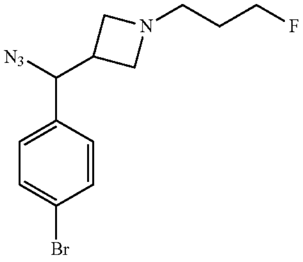

Step 2 of Intermediate 26 was prepared following a similar procedure to that of step 2 of Intermediate 25 from 3-((4-bromophenyl)chloromethyl)-1-(3-fluoropropyl)azetidine Isomer 2 to give 0.64 g (96%) of 3-(azido(4-bromophenyl)methyl)-1-(3-fluoropropyl)azetidine Isomer 2 as a yellow oil.

LC/MS (m/z, MH+): 327

Intermediate 27: 3-(4-Bromobenzyl)-1-(3,3-difluoropropyl)azetidine

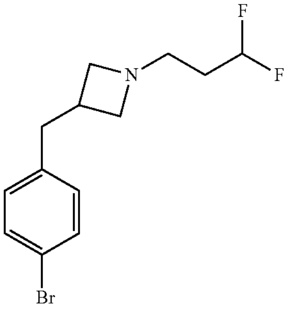 [SMILES: FC(F)CCN1CC(Cc2ccc(Br)cc2)C1]

Step 1: 3,3-Difluoropropyl Trifluoromethanesulfonate

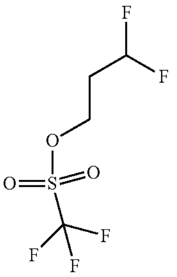 [SMILES: O=S(=O)(OCCC(F)F)C(F)(F)F]

To a solution of 3,3-difluoropropan-1-ol (1 g, 10.41 mmol) and 2,6-lutidine (2.66 mL, 22.9 mmol) in DCM (20 mL) at 0° C. was dropwise added trifluoromethanesulfonic anhydride (1.93 mL, 11.45 mmol). The mixture was stirred at 0° C. for 30 minutes. Ether and water were added. The aqueous layer was separated and extracted three times with ether. The combined organic layers were twice washed with a 10% aqueous solution of citric acid then water and dried over $Na_2SO_4$, filtered and concentrated under reduced pressure to give 2.06 g (86%) of 3,3-difluoropropyl trifluoromethanesulfonate which was used in the next step without further purification.

Step 2: 3-(4-Bromobenzyl)-1-(3,3-difluoropropyl)azetidine

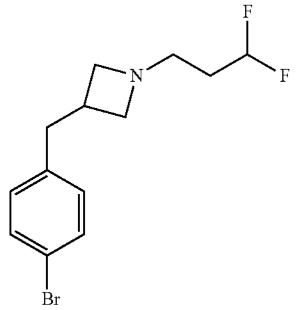 [SMILES: FC(F)CCN1CC(Cc2ccc(Br)cc2)C1]

To a suspension of 3-(4-bromobenzyl)azetidine para-toluene sulfonate (5 g, 12.55 mmol), 3,3-difluoropropyl trifluoromethanesulfonate (3.44 g, 15.06 mmol) in DCM (100 mL) was added a 1N aqueous solution of sodium hydroxide (31.38 mL, 31.38 mmol). The mixture was stirred at room temperature for 4 hours. Water (100 mL) was added. The aqueous layer was separated and extracted twice with ether (100 mL). The combined organic layers were dried over $Na_2SO_4$, filtered and concentrated under reduced pressure. The residue was purified by flash chromatography, eluting with a gradient of DCM/MeOH: from 100/0 to 80/20 to give 1.71 g (45%) of 3-(4-bromobenzyl)-1-(3,3-difluoropropyl)azetidine as a yellow oil.

LC/MS (m/z, MH+): 304

Intermediate 28: (3-(4-bromo-3-fluorobenzyl)-1-(3-fluoropropyl)azetidine

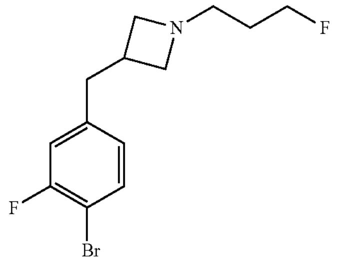 [SMILES: FCCCN1CC(Cc2ccc(Br)c(F)c2)C1]

Step 1: (tert-butyl(E)-3-((2-tosylhydrazono)methyl)azetidine-1-carboxylate

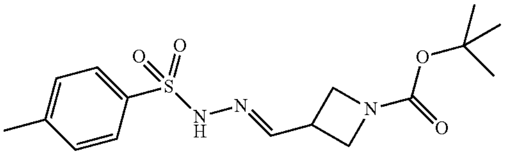 [SMILES: Cc1ccc(S(=O)(=O)N/N=C/C2CN(C(=O)OC(C)(C)C)C2)cc1]

A solution of 4-methylbenzenesulfonohydrazide (2.01 g, 10.80 mmol) and tert-butyl-3-formylazetidine-1-carboxylate (2 g, 10.80 mmol) in 1,4-dioxane (40 ml) was stirred at 80° C. for two hours. After cooling down to room temperature, the reaction mixture was concentrated under reduced pressure. The resulting residue was then transferred in a separating funnel containing an aqueous saturated solution of NaCl. The mixture was extracted three times with EtOAc. The combined organic layers were then dried over $MgSO_4$, filtered and concentrated to dryness to give 3.775 g (99%) of (tert-butyl(E)-3-((2-tosylhydrazono)methyl)azetidine-1-carboxylate.

LC/MS (m/z, MH+): 354

Step 2: (tert-butyl 3-(4-bromo-3-fluorobenzyl)azetidine-1-carboxylate

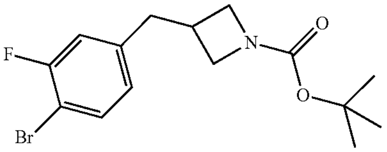 [SMILES: CC(C)(C)OC(=O)N1CC(Cc2ccc(Br)c(F)c2)C1]

To a solution of tert-butyl(E)-3-((2-tosylhydrazono)methyl)azetidine-1-carboxylate (623 mg, 1.76 mmol) in 1,4-dioxane (10 ml) were successively added $K_2CO_3$ (365.42 mg, 2.64 mmol) and (4-bromo-3-fluorophenyl)boronic acid (578.56 mg, 2.64 mmol). The reaction mixture was then refluxed for 16 hours. After cooling down to room temperature, the reaction mixture was transferred in a separating funnel containing an aqueous saturated solution of $NH_4Cl$, extracted three times with EtOAc. The combined organic layers were, dried over $MgSO_4$, filtered, and concentrated to dryness.

The resulting residue was then purified by flash chromatography eluting with a mixture of cyclohexane/EtOAc 80/20 to give 335 mg (55%) of (tert-butyl 3-(4-bromo-3-fluorobenzyl)azetidine-1-carboxylate.

LC/MS (m/z, MH+): 344

Step 3: 3-(4-bromo-3-fluorobenzyl)azetidine, Hydrochloride

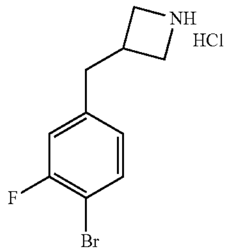 [SMILES: Fc1cc(CC2CNC2)ccc1Br ; Cl]

To a solution of tert-butyl 3-(4-bromo-3-fluorobenzyl) azetidine-1-carboxylate (326 mg, 947.06 μmol) in 1,4-dioxane (9 ml) was added dropwise 9.47 ml of a 4 M solution of HCl in 1,4-dioxane (37.88 mmol). The resulting reaction mixture was then stirred at room temperature overnight. The reaction mixture was concentrated to dryness to give 266 mg of 3-(4-bromo-3-fluorobenzyl)azetidine hydrochloride which was engaged in the next step without further purification.

LC/MS (m/z, MH+): 244

Step 4: (3-(4-bromo-3-fluorobenzyl)-1-(3-fluoropropyl)azetidine

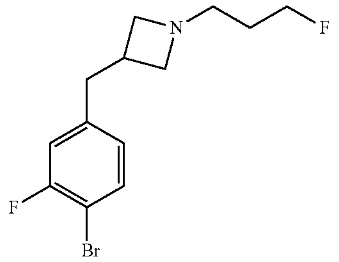 [SMILES: FCCCN1CC(Cc2ccc(Br)c(F)c2)C1]

Step 4 of Intermediate 28 was prepared following a similar procedure to that of Intermediate 23 from 3-(4-bromo-3-fluorobenzyl)azetidine hydrochloride to give 89 mg (18%) of (3-(4-bromo-3-fluorobenzyl)-1-(3-fluoropropyl)azetidine.

LC/MS (m/z, MH+): 304

Intermediate 29: Methyl 8-bromo-9-(2-fluoro-4-((1-(3-fluoropropyl)azetidin-3-yl)methyl)phenyl)-6,7-dihydro-5H-benzo[7]annulene-3-carboxylate

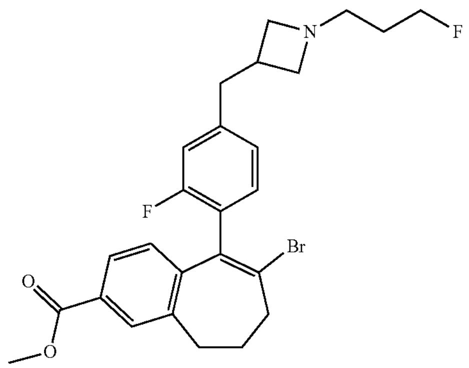 [SMILES: COC(=O)c1ccc2c(c1)CCCC(Br)=C2c1ccc(CC2CN(CCCF)C2)cc1F]

Step 1: Methyl 9-(2-fluoro-4-((1-(3-fluoropropyl) azetidin-3-yl)methyl)phenyl)-6,7-dihydro-5H-benzo [7]annulene-3-carboxylate

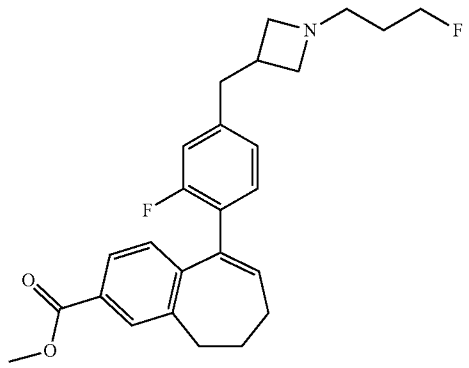 [SMILES: COC(=O)c1ccc2c(c1)CCCC=C2c1ccc(CC2CN(CCCF)C2)cc1F]

Step 1 of Intermediate 29 was prepared following a similar procedure to that of Step 1 of Intermediate 7 from methyl 9-(4,4,5,5-tetramethyl-1,3,2-dioxaborolan-2-yl)-6,7-dihydro-5H-benzo[7]annulene-3-carboxylate and (3-(4-bromo-3-fluorobenzyl)-1-(3-fluoropropyl)azetidine to give 1.28 g (100%) of methyl 9-(2-fluoro-4-((1-(3-fluoropropyl) azetidin-3-yl)methyl)phenyl)-6,7-dihydro-5H-benzo[7]annulene-3-carboxylate.

LC/MS (m/z, MH+): 426

Step 2: Methyl 8-bromo-9-(2-fluoro-4-((1-(3-fluoropropyl)azetidin-3-yl)methyl)phenyl)-6,7-dihydro-5H-benzo[7]annulene-3-carboxylate

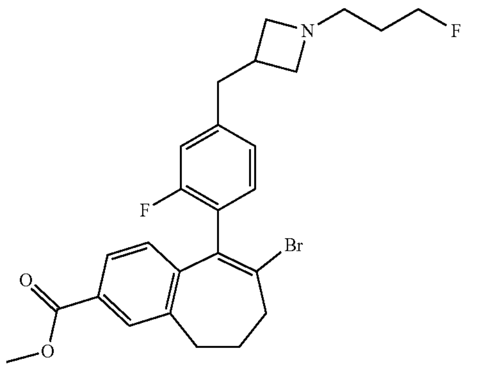 [SMILES: COC(=O)c1ccc2c(c1)CCCC(Br)=C2c1ccc(CC2CN(CCCF)C2)cc1F]

Step 2 of Intermediate 29 was prepared following a similar procedure to that of Step 2 of Intermediate 7 from methyl 9-(2-fluoro-4-((1-(3-fluoropropyl)azetidin-3-yl)methyl)phenyl)-6,7-dihydro-5H-benzo[7]annulene-3-carboxylate to give 840 mg (55%) of methyl 8-bromo-9-(2-fluoro-4-((1-(3-fluoropropyl)azetidin-3-yl)methyl)phenyl)-6,7-dihydro-5H-benzo[7]annulene-3-carboxylate.

LC/MS (m/z, MH+): 504

Intermediate 30: (3-(4-Bromo-2-methylbenzyl)-1-(3-fluoropropyl)azetidine

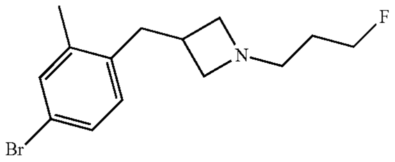 [SMILES: Cc1cc(Br)ccc1CC1CN(CCCF)C1]

Step 1: Tert-butyl 3-(4-bromo-2-methylbenzyl)azetidine-1-carboxylate

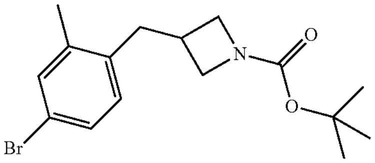 [SMILES: Cc1cc(Br)ccc1CC1CN(C(=O)OC(C)(C)C)C1]

Step 1 of Intermediate 30 was prepared following a similar procedure to that of step 2 of Intermediate 28 from (4-bromo-2-methylphenyl)boronic acid to give 593 mg (56%) of tert-butyl 3-(4-bromo-2-methylbenzyl)azetidine-1-carboxylate.

LC/MS (m/z, MH+): 341

Step 2: 3-(4-Bromo-2-methylbenzyl)azetidine Hydrochloride

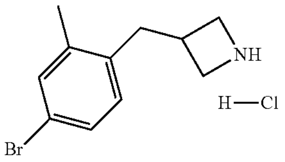

Step 2 of Intermediate 30 was prepared following a similar procedure to that of step 3 of Intermediate 28 from tert-butyl 3-(4-bromo-2-methylbenzyl)azetidine-1-carboxylate to give 480 mg (100%) of 3-(4-bromo-2-methylbenzyl)azetidine hydrochloride.

LC/MS (m/z, MH+): 241

Step 3: 3-(4-Bromo-2-methylbenzyl)-1-(3-fluoropropyl)azetidine

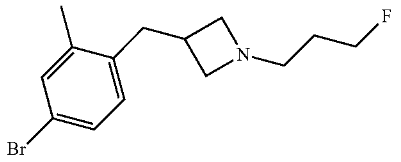 [SMILES: Cc1cc(Br)ccc1CC1CN(CCCF)C1]

Step 3 of Intermediate 30 was prepared following a similar procedure to that of Intermediate 23 from 3-(4-bromo-2-methylbenzyl)azetidine hydrochloride to give 86 mg (17%) of 3-(4-bromo-2-methylbenzyl)-1-(3-fluoropropyl)azetidine.

LC/MS (m/z, MH+): 301

Intermediate 31: 3-(4-Bromo-2-fluorobenzyl)-1-(3-fluoropropyl)azetidine

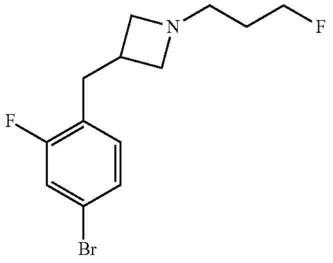 [SMILES: FCCCN1CC(Cc2ccc(Br)cc2F)C1]

Step 1: Tert-butyl 3-(4-bromo-2-fluorobenzyl)azetidine-1-carboxylate

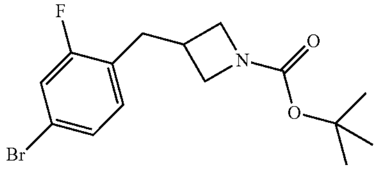 [SMILES: CC(C)(C)OC(=O)N1CC(Cc2ccc(Br)cc2F)C1]

Step 1 of Intermediate 31 was prepared following a similar procedure to that of step 2 of Intermediate 28 from (4-bromo-2-fluorophenyl)boronic acid to give 126 mg (26%) of tert-butyl 3-(4-bromo-2-fluorobenzyl)azetidine-1-carboxylate.

LC/MS (m/z, MH+): 344

Step 2: 3-(4-Bromo-2-fluorobenzyl)azetidine, Hydrochloride

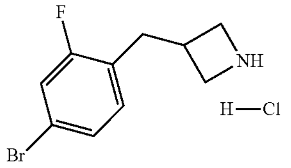

Step 2 of Intermediate 31 was prepared following a similar procedure to that of step 3 of Intermediate 28 from tert-butyl 3-(4-bromo-2-fluorobenzyl)azetidine-1-carboxylate to give 320 mg (100%) of 3-(4-bromo-2-fluorobenzyl)azetidine hydrochloride.

LC/MS (m/z, MH+): 244

Step 3: 3-(4-Bromo-2-fluorobenzyl)-1-(3-fluoropropyl)azetidine

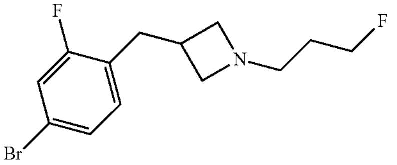 [SMILES: FCCCN1CC(Cc2ccc(Br)cc2F)C1]

Step 3 of Intermediate 31 was prepared following a similar procedure to that of Method 2 of Intermediate 1 from 3-(4-bromo-2-fluorobenzyl)azetidine hydrochloride to give 2.19 g (82%) of 3-(4-bromo-2-fluorobenzyl)-1-(3-fluoropropyl)azetidine.

LC/MS (m/z, MH+): 304

Intermediate 32: Methyl 8-bromo-9-(3-fluoro-4-((1-(3-fluoropropyl)azetidin-3-yl)methyl)phenyl)-6,7-dihydro-5H-benzo[7]annulene-3-carboxylate

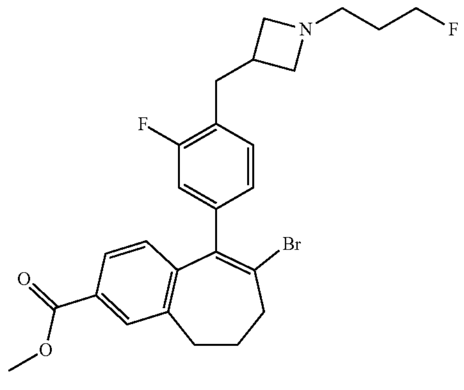 [SMILES: COC(=O)c1ccc2c(c1)CCCC(Br)=C2c1ccc(CC2CN(CCCF)C2)c(F)c1]

Step 1: Methyl 9-(3-fluoro-4-((1-(3-fluoropropyl)azetidin-3-yl)methyl)phenyl)-6,7-dihydro-5H-benzo[7]annulene-3-carboxylate

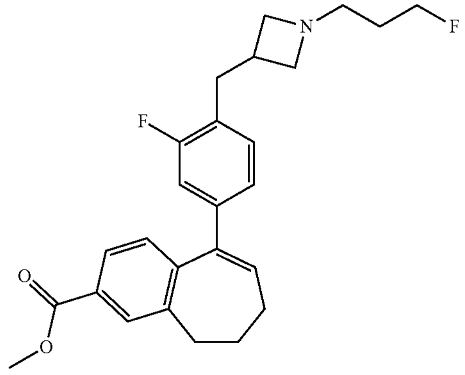 [SMILES: COC(=O)c1ccc2c(c1)CCCC=C2c1ccc(CC2CN(CCCF)C2)c(F)c1]

Step 1 of Intermediate 32 was prepared following a similar procedure to that of step 1 of Intermediate 7 from 3-(4-bromo-2-fluorobenzyl)-1-(3-fluoropropyl)azetidine (Intermediate 31) to give 2.58 g (84%) of methyl 9-(3-fluoro-4-((1-(3-fluoropropyl)azetidin-3-yl)methyl)phenyl)-6,7-dihydro-5H-benzo[7]annulene-3-carboxylate.

LC/MS (m/z, MH+): 426

Step 2: Methyl 8-bromo-9-(3-fluoro-4-((1-(3-fluoropropyl)azetidin-3-yl)methyl)phenyl)-6,7-dihydro-5H-benzo[7]annulene-3-carboxylate

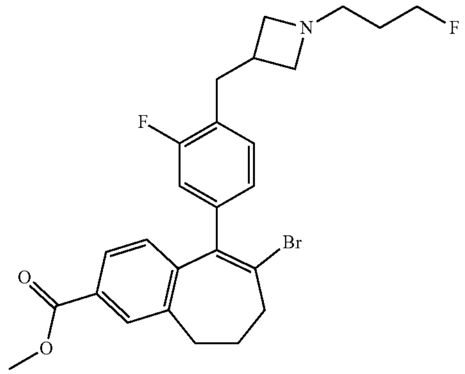 [SMILES: COC(=O)c1ccc2c(c1)CCCC(Br)=C2c1ccc(CC2CN(CCCF)C2)c(F)c1]

Step 2 of Intermediate 32 was prepared following a similar procedure to that of step 2 of Intermediate 7 from methyl 9-(3-fluoro-4-((1-(3-fluoropropyl)azetidin-3-yl)methyl)phenyl)-6,7-dihydro-5H-benzo[7]annulene-3-carboxylate to give 967 mg (82%) of methyl 8-bromo-9-(3-fluoro-4-((1-(3-fluoropropyl)azetidin-3-yl)methyl)phenyl)-6,7-dihydro-5H-benzo[7]annulene-3-carboxylate.

LC/MS (m/z, MH+): 504

Intermediate 33: 3-(4-Bromo-3-methylbenzyl)-1-(3-fluoropropyl)azetidine

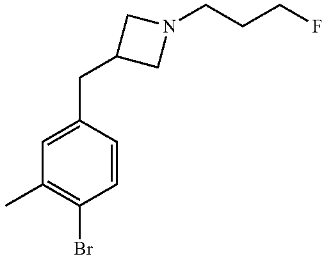 [SMILES: Cc1cc(CC2CN(CCCF)C2)ccc1Br]

Step 1: Tert-butyl 3-(4-bromo-3-methylbenzyl)azetidine-1-carboxylate

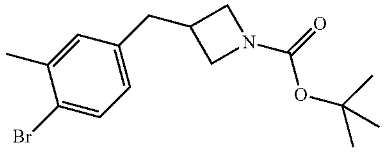 [SMILES: Cc1cc(CC2CN(C(=O)OC(C)(C)C)C2)ccc1Br]

Step 1 of Intermediate 33 was prepared following a similar procedure to that of step 2 of Intermediate 28 from (4-bromo-3-methylphenyl)boronic acid to give 850 mg (61%) of tert-butyl 3-(4-bromo-3-methylbenzyl)azetidine-1-carboxylate as a white solid.

Step 2: 3-(4-Bromo-3-methylbenzyl)azetidine, hydrochloride

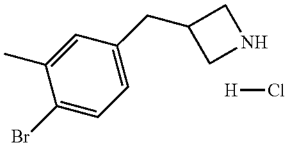

Step 2 of Intermediate 33 was prepared following a similar procedure to that of step 3 of Intermediate 28 from tert-butyl 3-(4-bromo-3-methylbenzyl)azetidine-1-carboxylate to give 0.84 g (100%) of 3-(4-bromo-3-methylbenzyl) azetidine hydrochloride which was used in the next step without further purification.

LC/MS (m/z, MH+): 240

Step 3: 3-(4-Bromo-3-methylbenzyl)-1-(3-fluoropropyl)azetidine

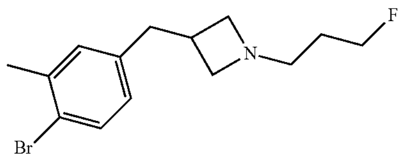 [SMILES: Cc1cc(CC2CN(CCCF)C2)ccc1Br]

Step 3 of Intermediate 33 was prepared following a similar procedure to that of Method 2 of Intermediate 1 from 3-(4-bromo-3-methylbenzyl)azetidine hydrochloride to give 63 mg (19%) of 3-(4-bromo-3-methylbenzyl)-1-(3-fluoropropyl)azetidine.

LC/MS (m/z, MH+): 300

Intermediate 34: 3-(4-Bromo-2,3-difluorobenzylidene)-1-(3-fluoropropyl)azetidine

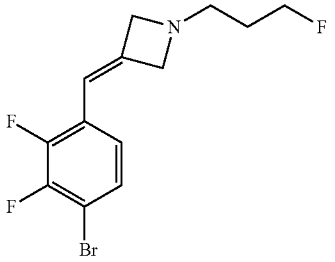 [SMILES: FCCCN1CC(=Cc2ccc(Br)c(F)c2F)C1]

Intermediate 34 was prepared following a similar procedure to that of Method 2 of Intermediate 1 from commercially available 3-(4-bromo-2,3-difluorobenzylidene)azetidine to give 0.65 g (34%) of 3-(4-bromo-2,3-difluorobenzylidene)-1-(3-fluoropropyl)azetidine as an orange oil.

LC/MS (m/z, MH+): 320

Intermediate 35: 3-(4-Bromo-2,6-difluorobenzylidene)-1-(3-fluoropropyl)azetidine

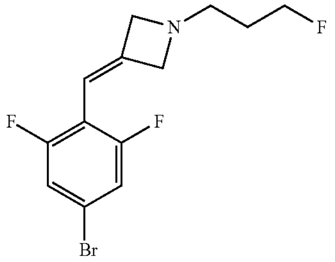 [SMILES: FCCCN1CC(=Cc2c(F)cc(Br)cc2F)C1]

Step 1: (4-Bromo-2,6-difluorophenyl)methanol

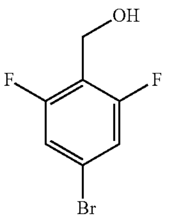 [SMILES: OCc1c(F)cc(Br)cc1F]

To a solution of 4-bromo-2,6-difluorobenzaldehyde (2 g, 9.05 mmol) in DCM (40 ml) and MeOH (10 ml) at 0° C. was portionwise added sodium borohydride (377 mg, 9.95 mmol). The reaction mixture was stirred at 0° C. for 1 hour then slowly quenched at 0° C. with a 1N aqueous solution of HCl. After stirring at 0° C. for 30 min, water was added and the mixture was transferred in a separating funnel and extracted three times with EtOAc. The combined organic layers were washed with brine, dried over $Na_2SO_4$, filtered, concentrated to dryness, triturated with pentane and filtered to give 1.83 g (91%) of (4-bromo-2,6-difluorophenyl) methanol as a pinkish solid.

LC/MS (m/z, MH+): 223

Step 2: 5-Bromo-2-(bromomethyl)-1,3-difluorobenzene

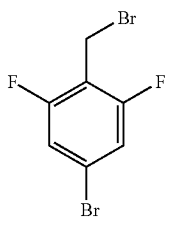 [SMILES: Fc1cc(Br)cc(F)c1CBr]

To a solution of (4-bromo-2,6-difluorophenyl)methanol (2.67 g, 11.99 mmol) in diethyl ether (60 ml) at 0° C. was dropwise added tribromophosphane (0.57 mL, 6 mmol). The reaction mixture was stirred for 12 hours at RT then slowly poured onto a saturated aqueous solution of $NaHCO_3$ under stirring. After stirring for 30 minutes, the mixture was transferred in a separating funnel and extracted three times with EtOAc. The combined organic layers were washed with brine, dried over $Na_2SO_4$, filtered and concentrated to dryness to give 3.04 g (88%) of 5-bromo-2-(bromomethyl)-1,3-difluorobenzene as a colorless oil which was used in the next step without further purification.

LC/MS (m/z, MH+): 285

Step 3: Diethyl (4-bromo-2,6-difluorobenzyl)phosphonate

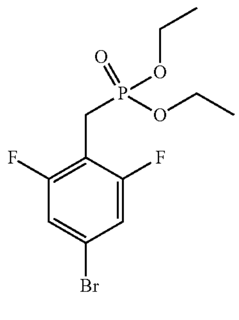 [SMILES: CCOP(=O)(Cc1c(F)cc(Br)cc1F)OCC]

A mixture of 5-bromo-2-(bromomethyl)-1,3-difluorobenzene (2.5 g, 8.74 mmol) and triethyl phosphite (2.25 ml, 13.12 mmol) was heated to 130° C. for 4 hours in a sealed tube. The resulting mixture was purified by flash chromatography eluting with a gradient of cyclohexane/EtOAc from 100/0 to 80/20 to give 2.95 g (98%) of diethyl (4-bromo-2,6-difluorobenzyl)phosphonate as a colorless oil.

LC/MS (m/z, MH+): 343

Step 4: Tert-butyl 3-(4-bromo-2,6-difluorobenzylidene)azetidine-1-carboxylate

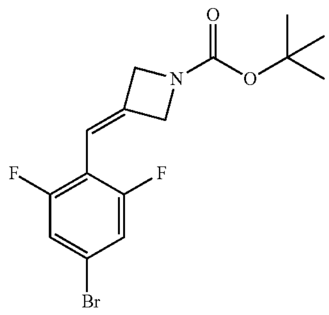 [SMILES: CC(C)(C)OC(=O)N1CC(=Cc2c(F)cc(Br)cc2F)C1]

To a solution of diisopropylamine (1.35 mL, 9.62 mmol) in THF (15 ml) at −78° C. under Ar atmosphere was dropwise added a 2.5 M solution of n-butyllithium in hexanes (3.5 mL, 8.74 mmol). The reaction mixture was stirred for 5 minutes then a solution of diethyl (4-bromo-2,6-difluorobenzyl)phosphonate (3 g, 8.74 mmol) in THF (15 ml) was added. After stirring for 45 minutes, a solution of tert-butyl 3-oxoazetidine-1-carboxylate (1.65 g, 9.62 mmol) in THF (30 ml) was added. The reaction mixture was stirred allowing the temperature to warm up to RT until completion. It was then transferred in a separating funnel containing an aqueous saturated solution of $NH_4Cl$, extracted three times with EtOAc. The combined organic layers were dried over $Na_2SO_4$, filtered, and concentrated to dryness. The resulting residue was then purified by flash chromatography eluting with a gradient of cyclohexane/EtOAc from 100/0 to 50/50 to give 1.67 g (53%) of tert-butyl 3-(4-bromo-2,6-difluorobenzylidene)azetidine-1-carboxylate as a colorless viscous oil.

LC/MS (m/z, MH+): 360

Step 5: 3-(4-Bromo-2,6-difluorobenzylidene)azetidine, Trifluoroacetic Acid

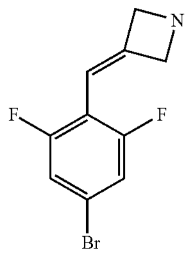

TFA

Step 5 of Intermediate 35 was prepared following a similar procedure to that of step 2 of Intermediate 11 from tert-butyl 3-(4-bromo-2,6-difluorobenzylidene)azetidine-1-carboxylate to give 1.65 g (98%) of 3-(4-bromo-2,6-difluorobenzylidene)azetidine, trifluoroacetic acid as a white solid.

LC/MS (m/z, MH+): 260

Step 6: 3-(4-Bromo-2,6-difluorobenzylidene)-1-(3-fluoropropyl)azetidine

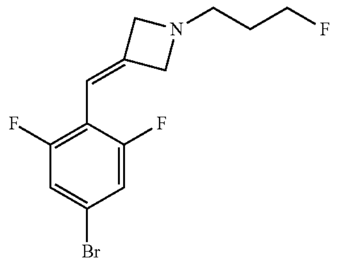 [SMILES: FCCCN1CC(=Cc2c(F)cc(Br)cc2F)C1]

Step 6 of Intermediate 35 was prepared following a similar procedure to that of Method 1 of Intermediate 1 from 3-(4-bromo-2,6-difluorobenzylidene)azetidine, trifluoroacetic acid to give 79 mg (18%) of 3-(4-bromo-2,6-difluorobenzylidene)-1-(3-fluoropropyl)azetidine.

LC/MS (m/z, MH+): 320

Intermediate 36: 3-(4-Bromo-2,6-dimethylbenzylidene)-1-(3-fluoropropyl)azetidine

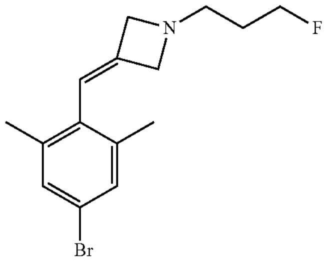 [SMILES: Cc1cc(Br)cc(C)c1C=C1CN(CCCF)C1]

Step 1: (4-Bromo-2,6-dimethylphenyl)methanol

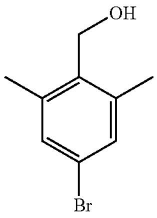

Step 1 of Intermediate 36 was prepared following a similar procedure to that of step 1 of Intermediate 35 from 4-bromo-2,6-dimethylbenzaldehyde to give 1.86 g (92%) of (4-bromo-2,6-dimethylphenyl)methanol as a white solid.

LC/MS (m/z, MH+): 215

Step 2: 5-Bromo-2-(bromomethyl)-1,3-dimethylbenzene

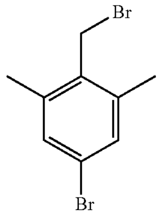

Step 2 of Intermediate 36 was prepared following a similar procedure to that of step 2 of Intermediate 35 from tert-butyl 3-(4-bromo-2,6-difluorobenzylidene)azetidine-1-carboxylate to give 1.27 g (98%) of 5-bromo-2-(bromomethyl)-1,3-dimethylbenzene as a white solid.

LC/MS (m/z, MH+): 277

Step 3: Diethyl (4-bromo-2,6-dimethylbenzyl)phosphonate

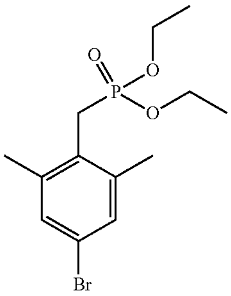 [SMILES: CCOP(=O)(Cc1c(C)cc(Br)cc1C)OCC]

Step 3 of Intermediate 36 was prepared following a similar procedure to that of step 3 of Intermediate 35 from 5-bromo-2-(bromomethyl)-1,3-dimethylbenzene to give 1.16 g (86%) of diethyl (4-bromo-2,6-dimethylbenzyl)phosphonate as a colorless oil.

LC/MS (m/z, MH+): 335

Step 4: Tert-butyl 3-(4-bromo-2,6-dimethylbenzylidene)azetidine-1-carboxylate

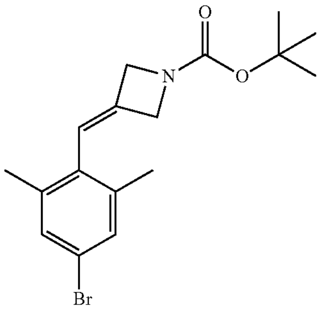 [SMILES: Cc1cc(Br)cc(C)c1C=C1CN(C(=O)OC(C)(C)C)C1]

Step 4 of Intermediate 36 was prepared following a similar procedure to that of step 4 of Intermediate 35 from diethyl (4-bromo-2,6-dimethylbenzyl)phosphonate to give 0.86 g (27%) of tert-butyl 3-(4-bromo-2,6-dimethylbenzylidene)azetidine-1-carboxylate as a colorless viscous oil.

LC/MS (m/z, MH+): 352

Step 5: 3-(4-Bromo-2,6-dimethylbenzylidene)azetidine, Trifluoroacetic Acid

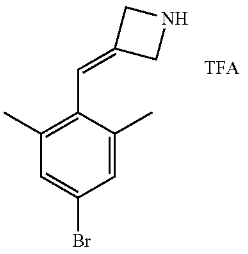

Step 5 of Intermediate 36 was prepared following a similar procedure to that of step 2 of Intermediate 11 from tert-butyl 3-(4-bromo-2,6-dimethylbenzylidene)azetidine-1-carboxylate to give 0.77 g (86%) of 3-(4-bromo-2,6-dimethylbenzylidene)azetidine, trifluoroacetic acid as a white solid.

LC/MS (m/z, MH+): 252

Step 6: 3-(4-Bromo-2,6-dimethylbenzylidene)-1-(3-fluoropropyl)azetidine

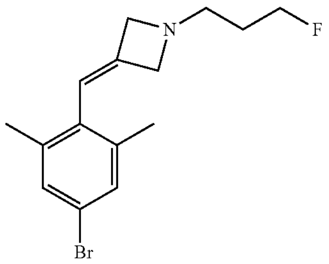 [SMILES: Cc1cc(Br)cc(C)c1C=C1CN(CCCF)C1]

Step 6 of Intermediate 36 was prepared following a similar procedure to that of Method 1 of Intermediate 1 from 3-(4-bromo-2,6-dimethylbenzylidene)azetidine, trifluoroacetic acid to give 0.7 mg (50%) of 3-(4-bromo-2,6-dimethylbenzylidene)-1-(3-fluoropropyl)azetidine.

LC/MS (m/z, MH+): 312

Intermediate 37: 3-(4-Bromo-2,5-difluorobenzylidene)-1-(3-fluoropropyl)azetidine

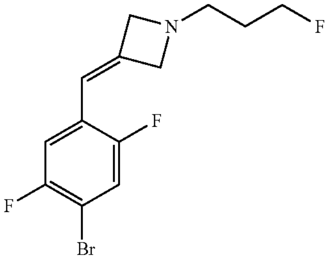 [SMILES: FCCCN1CC(=Cc2cc(F)c(Br)cc2F)C1]

Step 1: Diethyl (4-bromo-2,5-difluorobenzyl)phosphonate

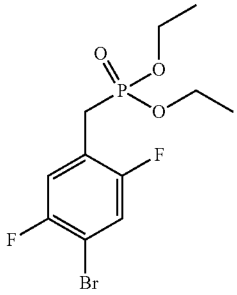 [SMILES: CCOP(=O)(Cc1cc(F)c(Br)cc1F)OCC]

Step 1 of Intermediate 37 was prepared following a similar procedure to that of step 3 of Intermediate 35 from commercially available 1-bromo-4-(bromomethyl)-2,5-difluorobenzene to give 6.48 g (87%) of diethyl (4-bromo-2,5-difluorobenzyl)phosphonate as a colorless oil.

LC/MS (m/z, MH+): 343

Step 2: Tert-butyl 3-(4-bromo-2,5-difluorobenzylidene)azetidine-1-carboxylate

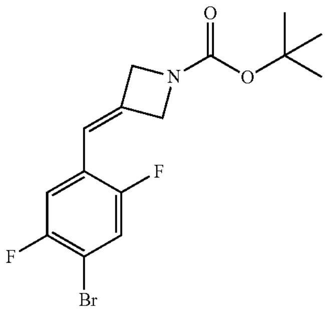 [SMILES: CC(C)(C)OC(=O)N1CC(=Cc2cc(F)c(Br)cc2F)C1]

Step 2 of Intermediate 37 was prepared following a similar procedure to that of step 4 of Intermediate 35 from diethyl (4-bromo-2,5-difluorobenzyl)phosphonate to give 1.16 g (73%) of tert-butyl 3-(4-bromo-2,5-difluorobenzylidene)azetidine-1-carboxylate as a white solid.

LC/MS (m/z, MH+): 360

Step 3: 3-(4-Bromo-2,5-difluorobenzylidene)azetidine, trifluoroacetic acid

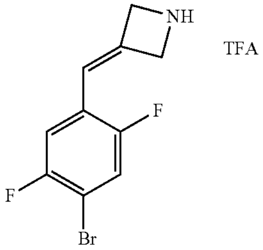

Step 3 of Intermediate 37 was prepared following a similar procedure to that of step 2 of Intermediate 11 from tert-butyl 3-(4-bromo-2,5-difluorobenzylidene)azetidine-1-carboxylate to give 1.07 g (89%) of 3-(4-bromo-2,5-difluorobenzylidene)azetidine, trifluoroacetic acid as a white solid.

LC/MS (m/z, MH+): 260

Step 4: 3-(4-Bromo-2,5-difluorobenzylidene)-1-(3-fluoropropyl)azetidine

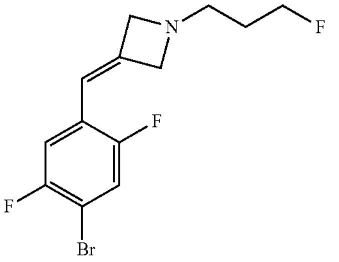 [SMILES: FCCCN1CC(=Cc2cc(F)c(Br)cc2F)C1]

Step 4 of Intermediate 37 was prepared following a similar procedure to that of Method 2 of Intermediate 1 from 3-(4-bromo-2,5-difluorobenzylidene)azetidine, trifluoroacetic acid to give 0.7 g (76%) of 3-(4-bromo-2,5-difluorobenzylidene)-1-(3-fluoropropyl)azetidine.

LC/MS (m/z, MH+): 320

Intermediate 38: Methyl 8-bromo-9-(4-((1-(3-fluoropropyl)azetidin-3-yl)methyl)phenyl)-4-methyl-6,7-dihydro-5H-benzo[7]annulene-3-carboxylate

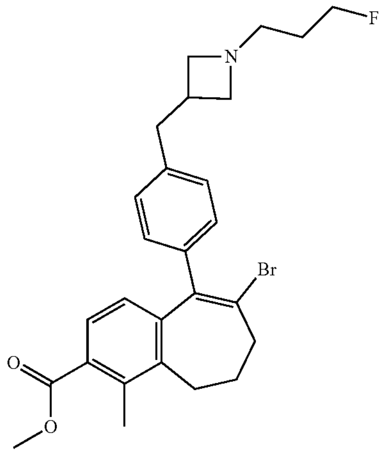 [SMILES: COC(=O)c1ccc2c(c1C)CCCC(Br)=C2c1ccc(CC2CN(CCCF)C2)cc1]

Step 1: 1-Bromo-2-methoxy-6,7,8,9-tetrahydro-5H-benzo[7]annulen-5-one and 3-bromo-2-methoxy-6,7,8,9-tetrahydro-5H-benzo[7]annulen-5-one

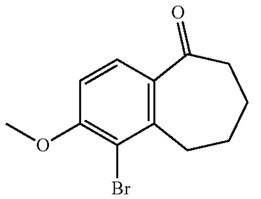
and
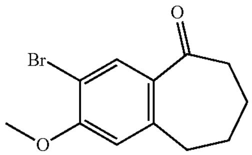

To a solution of 2-methoxy-6,7,8,9-tetrahydro-5H-benzo[7]annulen-5-one (500 mg, 2.63 mmol) and NBS (468 mg, 2.63 mmol) in $H_2O$ (5 ml) was added a solution of concentrated $H_2SO_4$ (286 µl, 5.26 mmol) in $H_2O$ (0.5 ml) and the mixture was stirred at 60° C. for 5 hours. The reaction mixture was extracted with EtOAc (30 mL) and after decantation, the organic layer was dried over anhydrous $Na_2SO_4$, filtered, and concentrated under reduced pressure. The residue was purified by flash chromatography eluting with a 0-15% Ethyl acetate gradient in Petroleum ether to give 260 mg (37%) of 1-bromo-2-methoxy-6,7,8,9-tetrahydro-5H-benzo[7]annulen-5-one and 130 mg (18%) of 3-bromo-2-methoxy-6,7,8,9-tetrahydro-5H-benzo[7]annulen-5-one.

LC/MS (m/z, MH+): 268

Step 2: 2-Methoxy-1-methyl-6,7,8,9-tetrahydro-5H-benzo[7]annulen-5-one

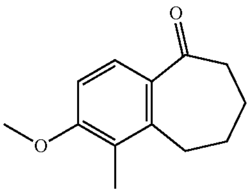

A mixture 1-bromo-2-methoxy-6,7,8,9-tetrahydro-5H-benzo[7]annulen-5-one (1 g, 3.72 mmol) in a mixture of dioxane (20 ml) and $H_2O$ (5 ml) was purged with Ar for 15 minutes. $K_2CO_3$ (1.54 g, 11.15 mmol), $MeB(OH)_2$ (266.90 mg, 4.46 mmol) and $Pd(PPh_3)_4$ (214.68 mg, 185.78 µmol) were added sequentially under $N_2$ atmosphere. The reaction mixture was sealed and heated to 100° C. for 2 hours. The mixture was poured into water (20 ml) and extracted three times with EtOAc (20 ml). The combined organic phases were dried over anhydrous $Na_2SO_4$, filtered, and concentrated in vacuo. The residue was purified by flash chromatography eluting with a 0-15% gradient of Ethyl acetate in Petroleum ether to give 880 mg (100%) of 2-methoxy-1-methyl-6,7,8,9-tetrahydro-5H-benzo[7]annulen-5-one.

LC/MS (m/z, MH+): 205

Step 3: 2-Hydroxy-1-methyl-6,7,8,9-tetrahydro-5H-benzo[7]annulen-5-one

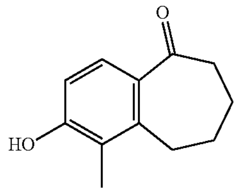

A mixture of 2-methoxy-1-methyl-6,7,8,9-tetrahydro-5H-benzo[7]annulen-5-one (760 mg, 3.72 mmol) in DCM (10 ml) was cooled to −60° C., $BBr_3$ (1.08 ml, 11.16 mmol) was added slowly. The mixture was stirred at 20° C. for 1 hour. The reaction mixture was quenched by addition of $H_2O$ (10 ml) and extracted twice with EtOAc (10 ml). The combined organic layers were dried over anhydrous $Na_2SO_4$, filtered, and concentrated under reduced pressure. The residue was purified by flash chromatography eluting with a 0-35% gradient of ethyl acetate in petroleum ether to give compound 500 mg (71%) of 2-hydroxy-1-methyl-6,7,8,9-tetrahydro-5H-benzo[7]annulen-5-one.

LC/MS (m/z, MH+): 191

Step 4: 1-Methyl-5-oxo-6,7,8,9-tetrahydro-5H-benzo[7]annulen-2-yl trifluoromethanesulfonate

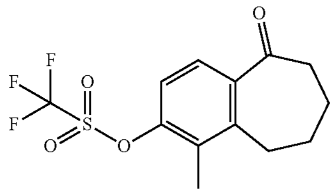 [SMILES: Cc1c(OS(=O)(=O)C(F)(F)F)ccc2c1CCCCC2=O]

Step 4 of Intermediate 38 was prepared following a similar procedure to that of Step 1 of Intermediate 9 from 2-hydroxy-1-methyl-6,7,8,9-tetrahydro-5H-benzo[7]annulen-5-one to give 610 mg (100%) of 1-methyl-5-oxo-6,7,8,9-tetrahydro-5H-benzo[7]annulen-2-yl trifluoromethanesulfonate.

LC/MS (m/z, MH+): 323

Step 5: Methyl 1-methyl-5-oxo-6,7,8,9-tetrahydro-5H-benzo[7]annulene-2-carboxylate

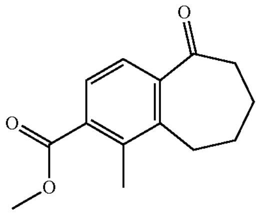 [SMILES: COC(=O)c1ccc2c(c1C)CCCCC2=O]

Step 5 of Intermediate 38 was prepared following a similar procedure to that of Step 2 of Intermediate 9 from 1-methyl-5-oxo-6,7,8,9-tetrahydro-5H-benzo[7]annulen-2-yl trifluoromethanesulfonate to give 70 mg (97%) of methyl 1-methyl-5-oxo-6,7,8,9-tetrahydro-5H-benzo[7]annulene-2-carboxylate.

LC/MS (m/z, MH+): 233.

Step 6: Methyl 4-methyl-9-(((trifluoromethyl)sulfonyl)oxy)-6,7-dihydro-5H-benzo[7]annulene-3-carboxylate

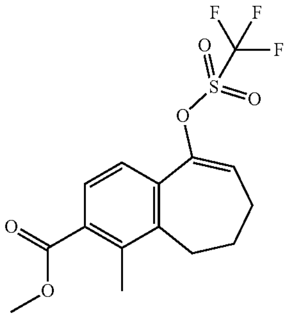 [SMILES: COC(=O)c1ccc2c(c1C)CCCC=C2OS(=O)(=O)C(F)(F)F]

Step 6 of Intermediate 38 was prepared following a similar procedure to that of Step 3 of Intermediate 9 from methyl 1-methyl-5-oxo-6,7,8,9-tetrahydro-5H-benzo[7]annulene-2-carboxylate to give 480 mg (93%) of methyl 4-methyl-9-(((trifluoromethyl)sulfonyl)oxy)-6,7-dihydro-5H-benzo[7]annulene-3-carboxylate.

LC/MS (m/z, MH+): 365

Step 7: methyl 9-(4-((1-(3-fluoropropyl)azetidin-3-yl)methyl)phenyl)-4-methyl-6,7-dihydro-5H-benzo[7]annulene-3-carboxylate

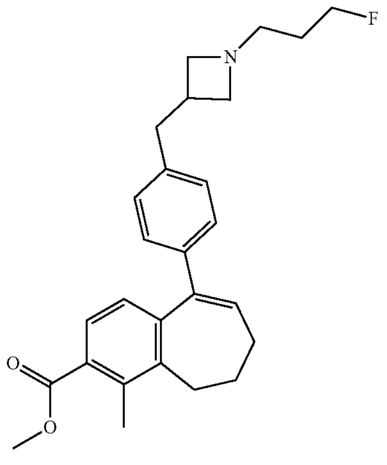 [SMILES: COC(=O)c1ccc2c(c1C)CCCC=C2c1ccc(CC2CN(CCCF)C2)cc1]

To a solution of methyl 4-methyl-9-(((trifluoromethyl)sulfonyl)oxy)-6,7-dihydro-5H-benzo[7]annulene-3-carboxylate (480 mg, 1.32 mmol), $Cs_2CO_3$ (1.5 M, 1.76 ml) and 1-(3-fluoropropyl)-3-(4-(4,4,5,5-tetramethyl-1,3,2-dioxaborolan-2-yl)benzyl)azetidine (Intermediate 2) (571 mg, 1.71 mmol) in dioxane (10 ml) was added Pd(dppf)$Cl_2$ (96.40 mg, 131.75 µmol). The mixture was stirred at 60° C. for 1 hour under Ar atmosphere. The residue was poured into water (20 ml) and extracted three times with EtOAc (20 ml). The combined organic phases were dried over anhydrous $Na_2SO_4$, filtered, and concentrated in vacuo. The residue was purified by flash chromatography eluting with a 0-10% gradient of DCM in MeOH to give 610 mg (91%) of methyl 9-(4-((1-(3-fluoropropyl)azetidin-3-yl)methyl)phenyl)-4-methyl-6,7-dihydro-5H-benzo[7]annulene-3-carboxylate.

LC/MS (m/z, MH+): 422

Step 8: Methyl 8-bromo-9-(4-((1-(3-fluoropropyl) azetidin-3-yl)methyl)phenyl)-4-methyl-6,7-dihydro-5H-benzo[7]annulene-3-carboxylate

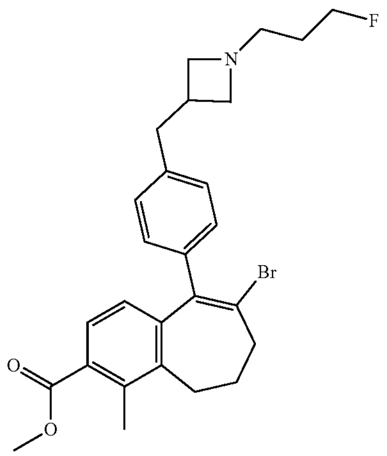 [SMILES: COC(=O)c1ccc2c(c1C)CCCC(Br)=C2c1ccc(CC2CN(CCCF)C2)cc1]

Step 8 of Intermediate 38 was prepared following a similar procedure to that of Step 2 of Intermediate 7 from methyl 9-(4-((1-(3-fluoropropyl)azetidin-3-yl)methyl)phenyl)-4-methyl-6,7-dihydro-5H-benzo[7]annulene-3-carboxylate to give 400 mg (77% yield) of methyl 8-bromo-9-(4-((1-(3-fluoropropyl)azetidin-3-yl)methyl)phenyl)-4-methyl-6,7-dihydro-5H-benzo[7]annulene-3-carboxylate.

LC/MS (m/z, MH+): 500

Intermediate 39: Methyl 8-bromo-9-(4-((1-(3-fluoropropyl)azetidin-3-yl)methyl)phenyl)-2-methyl-6,7-dihydro-5H-benzo[7]annulene-3-carboxylate

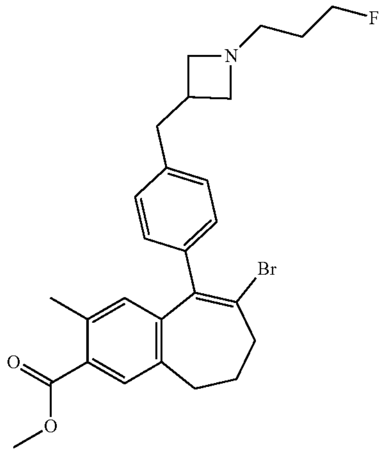 [SMILES: COC(=O)c1cc2c(cc1C)C(c1ccc(CC3CN(CCCF)C3)cc1)=C(Br)CCC2]

Step 1: 2-Methoxy-3-methyl-6,7,8,9-tetrahydro-5H-benzo[7]annulen-5-one

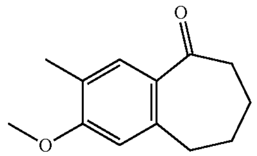

Step 1 of Intermediate 39 was prepared following a similar procedure to that of Step 2 of Intermediate 38 from 3-bromo-2-methoxy-6,7,8,9-tetrahydro-5H-benzo[7]annulen-5-one to give 183 mg (73%) of 2-methoxy-3-methyl-6,7,8,9-tetrahydro-5H-benzo[7]annulen-5-one.

LC/MS (m/z, MH+): 205

Step 2: 2-Hydroxy-3-methyl-6,7,8,9-tetrahydro-5H-benzo[7]annulen-5-one

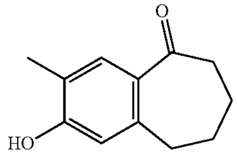

To a solution of 2-methoxy-3-methyl-6,7,8,9-tetrahydro-5H-benzo[7]annulen-5-one (310 mg, 1.52 mmol) in toluene (3 ml) was added $AlCl_3$ (1.01 g, 7.59 mmol) and the mixture was stirred at 80° C. for 3 hours. The residue was poured into water (10 ml) and extracted three times with EtOAc (10 ml). The combined organic phases were dried over anhydrous $Na_2SO_4$, filtered, and concentrated in vacuo. The residue was purified by flash chromatography eluting with a 0-50% gradient of Ethyl acetate in Petroleum ether to give 319 mg (99%) of 2-hydroxy-3-methyl-6,7,8,9-tetrahydro-5H-benzo[7]annulen-5-one.

LC/MS (m/z, MH+): 191

Step 3: 3-methyl-5-oxo-6,7,8,9-tetrahydro-5H-benzo[7]annulen-2-yl trifluoromethanesulfonate

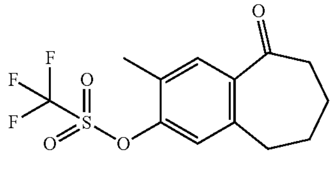 [SMILES: Cc1cc2c(cc1OS(=O)(=O)C(F)(F)F)CCCCC2=O]

Step 3 of Intermediate 39 was prepared following a similar procedure to that of Step 1 of Intermediate 9 from 2-hydroxy-3-methyl-6,7,8,9-tetrahydro-5H-benzo[7]annulen-5-one to give 437 mg (80%) of 3-methyl-5-oxo-6,7,8,9-tetrahydro-5H-benzo[7]annulen-2-yl trifluoromethanesulfonate.

LC/MS (m/z, MH+): 323

Step 4: Methyl 3-methyl-5-oxo-6,7,8,9-tetrahydro-5H-benzo[7]annulene-2-carboxylate

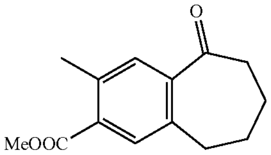 [SMILES: COC(=O)c1cc2c(cc1C)C(=O)CCCC2]

Step 4 of Intermediate 39 was prepared following a similar procedure to that of Step 2 of Intermediate 9 from 3-methyl-5-oxo-6,7,8,9-tetrahydro-5H-benzo[7]annulen-2-yl trifluoromethanesulfonate to give 300 mg (95%) of methyl 3-methyl-5-oxo-6,7,8,9-tetrahydro-5H-benzo[7]annulene-2-carboxylate.

LC/MS (m/z, MH+): 233

Step 5: Methyl 2-methyl-9-(((trifluoromethyl)sulfonyl)oxy)-6,7-dihydro-5H-benzo[7]annulene-3-carboxylate

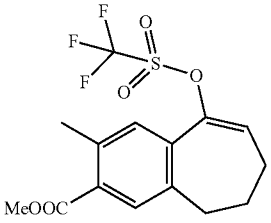 [SMILES: COC(=O)c1cc2c(cc1C)C(OS(=O)(=O)C(F)(F)F)=CCCC2]

Step 5 of Intermediate 39 was prepared following a similar procedure to that of Step 3 of Intermediate 9 from methyl 3-methyl-5-oxo-6,7,8,9-tetrahydro-5H-benzo[7]annulene-2-carboxylate to give compound 315 mg (67%) of methyl 2-methyl-9-(((trifluoromethyl)sulfonyl)oxy)-6,7-dihydro-5H-benzo[7]annulene-3-carboxylate.

LC/MS (m/z, MH+): 365

Step 6: Methyl 9-(4-((1-(3-fluoropropyl)azetidin-3-yl)methyl)phenyl)-2-methyl-6,7-dihydro-5H-benzo[7]annulene-3-carboxylate

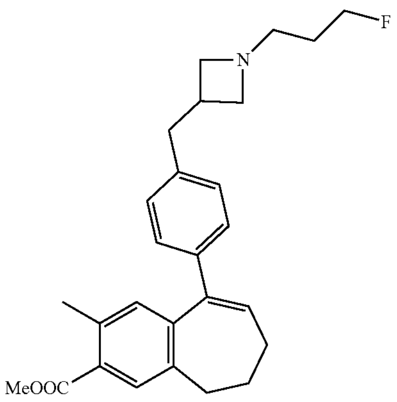 [SMILES: COC(=O)c1cc2c(cc1C)C(c1ccc(CC3CN(CCCF)C3)cc1)=CCCC2]

Step 6 of Intermediate 39 was prepared following a similar procedure to that of Step 7 of Intermediate 38 from methyl 2-methyl-9-(((trifluoromethyl)sulfonyl)oxy)-6,7-dihydro-5H-benzo[7]annulene-3-carboxylate to give 439 mg (96%) of methyl 9-(4-((1-(3-fluoropropyl)azetidin-3-yl)methyl)phenyl)-2-methyl-6,7-dihydro-5H-benzo[7]annulene-3-carboxylate.

LC/MS (m/z, MH+): 422

Step 7: Methyl 8-bromo-9-(4-((1-(3-fluoropropyl)azetidin-3-yl)methyl)phenyl)-2-methyl-6,7-dihydro-5H-benzo[7]annulene-3-carboxylate

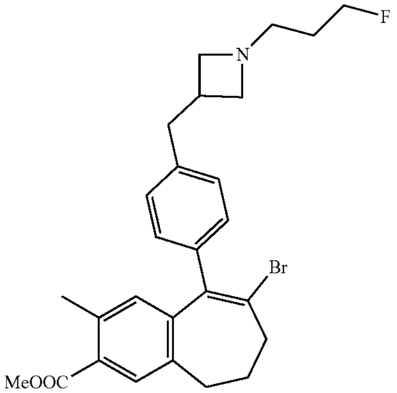 [SMILES: COC(=O)c1cc2c(cc1C)C(c1ccc(CC3CN(CCCF)C3)cc1)=C(Br)CCC2]

Step 7 of Intermediate 39 was prepared following a similar procedure to that of Step 2 of Intermediate 7 from methyl 9-(4-((1-(3-fluoropropyl)azetidin-3-yl)methyl)phenyl)-2-methyl-6,7-dihydro-5H-benzo[7]annulene-3-carboxylate to give 349 mg (72%) of methyl 8-bromo-9-(4-((1-(3-fluoropropyl)azetidin-3-yl)methyl)phenyl)-2-methyl-6,7-dihydro-5H-benzo[7]annulene-3-carboxylate.

LC/MS (m/z, MH+): 500

Intermediate 40: Methyl 8-bromo-4-chloro-9-(4-((1-(3-fluoropropyl)azetidin-3-yl)methyl)phenyl)-6,7-dihydro-5H-benzo[7]annulene-3-carboxylate

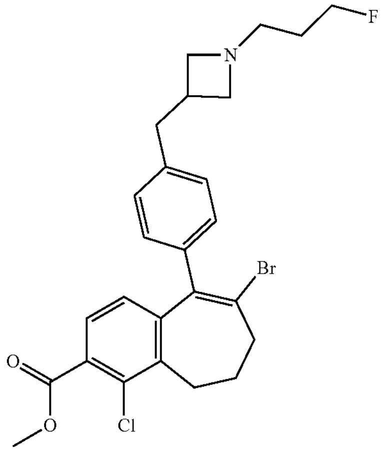

Step 1: 1-chloro-2-methoxy-6,7,8,9-tetrahydro-5H-benzo[7]annulen-5-one and 3-chloro-2-methoxy-6,7,8,9-tetrahydro-5H-benzo[7]annulen-5-one

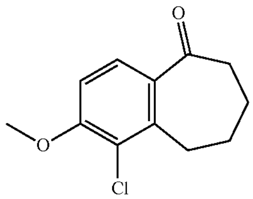

and

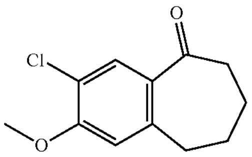

To a solution of 2-methoxy-6,7,8,9-tetrahydro-5H-benzo[7]annulen-5-one (10 g, 52.57 mmol) and N-chlorosuccinimide (7.72 g, 57.82 mmol) in $H_2O$ (100 ml) was added $H_2SO_4$ (5.72 ml, 105.13 mmol, 98% purity) in $H_2O$ (20 ml) and the mixture was stirred at 60° C. for 5 hours. The reaction mixture was extracted twice with EtOAc (200 ml) and the combined organic layers were dried over anhydrous $Na_2SO_4$, filtered and concentrated under reduced pressure. The residue was purified by flash chromatography eluting with a 0-15% gradient of Ethyl acetate in Petroleum ether to give 5.3 g (45%) of 1-chloro-2-methoxy-6,7,8,9-tetrahydro-5H-benzo[7]annulen-5-one and 4.8 g (20%) of 3-chloro-2-methoxy-6,7,8,9-tetrahydro-5H-benzo[7]annulen-5-one.

LC/MS (m/z, MH+): 225

Step 2: 1-Chloro-2-hydroxy-6,7,8,9-tetrahydro-5H-benzo[7]annulen-5-one

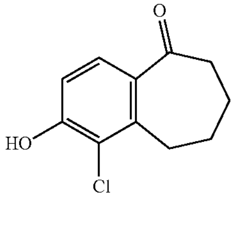 [SMILES: O=C1CCCCc2c1ccc(O)c2Cl]

Step 2 of Intermediate 40 was prepared following a similar procedure to that of Step 2 of Intermediate 39 from 1-chloro-2-methoxy-6,7,8,9-tetrahydro-5H-benzo[7]annulen-5-one to give 1.8 g (crude) of 1-chloro-2-hydroxy-6,7,8,9-tetrahydro-5H-benzo[7]annulen-5-one.

LC/MS (m/z, MH+): 211

Step 3: 1-chloro-2-fluorosulfonyloxy-5-oxo-6,7,8,9-tetrahydrobenzo[7]annulene

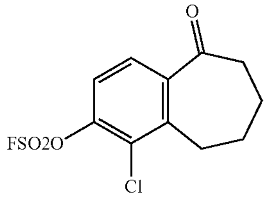

To a solution of 1-chloro-2-hydroxy-6,7,8,9-tetrahydro-5H-benzo[7]annulen-5-one (1.8 g, 8.54 mmol) in DCM (20 ml) was added TEA (2.16 g, 21.36 mmol, 2.97 ml). Then SO2F2 (gas) was introduced by needle from a balloon filled with the gas and the mixture was stirred at 25° C. for 1 hour. The residue was poured into $H_2O$ (10 ml) and extracted with DCM (40 ml). The organic phase was washed with brine (10 ml), dried over anhydrous $Na_2SO_4$, filtered, concentrated under reduced pressure and the residue obtained was purified by flash chromatography with 0-30% Ethyl acetate in Petroleum ether gradient to give 2 g (80%) of 1-chloro-2-fluorosulfonyloxy-5-oxo-6,7,8,9-tetrahydrobenzo[7]annulene.

LC/MS (m/z, MH+): 292

Step 4: Methyl 1-chloro-5-oxo-6,7,8,9-tetrahydro-5H-benzo[7]annulene-2-carboxylate

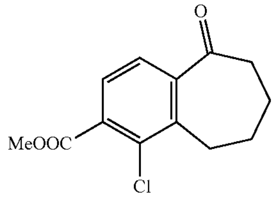 [SMILES: COC(=O)c1ccc2c(c1Cl)CCCCC2=O]

Step 4 of Intermediate 40 was prepared following a similar procedure to that of Step 2 of Intermediate 9 from 1-chloro-2-fluorosulfonyloxy-5-oxo-6,7,8,9-tetrahydrobenzo[7]annulene to give 900 mg (52%) of methyl 1-chloro-5-oxo-6,7,8,9-tetrahydro-5H-benzo[7]annulene-2-carboxylate.

LC/MS (m/z, MH+): 253

Step 5: Methyl 4-chloro-9-(((trifluoromethyl)sulfonyl)oxy)-6,7-dihydro-5H-benzo[7]annulene-3-carboxylate

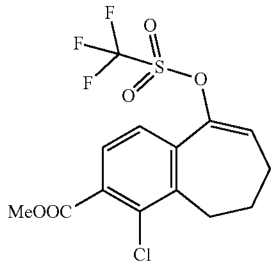 [SMILES: COC(=O)c1ccc2c(c1Cl)CCCC=C2OS(=O)(=O)C(F)(F)F]

To a solution of methyl 1-chloro-5-oxo-6,7,8,9-tetrahydro-5H-benzo[7]annulene-2-carboxylate (200 mg, 791 μmol) in THF (3 ml) was added NaHMDS (1 M, 950 μl) at −78° C. under Ar atmosphere. The mixture was stirred for 30 minutes and a mixture of 1,1,1-trifluoro-N-phenyl-N-(trifluoromethylsulfonyl)methanesulfonamide (368 mg, 1.03 mmol) in THF (1 ml) was added to the resulting mixture. The reaction mixture was slowly warmed up to 20° C. and stirred for 2 hours. The reaction mixture was quenched with saturated aqueous $NH_4Cl$ solution (5 ml), then diluted with $H_2O$ (15 ml) and extracted twice with EtOAc (20 ml). The combined organic layers were dried over anhydrous $Na_2SO_4$, filtered, and concentrated under reduced pressure. The residue was purified by flash chromatography with a 0-25% gradient of Ethyl acetate in Petroleum ether to give 250 mg (82%) of methyl 4-chloro-9-(((trifluoromethyl)sulfonyl)oxy)-6,7-dihydro-5H-benzo[7]annulene-3-carboxylate.

LC/MS (m/z, MH+): 385

Step 6: Methyl 4-chloro-9-(4-((1-(3-fluoropropyl)azetidin-3-yl)methyl)phenyl)-6,7-dihydro-5H-benzo[7]annulene-3-carboxylate

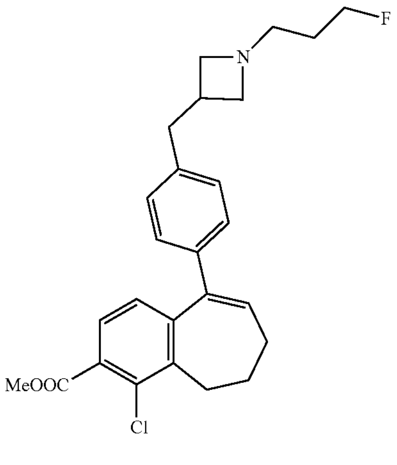 [SMILES: COC(=O)c1ccc2c(c1Cl)CCCC=C2c1ccc(CC2CN(CCCF)C2)cc1]

Step 6 of Intermediate 40 was prepared following a similar procedure to that of Step 7 of Intermediate 38 from methyl 4-chloro-9-(((trifluoromethyl)sulfonyl)oxy)-6,7-dihydro-5H-benzo[7]annulene-3-carboxylate to give 280 mg (93%) of methyl 4-chloro-9-(4-((1-(3-fluoropropyl)azetidin-3-yl)methyl)phenyl)-6,7-dihydro-5H-benzo[7]annulene-3-carboxylate.

LC/MS (m/z, MH+): 422

Step 7: Methyl 8-bromo-4-chloro-9-(4-((1-(3-fluoropropyl)azetidin-3-yl)methyl)phenyl)-6,7-dihydro-5H-benzo[7]annulene-3-carboxylate

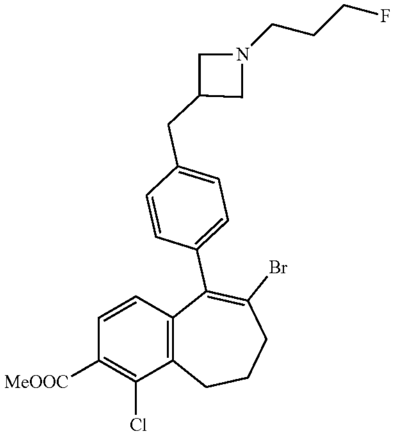 [SMILES: COC(=O)c1ccc2c(c1Cl)CCCC(Br)=C2c1ccc(CC2CN(CCCF)C2)cc1]

Step 7 of Intermediate 40 was prepared following a similar procedure to that of Step 2 of Intermediate 7 from methyl 4-chloro-9-(4-((1-(3-fluoropropyl)azetidin-3-yl)methyl)phenyl)-6,7-dihydro-5H-benzo[7]annulene-3-carboxylate to give 290 mg (83%) of methyl 8-bromo-4-chloro-9-(4-((1-(3-fluoropropyl)azetidin-3-yl)methyl)phenyl)-6,7-dihydro-5H-benzo[7]annulene-3-carboxylate.

LC/MS (m/z, MH+): 522

Intermediate 41: Methyl 8-bromo-2-chloro-9-(4-((1-(3-fluoropropyl)azetidin-3-yl)methyl)phenyl)-6,7-dihydro-5H-benzo[7]annulene-3-carboxylate

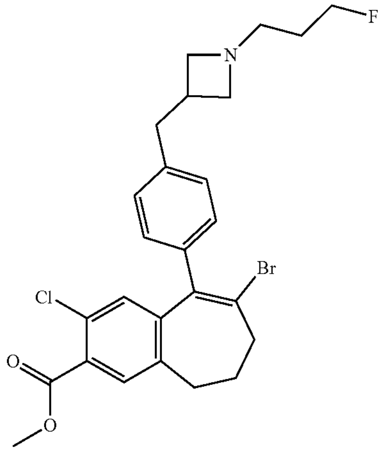

Step 1: 3-Chloro-2-hydroxy-6,7,8,9-tetrahydro-5H-benzo[7]annulen-5-one

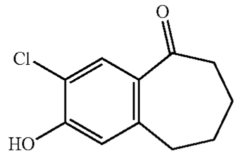

Step 1 of Intermediate 41 was prepared following a similar procedure to that of Step 2 of Intermediate 39 from 3-chloro-2-methoxy-6,7,8,9-tetrahydro-5H-benzo[7]annulen-5-one to give 650 mg (69.33%) of 3-chloro-2-hydroxy-6,7,8,9-tetrahydro-5H-benzo[7]annulen-5-one.

LC/MS (m/z, MH+): 211

Step 2: 3-chloro-2-fluorosulfonyloxy-5-oxo-6,7,8,9-tetrahydrobenzo[7]annulene

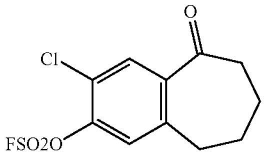

Step 2 of Intermediate 41 was prepared following a similar procedure to that of Step 3 of Intermediate 40 from 3-chloro-2-hydroxy-6,7,8,9-tetrahydro-5H-benzo[7]annulen-5-one to give 1.4 g (92%) of 3-chloro-2-fluorosulfonyloxy-5-oxo-6,7,8,9-tetrahydrobenzo[7]annulene LC/MS (m/z, MH+): 292

Step 3: Methyl 3-chloro-5-oxo-6,7,8,9-tetrahydro-5H-benzo[7]annulene-2-carboxylate

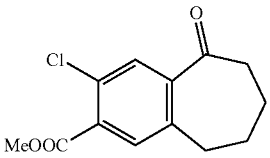 [SMILES: COC(=O)c1cc2c(cc1Cl)C(=O)CCCC2]

Step 3 of Intermediate 41 was prepared following a similar procedure to that of Step 2 of Intermediate 9 from 3-chloro-2-fluorosulfonyloxy-5-oxo-6,7,8,9-tetrahydrobenzo[7]annulene to give 700 mg (58%) of methyl 3-chloro-5-oxo-6,7,8,9-tetrahydro-5H-benzo[7]annulene-2-carboxylate.

LC/MS (m/z, MH+): 253

Step 4: Methyl 2-chloro-9-(((trifluoromethyl)sulfonyl)oxy)-6,7-dihydro-5H-benzo[7]annulene-3-carboxylate

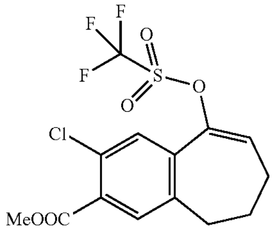 [SMILES: COC(=O)c1cc2c(cc1Cl)C(OS(=O)(=O)C(F)(F)F)=CCCC2]

Step 4 of Intermediate 41 was prepared following a similar procedure to that of Step 5 of Intermediate 40 from methyl 3-chloro-5-oxo-6,7,8,9-tetrahydro-5H-benzo[7]annulene-2-carboxylate to give 40 mg (53%) of methyl 2-chloro-9-(((trifluoromethyl)sulfonyl)oxy)-6,7-dihydro-5H-benzo[7]annulene-3-carboxylate.

LC/MS (m/z, MH+): 385

Step 5: Methyl 2-chloro-9-(4-((1-(3-fluoropropyl)azetidin-3-yl)methyl)phenyl)-6,7-dihydro-5H-benzo[7]annulene-3-carboxylate

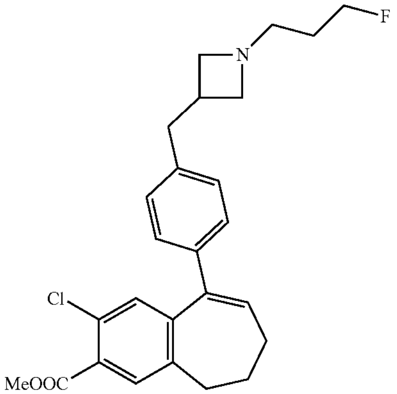

Step 5 of Intermediate 41 was prepared following a similar procedure to that of Step 7 of Intermediate 38 from methyl 2-chloro-9-(((trifluoromethyl)sulfonyl)oxy)-6,7-dihydro-5H-benzo[7]annulene-3-carboxylate to give 300 mg (crude) of methyl 2-chloro-9-(4-((1-(3-fluoropropyl)azetidin-3-yl)methyl)phenyl)-6,7-dihydro-5H-benzo[7]annulene-3-carboxylate.

LC/MS (m/z, MH+): 442

Step 6: Methyl 8-bromo-2-chloro-9-(4-((1-(3-fluoropropyl)azetidin-3-yl)methyl)phenyl)-6,7-dihydro-5H-benzo[7]annulene-3-carboxylate

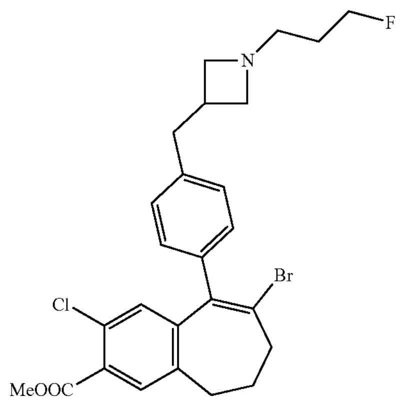 [SMILES: COC(=O)c1cc2c(cc1Cl)C(c1ccc(CC3CN(CCCF)C3)cc1)=C(Br)CCC2]

Step 6 of Intermediate 41 was prepared following a similar procedure to that of Step 2 of Intermediate 7 from methyl 2-chloro-9-(4-((1-(3-fluoropropyl)azetidin-3-yl)methyl)phenyl)-6,7-dihydro-5H-benzo[7]annulene-3-carboxylate to give 260 mg (crude) of methyl 8-bromo-2-chloro-9-(4-((1-(3-fluoropropyl)azetidin-3-yl)methyl)phenyl)-6,7-dihydro-5H-benzo[7]annulene-3-carboxylate.

LC/MS (m/z, MH+): 522

Intermediate 42: Methyl 8-bromo-4-cyano-9-(4-((1-(3-fluoropropyl)azetidin-3-yl)methyl)phenyl)-6,7-dihydro-5H-benzo[7]annulene-3-carboxylate

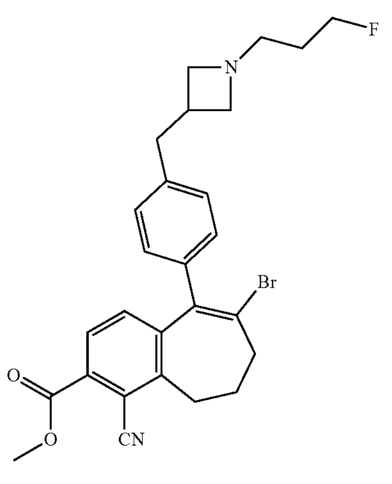 [SMILES: COC(=O)c1ccc2c(c1C#N)CCCC(Br)=C2c1ccc(CC2CN(CCCF)C2)cc1]

Step 1: Methyl 1-cyano-5-oxo-6,7,8,9-tetrahydro-5H-benzo[7]annulene-2-carboxylate

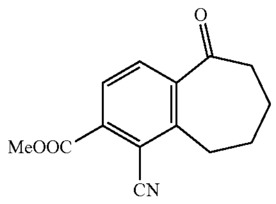 [SMILES: COC(=O)c1ccc2c(c1C#N)CCCCC2=O]

To a solution of methyl 1-chloro-5-oxo-6,7,8,9-tetrahydro-5H-benzo[7]annulene-2-carboxylate (2.1 g, 8.31 mmol), Zn (163 mg, 2.49 mmol), $Zn(CN)_2$ (976 mg, 8.31 mmol) and dppf (461 mg, 831 μmol) in DMA (25 ml) was added $Pd_2(dba)_3$ (761 mg, 0.83 mmol). The mixture was stirred at 150° C. for 2 hours. The residue was poured into $H_2O$ (20 ml) and extracted three times with EtOAc (30 ml). The combined organic phases were dried over anhydrous $Na_2SO_4$, filtered, and concentrated in vacuo. The residue was purified by flash chromatography eluting with a 0-40% gradient of Ethyl acetate in Petroleum ether to give 750 mg (37%) of methyl 1-cyano-5-oxo-6,7,8,9-tetrahydro-5H-benzo[7]annulene-2-carboxylate.

LC/MS (m/z, MH+): 244

Step 2: Methyl 4-cyano-9-(((trifluoromethyl)sulfonyl)oxy)-6,7-dihydro-5H-benzo[7]annulene-3-carboxylate

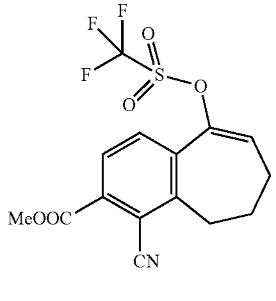 [SMILES: COC(=O)c1ccc2c(c1C#N)CCCC=C2OS(=O)(=O)C(F)(F)F]

Step 2 of Intermediate 42 was prepared following a similar procedure to that of Step 5 of Intermediate 40 from methyl 1-cyano-5-oxo-6,7,8,9-tetrahydro-5H-benzo[7]annulene-2-carboxylate to give 500 mg (88%) of methyl 4-cyano-9-(((trifluoromethyl)sulfonyl)oxy)-6,7-dihydro-5H-benzo[7]annulene-3-carboxylate.

LC/MS (m/z, MH+): 376

Step 3: Methyl 4-cyano-9-(4-((1-(3-fluoropropyl)azetidin-3-yl)methyl)phenyl)-6,7-dihydro-5H-benzo[7]annulene-3-carboxylate

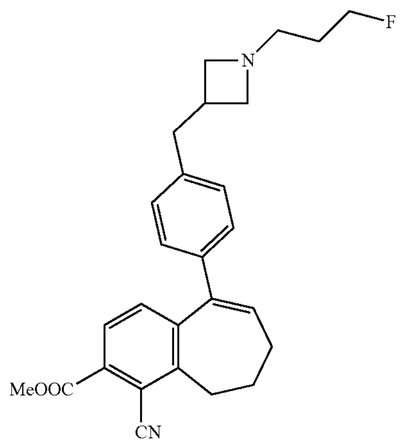 [SMILES: COC(=O)c1ccc2c(c1C#N)CCCC=C2c1ccc(CC2CN(CCCF)C2)cc1]

Step 3 of Intermediate 42 was prepared following a similar procedure to that of Step 7 of Intermediate 38 from methyl 4-cyano-9-(((trifluoromethyl)sulfonyl)oxy)-6,7-dihydro-5H-benzo[7]annulene-3-carboxylate to give 350 mg (80%) of methyl 4-cyano-9-(4-((1-(3-fluoropropyl)azetidin-3-yl)methyl)phenyl)-6,7-dihydro-5H-benzo[7]annulene-3-carboxylate.

LC/MS (m/z, MH+): 433

Step 4: Methyl 8-bromo-4-cyano-9-(4-((1-(3-fluoropropyl)azetidin-3-yl)methyl)phenyl)-6,7-dihydro-5H-benzo[7]annulene-3-carboxylate

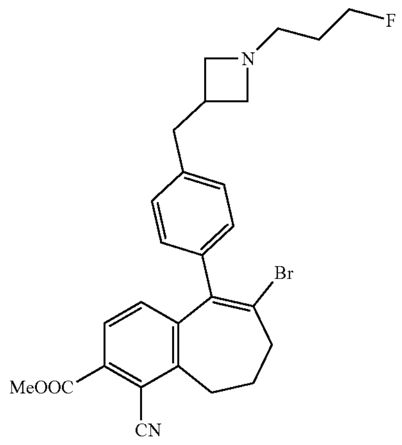 [SMILES: COC(=O)c1ccc2c(c1C#N)CCCC(Br)=C2c1ccc(CC2CN(CCCF)C2)cc1]

Step 4 of Intermediate 42 was prepared following a similar procedure to that of Step 2 of Intermediate 7 from methyl 4-cyano-9-(4-((1-(3-fluoropropyl)azetidin-3-yl)methyl)phenyl)-6,7-dihydro-5H-benzo[7]annulene-3-carboxylate to give 440 mg (91%) of methyl 8-bromo-4-cyano-9-(4-((1-(3-fluoropropyl)azetidin-3-yl)methyl)phenyl)-6,7-dihydro-5H-benzo[7]annulene-3-carboxylate.

LC/MS (m/z, MH+): 513

Intermediate 43: Methyl 8-bromo-2-cyano-9-(4-((1-(3-fluoropropyl)azetidin-3-yl)methyl)phenyl)-6,7-dihydro-5H-benzo[7]annulene-3-carboxylate

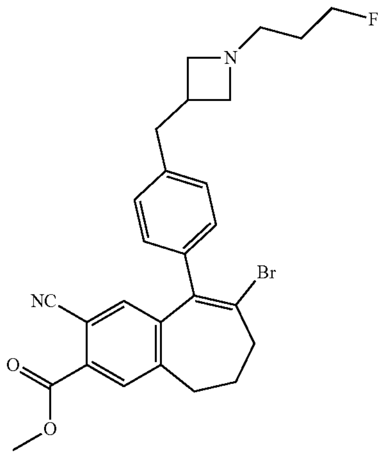 [SMILES: COC(=O)c1cc2c(cc1C#N)C(c1ccc(CC3CN(CCCF)C3)cc1)=C(Br)CCC2]

Step 1: Methyl 3-cyano-5-oxo-6,7,8,9-tetrahydro-5H-benzo[7]annulene-2-carboxylate

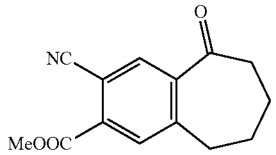 [SMILES: COC(=O)c1cc2c(cc1C#N)C(=O)CCCC2]

Step 1 of Intermediate 43 was prepared following a similar procedure to that of Step 1 of Intermediate 42 from methyl 3-chloro-5-oxo-6,7,8,9-tetrahydro-5H-benzo[7]annulene-2-carboxylate to give 360 mg (36%) of methyl 3-cyano-5-oxo-6,7,8,9-tetrahydro-5H-benzo[7]annulene-2-carboxylate.

LC/MS (m/z, MH+): 244

Step 2: Methyl 2-cyano-9-(((trifluoromethyl)sulfonyl)oxy)-6,7-dihydro-5H-benzo[7]annulene-3-carboxylate

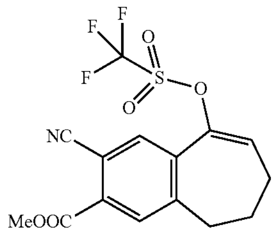 [SMILES: COC(=O)c1cc2c(cc1C#N)C(OS(=O)(=O)C(F)(F)F)=CCCC2]

Step 2 of Intermediate 43 was prepared following a similar procedure to that of Step 5 of Intermediate 40 from methyl 3-cyano-5-oxo-6,7,8,9-tetrahydro-5H-benzo[7]annulene-2-carboxylate to give 200 mg (47%) of methyl 2-cyano-9-(((trifluoromethyl)sulfonyl)oxy)-6,7-dihydro-5H-benzo[7]annulene-3-carboxylate.

LC/MS (m/z, MH+): 376

Step 3: Methyl 2-cyano-9-(4-((1-(3-fluoropropyl) azetidin-3-yl)methyl)phenyl)-6,7-dihydro-5H-benzo [7]annulene-3-carboxylate

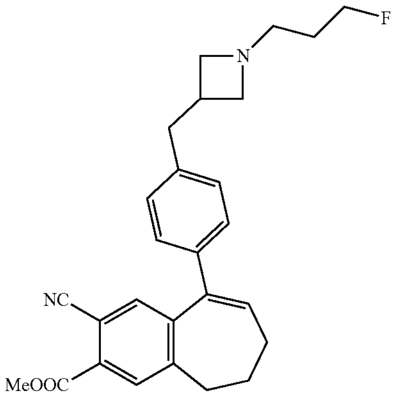 [SMILES: COC(=O)c1cc2c(cc1C#N)C(c1ccc(CC3CN(CCCF)C3)cc1)=CCCC2]

Step 3 of Intermediate 43 was prepared following a similar procedure to that of Step 7 of Intermediate 38 from methyl 2-cyano-9-(((trifluoromethyl)sulfonyl)oxy)-6,7-dihydro-5H-benzo[7]annulene-3-carboxylate to give 200 mg (crude) of methyl 2-cyano-9-(4-((1-(3-fluoropropyl)azetidin-3-yl)methyl)phenyl)-6,7-dihydro-5H-benzo[7]annulene-3-carboxylate.

LC/MS (m/z, MH+): 433

Step 4: Methyl 8-bromo-2-cyano-9-(4-((1-(3-fluoropropyl)azetidin-3-yl)methyl)phenyl)-6,7-dihydro-5H-benzo[7]annulene-3-carboxylate

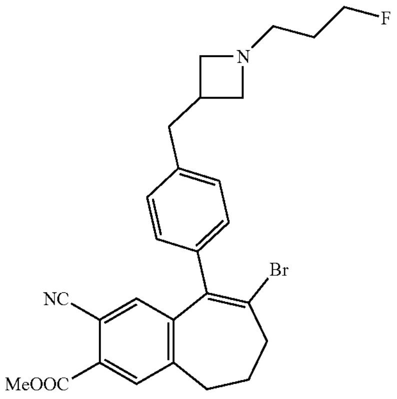

Step 4 of Intermediate 43 was prepared following a similar procedure to that of Step 2 of Intermediate 7 from methyl 2-cyano-9-(4-((1-(3-fluoropropyl)azetidin-3-yl)methyl)phenyl)-6,7-dihydro-5H-benzo[7]annulene-3-carboxylate to give 100 mg (64%) of methyl 8-bromo-2-cyano-9-(4-((1-(3-fluoropropyl)azetidin-3-yl)methyl)phenyl)-6,7-dihydro-5H-benzo[7]annulene-3-carboxylate.

LC/MS (m/z, MH+): 513

Intermediate 44: Methyl 8-bromo-2-fluoro-9-(4-((1-(3-fluoropropyl)azetidin-3-yl)methyl)phenyl)-6,7-dihydro-5H-benzo[7]annulene-3-carboxylate

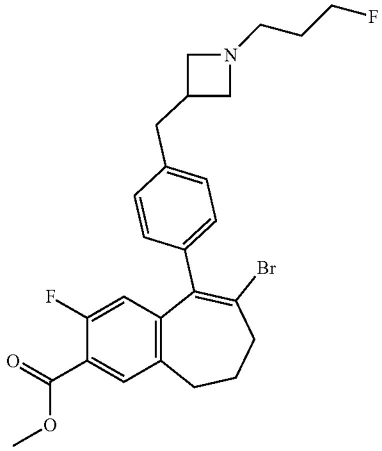 [SMILES: COC(=O)c1cc2c(cc1F)C(c1ccc(CC3CN(CCCF)C3)cc1)=C(Br)CCC2]

Step 1: 3-Fluoro-5-oxo-6,7,8,9-tetrahydro-5H-benzo [7]annulen-2-yl trifluoromethanesulfonate

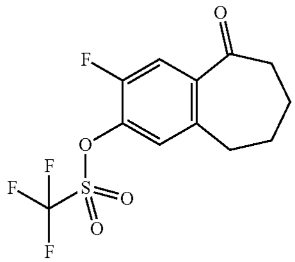 [SMILES: O=C1CCCCc2cc(OS(=O)(=O)C(F)(F)F)c(F)cc21]

Step 1 of Intermediate 44 was prepared following a similar procedure to that of step 1 of Intermediate 9 from 3-fluoro-2-hydroxy-6,7,8,9-tetrahydro-5H-benzo[7]annulen-5-one to give 4.2 g (81%) of 3-fluoro-5-oxo-6,7,8,9-tetrahydro-5H-benzo[7]annulen-2-yl trifluoromethanesulfonate.

LC/MS (m/z, MH+): 327

Step 2: Methyl 3-fluoro-5-oxo-6,7,8,9-tetrahydro-5H-benzo[7]annulene-2-carboxylate

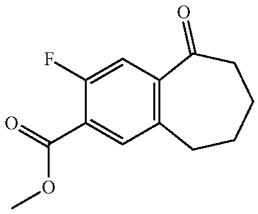 [SMILES: COC(=O)c1cc2c(cc1F)C(=O)CCCC2]

Step 2 of Intermediate 44 was prepared following a similar procedure to that of step 2 Intermediate 9 from 3-fluoro-5-oxo-6,7,8,9-tetrahydro-5H-benzo[7]annulen-2-yl trifluoromethanesulfonate to give 2.9 g (95%) of methyl 3-fluoro-5-oxo-6,7,8,9-tetrahydro-5H-benzo[7]annulene-2-carboxylate.

LC/MS (m/z, MH+): 237

Step 3: Methyl 2-fluoro-9-(((trifluoromethyl)sulfonyl)oxy)-6,7-dihydro-5H-benzo[7]annulene-3-carboxylate

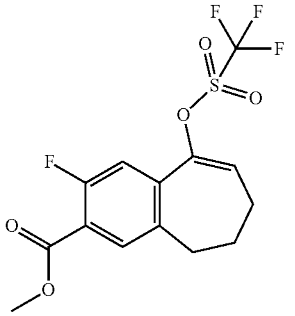 [SMILES: COC(=O)c1cc2c(cc1F)C(OS(=O)(=O)C(F)(F)F)=CCCC2]

Step 3 of Intermediate 44 was prepared following a similar procedure to that of Step 3 of Intermediate 9 from methyl 3-fluoro-5-oxo-6,7,8,9-tetrahydro-5H-benzo[7]annulene-2-carboxylate to give 3.6 g (80%) of methyl 2-fluoro-9-(((trifluoromethyl)sulfonyl)oxy)-6,7-dihydro-5H-benzo[7]annulene-3-carboxylate.

LC/MS (m/z, MH+): 369

Step 4: Methyl 2-fluoro-9-(4,4,5,5-tetramethyl-1,3,2-dioxaborolan-2-yl)-6,7-dihydro-5H-benzo[7]annulene-3-carboxylate

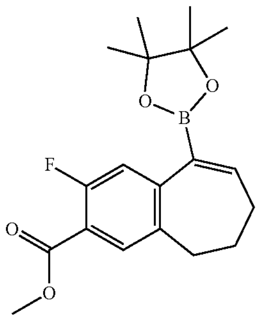 [SMILES: COC(=O)c1cc2c(cc1F)C(B1OC(C)(C)C(C)(C)O1)=CCCC2]

Step 4 of Intermediate 44 was prepared following a similar procedure to that of Intermediate 4 from methyl 2-fluoro-9-(((trifluoromethyl)sulfonyl)oxy)-6,7-dihydro-5H-benzo[7]annulene-3-carboxylate to give 4.3 g (100% yield) of methyl 2-fluoro-9-(4,4,5,5-tetramethyl-1,3,2-dioxaborolan-2-yl)-6,7-dihydro-5H-benzo[7]annulene-3-carboxylate.

LC/MS (m/z, MH+): 347

Step 5: Methyl 2-fluoro-9-(4-((1-(3-fluoropropyl)azetidin-3-yl)methyl)phenyl)-6,7-dihydro-5H-benzo[7]annulene-3-carboxylate

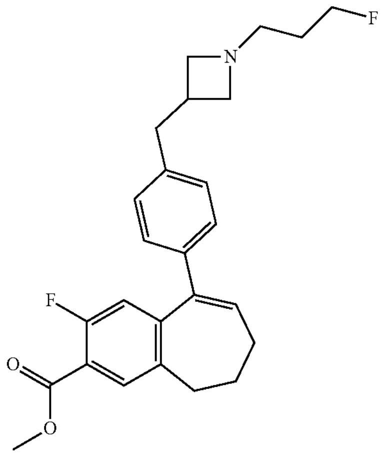 [SMILES: COC(=O)c1cc2c(cc1F)C(c1ccc(CC3CN(CCCF)C3)cc1)=CCCC2]

Step 5 of Intermediate 44 was prepared following a similar procedure to that of Step 1 of Intermediate 7 from methyl 2-fluoro-9-(4,4,5,5-tetramethyl-1,3,2-dioxaborolan-2-yl)-6,7-dihydro-5H-benzo[7]annulene-3-carboxylate to give 827 mg (38% yield) of methyl 2-fluoro-9-(4-((1-(3-fluoropropyl)azetidin-3-yl)methyl)phenyl)-6,7-dihydro-5H-benzo[7]annulene-3-carboxylate.

LC/MS (m/z, MH+): 426

Step 6: Methyl 8-bromo-2-fluoro-9-(4-((1-(3-fluoropropyl)azetidin-3-yl)methyl)phenyl)-6,7-dihydro-5H-benzo[7]annulene-3-carboxylate

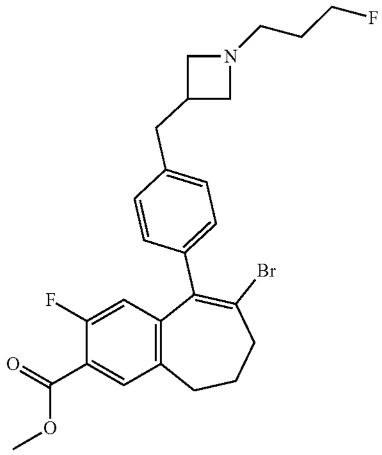 [SMILES: COC(=O)c1cc2c(cc1F)C(c1ccc(CC3CN(CCCF)C3)cc1)=C(Br)CCC2]

Step 6 of Intermediate 44 was prepared following a similar procedure to that of Step 2 of Intermediate 7 from methyl 2-fluoro-9-(4-((1-(3-fluoropropyl)azetidin-3-yl)methyl)phenyl)-6,7-dihydro-5H-benzo[7]annulene-3-carboxylate to give 405 mg (41% yield) of methyl 8-bromo-2-fluoro-9-(4-((1-(3-fluoropropyl)azetidin-3-yl)methyl)phenyl)-6,7-dihydro-5H-benzo[7]annulene-3-carboxylate.

LC/MS (m/z, MH+): 504

Intermediate 45: Methyl 8-bromo-4-fluoro-9-(4-((1-(3-fluoropropyl)azetidin-3-yl)methyl)phenyl)-6,7-dihydro-5H-benzo[7]annulene-3-carboxylate

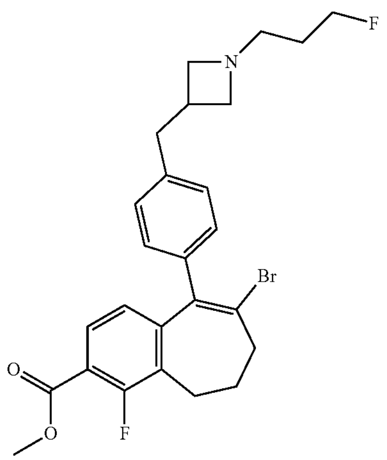 [SMILES: COC(=O)c1ccc2c(c1F)CCCC(Br)=C2c1ccc(CC2CN(CCCF)C2)cc1]

Step 1: Methyl 4-fluoro-9-(4,4,5,5-tetramethyl-1,3,2-dioxaborolan-2-yl)-6,7-dihydro-5H-benzo[7]annulene-3-carboxylate

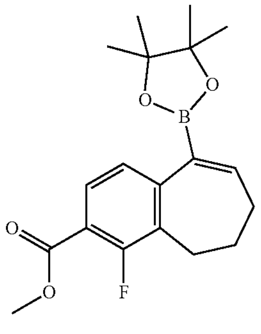 [SMILES: COC(=O)c1ccc2c(c1F)CCCC=C2B1OC(C)(C)C(C)(C)O1]

Step 1 of Intermediate 45 was prepared following a similar procedure to that of Intermediate 4 from methyl 4-fluoro-9-(((trifluoromethyl)sulfonyl)oxy)-6,7-dihydro-5H-benzo[7]annulene-3-carboxylate (prepared according to WO2017140669) to give 3.1 g (67% yield) of methyl 4-fluoro-9-(4,4,5,5-tetramethyl-1,3,2-dioxaborolan-2-yl)-6,7-dihydro-5H-benzo[7]annulene-3-carboxylate.

LC/MS (m/z, MH+): 347

Step 2: Methyl 4-fluoro-9-(4-((1-(3-fluoropropyl)azetidin-3-yl)methyl)phenyl)-6,7-dihydro-5H-benzo[7]annulene-3-carboxylate

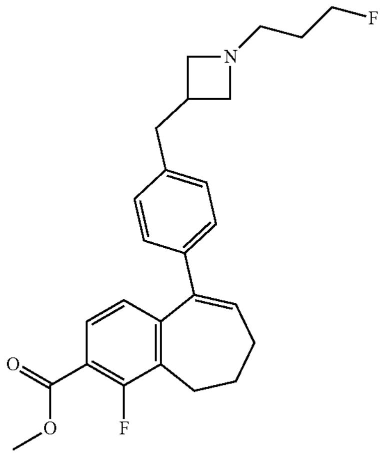 [SMILES: COC(=O)c1ccc2c(c1F)CCCC=C2c1ccc(CC2CN(CCCF)C2)cc1]

Step 2 of Intermediate 45 was prepared following a similar procedure to that of Step 1 of Intermediate 7 from methyl 4-fluoro-9-(4,4,5,5-tetramethyl-1,3,2-dioxaborolan-2-yl)-6,7-dihydro-5H-benzo[7]annulene-3-carboxylate to give 1.9 g (40% yield) of methyl 4-fluoro-9-(4-((1-(3-fluoropropyl)azetidin-3-yl)methyl)phenyl)-6,7-dihydro-5H-benzo[7]annulene-3-carboxylate.

LC/MS (m/z, MH+): 426

Step 3: Methyl 8-bromo-4-fluoro-9-(4-((1-(3-fluoropropyl)azetidin-3-yl)methyl)phenyl)-6,7-dihydro-5H-benzo[7]annulene-3-carboxylate

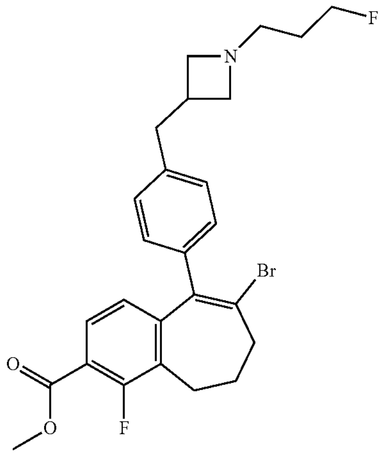 [SMILES: COC(=O)c1ccc2c(c1F)CCCC(Br)=C2c1ccc(CC2CN(CCCF)C2)cc1]

Step 3 of Intermediate 45 was prepared following a similar procedure to that of Step 2 of Intermediate 7 from methyl 4-fluoro-9-(4-((1-(3-fluoropropyl)azetidin-3-yl)methyl)phenyl)-6,7-dihydro-5H-benzo[7]annulene-3-carboxylate to give 1.24 g (55% yield) of methyl 8-bromo-4-fluoro-9-(4-((1-(3-fluoropropyl)azetidin-3-yl)methyl)phenyl)-6,7-dihydro-5H-benzo[7]annulene-3-carboxylate.

LC/MS (m/z, MH+): 504

Intermediate 46: Methyl 8-bromo-2,4-difluoro-9-(4-((1-(3-fluoropropyl)azetidin-3-yl)methyl)phenyl)-6,7-dihydro-5H-benzo[7]annulene-3-carboxylate

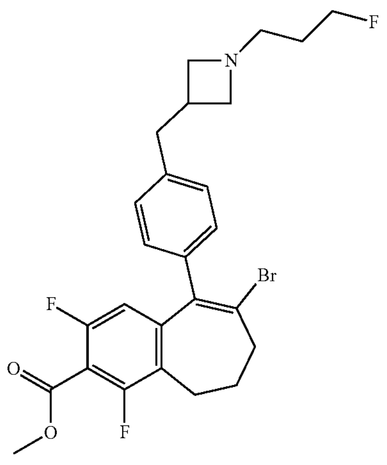 [SMILES: COC(=O)c1c(F)cc2c(c1F)CCCC(Br)=C2c1ccc(CC2CN(CCCF)C2)cc1]

Step 1: Ethyl (Z)-5-(2,4-difluoro-3-methoxyphenyl)pent-4-enoate

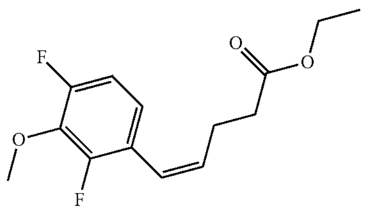 [SMILES: CCOC(=O)CC/C=C\c1ccc(F)c(OC)c1F]

To a solution of [3-(ethoxycarbonyl)propyl]triphenylphosphonium bromide (5.42 g, 11.5 mmol) in THF (40 mL) at −78° C. was slowly added a 1 M solution of potassium bis(trimethylsilyl)amide THF (11.5 mL, 11.5 mmol). The reaction mixture was stirred 1 hour at −78° C. and a solution of 2,4-difluoro-3-methoxybenzaldehyde (1 g, 5.75 mmol) in THF (5 mL) was added. The reaction mixture was stirred at −78° C. for 1 h and then allowed to reach room temperature overnight under stirring. The mixture was poured into water and extracted with DCM. The aqueous layer was separated and extracted twice with DCM. The combined organic layers were washed with brine, dried over $MgSO_4$, filtered and concentrated under reduced pressure. The residue was purified by flash chromatography eluting with a gradient of heptane/ethyl acetate: from 100/0 to 90/10 to give 1.1 g (71%) of ethyl (Z)-5-(2,4-difluoro-3-methoxyphenyl)pent-4-enoate.

LC/MS (m/z, MH+): 271

Step 2: Ethyl 5-(2,4-difluoro-3-methoxyphenyl)pentanoate

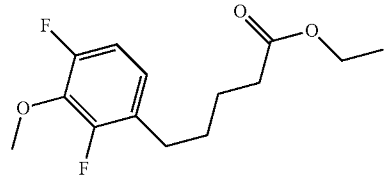 [SMILES: CCOC(=O)CCCCc1ccc(F)c(OC)c1F]

To a solution of ethyl (Z)-5-(2,4-difluoro-3-methoxyphenyl)pent-4-enoate (8.4 g, 31 mmol) in ethanol (40 mL) was added Pd/C 10% (0.33 g). The black suspension was hydrogenated in an autoclave at room temperature under 3.5 bars of hydrogen for 1 hour. The mixture was filtered with ethanol washes then the filtrate was concentrated under reduced pressure to give 8.4 g (99%) of ethyl 5-(2,4-difluoro-3-methoxyphenyl)pentanoate as a colorless oil.

LC/MS (m/z, MH+): 273

Step 3: 5-(2,4-Difluoro-3-methoxyphenyl)pentanoic Acid

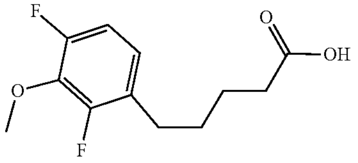 [SMILES: COc1c(F)ccc(CCCCC(=O)O)c1F]

To a solution of ethyl 5-(2,4-difluoro-3-methoxyphenyl)pentanoate (5.7 g, 20.9 mmol) in ethanol (15 mL) were added aqueous NaOH (8.8 mL, 44 mmol). The reaction mixture was stirred for 40 minutes at 50° C. After cooling to room temperature, ice was added then the reaction mixture was acidified with 1 M aqueous HCl to pH 3 and extracted three times with EtOAc. The combined organic layers were dried over $MgSO_4$, filtered and concentrated under reduced pressure to give 5.1 g (99%) of 5-(2,4-difluoro-3-methoxyphenyl)pentanoic acid.

LC/MS (m/z, MH+): 245

Step 4: 1,3-Difluoro-2-methoxy-6,7,8,9-tetrahydro-5H-benzo[7]annulen-5-one

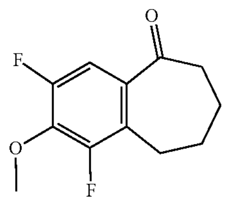 [SMILES: COc1c(F)cc2c(c1F)CCCCC2=O]

A mixture of 5-(2,4-difluoro-3-methoxyphenyl)pentanoic acid (5.5 g, 22.5 mmol) and Eaton's reagent (143 mL, 0.9 mol) was stirred at room temperature for 12 hours then ice was added. Saturated aqueous solution of $NaHCO_3$ and DCM were added. The organic layer was separated and the aqueous layer extracted three times with DCM. The combined organic layers were dried over $MgSO_4$, filtered and concentrated under reduced pressure to give 5 g (98%) of 1,3-difluoro-2-methoxy-6,7,8,9-tetrahydro-5H-benzo[7]annulen-5-one.

LC/MS (m/z, MH+): 227

Step 5: 1,3-Difluoro-2-hydroxy-6,7,8,9-tetrahydro-5H-benzo[7]annulen-5-one

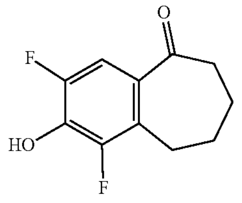 [SMILES: O=C1CCCCc2c1cc(F)c(O)c2F]

To 1,3-difluoro-2-methoxy-6,7,8,9-tetrahydro-5H-benzo[7]annulen-5-one (6.79 g, 30 mmol) was slowly added a 33% solution of hydrobromic acid in acetic acid (34 mL, 0.6 mol). The brown reaction mixture was heated at 75° C. overnight. An additional 33% solution of hydrobromic acid in acetic acid (17 mL, 0.3 mol) was added and the mixture was heated at 75° C. for 2 days. After cooling down to room temperature, the mixture was poured onto ice. Saturated aqueous solution of $NaHCO_3$ and ethyl acetate were added. The organic layer was separated and the aqueous layer extracted twice with ethyl acetate. The combined organic layers were dried over $MgSO_4$, filtered and concentrated under reduced pressure. The residue was purified by flash chromatography eluting with a gradient of heptane/ethyl acetate: from 95/5 to 50/50 to give 4.2 g (66%) of 1,3-difluoro-2-hydroxy-6,7,8,9-tetrahydro-5H-benzo[7]annulen-5-one as a yellow solid.

LC/MS (m/z, M-H−): 211

Step 6: 1,3-Difluoro-5-oxo-6,7,8,9-tetrahydro-5H-benzo[7]annulen-2-yl trifluoromethanesulfonate

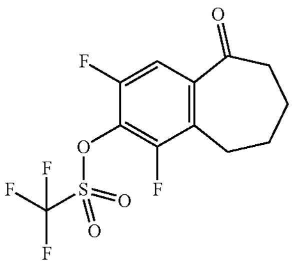 [SMILES: O=C1CCCCc2c1cc(F)c(OS(=O)(=O)C(F)(F)F)c2F]

Step 6 of Intermediate 46 was prepared following a similar procedure to that of step 1 of Intermediate 9 from 1,3-difluoro-2-hydroxy-6,7,8,9-tetrahydro-5H-benzo[7]annulen-5-one to give 6.1 g (89%) of 1,3-difluoro-5-oxo-6,7,8,9-tetrahydro-5H-benzo[7]annulen-2-yl trifluoromethanesulfonate as a yellow oil.

LC/MS (m/z, MH+): 345

Step 7: Methyl 1,3-difluoro-5-oxo-6,7,8,9-tetrahydro-5H-benzo[7]annulene-2-carboxylate

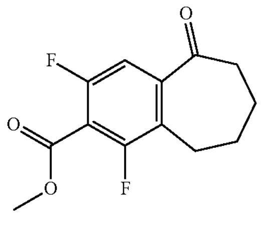 [SMILES: COC(=O)c1c(F)cc2c(c1F)CCCCC2=O]

Step 7 of Intermediate 46 was prepared following a similar procedure to that of step 2 Intermediate 9 from 1,3-difluoro-5-oxo-6,7,8,9-tetrahydro-5H-benzo[7]annulen-2-yl trifluoromethanesulfonate to give 3 g (66%) of methyl 1,3-difluoro-5-oxo-6,7,8,9-tetrahydro-5H-benzo[7]annulene-2-carboxylate as a colorless oil.

LC/MS (m/z, MH+): 255

Step 8: Methyl 2,4-difluoro-9-(((trifluoromethyl)sulfonyl)oxy)-6,7-dihydro-5H-benzo[7]annulene-3-carboxylate

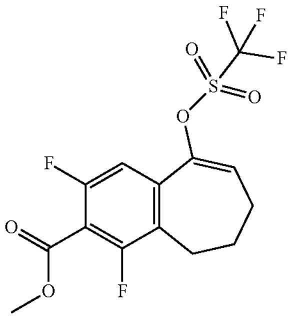 [SMILES: COC(=O)c1c(F)cc2c(c1F)CCCC=C2OS(=O)(=O)C(F)(F)F]

Step 8 of Intermediate 46 was prepared following a similar procedure to that of Step 3 of Intermediate 9 from methyl 1,3-difluoro-5-oxo-6,7,8,9-tetrahydro-5H-benzo[7]annulene-2-carboxylate to give 1 g (37%) of methyl 2,4-difluoro-9-(((trifluoromethyl)sulfonyl)oxy)-6,7-dihydro-5H-benzo[7]annulene-3-carboxylate.

Step 9: Methyl 2,4-difluoro-9-(4,4,5,5-tetramethyl-1,3,2-dioxaborolan-2-yl)-6,7-dihydro-5H-benzo[7]annulene-3-carboxylate

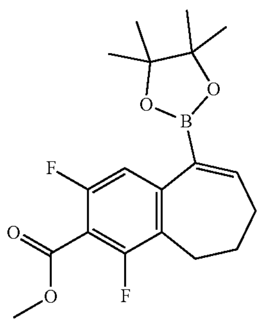 [SMILES: COC(=O)c1c(F)cc2c(c1F)CCCC=C2B1OC(C)(C)C(C)(C)O1]

Step 9 of Intermediate 46 was prepared following a similar procedure to that of Intermediate 4 from methyl 2,4-difluoro-9-(((trifluoromethyl)sulfonyl)oxy)-6,7-dihydro-5H-benzo[7]annulene-3-carboxylate to give 0.75 g (80% yield) of methyl 2,4-difluoro-9-(4,4,5,5-tetramethyl-1,3,2-dioxaborolan-2-yl)-6,7-dihydro-5H-benzo[7]annulene-3-carboxylate.

LC/MS (m/z, MH+): 365

Step 10: Methyl 2,4-difluoro-9-(4-((1-(3-fluoropropyl)azetidin-3-yl)methyl)phenyl)-6,7-dihydro-5H-benzo[7]annulene-3-carboxylate

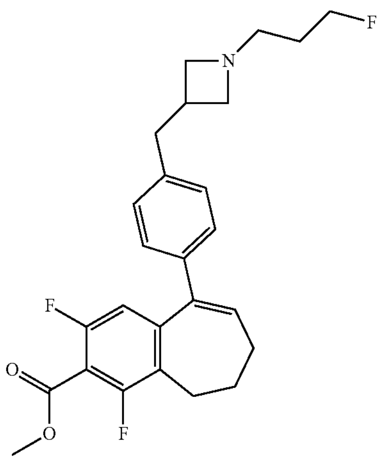 [SMILES: COC(=O)c1c(F)cc2c(c1F)CCCC=C2c1ccc(CC2CN(CCCF)C2)cc1]

Step 10 of Intermediate 46 was prepared following a similar procedure to that of Step 1 of Intermediate 7 from methyl 2,4-difluoro-9-(4,4,5,5-tetramethyl-1,3,2-dioxaborolan-2-yl)-6,7-dihydro-5H-benzo[7]annulene-3-carboxylate to give 1.28 g (93% yield) of methyl 2,4-difluoro-9-(4-((1-(3-fluoropropyl)azetidin-3-yl)methyl)phenyl)-6,7-dihydro-5H-benzo[7]annulene-3-carboxylate.

LC/MS (m/z, MH+): 444

Step 11: Methyl 8-bromo-2,4-difluoro-9-(4-((1-(3-fluoropropyl)azetidin-3-yl)methyl)phenyl)-6,7-dihydro-5H-benzo[7]annulene-3-carboxylate

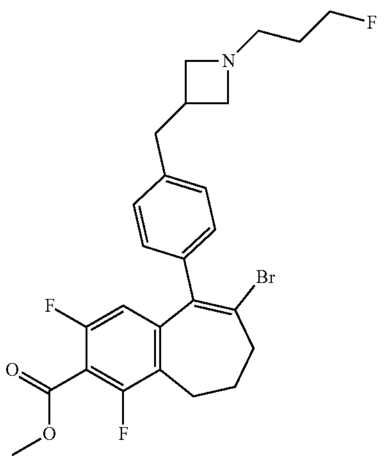 [SMILES: COC(=O)c1c(F)cc2c(c1F)CCCC(Br)=C2c1ccc(CC2CN(CCCF)C2)cc1]

Step 11 of Intermediate 46 was prepared following a similar procedure to that of Step 2 of Intermediate 7 from methyl 2,4-difluoro-9-(4-((1-(3-fluoropropyl)azetidin-3-yl)methyl)phenyl)-6,7-dihydro-5H-benzo[7]annulene-3-carboxylate to give 0.67 g (46% yield) of methyl 8-bromo-2,4-difluoro-9-(4-((1-(3-fluoropropyl)azetidin-3-yl)methyl)phenyl)-6,7-dihydro-5H-benzo[7]annulene-3-carboxylate as a brownish foam.

LC/MS (m/z, MH+): 522

Intermediate 47: 3-(4-Bromobenzylidene)-1-(3-fluoropropyl)azetidine

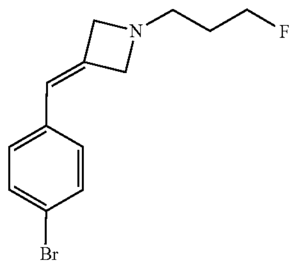 [SMILES: FCCCN1CC(=Cc2ccc(Br)cc2)C1]

Intermediate 47 was prepared following a similar procedure to that of Method 2 of Intermediate 1 from 3-(4-bromobenzylidene)azetidine hydrochloride to give 0.34 g (40%) of 3-(4-bromobenzylidene)-1-(3-fluoropropyl)azetidine LC/MS (m/z, MH+): 284

Intermediate 48: Tert-butyl 3-((6-(8-bromo-3-(methoxycarbonyl)-6,7-dihydro-5H-benzo[7]annulen-9-yl)pyridin-3-yl)methyl)azetidine-1-carboxylate

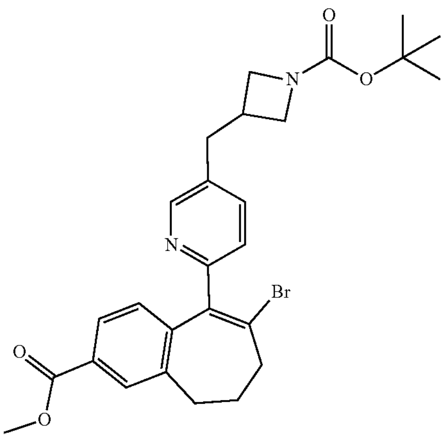 [SMILES: COC(=O)c1ccc2c(c1)CCCC(Br)=C2c1ccc(CC2CN(C(=O)OC(C)(C)C)C2)cn1]

Step 1: Tert-butyl 3-((6-bromopyridin-3-yl)methyl)azetidine-1-carboxylate

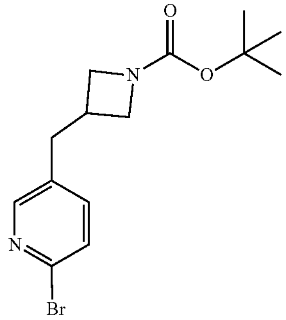 [SMILES: CC(C)(C)OC(=O)N1CC(Cc2ccc(Br)nc2)C1]

To a solution of tert-butyl 3-methyleneazetidine-1-carboxylate (2.54 g, 15 mmol) in anhydrous THF (30 mL) under Ar atmosphere was added 9-BBN (33 mL, 16.5 mmol). The resulting mixture was heated to 75° C. for 2 hours. After allowing the temperature to cool down to room temperature, 2-bromo-5-iodopyridine (3.84 g, 13.5 mmol), $K_2CO_3$ (910 mg, 6.58 mmol), anhydrous DMF (21 mL) and $Pd(dppf)Cl_2$ (0.33 g, 0.45 mmol) were added and the mixture was heated to 60° C. overnight under Ar atmosphere. After allowing the temperature to cool down to room temperature, EtOAc and water were added. The layers were separated and the aqueous layer was extracted twice with EtOAc. The combined organic layers were dried over $Na_2SO_4$, filtered, and concentrated under reduced pressure. The residue obtained was purified by flash chromatography eluting with a gradient of cyclohexane/EtOAc from 100/00 to 50/50 to give 2.07 g (42%) of tert-butyl 3-((6-bromopyridin-3-yl)methyl)azetidine-1-carboxylate.

LC/MS (m/z, MH+): 327

Step 2: Tert-butyl 3-((6-(3-(methoxycarbonyl)-6,7-dihydro-5H-benzo[7]annulen-9-yl)pyridin-3-yl)methyl)azetidine-1-carboxylate

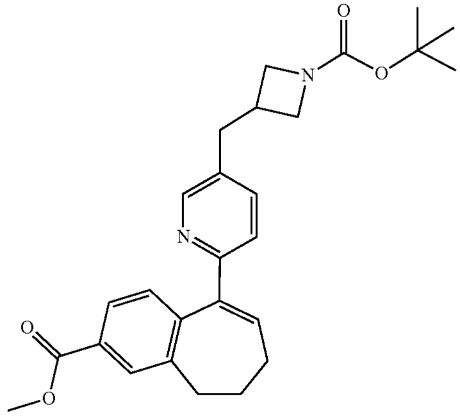 [SMILES: COC(=O)c1ccc2c(c1)CCCC=C2c1ccc(CC2CN(C(=O)OC(C)(C)C)C2)cn1]

Step 2 of Intermediate 48 was prepared following a similar procedure to that of step 1 of Intermediate 7 from tert-butyl 3-((6-bromopyridin-3-yl)methyl)azetidine-1-carboxylate to give 0.4 g (58%) of tert-butyl 3-((6-(3-(methoxycarbonyl)-6,7-dihydro-5H-benzo[7]annulen-9-yl)pyridin-3-yl)methyl)azetidine-1-carboxylate as a brownish foam.

LC/MS (m/z, MH+): 449

Step 3: Tert-butyl 3-((6-(8-bromo-3-(methoxycarbonyl)-6,7-dihydro-5H-benzo[7]annulen-9-yl)pyridin-3-yl)methyl)azetidine-1-carboxylate

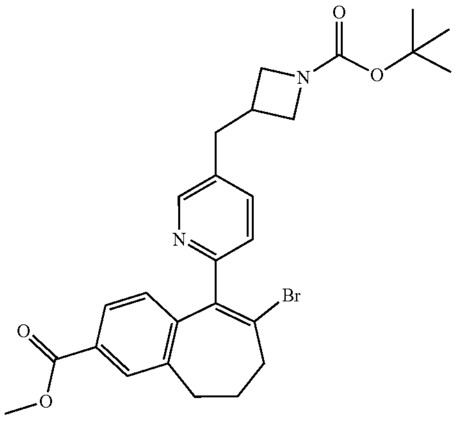 [SMILES: COC(=O)c1ccc2c(c1)CCCC(Br)=C2c1ccc(CC2CN(C(=O)OC(C)(C)C)C2)cn1]

Step 3 of Intermediate 48 was prepared following a similar procedure to that of step 2 of Intermediate 7 from tert-butyl 3-((6-(3-(methoxycarbonyl)-6,7-dihydro-5H-benzo[7]annulen-9-yl)pyridin-3-yl)methyl)azetidine-1-carboxylate to give 60 mg (27%) of tert-butyl 3-((6-(8-bromo-3-(methoxycarbonyl)-6,7-dihydro-5H-benzo[7]annulen-9-yl)pyridin-3-yl)methyl)azetidine-1-carboxylate as a yellowish foam.

LC/MS (m/z, MH+): 527

Intermediate 49: 8-Bromo-9-(4-((1-(3-fluoropropyl)azetidin-3-yl)methyl)phenyl)-6,7-dihydro-5H-benzo[7]annulen-3-ol

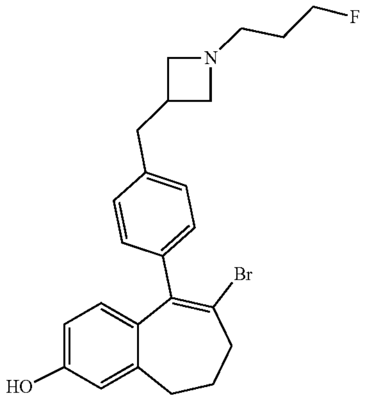 [SMILES: Oc1ccc2c(c1)CCCC(Br)=C2c1ccc(CC2CN(CCCF)C2)cc1]

Step 1: 9-(4-((1-(3-fluoropropyl)azetidin-3-yl)methyl)phenyl)-6,7-dihydro-5H-benzo[7]annulen-3-yl Pivalate

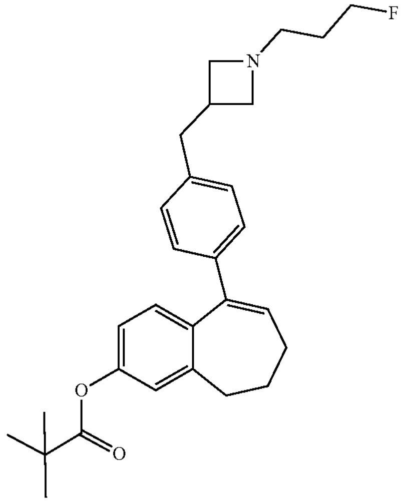 [SMILES: CC(C)(C)C(=O)Oc1ccc2c(c1)CCCC=C2c1ccc(CC2CN(CCCF)C2)cc1]

Step 1 of Intermediate 49 was prepared following a similar procedure to that of step 1 of Intermediate 7 from 9-(4,4,5,5-tetramethyl-1,3,2-dioxaborolan-2-yl)-6,7-dihydro-5H-benzo[7]annulen-3-yl pivalate (prepared according to WO2018091153) and 3-(4-bromobenzyl)-1-(3-fluoropropyl)azetidine to give 1.27 g (70%) of 9-(4-((1-(3-fluoropropyl)azetidin-3-yl)methyl)phenyl)-6,7-dihydro-5H-benzo[7]annulen-3-yl pivalate.

LC/MS (m/z, MH+): 450

Step 2: 8-Bromo-9-(4-((1-(3-fluoropropyl)azetidin-3-yl)methyl)phenyl)-6,7-dihydro-5H-benzo[7]annulen-3-yl pivalate

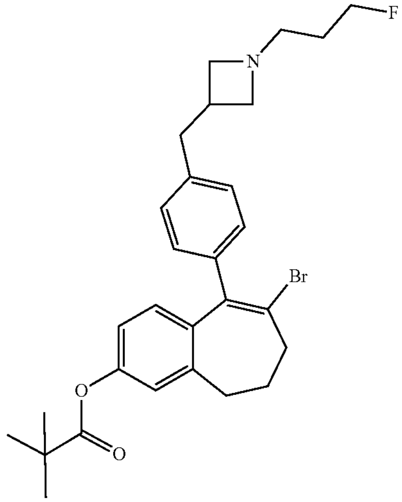 [SMILES: CC(C)(C)C(=O)Oc1ccc2c(c1)CCCC(Br)=C2c1ccc(CC2CN(CCCF)C2)cc1]

Step 2 of Intermediate 49 was prepared following a similar procedure to that of step 2 of Intermediate 7 from 9-(4-((1-(3-fluoropropyl)azetidin-3-yl)methyl)phenyl)-6,7-dihydro-5H-benzo[7]annulen-3-yl pivalate to give 1.7 g (89%) of 8-bromo-9-(4-((1-(3-fluoropropyl)azetidin-3-yl)methyl)phenyl)-6,7-dihydro-5H-benzo[7]annulen-3-yl pivalate.

LC/MS (m/z, MH+): 528

Step 3: 8-Bromo-9-(4-((1-(3-fluoropropyl)azetidin-3-yl)methyl)phenyl)-6,7-dihydro-5H-benzo[7]annulen-3-ol

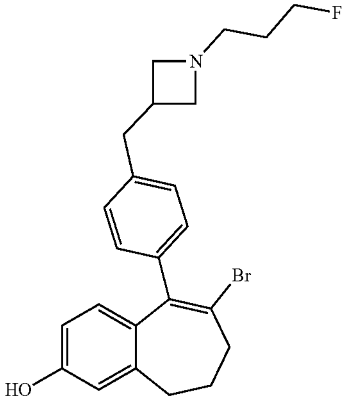 [SMILES: Oc1ccc2c(c1)CCCC(Br)=C2c1ccc(CC2CN(CCCF)C2)cc1]

To a solution of 8-bromo-9-(4-((1-(3-fluoropropyl)azetidin-3-yl)methyl)phenyl)-6,7-dihydro-5H-benzo[7]annulen-3-yl pivalate (0.8 g, 1.51 mmol) in MeOH (15 mL) was added a solution of NaOH (1.51 mL, 1 M) and the reaction mixture was heated to 50° C. for 1 hour. After cooling, EtOAC and water were added and pH was adjusted to 4 with HCl 5N. After separation, the aqueous layer was extracted twice with EtOAc. The combined organic layers were washed with water, dried over $MgSO_4$, filtered and concentrated under reduced pressure to give 0.6 g (90%) of 8-bromo-9-(4-((1-(3-fluoropropyl)azetidin-3-yl)methyl)phenyl)-6,7-dihydro-5H-benzo[7]annulen-3-ol as a brown solid.

LC/MS (m/z, MH+): 444

Intermediate 50: 3-(4-Bromobenzyl)-1-(2,3-difluoropropyl)azetidine

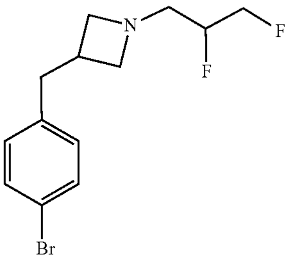 [SMILES: FCC(F)CN1CC(Cc2ccc(Br)cc2)C1]

Intermediate 50 was prepared following a similar procedure to that of step 2 of Intermediate 27 from 2,3-difluoropropyl trifluoromethanesulfonate to give 211 mg (40%) of 3-(4-bromobenzyl)-1-(2,3-difluoropropyl)azetidine.

LC/MS (m/z, MH+): 304

Intermediate 51: Methyl 8-bromo-9-(4-((1-(3,3,3-trifluoropropyl)azetidin-3-yl)methyl)phenyl)-6,7-dihydro-5H-benzo[7]annulene-3-carboxylate

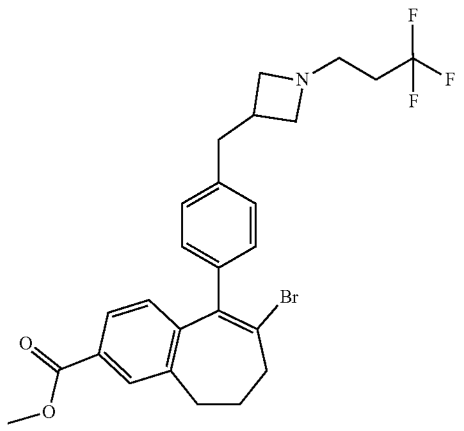 [SMILES: COC(=O)c1ccc2c(c1)CCCC(Br)=C2c1ccc(CC2CN(CCC(F)(F)F)C2)cc1]

Step 1: 3-(4-Bromobenzyl)-1-(3,3,3-trifluoropropyl) azetidine

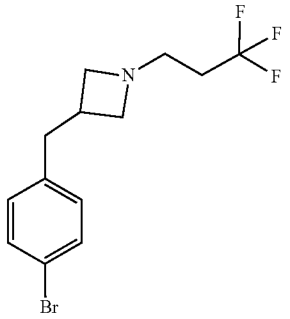 [SMILES: FC(F)(F)CCN1CC(Cc2ccc(Br)cc2)C1]

Step 1 of Intermediate 51 was prepared following a similar procedure to that of Intermediate 23 from 3-(4-bromobenzyl)azetidine, 4-methylbenzenesulfonic acid and 1,1,1-trifluoro-3-iodopropane to give 0.8 g (49%) of 3-(4-bromobenzyl)-1-(3,3,3-trifluoropropyl)azetidine.

LC/MS (m/z, MH+): 322

Step 2: Methyl 9-(4-((1-(3,3,3-trifluoropropyl)azetidin-3-yl)methyl)phenyl)-6,7-dihydro-5H-benzo[7] annulene-3-carboxylate

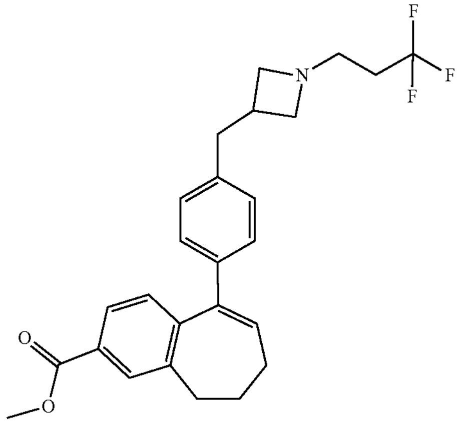 [SMILES: COC(=O)c1ccc2c(c1)CCCC=C2c1ccc(CC2CN(CCC(F)(F)F)C2)cc1]

Step 2 of Intermediate 51 was prepared following a similar procedure to that of step 1 of Intermediate 7 from methyl 9-(4,4,5,5-tetramethyl-1,3,2-dioxaborolan-2-yl)-6,7-dihydro-5H-benzo[7]annulene-3-carboxylate (Intermediate 4) and 3-(4-bromobenzyl)-1-(3,3,3-trifluoropropyl)azetidine to give 1.4 g (86%) of methyl 9-(4-((1-(3,3,3-trifluoropropyl)azetidin-3-yl)methyl)phenyl)-6,7-dihydro-5H-benzo[7] annulene-3-carboxylate.

LC/MS (m/z, MH+): 444

Step 3: Methyl 8-bromo-9-(4-((1-(3,3,3-trifluoropropyl)azetidin-3-yl)methyl)phenyl)-6,7-dihydro-5H-benzo[7]annulene-3-carboxylate

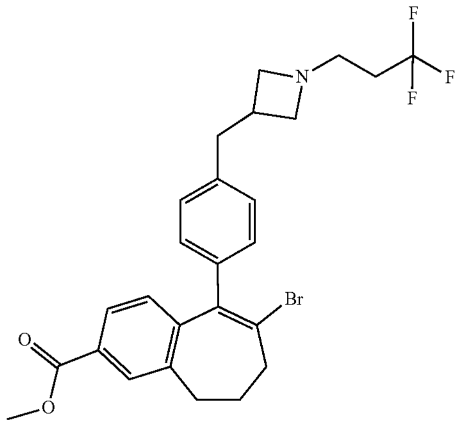 [SMILES: COC(=O)c1ccc2c(c1)CCCC(Br)=C2c1ccc(CC2CN(CCC(F)(F)F)C2)cc1]

Step 3 of Intermediate 51 was prepared following a similar procedure to that of step 2 of Intermediate 7 from methyl 9-(4-((1-(3,3,3-trifluoropropyl)azetidin-3-yl)methyl) phenyl)-6,7-dihydro-5H-benzo[7]annulene-3-carboxylate to give 1.2 g (73%) of methyl 8-bromo-9-(4-((1-(3,3,3-trifluoropropyl)azetidin-3-yl)methyl)phenyl)-6,7-dihydro-5H-benzo[7]annulene-3-carboxylate as a brown foam.

LC/MS (m/z, MH+): 522

Intermediate 52: Methyl 6-(2,4-dichlorophenyl)-5-(((trifluoromethyl)sulfonyl)oxy)-7,8-dihydronaphthalene-2-carboxylate

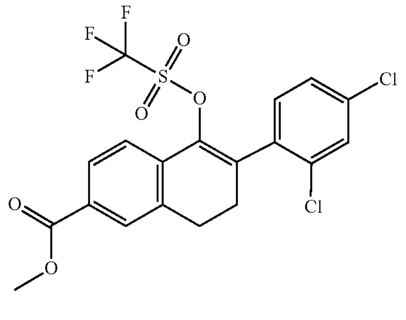 [SMILES: COC(=O)c1ccc2c(c1)CCC(c1ccc(Cl)cc1Cl)=C2OS(=O)(=O)C(F)(F)F]

Step 1: Methyl 6-(2,4-dichlorophenyl)-5-oxo-5,6,7,8-tetrahydronaphthalene-2-carboxylate

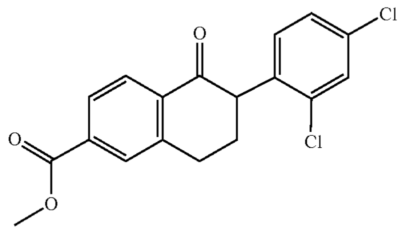 [SMILES: COC(=O)c1ccc2c(c1)CCC(c1ccc(Cl)cc1Cl)C2=O]

Step 1 of Intermediate 52 was prepared following a similar procedure to that of step 1 of Intermediate 6 from methyl 1-oxotetralin-6-carboxylate to give 459 mg (19%) of methyl 6-(2,4-dichlorophenyl)-5-oxo-5,6,7,8-tetrahydronaphthalene-2-carboxylate.

LC/MS (m/z, MH+): 349

Step 2: Methyl 6-(2,4-dichlorophenyl)-5-(((trifluoromethyl)sulfonyl)oxy)-7,8-dihydronaphthalene-2-carboxylate

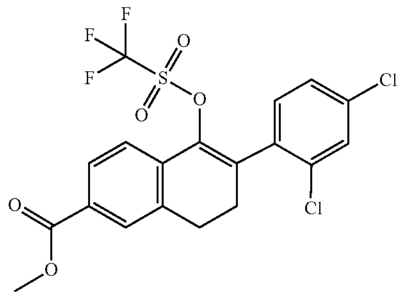 [SMILES: COC(=O)c1ccc2c(c1)CCC(c1ccc(Cl)cc1Cl)=C2OS(=O)(=O)C(F)(F)F]

To a solution of methyl 6-(2,4-dichlorophenyl)-5-oxo-5,6,7,8-tetrahydronaphthalene-2-carboxylate (0.29 g, 0.83 mmol) in THF (5 mL) at −78° C. under Ar atmosphere was added N,N-bis(trifluoromethylsulfonyl)aniline (0.39 g, 1.08 mmol) followed by KHMDS (1 M, 1.08 mL, 1.08 mmol). The reaction mixture was stirred for 5 hours allowing the temperature to warm up to −10° C. then it was poured into brine and extracted with EtOAc. The combined organic layers were dried over anhydrous $Na_2SO_4$, filtered, and concentrated under reduced pressure. The residue was purified by flash chromatography with a 0-10% gradient of Ethyl acetate in cyclohexane to give 0.33 g (82%) of methyl 6-(2,4-dichlorophenyl)-5-(((trifluoromethyl)sulfonyl)oxy)-7,8-dihydronaphthalene-2-carboxylate.

LC/MS (m/z, MH+): 481

Intermediate 53: 8-Bromo-2,4-difluoro-9-(4-((1-(3-fluoropropyl)azetidin-3-yl)methyl)phenyl)-6,7-dihydro-5H-benzo[7]Annulen-3-yl Pivalate

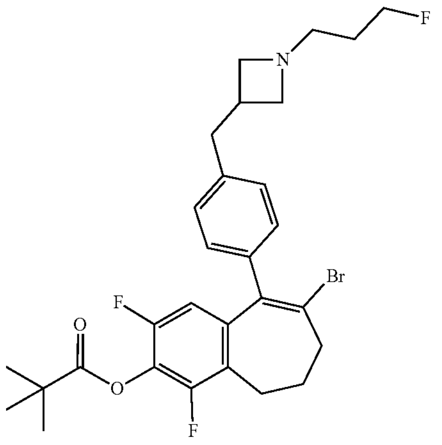 [SMILES: CC(C)(C)C(=O)Oc1c(F)cc2c(c1F)CCCC(Br)=C2c1ccc(CC2CN(CCCF)C2)cc1]

Step 1: 1,3-Difluoro-5-oxo-6,7,8,9-tetrahydro-5H-benzo[7]annulen-2-yl Pivalate

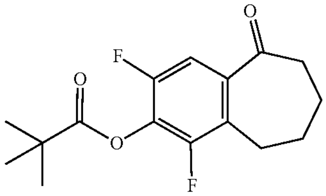 [SMILES: CC(C)(C)C(=O)Oc1c(F)cc2c(c1F)CCCCC2=O]

To a suspension of 1,3-difluoro-2-hydroxy-6,7,8,9-tetrahydro-5H-benzo[7]annulen-5-one (step 5 of Intermediate 46) (2.3 g, 10.84 mmol) and $K_2CO_3$ (3.75 g, 27.1 mmol) in acetone (150 mL) was dropwise 2,2-dimethylpropanoyl chloride (3.18 mL, 23.85 mmol). The reaction mixture was stirred at RT for 20 minutes. Water was added and the reaction mixture was extracted three times with EtOAc. The organic phases were gathered, washed with brine, dried over $MgSO_4$, filtered and concentrated under reduced pressure. The residue obtained was purified by flash chromatography, eluting with a gradient of DCM/MeOH: from 100/00 to 97/03 to give 3 g (93%) of 1,3-difluoro-5-oxo-6,7,8,9-tetrahydro-5H-benzo[7]annulen-2-yl pivalate as a yellow oil.

LC/MS (m/z, MH+): 297

Step 2: 2,4-Difluoro-9-(((trifluoromethyl)sulfonyl)oxy)-6,7-dihydro-5H-benzo[7]annulen-3-yl Pivalate

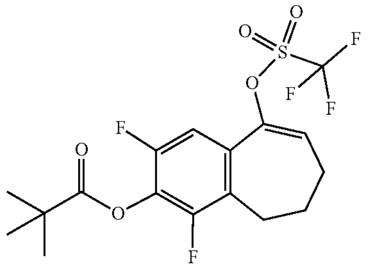 [SMILES: CC(C)(C)C(=O)Oc1c(F)cc2c(c1F)CCCC=C2OS(=O)(=O)C(F)(F)F]

Step 2 of Intermediate 53 was prepared following a similar procedure to that of step 3 of Intermediate 9 from 1,3-difluoro-5-oxo-6,7,8,9-tetrahydro-5H-benzo[7]annulen-2-yl pivalate to give 1.35 g (31%) of 2,4-difluoro-9-(((trifluoromethyl)sulfonyl)oxy)-6,7-dihydro-5H-benzo[7]annulen-3-yl pivalate.

LC/MS (m/z, MH+): 429

Step 3: 2,4-Difluoro-9-(4,4,5,5-tetramethyl-1,3,2-dioxaborolan-2-yl)-6,7-dihydro-5H-benzo[7]annulen-3-yl pivalate

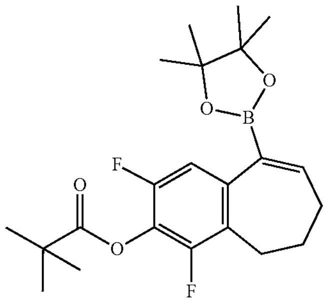 [SMILES: CC(C)(C)C(=O)Oc1c(F)cc2c(c1F)CCCC=C2B1OC(C)(C)C(C)(C)O1]

Step 3 of Intermediate 53 was prepared following a similar procedure to that of Intermediate 4 from 1,3-difluoro-5-oxo-6,7,8,9-tetrahydro-5H-benzo[7]annulen-2-yl pivalate to give 310 mg (63%) of 2,4-difluoro-9-(4,4,5,5-tetramethyl-1,3,2-dioxaborolan-2-yl)-6,7-dihydro-5H-benzo[7]annulen-3-yl pivalate.

LC/MS (m/z, MH+): 407

Step 4: 2,4-Difluoro-9-(4-((1-(3-fluoropropyl)azetidin-3-yl)methyl)phenyl)-6,7-dihydro-5H-benzo[7]annulen-3-yl Pivalate

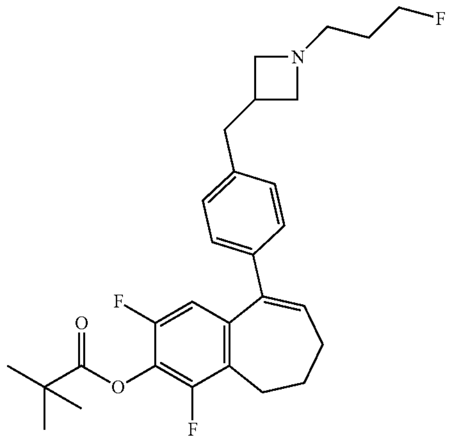 [SMILES: CC(C)(C)C(=O)Oc1c(F)cc2c(c1F)CCCC=C2c1ccc(CC2CN(CCCF)C2)cc1]

Step 4 of Intermediate 53 was prepared following a similar procedure to that of step 1 of Intermediate 7 from 2,4-difluoro-9-(4,4,5,5-tetramethyl-1,3,2-dioxaborolan-2-yl)-6,7-dihydro-5H-benzo[7]annulen-3-yl pivalate to give 180 mg (43%) of 2,4-difluoro-9-(4-((1-(3-fluoropropyl)azetidin-3-yl)methyl)phenyl)-6,7-dihydro-5H-benzo[7]annulen-3-yl pivalate.

LC/MS (m/z, MH+): 486

Step 5: 8-Bromo-2,4-difluoro-9-(4-((1-(3-fluoropropyl)azetidin-3-yl)methyl)phenyl)-6,7-dihydro-5H-benzo[7]annulen-3-yl Pivalate

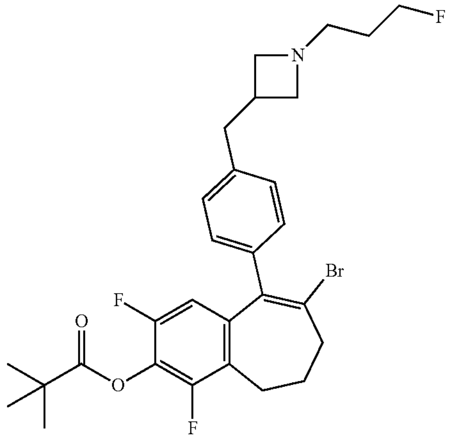 [SMILES: CC(C)(C)C(=O)Oc1c(F)cc2c(c1F)CCCC(Br)=C2c1ccc(CC2CN(CCCF)C2)cc1]

Step 5 of Intermediate 53 was prepared following a similar procedure to that of step 2 of Intermediate 7 from 2,4-difluoro-9-(4-((1-(3-fluoropropyl)azetidin-3-yl)methyl)phenyl)-6,7-dihydro-5H-benzo[7]annulen-3-yl pivalate to give 210 mg (76%) of 8-bromo-2,4-difluoro-9-(4-((1-(3-fluoropropyl)azetidin-3-yl)methyl)phenyl)-6,7-dihydro-5H-benzo[7]annulen-3-yl pivalate.

LC/MS (m/z, MH+): 564

Intermediate 54: Methyl 8-bromo-9-(4-((1-(3-fluoropropyl)azetidin-3-yl)methyl)phenyl)-4-methoxy-6,7-dihydro-5H-benzo[7]annulene-3-carboxylate

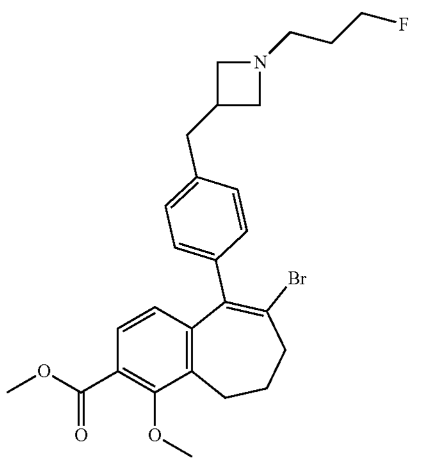 [SMILES: COC(=O)c1ccc2c(c1OC)CCCC(Br)=C2c1ccc(CC2CN(CCCF)C2)cc1]

Step 1: 3-Formyl-2-methoxyphenyl Pivalate

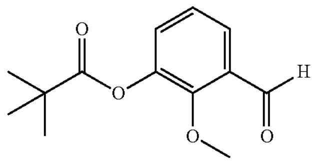 [SMILES: COc1c(C=O)cccc1OC(=O)C(C)(C)C]

Step 1 of Intermediate 54 was prepared following a similar procedure to that step 1 of Intermediate 53 from 3-hydroxy-2-methoxy-benzaldehyde to give 11.5 g (74%) of 3-formyl-2-methoxyphenyl pivalate.

LC/MS (m/z, MH+): 237

Step 2: Ethyl (Z)-5-(2-methoxy-3-(pivaloyloxy)phenyl)pent-4-enoate

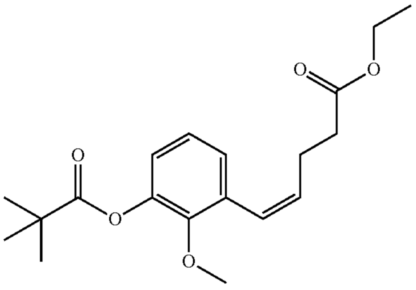 [SMILES: CCOC(=O)CC/C=C\c1cccc(OC(=O)C(C)(C)C)c1OC]

Step 2 of Intermediate 54 was prepared following a similar procedure to that step 1 of Intermediate 46 from 3-formyl-2-methoxyphenyl pivalate to give 11 g (67%) of ethyl (Z)-5-(2-methoxy-3-(pivaloyloxy)phenyl)pent-4-enoate.

LC/MS (m/z, MH+): 335

Step 3: Ethyl 5-(2-methoxy-3-(pivaloyloxy)phenyl)pentanoate

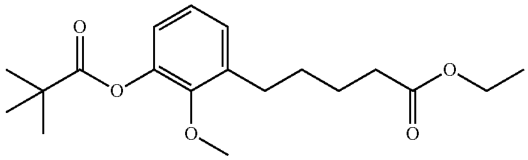 [SMILES: CCOC(=O)CCCCc1cccc(OC(=O)C(C)(C)C)c1OC]

Step 3 of Intermediate 54 was prepared following a similar procedure to that step 2 of Intermediate 46 from ethyl (Z)-5-(2-methoxy-3-(pivaloyloxy)phenyl)pent-4-enoate to give 11 g (99%) of ethyl 5-(2-methoxy-3-(pivaloyloxy)phenyl)pentanoate.

LC/MS (m/z, MH+): 337

Step 4: 2-Hydroxy-1-methoxy-6,7,8,9-tetrahydro-5H-benzo[7]annulen-5-one

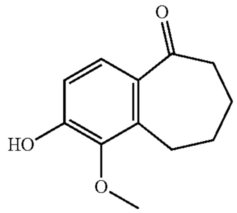

Step 4 of Intermediate 54 was prepared following a similar procedure to that step 4 of Intermediate 46 from ethyl 5-(2-methoxy-3-(pivaloyloxy)phenyl)pentanoate to give 3.6 g (53%) of 2-hydroxy-1-methoxy-6,7,8,9-tetrahydro-5H-benzo[7]annulen-5-one.

LC/MS (m/z, MH+): 207

Step 5: 1-Methoxy-5-oxo-6,7,8,9-tetrahydro-5H-benzo[7]annulen-2-yl trifluoromethanesulfonate

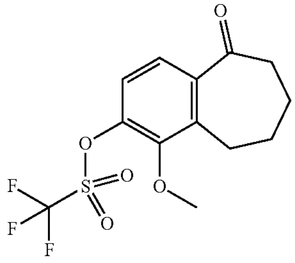 [SMILES: COc1c(OS(=O)(=O)C(F)(F)F)ccc2c1CCCCC2=O]

Step 5 of Intermediate 54 was prepared following a similar procedure to that of step 1 of Intermediate 9 from 2-hydroxy-1-methoxy-6,7,8,9-tetrahydro-5H-benzo[7]annulen-5-one to give 4.6 g (70%) of 1-methoxy-5-oxo-6,7,8,9-tetrahydro-5H-benzo[7]annulen-2-yl trifluoromethanesulfonate.

LC/MS (m/z, MH+): 339

Step 6: Methyl 1-methoxy-5-oxo-6,7,8,9-tetrahydro-5H-benzo[7]annulene-2-carboxylate

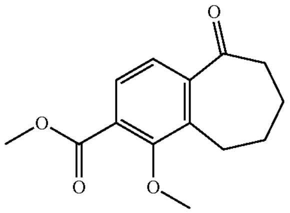 [SMILES: COC(=O)c1ccc2c(c1OC)CCCCC2=O]

Step 6 of Intermediate 54 was prepared following a similar procedure to that of step 2 Intermediate 9 from 1-methoxy-5-oxo-6,7,8,9-tetrahydro-5H-benzo[7]annulen-2-yl trifluoromethanesulfonate to give 2.4 g (70%) of methyl 1-methoxy-5-oxo-6,7,8,9-tetrahydro-5H-benzo[7]annulene-2-carboxylate.

LC/MS (m/z, MH+): 249

Step 7: Methyl 4-methoxy-9-(((trifluoromethyl) sulfonyl)oxy)-6,7-dihydro-5H-benzo[7]annulene-3-carboxylate

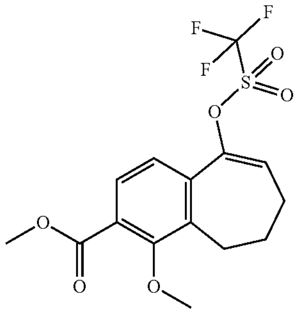 [SMILES: COC(=O)c1ccc2c(c1OC)CCCC=C2OS(=O)(=O)C(F)(F)F]

Step 7 of Intermediate 54 was prepared following a similar procedure to that of step 3 of Intermediate 9 from methyl 1-methoxy-5-oxo-6,7,8,9-tetrahydro-5H-benzo[7]annulene-2-carboxylate to give 3.8 g (100%) of methyl 4-methoxy-9-(((trifluoromethyl)sulfonyl)oxy)-6,7-dihydro-5H-benzo[7]annulene-3-carboxylate.

LC/MS (m/z, MH+): 381

Step 8: Methyl 4-methoxy-9-(4,4,5,5-tetramethyl-1,3,2-dioxaborolan-2-yl)-6,7-dihydro-5H-benzo[7]annulene-3-carboxylate

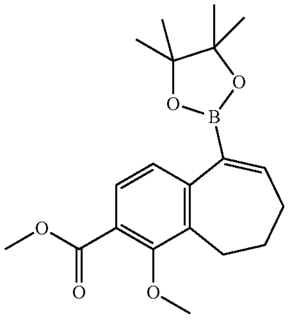 [SMILES: COC(=O)c1ccc2c(c1OC)CCCC=C2B1OC(C)(C)C(C)(C)O1]

Step 8 of Intermediate 54 was prepared following a similar procedure to that of Intermediate 4 from methyl 4-methoxy-9-(((trifluoromethyl)sulfonyl)oxy)-6,7-dihydro-5H-benzo[7]annulene-3-carboxylate to give 2 g (56%) of methyl 4-methoxy-9-(4,4,5,5-tetramethyl-1,3,2-dioxaborolan-2-yl)-6,7-dihydro-5H-benzo[7]annulene-3-carboxylate.

LC/MS (m/z, MH+): 359

Step 9: Methyl 9-(4-((1-(3-fluoropropyl)azetidin-3-yl)methyl)phenyl)-4-methoxy-6,7-dihydro-5H-benzo[7]annulene-3-carboxylate

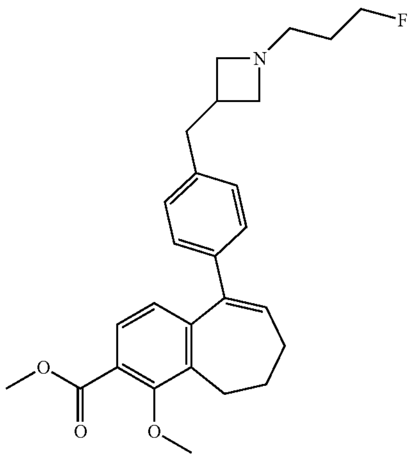 [SMILES: COC(=O)c1ccc2c(c1OC)CCCC=C2c1ccc(CC2CN(CCCF)C2)cc1]

Step 9 of Intermediate 54 was prepared following a similar procedure to that of step 1 of Intermediate 7 from methyl 4-methoxy-9-(4,4,5,5-tetramethyl-1,3,2-dioxaborolan-2-yl)-6,7-dihydro-5H-benzo[7]annulene-3-carboxylate to give 180 mg (43%) of methyl 9-(4-((1-(3-fluoropropyl) azetidin-3-yl)methyl)phenyl)-4-methoxy-6,7-dihydro-5H-benzo[7]annulene-3-carboxylate.

LC/MS (m/z, MH+): 438

Step 10: Methyl 8-bromo-9-(4-((1-(3-fluoropropyl) azetidin-3-yl)methyl)phenyl)-4-methoxy-6,7-dihydro-5H-benzo[7]annulene-3-carboxylate

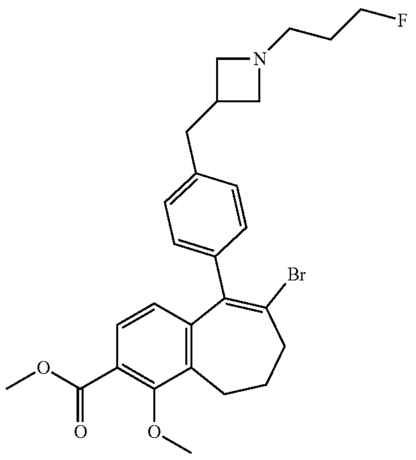 [SMILES: COC(=O)c1ccc2c(c1OC)CCCC(Br)=C2c1ccc(CC2CN(CCCF)C2)cc1]

Step 10 of Intermediate 54 was prepared following a similar procedure to that of step 2 of Intermediate 7 from methyl 9-(4-((1-(3-fluoropropyl)azetidin-3-yl)methyl)phenyl)-4-methoxy-6,7-dihydro-5H-benzo[7]annulene-3-carboxylate to give 576 mg (62%) of methyl 8-bromo-9-(4-((1-(3-fluoropropyl)azetidin-3-yl)methyl)phenyl)-4-methoxy-6,7-dihydro-5H-benzo[7]annulene-3-carboxylate.

LC/MS (m/z, MH+): 516

Intermediate 55: Methyl 8-bromo-9-(4-((1-(3,3-difluoropropyl)azetidin-3-yl)methyl)phenyl)-6,7-dihydro-5H-benzo[7]annulene-3-carboxylate

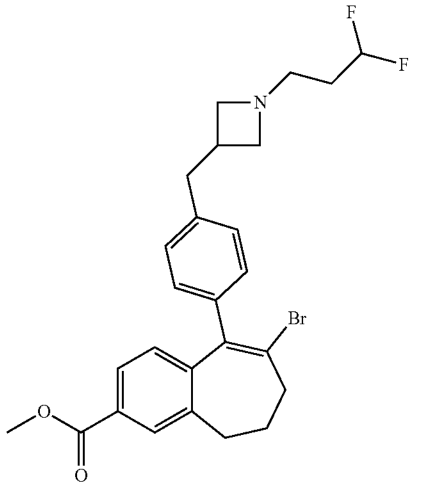 [SMILES: COC(=O)c1ccc2c(c1)CCCC(Br)=C2c1ccc(CC2CN(CCC(F)F)C2)cc1]

Step 1: Methyl 9-(4-((1-(3,3-difluoropropyl)azetidin-3-yl)methyl)phenyl)-6,7-dihydro-5H-benzo[7]annulene-3-carboxylate

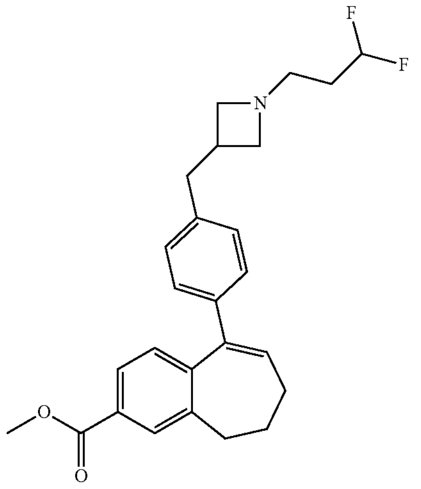 [SMILES: COC(=O)c1ccc2c(c1)CCCC=C2c1ccc(CC2CN(CCC(F)F)C2)cc1]

Step 1 of Intermediate 55 was prepared following a similar procedure to that of step 1 of Intermediate 7 from methyl 9-(4,4,5,5-tetramethyl-1,3,2-dioxaborolan-2-yl)-6,7-dihydro-5H-benzo[7]annulene-3-carboxylate (Intermediate 4) and 3-(4-bromobenzyl)-1-(3,3-difluoropropyl)azetidine (Intermediate 27) to give 4.7 g (98%) of methyl 9-(4-((1-(3,3-difluoropropyl)azetidin-3-yl)methyl)phenyl)-6,7-dihydro-5H-benzo[7]annulene-3-carboxylate.

LC/MS (m/z, MH+): 426

Step 2: Methyl 8-bromo-9-(4-((1-(3,3-difluoropropyl)azetidin-3-yl)methyl)phenyl)-6,7-dihydro-5H-benzo[7]annulene-3-carboxylate

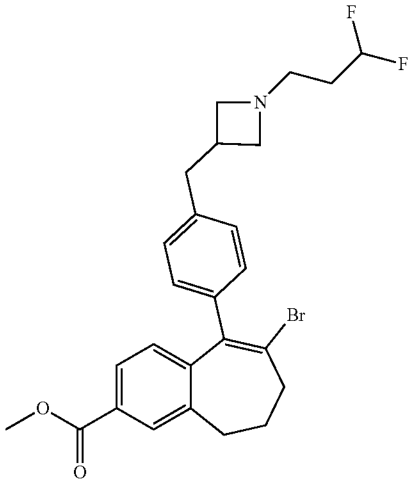 [SMILES: COC(=O)c1ccc2c(c1)CCCC(Br)=C2c1ccc(CC2CN(CCC(F)F)C2)cc1]

Step 2 of Intermediate 55 was prepared following a similar procedure to that of step 2 of Intermediate 7 from methyl 9-(4-((1-(3,3-difluoropropyl)azetidin-3-yl)methyl)phenyl)-6,7-dihydro-5H-benzo[7]annulene-3-carboxylate to give 3.4 g (61%) of methyl 8-bromo-9-(4-((1-(3,3-difluoropropyl)azetidin-3-yl)methyl)phenyl)-6,7-dihydro-5H-benzo[7]annulene-3-carboxylate.

LC/MS (m/z, MH+): 504

Intermediate 56: Methyl 9-(4-((1-(3,3-difluoropropyl)azetidin-3-yl)methyl)phenyl)-8-(4,4,5,5-tetramethyl-1,3,2-dioxaborolan-2-yl)-6,7-dihydro-5H-benzo[7]annulene-3-carboxylate

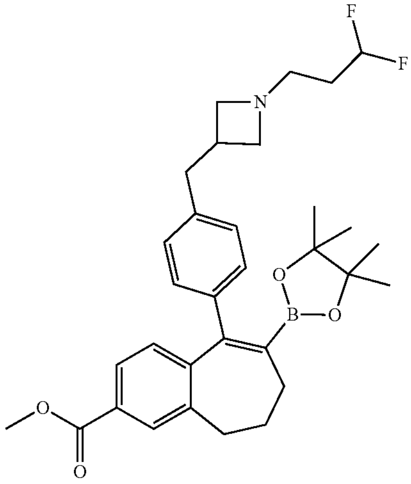 [SMILES: COC(=O)c1ccc2c(c1)CCCC(B1OC(C)(C)C(C)(C)O1)=C2c1ccc(CC2CN(CCC(F)F)C2)cc1]

Intermediate 56 was prepared following a similar procedure to that of Intermediate 8 from methyl 8-bromo-9-(4-

((1-(3,3-difluoropropyl)azetidin-3-yl)methyl)phenyl)-6,7-dihydro-5H-benzo[7]annulene-3-carboxylate (Intermediate 55) to give 164 mg (50%) of methyl 9-(4-((1-(3,3-difluoropropyl)azetidin-3-yl)methyl)phenyl)-8-(4,4,5,5-tetramethyl-1,3,2-dioxaborolan-2-yl)-6,7-dihydro-5H-benzo[7]annulene-3-carboxylate.

LC/MS (m/z, MH+): 552

Intermediate 57: Methyl 8-bromo-9-(4-((1-(3,3-difluoropropyl)azetidin-3-yl)methyl)phenyl)-6,7-dihydro-5H-benzo[7]annulene-3-carboxylate

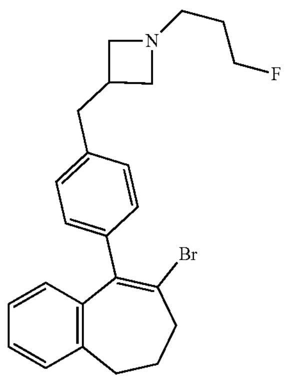 [SMILES: FCCCN1CC(Cc2ccc(C3=C(Br)CCCc4ccccc43)cc2)C1]

Step 1: 6,7-Dihydro-5H-benzo[7]Annulen-9-yl Trifluoromethanesulfonate

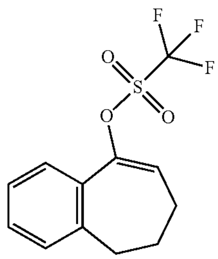 [SMILES: O=S(=O)(OC1=CCCCc2ccccc21)C(F)(F)F]

Step 1 of Intermediate 57 was prepared following a similar procedure to that of step 3 of Intermediate 9 from 6,7,8,9-tetrahydro-5H-benzo[7]annulen-5-one to give 1.68 g (85%) of 6,7-dihydro-5H-benzo[7]annulen-9-yl trifluoromethanesulfonate.

LC/MS (m/z, MH+): 293

Step 2: 2-(6,7-Dihydro-5H-benzo[7]annulen-9-yl)-4,4,5,5-tetramethyl-1,3,2-dioxaborolane

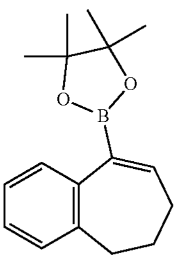 [SMILES: CC1(C)OB(C2=CCCCc3ccccc32)OC1(C)C]

Step 2 of Intermediate 57 was prepared following a similar procedure to that of Intermediate 4 from 6,7-dihydro-5H-benzo[7]annulen-9-yl trifluoromethanesulfonate to give 91 mg (65%) of 2-(6,7-dihydro-5H-benzo[7]annulen-9-yl)-4,4,5,5-tetramethyl-1,3,2-dioxaborolane.

LC/MS (m/z, MH+): 271

Step 3: 3-(4-(8-Bromo-6,7-dihydro-5H-benzo[7]annulen-9-yl)benzyl)-1-(3-fluoropropyl)azetidine

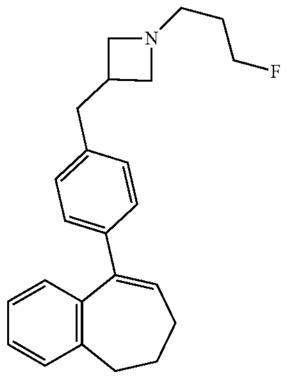 [SMILES: FCCCN1CC(Cc2ccc(C3=CCCCc4ccccc43)cc2)C1]

Step 3 of Intermediate 57 was prepared following a similar procedure to that of step 1 of Intermediate 7 from 2-(6,7-dihydro-5H-benzo[7]annulen-9-yl)-4,4,5,5-tetramethyl-1,3,2-dioxaborolane and 3-(4-bromobenzyl)-1-(3,3-difluoropropyl)azetidine (Intermediate 27) to give 782 mg (59%) of 3-(4-(6,7-dihydro-5H-benzo[7]annulen-9-yl)benzyl)-1-(3-fluoropropyl)azetidine.

LC/MS (m/z, MH+): 350

Step 4: 3-(4-(8-Bromo-6,7-dihydro-5H-benzo[7]annulen-9-yl)benzyl)-1-(3-fluoropropyl)azetidine

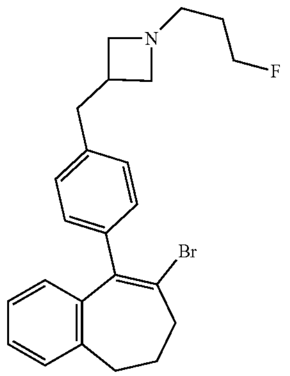 [SMILES: FCCCN1CC(Cc2ccc(C3=C(Br)CCCc4ccccc43)cc2)C1]

Step 4 of Intermediate 57 was prepared following a similar procedure to that of step 2 of Intermediate 7 from 3-(4-(6,7-dihydro-5H-benzo[7]annulen-9-yl)benzyl)-1-(3-fluoropropyl)azetidine to give 211 g (86%) of 3-(4-(8-bromo-6,7-dihydro-5H-benzo[7]annulen-9-yl)benzyl)-1-(3-fluoropropyl)azetidine.

LC/MS (m/z, MH+): 428

Intermediate 58: Methyl 8-bromo-9-(4-((1-(3-fluoropropyl)azetidin-3-yl)methyl)phenyl)-7-methyl-6,7-dihydro-5H-benzo[7]annulene-3-carboxylate, Isomer 1 and isomer 2

Isomer 1

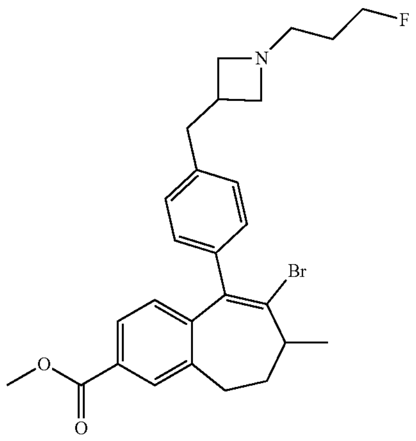

Isomer 2

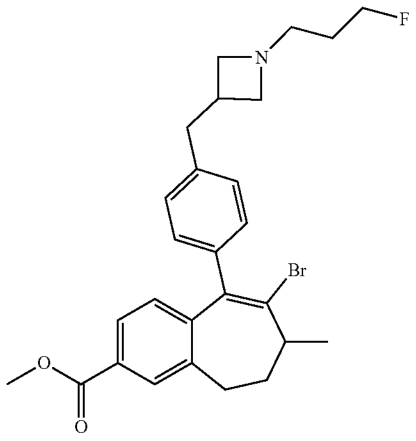

Step 1: Methyl 6-bromo-5-oxo-6,7,8,9-tetrahydro-5H-benzo[7]annulene-2-carboxylate

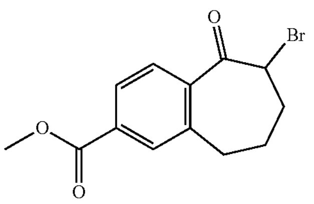 [SMILES: COC(=O)c1ccc2c(c1)CCCC(Br)C2=O]

To a mixture of methyl 5-oxo-6,7,8,9-tetrahydro-5H-benzo[7]annulene-2-carboxylate (9.42 g, 43.2 mmol) in DCM (400 mL) was portionwise added pyridinium tribromide (16.12 g, 45.4 mmol). The reaction mixture was stirred overnight at room temperature. Water (500 ml) and ether (1 L) were added. The organic phase was separated and washed twice with water, dried over $MgSO_4$, filtered and concentrated under reduced pressure to give 14.4 g (90%) of methyl 6-bromo-5-oxo-6,7,8,9-tetrahydro-5H-benzo[7]annulene-2-carboxylate.

LC/MS (m/z, MH+): 297

Step 2: Methyl 5-oxo-8,9-dihydro-5H-benzo[7]annulene-2-carboxylate

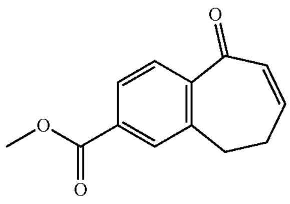 [SMILES: COC(=O)c1ccc2c(c1)CCC=CC2=O]

To a solution of methyl 6-bromo-5-oxo-6,7,8,9-tetrahydro-5H-benzo[7]annulene-2-carboxylate (10 g, 33.66 mmol) in acetonitrile (100 mL) was added DABCO (7.4 mL, 67.32 mmol). The reaction mixture was heated to 55° C. for 2.5 hours under Ar. Ether and 1N HCl were added. The organic phase was separated and washed twice with water, with brine, dried over $MgSO_4$, filtered and concentrated under reduced pressure. The resulting residue was then purified by flash chromatography eluting with a mixture of cyclohexane/EtOAc 85/15 to give 1.88 g (26%) of methyl 5-oxo-8,9-dihydro-5H-benzo[7]annulene-2-carboxylate.

LC/MS (m/z, MH+): 217

Step 3: Methyl 7-methyl-5-oxo-6,7,8,9-tetrahydro-5H-benzo[7]annulene-2-carboxylate, Racemic Mixture

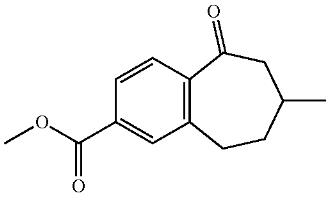

To a solution of methyl 5-oxo-8,9-dihydro-5H-benzo[7]annulene-2-carboxylate (1.88 g, 8.6 mmol) in THF (30 mL) under Ar at 0° C. was added a 0.328 M cuprate solution (35 mL, 11.5 mmol) prepared by addition of 15 mL of a 1.6N solution of methyl lithium in ether to a suspension of 2.5 g of CuI (13 mmol) in 25 mL of ether under Ar at 0° C. The reaction mixture was stirred for 30 minutes at 0° C. Ether (200 mL) and 1N HCl (200 mL) were added. The organic phase was separated and the aqueous phase extracted with ether. The combined organic phases were washed with water, dried over $MgSO_4$, filtered and concentrated under reduced pressure. The resulting residue was then purified by flash chromatography eluting with a mixture of cyclohexane/EtOAc 95/5 to give 1.95 g (86%) of methyl 7-methyl-5-oxo-6,7,8,9-tetrahydro-5H-benzo[7]annulene-2-carboxylate as a racemic mixture.

LC/MS (m/z, MH+): 233

Step 4: Methyl 7-methyl-9-(((trifluoromethyl)sulfonyl)oxy)-6,7-dihydro-5H-benzo[7]annulene-3-carboxylate, Racemic Mixture

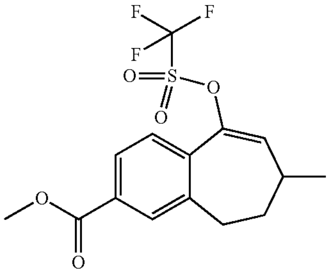

Step 4 of Intermediate 58 was prepared following a similar procedure to that of step 3 of Intermediate 9 from methyl 7-methyl-5-oxo-6,7,8,9-tetrahydro-5H-benzo[7]annulene-2-carboxylate (racemic mixture) to give 2.5 g (86%) of methyl 7-methyl-9-(((trifluoromethyl)sulfonyl)oxy)-6,7-dihydro-5H-benzo[7]annulene-3-carboxylate as a racemic mixture.

LC/MS (m/z, MH+): 365

Step 5: Methyl 9-(4-((1-(3-fluoropropyl)azetidin-3-yl)methyl)phenyl)-7-methyl-6,7-dihydro-5H-benzo[7]annulene-3-carboxylate, Racemic Mixture

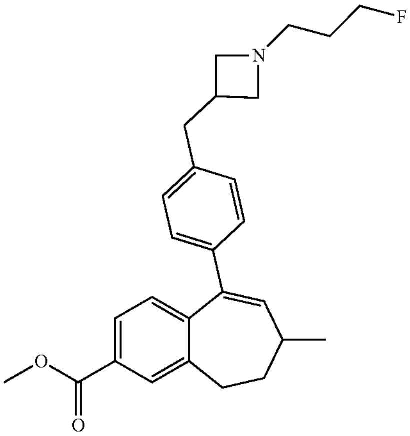 [SMILES: COC(=O)c1ccc2c(c1)CCC(C)C=C2c1ccc(CC2CN(CCCF)C2)cc1]

Step 5 of Intermediate 58 was prepared following a similar procedure to that of Step 7 of Intermediate 38 from methyl 7-methyl-9-(((trifluoromethyl)sulfonyl)oxy)-6,7-dihydro-5H-benzo[7]annulene-3-carboxylate (racemic mixture) to give 1.1 g (95%) of methyl 9-(4-((1-(3-fluoropropyl)azetidin-3-yl)methyl)phenyl)-7-methyl-6,7-dihydro-5H-benzo[7]annulene-3-carboxylate as a racemic mixture.

LC/MS (m/z, MH+): 422

Step 6: Methyl 8-bromo-9-(4-((1-(3-fluoropropyl)azetidin-3-yl)methyl)phenyl)-7-methyl-6,7-dihydro-5H-benzo[7]annulene-3-carboxylate, Isomer 1 and Isomer 2

Isomer 1

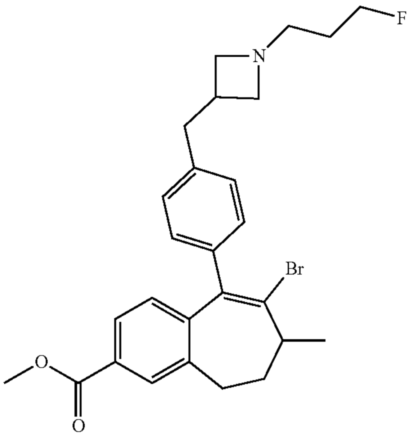

Isomer 2

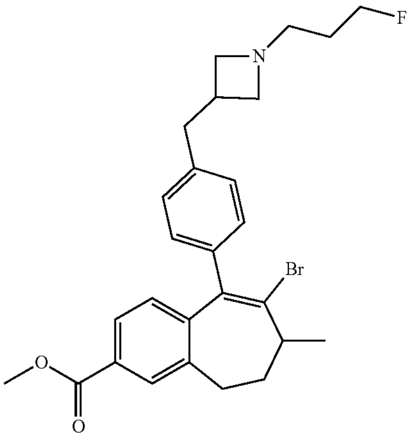

Step 6 of Intermediate 58 was prepared following a similar procedure to that of Step 2 of Intermediate 7 from methyl 9-(4-((1-(3-fluoropropyl)azetidin-3-yl)methyl)phenyl)-7-methyl-6,7-dihydro-5H-benzo[7]annulene-3-carboxylate (racemic mixture) to give 1.4 g (100% yield) of methyl 8-bromo-9-(4-((1-(3-fluoropropyl)azetidin-3-yl)methyl)phenyl)-7-methyl-6,7-dihydro-5H-benzo[7]annulene-3-carboxylate as a racemic mixture.

LC/MS (m/z, MH+): 500

The mixture of two isomers of methyl 8-bromo-9-(4-((1-(3-fluoropropyl)azetidin-3-yl)methyl)phenyl)-7-methyl-6,7-dihydro-5H-benzo[7]annulene-3-carboxylate was separated by SFC (conditions: column DAICEL IH (250×50 mm, 5 μm); supercritical $CO_2$ 87%/MeOH 13%/[0.1% $Et_3N$ in EtOH]; 40° C.; 100 bars) to give 217 mg of isomer 1 and 174 mg of isomer 2.

Intermediate 59: Methyl 8-benzyl-9-(((trifluoromethyl)sulfonyl)oxy)-6,7-dihydro-5H-benzo[7]annulene-3-carboxylate

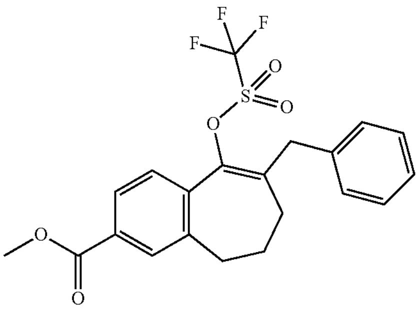 [SMILES: COC(=O)c1ccc2c(c1)CCCC(Cc1ccccc1)=C2OS(=O)(=O)C(F)(F)F]

Step 1: Methyl 9-acetoxy-8-bromo-6,7-dihydro-5H-benzo[7]annulene-3-carboxylate

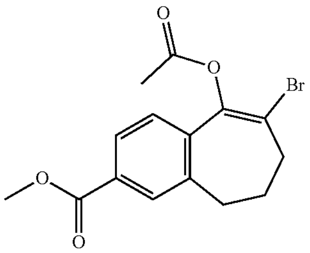 [SMILES: COC(=O)c1ccc2c(c1)CCCC(Br)=C2OC(C)=O]

To a solution of methyl 6-bromo-5-oxo-6,7,8,9-tetrahydro-5H-benzo[7]annulene-2-carboxylate (7.4 g, 25 mmol) in THF (80 mL) at −78° C. under Ar atmosphere was added LiHMDS (1 M, 27 mL). The mixture was stirred for 2 hours then treated with acetic anhydride (8.8 mL, 75 mmol) allowing the temperature to warmed up to 0° C. After pouring onto diisopropyl ether and water, the aqueous layer was separated and extracted with diisopropyl ether. The combined organic layers were washed with water, dried over $Na_2SO_4$, filtered, and concentrated under reduced pressure. The residue was purified by flash chromatography with a 0-50% gradient of ethyl acetate in cyclohexane to give 6.97 g (83%) of methyl 9-acetoxy-8-bromo-6,7-dihydro-5H-benzo[7]annulene-3-carboxylate.

LC/MS (m/z, MH+): 339

Step 2: Methyl 9-acetoxy-8-benzyl-6,7-dihydro-5H-benzo[7]annulene-3-carboxylate

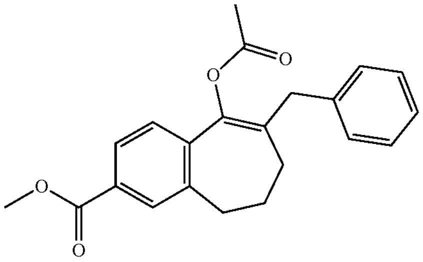 [SMILES: COC(=O)c1ccc2c(c1)CCCC(Cc1ccccc1)=C2OC(C)=O]

A mixture of methyl 9-acetoxy-8-bromo-6,7-dihydro-5H-benzo[7]annulene-3-carboxylate (300 mg, 0.89 mmol), potassium benzyltrifluoroborate (193 mg, 0.97 mmol), $Cs_2CO_3$ (874 mg, 2.63 mmol), and Pd(dppf)$Cl_2$, complex with DCM (74 mg, 88 μmol) in toluene (9 mL) and water (3 mL) was heated to 90° C. in a sealed tube for 30 minutes. After cooling to room temperature, the reaction mixture was extracted with EtOAc (200 mL). The organic layer were washed twice with water (50 mL), dried over $Na_2SO_4$, filtered and concentrated under reduced pressure. The residue was purified by flash chromatography with a 0-100% gradient of ethyl acetate in cyclohexane to give 285 mg (92%) of methyl 9-acetoxy-8-bromo-6,7-dihydro-5H-benzo[7]annulene-3-carboxylate.

LC/MS (m/z, MH+): 351

Step 3: Methyl 6-benzyl-5-oxo-6,7,8,9-tetrahydro-5H-benzo[7]annulene-2-carboxylate

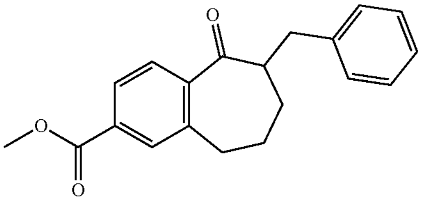 [SMILES: COC(=O)c1ccc2c(c1)CCCC(Cc1ccccc1)C2=O]

To a solution of methyl 9-acetoxy-8-bromo-6,7-dihydro-5H-benzo[7]annulene-3-carboxylate (285 mg, 0.81 mmol) in methanol (8 mL) and DCM (4 mL) was added a 12N solution of HCl (0.44 mL, 5.29 mmol). The resulting reaction mixture was heated to reflux for 7 hours then stirred overnight at room temperature. After pouring onto diisopropyl ether and water, the aqueous layer was separated and extracted with diisopropyl ether. The combined organic layers were washed with water, a 5% aqueous solution of $Na_2CO_3$ and water then dried over $Na_2SO_4$, filtered, and concentrated under reduced pressure to give 220 mg (88%) of methyl 6-benzyl-5-oxo-6,7,8,9-tetrahydro-5H-benzo[7]annulene-2-carboxylate which was used in the next step without further purification.

LC/MS (m/z, MH+): 309

Step 4: Methyl 8-benzyl-9-(((trifluoromethyl)sulfonyl)oxy)-6,7-dihydro-5H-benzo[7]annulene-3-carboxylate

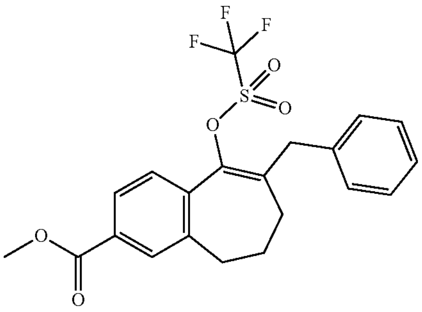 [SMILES: COC(=O)c1ccc2c(c1)CCCC(Cc1ccccc1)=C2OS(=O)(=O)C(F)(F)F]

Step 4 of Intermediate 59 was prepared following a similar procedure to that of step 2 of Intermediate 52 from methyl 6-benzyl-5-oxo-6,7,8,9-tetrahydro-5H-benzo[7]annulene-2-carboxylate to give 249 mg (79%) of methyl 8-benzyl-9-(((trifluoromethyl)sulfonyl)oxy)-6,7-dihydro-5H-benzo[7]annulene-3-carboxylate.

LC/MS (m/z, MH+): 441

Intermediate 60: Methyl 3-bromo-4-(4-((1-(3-fluoropropyl)azetidin-3-yl)methyl)phenyl)-2H-thiochromene-7-carboxylate

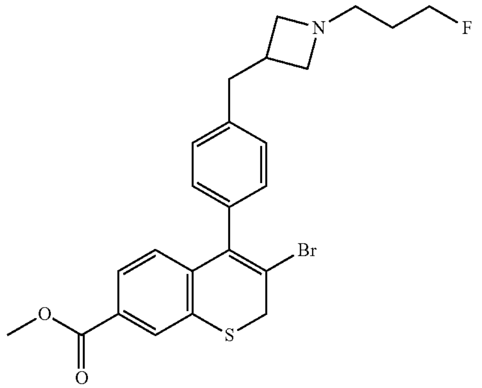 [SMILES: COC(=O)c1ccc2c(c1)SCC(Br)=C2c1ccc(CC2CN(CCCF)C2)cc1]

Step 1: 4-Oxothiochroman-7-yl trifluoromethanesulfonate

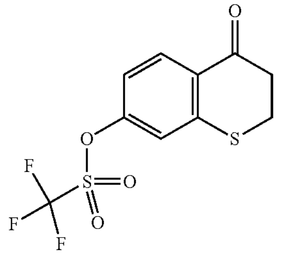 [SMILES: O=C1CCSc2cc(OS(=O)(=O)C(F)(F)F)ccc21]

Step 1 of Intermediate 60 was prepared following a similar procedure to that of step 1 of Intermediate 9 from 7-hydroxythiochroman-4-one (prepared according to WO2018091153) to give 1.14 g (33%) of 4-oxothiochroman-7-yl trifluoromethanesulfonate.

LC/MS (m/z, MH+): 313

Step 2: Methyl 4-oxothiochromane-7-carboxylate

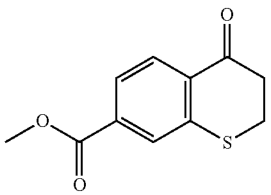

Step 2 of Intermediate 60 was prepared following a similar procedure to that of step 2 of Intermediate 9 from 4-oxothiochroman-7-yl trifluoromethanesulfonate to give 0.61 g (76%) of methyl 4-oxothiochromane-7-carboxylate.

LC/MS (m/z, MH+): 223

Step 3: Methyl 4-(((trifluoromethyl)sulfonyl)oxy)-2H-thiochromene-7-carboxylate

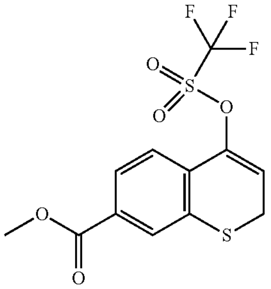 [SMILES: COC(=O)c1ccc2c(c1)SCC=C2OS(=O)(=O)C(F)(F)F]

Step 3 of Intermediate 60 was prepared following a similar procedure to that of step 2 of Intermediate 52 from methyl 4-oxothiochromane-7-carboxylate to give 199 mg (41%) of methyl 4-(((trifluoromethyl)sulfonyl)oxy)-2H-thiochromene-7-carboxylate.

LC/MS (m/z, MH+): 355

Step 4: Methyl 4-(4-((1-(3-fluoropropyl)azetidin-3-yl)methyl)phenyl)-2H-thiochromene-7-carboxylate

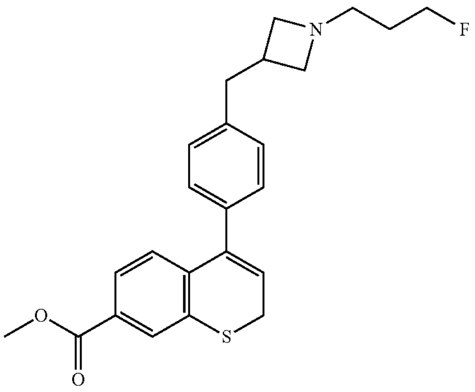 [SMILES: COC(=O)c1ccc2c(c1)SCC=C2c1ccc(CC2CN(CCCF)C2)cc1]

Step 4 of Intermediate 60 was prepared following a similar procedure to that of step 7 of Intermediate 38 from methyl 4-(((trifluoromethyl)sulfonyl)oxy)-2H-thiochromene-7-carboxylate to give 72 mg (62%) of methyl 4-(4-((1-(3-fluoropropyl)azetidin-3-yl)methyl)phenyl)-2H-thiochromene-7-carboxylate.

LC/MS (m/z, MH+): 412

Step 5: Methyl 3-bromo-4-(4-((1-(3-fluoropropyl)azetidin-3-yl)methyl)phenyl)-2H-thiochromene-7-carboxylate

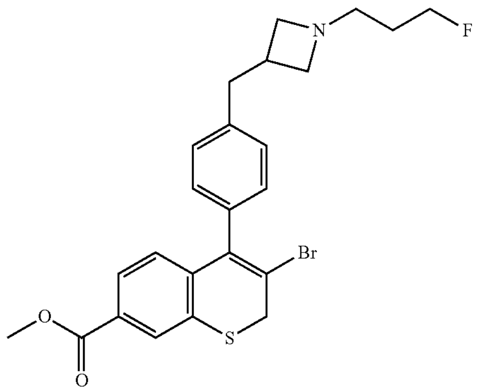 [SMILES: COC(=O)c1ccc2c(c1)SCC(Br)=C2c1ccc(CC2CN(CCCF)C2)cc1]

Step 5 of Intermediate 60 was prepared following a similar procedure to that of step 2 of Intermediate 7 from methyl 4-(4-((1-(3-fluoropropyl)azetidin-3-yl)methyl)phenyl)-2H-thiochromene-7-carboxylate to give 923 mg (80%) of methyl 3-bromo-4-(4-((1-(3-fluoropropyl)azetidin-3-yl)methyl)phenyl)-2H-thiochromene-7-carboxylate.

LC/MS (m/z, MH+): 490

Intermediate 61: Methyl 8-bromo-9-(4-((1-(3-fluoropropyl)azetidin-3-yl)methyl)phenyl)-7-ethyl-6,7-dihydro-5H-benzo[7]annulene-3-carboxylate, Isomer 1 and Isomer 2

Isomer 1

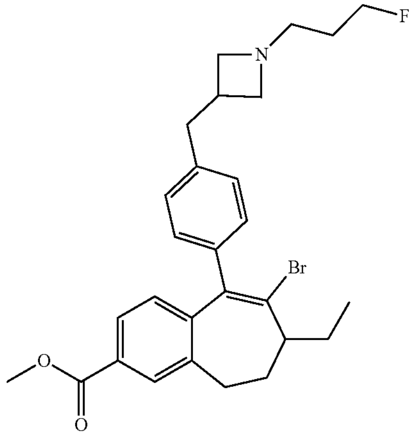

-continued

Isomer 2

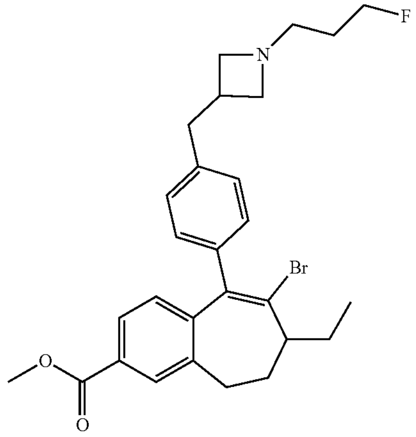

Step 1: Methyl 7-ethyl-5-oxo-6,7,8,9-tetrahydro-5H-benzo[7]annulene-2-carboxylate, Racemic Mixture

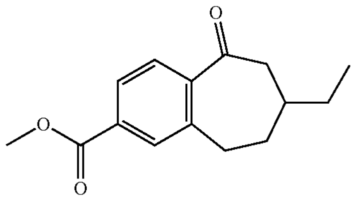 [SMILES: CCC1CCc2cc(C(=O)OC)ccc2C(=O)C1]

Step 1 of Intermediate 61 was prepared following a similar procedure to that of Step 3 of Intermediate 58 from methyl 5-oxo-8,9-dihydro-5H-benzo[7]annulene-2-carboxylate and lithium diethylcopper to give 0.4 g (80%) of methyl 7-ethyl-5-oxo-6,7,8,9-tetrahydro-5H-benzo[7]annulene-2-carboxylate as a racemic mixture.

LC/MS (m/z, MH+): 247

Step 2: Methyl 7-ethyl-9-(((trifluoromethyl)sulfonyl)oxy)-6,7-dihydro-5H-benzo[7]annulene-3-carboxylate, Racemic Mixture

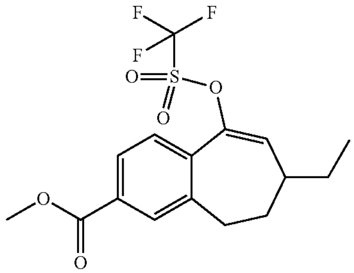 [SMILES: CCC1C=C(OS(=O)(=O)C(F)(F)F)c2ccc(C(=O)OC)cc2CC1]

Step 2 of Intermediate 61 was prepared following a similar procedure to that of step 3 of Intermediate 9 from methyl 7-ethyl-5-oxo-6,7,8,9-tetrahydro-5H-benzo[7]annulene-2-carboxylate (racemic mixture) to give 0.62 g (98%) of methyl 7-ethyl-9-(((trifluoromethyl)sulfonyl)oxy)-6,7-dihydro-5H-benzo[7]annulene-3-carboxylate as a racemic mixture.

LC/MS (m/z, MH+): 379

Step 3: Methyl 9-(4-((1-(3-fluoropropyl)azetidin-3-yl)methyl)phenyl)-7-ethyl-6,7-dihydro-5H-benzo[7]annulene-3-carboxylate, Racemic Mixture

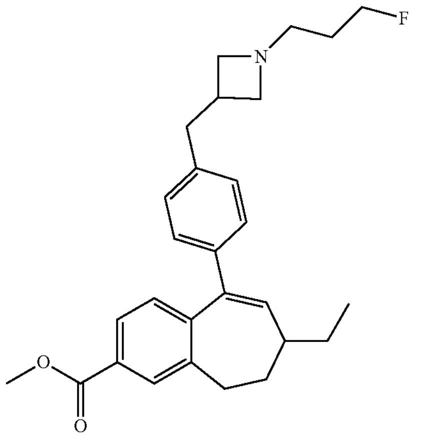 [SMILES: CCC1C=C(c2ccc(CC3CN(CCCF)C3)cc2)c2ccc(C(=O)OC)cc2CC1]

Step 3 of Intermediate 61 was prepared following a similar procedure to that of Step 7 of Intermediate 38 from methyl 7-ethyl-9-(((trifluoromethyl)sulfonyl)oxy)-6,7-dihydro-5H-benzo[7]annulene-3-carboxylate (racemic mixture) to give 0.67 g (94%) of methyl 9-(4-((1-(3-fluoropropyl)azetidin-3-yl)methyl)phenyl)-7-ethyl-6,7-dihydro-5H-benzo[7]annulene-3-carboxylate as a racemic mixture.

LC/MS (m/z, MH+): 436

Step 4: Methyl 8-bromo-9-(4-((1-(3-fluoropropyl)azetidin-3-yl)methyl)phenyl)-7-ethyl-6,7-dihydro-5H-benzo[7]annulene-3-carboxylate, Isomer 1 and Isomer 2

Isomer 1

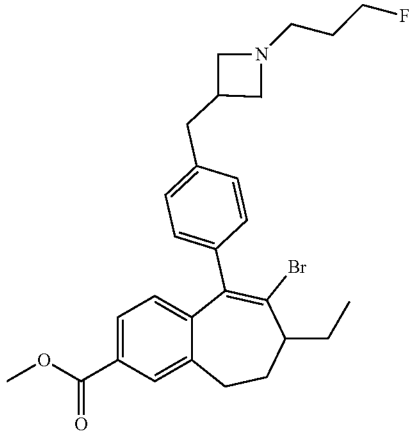

-continued

Isomer 2

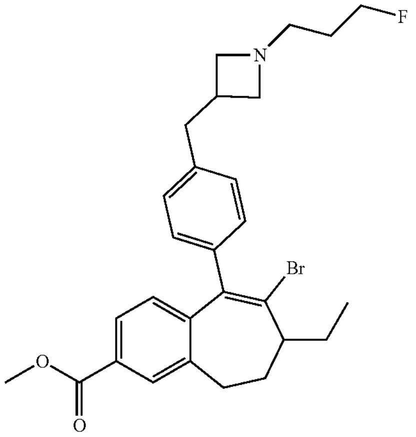

Step 4 of Intermediate 61 was prepared following a similar procedure to that of Step 2 of Intermediate 7 from methyl 9-(4-((1-(3-fluoropropyl)azetidin-3-yl)methyl)phenyl)-7-methyl-6,7-dihydro-5H-benzo[7]annulene-3-carboxylate (racemic mixture) to give 0.66 g (100% yield) of methyl 8-bromo-9-(4-((1-(3-fluoropropyl)azetidin-3-yl)methyl)phenyl)-7-ethyl-6,7-dihydro-5H-benzo[7]annulene-3-carboxylate as a racemic mixture.

LC/MS (m/z, MH+): 514

The mixture of two isomers of methyl 8-bromo-9-(4-((1-(3-fluoropropyl)azetidin-3-yl)methyl)phenyl)-7-ethyl-6,7-dihydro-5H-benzo[7]annulene-3-carboxylate was separated by chiral HPLC (conditions: column CHIRALPACK AD (350×76.5 mm, 20 μm); Heptane 90%/EtOH 10%/[0.1% $Et_3N$ in MeOH]; 400 mL/min) to give 220 mg of isomer 1 and 220 mg of isomer 2.

Intermediate 62: Methyl 8-bromo-9-(4-((1-(3-fluoropropyl)azetidin-3-yl)methyl)phenyl)-7-isopropyl-6,7-dihydro-5H-benzo[7]annulene-3-carboxylate, Isomer 1 and Isomer 2

Isomer 1

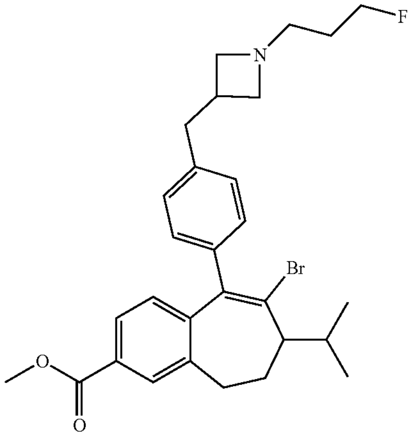

-continued

Isomer 2

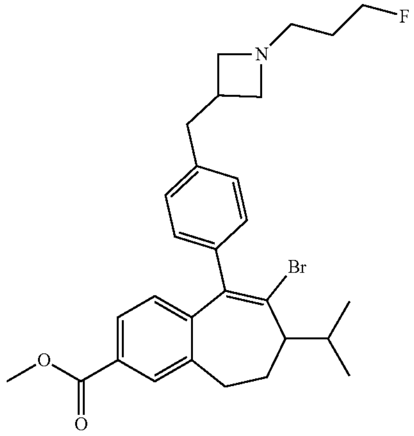

Step 1: Methyl 7-isopropyl-5-oxo-6,7,8,9-tetrahydro-5H-benzo[7]annulene-2-carboxylate, Racemic Mixture

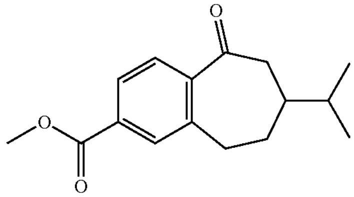 [SMILES: COC(=O)c1ccc2c(c1)CCC(C(C)C)CC2=O]

Step 1 of Intermediate 62 was prepared following a similar procedure to that of Step 3 of Intermediate 58 from methyl 5-oxo-8,9-dihydro-5H-benzo[7]annulene-2-carboxylate and lithium diisopropylcopper to give 0.37 g (77%) of methyl 7-isopropyl-5-oxo-6,7,8,9-tetrahydro-5H-benzo[7]annulene-2-carboxylate as a racemic mixture.

LC/MS (m/z, MH+): 261

Step 2: Methyl 7-isopropyl-9-(((trifluoromethyl)sulfonyl)oxy)-6,7-dihydro-5H-benzo[7]annulene-3-carboxylate, Racemic Mixture

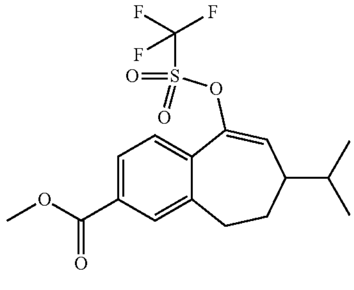 [SMILES: COC(=O)c1ccc2c(c1)CCC(C(C)C)C=C2OS(=O)(=O)C(F)(F)F]

Step 2 of Intermediate 62 was prepared following a similar procedure to that of step 3 of Intermediate 9 from methyl 7-isopropyl-5-oxo-6,7,8,9-tetrahydro-5H-benzo[7]annulene-2-carboxylate (racemic mixture) to give 0.56 g (100%) of methyl 7-isopropyl-9-(((trifluoromethyl)sulfonyl)oxy)-6,7-dihydro-5H-benzo[7]annulene-3-carboxylate as a racemic mixture.

LC/MS (m/z, MH+): 393

Step 3: Methyl 9-(4-((1-(3-fluoropropyl)azetidin-3-yl)methyl)phenyl)-7-isopropyl-6,7-dihydro-5H-benzo[7]annulene-3-carboxylate, Racemic Mixture

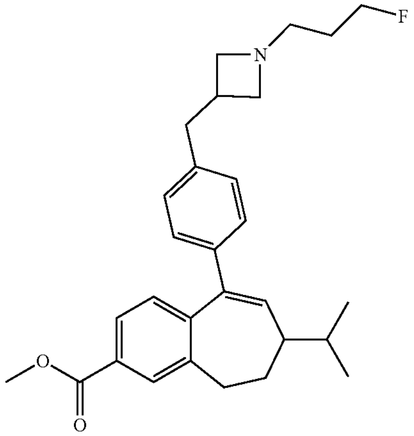 [SMILES: COC(=O)c1ccc2c(c1)CCC(C(C)C)C=C2c1ccc(CC2CN(CCCF)C2)cc1]

Step 3 of Intermediate 62 was prepared following a similar procedure to that of Step 7 of Intermediate 38 from methyl 7-isopropyl-9-(((trifluoromethyl)sulfonyl)oxy)-6,7-dihydro-5H-benzo[7]annulene-3-carboxylate (racemic mixture) to give 0.507 g (79%) of methyl 9-(4-((1-(3-fluoropropyl)azetidin-3-yl)methyl)phenyl)-7-isopropyl-6,7-dihydro-5H-benzo[7]annulene-3-carboxylate as a racemic mixture.

LC/MS (m/z, MH+): 450

Step 4: Methyl 8-bromo-9-(4-((1-(3-fluoropropyl)azetidin-3-yl)methyl)phenyl)-7-isopropyl-6,7-dihydro-5H-benzo[7]annulene-3-carboxylate, Isomer 1 and Isomer 2

Isomer 1

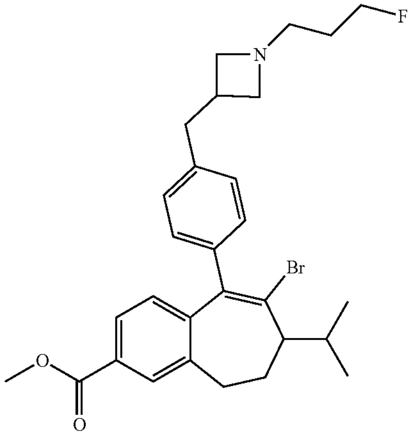

-continued

Isomer 2

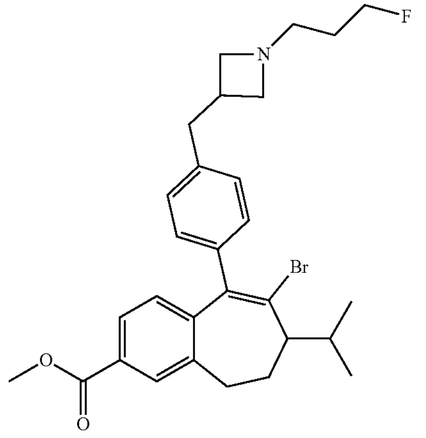

Step 4 of Intermediate 62 was prepared following a similar procedure to that of Step 2 of Intermediate 7 from methyl 9-(4-((1-(3-fluoropropyl)azetidin-3-yl)methyl)phenyl)-7-isopropyl-6,7-dihydro-5H-benzo[7]annulene-3-carboxylate (racemic mixture) to give 0.453 g (76% yield) of methyl 8-bromo-9-(4-((1-(3-fluoropropyl)azetidin-3-yl)methyl)phenyl)-7-isopropyl-6,7-dihydro-5H-benzo[7]annulene-3-carboxylate as a racemic mixture.

LC/MS (m/z, MH+): 528

The mixture of two isomers of methyl 8-bromo-9-(4-((1-(3-fluoropropyl)azetidin-3-yl)methyl)phenyl)-7-isopropyl-6,7-dihydro-5H-benzo[7]annulene-3-carboxylate was separated by SFC (conditions: column CHIRALCEL OD-H (250×30 mm, 5 μm); supercritical $CO_2$ 85%/MeOH 15%/[0.1% $Et_3N$ in MeOH]; 120 mL/min; 40° C.; 100 bars) to give 99 mg of isomer 1 and 100 mg of isomer 2.

Intermediate 63: Methyl 8-bromo-7-cyclopropyl-9-(4-((1-(3-fluoropropyl)azetidin-3-yl)methyl)phenyl)-6,7-dihydro-5H-benzo[7]annulene-3-carboxylate, Racemic Mixture

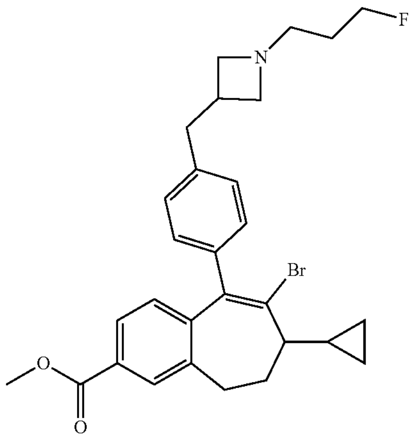 [SMILES: COC(=O)c1ccc2c(c1)CCC(C1CC1)C(Br)=C2c1ccc(CC2CN(CCCF)C2)cc1]

Step 1: Methyl 7-cyclopropyl-5-oxo-6,7,8,9-tetrahydro-5H-benzo[7]annulene-2-carboxylate, Racemic Mixture

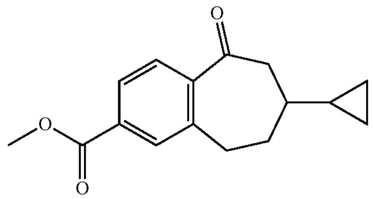 [SMILES: COC(=O)c1ccc2c(c1)CCC(C1CC1)CC2=O]

Step 1 of Intermediate 63 was prepared following a similar procedure to that of Step 3 of Intermediate 58 from methyl 5-oxo-8,9-dihydro-5H-benzo[7]annulene-2-carboxylate and lithium dicyclopropylcopper to give 0.175 g (37%) of methyl 7-cyclopropyl-5-oxo-6,7,8,9-tetrahydro-5H-benzo[7]annulene-2-carboxylate as a racemic mixture.

LC/MS (m/z, MH+): 259

Step 2: Methyl 7-cyclopropyl-9-(((trifluoromethyl)sulfonyl)oxy)-6,7-dihydro-5H-benzo[7]annulene-3-carboxylate, Racemic Mixture

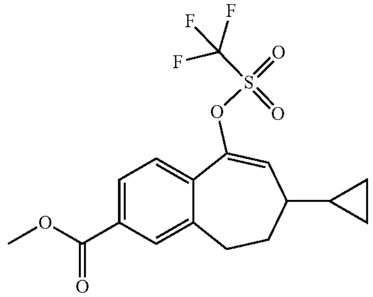 [SMILES: COC(=O)c1ccc2c(c1)CCC(C1CC1)C=C2OS(=O)(=O)C(F)(F)F]

Step 2 of Intermediate 63 was prepared following a similar procedure to that of step 3 of Intermediate 9 from methyl 7-cyclopropyl-5-oxo-6,7,8,9-tetrahydro-5H-benzo[7]annulene-2-carboxylate (racemic mixture) to give 0.16 g (61%) of methyl 7-cyclopropyl-9-(((trifluoromethyl)sulfonyl)oxy)-6,7-dihydro-5H-benzo[7]annulene-3-carboxylate as a racemic mixture.

LC/MS (m/z, MH+): 391

Step 3: Methyl 7-cyclopropyl-9-(4-((1-(3-fluoropropyl)azetidin-3-yl)methyl)phenyl)-6,7-dihydro-5H-benzo[7]annulene-3-carboxylate, Racemic Mixture

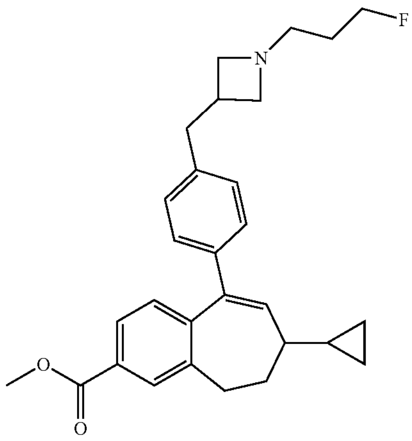 [SMILES: COC(=O)c1ccc2c(c1)CCC(C1CC1)C=C2c1ccc(CC2CN(CCCF)C2)cc1]

Step 3 of Intermediate 63 was prepared following a similar procedure to that of Step 7 of Intermediate 38 from methyl 7-cyclopropyl-9-(((trifluoromethyl)sulfonyl)oxy)-6,7-dihydro-5H-benzo[7]annulene-3-carboxylate (racemic mixture) to give 0.145 g (100%) of methyl 7-cyclopropyl-9-(4-((1-(3-fluoropropyl)azetidin-3-yl)methyl)phenyl)-6,7-dihydro-5H-benzo[7]annulene-3-carboxylate as a racemic mixture.

LC/MS (m/z, MH+): 448

Step 4: Methyl 8-bromo-7-cyclopropyl-9-(4-((1-(3-fluoropropyl)azetidin-3-yl)methyl)phenyl)-6,7-dihydro-5H-benzo[7]annulene-3-carboxylate, Racemic Mixture

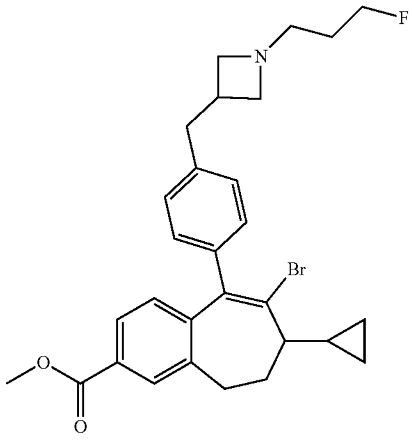 [SMILES: COC(=O)c1ccc2c(c1)CCC(C1CC1)C(Br)=C2c1ccc(CC2CN(CCCF)C2)cc1]

Step 4 of Intermediate 63 was prepared following a similar procedure to that of Step 2 of Intermediate 7 from methyl 7-cyclopropyl-9-(4-((1-(3-fluoropropyl)azetidin-3-yl)methyl)phenyl)-6,7-dihydro-5H-benzo[7]annulene-3-carboxylate (racemic mixture) to give 0.268 g (82% yield) of methyl 8-bromo-7-cyclopropyl-9-(4-((1-(3-fluoropropyl)azetidin-3-yl)methyl)phenyl)-6,7-dihydro-5H-benzo[7]annulene-3-carboxylate as a racemic mixture.

LC/MS (m/z, MH+): 526

Intermediate 64: Methyl 8-(bicyclo[3.2.1]octan-3-yl)-9-(((trifluoromethyl)sulfonyl)oxy)-6,7-dihydro-5H-benzo[7]annulene-3-carboxylate

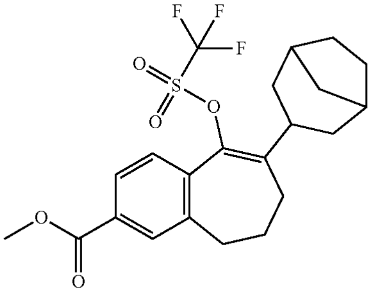 [SMILES: COC(=O)c1ccc2c(c1)CCCC(C1CC3CCC(C3)C1)=C2OS(=O)(=O)C(F)(F)F]

Step 1: Methyl 9-acetoxy-8-(bicyclo[3.2.1]oct-2-en-3-yl)-6,7-dihydro-5H-benzo[7]annulene-3-carboxylate

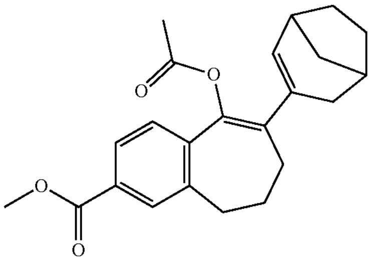 [SMILES: COC(=O)c1ccc2c(c1)CCCC(C1=CC3CCC(C1)C3)=C2OC(C)=O]

Step 1 of Intermediate 64 was prepared following a similar procedure to that of Step 7 of Intermediate 38 from methyl 9-acetoxy-8-bromo-6,7-dihydro-5H-benzo[7]annulene-3-carboxylate to give 1.07 g (99%) of methyl 9-acetoxy-8-(bicyclo[3.2.1]oct-2-en-3-yl)-6,7-dihydro-5H-benzo[7]annulene-3-carboxylate.

LC/MS (m/z, MH+): 367

Step 2: Methyl 9-acetoxy-8-(bicyclo[3.2.1]octan-3-yl)-6,7-dihydro-5H-benzo[7]annulene-3-carboxylate

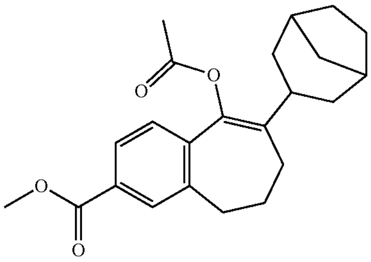 [SMILES: COC(=O)c1ccc2c(c1)CCCC(C1CC3CCC(C3)C1)=C2OC(C)=O]

A mixture of methyl 9-acetoxy-8-(bicyclo[3.2.1]oct-2-en-3-yl)-6,7-dihydro-5H-benzo[7]annulene-3-carboxylate (1.07 g, 2.92 mmol) and Pd/C 10% (50 mg, 4.68 mmol) in EtOAc (10 ml) was hydrogenated at room temperature and 3.5 bars of $H_2$ for 4 hours. The reaction mixture was filtered. The filtrate was evaporated under reduced pressure and the residue was purified by flash chromatography eluting with a gradient of EtOAc in cyclohexane (99/01 to 90/10, v/v) to give 580 mg (54%) of methyl 9-acetoxy-8-(bicyclo[3.2.1]octan-3-yl)-6,7-dihydro-5H-benzo[7]annulene-3-carboxylate.

LC/MS (m/z, MH+): 369

Step 3: Methyl 6-(bicyclo[3.2.1]octan-3-yl)-5-oxo-6,7,8,9-tetrahydro-5H-benzo[7]annulene-2-carboxylate

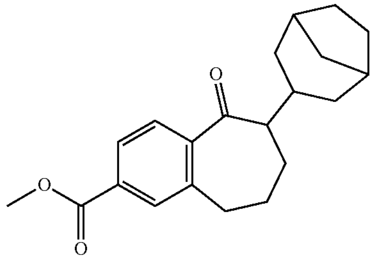 [SMILES: COC(=O)c1ccc2c(c1)CCCC(C1CC3CCC(C3)C1)C2=O]

Step 3 of Intermediate 64 was prepared following a similar procedure to that of Step 3 of Intermediate 59 from methyl 9-acetoxy-8-(bicyclo[3.2.1]octan-3-yl)-6,7-dihydro-5H-benzo[7]annulene-3-carboxylate to give 509 mg (99%) of methyl 6-(bicyclo[3.2.1]octan-3-yl)-5-oxo-6,7,8,9-tetrahydro-5H-benzo[7]annulene-2-carboxylate.

LC/MS (m/z, MH+): 327

Step 4: Methyl 8-(bicyclo[3.2.1]octan-3-yl)-9-(((trifluoromethyl)sulfonyl)oxy)-6,7-dihydro-5H-benzo[7]annulene-3-carboxylate

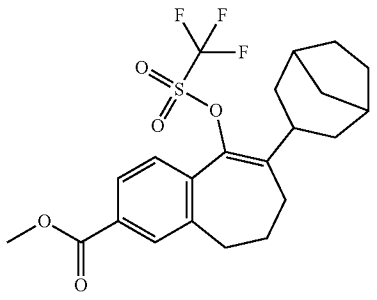 [SMILES: COC(=O)c1ccc2c(c1)CCCC(C1CC3CCC(C3)C1)=C2OS(=O)(=O)C(F)(F)F]

Step 4 of Intermediate 64 was prepared following a similar procedure to that of step 2 of Intermediate 52 from methyl 6-(bicyclo[3.2.1]octan-3-yl)-5-oxo-6,7,8,9-tetrahydro-5H-benzo[7]annulene-2-carboxylate to give 480 mg (67%) of methyl 8-(bicyclo[3.2.1]octan-3-yl)-9-(((trifluoromethyl)sulfonyl)oxy)-6,7-dihydro-5H-benzo[7]annulene-3-carboxylate.

LC/MS (m/z, MH+): 459

EXAMPLES

Method A:

Example 1. 9-(4-((1-(3-Fluoropropyl)azetidin-3-yl)methyl)phenyl)-8-phenyl-6,7-dihydro-5H-benzo[7]annulene-3-carboxylic Acid Hydrochloride

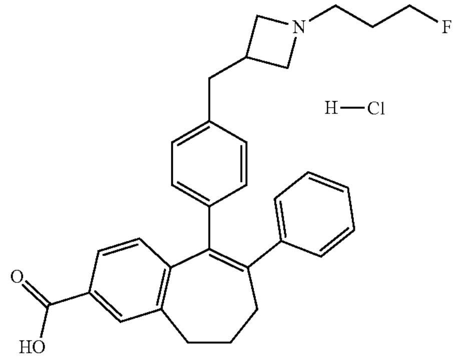

Step 1: Methyl 9-(4-((1-(3-fluoropropyl)azetidin-3-yl)methyl)phenyl)-8-phenyl-6,7-dihydro-5H-benzo[7]annulene-3-carboxylate

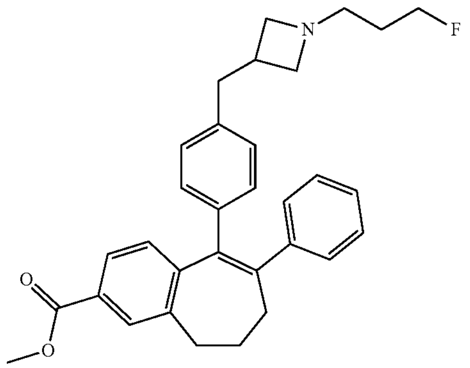 [SMILES: COC(=O)c1ccc2c(c1)CCCC(c1ccccc1)=C2c1ccc(CC2CN(CCCF)C2)cc1]

A mixture of methyl 8-bromo-9-(4-((1-(3-fluoropropyl)azetidin-3-yl)methyl)phenyl)-6,7-dihydro-5H-benzo[7]annulene-3-carboxylate (Intermediate 7) (103 mg, 212.45 µmol), phenyl-boronic acid (37.14 mg, 298.51 µmol), $Cs_2CO_3$ (224 mg, 673.75 µmol), and Pd(dppf)$Cl_2$, complex with DCM (13.15 mg, 15.46 µmol) in dioxane (1 ml) and water (0.4 ml) was microwaved at 80° C. for 30 minutes. Water (2 ml) and DCM (5 ml) were added. After hydrophobic column decantation, the organic phase was concentrated under reduced pressure and the residue was treated on SCX column. The residue obtained was purified by flash chromatography eluting with a gradient of MeOH in DCM (100/0 to 95/05, v/v) to give 41 mg (40%) of methyl 9-(4-((1-(3-fluoropropyl)azetidin-3-yl)methyl)phenyl)-8-phenyl-6,7-dihydro-5H-benzo[7]annulene-3-carboxylate.

LC/MS (m/z, MH+): 484

Step 2: 9-(4-((1-(3-fluoropropyl)azetidin-3-yl)methyl)phenyl)-8-phenyl-6,7-dihydro-5H-benzo[7]annulene-3-carboxylic Acid Hydrochloride

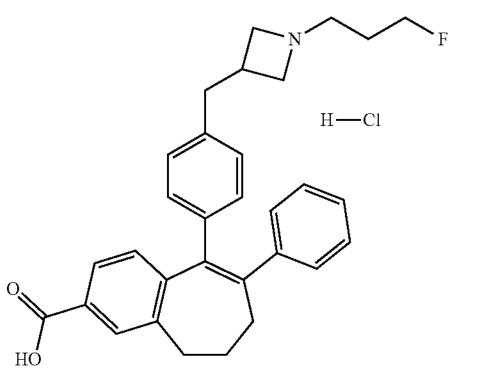

To a solution of methyl 9-(4-((1-(3-fluoropropyl)azetidin-3-yl)methyl)phenyl)-8-phenyl-6,7-dihydro-5H-benzo[7]annulene-3-carboxylate (40.8 mg, 84.45 μmol) in MeOH (1.5 ml) was added a solution of NaOH (300 μl, 1 M) and the reaction mixture was heated to reflux for 50 minutes. After cooling, water (5 ml) and DCM (5 ml) were added and pH was adjusted to 2 with HCl 1N. After hydrophobic column decantation, the organic phase was concentrated under reduced pressure and the residue was purified by flash chromatography eluting with a gradient of MeOH in DCM (100/0 to 90/10, v/v) to give 30 mg (70.8%) of 9-(4-((1-(3-fluoropropyl)azetidin-3-yl)methyl)phenyl)-8-phenyl-6,7-dihydro-5H-benzo[7]annulene-3-carboxylic acid hydrochloride.

Example 2. 8-(2,4-dichlorophenyl)-9-(4-((1-(3-fluoropropyl)azetidin-3-yl)methyl)phenyl)-6,7-dihydro-5H-benzo[7]annulene-3-carboxylic Acid (2)

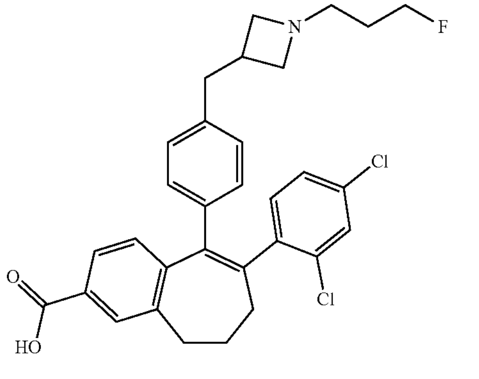 [SMILES: O=C(O)c1ccc2c(c1)CCCC(c1ccc(Cl)cc1Cl)=C2c1ccc(CC2CN(CCCF)C2)cc1]

Step 1: Methyl 8-(2,4-dichlorophenyl)-9-(4-((1-(3-fluoropropyl)azetidin-3-yl)methyl)phenyl)-6,7-dihydro-5H-benzo[7]annulene-3-carboxylate

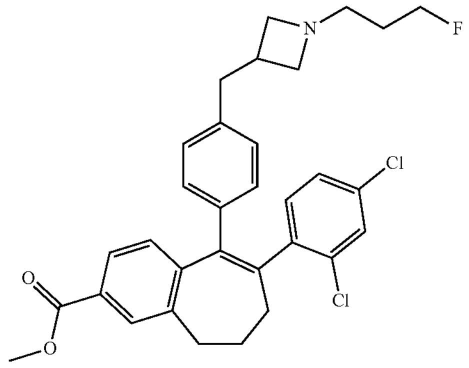 [SMILES: COC(=O)c1ccc2c(c1)CCCC(c1ccc(Cl)cc1Cl)=C2c1ccc(CC2CN(CCCF)C2)cc1]

Step 1 of Example 2 was prepared following a similar procedure to that of step 1 of Example 1 from methyl 8-bromo-9-(4-((1-(3-fluoropropyl)azetidin-3-yl)methyl)phenyl)-6,7-dihydro-5H-benzo[7]annulene-3-carboxylate (Intermediate 7) and 2,4-dichlorophenyl-boronic acid to give 100 mg (62%) of methyl 8-(2,4-dichlorophenyl)-9-(4-((1-(3-fluoropropyl)azetidin-3-yl)methyl)phenyl)-6,7-dihydro-5H-benzo[7]annulene-3-carboxylate.

LC/MS (m/z, MH+): 552

Step 2: 8-(2,4-dichlorophenyl)-9-(4-((1-(3-fluoropropyl)azetidin-3-yl)methyl)phenyl)-6,7-dihydro-5H-benzo[7]annulene-3-carboxylic Acid

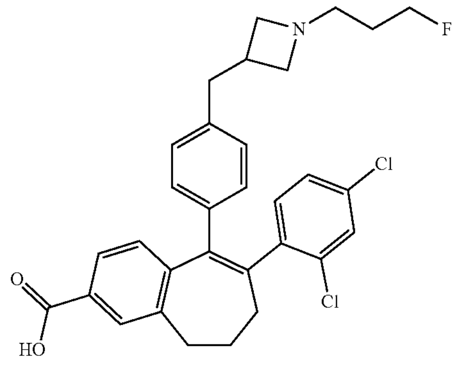 [SMILES: O=C(O)c1ccc2c(c1)CCCC(c1ccc(Cl)cc1Cl)=C2c1ccc(CC2CN(CCCF)C2)cc1]

To a solution of methyl 8-(2,4-dichlorophenyl)-9-(4-((1-(3-fluoropropyl)azetidin-3-yl)methyl)phenyl)-6,7-dihydro-5H-benzo[7]annulene-3-carboxylate (100 mg, 181 μmol) in MeOH (3 ml) was added a solution of NaOH (250 μl, 1 M) and the reaction mixture was heated to reflux for 2.5 hours. After cooling, water (5 ml) and DCM (5 ml) were added and pH was adjusted to 5 with HCl 1N. After hydrophobic Column decantation, the organic phase was concentrated under reduced pressure and the residue was purified by flash chromatography eluting with a gradient of MeOH in DCM (100/0 to 90/10, v/v) to give 48 mg (49%) of 8-(2,4-dichlorophenyl)-9-(4-((1-(3-fluoropropyl)azetidin-3-yl)methyl)phenyl)-6,7-dihydro-5H-benzo[7]annulene-3-carboxylic acid.

Method B:

Example 148. 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylic Acid

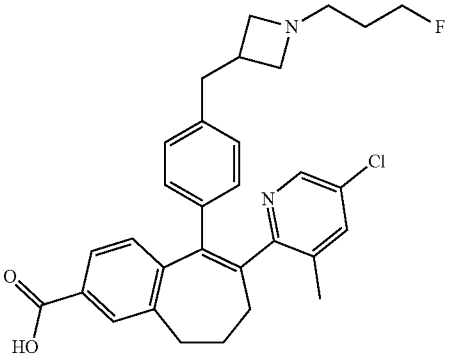 [SMILES: Cc1cc(Cl)cnc1C1=C(c2ccc(CC3CN(CCCF)C3)cc2)c2ccc(C(=O)O)cc2CCC1]

Step 1: Methyl 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylate

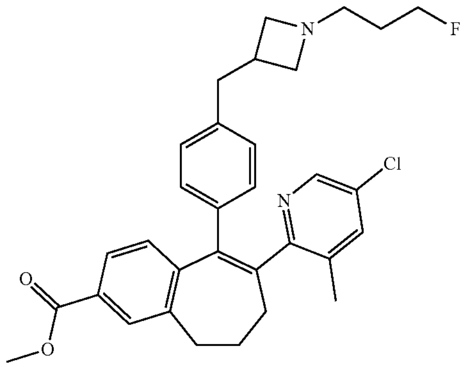 [SMILES: COC(=O)c1ccc2c(c1)CCCC(c1ncc(Cl)cc1C)=C2c1ccc(CC2CN(CCCF)C2)cc1]

Step 1 of Example 148 was prepared following a similar procedure to that of step 1 of Example 1 from methyl 9-(4-((1-(3-fluoropropyl)azetidin-3-yl)methyl)phenyl)-8-(4,4,5,5-tetramethyl-1,3,2-dioxaborolan-2-yl)-6,7-dihydro-5H-benzo[7]annulene-3-carboxylate (Intermediate 8) and 2-bromo-5-chloro-3-methyl-pyridine to give 71 mg (47%) of methyl 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylate.

LC/MS (m/z, MH+): 533

Step 2: 8-(5-Chloro-3-methylpyridin-2-yl)-9-(4-((1-(3-fluoropropyl)azetidin-3-yl)methyl)phenyl)-6,7-dihydro-5H-benzo[7]annulene-3-carboxylic Acid

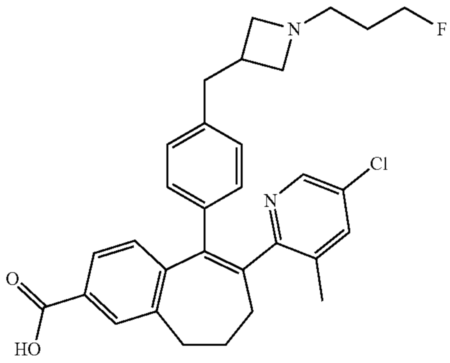 [SMILES: Cc1cc(Cl)cnc1C1=C(c2ccc(CC3CN(CCCF)C3)cc2)c2ccc(C(=O)O)cc2CCC1]

Step 2 of example 148 was prepared following a similar procedure to that of step 2 of Example 2 from methyl 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylate to give 21 mg (30%) of 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylic acid.

Method C:

Example 4. 8-(4,4-Difluorocyclohexyl)-9-(4-((1-(3-fluoropropyl)azetidin-3-yl)methyl)phenyl)-6,7-dihydro-5H-benzo[7]Annulene-3-carboxylic Acid Hydrochloride

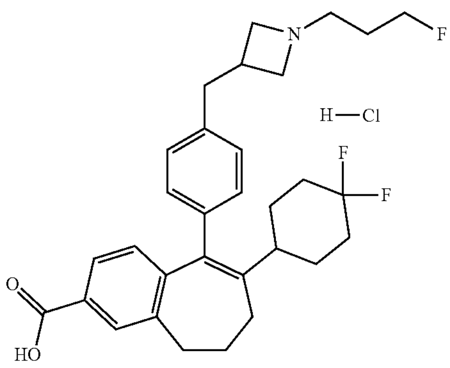

Step 1: Methyl 8-(4,4-difluorocyclohex-1-en-1-yl)-9-(4-((1-(3-fluoropropyl)azetidin-3-yl)methyl)phenyl)-6,7-dihydro-5H-benzo[7]Annulene-3-carboxylate

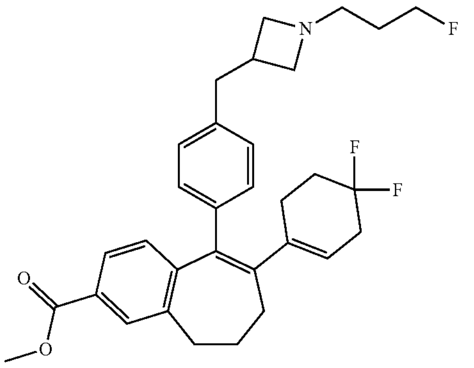 [SMILES: COC(=O)c1ccc2c(c1)CCCC(C1=CCC(F)(F)CC1)=C2c1ccc(CC2CN(CCCF)C2)cc1]

Step 1 of Example 4 was prepared following a similar procedure to that of step 1 of Example 1 from methyl 8-bromo-9-(4-((1-(3-fluoropropyl)azetidin-3-yl)methyl)phenyl)-6,7-dihydro-5H-benzo[7]annulene-3-carboxylate (Intermediate 7) and (4,4-difluorocyclohex-1-en-1-yl)boronic acid to give 55 mg (347%) of methyl 8-(4,4-difluorocyclohex-1-en-1-yl)-9-(4-((1-(3-fluoropropyl)azetidin-3-yl)methyl)phenyl)-6,7-dihydro-5H-benzo[7]annulene-3-carboxylate.

LC/MS (m/z, MH+): 524.

Step 2: Methyl 8-(4,4-difluorocyclohexyl)-9-(4-((1-(3-fluoropropyl)azetidin-3-yl)methyl)phenyl)-6,7-dihydro-5H-benzo[7]annulene-3-carboxylate

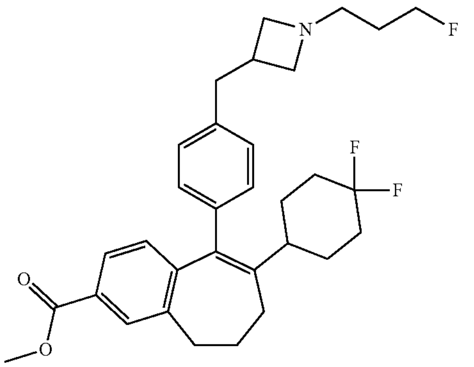 [SMILES: COC(=O)c1ccc2c(c1)CCCC(C1CCC(F)(F)CC1)=C2c1ccc(CC2CN(CCCF)C2)cc1]

A mixture of methyl 8-(4,4-difluorocyclohex-1-en-1-yl)-9-(4-((1-(3-fluoropropyl)azetidin-3-yl)methyl)phenyl)-6,7-dihydro-5H-benzo[7]annulene-3-carboxylate (55 mg, 105 μmol), Pd/C 10% (18.67 mg, 175 μmol) in MeOH (3 ml) and EtOAc (2 ml) was hydrogenated at 50° C. and 5 bars of $H_2$ for 15 hours. The reaction mixture was filtered, the filtrate was evaporated under reduced pressure and the residue was purified by flash chromatography eluting with a gradient of MeOH in DCM (100/0 to 95/05, v/v) to give 55 mg (99%) of methyl 8-(4,4-difluorocyclohexyl)-9-(4-((1-(3-fluoropropyl)azetidin-3-yl)methyl)phenyl)-6,7-dihydro-5H-benzo[7]annulene-3-carboxylate.

LC/MS (m/z, MH+): 526

Step 3: 8-(4,4-difluorocyclohexyl)-9-(4-((1-(3-fluoropropyl)azetidin-3-yl)methyl)phenyl)-6,7-dihydro-5H-benzo[7]annulene-3-carboxylic Acid Hydrochloride

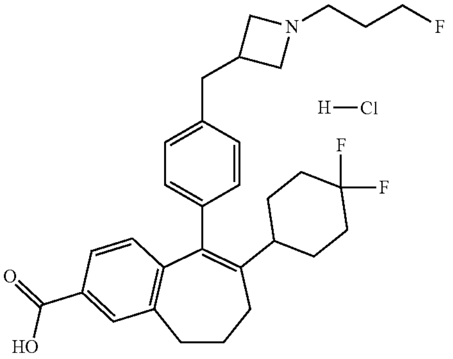

Step 3 of Example 4 was prepared following a similar procedure to that of step 2 of Example 1 from methyl 8-(4,4-difluorocyclohexyl)-9-(4-((1-(3-fluoropropyl)azetidin-3-yl)methyl)phenyl)-6,7-dihydro-5H-benzo[7]annulene-3-carboxylate to give 46 mg (80.6%) of 8-(4,4-difluorocyclohexyl)-9-(4-((1-(3-fluoropropyl)azetidin-3-yl)methyl)phenyl)-6,7-dihydro-5H-benzo[7]annulene-3-carboxylic acid hydrochloride.

Method D:

Example 39. 8-(2,4-Dichlorophenyl)-9-(4-(1-(3-fluoropropyl)azetidine-3-carbonyl)phenyl)-6,7-dihydro-5H-benzo[7]annulene-3-carboxylic Acid

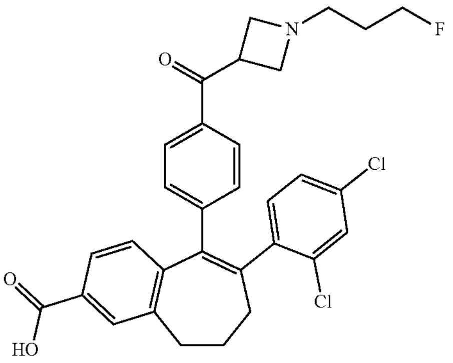 [SMILES: O=C(O)c1ccc2c(c1)CCCC(c1ccc(Cl)cc1Cl)=C2c1ccc(C(=O)C2CN(CCCF)C2)cc1]

Step 1: Methyl 8-(2,4-dichlorophenyl)-9-(4-(1-(3-fluoropropyl)azetidine-3-carbonyl)phenyl)-6,7-dihydro-5H-benzo[7]annulene-3-carboxylate

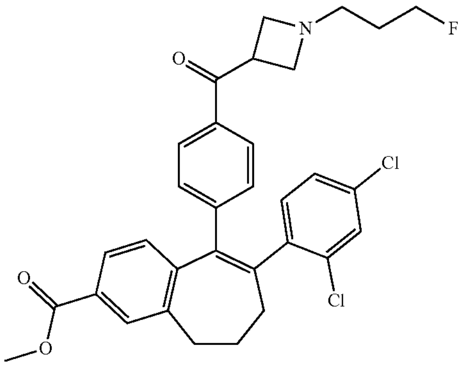 [SMILES: COC(=O)c1ccc2c(c1)CCCC(c1ccc(Cl)cc1Cl)=C2c1ccc(C(=O)C2CN(CCCF)C2)cc1]

Step 1 of Example 39 was prepared following a similar procedure to that of step 1 of Example 1 from methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) and (4-bromobenzyl)(1-(3-fluoropropyl)azetidin-3yl)methanone (Intermediate 11) to give 111 mg (46%) of methyl 8-(2,4-dichlorophenyl)-9-(4-(1-(3-fluoropropyl)azetidine-3-carbonyl)phenyl)-6,7-dihydro-5H-benzo[7]annulene-3-carboxylate as an orange viscous oil.

LC/MS (m/z, MH+): 566

Step 2: 8-(2,4-dichlorophenyl)-9-(4-(1-(3-fluoropropyl)azetidine-3-carbonyl)phenyl)-6,7-dihydro-5H-benzo[7]annulene-3-carboxylic Acid

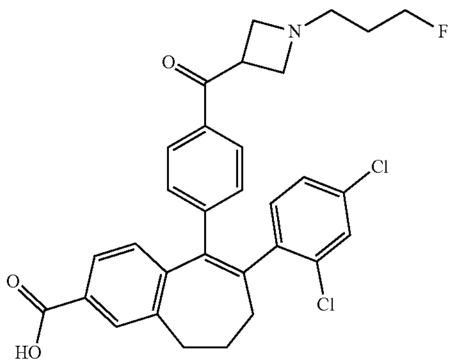 [SMILES: O=C(O)c1ccc2c(c1)CCCC(c1ccc(Cl)cc1Cl)=C2c1ccc(C(=O)C2CN(CCCF)C2)cc1]

Step 2 of Example 39 was prepared following a similar procedure to that of step 2 of Example 2 from methyl 8-(2,4-dichlorophenyl)-9-(4-(1-(3-fluoropropyl)azetidine-3-carbonyl)phenyl)-6,7-dihydro-5H-benzo[7]annulene-3-carboxylate to give 69 mg (63%) of 8-(2,4-dichlorophenyl)-9-(4-(1-(3-fluoropropyl)azetidine-3-carbonyl)phenyl)-6,7-dihydro-5H-benzo[7]annulene-3-carboxylic acid.

Method E:

Example 231. 8-(2-Ethylbutyl)-9-(4-((1-(3-fluoropropyl)azetidin-3-yl)methyl)phenyl)-6,7-dihydro-5H-benzo[7]annulene-3-carboxylic Acid

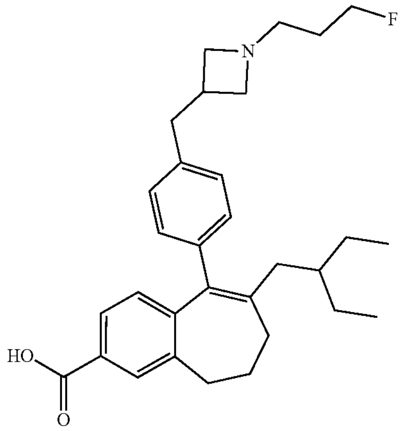 [SMILES: CCC(CC)CC1=C(c2ccc(CC3CN(CCCF)C3)cc2)c2ccc(C(=O)O)cc2CCC1]

Step 1: Methyl 8-(2-ethylbutyl)-9-(4-((1-(3-fluoropropyl)azetidin-3-yl)methyl)phenyl)-6,7-dihydro-5H-benzo[7]annulene-3-carboxylate

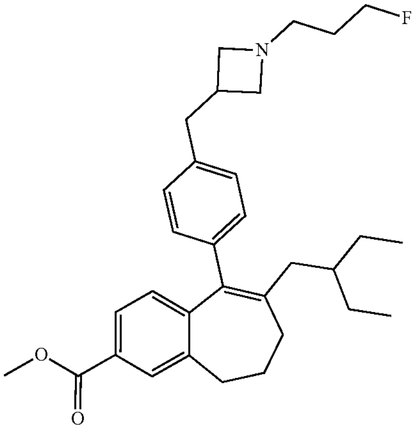 [SMILES: CCC(CC)CC1=C(c2ccc(CC3CN(CCCF)C3)cc2)c2ccc(C(=O)OC)cc2CCC1]

To a mixture of methyl 8-bromo-9-(4-((1-(3-fluoropropyl)azetidin-3-yl)methyl)phenyl)-6,7-dihydro-5H-benzo[7]annulene-3-carboxylate (Intermediate 7) (50 mg, 103 μmol) in THF (1 ml) were added nickel(II) chloride ethylene glycol dimethyl ether complex (1 mg, 5 μmol), 4,4'-di-tert-butyl-2,2'-bipyridine (1.38 mg, 5.14 μmol), sodium carbonate (21.79 mg, 205.58 μmol), (Ir[dF($CF_3$)ppy]2(dtbpy))$PF_6$ (1.15 mg, 1.03 μmol), 3-(bromomethyl)pentane (63 μl, 308 μmol) and tris(trimethylsilyl)silane (30 μl, 150 μmol). The degassed reaction mixture was irradiated under LED blue light (Photoreactor Penn OC ml) for 2 hours. Potassium fluoride 1 M (2 ml) and EtOAc were added. The organic layer was separated, washed with brine, dried over $Na_2SO_4$, filtered and concentrated under reduced pressure. The residue obtained was purified by flash chromatography eluting with a gradient of DCM/EtOAc/MeOH from 100/0/0 to 50/45/05 to give 21 mg (42%) of methyl 8-(2-ethylbutyl)-9-(4-((1-(3-fluoropropyl)azetidin-3-yl)methyl)phenyl)-6,7-dihydro-5H-benzo[7]annulene-3-carboxylate.

LC/MS (m/z, MH+): 492

Step 2: 8-(2-Ethylbutyl)-9-(4-((1-(3-fluoropropyl)azetidin-3-yl)methyl)phenyl)-6,7-dihydro-5H-benzo[7]annulene-3-carboxylic Acid

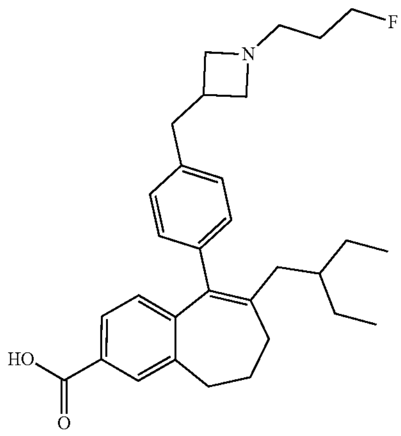 [SMILES: CCC(CC)CC1=C(c2ccc(CC3CN(CCCF)C3)cc2)c2ccc(C(=O)O)cc2CCC1]

Step 2 of Example 231 was prepared following a similar procedure to that of step 2 of Example 2 from methyl 8-(2-ethylbutyl)-9-(4-((1-(3-fluoropropyl)azetidin-3-yl)methyl)phenyl)-6,7-dihydro-5H-benzo[7]annulene-3-carboxylate to give 17 mg (87%) of 8-(2-ethylbutyl)-9-(4-((1-(3-fluoropropyl)azetidin-3-yl)methyl)phenyl)-6,7-dihydro-5H-benzo[7]annulene-3-carboxylic acid.

Method F

Example 115. 8-(2,4-Dichlorophenyl)-9-(2,3-difluoro-4-((1-(3-fluoropropyl)azetidin-3-yl)methyl)phenyl)-6,7-dihydro-5H-benzo[7]annulene-3-carboxylic Acid Hydrochloride

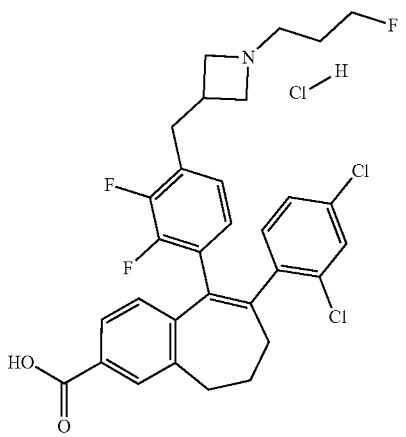

Step 1: Methyl 8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylate

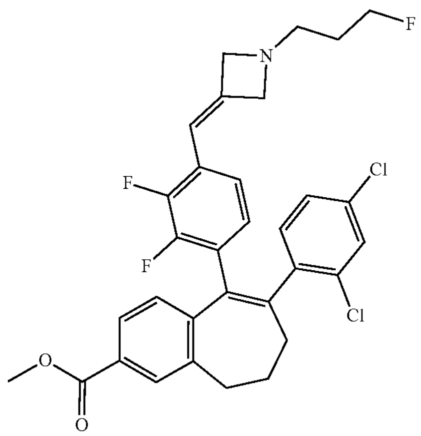 [SMILES: COC(=O)c1ccc2c(c1)CCCC(c1ccc(Cl)cc1Cl)=C2c1ccc(C=C2CN(CCCF)C2)c(F)c1F]

Step 1 of Example 115 was prepared following a similar procedure to that of step 1 of Example 1 from methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) and 3-(4-bromo-2,3-difluorobenzylidene)-1-(3-fluoropropyl)azetidine (Intermediate 34) to give 215 mg (58%) of methyl 8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylate as an orange oil.

LC/MS (m/z, MH+): 586

Step 2: Methyl 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylate

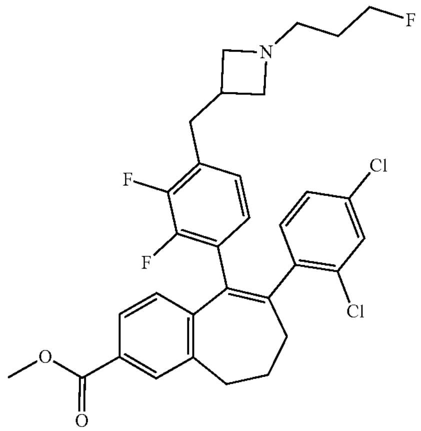 [SMILES: COC(=O)c1ccc2c(c1)CCCC(c1ccc(Cl)cc1Cl)=C2c1ccc(CC2CN(CCCF)C2)c(F)c1F]

To a solution of methyl 8-(2,4-dichlorophenyl)-9-(2,3-difluoro-4-((1-(3-fluoropropyl)azetidin-3-ylidene)methyl)phenyl)-6,7-dihydro-5H-benzo[7]annulene-3-carboxylate (165 mg, 0.281 mmol) in ethanol (30 mL) was added $PtO_2$ (32 mg, 0.14 mmol). The suspension was hydrogenated in an autoclave at room temperature under 2 bars of hydrogen for 2 hours. The mixture was filtered with ethanol washes then the filtrate was concentrated under reduced pressure. The residue was purified by flash chromatography eluting with DCM/MeOH: 90/10 to give 140 mg (84%) of methyl 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylate.

LC/MS (m/z, MH+): 588

Step 3: 8-(2,4-Dichlorophenyl)-9-(2,3-difluoro-4-((1-(3-fluoropropyl)azetidin-3-yl)methyl)phenyl)-6,7-dihydro-5H-benzo[7]annulene-3-carboxylic Acid Hydrochloride

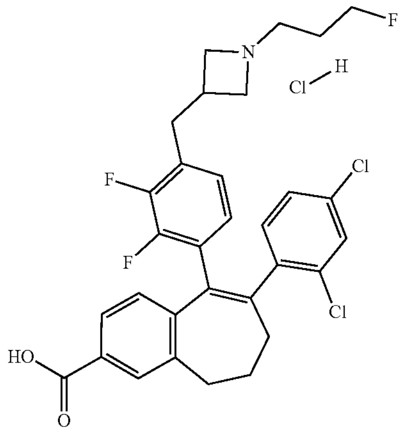

To a solution of methyl 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylate (140 g, 0.238 mmol) in methanol (2 mL), THF (1 mL) and water (0.5 mL) was added LiOH (59 mg, 2.38 mmol). The reaction mixture was stirred at room temperature overnight. The mixture was concentrated under reduced pressure, taken into water and acidified with 1N aqueous HCl to pH 3. The resulting precipitate was filtered and dried to give 44 mg (30%) of 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylic acid hydrochloride as a white solid.

Method G:

Example 262. 6-(2,4-Dichlorophenyl)-5-(4-((1-(3-fluoropropyl)azetidin-3-yl)methyl)phenyl)-7,8-dihydronaphthalene-2-carboxylic Acid Hydrochloride

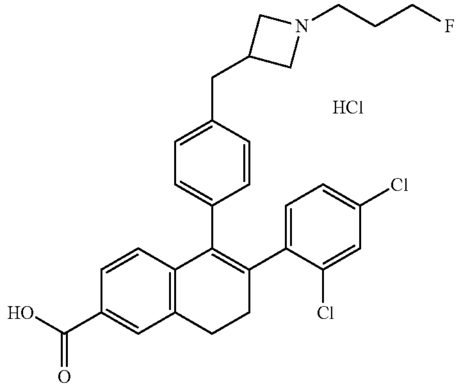 [SMILES: O=C(O)c1ccc2c(c1)CCC(c1ccc(Cl)cc1Cl)=C2c1ccc(CC2CN(CCCF)C2)cc1 ; Cl]

Step 1: Methyl 6-(2,4-dichlorophenyl)-5-[4-[[1-(3-fluoropropyl)azetidin-3-yl]methyl]phenyl]-7,8-dihydronaphthalene-2-carboxylate

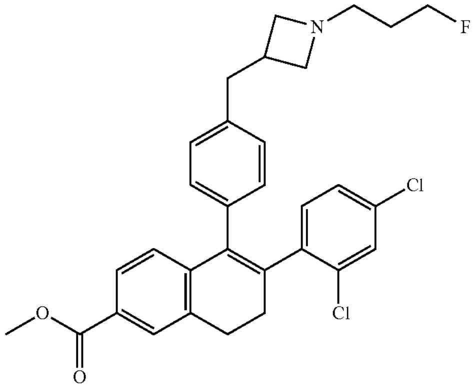 [SMILES: COC(=O)c1ccc2c(c1)CCC(c1ccc(Cl)cc1Cl)=C2c1ccc(CC2CN(CCCF)C2)cc1]

Step 1 of Example 262 was prepared following a similar procedure to that of step 1 of Example 1 from methyl 6-(2,4-dichlorophenyl)-5-(((trifluoromethyl)sulfonyl)oxy)-7,8-dihydronaphthalene-2-carboxylate (Intermediate 52) and 1-(3-fluoropropyl)-3-(4-(4,4,5,5-tetramethyl-1,3,2-dioxaborolan-2-yl)benzyl)azetidine (Intermediate 2), to give 48 mg (43%) of methyl 6-(2,4-dichlorophenyl)-5-[4-[[1-(3-fluoropropyl)azetidin-3-yl]methyl]phenyl]-7,8-dihydronaphthalene-2-carboxylate.

LC/MS (m/z, MH+): 538

Step 2: 6-(2,4-Dichlorophenyl)-5-(4-((1-(3-fluoropropyl)azetidin-3-yl)methyl)phenyl)-7,8-dihydronaphthalene-2-carboxylic Acid Hydrochloride

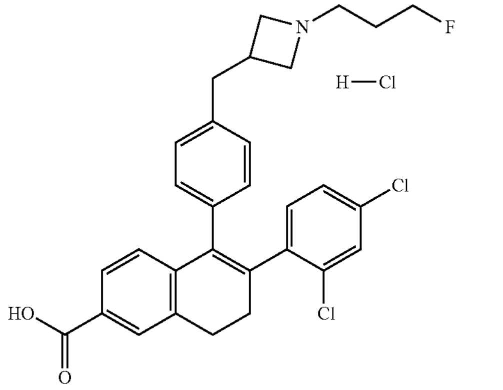

Step 2 of Example 262 was prepared following a similar procedure to that of step 2 of Example 2 from methyl 6-(2,4-dichlorophenyl)-5-[4-[[1-(3-fluoropropyl)azetidin-3-yl]methyl]phenyl]-7,8-dihydronaphthalene-2-carboxylate to give 22 mg (47%) of 6-(2,4-dichlorophenyl)-5-(4-((1-(3-fluoropropyl)azetidin-3-yl)methyl)phenyl)-7,8-dihydronaphthalene-2-carboxylic acid hydrochloride.

Method H:

Example 77. 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic Acid, Hydrochloride Isomer 1

Isomer 1

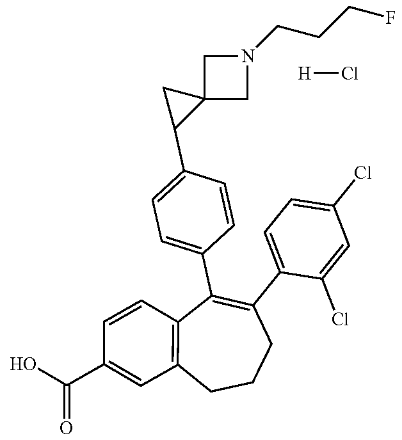

-continued

Isomer 2

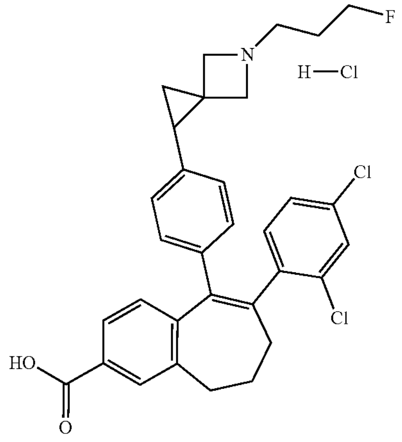

Step 1: Methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate

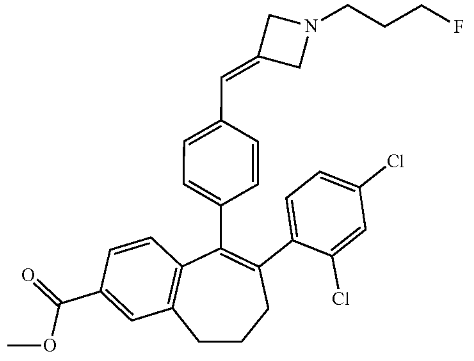 [SMILES: COC(=O)c1ccc2c(c1)CCCC(c1ccc(Cl)cc1Cl)=C2c1ccc(C=C2CN(CCCF)C2)cc1]

Step 1 of Example 77 was prepared following a similar procedure to that of step 1 of Example 1 from methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) and 3-(4-bromobenzylidene)-1-(3-fluoropropyl)azetidine (Intermediate 47) to give 101 mg (86%) of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate.

LC/MS (m/z, MH+): 550

Step 2: Methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate Isomer 1

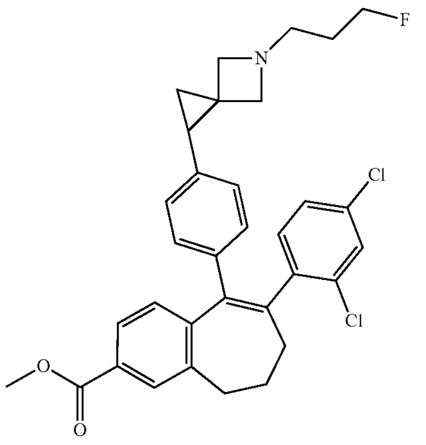

Isomer 2

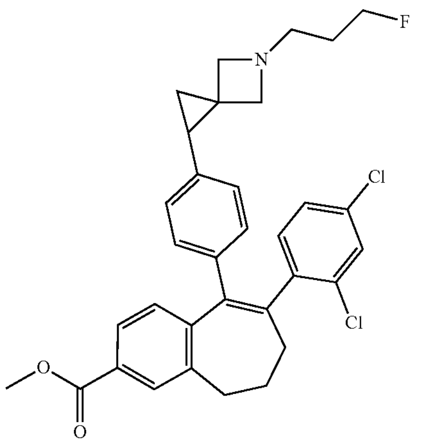

To a solution of diethylzinc (1.13 mL, 1.13 mmol, 1 M in hexanes) at 0° C. under Argon atmosphere was added a solution of diiodomethane (90 μL, 1.13 mmol) in DCM (1 mL). The mixture was stirred at 0° C. for 30 minutes then a solution of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate (310 mg, 0.563 mmol) in DCM (6 mL) was dropwise added. The resulting mixture was stirred overnight allowing the temperature to warm up to room temperature then quenched with a 1N aqueous HCl solution (10 mL) and diluted with water. The aqueous layer was separated and extracted three times with DCM. The combined organic layers were washed with a saturated aqueous solution of $NaHCO_3$, brine, dried over $Na_2SO_4$, filtered and concentrated under reduced pressure. The residue obtained was purified by flash chromatography eluting with a gradient of MeOH in DCM (100/0 to 80/20, v/v) to give 132 mg (33%) of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate as a mixture of two isomers.

LC/MS (m/z, MH+): 550

The mixture of two isomers of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate was separated by chiral HPLC (conditions: flash Chiralcel OD-H 250×30 mm, 5 μm; Heptane 95%/Isopropanol 5%/TEA 0.1%; 45 mL/min) to give 54 mg of isomer 1 and 43 mg of isomer 2.

Step 3: 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic Acid, Hydrochloride Isomer 1

Isomer 1

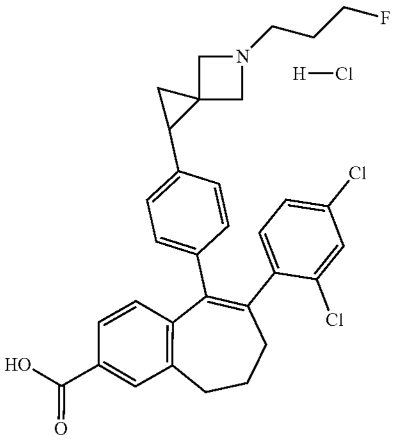

To a solution of methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate Isomer 1 (43 mg, 80 μmol) in methanol (9 mL)/THF (3 mL)/water (3 mL) was added LiOH (30.5 mg, 1.27 mmol). The reaction mixture was stirred at room temperature overnight then quenched with 1N aqueous HCl to pH 1 and extracted three times with DCM. The combined organic layers were washed with brine, dried over $Na_2SO_4$, filtered and concentrated under reduced pressure to give 31 mg (74%) of 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid, hydrochloride Isomer 1 as a white solid.

Example 78. 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic Acid, Hydrochloride Isomer 2

Isomer 2

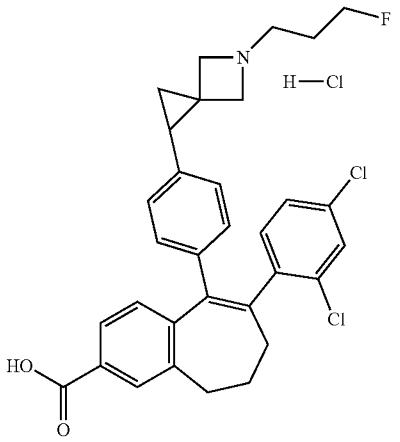

Example 78 was prepared following a similar procedure to that of step 3 of Example 77 from methyl 8-(2,4-dichlorophenyl)-9-(4-((1-(3-fluoropropyl)azetidin-3-ylidene)methyl)phenyl)-6,7-dihydro-5H-benzo[7]annulene-3-carboxylate Isomer 2 to give 41 mg (78%) of 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid, hydrochloride Isomer 2 as a white solid.

Example 105. 8-(2-carbamoylpyridin-4-yl)-9-(4-((1-(3-fluoropropyl)azetidin-3-yl)methyl)phenyl)-6,7-dihydro-5H-benzo[7]annulene-3-carboxylic Acid Hydrochloride

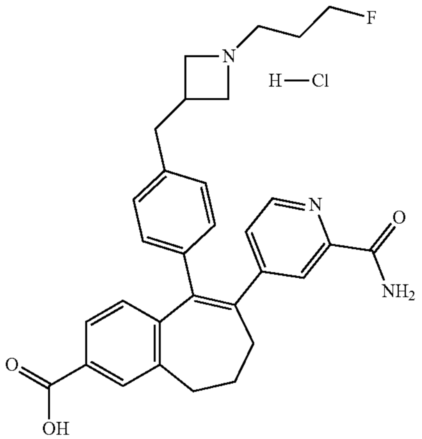

Step 1: methyl 8-(2-cyanopyridin-4-yl)-9-(4-((1-(3-fluoropropyl)azetidin-3-yl)methyl)phenyl)-6,7-dihydro-5H-benzo[7]annulene-3-carboxylate

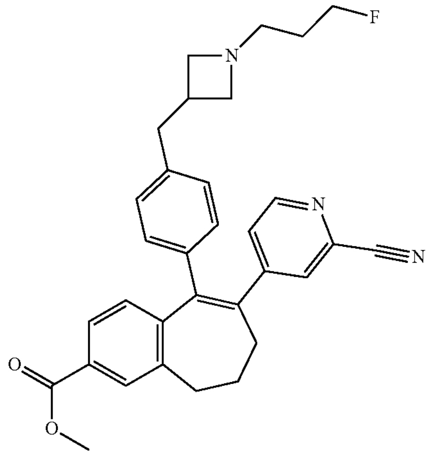 [SMILES: COC(=O)c1ccc2c(c1)CCCC(c1ccnc(C#N)c1)=C2c1ccc(CC2CN(CCCF)C2)cc1]

Step 1 of Example 105 was prepared following a similar procedure to that of step 1 of Example 1 from methyl 8-bromo-9-(4-((1-(3-fluoropropyl)azetidin-3-yl)methyl)phenyl)-6,7-dihydro-5H-benzo[7]annulene-3-carboxylate (Intermediate 7) and 2-cyanopyridine-4-boronic acid pinacol ester to give 227 mg (44%) of methyl 8-(2-cyanopyridin-4-yl)-9-(4-((1-(3-fluoropropyl)azetidin-3-yl)methyl)phenyl)-6,7-dihydro-5H-benzo[7]annulene-3-carboxylate.

LC/MS (m/z, MH+): 510

Step 2: 8-(2-carbamoylpyridin-4-yl)-9-(4-((1-(3-fluoropropyl)azetidin-3-yl)methyl)phenyl)-6,7-dihydro-5H-benzo[7]annulene-3-carboxylic Acid Hydrochloride

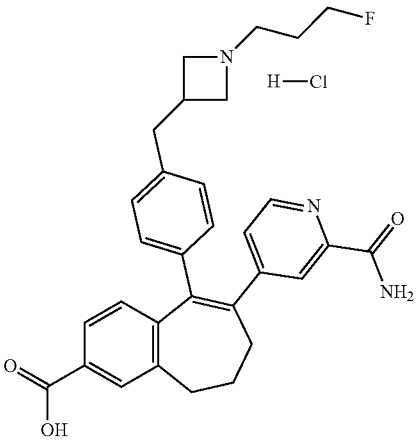

To a solution of methyl 8-(2-cyanopyridin-4-yl)-9-(4-((1-(3-fluoropropyl)azetidin-3-yl)methyl)phenyl)-6,7-dihydro-5H-benzo[7]annulene-3-carboxylate (227 mg, 445 μmol) in MeOH (10 ml) was added a 1 M solution of NaOH (2.8 ml, 2.8 mmol) and the reaction mixture was heated to reflux for 1 hour. After cooling, water (5 ml) and DCM (5 ml) were added and pH was adjusted to 2 with HCl 1N. After hydrophobic column decantation, the organic phase was concentrated under reduced pressure and the residue was purified by flash chromatography eluting with a gradient of MeOH in DCM (100/0 to 90/10, v/v) to give 94 mg (41%) of 8-(2-carbamoylpyridin-4-yl)-9-(4-((1-(3-fluoropropyl)azetidin-3-yl)methyl)phenyl)-6,7-dihydro-5H-benzo[7]annulene-3-carboxylic acid hydrochloride.

Example 110. 9-(4-((1-(3-fluoropropyl)azetidin-3-yl)methyl)phenyl)-8-(1H-pyrrol-2-yl)-6,7-dihydro-5H-benzo[7]annulene-3-carboxylic acid, Hydrochloride

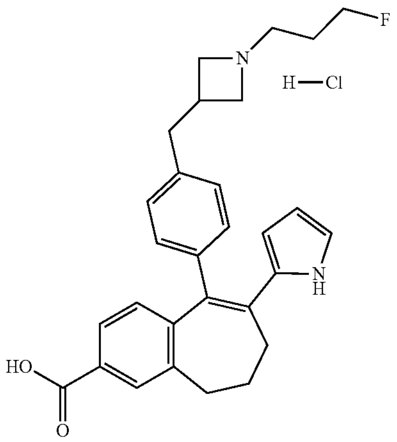

Step 1: tert-butyl 2-(9-(4-((1-(3-fluoropropyl)azetidin-3-yl)methyl)phenyl)-3-(methoxycarbonyl)-6,7-dihydro-5H-benzo[7]annulen-8-yl)-1H-pyrrole-1-carboxylate

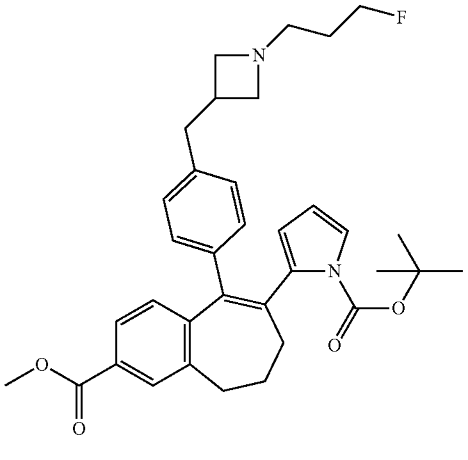 [SMILES: COC(=O)c1ccc2c(c1)CCCC(c1cccn1C(=O)OC(C)(C)C)=C2c1ccc(CC2CN(CCCF)C2)cc1]

Step 1 of Example 110 was prepared following a similar procedure to that of step 1 of Example 1 from methyl 8-bromo-9-(4-((1-(3-fluoropropyl)azetidin-3-yl)methyl)phenyl)-6,7-dihydro-5H-benzo[7]annulene-3-carboxylate (Intermediate 7) and N-Boc-2-pyrroleboronic acid to give 223 mg (89%) of tert-butyl 2-(9-(4-((1-(3-fluoropropyl)azetidin-3-yl)methyl)phenyl)-3-(methoxycarbonyl)-6,7-dihydro-5H-benzo[7]annulen-8-yl)-1H-pyrrole-1-carboxylate.

LC/MS (m/z, MH+): 573

Step 2: 9-(4-((1-(3-fluoropropyl)azetidin-3-yl)methyl)phenyl)-8-(1H-pyrrol-2-yl)-6,7-dihydro-5H-benzo[7]annulene-3-carboxylic acid, Hydrochloride

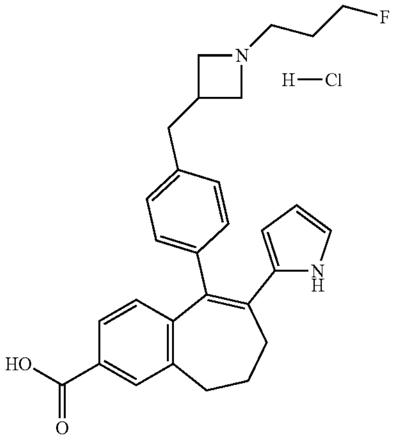

To a solution of tert-butyl 2-(9-(4-((1-(3-fluoropropyl)azetidin-3-yl)methyl)phenyl)-3-(methoxycarbonyl)-6,7-dihydro-5H-benzo[7]annulen-8-yl)-1H-pyrrole-1-carboxylate (93 mg, 162 μmol) in MeOH (10 ml) was added a solution of NaOH (1.02 ml, 1.02 mmol) and the reaction mixture was heated to reflux for 1 hour. After cooling, water (5 ml) and DCM (5 ml) were added, and pH was adjusted to 2 with HCl 1N. After hydrophobic column decantation, the organic phase was concentrated under reduced pressure and the residue was purified by flash chromatography eluting with a gradient of MeOH in DCM (100/0 to 90/10, v/v) to give 30 mg (32%) of 8-(1-(tert-butoxycarbonyl)-1H-pyrrol-2-yl)-9-(4-((1-(3-fluoropropyl)azetidin-3-yl)methyl)phenyl)-6,7-dihydro-5H-benzo[7]annulene-3-carboxylic acid, hydrochloride and 12 mg (16%) of 9-(4-((1-(3-fluoropropyl)azetidin-3-yl)methyl)phenyl)-8-(1H-pyrrol-2-yl)-6,7-dihydro-5H-benzo[7]annulene-3-carboxylic acid, hydrochloride.

Example 175. 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic Acid Hydrochloride Isomer 1

Isomer 1

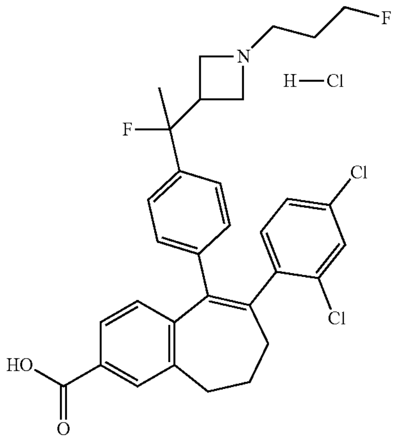

Step 1: Methyl 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylate

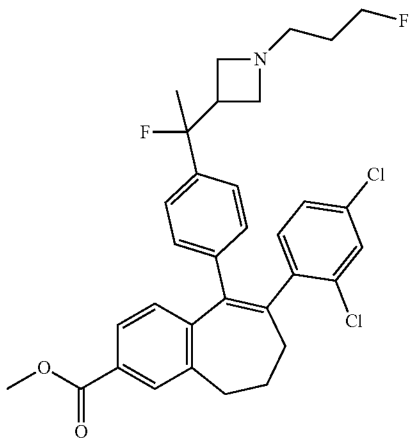 [SMILES: COC(=O)c1ccc2c(c1)CCCC(c1ccc(Cl)cc1Cl)=C2c1ccc(C(C)(F)C2CN(CCCF)C2)cc1]

To a solution of methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate (Step 1 of Example 235) (200 mg, 343 μmol) in DCM (5 mL) at −78° C. was added diethylaminosulfur trifluoride (90 μl, 0.69 mmol). The mixture was stirred for 1 hour at −78° C. then for 6 hours allowing the temperature to warm up to room temperature. Saturated aqueous solution of $NaHCO_3$ and DCM were added. The combined organic layers were washed with brine, dried over $Na_2SO_4$, filtered, and concentrated under reduced pressure. The residue obtained was purified by flash chromatography eluting with a gradient of gradient of DCM/MeOH/$NH_4$OH from 100/0/0 to 90/10/1 to give 153 mg (77%) of methyl 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylate as mixture of two isomers.

LC/MS (m/z, MH+): 584

The mixture of two isomers of methyl 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylate was separated by chiral SFC (conditions: flash Chiralcel OD-H (250×30 mm, 5 μm); supercritical $CO_2$ 80%/[0.1% TEA/MeOH] 20%; 3 mL/min) to give 35 mg of isomer 1 and 37 mg of isomer 2.

Step 2: 8-(2,4-Dichlorophenyl)-9-(4-(1-fluoro-1-(1-(3-fluoropropyl)azetidin-3-yl)ethyl)phenyl)-6,7-dihydro-5H-benzo[7]annulene-3-carboxylic Acid Hydrochloride Isomer 1

Isomer 1

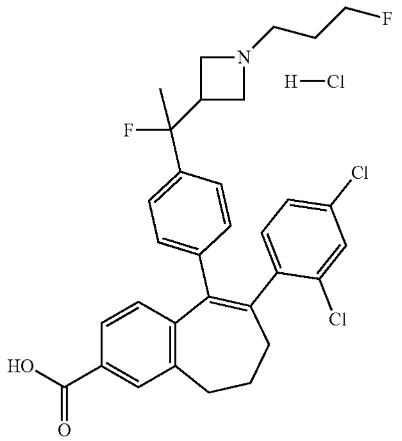

Example 175 was prepared following a similar procedure to that of step 3 of Example 77 from methyl 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylate Isomer 1 to give 31 mg (82%) of 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 1.

Example 176. 8-(2,4-Dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 2

Isomer 2

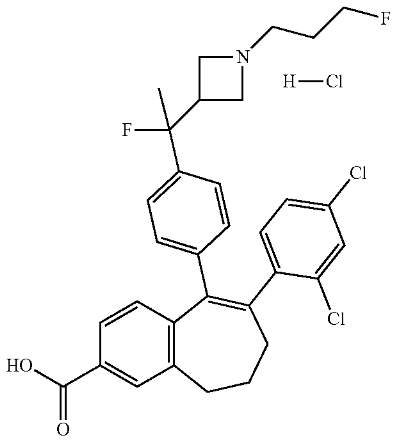

Example 176 was prepared following a similar procedure to that of step 3 of Example 77 from methyl 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylate Isomer 2 to give 26 mg (75%) of 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride Isomer 2.

Example 235. 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, Hydrochloride Isomer 1

Isomer 1

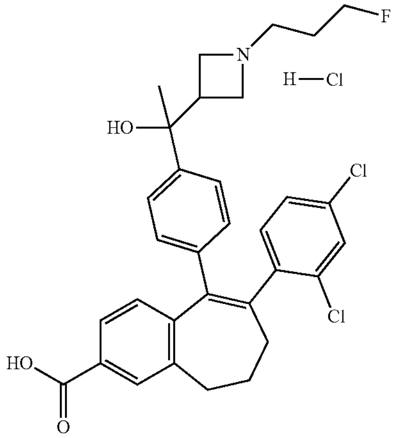

Step 1: Methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate

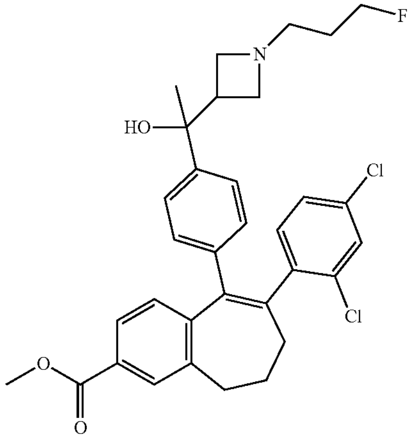 [SMILES: COC(=O)c1ccc2c(c1)CCCC(c1ccc(Cl)cc1Cl)=C2c1ccc(C(C)(O)C2CN(CCCF)C2)cc1]

To a solution of 8-(2,4-dichlorophenyl)-9-(4-(1-(3-fluoropropyl)azetidine-3-carbonyl)phenyl)-6,7-dihydro-5H-benzo[7]annulene-3-carboxylic acid (Step 1 of Example 39) (100 mg, 176 μmol) in THF (5 mL) at −10° C. was added a 3 M solution of methyl magnesium bromide in ether (180 μL, 530 μmol). The mixture was stirred at −10° C. for 45 minutes. The reaction mixture was slowly quenched by addition of a saturated aqueous solution of $NH_4Cl$ and extracted three times with EtOAc. The combined organic layers were washed with brine, dried over $Na_2SO_4$, filtered, and concentrated under reduced pressure to give 102 mg (99%) of methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate as mixture of two isomers.

LC/MS (m/z, MH+): 582

The mixture of two isomers of methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate was separated by chiral HPLC (conditions: flash Chiralpak AY-H 250×4.6 mm, 5 μm; Heptane 89/EtOH 10/MeOH 1/TEA 0.2; 45 mL/min) to give 20 mg of isomer 1 and 19 mg of isomer 2.

Step 2: 8-(2,4-Dichlorophenyl)-9-(4-(1-(1-(3-fluoropropyl)azetidin-3-yl)-1-hydroxyethyl)phenyl)-6,7-dihydro-5H-benzo[7]annulene-3-carboxylic Acid, Hydrochloride Isomer 1

Isomer 1

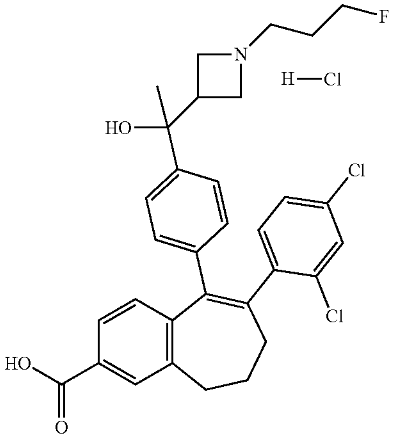

Example 235 was prepared following a similar procedure to that of step 3 of Example 77 from methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate Isomer 1 to give 4 mg (21%) of 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, hydrochloride Isomer 1.

Example 236. 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic Acid, Hydrochloride Isomer 2

Isomer 2

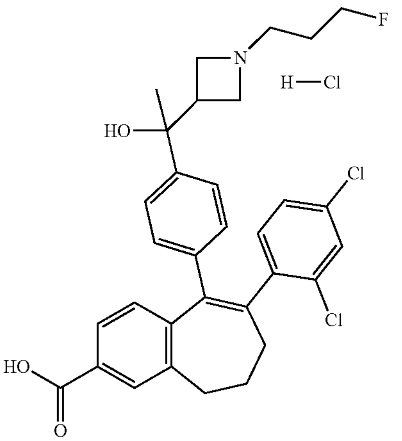

Example 236 was prepared following a similar procedure to that of step 3 of Example 77 from methyl 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylate Isomer 2 to give 7 mg (35%) of 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, hydrochloride Isomer 2.

Example 194. 8-(2,4-Dichlorophenyl)-9-(4-((1-(2,3-difluoropropyl)azetidin-3-yl)methyl)phenyl)-6,7-dihydro-5H-benzo[7]annulene-3-carboxylic Acid Isomer 1

Isomer 1

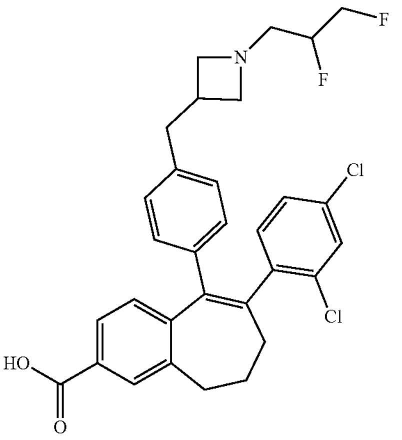

Step 12: Methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate Isomer 1 and Isomer 2

Isomer 1

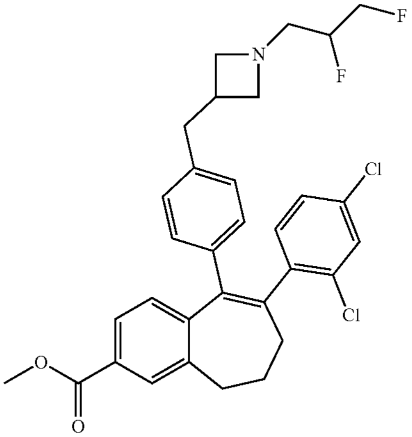

and

Isomer 2

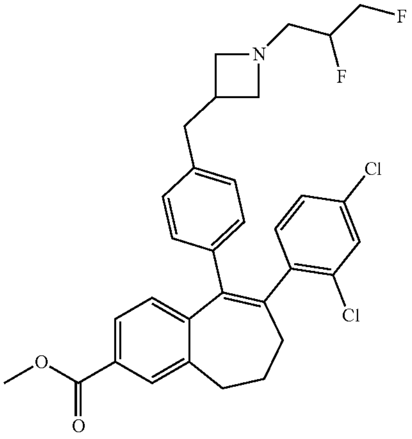

Step 1 of Example 194 Isomer 1 and Isomer 2 were prepared following a similar procedure to that of step 1 of Example 1 from 3-(4-bromobenzyl)-1-(2,3-difluoropropyl)azetidine (Intermediate 50) and methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) to give 278 mg (66%) as a mixture of methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate Isomer 1 and Isomer 2.

The mixture of two isomers was separated by chiral chromatography (condition: flash Chiralpak IF 5 m (250×30 mm), eluent: Heptane 95 EtOH 5 TEA 0.1 to give 91 mg of methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate Isomer 1 and 94 mg of methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate Isomer 2.

LC/MS (m/z, MH+): 570

Step 2: 8-(2,4-dichlorophenyl)-9-(4-((1-(2,3-difluoropropyl)azetidin-3-yl)methyl)phenyl)-6,7-dihydro-5H-benzo[7]annulene-3-carboxylic Acid Isomer 1

Isomer 1

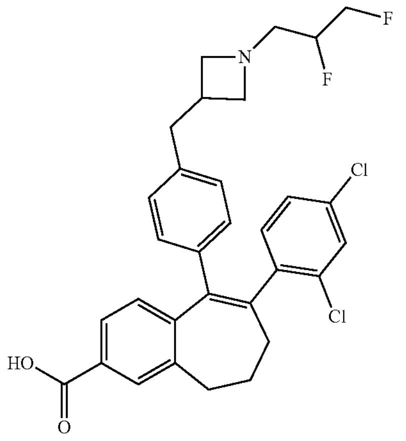

Step 2 of Example 194 Isomer 1 was prepared following a similar procedure to that of step 2 of Example 2 from methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate Isomer 1 to give 75 mg (84%) of 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 1.

Example 195. 8-(2,4-dichlorophenyl)-9-(4-((1-(2,3-difluoropropyl)azetidin-3-yl)methyl)phenyl)-6,7-dihydro-5H-benzo[7]annulene-3-carboxylic Acid Isomer 2

Isomer 2

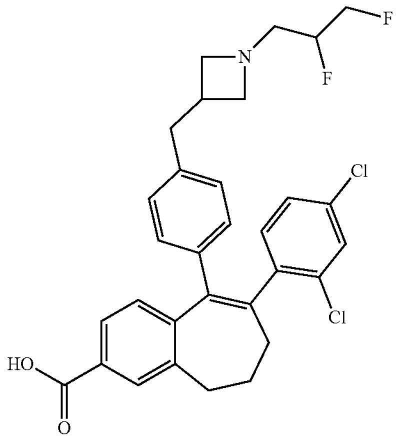

Example 195 was prepared following a similar procedure to that of step 2 of Example 2 from methyl 8-(2,4-dichlorophenyl)-9-(4-((1-(2,3-difluoropropyl)azetidin-3-yl)methyl)phenyl)-6,7-dihydro-5H-benzo[7]annulene-3-carboxylate isomer 2 to give 90 mg (98%) of 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid Isomer 2.

Example 196. (E)-8-(2,4-Dichlorophenyl)-9-(4-((1-(3-fluoropropyl)azetidin-3-yl)(methoxyimino)methyl)phenyl)-6,7-dihydro-5H-benzo[7]annulene-3-carboxylic Acid, Trifluoroacetic Acid

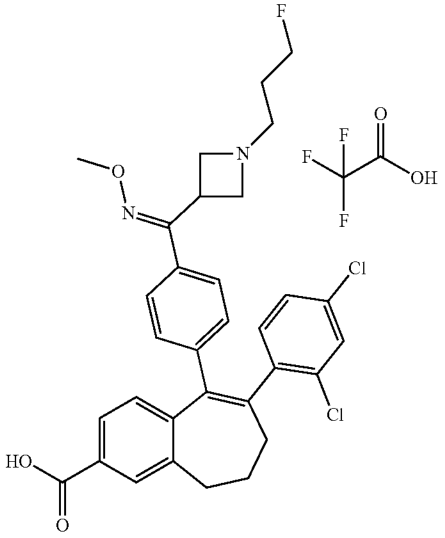

Step 1: Methyl(E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate and methyl (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate

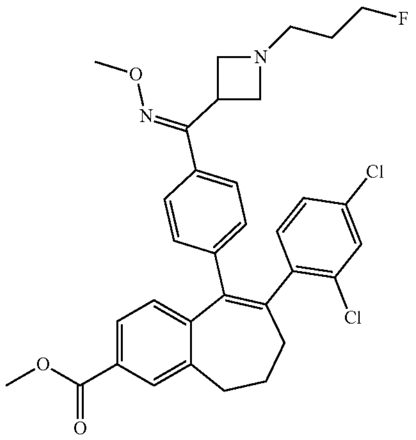

and

-continued

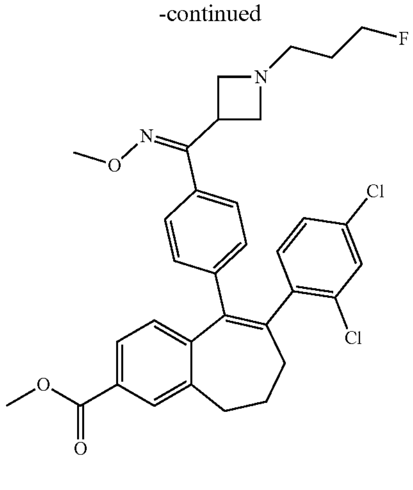

A mixture of methyl 8-(2,4-dichlorophenyl)-9-(4-(1-(3-fluoropropyl)azetidine-3-carbonyl)phenyl)-6,7-dihydro-5H-benzo[7]annulene-3-carboxylate acid (Step 1 of Example 39) (500 mg, 882 μmol) and O-methylhydroxylamine hydrochloride (184 mg, 2.21 mmol) in pyridine (5 ml) was stirred at room temperature for 24 hours. The reaction mixture was concentrated under reduced pressure. The 2 isomers were separated by SFC (condition: flash Chiralpak IG 5 μm (3×25 cm), eluent $CO_2$/11% (MeOH+0.1% DEA) to give 111 mg (21%) of methyl(E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate and 34 mg (6%) of methyl (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate.

LC/MS (m/z, MH+): 595

Step 2: (E)-8-(2,4-Dichlorophenyl)-9-(4-((1-(3-fluoropropyl)azetidin-3-yl)(methoxyimino)methyl)phenyl)-6,7-dihydro-5H-benzo[7]annulene-3-carboxylic Acid, Trifluoroacetic Acid

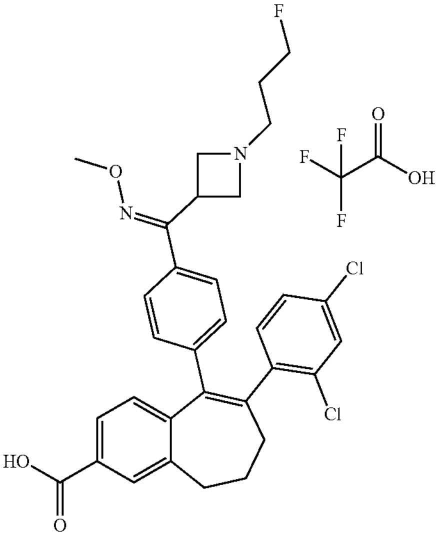

Step 2 of Example 196 isomer 1 was prepared following a similar procedure to that of step 2 of Example 2 from methyl(E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate to give 86 mg (66%) of (E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid.

Example 197. (Z)-8-(2,4-Dichlorophenyl)-9-(4-((1-(3-fluoropropyl)azetidin-3-yl)(methoxyimino)methyl)phenyl)-6,7-dihydro-5H-benzo[7]annulene-3-carboxylic Acid, Trifluoroacetic Acid

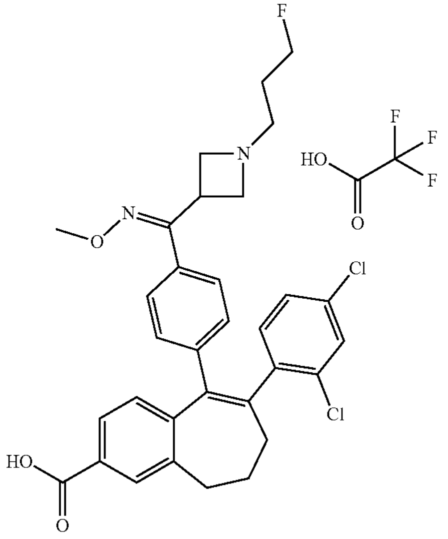

Example 197 was prepared following a similar procedure to that of step 2 of Example 2 from methyl (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylate to give 12 mg (30%) of (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acetate.

Example 227. 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic Acid Isomer 1

Isomer 1

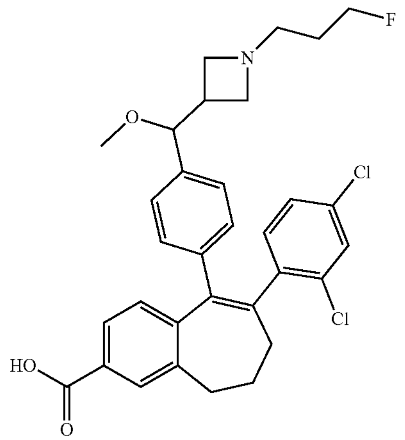

Step 1: Methyl 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylate Isomer 1

Isomer 1

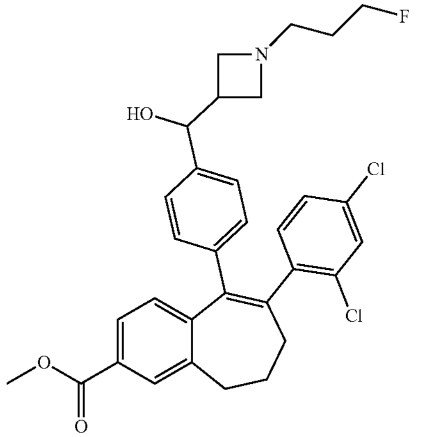

Step 1 of Example 227 was prepared following a similar procedure to that of step 1 of Example 1 from methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) and (4-bromophenyl)(1-(3-fluoropropyl)azetidin-3-yl)methanol Isomer 1 (Intermediate 14) to give 191 mg (64%) of methyl 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylate Isomer 1.

LC/MS (m/z, MH+): 568

Step 2: Methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 1

Isomer 1

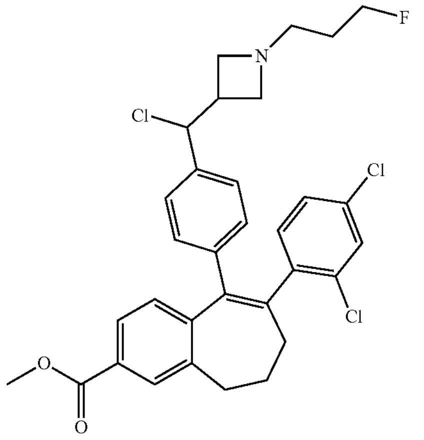

Step 3: 8-(2,4-Dichlorophenyl)-9-(4-((1-(3-fluoropropyl)azetidin-3-yl)(methoxy)methyl)phenyl)-6,7-dihydro-5H-benzo[7]annulene-3-carboxylic Acid Isomer 1

Isomer 1

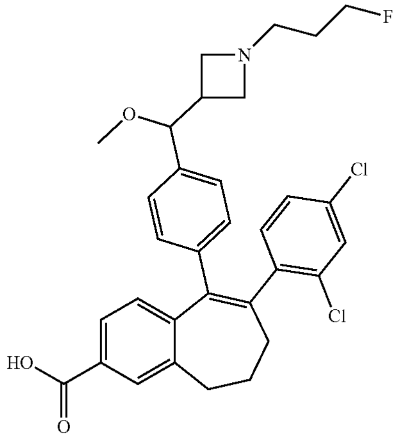

To a solution of methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 1 (100 mg, 170 μmol) in methanol (5 mL) and water (1 mL) was added LiOH (12 mg, 511 μmol). The reaction mixture was stirred at room temperature for 3 hours then quenched with 1N aqueous HCl to pH 6-7 and extracted three times with EtOAc. The organic layer was washed with brine, dried over $Na_2SO_4$, filtered, concentrated under reduced pressure and the residue obtained was purified by flash chromatography eluting with a gradient of DCM/MeOH from 100/00 to 95/05 to give 28 mg (29%) of 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 1.

Example 228. 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic Acid Isomer 2

Isomer 2

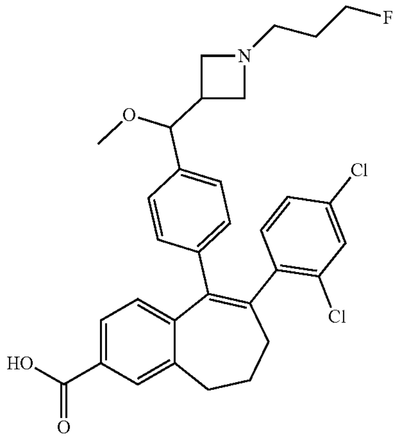

Step 1: Methyl 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylate Isomer 2

Isomer 2

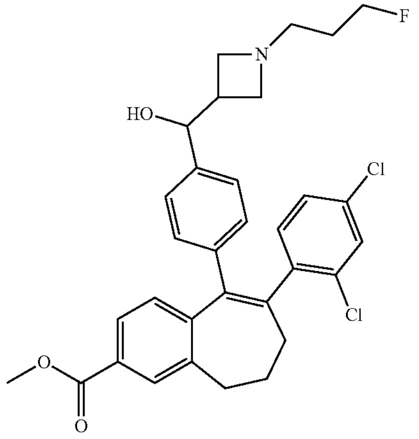

Step 1 of Example 228 was prepared following a similar procedure to that of step 1 of Example 1 from methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) and (4-bromophenyl)(1-(3-fluoropropyl)azetidin-3-yl)methanol Isomer 2 (Intermediate 15) to give 186 mg (62%) of methyl 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylate Isomer 2.

LC/MS (m/z, MH+): 568

Step 2: Methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 2

Isomer 2

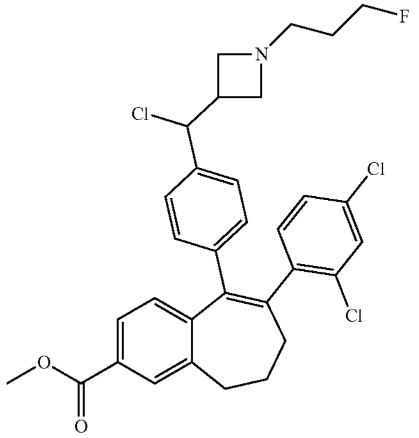

Step 2 of Example 228 was prepared following a similar procedure to that of step 2 of Example 227 from methyl 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylate Isomer 2 to give 175 mg (91%) of methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 2.

LC/MS (m/z, MH+): 586

Step 3: 8-(2,4-Dichlorophenyl)-9-(4-((1-(3-fluoropropyl)azetidin-3-yl)(methoxy)methyl)phenyl)-6,7-dihydro-5H-benzo[7]annulene-3-carboxylic Acid Isomer 2

Isomer 2

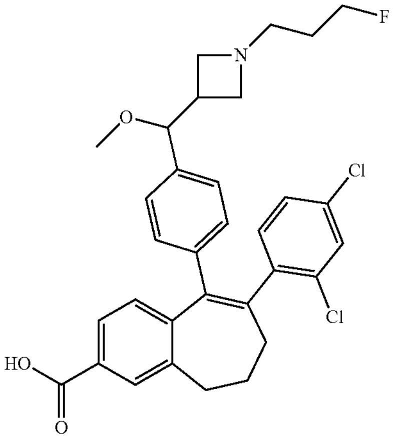

Step 3 of Example 228 was prepared following a similar procedure to that of step 3 of Example 227 from methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 2 to give 25 mg (26%) of 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 2.

Example 229. 8-(2,4-dichlorophenyl)-9-(4-(ethoxy(1-(3-fluoropropyl)azetidin-3-yl)methyl)phenyl)-6,7-dihydro-5H-benzo[7]annulene-3-carboxylic Acid Isomer 1

Isomer 1

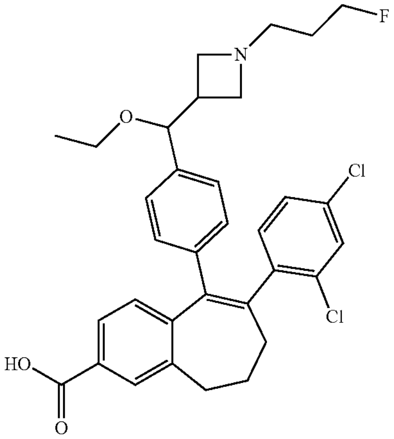

Example 229 was prepared following a similar procedure to that of step 3 of Example 227 from methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 1 and EtOH to give 15 mg (30%) of 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 1.

Example 230. 8-(2,4-dichlorophenyl)-9-(4-(ethoxy(1-(3-fluoropropyl)azetidin-3-yl)methyl)phenyl)-6,7-dihydro-5H-benzo[7]annulene-3-carboxylic Acid Isomer 2

Isomer 2

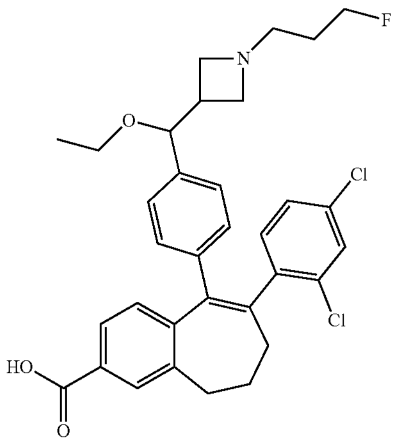

Example 230 was prepared following a similar procedure to that of step 3 of Example 227 from methyl 9-(4-(chloro(1-(3-fluoropropyl)azetidin-3-yl)methyl)phenyl)-8-(2,4-dichlorophenyl)-6,7-dihydro-5H-benzo[7]annulene-3-carboxylate Isomer 2 and EtOH to give 34 mg (34%) of 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid Isomer 2.

Example 243. 9-(4-(amino(1-(3-fluoropropyl)azetidin-3-yl)methyl)phenyl)-8-(2,4-dichlorophenyl)-6,7-dihydro-5H-benzo[7]annulene-3-carboxylic Acid Isomer 1

Isomer 1

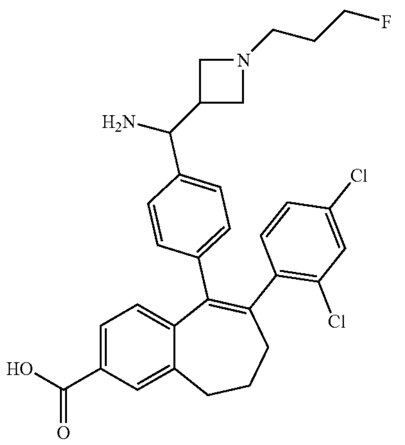

Step 1: Methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 1

Isomer 1

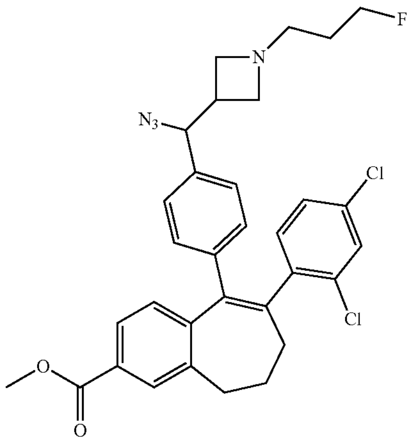

Step 1 of Example 243 was prepared following a similar procedure to that of step 1 of Example 1 from 3-(azido(4-bromophenyl)methyl)-1-(3-fluoropropyl)azetidine Isomer 1 (Intermediate 25) and methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) to give 500 mg (99%) of methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 1.

LC/MS (m/z, MH+): 593

Step 2: Methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 1

Isomer 1

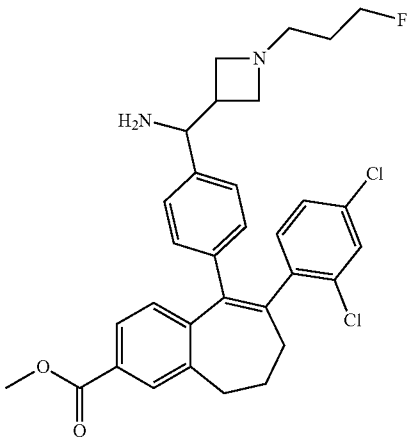

A mixture of methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 1 (300 mg, 505 μmol) and triphenylphosphine (132 mg, 505 μmol) in THF (4 ml) was stirred at room temperature for 24 hours. DCM (100 ml) and water (100 ml) were added. After decantation, the organic layer was dried over $Na_2SO_4$, filtered, concentrated under reduced pressure and the residue obtained purified by flash chromatography eluting with a gradient of DCM/MeOH from 100/00 to 80/20 to give 44 mg (15%) of methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 1.

LC/MS (m/z, MH+): 567

Step 3: 9-(4-(Amino(1-(3-fluoropropyl)azetidin-3-yl)methyl)phenyl)-8-(2,4-dichlorophenyl)-6,7-dihydro-5H-benzo[7]annulene-3-carboxylic Acid Isomer 1

Isomer 1

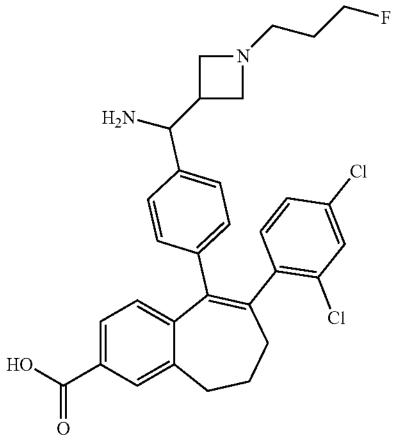

Step 3 of Example 243 was prepared following a similar procedure to that of step 2 of Example 2 from methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 1 to give 33 mg (79%) of 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 1.

Example 244. 9-(4-(Amino(1-(3-fluoropropyl)azetidin-3-yl)methyl)phenyl)-8-(2,4-dichlorophenyl)-6,7-dihydro-5H-benzo[7]annulene-3-carboxylic Acid Isomer 2

Isomer 2

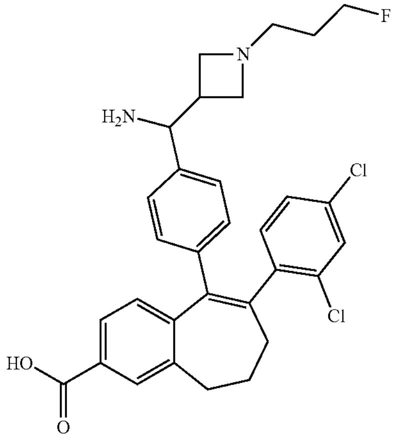

Step 1: Methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 2

Isomer 2

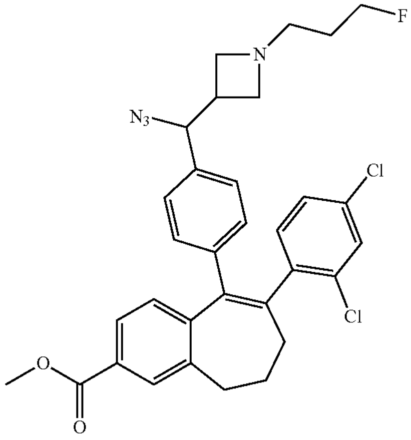

Step 1 of Example 244 was prepared following a similar procedure to that of step 1 of Example 1 from 3-(azido(4-bromophenyl)methyl)-1-(3-fluoropropyl)azetidine isomer 2 (Intermediate 26) and methyl 8-(2,4-dichlorophenyl)-9-(4,4,5,5-tetramethyl-1,3,2-dioxaborolan-2-yl)-6,7-dihydro-5H-benzo[7]annulene-3-carboxylate (Intermediate 5) to give 550 mg (97%) of methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 2.

LC/MS (m/z, MH+): 593

Step 2: Methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 2

Isomer 2

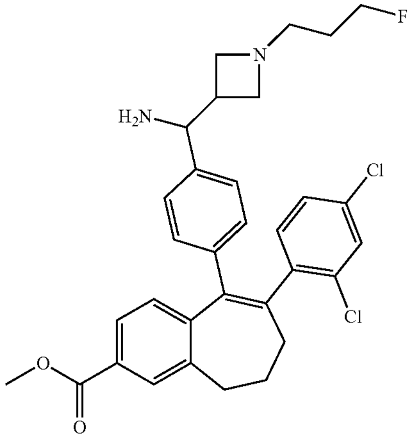

Step 2 of Example 244 was prepared following a similar procedure to that of step 2 of Example 243 from methyl 9-(4-(azido(1-(3-fluoropropyl)azetidin-3-yl)methyl)phenyl)-8-(2,4-dichlorophenyl)-6,7-dihydro-5H-benzo[7]annulene-3-carboxylate Isomer 2 to give 140 mg (44%) of methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 2.

LC/MS (m/z, MH+): 567

Step 3: 9-(4-(Amino(1-(3-fluoropropyl)azetidin-3-yl)methyl)phenyl)-8-(2,4-dichlorophenyl)-6,7-dihydro-5H-benzo[7]annulene-3-carboxylic Acid Isomer 1

Isomer 2

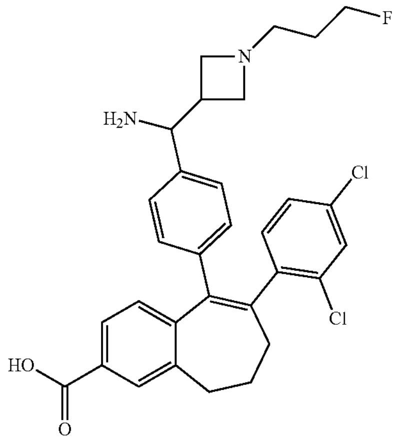

Step 3 of Example 244 was prepared following a similar procedure to that of step 2 of Example 2 from methyl 9-(4-(amino(1-(3-fluoropropyl)azetidin-3-yl)methyl)phenyl)-8-(2,4-dichlorophenyl)-6,7-dihydro-5H-benzo[7]annulene-3-carboxylate Isomer 2 to give 22 mg (52%) of 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid Isomer 2.

Example 252. 8-(2-chlorophenyl)-9-(5-((1-(3-fluoropropyl)azetidin-3-yl)methyl)pyridin-2-yl)-6,7-dihydro-5H-benzo[7]annulene-3-carboxylic Acid

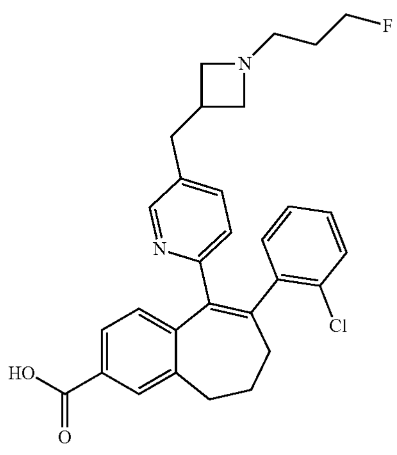 [SMILES: O=C(O)c1ccc2c(c1)CCCC(c1ccccc1Cl)=C2c1ccc(CC2CN(CCCF)C2)cn1]

Step 1: tert-butyl 3-((6-(8-(2-chlorophenyl)-3-(methoxycarbonyl)-6,7-dihydro-5H-benzo[7]annulen-9-yl)pyridin-3-yl)methyl)azetidine-1-carboxylate

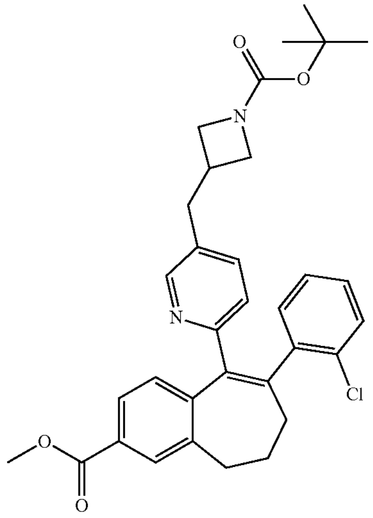 [SMILES: COC(=O)c1ccc2c(c1)CCCC(c1ccccc1Cl)=C2c1ccc(CC2CN(C(=O)OC(C)(C)C)C2)cn1]

Step 1 of Example 252 was prepared following a similar procedure to that of step 1 of Example 1 from tert-butyl 3-((6-(8-bromo-3-(methoxycarbonyl)-6,7-dihydro-5H-benzo[7]annulen-9-yl)pyridin-3-yl)methyl)azetidine-1-carboxylate (Intermediate 48) and (2-chlorophenyl)boronic acid to give 87 mg (41%) of tert-butyl 3-((6-(8-(2-chlorophenyl)-3-(methoxycarbonyl)-6,7-dihydro-5H-benzo[7]annulen-9-yl)pyridin-3-yl)methyl)azetidine-1-carboxylate.

LC/MS (m/z, MH+): 559

Step 2: methyl 9-(5-(azetidin-3-ylmethyl)pyridin-2-yl)-8-(2-chlorophenyl)-6,7-dihydro-5H-benzo[7]annulene-3-carboxylate, Trifluoroacetic Acid

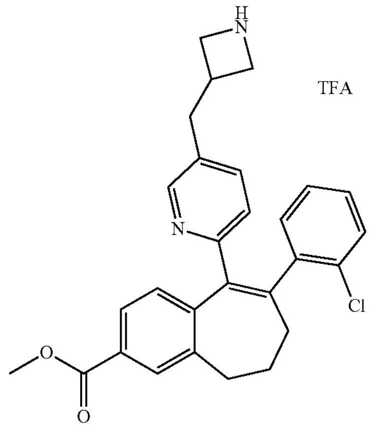 [SMILES: COC(=O)c1ccc2c(c1)CCCC(c1ccccc1Cl)=C2c1ccc(CC2CNC2)cn1]

Step 2 of Example 252 was prepared following a similar procedure to that of step 2 of Intermediate 11 from tert-butyl 3-((6-(8-(2-chlorophenyl)-3-(methoxycarbonyl)-6,7-dihydro-5H-benzo[7]annulen-9-yl)pyridin-3-yl)methyl)azetidine-1-carboxylate to give methyl 9-(5-(azetidin-3-ylmethyl)pyridin-2-yl)-8-(2-chlorophenyl)-6,7-dihydro-5H- benzo[7]annulene-3-carboxylate, trifluoroacetic acid which was used in the next step without further purification.

Step 3: methyl 8-(2-chlorophenyl)-9-(5-((1-(3-fluoropropyl)azetidin-3-yl)methyl)pyridin-2-yl)-6,7-dihydro-5H-benzo[7]annulene-3-carboxylate

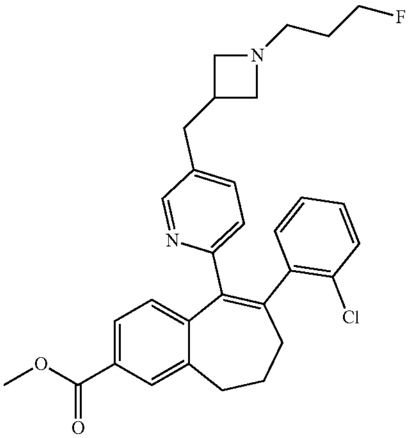 [SMILES: COC(=O)c1ccc2c(c1)CCCC(c1ccccc1Cl)=C2c1ccc(CC2CN(CCCF)C2)cn1]

Step 3 of Example 252 was prepared following a similar procedure to that of step 4 of Intermediate 28 from methyl 9-(5-(azetidin-3-ylmethyl)pyridin-2-yl)-8-(2-chlorophenyl)-6,7-dihydro-5H-benzo[7]annulene-3-carboxylate, trifluoroacetic acid to give 35 mg (43%) of methyl 8-(2-chlorophenyl)-9-(5-((1-(3-fluoropropyl)azetidin-3-yl)methyl)pyridin-2-yl)-6,7-dihydro-5H-benzo[7]annulene-3-carboxylate.

LC/MS (m/z, MH+): 519

Step 4: 8-(2-chlorophenyl)-9-(5-((1-(3-fluoropropyl)azetidin-3-yl)methyl)pyridin-2-yl)-6,7-dihydro-5H-benzo[7]annulene-3-carboxylic Acid

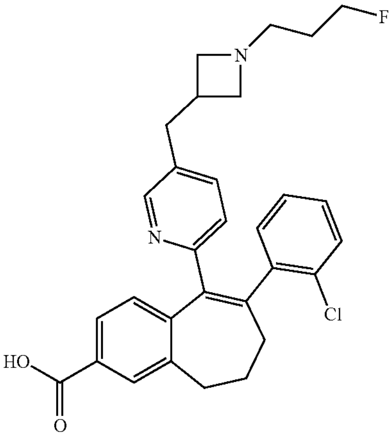 [SMILES: O=C(O)c1ccc2c(c1)CCCC(c1ccccc1Cl)=C2c1ccc(CC2CN(CCCF)C2)cn1]

Step 4 of Example 252 was prepared following a similar procedure to that of step 2 of Example 2 from methyl 8-(2-chlorophenyl)-9-(5-((1-(3-fluoropropyl)azetidin-3-yl)methyl)pyridin-2-yl)-6,7-dihydro-5H-benzo[7]annulene-3-carboxylate to give 32 mg (44%) of 8-(2-chlorophenyl)-9-(5-((1-(3-fluoropropyl)azetidin-3-yl)methyl)pyridin-2-yl)-6,7-dihydro-5H-benzo[7]annulene-3-carboxylic acid.

Example 253. 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic Acid

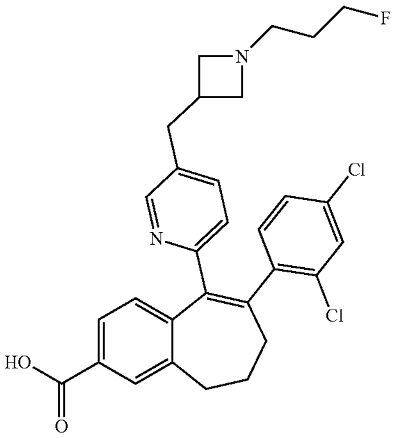 [SMILES: O=C(O)c1ccc2c(c1)CCCC(c1ccc(Cl)cc1Cl)=C2c1ccc(CC2CN(CCCF)C2)cn1]

Step 1: tert-butyl 3-((6-(8-(2,4-dichlorophenyl)-3-(methoxycarbonyl)-6,7-dihydro-5H-benzo[7]annulen-9-yl)pyridin-3-yl)methyl)azetidine-1-carboxylate

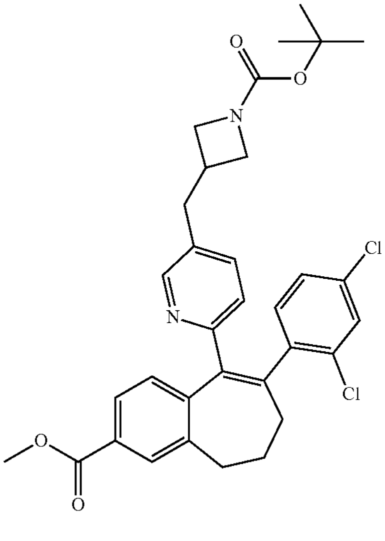 [SMILES: COC(=O)c1ccc2c(c1)CCCC(c1ccc(Cl)cc1Cl)=C2c1ccc(CC2CN(C(=O)OC(C)(C)C)C2)cn1]

Step 1 of Example 253 was prepared following a similar procedure to that of step 1 of Example 1 from tert-butyl 3-((6-(8-bromo-3-(methoxycarbonyl)-6,7-dihydro-5H-benzo[7]annulen-9-yl)pyridin-3-yl)methyl)azetidine-1-carboxylate (Intermediate 48) and (2,4-dichlorophenyl)boronic acid to give 105 mg (47%) of tert-butyl 3-((6-(8-(2,4-dichlorophenyl)-3-(methoxycarbonyl)-6,7-dihydro-5H-benzo[7]annulen-9-yl)pyridin-3-yl)methyl)azetidine-1-carboxylate.

LC/MS (m/z, MH+): 593

Step 2: methyl 9-(5-(azetidin-3-ylmethyl)pyridin-2-yl)-8-(2,4-dichlorophenyl)-6,7-dihydro-5H-benzo[7]annulene-3-carboxylate, Trifluoroacetic Acid

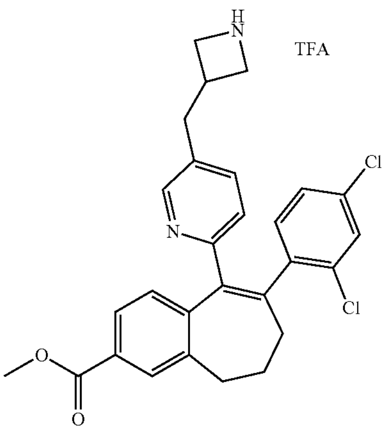 [SMILES: COC(=O)c1ccc2c(c1)CCCC(c1ccc(Cl)cc1Cl)=C2c1ccc(CC2CNC2)cn1]

Step 2 of Example 253 was prepared following a similar procedure to that of step 2 of Intermediate 11 from tert-butyl 3-((6-(8-(2,4-dichlorophenyl)-3-(methoxycarbonyl)-6,7-dihydro-5H-benzo[7]annulen-9-yl)pyridin-3-yl)methyl)azetidine-1-carboxylate to give methyl 9-(5-(azetidin-3-ylmethyl)pyridin-2-yl)-8-(2,4-dichlorophenyl)-6,7-dihydro-5H-benzo[7]annulene-3-carboxylate, trifluoroacetic acid which was used in the next step without further purification.

Step 3: methyl 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylate

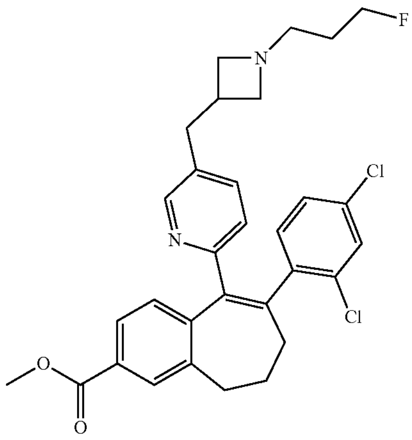 [SMILES: COC(=O)c1ccc2c(c1)CCCC(c1ccc(Cl)cc1Cl)=C2c1ccc(CC2CN(CCCF)C2)cn1]

Step 3 of Example 253 was prepared following a similar procedure to that of step 4 of Intermediate 28 from methyl 9-(5-(azetidin-3-ylmethyl)pyridin-2-yl)-8-(2,4-dichlorophenyl)-6,7-dihydro-5H-benzo[7]annulene-3-carboxylate, trifluoroacetic acid to give methyl 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylate.

LC/MS (m/z, MH+): 553

Step 4: 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic Acid

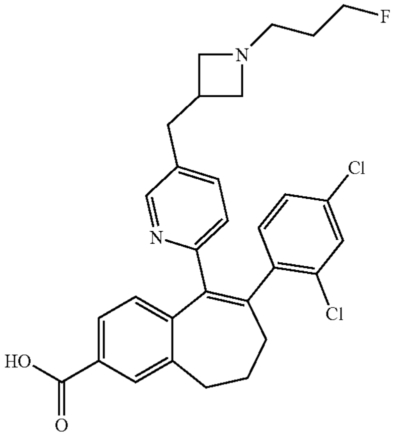 [SMILES: O=C(O)c1ccc2c(c1)CCCC(c1ccc(Cl)cc1Cl)=C2c1ccc(CC2CN(CCCF)C2)cn1]

Step 4 of Example 253 was prepared following a similar procedure to that of step 2 of Example 2 from methyl 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylate to give 17 mg (18% for two last steps) of 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic acid.

Example 254. 8-(2,4-dichlorophenyl)-9-(4-((1-(3-fluoropropyl)azetidin-3-yl)methyl)phenyl)-6,7-dihydro-5H-benzo[7]annulen-3-ol

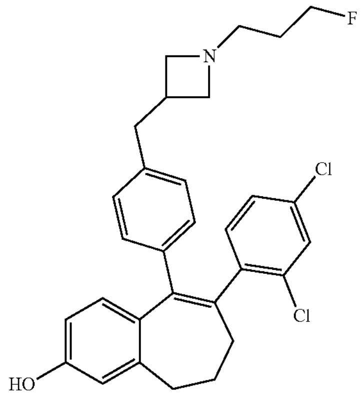 [SMILES: Oc1ccc2c(c1)CCCC(c1ccc(Cl)cc1Cl)=C2c1ccc(CC2CN(CCCF)C2)cc1]

Example 254 was prepared following a similar procedure to that of step 1 of Example 1 from 8-bromo-9-(4-((1-(3-fluoropropyl)azetidin-3-yl)methyl)phenyl)-6,7-dihydro-5H-benzo[7]annulen-3-ol (Intermediate 49) and 2,4-dichlorophenyl-boronic acid to give 120 mg (52%) of 8-(2,4-dichlorophenyl)-9-(4-((1-(3-fluoropropyl)azetidin-3-yl)methyl)phenyl)-6,7-dihydro-5H-benzo[7]annulen-3-ol as an off-white solid.

Example 255. 8-(2-chlorophenyl)-9-(4-((1-(3-fluoropropyl)azetidin-3-yl)methyl)phenyl)-6,7-dihydro-5H-benzo[7]annulen-3-ol

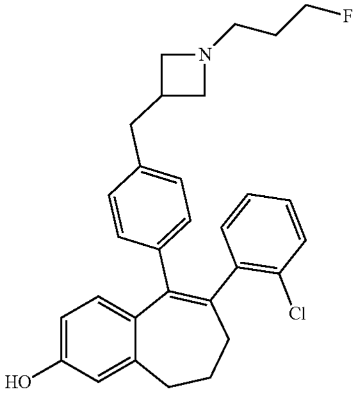 [SMILES: Oc1ccc2c(c1)CCCC(c1ccccc1Cl)=C2c1ccc(CC2CN(CCCF)C2)cc1]

Example 255 was prepared following a similar procedure to that of step 1 of Example 1 from 8-bromo-9-(4-((1-(3-fluoropropyl)azetidin-3-yl)methyl)phenyl)-6,7-dihydro-5H-benzo[7]annulen-3-ol (Intermediate 49) and 2-chlorophenyl-boronic acid to give 130 mg (61%) of 8-(2-chlorophenyl)-9-(4-((1-(3-fluoropropyl)azetidin-3-yl) methyl)phenyl)-6,7-dihydro-5H-benzo[7]annulen-3-ol as a brownish solid.

The compounds according to Table 1a above were subjected to pharmacological tests for determining their degradation effects on estrogen receptors.

Test: Estrogen Receptor Degradation Activity

Said test involves measuring the in vitro degradation activity of the compounds of the Table 1a.

The measurements of the degradation activities were made using a breast cancer cell ERα in cell western assay as described hereunder.

MCF7 cells (ATCC) were seeded in 384 wells microplate (collagen coated) at a concentration of 10000 cells/30 μL per well in red phenol free MEM alpha medium (invitrogen) containing 5% charcoal dextran striped FBS. The following day, 9 points serial 1:5 dilution of each compound was added to the cells in 2.5p L at final concentrations ranging from 0.3-0.0000018 μM (in table 2), or 0.1 μM for fulvestrant (using as positive control). At 4 hours post compound addition the cells were fixed by adding 25 μL of formalin (final concentration 5% formalin containing 0.1% triton) for 10 minutes at room temperature and then washed twice with PBS. Then, 50 μL of LI-COR blocking buffer containing 0.1% Triton was added to plate for 30 minutes at room temperature. LI-COR blocking buffer was removed and cells were incubated overnight at cold room with 50 μL anti-ER rabbit monoclonal antibody (Thermo scientific MA1-39540) diluted at 1:1000 in LI-COR blocking buffer containing 0.1% tween-20. Wells which were treated with blocking buffer but no antibody were used as background control. Wells were washed twice with PBS (0.1% tween-20) and incubated at 37° C. for 60 minutes in LI-COR (0.1% tween-20) containing goat anti-rabbit antibody Alexa 488 (1:1000) and Syto-64 a DNA dye (2 μM final concentration). Cells were then washed 3 times in PBS and scanned in ACUMEN explorer (TTP-Labtech). Integrated intensities in the green fluorescence and red fluorescence were measured to determine the levels of ERα and DNA respectively.

The degradation activity with respect to estrogen receptors in this test is given by the concentration which degrades 50% of the estrogen receptor (or $IC_{50}$) in nM.

The % of ERα levels decrease were determined as follows: % inhibition=100*(1−(sample−fulvestrant: DMSO−fulvestrant)).

The Table 2 below indicates the estrogen receptor degradation activity results for the compounds of Table 1a tested at 0.3 μM, and demonstrates that said compounds have a significant degradation activity on estrogen receptors.

TABLE 2

| Compound No. | Degradation $IC_{50}$ (nM) | % Degradation At 0.3 μM |
|---|---|---|
| 1 | 0.4 | 83 |
| 2 | 0.3 | 91 |
| 3 | 0.3 | 89 |
| 4 | 0.9 | 85 |
| 5 | 0.5 | 86 |
| 6 | 0.8 | 82 |
| 7 | 0.5 | 90 |
| 8 | 0.4 | 92 |
| 9 | 0.3 | 92 |
| 10 | 0.3 | 92 |
| 11 | 0.4 | 91 |
| 12 | 0.4 | 93 |
| 13 | 0.3 | 85 |
| 14 | 0.8 | 80 |
| 15 | 4 | 86 |
| 16 | 0.4 | 94 |
| 17 | 0.3 | 90 |
| 18 | 1.6 | 95 |
| 19 | 0.3 | 91 |
| 20 | 0.3 | 91 |
| 21 | 2.1 | 89 |
| 22 | 0.3 | 92 |
| 23 | 0.2 | 91 |
| 24 | 0.4 | 92 |
| 25 | 0.3 | 91 |
| 26 | 0.3 | 92 |
| 27 | 0.5 | 94 |
| 28 | 0.4 | 93 |
| 29 | 0.6 | 98 |
| 30 | 0.4 | 94 |
| 31 | 0.3 | 89 |
| 32 | 0.6 | 94 |
| 33 | 0.2 | 89 |
| 34 | 0.2 | 79 |
| 35 | 0.4 | 91 |
| 36 | 0.6 | 89 |
| 37 | 0.4 | 87 |
| 38 | 7 | 83 |
| 39 | 1.2 | 92 |
| 40 | 0.4 | 91 |
| 41 | 1.6 | 95 |
| 42 | 3.3 | 94 |
| 43 | 0.4 | 90 |
| 44 | 0.5 | 90 |
| 45 | 0.3 | 86 |
| 46 | 0.6 | 88 |
| 47 | 0.4 | 93 |
| 48 | 0.5 | 86 |
| 49 | 3.4 | 82 |
| 50 | 10.5 | 88 |
| 51 | 0.7 | 89 |
| 52 | 255 | 54 |
| 53 | 0.4 | 91 |
| 54 | 0.6 | 94 |
| 55 | 0.5 | 93 |
| 565 | 0.7 | 90 |
| 206 | 0.4 | 86 |
| 207 | 1.1 | 92 |
| 208 | 0.2 | 95 |
| 209 | 88.7 | 100 |
| 210 | 0.3 | 88 |
| 211 | 0.1 | 96 |

TABLE 2-continued

| Compound No. | Degradation $IC_{50}$ (nM) | % Degradation At 0.3 μM |
|---|---|---|
| 212 | 0.1 | 87 |
| 213 | 0.2 | 94 |
| 214 | 2.8 | 86 |
| 215 | 0.3 | 67 |
| 216 | 13.2 | 83 |
| 217 | 6.2 | 86 |
| 218 | 0.5 | 92 |
| 219 | 6.5 | 92 |
| 220 | 0.3 | 87 |
| 221 | 0.2 | 91 |
| 222 | 2.4 | 88 |
| 223 | 0.2 | 92 |
| 224 | 43.0 | 82 |
| 225 | 6.6 | 82 |
| 226 | 0.1 | 90 |
| 227 | 0.6 | 75 |
| 228 | 0.6 | 76 |
| 229 | 0.6 | 77 |
| 230 | 0.7 | 78 |
| 231 | 0.3 | 83 |
| 232 | 0.1 | 88 |
| 233 | 0.5 | 85 |
| 234 | 1.3 | 84 |
| 235 | 4.5 | 62 |
| 236 | 0.4 | 100 |
| 237 | 5.8 | 88 |
| 238 | 1.2 | 81 |
| 239 | 0.4 | 93 |
| 240 | 0.5 | 85 |
| 241 | 3.7 | 92 |
| 242 | 1.7 | 78 |
| 243 | 15.6 | 78 |
| 244 | 13.6 | 86 |
| 245 | 269.0 | 100 |
| 246 | 31.6 | 73 |
| 247 | 1.8 | 97 |
| 248 | 2.2 | 90 |
| 249 | 0.4 | 90 |
| 250 | 0.6 | 90 |
| 251 | 0.7 | 87 |
| 252 | 48.6 | 67 |
| 253 | 4.0 | 89 |
| 254 | 1.4 | 85 |
| 255 | 0.6 | 74 |
| 256 | 1 | 82 |
| 257 | 0.7 | 83 |
| 258 | 0.8 | 87 |
| 259 | 0.4 | 87 |
| 260 | 0.6 | 86 |
| 261 | 0.8 | 89 |
| 262 | 1.6 | 91 |
| 263 | 0.8 | 90 |
| 264 | 1.1 | 95 |
| 265 | 0.4 | 83 |
| 266 | 0.3 | 90 |
| 267 | 0.8 | 89 |
| 268 | 0.5 | 89 |
| 269 | 180 | 100 |
| 270 | 225 | 100 |
| 271 | 16.2 | 83 |
| 272 | 0.6 | 90 |
| 273 | 0.6 | 89 |
| 274 | 6.5 | 84 |
| 275 | 0.4 | 89 |
| 276 | 0.4 | 85 |
| 277 | 0.3 | 82 |
| 278 | 0.2 | 84 |
| 279 | 0.2 | 84 |
| 280 | 0.3 | 86 |
| 281 | 0.4 | 84 |
| 282 | 0.4 | 86 |
| 283 | 93.3 | 90 |
| 284 | 0.3 | 96 |
| 285 | 0.4 | 89 |
| 286 | 0.3 | 88 |
| 287 | 0.4 | 86 |

TABLE 2-continued

| Compound No. | Degradation $IC_{50}$ (nM) | % Degradation At 0.3 μM |
|---|---|---|
| 288 | 0.5 | 81 |
| 289 | 0.3 | 86 |
| 290 | 0.8 | 84 |
| 291 | 0.8 | 84 |
| 292 | 0.4 | 93 |
| 293 | 0.6 | 86 |
| 294 | 0.2 | 92 |
| 295 | 0.7 | 86 |
| 296 | 0.7 | 91 |
| 297 | 0.7 | 81 |
| 298 | 0.5 | 82 |
| 299 | 0.7 | 90 |
| 300 | 11.2 | 88 |
| 301 | 0.5 | 89 |
| 302 | 0.6 | 90 |
| 303 | 0.4 | 90 |
| 304 | 17.4 | 89 |
| 305 | 1.2 | 85 |
| 306 | 25.8 | 82 |
| 307 | 0.4 | 84 |
| 308 | 1.4 | 94 |
| 309 | 0.4 | 88 |
| 310 | 0.4 | 85 |
| 311 | 9 | 73 |
| 312 | 0.3 | 91 |
| 313 | 0.3 | 90 |
| 314 | 3 | 87 |
| 315 | 1 | 87 |
| 316 | 1.2 | 81 |
| 317 | 1.6 | 87 |
| 318 | 0.6 | 94 |
| 319 | 48 | 73 |
| 320 | 110 | 80 |
| 321 | 0.5 | 88 |
| 322 | 0.6 | 87 |
| 323 | 0.6 | 84 |
| 324 | 0.8 | 86 |
| 325 | 0.5 | 89 |
| 326 | 0.7 | 91 |
| 327 | 4.7 | 86 |
| 328 | 0.4 | 88 |
| 329 | 1.3 | 89 |
| 330 | 7 | 91 |
| 331 | 10.7 | 77 |
| 332 | 0.4 | 85 |
| 333 | 0.4 | 87 |
| 334 | 0.4 | 91 |
| 335 | 0.6 | 93 |
| 336 | 0.9 | 86 |

It is therefore apparent that the tested compounds have degradation activities for estrogen receptors, with IC50 less than 1 μM and with degradation levels greater than 50%. The compounds of formula (I) can therefore be used for preparing medicaments, especially medicaments which are degraders of estrogen receptors.

Accordingly, also provided herein are medicaments which comprise a compound of the formula (I), or a pharmaceutically acceptable salt thereof.

Herein are also provided the compounds of formula (I) defined above, or pharmaceutically acceptable salts thereof, for use as medicines.

Herein are also provided the compounds of formula (I) defined above, or pharmaceutically acceptable salt thereof, for use in therapy, especially as inhibitors and degraders of estrogen receptors.

Herein are also provided the compounds of formula (I) defined above, or a pharmaceutically acceptable salts thereof, for use in the treatment of ovulatory dysfunction, cancer, endometriosis, osteoporosis, benign prostatic hypertrophy or inflammation.

A particular aspect is a compound of formula (I) defined above, or a pharmaceutically acceptable salt thereof, for use in the treatment of cancer.

In an embodiment, the cancer is a hormone dependent cancer.

In another embodiment, the cancer is an estrogen receptor dependent cancer, particularly the cancer is an estrogen receptor a dependent cancer.

In another embodiment, the cancer is selected from breast, ovarian, endometrial, prostate, uterine, cervical and lung cancer, or a metastasis thereof.

In another embodiment, the metastasis is a cerebral metastasis.

In another embodiment, the cancer is breast cancer. Particularly, the breast cancer is an estrogen receptor positive breast cancer (ERα positive breast cancer).

In another embodiment, the cancer is resistant to anti-hormonal treatment.

In a further embodiment, the compound of formula (I) is as used as single agent or in combination with other agents such as CDK4/6, mTOR or PI3K inhibitors.

According to another aspect, herein is provided a method of treating the pathological conditions indicated above, comprising administering to a subject in need thereof a therapeutically effective amount of a compound of formula (I), or a pharmaceutically acceptable salt thereof. In an embodiment of this method of treatment, the subject is a human.

Herein is also provided the use of a compound of the formula (I), or a pharmaceutically acceptable salt thereof, for the manufacture of a medicament useful in treating any of the pathological conditions indicated above, more particularly useful in treating cancer.

Herein are also provided the pharmaceutical compositions comprising as active principle a compound of formula (I). These pharmaceutical compositions comprise an effective dose of at least one compound of formula (I), or a pharmaceutically acceptable salt thereof, and also at least one pharmaceutically acceptable excipient.

The said excipients are selected, in accordance with the pharmaceutical form and method of administration desired, from the customary excipients, which are known to a person skilled in the art.

In the pharmaceutical compositions for oral, sublingual, subcutaneous, intramuscular, intravenous, topical, local, intra-tracheal, intranasal, transdermal or rectal administration, the active principle of formula (I) above, or its base, acid, zwitterion or salt thereof, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds of formula (I) in creams, gels, ointments or lotions.

As an example, a unit administration form of a compound of formula (I) in tablet form may comprise the following components:

| | |
|---|---|
| Compound of formula (I) | 50.0 Mg |
| Mannitol | 223.75 Mg |
| Sodium croscarmellose | 6.0 Mg |
| Corn starch | 15.0 Mg |
| Hydroxypropylmethylcellulose | 2.25 Mg |
| Magnesium stearate | 3.0 Mg |

There may be particular cases in which higher or lower dosages are appropriate. According to usual practice, the dosage that is appropriate for each patient is determined by the doctor according to the mode of administration and the weight and response of the said patient.

The invention claimed is:

1. A compound of the formula (I) or a pharmaceutically acceptable salt thereof:

(I)

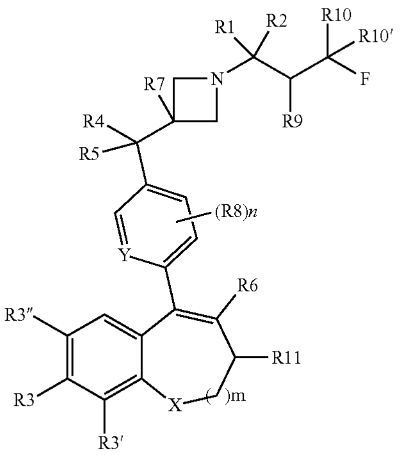

wherein:

R1 and R2 independently represent a hydrogen atom or a deuterium atom;

R3 represents a hydrogen atom, a —COOH group or a —OH group;

R3' and R3" independently represent a hydrogen atom, a methyl group, a methoxy group, a chlorine atom, a fluorine atom, or a cyano group;

R4 and R5 independently represent a hydrogen atom, a fluorine atom, a —$NH_2$ group, a $(C_1-C_3)$alkyl group, a $(C_1-C_3)$alkoxy group, or a —OH group; or R4 and R5 together form an oxo group or R4 and R5 together form a =$NOCH_3$ group or a $(C_3-C_5)$cycloalkyl group with the carbon atom to which they are attached;

R7 represents a hydrogen atom, a methyl group, a —OH group or a fluorine atom; or alternatively R4 and R7 together form a cyclopropyl group together with the bond to which they are attached such that, with the adjacent azetidine group, results in an azaspiro[2.3] hexane;

R6 represents a group selected from:

a phenyl group, said phenyl group being optionally substituted by 1 to 3 substituents independently selected from a halogen atom; a $(C_1-C_6)$alkyl group optionally substituted with a cyano group or a —OH group; a $(C_1-C_6)$fluoroalkyl group; a $(C_3-C_6)$cycloalkyl group; a $(C_1-C_6)$alkoxy group; a $(C_1-C_6)$fluoroalkoxy group; a cyano group; a trifluoromethylsulfonyl group; a $(C_1-C_4)$alkylthio group; a $(C_1-C_4)$ fluoroalkylthio group; a $(C_1-C_4)$alkylsulfonyl group; and a —OH group;

a fused phenyl group, selected from phenyl groups fused with a $(C_3-C_6)$cycloalkyl, wherein the $(C_3-C_6)$ cycloalkyl ring optionally comprises an unsaturation and, wherein the fused phenyl is optionally substituted with 1 to 3 substituents independently selected from a $(C_1-C_3)$alkyl group, a hydroxy group, a halogen atom, a $(C_1-C_6)$fluoroalkyl group and a $(C_1-C_3)$alkoxy group;

a bicyclic group comprising 5 to 12 carbon atoms, optionally comprising 1 to 2 double bonds and optionally substituted with 1 to 4 substituents independently selected from: a fluorine atom, a —OH group, a $(C_1-C_3)$-alkyl group, a $(C_1-C_3)$fluoroalkyl group, a $(C_1-C_3)$alkoxy group, a $(C_1-C_3)$fluoroalkoxy group and an oxo group;

a heteroaryl group comprising 2 to 9 carbon atoms and comprising from 1 to 3 heteroatoms independently selected from oxygen, nitrogen and sulfur, and at least 5 atoms including carbon atoms and heteroatoms, said heteroaryl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a cyano group, a carbamoyl group and a —OH group;

a cycloalkyl group comprising 3 to 7 carbon atoms, said cycloalkyl group being saturated or partially saturated and being optionally substituted with 1 to 4 substituents independently selected from:

a fluorine atom, a —OH group, a $(C_1-C_3)$alkyl group, a $(C_1-C_3)$fluoroalkyl group, a $(C_1-C_3)$ alkoxy group, a $(C_1-C_3)$fluoroalkoxy group, an oxo group, a $(C_3-C_6)$cycloalkyl group, and a phenyl group, said $(C_3-C_6)$cycloalkyl or phenyl groups being optionally substituted with one or two halogen atom(s) or $(C_1-C_3)$alkyl group(s);

a $(C_3-C_6)$cycloalkyl$(C_1-C_3)$alkyl group, optionally substituted on the cycloalkyl with 1 to 4 substituents independently selected from: a fluorine atom, a —OH group, a $(C_1-C_4)$alkyl group, a $(C_1-C_3)$fluoroalkyl group, a $(C_1-C_3)$fluoroalkoxy group and an oxo group;

a 3 to 8 membered-heterocycloalkyl group comprising 1 or 2 heteroatoms independently selected from oxygen, nitrogen and sulfur, said heterocycloalkyl group being saturated or partially saturated and being optionally substituted with 1 to 3 substituents independently selected from: a fluorine atom, a $(C_1-C_3)$ alkyl group, a $(C_1-C_3)$fluoroalkyl group, a $(C_1-C_3)$ fluoroalkoxy group, an oxo group, a $(C_1-C_3)$alkoxy group and a —OH group;

a $(C_1-C_6)$alkyl group, said alkyl group being optionally substituted with 1 to 4 substituents independently selected from: a fluorine atom, a $(C_1-C_3)$alkoxy group, a $(C_1-C_3)$fluoroalkoxy group and a —OH group; and a phenyl$(C_1-C_2)$alkyl group, said phenyl group being optionally substituted with 1 to 3 substituents independently selected from a halogen atom; a $(C_1-C_3)$ alkyl group; a $(C_1-C_3)$fluoroalkyl group; a $(C_1-C_3)$ alkoxy group; a $(C_1-C_3)$fluoroalkoxy group; a cyano group; and a —OH group;

X represents $—CH_2—$, —O— or —S—;

Y represents —CH═, —N═ or —CR"═, wherein R" represents a $(C_1-C_3)$alkyl group or a halogen atom, a cyano group, or a $(C_1-C_3)$fluoroalkyl group;

R8 independently represents a $(C_1-C_3)$alkyl group, a halogen atom, a cyano group, or a $(C_1-C_3)$fluoroalkyl group;

R9 represents a hydrogen atom or a fluorine atom;

R10 and R10' independently represent a hydrogen atom or a fluorine atom;

R11 represents a hydrogen atom, a $(C_1-C_3)$alkyl group or a cyclopropyl;

n is 0, 1 or 2, and m is 0 or 1.

2. The compound of formula (I) according to claim 1, or a pharmaceutically acceptable salt thereof, wherein R1 and R2 are each a hydrogen atom.

3. The compound of formula (I) according to claim 1, or a pharmaceutically acceptable salt thereof, wherein R3 is —COOH.

4. The compound of formula (I) according to claim 1, or a pharmaceutically acceptable salt thereof, wherein X is $—CH_2—$.

5. The compound of formula (I) according to claim 1, or a pharmaceutically acceptable salt thereof, wherein R4 and R5 represent independently from each other a hydrogen atom, a fluorine atom, a methyl group, a methoxy group, an ethoxy group, a $—NH_2$ group or a —OH group; or R4 and R5 together form an oxo group, a $═NOCH_3$ group or a cyclopropyl group with the carbon atom to which they are attached; or alternatively R4 and R7 together form a cyclopropyl group together with the bond to which they are attached.

6. The compound of formula (I) according to claim 1, or a pharmaceutically acceptable salt thereof, wherein R7 represents a hydrogen atom, a —OH group, a methyl group or a fluorine atom.

7. The compound of formula (I) according to claim 1, wherein R6 represents a phenyl group, said phenyl group being optionally substituted with 1 to 3 substituents independently selected from a chlorine atom, a fluorine atom, a methyl group, an ethyl group, a trifluoromethyl group, a 2,2,2-trifluoroethyl group, a hydroxy methyl group, a 2-hydroxyethyl group, a fluoromethyl group, a difluoromethyl group, a 2,2-difluoroethyl group, a methoxy group, an ethoxy group, a cyano group, a cyanomethyl group, a trifluoromethylsulfonyl group, a methylsulfanyl group, a difluoromethylsulfanyl group, a methylsulfonyl group and a difluoromethoxy group.

8. The compound of formula (I) according to claim 1, wherein R6 represents a fused phenyl group selected from a bicyclo[4.2.0]octa-trienyl group and an indanyl group, said group being optionally substituted with one or two fluorine atoms.

9. The compound of formula (I) according to claim 1, wherein R6 represents:

a pyridyl group, said pyridyl group being optionally substituted with 1 to 3 substituents independently selected from a halogen atom, a $(C_1-C_6)$alkyl group, a $(C_1-C_6)$fluoroalkyl group, a $(C_1-C_6)$alkoxy group, a $(C_1-C_6)$fluoroalkoxy group, a carbamoyl and a —OH group;

a pyridone, optionally substituted with 1 to 3 substituents independently selected from a halogen atom, a $(C_1-C_3)$ alkyl group, a $(C_1-C_3)$fluoroalkyl group, a $(C_1-C_3)$ alkoxy group and a $(C_1-C_3)$fluoroalkoxy group; or a pyrrole group, optionally substituted with 1 or 2 substituents selected from a $(C_1-C_6)$alkyl group.

10. The compound of formula (I) according to claim 1, wherein R6 represents a cycloalkyl group selected from a cyclohexyl group, a cyclopentyl group, a cycloheptyl group, a cycloheptenyl group and a cyclohexenyl group, said cycloalkyl group being optionally substituted with 1 to 4 substituents independently selected from a fluorine atom, a —OH group, a $(C_1-C_3)$alkyl group, a $(C_1-C_3)$fluoroalkyl group, a $(C_1-C_3)$alkoxy group, a $(C_1-C_3)$fluoroalkoxy group, an oxo group, a $(C_3-C_6)$cycloalkyl group and a phenyl group, said $(C_3-C_6)$cycloalkyl or phenyl groups being optionally substituted with one or two halogen atom(s) or a $(C_1-C_3)$alkyl group, said cycloalkyl being optionally substituted with 1 to 2 substituents independently selected from:

a fluorine atom, a methyl group, and a cyclohexyl group substituted by two halogen atoms.

11. The compound of formula (I) according to claim 1, wherein R6 represents a heterocycloalkyl group, said heterocycloalkyl group being optionally substituted with 1 to 3 substituents independently selected from a $(C_1-C_6)$alkyl group, a fluorine atom and a —OH group.

12. The compound of formula (I) according to claim 1, wherein R6 represents a bicyclic group selected from:

a spiro[3.3]hept-1-ene or a spiro[3.3]hept-2-ane group, said group being optionally substituted with 1 to 4 substituents independently selected from a $(C_1-C_3)$alkyl group, a fluorine atom, a $(C_1-C_3)$alkoxy group, a $(C_1-C_3)$fluoroalkoxy group and a —OH group; and a bicyclo[2.2.1]heptan-2-yl or a bicyclo[3.2.1]octan-3-yl group, said group being optionally substituted with 1 to 4 substituents independently selected from a $(C_1-C_3)$alkyl group, a fluorine atom, a $(C_1-C_3)$alkoxy group, a $(C_1-C_3)$fluoroalkoxy group and a —OH group.

13. The compound of formula (I) according to claim 1, wherein R6 represents a $(C_1-C_6)$alkyl group selected from an ethyl, an isobutyl group and an ethylbutyl, said alkyl group being optionally substituted with 1 to 4 substituents independently selected from a fluorine atom, a $(C_1-C_3)$alkoxy group, a $(C_1-C_3)$fluoroalkoxy group and a —OH group.

14. The compound of formula (I) according to claim 1, wherein R6 represents a cis-1,3a,4,5,6,6a-hexahydropentalenyl group or a octahydropentalenyl group.

15. The compound of formula (I) according to claim 1, wherein R6 represents a cyclobutylmethyl group.

16. The compound of formula (I) according to claim 1, wherein R6 represents a phenyl$(C_1-C_2)$alkyl group.

17. The compound of formula (I) according to claim 1, wherein R3' and R3" each represent a hydrogen atom.

18. The compound of formula (I) according to claim 1, wherein R8 independently represents a methyl group or a fluorine atom and n is 0, 1 or 2.

19. The compound of formula (I) according to claim 1, wherein Y represents —CH═, —$C(CH_3)$═, —CF═ or —N═.

20. The compound of formula (I) according to claim 1, wherein R9 represents a hydrogen atom.

21. The compound of formula (I) according to claim 1, wherein R10 and R10' each represent a hydrogen atom.

22. The compound of formula (I) according to claim 1, wherein R11 represents a hydrogen atom.

23. The compound of formula (I) according to claim 1, wherein m is 1.

24. The compound of formula (I) according to claim 1, or a pharmaceutically acceptable salt thereof selected from the following compounds:

9-(4-((1-(3-fluoropropyl)azetidin-3-yl)methyl)phenyl)-8-phenyl-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-6,7-dihydro-5H-benzo[7]annulene-3-carboxylic acid, 8-(2-chlorophenyl)-9-(4-((1-(3-fluoropropyl)azetidin-3-yl)methyl)phenyl)-6,7-dihydro-5H-benzo[7]annulene-3-carboxylic acid, 8-(4,4-difluorocyclohexyl)-9-(4-((1-(3-fluoropropyl)azetidin-3-yl)methyl)phenyl)-6,7-dihydro-5H-benzo[7]annulene-3-carboxylic acid, 8-(4,4-difluorocyclohex-1-en-1-yl)-9-(4-((1-(3-fluoropropyl)azetidin-3-yl)methyl)phenyl)-6,7-dihydro-5H-benzo[7]annulene-3-carboxylic acid, 8-cyclopentyl-9-(4-((1-(3-fluoropropyl)azetidin-3-yl)methyl)phenyl)-6,7-dihydro-5H-benzo[7]annulene-3-carboxylic acid, 8-(2-chloro-4-methylphenyl)-9-(4-((1-(3-fluoropropyl)azetidin-3-yl)methyl)phenyl)-6,7-dihydro-5H-benzo[7]annulene-3-carboxylic acid, 8-(2-chloro-4-fluorophenyl)-9-(4-((1-(3-fluoropropyl)azetidin-3-yl)methyl)phenyl)-6,7-dihydro-5H-benzo[7]annulene-3-carboxylic acid, 8-(2-chloro-3-fluorophenyl)-9-(4-((1-(3-fluoropropyl)azetidin-3-yl)methyl)phenyl)-6,7-dihydro-5H-benzo[7]annulene-3-carboxylic acid, 8-(2,4-dimethylphenyl)-9-(4-((1-(3-fluoropropyl)azetidin-3-yl)methyl)phenyl)-6,7-dihydro-5H-benzo[7]annulene-3-carboxylic acid, 8-(2-fluoro-4-methylphenyl)-9-(4-((1-(3-fluoropropyl)azetidin-3-yl)methyl)phenyl)-6,7-dihydro-5H-benzo[7]annulene-3-carboxylic acid, 8-(4-chloro-2-fluorophenyl)-9-(4-((1-(3-fluoropropyl)azetidin-3-yl)methyl)phenyl)-6,7-dihydro-5H-benzo[7]annulene-3-carboxylic acid, 8-(4,4-dimethylcyclohexyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-((1s,4s)-4-methylcyclohexyl)-6,7-dihydro-5H-benzo[7]annulene-3-carboxylic acid, 9-(4-((1-(3-fluoropropyl)azetidin-3-yl)methyl)phenyl)-8-((1r,4r)-4-methylcyclohexyl)-6,7-dihydro-5H-benzo[7]annulene-3-carboxylic acid, 8-(2-fluoro-4-methoxyphenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(2-methyl-4-(trifluoromethyl)phenyl)-6,7-dihydro-5H-benzo[7]annulene-3-carboxylic acid, 9-(4-((1-(3-fluoropropyl)azetidin-3-yl)methyl)phenyl)-8-(6-methoxypyridin-3-yl)-6,7-dihydro-5H-benzo[7]annulene-3-carboxylic acid, 8-(2,3-dichlorophenyl)-9-(4-((1-(3-fluoropropyl)azetidin-3-yl)methyl)phenyl)-6,7-dihydro-5H-benzo[7]annulene-3-carboxylic acid, 8-(4-(difluoromethoxy)-2-methylphenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(2-methoxypyridin-4-yl)-6,7-dihydro-5H-benzo[7]annulene-3-carboxylic acid, 8-(2,3-difluorophenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(2-(trifluoromethyl)phenyl)-6,7-dihydro-5H-benzo[7]annulene-3-carboxylic acid, 8-(2-chloro-4-methoxyphenyl)-9-(4-((1-(3-fluoropropyl)azetidin-3-yl)methyl)phenyl)-6,7-dihydro-5H-benzo[7]annulene-3-carboxylic acid, 8-(4-chloro-2-methylphenyl)-9-(4-((1-(3-fluoropropyl)azetidin-3-yl)methyl)phenyl)-6,7-dihydro-5H-benzo[7]annulene-3-carboxylic acid, 8-(4-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(4-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(3-fluoro-2-methylphenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(4-methoxy-2-methylphenyl)-6,7-dihydro-5H-benzo[7]annulene-3-carboxylic acid, 8-(2-chloro-3-methylphenyl)-9-(4-((1-(3-fluoropropyl)azetidin-3-yl)methyl)phenyl)-6,7-dihydro-5H-benzo[7]annulene-3-carboxylic acid, 8-(2-fluoro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(3-chloro-2-fluorophenyl)-9-(4-((1-(3-fluoropropyl)azetidin-3-yl)methyl)phenyl)-6,7-dihydro-5H-benzo[7]annulene-3-carboxylic acid, 8-(4-fluoro-2-methylphenyl)-9-(4-((1-(3-fluoropropyl)azetidin-3-yl)methyl)phenyl)-6,7-dihydro-5H-benzo[7]annulene-3-carboxylic acid, 8-(2-chloro-6-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(2-fluorophenyl)-9-(4-((1-(3-fluoropropyl)azetidin-3-yl)methyl)phenyl)-6,7-dihydro-5H-benzo[7]annulene-3-carboxylic acid, 8-(4-fluoro-2-methoxyphenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-isobutyl-6,7-dihydro-5H-benzo[7]annulene-3-carboxylic acid, dihydro-5H-benzo[7]annulene-3-carboxylic acid, 8-(2,4-dichlorophenyl)-9-(4-(1-(3-fluoropropyl)azetidine-3-carbonyl)phenyl)-6,7-dihydro-5H-benzo[7]annulene-3-carboxylic acid, 8-(2,4-dichlorophenyl)-9-(4-(difluoro(1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)(hydroxy)methyl)phenyl)-6,7-dihydro-5H-benzo[7]annulene-3-carboxylic acid, 8-(2,4-dichlorophenyl)-9-(4-(fluoro(1-(3-fluoropropyl)azetidin-3-yl)methyl)phenyl)-6,7-dihydro-5H-benzo[7]annulene-3-carboxylic acid, 8-(3,4-difluorophenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((3-fluoro-1-(3-fluoropropyl)azetidin-3-yl)methyl)phenyl)-6,7-dihydro-5H-benzo[7]annulene-3-carboxylic acid, 8-(2,4-dichlorophenyl)-9-(2-fluoro-4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)-3-methylphenyl)-6,7-dihydro-5H-benzo[7]annulene-3-carboxylic acid, 4-(2-chlorophenyl)-5-(4-((1-(3-fluoropropyl)azetidin-3-yl)methyl)phenyl)-2,3-dihydrobenzo[b]oxepine-8-carboxylic acid, 8-(6,6-difluorospiro[3.3]hept-1-en-2-yl)-9-(4-((1-(3-fluoropropyl)azetidin-3-yl)methyl)phenyl)-6,7-dihydro-5H-benzo[7]annulene-3-carboxylic acid, 8-(6,6-difluorospiro[3.3]heptan-2-yl)-9-(4-((1-(3-fluoropropyl)azetidin-3-yl)methyl)phenyl)-6,7-dihydro-5H-benzo[7]annulene-3-carboxylic acid, 4-(2,4-dichlorophenyl)-5-(4-((1-(3-fluoropropyl)azetidin-3-yl)methyl)phenyl)-2,3-dihydrobenzo[b]thiepine-8-carboxylic acid, 8-(bicyclo[4.2.0]octa-1(6),2,4-trien-2-yl)-9-(4-((1-(3-fluoropropyl)azetidin-3-yl)methyl)phenyl)-6,7-dihydro-5H-benzo[7]annulene-3-carboxylic acid, 8-(1,1-difluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride, 8-(7-fluoro-2,3-dihydro-1H-inden-4-yl)-9-(4-((1-(3-fluoropropyl)azetidin-3-yl)methyl)phenyl)-6,7-dihydro-5H-benzo[7]annulene-3-carboxylic acid hydrochloride, 8-(5-fluoro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, 8-(2-(difluoromethyl)-4-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(3-chloro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid, 8-(2-chloro-4-fluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride, 8-(3-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid, 8-(3,4-bis(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid, 8-(4-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid, formic acid, 9-(4-(difluoro(1-(3-fluoropropyl)azetidin-3-yl)methyl)phenyl)-8-(cis-4-methylcyclohexyl)-6,7-dihydro-5H-benzo[7]annulene-3-carboxylic acid, 9-(4-(difluoro(1-(3-fluoropropyl)azetidin-3-yl)methyl)phenyl)-8-(trans-4-methylcyclohexyl)-6,7-dihydro-5H-benzo[7]annulene-3-carboxylic acid, 8-(3-fluorophenyl)-9-(4-((1-(3-fluoropropyl)azetidin-3-yl)methyl)phenyl)-6,7-dihydro-5H-benzo[7]annulene-3-carboxylic acid, 8-(3-fluoro-2-(trifluoromethyl)phenyl)-9-(3-fluoro-4-((1-(3-fluoropropyl)azetidin-3-yl)methyl)phenyl)-6,7-dihydro-5H-benzo[7]annulene-3-carboxylic acid, 8-(3-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(2-methyl-3-(trifluoromethyl)phenyl)-6,7-dihydro-5H-benzo[7]annulene-3-carboxylic acid hydrochloride, 8-(4-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid, 8-(5-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid, 8-(3-fluoro-2-methoxypyridin-4-yl)-9-(3-fluoro-4-((1-(3-fluoropropyl)azetidin-3-yl)methyl)phenyl)-6,7-dihydro-5H-benzo[7]annulene-3-carboxylic acid, 8-(5-chloro-3-(trifluoromethyl)pyridin-2-yl)-9-(3-fluoro-4-((1-(3-fluoropropyl)azetidin-3-yl)methyl)phenyl)-6,7-dihydro-5H-benzo[7]annulene-3-carboxylic acid, 8-(4-chloro-3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid, 8-(4-chloro-3-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-chloro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 8-(4-chloro-2-(difluoromethyl)phenyl)-4-fluoro-9-(4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-9-(4-(5-(3-fluoropropyl)-5-azaspiro[2.3]hexan-1-yl)phenyl)-6,7-dihydro-5H-benzo[7]annulene-3-carboxylic acid, 8-(4-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-fluoro-3-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-difluorophenyl)-9-(2-fluoro-4-((1-(3-fluoropropyl)azetidin-3-yl)methyl)phenyl)-6,7-dihydro-5H-benzo[7]annulene-3-carboxylic acid hydrochloride, 8-(5-chloro-3-(difluoromethyl)pyridin-2-yl)-9-(4-((1-(3-fluoropropyl)azetidin-3-yl)methyl)phenyl)-6,7-dihydro-5H-benzo[7]annulene-3-carboxylic acid hydrochloride, 8-(3-fluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(3-chloro-4-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(3,4-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(3-chloro-2-(trifluoromethyl)phenyl)-9-(2-fluoro-4-((1-(3-fluoropropyl)azetidin-3-yl)methyl)phenyl)-6,7-dihydro-5H-benzo[7]annulene-3-carboxylic acid hydrochloride, 8-(2-chloro-3-fluorophenyl)-4-fluoro-9-(4-((1-(3-fluoropropyl)azetidin-3-yl)methyl)phenyl)-6,7-dihydro-5H-benzo[7]annulene-3-carboxylic acid, formic acid, 8-(3-chloro-4-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, formic acid, 8-(5-chloro-4-(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid, formic acid, 8-(3-chloro-4-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(2-fluoro-3-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid, 8-(6-(difluoromethyl)-2,3-difluorophenyl)-9-(4-((1-(3-fluoropropyl)azetidin-3-yl)methyl)phenyl)-6,7-dihydro-5H-benzo[7]annulene-3-carboxylic acid, formic acid, 8-(3-chlorophenyl)-4-fluoro-9-(4-((1-(3-fluoropropyl)azetidin-3-yl)methyl)phenyl)-6,7-dihydro-5H-benzo[7]annulene-3-carboxylic acid, formic acid, 8-(6-(difluoromethyl)-4-methylpyridin-3-yl)-9-(4-((1-(3-fluoropropyl)azetidin-3-yl)methyl)phenyl)-6,7-dihydro-5H-benzo[7]annulene-3-carboxylic acid, 8-(3,3-dimethylcyclohexyl)-9-(4-((1-(3-fluoropropyl)azetidin-3-yl)methyl)phenyl)-6,7-dihydro-5H-benzo[7]annulene-3-carboxylic acid hydrochloride, 8-(5-fluoro-2-methylphenyl)-9-(4-((1-(3-fluoropropyl)azetidin-3-yl)methyl)phenyl)-6,7-dihydro-5H-benzo[7]annulene-3-carboxylic acid, formic acid, 8-(4-(difluoromethyl)-2-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(2-cyano-4-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(4-chloro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(3-fluoro-2-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride, 8-(2-carbamoylpyridin-4-yl)-9-(4-((1-(3-fluoropropyl)azetidin-3-yl)methyl)phenyl)-6,7-dihydro-5H-benzo[7]annulene-3-carboxylic acid hydrochloride, 9-(4-((l-(3-fluoropropyl)azetidin-3-yl)methyl)phenyl)-8-(trans-3-methylcyclohexyl)-6,7-dihydro-5H-benzo[7]annulene-3-carboxylic acid hydrochloride, 9-(4-((1-(3-fluoropropyl)azetidin-3-yl)methyl)phenyl)-8-(cis-3-methylcyclohexyl)-6,7-dihydro-5H-benzo[7]annulene-3-carboxylic acid hydrochloride, 9-(4-((1-(3-fluoropropyl)azetidin-3-yl)methyl)phenyl)-8-(1H-pyrrol-2-yl)-6,7-dihydro-5H-benzo[7]annulene-3-carboxylic acid, 8-(4-ethyl-2-methylphenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(4-((trifluoromethyl)sulfonyl)phenyl)-6,7-dihydro-5H-benzo[7]annulene-3-carboxylic acid hydrochloride, 8-(2,4-dichlorophenyl)-9-(2,3-difluoro-4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-mesityl-6,7-dihydro-5H-benzo[7]annulene-3-carboxylic acid, 8-(4-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 8-(3-chlorophenyl)-9-(4-((1-(3-fluoropropyl)azetidin-3-yl)methyl)phenyl)-6,7-dihydro-5H-benzo[7]annulene-3-carboxylic acid hydrochloride, 8-(4-cyano-2-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-fluoro-4-(methylthio)phenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-9-(2,5-difluoro-4-((1-(3-fluoropropyl)azetidin-3-yl)methyl)phenyl)-6,7-dihydro-5H-benzo[7]annulene-3-carboxylic acid, 8-(2-chloro-4-methylphenyl)-9-(2-fluoro-4-((1-(3-fluoropropyl)azetidin-3-yl)methyl)phenyl)-6,7-dihydro-5H-benzo[7]annulene-3-carboxylic acid hydrochloride, 8-(4-chloro-3-fluoro-2-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(3,4-difluoro-2-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-fluoro-4-(methylsulfonyl)phenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(1-methyl-1H-pyrrol-2-yl)-6,7-dihydro-5H-benzo[7]annulene-3-carboxylic acid hydrochloride, 8-(2,6-dimethylpyridin-3-yl)-9-(3-fluoro-4-((1-(3-fluoropropyl)azetidin-3-yl)methyl)phenyl)-6,7-dihydro-5H-benzo[7]annulene-3-carboxylic acid, 8-(4-chloro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, formic acid, 8-(2,5-difluorophenyl)-9-(4-((1-(3-fluoropropyl)azetidin-3-yl)methyl)phenyl)-6,7-dihydro-5H-benzo[7]annulene-3-carboxylic acid, formic acid, 9-(3-fluoro-4-((1-(3-fluoropropyl)azetidin-3-yl)methyl)phenyl)-8-(2-fluoro-4-methylphenyl)-6,7-dihydro-5H-benzo[7]annulene-3-carboxylic acid, 8-(4-fluoro-2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(3-cyano-2-methylphenyl)-9-(4-((1-(3-fluoropropyl)azetidin-3-yl)methyl)phenyl)-6,7-dihydro-5H-benzo[7]annulene-3-carboxylic acid, 8-(4-((difluoromethyl)thio)phenyl)-9-(4-((1-(3-fluoropropyl)azetidin-3-yl)methyl)phenyl)-6,7-dihydro-5H-benzo[7]annulene-3-carboxylic acid hydrochloride, 8-(4-fluoro-2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(4-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(2,6-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-9-(3,5-difluoro-4-((1-(3-fluoropropyl)azetidin-3-yl)methyl)phenyl)-6,7-dihydro-5H-benzo[7]annulene-3-carboxylic acid, 8-(2,6-dimethylpyridin-3-yl)-9-(4-((1-(3-fluoropropyl)azetidin-3-yl)methyl)phenyl)-6,7-dihydro-5H-benzo[7]annulene-3-carboxylic acid hydrochloride, 8-(4-chloro-2-(cyanomethyl)phenyl)-9-(4-((1-(3-fluoropropyl)azetidin-3-yl)methyl)phenyl)-6,7-dihydro-5H-benzo[7]annulene-3-carboxylic acid, formic acid, 8-(2-chloro-4-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(2-(fluoromethyl)phenyl)-9-(4-((1-(3-fluoropropyl)azetidin-3-yl)methyl)phenyl)-6,7-dihydro-5H-benzo[7]annulene-3-carboxylic acid, 8-(3-cyanophenyl)-9-(4-((1-(3-fluoropropyl)azetidin-3-yl)methyl)phenyl)-6,7-dihydro-5H-benzo[7]annulene-3-carboxylic acid, formic acid, 8-(5-chloro-3-methylpyridin-2-yl)-9-(4-((1-(3-fluoropropyl)azetidin-3-yl)methyl)phenyl)-6,7-dihydro-5H-benzo[7]annulene-3-carboxylic acid, 8-(2-ethyl-4-fluorophenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(o-tolyl)-6,7-dihydro-5H-benzo[7]annulene-3-carboxylic acid hydrochloride, 8-(2,3-dimethylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-ethylphenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(2,4,6-trifluorophenyl)-6,7-dihydro-5H-benzo[7]annulene-3-carboxylic acid hydrochloride, 8-(4-chloro-2-methylphenyl)-9-(3-fluoro-4-((1-(3-fluoropropyl)azetidin-3-yl)methyl)phenyl)-6,7-dihydro-5H-benzo[7]annulene-3-carboxylic acid, 8-(2-cyano-5-methylphenyl)-9-(4-((1-(3-fluoropropyl)azetidin-3-yl)methyl)phenyl)-6,7-dihydro-5H-benzo[7]annulene-3-carboxylic acid, 8-(5-cyano-2-methylphenyl)-9-(4-((1-(3-fluoropropyl)azetidin-3-yl)methyl)phenyl)-6,7-dihydro-5H-benzo[7]annulene-3-carboxylic acid, 8-(2-cyano-6-methylphenyl)-9-(4-((1-(3-fluoropropyl)azetidin-3-yl)methyl)phenyl)-6,7-dihydro-5H-benzo[7]annulene-3-carboxylic acid, 8-(2-cyano-4-methylphenyl)-9-(4-((1-(3-fluoropropyl)azetidin-3-yl)methyl)phenyl)-6,7-dihydro-5H-benzo[7]annulene-3-carboxylic acid, 8-(4,6-bis(trifluoromethyl)pyridin-3-yl)-9-(4-((1-(3-fluoropropyl)azetidin-3-yl)methyl)phenyl)-6,7-dihydro-5H-benzo[7]annulene-3-carboxylic acid, 8-(2-chloro-4-fluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(2,3-difluorophenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(cyclohept-1-en-1-yl)-9-(4-((1-(3-fluoropropyl)azetidin-3-yl)methyl)phenyl)-6,7-dihydro-5H-benzo[7]annulene-3-carboxylic acid, 8-cycloheptyl-9-(4-((1-(3-fluoropropyl)azetidin-3-yl)methyl)phenyl)-6,7-dihydro-5H-benzo[7]annulene-3-carboxylic acid hydrochloride, 8-(2-(difluoromethyl)-4-fluorophenyl)-9-(4-((1-(3-fluoropropyl)azetidin-3-yl)methyl)phenyl)-6,7-dihydro-5H-benzo[7]annulene-3-carboxylic acid, 8-(3-fluoro-2-(fluoromethyl)phenyl)-9-(4-((1-(3-fluoropropyl)azetidin-3-yl)methyl)phenyl)-6,7-dihydro-5H-benzo[7]annulene-3-carboxylic acid, 8-(2-cyano-3-methylphenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)-3,5-dimethylphenyl)-6,7-dihydro-5H-benzo[7]annulene-3-carboxylic acid hydrochloride, 9-(4-(difluoro(1-(3-fluoropropyl)azetidin-3-yl)methyl)phenyl)-8-isobutyl-6,7-dihydro-5H-benzo[7]annulene-3-carboxylic acid, 8-(2,4-difluorophenyl)-9-(4-((1-(3-fluoropropyl)azetidin-3-yl)methyl)phenyl)-6,7-dihydro-5H-benzo[7]annulene-3-carboxylic acid hydrochloride, 8-(4-chloro-2-cyanophenyl)-9-(4-((1-(3-fluoropropyl)azetidin-3-yl)methyl)phenyl)-6,7-dihydro-5H-benzo[7]annulene-3-carboxylic acid hydrochloride, 8-(4-chloro-2,3-difluorophenyl)-9-(4-((1-(3-fluoropropyl)azetidin-3-yl)methyl)phenyl)-6,7-dihydro-5H-benzo[7]annulene-3-carboxylic acid hydrochloride, 8-(3-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(2-chloro-3-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(4-fluoro-2-methylphenyl)-9-(3-fluoro-4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-9-(4-(1-fluoro-1-(1-(3-fluoropropyl)azetidin-3-yl)ethyl)phenyl)-6,7-dihydro-5H-benzo[7]annulene-3-carboxylic acid hydrochloride, 9-(4-(fluoro(1-(3-fluoropropyl)azetidin-3-yl)methyl)phenyl)-8-(2-fluoro-4-methylphenyl)-6,7-dihydro-5H-benzo[7]annulene-3-carboxylic acid, 8-(4-chloro-2-fluorophenyl)-9-(4-(fluoro(1-(3-fluoropropyl)azetidin-3-yl)methyl)phenyl)-6,7-dihydro-5H-benzo[7]annulene-3-carboxylic acid, 8-(2-chloro-4-methylphenyl)-9-(4-(fluoro(1-(3-fluoropropyl)azetidin-3-yl)methyl)phenyl)-6,7-dihydro-5H-benzo[7]annulene-3-carboxylic acid, 8-(2-(difluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dimethylphenyl)-9-(4-(fluoro(1-(3-fluoropropyl)azetidin-3-yl)methyl)phenyl)-6,7-dihydro-5H-benzo[7]annulene-3-carboxylic acid, 8-(2-chloro-3-fluorophenyl)-9-(4-(fluoro(1-(3-fluoropropyl)azetidin-3-yl)methyl)phenyl)-6,7-dihydro-5H-benzo[7]annulene-3-carboxylic acid, 8-(4-chloro-2-methylphenyl)-9-(4-(fluoro(1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)-3-methylazetidin-3-yl)methyl)phenyl)-6,7-dihydro-5H-benzo[7]annulene-3-carboxylic acid, 9-(4-(fluoro(1-(3-fluoropropyl)azetidin-3-yl)methyl)phenyl)-8-(3-fluoro-2-methylphenyl)-6,7-dihydro-5H-benzo[7]annulene-3-carboxylic acid, 9-(4-(fluoro(1-(3-fluoropropyl)azetidin-3-yl)methyl)phenyl)-8-(4-fluoro-2-methylphenyl)-6,7-dihydro-5H-benzo[7]annulene-3-carboxylic acid, 8-(2-chloro-4-fluorophenyl)-9-(4-(fluoro(1-(3-fluoropropyl)azetidin-3-yl)methyl)phenyl)-6,7-dihydro-5H-benzo[7]annulene-3-carboxylic acid, 8-(2-chloro-3-methylphenyl)-9-(4-(fluoro(1-(3-fluoropropyl)azetidin-3-yl)methyl)phenyl)-6,7-dihydro-5H-benzo[7]annulene-3-carboxylic acid, 8-(2-chloro-4-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 9-(4-(difluoro(1-(3-fluoropropyl)azetidin-3-yl)methyl)phenyl)-8-(4-fluoro-2-(trifluoromethyl)phenyl)-6,7-dihydro-5H-benzo[7]annulene-3-carboxylic acid, 9-(4-(difluoro(1-(3-fluoropropyl)azetidin-3-yl)methyl)phenyl)-8-(2-(trifluoromethyl)phenyl)-6,7-dihydro-5H-benzo[7]annulene-3-carboxylic acid, 8-(4-chlorophenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(4-methylpyridin-3-yl)-6,7-dihydro-5H-benzo[7]annulene-3-carboxylic acid, 8-(2,4-dichlorophenyl)-9-(4-((1-(2,3-difluoropropyl)azetidin-3-yl)methyl)phenyl)-6,7-dihydro-5H-benzo[7]annulene-3-carboxylic acid, (E)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid, (Z)-8-(2,4-dichlorophenyl)-9-(4-((1-(3-fluoropropyl)azetidin-3-yl)(methoxyimino)methyl)phenyl)-6,7-dihydro-5H-benzo[7]annulene-3-carboxylic acid, trifluoroacetic acid, 9-(4-(difluoro(1-(3-fluoropropyl)azetidin-3-yl)methyl)phenyl)-8-(3-fluoro-2-methylphenyl)-6,7-dihydro-5H-benzo[7]annulene-3-carboxylic acid, 8-(4-chloro-2-methylphenyl)-9-(4-(difluoro(1-(3-fluoropropyl)azetidin-3-yl)methyl)phenyl)-6,7-dihydro-5H-benzo[7]annulene-3-carboxylic acid, 9-(4-(difluoro(1-(3-fluoropropyl)azetidin-3-yl)methyl)phenyl)-8-(4-fluoro-2-methylphenyl)-6,7-dihydro-5H-benzo[7]annulene-3-carboxylic acid, 8-(4-ethoxy-2-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(5-chloro-2-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(5-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 8-(2-fluoro-5-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2-chlorophenyl)-2-fluoro-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-2-fluoro-9-(4-((1-(3-fluoropropyl)azetidin-3-yl)methyl)phenyl)-6,7-dihydro-5H-benzo[7]annulene-3-carboxylic acid, 8-(3,4-dichlorophenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dichlorophenyl)-9-(4-((1-(3-fluoropropyl-1,1-d2)azetidin-3-yl)methyl)phenyl)-6,7-dihydro-5H-benzo[7]annulene-3-carboxylic acid hydrochloride, 8-(1,5-dimethyl-6-oxo-1,6-dihydropyridin-3-yl)-9-(4-((1-(3-fluoropropyl)azetidin-3-yl)methyl)phenyl)-6,7-dihydro-5H-benzo[7]annulene-3-carboxylic acid, 8-(2,3-difluoro-4-methylphenyl)-9-(4-((1-(3-fluoropropyl)azetidin-3-yl)methyl)phenyl)-6,7-dihydro-5H-benzo[7]annulene-3-carboxylic acid hydrochloride, 8-(2,4-dichloro-3-fluorophenyl)-9-(4-((1-(3-fluoropropyl)azetidin-3-yl)methyl)phenyl)-6,7-dihydro-5H-benzo[7]annulene-3-carboxylic acid hydrochloride, 8-(3-chloro-2-methylphenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(4-methyl-2-(trifluoromethyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(4-(trifluoromethyl)pyridin-3-yl)-6,7-dihydro-5H-benzo[7]annulene-3-carboxylic acid, 8-(2,4-dichlorophenyl)-9-(4-(1-(1-(3-fluoropropyl)azetidin-3-yl)cyclopropyl)phenyl)-6,7-dihydro-5H-benzo[7]annulene-3-carboxylic acid hydrochloride, 8-(2-chloro-4-fluorophenyl)-2,4-difluoro-9-(4-((1-(3-fluoropropyl)azetidin-3-yl)methyl)phenyl)-6,7-dihydro-5H-benzo[7]annulene-3-carboxylic acid, 8-(2-chloro-4-methylphenyl)-2,4-difluoro-9-(4-((1-(3-fluoropropyl)azetidin-3-yl)methyl)phenyl)-6,7-dihydro-5H-benzo[7]annulene-3-carboxylic acid, 8-(5-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, 8-(5-chloro-3-fluoropyridin-2-yl)-9-(4-((1-(3-fluoropropyl)azetidin-3-yl)methyl)phenyl)-6,7-dihydro-5H-benzo[7]annulene-3-carboxylic acid, 8-(2-chloro-6-fluorophenyl)-9-(4-((1-(3-fluoropropyl)azetidin-3-yl)methyl)phenyl)-6,7-dihydro-5H-benzo[7]annulene-3-carboxylic acid, 8-(4-chloro-2-(difluoromethyl)phenyl)-9-(4-((1-(3-fluoropropyl)azetidin-3-yl)methyl)phenyl)-6,7-dihydro-5H-benzo[7]annulene-3-carboxylic acid, 8-(2,6-difluorophenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3,3-difluoropropyl)azetidin-3-yl)methyl)phenyl)-6,7-dihydro-5H-benzo[7]annulene-3-carboxylic acid, 8-(2-chlorophenyl)-2,4-difluoro-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-2,4-difluoro-9-(4-((1-(3-fluoropropyl)azetidin-3-yl)methyl)phenyl)-6,7-dihydro-5H-benzo[7]annulene-3-carboxylic acid, 8-(3-chloro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)(methoxy)methyl)phenyl)-6,7-dihydro-5H-benzo[7]annulene-3-carboxylic acid, 8-(2,4-dichlorophenyl)-9-(4-(ethoxy(1-(3-fluoropropyl)azetidin-3-yl)methyl)phenyl)-6,7-dihydro-5H-benzo[7]annulene-3-carboxylic acid, 8-(2-ethylbutyl)-9-(4-((1-(3-fluoropropyl)azetidin-3-yl)methyl)phenyl)-6,7-dihydro-5H-benzo[7]annulene-3-carboxylic acid, 8-(3-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)-3-hydroxyazetidin-3-yl)methyl)phenyl)-6,7-dihydro-5H-benzo[7]annulene-3-carboxylic acid, 8-(3,5-dichloropyridin-2-yl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-(1-(1-(3-fluoropropyl)azetidin-3-yl)-1-hydroxyethyl)phenyl)-6,7-dihydro-5H-benzo[7]annulene-3-carboxylic acid, 8-(4-chloro-2-(trifluoromethyl)phenyl)-9-(4-((3-fluoro-1-(3-fluoropropyl)azetidin-3-yl)methyl)phenyl)-6,7-dihydro-5H-benzo[7]annulene-3-carboxylic acid, 9-(4-((3-fluoro-1-(3-fluoropropyl)azetidin-3-yl)methyl)phenyl)-8-(2-(trifluoromethyl)phenyl)-6,7-dihydro-5H-benzo[7]annulene-3-carboxylic acid, 8-(2,4-dichlorophenyl)-9-(3-fluoro-4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)-2-methylphenyl)-6,7-dihydro-5H-benzo[7]annulene-3-carboxylic acid, 9-(4-((3-fluoro-1-(3-fluoropropyl)azetidin-3-yl)methyl)phenyl)-8-(4-fluoro-2-(trifluoromethyl)phenyl)-6,7-dihydro-5H-benzo[7]annulene-3-carboxylic acid, 8-(2-chloro-4-fluorophenyl)-9-(4-((3-fluoro-1-(3-fluoropropyl)azetidin-3-yl)methyl)phenyl)-6,7-dihydro-5H-benzo[7]annulene-3-carboxylic acid, 9-(4-(amino(1-(3-fluoropropyl)azetidin-3-yl)methyl)phenyl)-8-(2,4-dichlorophenyl)-6,7-dihydro-5H-benzo[7]annulene-3-carboxylic acid, 2-cyano-8-(2,4-dichlorophenyl)-9-(4-((1-(3-fluoropropyl)azetidin-3-yl)methyl)phenyl)-6,7-dihydro-5H-benzo[7]annulene-3-carboxylic acid, 4-cyano-8-(2,4-dichlorophenyl)-9-(4-((1-(3-fluoropropyl)azetidin-3-yl)methyl)phenyl)-6,7-dihydro-5H-benzo[7]annulene-3-carboxylic acid, formic acid, 4-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid, 2-chloro-8-(2,4-dichlorophenyl)-9-(4-((1-(3-fluoropropyl)azetidin-3-yl)methyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-2-methyl-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-4-methyl-6,7-dihydro-5H-benzo[7]annulene-3-carboxylic acid hydrochloride, sodium 8-(3-(difluoromethyl)-5-fluorophenyl)-9-(4-((1-(3-fluoropropyl)azetidin-3-yl)methyl)phenyl)-6,7-dihydro-5H-benzo[7]annulene-3-carboxylate, 8-(2-chlorophenyl)-9-(5-((1-(3-fluoropropyl)azetidin-3-yl)methyl)pyridin-2-yl)-6,7-dihydro-5H-benzo[7]annulene-3-carboxylic acid, 8-(2,4-dichlorophenyl)-9-(5-((1-(3-fluoropropyl)azetidin-3-yl)methyl)pyridin-2-yl)-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-6,7-dihydro-5H-benzo[7]annulen-3-ol, 8-(2-chlorophenyl)-9-(4-((1-(3-fluoropropyl)azetidin-3-yl)methyl)phenyl)-6,7-dihydro-5H-benzo[7]annulen-3-ol, 8-(2-methyl-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid, 8-(2-chloro-3-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid, 8-(4-fluoro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid, 8-(3-chloro-2-(trifluoromethyl)phenyl)-9-(4-((1-(3,3,3-trifluoropropyl)azetidin-3-yl)methyl)phenyl)-6,7-dihydro-5H-benzo[7]annulene-3-carboxylic acid, 8-(3-chloro-2-methylphenyl)-9-(4-((1-(3,3,3-trifluoropropyl)azetidin-3-yl)methyl)phenyl)-6,7-dihydro-5H-benzo[7]annulene-3-carboxylic acid, 8-(2,4-dichlorophenyl)-9-(4-((1-(3,3,3-trifluoropropyl)azetidin-3-yl)methyl)phenyl)-6,7-dihydro-5H-benzo[7]annulene-3-carboxylic acid, 6-(2,4-dichlorophenyl)-5-(4-((1-(3-fluoropropyl)azetidin-3-yl)methyl)phenyl)-7,8-dihydronaphthalene-2-carboxylic acid hydrochloride, 4-(4-chloro-2-methylphenyl)-5-(4-((1-(3-fluoropropyl)azetidin-3-yl)methyl)phenyl)-2,3-dihydrobenzo[b]oxepine-8-carboxylic acid, sodium 4-(2-chloro-4-fluorophenyl)-5-(4-((1-(3-fluoropropyl)azetidin-3-yl)methyl)phenyl)-2,3-dihydrobenzo[b]oxepine-8-carboxylate, 8-(2-chloro-4-methylphenyl)-2,4-difluoro-9-(4-((1-(3-fluoropropyl)azetidin-3-yl)methyl)phenyl)-6,7-dihydro-5H-benzo[7]annulen-3-ol, 8-(3,5-difluorophenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(3,4,5-trifluorophenyl)-6,7-dihydro-5H-benzo[7]annulene-3-carboxylic acid, 9-(4-((1-(3-fluoropropyl)azetidin-3-yl)methyl)phenyl)-8-(2-methoxy-6-(trifluoromethyl)pyridin-3-yl)-6,7-dihydro-5H-benzo[7]annulene-3-carboxylic acid, 8-(4-fluoro-2-methylphenyl)-9-(4-((1-(3-fluoropropyl)azetidin-3-yl)methyl)phenyl)-4-methoxy-6,7-dihydro-5H-benzo[7]annulene-3-carboxylic acid, 8-(2,4-difluorophenyl)-9-(4-((1-(3-fluoropropyl)azetidin-3-yl)methyl)phenyl)-4-methoxy-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-4-methoxy-6,7-dihydro-5H-benzo[7]annulene-3-carboxylic acid, 8-(4-fluoro-2-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, sodium 8-(5-(difluoromethyl)-2-fluorophenyl)-9-(4-((1-(3-fluoropropyl)azetidin-3-yl)methyl)phenyl)-6,7-dihydro-5H-benzo[7]annulene-3-carboxylate, sodium 9-(4-((1-(3-fluoropropyl)azetidin-3-yl)methyl)phenyl)-8-(2-methoxy-6-(trifluoromethyl)pyridin-4-yl)-6,7-dihydro-5H-benzo[7]annulene-3-carboxylate, 8-(3,4-difluoro-2-methylphenyl)-9-(4-((1-(3,3-difluoropropyl)azetidin-3-yl)methyl)phenyl)-6,7-dihydro-5H-benzo[7]annulene-3-carboxylic acid, 9-(4-((1-(3,3-difluoropropyl)azetidin-3-yl)methyl)phenyl)-8-(4-fluoro-2-(trifluoromethyl)phenyl)-6,7-dihydro-5H-benzo[7]annulene-3-carboxylic acid, 8-(2-chloro-3-methylphenyl)-9-(4-((1-(3,3-difluoropropyl)azetidin-3-yl)methyl)phenyl)-6,7-dihydro-5H-benzo[7]annulene-3-carboxylic acid, 9-(4-((1-(3,3-difluoropropyl)azetidin-3-yl)methyl)phenyl)-8-(3-fluoro-2-(trifluoromethyl)phenyl)-6,7-dihydro-5H-benzo[7]annulene-3-carboxylic acid, 9-(4-((1-(3,3-difluoropropyl)azetidin-3-yl)methyl)phenyl)-8-(4-fluoro-2-methylphenyl)-6,7-dihydro-5H-benzo[7]annulene-3-carboxylic acid, 8-(3-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid, 8-(2,4-difluorophenyl)-9-(4-((1-(3,3-difluoropropyl)azetidin-3-yl)methyl)phenyl)-6,7-dihydro-5H-benzo[7]annulene-3-carboxylic acid, 8-(4-chloro-2-methylphenyl)-9-(4-((1-(3,3-difluoropropyl)azetidin-3-yl)methyl)phenyl)-6,7-dihydro-5H-benzo[7]annulene-3-carboxylic acid, 8-(4-fluoro-2-(trifluoromethyl)phenyl)-9-(4-((1-(3-fluoropropyl)azetidin-3-yl)methyl)phenyl)-4-methoxy-6,7-dihydro-5H-benzo[7]annulene-3-carboxylic acid hydrochloride, 8-(2-(difluoromethyl)-4,6-difluorophenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3,3-difluoropropyl)azetidin-3-yl)methyl)phenyl)-8-(4-fluoro-2,3-dimethylphenyl)-6,7-dihydro-5H-benzo[7]annulene-3-carboxylic acid, 8-(2-chloro-3-(trifluoromethyl)phenyl)-9-(4-((1-(3,3-difluoropropyl)azetidin-3-yl)methyl)phenyl)-6,7-dihydro-5H-benzo[7]annulene-3-carboxylic acid, 9-(4-((1-(3,3-difluoropropyl)azetidin-3-yl)methyl)phenyl)-8-(2-methyl-3-(trifluoromethyl)phenyl)-6,7-dihydro-5H-benzo[7]annulene-3-carboxylic acid, 9-(4-((1-(3,3-difluoropropyl)azetidin-3-yl)methyl)phenyl)-8-(2-fluoro-3-(trifluoromethyl)phenyl)-6,7-dihydro-5H-benzo[7]annulene-3-carboxylic acid, 8-(4-chloro-2-(trifluoromethyl)phenyl)-9-(4-((1-(3,3-difluoropropyl)azetidin-3-yl)methyl)phenyl)-6,7-dihydro-5H-benzo[7]annulene-3-carboxylic acid, 8-(4-fluoro-3-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, 8-(5-chloro-3-(trifluoromethyl)pyridin-2-yl)-9-(4-((1-(3,3-difluoropropyl)azetidin-3-yl)methyl)phenyl)-6,7-dihydro-5H-benzo[7]annulene-3-carboxylic acid, 8-(4-chloro-3-fluoro-2-methylphenyl)-9-(4-((1-(3,3-difluoropropyl)azetidin-3-yl)methyl)phenyl)-6,7-dihydro-5H-benzo[7]annulene-3-carboxylic acid, 8-(3-chloro-2-methylphenyl)-9-(4-((1-(3,3-difluoropropyl)azetidin-3-yl)methyl)phenyl)-6,7-dihydro-5H-benzo[7]annulene-3-carboxylic acid, 8-(cyclobutylmethyl)-9-(4-((1-(3-fluoropropyl)azetidin-3-yl)methyl)phenyl)-6,7-dihydro-5H-benzo[7]annulene-3-carboxylic acid, 8-(2-fluoro-5-(2,2,2-trifluoroethyl)phenyl)-9-(4-((1-(3-fluoropropyl)azetidin-3-yl)methyl)phenyl)-6,7-dihydro-5H-benzo[7]annulene-3-carboxylic acid, 8-(2-(difluoromethyl)-3-fluorophenyl)-9-(4-((1-(3-fluoropropyl)azetidin-3-yl)methyl)phenyl)-6,7-dihydro-5H-benzo[7]annulene-3-carboxylic acid, 8-(3-(2,2-difluoroethyl)phenyl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(3-(2,2,2-trifluoroethyl)phenyl)-6,7-dihydro-5H-benzo[7]annulene-3-carboxylic acid, sodium 9-(4-((1-(3-fluoropropyl)azetidin-3-yl)methyl)phenyl)-8-(cis-1,3a,4,5,6,6a-hexahydropentalen-2-yl)-6,7-dihydro-5H-benzo[7]annulene-3-carboxylate, 8-(6-chloro-3-(trifluoromethyl)pyridin-2-yl)-9-(4-((1-(3-fluoropropyl)azetidin-3-yl)methyl)phenyl)-6,7-dihydro-5H-benzo[7]annulene-3-carboxylic acid, 9-(4-((1-(3-fluoropropyl)azetidin-3-yl)methyl)phenyl)-8-(2-(2,2,2-trifluoroethyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-7-methyl-6,7-dihydro-5H-benzo[7]annulene-3-carboxylic acid, 3-(4-(8-(2-chlorophenyl)-6,7-dihydro-5H-benzo[7]annulen-9-yl)benzyl)-1-(3-fluoropropyl)azetidine, 8-(2,4-dichlorophenyl)-2,4-difluoro-9-(4-((1-(3-fluoropropyl)azetidin-3-yl)methyl)phenyl)-6,7-dihydro-5H-benzo[7]annulen-3-ol, 9-(4-((1-(3-fluoropropyl)azetidin-3-yl)methyl)phenyl)-8-(6-methoxy-5-(trifluoromethyl)pyridin-3-yl)-6,7-dihydro-5H-benzo[7]annulene-3-carboxylic acid, 8-(bicyclo[2.2.1]heptan-2-yl)-9-(4-((1-(3-fluoropropyl)azetidin-3-yl)methyl)phenyl)-6,7-dihydro-5H-benzo[7]annulene-3-carboxylic acid, 3-(2,4-dichlorophenyl)-4-(4-((1-(3-fluoropropyl)azetidin-3-yl)methyl)phenyl)-2H-thiochromene-7-carboxylic acid, 8-(4-fluoro-2,3-dimethylphenyl)-9-(4-((1-(3-fluoropropyl)azetidin-3-yl)methyl)phenyl)-7-methyl-6,7-dihydro-5H-benzo[7]annulene-3-carboxylic acid, 9-(4-((1-(3-fluoropropyl)azetidin-3-yl)methyl)phenyl)-7-methyl-8-(2-methyl-3-(trifluoromethyl)phenyl)-6,7-dihydro-5H-benzo[7]annulene-3-carboxylic acid, 8-benzyl-9-(4-((1-(3-fluoropropyl)azetidin-3-yl)methyl)phenyl)-6,7-dihydro-5H-benzo[7]annulene-3-carboxylic acid, 8-(4-fluoro-2-(trifluoromethyl)phenyl)-9-(4-((1-(3-fluoropropyl)azetidin-3-yl)methyl)phenyl)-7-methyl-6,7-dihydro-5H-benzo[7]annulene-3-carboxylic acid, 9-(4-((1-(3-fluoropropyl)azetidin-3-yl)methyl)phenyl)-8-(3-methyl-2-(trifluoromethyl)phenyl)-6,7-dihydro-5H-benzo[7]annulene-3-carboxylic acid hydrochloride, 3-(2,4-difluorophenyl)-4-(4-((1-(3-fluoropropyl)azetidin-3-yl)methyl)phenyl)-2H-thiochromene-7-carboxylic acid, 8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, 8-(bicyclo[3.2.1]octan-3-yl)-9-(4-((1-(3-fluoropropyl)azetidin-3-yl)methyl)phenyl)-6,7-dihydro-5H-benzo[7]annulene-3-carboxylic acid, 8-(4-chlorophenyl)-9-(4-((1-(3-fluoropropyl)azetidin-3-yl)methyl)phenyl)-7-isopropyl-6,7-dihydro-5H-benzo[7]annulene-3-carboxylic acid, 9-(4-((1-(3-fluoropropyl)azetidin-3-yl)methyl)phenyl)-8-(4-(trifluoromethyl)phenyl)-6,7-dihydro-5H-benzo[7]annulene-3-carboxylic acid hydrochloride, 9-(4-((1-(3-fluoropropyl)azetidin-3-yl)methyl)phenyl)-8-(3-(2-hydroxyethyl)phenyl)-6,7-dihydro-5H-benzo[7]annulene-3-carboxylic acid, 9-(4-((1-(3-fluoropropyl)azetidin-3-yl)methyl)phenyl)-8-(3-(hydroxymethyl)phenyl)-6,7-dihydro-5H-benzo[7]annulene-3-carboxylic acid, 8-(2,4-dichlorophenyl)-9-(4-((1-(3-fluoropropyl)azetidin-3-yl)methyl)phenyl)-7-isopropyl-6,7-dihydro-5H-benzo[7]annulene-3-carboxylic acid, 9-(4-((1-(3-fluoropropyl)azetidin-3-yl)methyl)phenyl)-8-(3-(trifluoromethyl)phenyl)-6,7-dihydro-5H-benzo[7]annulene-3-carboxylic acid, 8-(4-chlorophenyl)-7-cyclopropyl-9-(4-((1-(3-fluoropropyl)azetidin-3-yl)methyl)phenyl)-6,7-dihydro-5H-benzo[7]annulene-3-carboxylic acid, 8-(4-fluorophenyl)-9-(4-((1-(3-fluoropropyl)azetidin-3-yl)methyl)phenyl)-7-methyl-6,7-dihydro-5H-benzo[7]annulene-3-carboxylic acid, 8-(3,4-difluorophenyl)-9-(4-((1-(3-fluoropropyl)azetidin-3-yl)methyl)phenyl)-7-methyl-6,7-dihydro-5H-benzo[7]annulene-3-carboxylic acid, 8-(4-chlorophenyl)-9-(4-((1-(3-fluoropropyl)azetidin-3-yl)methyl)phenyl)-7-methyl-6,7-dihydro-5H-benzo[7]annulene-3-carboxylic acid, 8-(4-chlorophenyl)-7-ethyl-9-(4-((1-(3-fluoropropyl)azetidin-3-yl)methyl)phenyl)-6,7-dihydro-5H-benzo[7]annulene-3-carboxylic acid, 8-((1R,2S)-2-(4,4-difluorocyclohexyl)cyclopropyl)-9-(4-((1-(3-fluoropropyl)azetidin-3-yl)methyl)phenyl)-6,7-dihydro-H-benzo[7]annulene-3-carboxylic acid, 8-(5-fluoro-2-(trifluoromethyl)phenyl)-9-(4-((1-(3-fluoropropyl)azetidin-3-yl)methyl)phenyl)-6,7-dihydro-5H-benzo[7]annulene-3-carboxylic acid hydrochloride, 9-(4-((1-(3-fluoropropyl)azetidin-3-yl)methyl)phenyl)-7-methyl-8-(3-(trifluoromethyl)phenyl)-6,7-dihydro-5H-benzo[7]annulene-3-carboxylic acid, 8-(3-chloro-2-methoxyphenyl)-9-(4-((1-(3-fluoropropyl)azetidin-3-yl)methyl)phenyl)-6,7-dihydro-5H-benzo[7]annulene-3-carboxylic acid, and 8-(3-fluoro-2-methoxyphenyl)-9-(4-((1-(3-fluoropropyl)azetidin-3-yl)methyl)phenyl)-6,7-dihydro-5H-benzo[7]annulene-3-carboxylic acid.

25. A compound selected from a compound of formula 1E, 1F, 1G and 1Fa, or a pharmaceutically acceptable salt thereof,

1E

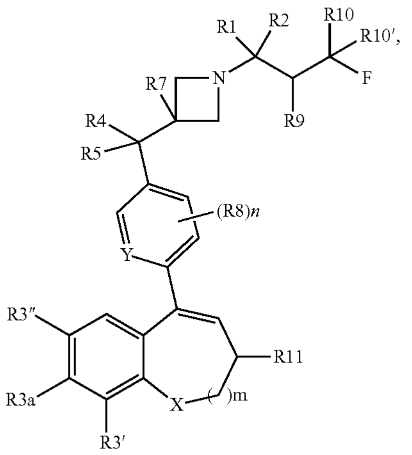

1F

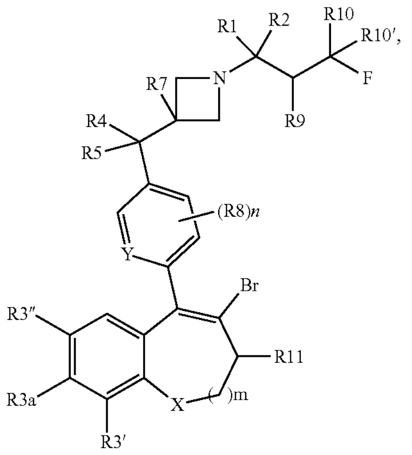

-continued

1G

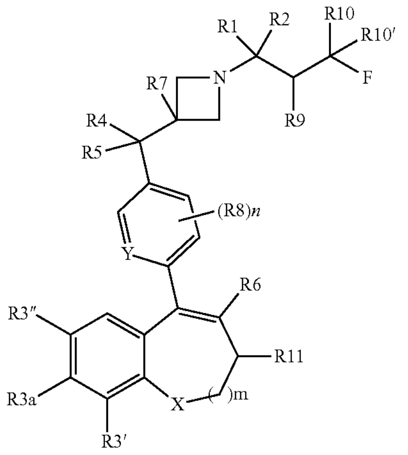

and

1Fa

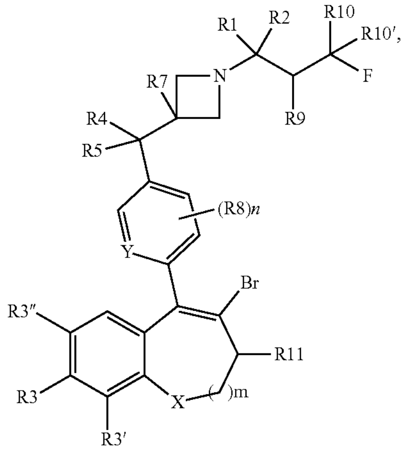

wherein R1, R2, R3, R3', R3", R4, R5, R6, R7, Y, R8, R9, R10, R10', R11, n, m, and X are as described in claim 1 and R3a is a carboxylic ester or a protected OH.

26. A compound of formula 1D or 1D', or a pharmaceutically acceptable salt thereof,

1D

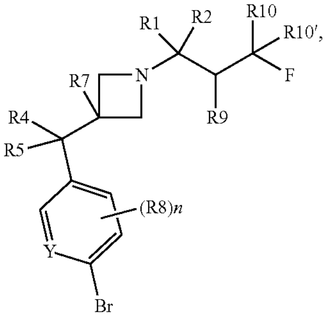

-continued

1D'

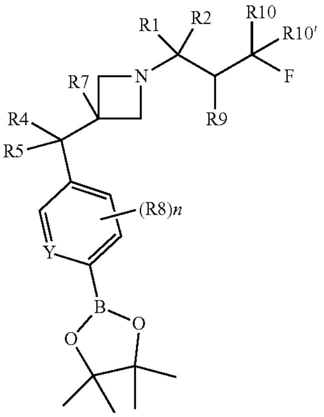

wherein R1, R2, R4, R5, R7, R8, R9, R10, R10', Y and n are as described in claim 1.

27. A process for preparing the compound of formula (I) according to claim 1, wherein a compound of formula 1G

1G

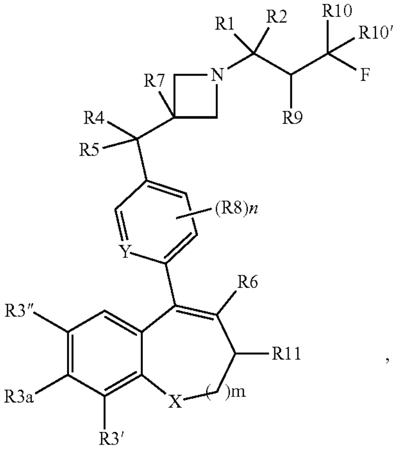

, wherein R1, R2, R3', R3", R4, R5, R6, R7, Y, R8, R9, R10, R10', R11, n, m, and X are as described in claim 1 and R3a is a carboxylic ester or a protected OH, is converted to compound of formula (I) in a first step, in the presence of a source of hydroxide ions, said first step being optionally preceded by a step for obtaining compound 1G, wherein a compound of formula 1F

1F

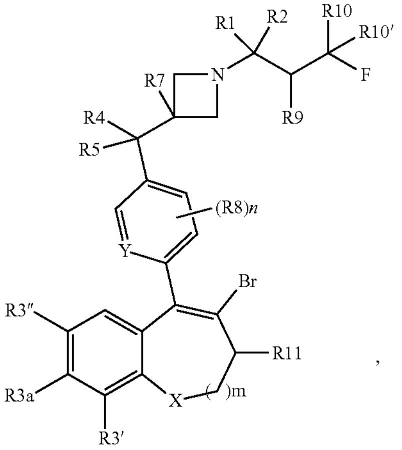

, wherein R1, R2, R3', R3", R4, R5, R7, Y, R8, R9, R10, R10', R11, n, m, and X are as described in claim 1 and R3a is as defined above, is subjected to a Suzuki coupling with a boronic reagent $R6B(OR')_2$, wherein —$B(OR')_2$ is a boronic acid or a pinacolate ester and R6 is as defined in claim 1.

28. A process for preparing the compound of formula (I) according to claim 1, wherein a compound of formula 1Fa 1Fa

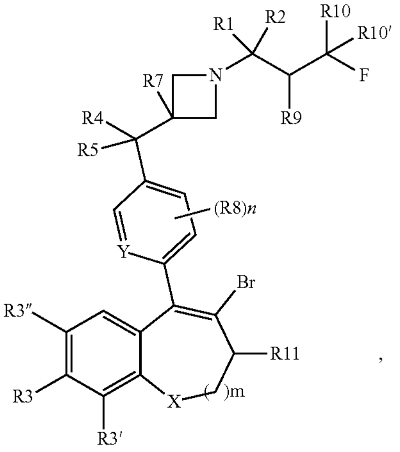

, wherein R1, R2, R3, R3', R3", R4, R5, R7, Y, R8, R9, R10, R10', n, m, and X are as described in claim 1, is submitted to a Suzuki coupling with a boronic reagent $R6B(OR')_2$ in a first step, wherein —$B(OR')_2$ is a boronic acid or a pinacolate ester and R6 is defined as in claim 1, said first step being optionally preceded by a step for obtaining compound 1Fa, wherein a compound of formula 1F

1F

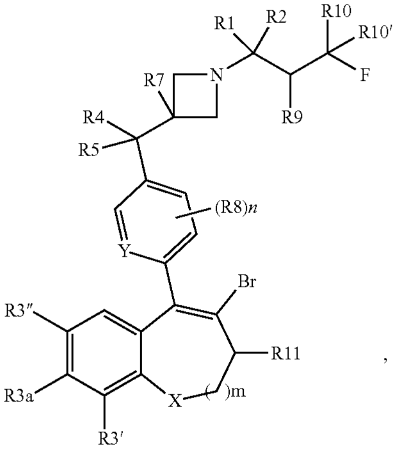

, wherein R1, R2, R3', R3", R4, R5, R7, Y, R8, R9, R10, R10', R11, n, m, and X are as described in claim 1 and R3a is a carboxylic ester or a protected OH, is converted to a compound 1Fa in the presence of a source of hydroxide ions, in solution in methanol.

29. A pharmaceutical composition comprising a compound of formula (I) according to claim 1, or a pharmaceutically acceptable salt thereof, and at least one pharmaceutically acceptable excipient.

30. A method of inhibiting and/or degrading an estrogen receptor, comprising administering to a subject in need thereof a compound of formula (I) according to claim 1, or a pharmaceutically acceptable salt thereof.

31. A method of treating a disease or condition, comprising administering to the subject a compound of formula (I) according to claim 1, or a pharmaceutically acceptable salt thereof, wherein the disease or condition is chosen from ovulatory dysfunction, cancer, endometriosis, osteoporosis, benign prostatic hypertrophy or inflammation.

32. The method according to claim 31, wherein the disease or condition is cancer.

* * * * *